United States Patent
Matsunaga et al.

(10) Patent No.: US 11,130,752 B2
(45) Date of Patent: Sep. 28, 2021

(54) AMINOPYRIMIDINE COMPOUND

(71) Applicant: Cardurion Pharmaceuticals, LLC, Cambridge, MA (US)

(72) Inventors: Nobuyuki Matsunaga, Kanagawa (JP); Yasufumi Miyamoto, Kanagawa (JP); Junya Shirai, Kanagawa (JP); Takashi Nakahata, Kanagawa (JP); Zenyu Shiokawa, Kanagawa (JP); Tomohiro Okawa, Kanagawa (JP); Akito Shibuya, Kanagawa (JP); Malcolm MacCoss, Seabrook Island, SC (US)

(73) Assignee: Cardurion Pharmaceuticals, LLC, Cambridge, MA (US)

( * ) Notice: Subject to any disclaimer, the term of this patent is extended or adjusted under 35 U.S.C. 154(b) by 0 days.

(21) Appl. No.: 16/580,984

(22) Filed: Sep. 24, 2019

(65) Prior Publication Data

US 2020/0095240 A1    Mar. 26, 2020

Related U.S. Application Data

(60) Provisional application No. 62/735,897, filed on Sep. 25, 2018.

(51) Int. Cl.
| | |
|---|---|
| C07D 401/14 | (2006.01) |
| A61K 31/505 | (2006.01) |
| A61P 9/00 | (2006.01) |
| C07D 413/14 | (2006.01) |
| C07D 417/14 | (2006.01) |
| C07D 498/08 | (2006.01) |

(52) U.S. Cl.
CPC .............. *C07D 413/14* (2013.01); *A61P 9/00* (2018.01); *C07D 417/14* (2013.01); *C07D 498/08* (2013.01)

(58) Field of Classification Search
CPC ........ C07D 401/14; A61K 31/505; A61P 9/00
See application file for complete search history.

(56) References Cited

U.S. PATENT DOCUMENTS

| | | |
|---|---|---|
| 8,530,480 B2 | 9/2013 | Kamenecka et al. |
| 9,187,453 B2 | 11/2015 | Tsukamoto et al. |
| 9,212,173 B2 | 12/2015 | Baker-glenn et al. |
| 10,543,212 B2 | 1/2020 | Matsunaga et al. |
| 2007/0021419 A1 | 1/2007 | Wang et al. |
| 2009/0181991 A1 | 7/2009 | Zhang et al. |
| 2017/0239264 A1 | 8/2017 | Fensome et al. |
| 2018/0280389 A1* | 10/2018 | Matsunaga ............... A61P 9/06 |
| 2020/0230137 A1* | 7/2020 | Matsunaga .......... A61K 31/506 |

FOREIGN PATENT DOCUMENTS

| | | |
|---|---|---|
| WO | 200211724 A2 | 2/2002 |
| WO | 2002024681 A2 | 3/2002 |
| WO | 2005021529 A1 | 3/2005 |
| WO | 2009032703 A1 | 3/2009 |
| WO | 2010057833 A1 | 5/2010 |
| WO | 2012062704 A1 | 5/2012 |
| WO | 2013052394 A1 | 4/2013 |
| WO | 2013157540 A1 | 10/2013 |
| WO | 2018183112 A1 | 10/2018 |
| WO | 2020068846 A1 | 4/2020 |

OTHER PUBLICATIONS

International Search Report and Written Opinion issued in International Application No. PCT/US18/24043, dated Jul. 10, 2018, 7 pages.
Backs et al. (Feb. 17, 2009) "The δ Isoform of CaM Kinase II is Required for Pathological Cardiac Hypertrophy and Remodeling After Pressure Overload", Proceedings of the National Academy of Sciences, 106(7):2342-2347.
Colomer et al. (Feb. 2003) "Pressure Overload Selectively Up-Regulates Ca2+/Calmodulin-Dependent Protein Kinase II in Vivo", Molecular Endocrinology, 17(2):183-192.
Degorce et al. (2016) "Discovery of a Potent, Selective, Orally Bioavailable, and Efficacious Novel 2-(Pyrazol-4-ylamino)-pyrimidine Inhibitor of the Insulin-like Growth Factor-1 Receptor (IGF-1R)", Journal of Medicinal Chemistry, 59 (10):4859-4866.
Erickson et al. (Oct. 17, 2013) "Diabetic Hyperglycaemia Activates CaMKII and Arrhythmias by O-linked Glycosylation", Nature, 502:372-376.

(Continued)

*Primary Examiner* — Bruck Kifle
(74) *Attorney, Agent, or Firm* — Mintz Levin Cohn Ferris Glovsky and Popeo, P.C.

(57) ABSTRACT

The present invention provides a compound having a CaMKII inhibitory action, which is expected to be useful as an agent for the prophylaxis or treatment of cardiac diseases (particularly catecholaminergic polymorphic ventricular tachycardia, postoperative atrial fibrillation, heart failure, fatal arrhythmia) and the like.
The present invention relates to a compound represented by the formula (I):

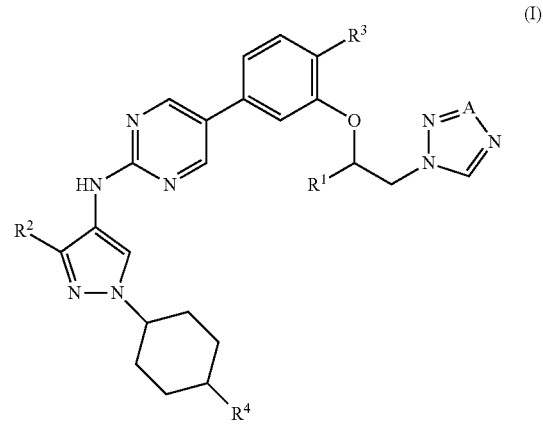

wherein each symbol is as defined in the specification, or a salt thereof.

5 Claims, No Drawings

(56) References Cited

OTHER PUBLICATIONS

Fischer et al. (Sep. 8, 2014) "Ca(2+)/Calmodulin-Dependent Protein Kinase II Equally Induces Sarcoplasmic Reticulum Ca(2+) Leak in Human Ischaemic and Dilated Cardiomyopathy", European Journal of Heart Failure, 16 (12):1292-1300.
Hackam et al. (Oct. 11, 2006) "Translation of Research Evidence From Animals to Humans", JAMA, 296 (14):1731-1732.
Hoch et al. (Apr. 2, 1999) "Identification and Expression of δ-Isoforms of the Multifunctional Ca2+/Calmodulin-Dependent Protein Kinase in Failing and Nonfailing Human Myocardium", Circulation Research, 84(6):713-721.
House et al. (Dec. 20, 2007) "CaMKII-δ Isoform Regulation of Neointima Formation After Vascular Injury", Arteriosclerosis, Thrombosis, and Vascular Biology, 28(3):441-447.
Jordan Craig V. (2003) "Tamoxifen: A Most Unlikely Pioneering Medicine", Nature Reviews Drug Discovery, 2 (3):205-213.
Ling et al. (Mar. 15, 2013) "Ca2+/Calmodulin-Dependent Protein Kinase II δ Mediates Myocardial Ischemia/Reperfusion Injury Through Nuclear Factor-κB", Circulation Research, 112(6):935-944.
Liu et al. (Jan. 2011) "Calmodulin kinase II inhibition prevents arrhythmias in RyR2R4496C+/− mice with catecholaminergic polymorphic ventricular tachycardia", Journal of Molecular and Cellular Cardiology, 50(1):214-222.
Luo et al. (Apr. 2008) "Reversal of Chronic Inflammatory Pain by Acute Inhibition of Ca2+/Calmodulin-Dependent Protein Kinase II", Journal of Pharmacology and Experimental Therapeutics, 325(1):267-275.
Mavunkel et al. {Apr. 1, 2008, e-Pub (Mar. 4, 2008)} "Pyrimidine-Based Inhibitors of CaMKIIdelta", Bioorganic & Medicinal Chemistry Letters, 18(7):2404-2408.
Pellicena et al. (Feb. 2014) "CaMKII Inhibitors: From Research Tools to Therapeutic Agents", Frontiers in Pharmacology, 5(21):1-10 pages.
Soliman et al. (Mar. 2009) "Intracellular Calcium Signals Regulate Growth of Hepatic Stellate Cells Via Specific Effects on Cell Cycle Progression", Cell Calcium, 45(3):284-292.
Timmins et al. (Oct. 2009) "Calcium/Calmodulin-Dependent Protein Kinase II links ER Stress with Fas and Mitochondrial Apoptosis Pathways", The Journal of Clinical Investigation, 119(10):2925-2941.
Vest et al. (Jul. 2, 2010) "Effective Post-insult Neuroprotection by a Novel Ca2+/Calmodulin-Dependent Protein Kinase II (CaMKII) Inhibitor", Journal of Biological Chemistry, 285(27):20675-20682.
Wang et al. (2015) "The Emerging Role of CaMKII in Cancer", Oncotarget, 6(14):11725-11734.
Westra et al. (2010) "Expression and regulation of HIF-1alpha in macrophages under inflammatory conditions; significant reduction of VEGF by CaMKII inhibitor", BMC Musculoskeletal Disorders, 30:11 pages.
Zhang et al. (May 2, 2003) "The δc Isoform of CaMKII Is Activated in Cardiac Hypertrophy and Induces Dilated Cardiomyopathy and Heart Failure", Circulation Research, 92(8):912-919.
International Search Report and Written Opinion issued in PCT Application No. PCT/US2019/52730, dated Dec. 16, 2019, 7 pages.

\* cited by examiner

AMINOPYRIMIDINE COMPOUND

This non-provisional application claims the benefit of U.S. Provisional Application Ser. No. 62/735,897 filed Sep. 25, 2018, hereby incorporated by reference in its entirety.

TECHNICAL FIELD

The present invention relates to an aminopyrimidine compound having a calcium/calmodulin-dependent protein kinase II (sometimes to be abbreviated as "CaMKII" in the present specification) inhibitory action, which is expected to be useful as an agent for the prophylaxis or treatment of cardiac diseases (particularly catecholaminergic polymorphic ventricular tachycardia, postoperative atrial fibrillation, heart failure, fatal arrhythmia) and the like.

BACKGROUND

Cardiac diseases include heart failure, arrhythmia, myocardial infarction, angina, valvular heart disease and the like, and they are high-mortality diseases. In treatment of cardiac diseases with a drug, the symptoms are improved by control of each risk factor and symptomatic therapy. However, the satisfaction with treatment remains low level, and there is now no definitive therapy.

Calcium-calmodulin complex binds to $Ca^{2+}$/calmodulin-dependent protein kinase (CaMK) included in serine/threonine protein kinase, and activates the kinase. The CaMK family includes CaMKII, and four isoforms ($\alpha$, $\beta$, $\gamma$ and $\delta$) exist as CaMKII. CaMKII $\alpha$ and CaMKII $\beta$ are expressed mainly in cerebral tissue, and CaMKII $\gamma$ and CaMKII $\delta$ are expressed in many tissues including heart. CaMKII is activated by amino acid-modification due to oxidative stress or hyperglycemia, in addition to the binding of calcium-calmodulin complex. CaMKII regulates cell functions by phosphorylation of a transcription factor which is a substrate, a protein that plays a function in organelle uptake/excretion of $Ca^{2+}$, a protein that regulates contract and relax of muscles, a channel that regulates an intracellular ion concentration, and the like, due to its kinase activation.

Some documents suggest that CaMKII plays a harmful role in progress of cardiac disease conditions. Expression and activity of CaMKII are increased in heart of human patient or animal with heart failure (Non-Patent Documents 1-4). In transgenic mouse overexpressing CaMKII $\delta$ in heart, onsets of cardiac hypertrophy and heart failure are reported (Non-Patent Document 4). By studies using an inhibitor by a pharmacological method, and studies using a gene deletion by genetic method, protecting effects on heart failure, cardiac hypertrophy, myocardial infarction and arrhythmia by an inhibition of CaMKII and an overexpression of CaMKII inhibitory protein are reported in mouse (Non-Patent Documents 5-7). For catecholaminergic polymorphic ventricular tachycardia, improving effects on disease conditions by CaMKII inhibitor in mutant ryanodine knock-in mouse ($RyR2^{R4496C+/-}$ mouse) are reported (Non-Patent Document 8). These findings suggest availabilities of CaMKII inhibitors in the prophylaxis and/or treatment of cardiac diseases including heart failure, cardiac hypertrophy, myocardial infarction and cardiac arrhythmia.

Recently, CaMKII exacerbating action on growth or metastasis of a certain type of cancer is suggested (Non-Patent Document 9). In addition, therapeutic effect on acute renal failure, intimal hypertrophy, hepatic fibrosis, stroke, pain, rheumatoid arthritis and the like by CaMKII inhibition are also indicated (Non-Patent Documents 10-15).

However, genetic methods achieve only deficiency of protein or overexpression of inhibitory protein, and they are different from a mechanism which inhibits temporarily kinase activity, and therefore, effects by kinase inhibitor cannot be always expected. In addition, inhibitors which have been already reported are not suitable for application as a medicament for a CaMKII selective inhibitor, because they have a low kinase selectivity to CaMKII, or they are not suitable for oral administration or chronic administration.

As a heterocyclic compound, the following compounds are known. Patent Document 1 describes that a compound represented by the following formula (I):

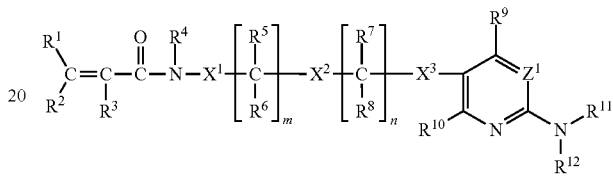

[1]

wherein each symbol is as defined in Patent Document 1, is a FLT3 inhibitor and useful for the treatment of acute myelogenous leukemia and the like.

Patent Document 2 describes that a compound represented by the following formula (I):

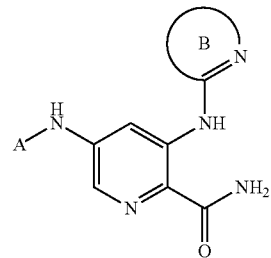

(I)

wherein each symbol is as defined in Patent Document 2, is a Syk (Spleen tyrosine kinase) inhibitor and useful for the treatment of diseases or conditions mediated by Syk (e.g., rheumatism).

Patent Document 3 describes that a compound represented by the following formula (I):

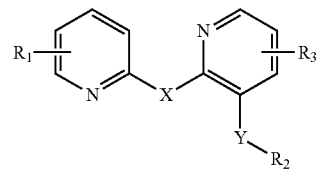

wherein each symbol is as defined in Patent Document 3, is a mGluR (metabotropic glutamate receptors)5 modulator and useful for the treatment or prophylaxis of diseases or conditions in which mGluR5 is involved (e.g., pain disorder, anxiety, depression, Alzheimer's disease, Parkinson's disease, etc.).

Patent Document 4 describes that a compound represented by the following formula (I):

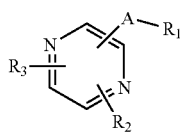

wherein each symbol is as defined in Patent Document 4, is a kinase inhibitor (particularly an inhibitor of kinase domain in VEGF receptor (VEGF receptor tyrosine kinase inhibitor)) and useful for the treatment of vascular abnormality, tumor, diabetic retinopathy, rheumatism, endometriosis, psoriasis and the like.

Patent Document 5 describes that a compound represented by the following formula (I):

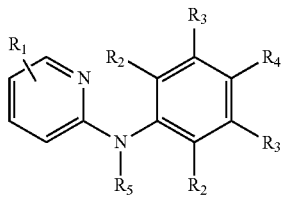

wherein each symbol is as defined in Patent Document 5, is a kinase (p38 kinase, etc.) inhibitor and useful for reduction of ischemic cell death (particularly reduction of traumatic neuronal cell death).

Patent Document 6 describes that a compound represented by the following formula (I):

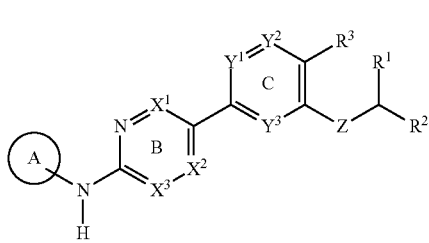

wherein each symbol is as defined in Patent Document 6, is a CaMKII inhibitor and useful for treatment of cardiac diseases (particularly catecholaminergic polymorphic ventricular tachycardia, postoperative atrial fibrillation, heart failure, fatal arrhythmia) and the like.

DOCUMENT LIST

Patent Document

Patent Document 1: WO 2013/157540
Patent Document 2: WO 2013/052394
Patent Document 3: WO 2005/021529
Patent Document 4: WO 2002/024681
Patent Document 5: WO 2002/011724
Patent Document 6: WO 2018/183112

Non-Patent Document

Non-Patent Document 1: European Journal of Heart Failure, vol. 16, p. 1292-1300
Non-Patent Document 2: Circulation Research, vol. 84, p. 713-721
Non-Patent Document 3: Molecular Endocrinology, vol. 17, p. 183-192
Non-Patent Document 4: Circulation Research, vol. 92, p. 912-919
Non-Patent Document 5: Proceedings of the National Academy of Sciences, vol. 106, p. 2342-2347
Non-Patent Document 6: Circulation Research, vol. 112, p. 935-944
Non-Patent Document 7: Nature, vol. 502, p. 372-376
Non-Patent Document 8: Journal of Molecular and Cellular Cardiology, vol. 50, p. 214-222
Non-Patent Document 9: Oncotarget, vol. 20, p. 11725-11734 Non-Patent Document 10: Arterioscler Thromb Vasc Biol, vol. 28, p. 441-447 Non-Patent Document 11: Cell Calcium, vol. 45, p. 284-292 Non-Patent Document 12: J Clin Invest, vol. 119, p. 2925-2941 Non-Patent Document 13: J Biol Chem, vol. 285, p. 20675-20682 Non-Patent Document 14: J Pharmacol Exp Ther, vol. 325, p. 267-275 Non-Patent Document 15: BMC Musculoskelet Disord, vol. 30, p. 61

SUMMARY

An object of the present invention is to provide a compound having a CaMKII inhibitory action, which is expected to be useful as an agent for the prophylaxis or treatment of cardiac diseases (particularly catecholaminergic polymorphic ventricular tachycardia, postoperative atrial fibrillation, heart failure, fatal arrhythmia) and the like.

The present inventors have conducted intensive studies in an attempt to solve the above-mentioned problems and found that a compound represented by the following formula (I) has a CaMKII inhibitory action, and therefore, is expected to be useful as an agent for the prophylaxis or treatment of cardiac diseases (particularly catecholaminergic polymorphic ventricular tachycardia, postoperative atrial fibrillation, heart failure, fatal arrhythmia) and the like, which resulted in the completion of the present invention.

Accordingly, the present invention provides the following.

[1] A compound represented by the formula (I):

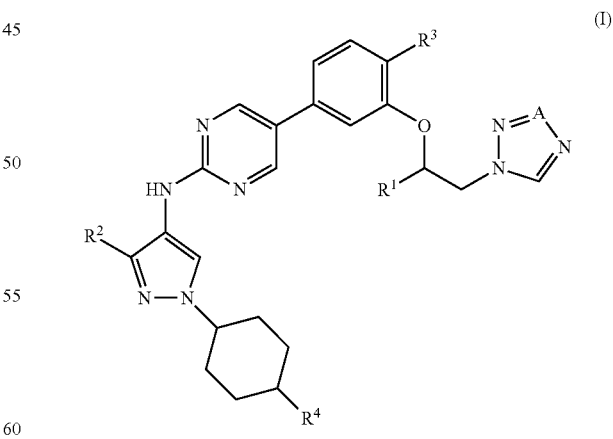

wherein
A is CH or N;
$R^1$ is a $C_{1-3}$ alkyl group;
$R^2$ is
(1) a group represented by the formula: $-O-X^1-X^2-O-(CH_2-CH_2-O)_p-Y$:

wherein
X$^1$ is a C$_{1-6}$ alkylene group optionally substituted by 1 to 4 halogen atoms,
X$^2$ is
(i) a bond, or
(ii) a group represented by the formula:

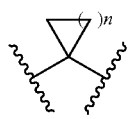

wherein n is an integer of 1 to 4,
p is an integer of 0 to 7, and
Y is
(i) a hydrogen atom, or
(ii) a C$_{1-6}$ alkyl group optionally substituted by 1 to 3 halogen atoms,
(2) a group represented by the formula: —O—X$^3$—Z$^1$:
wherein
X$^3$ is a C$_{1-6}$ alkylene group optionally substituted by 1 to 4 halogen atoms, and
Z$^1$ is
(i) a cyano group,
(ii) a C$_{1-6}$ alkylsulfonyl group, or
(iii) a 3- to 8-membered monocyclic non-aromatic heterocyclic group,
(3) a group represented by the formula: —O—X$^4$—Z$^2$:
wherein
X$^4$ is a bond or a C$_{1-6}$ alkylene group optionally substituted by 1 to 4 halogen atoms, and
Z$^2$ is a 5- or 6-membered monocyclic aromatic heterocyclic group optionally substituted by 1 to 3 C$_{1-6}$ alkyl groups, or
(4) a hydroxy group;
R$^3$ is a cyano group or a halogen atom; and
R$^4$ is a morpholinyl group or a bridged morpholinyl group, each optionally substituted by 1 to 3 C$_{1-6}$ alkyl groups; or a salt thereof (hereinafter sometimes to be referred to as "compound (I)").
[1a] A compound represented by the formula (I):

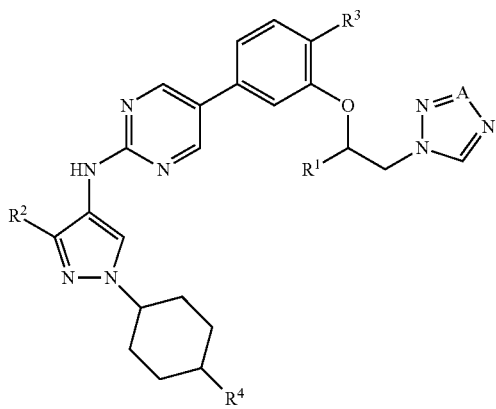

(I)

wherein
A is CH or N;
R$^1$ is a C$_{1-3}$ alkyl group;

R$^2$ is
(1) a group represented by the formula: —O—[X$^1$—X$^2$—O]$_m$—Y:
wherein
each of X$^1$ is independently a C$_{1-6}$ alkylene group optionally substituted by 1 to 4 halogen atoms,
each of X$^2$ is independently
(i) a bond, or
(ii) a group represented by the formula:

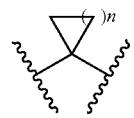

wherein n is an integer of 1 to 4,
m is an integer of 0 to 8, and
Y is
(i) a hydrogen atom, or
(ii) a C$_{1-6}$ alkyl group optionally substituted by 1 to 3 halogen atoms,
(2) a group represented by the formula: —O—X$^3$—Z$^1$:
wherein
X$^3$ is a C$_{1-6}$ alkylene group optionally substituted by 1 to 4 halogen atoms, and
Z$^1$ is
(i) a cyano group,
(ii) a C$_{1-6}$ alkylsulfonyl group, or
(iii) a 3- to 8-membered monocyclic non-aromatic heterocyclic group, or
(3) a group represented by the formula: —O—X$^4$—Z$^2$:
wherein
X$^4$ is a bond or a C$_{1-6}$ alkylene group optionally substituted by 1 to 4 halogen atoms, and
Z$^2$ is a 5- or 6-membered monocyclic aromatic heterocyclic group optionally substituted by 1 to 3 C$_{1-6}$ alkyl groups;
R$^3$ is a cyano group or a halogen atom; and
R$^4$ is a morpholinyl group or a bridged morpholinyl group, each optionally substituted by 1 to 3 C$_{1-6}$ alkyl groups;
provided that when m is 0, then Y is a hydrogen atom, or a salt thereof.
[2] The compound or salt of the above-mentioned[1], wherein
R$^1$ is a methyl group;
R$^2$ is
(1) a group represented by the formula: —O—X$^1$—X$^2$—O—(CH$_2$—CH$_2$—O)$_p$—Y:
wherein
X$^1$ is a C$_{1-6}$ alkylene group,
X$^2$ is a bond,
p is an integer of 0 or 1, and
Y is
(i) a hydrogen atom, or
(ii) a C$_{1-3}$ alkyl group optionally substituted by 1 to 3 halogen atoms,
(2) a group represented by the formula: —O—X$^3$—Z$^1$:
wherein
X$^3$ is a C$_{1-3}$ alkylene group, and
Z$^1$ is
(i) a cyano group,
(ii) a C$_{1-3}$ alkylsulfonyl group, or
(iii) a 3- to 6-membered monocyclic non-aromatic heterocyclic group, (3) a group represented by the formula: —O—X$^4$—Z$^2$:
wherein
X$^4$ is a C$_{1-3}$ alkylene group, and
Z$^2$ is a 5- or 6-membered monocyclic aromatic heterocyclic group optionally substituted by 1 to 3 C$_{1-3}$ alkyl groups, or
(4) a hydroxy group;
R$^3$ is a cyano group or a chlorine atom; and
R$^4$ is a morpholino group or a 3-oxa-8-azabicyclo[3.2.1]octan-8-yl group, each optionally substituted by 1 to 3 C$_{1-6}$ alkyl groups.

[3] The compound or salt of the above-mentioned[1], wherein
R$^1$ is a methyl group;
R$^2$ is
(1) a group represented by the formula: —O—X$^1$—X$^2$—O—(CH$_2$—CH$_2$—O)$_p$—Y:
wherein
X$^1$ is a C$_{1-6}$ alkylene group,
X$^2$ is a bond,
p is an integer of 0 or 1, and
Y is
  (i) a hydrogen atom, or
  (ii) a C$_{1-3}$ alkyl group, or
(2) a group represented by the formula: —O—X$^3$—Z$^1$:
wherein
X$^3$ is a C$_{1-3}$ alkylene group, and
Z$^1$ is a 3- to 6-membered monocyclic non-aromatic heterocyclic group;
R$^3$ is a cyano group or a chlorine atom; and
R$^4$ is a morpholino group, a morpholino group substituted by 1 or 2 C$_{1-6}$ alkyl groups, or a 3-oxa-8-azabicyclo[3.2.1]octan-8-yl group.

[4] The compound or salt of the above-mentioned[3], wherein R$^2$ is
(1) a group represented by the formula: —O—X$^1$—X$^2$—O—(CH$_2$—CH$_2$—O)$_p$—Y:
wherein
X$^1$ is —(CH$_2$) 2-, —(CH$_2$) 3- or *—CH$_2$—CH$_2$—C(CH$_3$) 2-**, wherein * is the bonding site to the oxygen atom, and ** is the bonding site to X$^2$,
X$^2$ is a bond,
p is an integer of 0 or 1, and
Y is a hydrogen atom, a methyl group or an ethyl group, or
(2) a group represented by the formula: —O—X$^3$—Z$^1$:
wherein
X$^3$ is —CH$_2$— or —(CH$_2$)$_2$—, and
Z$^1$ is an oxetanyl group or a tetrahydropyranyl group.

[5] A compound selected from
2-(((S)-1-(1H-tetrazol-1-yl)propan-2-yl)oxy)-4-(2-((1-((1r,4r)-4-((1R,5S)-3-oxa-8-azabicyclo[3.2.1]octan-8-yl)cyclohexyl)-3-(2-ethoxyethoxy)-1H-pyrazol-4-yl)amino)pyrimidin-5-yl)benzonitrile,
2-(((S)-1-(1H-tetrazol-1-yl)propan-2-yl)oxy)-4-(2-((3-(3-methoxypropoxy)-1-((1r,4r)-4-morpholinocyclohexyl)-1H-pyrazol-4-yl)amino)pyrimidin-5-yl)benzonitrile,
2-(((S)-1-(1H-tetrazol-1-yl)propan-2-yl)oxy)-4-(2-((1-((1r,4r)-4-((1R,5S)-3-oxa-8-azabicyclo[3.2.1]octan-8-yl)cyclohexyl)-3-(3-methoxypropoxy)-1H-pyrazol-4-yl)amino)pyrimidin-5-yl)benzonitrile,
2-(((S)-1-(1H-tetrazol-1-yl)propan-2-yl)oxy)-4-(2-((3-(3-ethoxypropoxy)-1-((1r,4r)-4-morpholinocyclohexyl)-1H-pyrazol-4-yl)amino)pyrimidin-5-yl)benzonitrile,
2-(((S)-1-(1H-tetrazol-1-yl)propan-2-yl)oxy)-4-(2-((1-((1r,4r)-4-((1R,5S)-3-oxa-8-azabicyclo[3.2.1]octan-8-yl)cyclohexyl)-3-(3-ethoxypropoxy)-1H-pyrazol-4-yl)amino)pyrimidin-5-yl)benzonitrile,
2-(((S)-1-(1H-tetrazol-1-yl)propan-2-yl)oxy)-4-(2-((1-((1r,4r)-4-((2S,6R)-2,6-dimethylmorpholino)cyclohexyl)-3-(3-methoxypropoxy)-1H-pyrazol-4-yl)amino)pyrimidin-5-yl)benzonitrile,
2-(((S)-1-(1H-tetrazol-1-yl)propan-2-yl)oxy)-4-(2-((1-((1r,4r)-4-((2S,6R)-2, 6-dimethylmorpholino)cyclohexyl)-3-(2-(2-methoxyethoxy)ethoxy)-1H-pyrazol-4-yl)amino)pyrimidin-5-yl)benzonitrile hydrochloride,
2-(3-((4-((5-(3-(((S)-1-(1H-tetrazol-1-yl) propan-2-yl)oxy)-4-chlorophenyl)pyrimidin-2-yl)amino)-1-((1r,4r)-4-((2S,6R)-2,6-dimethylmorpholino)cyclohexyl)-1H-pyrazol-3-yl)oxy)propoxy)ethan-1-ol,
2-(((S)-1-(1H-tetrazol-1-yl)propan-2-yl)oxy)-4-(2-((1-((1r,4r)-4-((2S,6R)-2,6-dimethylmorpholino)cyclohexyl)-3-(2-(oxetan-3-yl)ethoxy)-1H-pyrazol-4-yl)amino)pyrimidin-5-yl)benzonitrile,
2-(((S)-1-(1H-tetrazol-1-yl)propan-2-yl)oxy)-4-(2-((1r,4r)-4-((2S,6R)-2,6-dimethylmorpholino)cyclohexyl)-3-(oxetan-3-ylmethoxy)-1H-pyrazol-4-yl)amino)pyrimidin-5-yl)benzonitrile,
2-(((S)-1-(1H-tetrazol-1-yl)propan-2-yl)oxy)-4-(2-((1r,4r)-4-((2S,6R)-2,6-dimethylmorpholino)cyclohexyl)-3-((tetrahydro-2H-pyran-4-yl)methoxy)-1H-pyrazol-4-yl)amino)pyrimidin-5-yl)benzonitrile,
2-(((S)-1-(1H-tetrazol-1-yl)propan-2-yl)oxy)-4-(2-((1-((1r,4r)-4-((2S,6R)-2,6-dimethylmorpholino)cyclohexyl)-3-(3-hydroxy-3-methylbutoxy)-1H-pyrazol-4-yl)amino)pyrimidin-5-yl)benzonitrile,
4-((4-((5-(3-(((S)-1-(1H-tetrazol-1-yl)propan-2-yl)oxy)-4-chlorophenyl)pyrimidin-2-yl)amino)-1-((1r,4r)-4-((2S,6R)-2,6-dimethylmorpholino)cyclohexyl)-1H-pyrazol-3-yl)oxy)-2-methylbutan-2-ol,
5-(3-(((S)-1-(1H-tetrazol-1-yl) propan-2-yl)oxy)-4-chlorophenyl)-N-(1-((1r,4r)-4-((2S,6R)-2,6-dimethylmorpholino)cyclohexyl)-3-(3-(2-methoxyethoxy)propoxy)-1H-pyrazol-4-yl)pyrimidin-2-amine,
2-(((S)-1-(1H-tetrazol-1-yl)propan-2-yl)oxy)-4-(2-((1-((1r,4r)-4-((2S,6R)-2,6-dimethylmorpholino)cyclohexyl)-3-(3-(2-methoxyethoxy)propoxy)-1H-pyrazol-4-yl)amino)pyrimidin-5-yl)benzonitrile, and
5-(3-(((S)-1-(1H-tetrazol-1-yl)propan-2-yl)oxy)-4-chlorophenyl)-N-(1-((1r,4r)-4-((2S,6R)-2,6-dimethylmorpholino)cyclohexyl)-3-(3-methoxypropoxy)-1H-pyrazol-4-yl)pyrimidin-2-amine,
or a salt thereof.

[6] A medicament comprising the compound or salt of the above-mentioned[1].
[7] The medicament of the above-mentioned[6], which is a calcium/calmodulin-dependent protein kinase II inhibitor.
[8] The medicament of the above-mentioned[6], which is an agent for the prophylaxis or treatment of cardiac diseases.
[9] The medicament of the above-mentioned[8], wherein the cardiac disease is selected from catecholaminergic polymorphic ventricular tachycardia, postoperative atrial fibrillation, heart failure and fatal arrhythmia.
[10] The compound or salt of the above-mentioned[1] for use in the prophylaxis or treatment of cardiac diseases.
[11] The compound or salt of the above-mentioned[10], wherein the cardiac disease is selected from catecholaminergic polymorphic ventricular tachycardia, postoperative atrial fibrillation, heart failure and fatal arrhythmia.
[12] A method of inhibiting calcium/calmodulin-dependent protein kinase II in a mammal, which comprises administering an effective amount of the compound or salt of the above-mentioned[1] to the mammal.
[13] A method for the prophylaxis or treatment of cardiac diseases in a mammal, which comprises administering an effective amount of the compound or salt of the above-mentioned [1] to the mammal.

[14] The method of the above-mentioned[13], wherein the cardiac disease is selected from catecholaminergic polymorphic ventricular tachycardia, postoperative atrial fibrillation, heart failure and fatal arrhythmia.

[15] Use of the compound or salt of the above-mentioned[1] for the production of an agent for the prophylaxis or treatment of cardiac diseases.

[16] The use of the above-mentioned[15], wherein the cardiac disease is selected from catecholaminergic polymorphic ventricular tachycardia, postoperative atrial fibrillation, heart failure and fatal arrhythmia.

According to the present invention, a compound having a superior CaMKII inhibitory action, which is expected to be useful as an agent for the prophylaxis or treatment of cardiac diseases (particularly catecholaminergic polymorphic ventricular tachycardia, postoperative atrial fibrillation, heart failure, fatal arrhythmia) and the like can be provided.

DETAILED DESCRIPTION

The present invention is explained in detail in the following.

The definition of each substituent used in the present specification is described in detail in the following. Unless otherwise specified, each substituent has the following definition.

In the present specification, examples of the "halogen atom" include fluorine, chlorine, bromine and iodine.

In the present specification, examples of the "$C_{1-3}$ alkyl group" include methyl, ethyl, propyl and isopropyl.

In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl. Preferred is a $C_{1-3}$ alkyl group.

In the present specification, examples of the "$C_{1-6}$ alkylsulfonyl group" include methylsulfonyl, ethylsulfonyl, propylsulfonyl, isopropylsulfonyl, butylsulfonyl, isobutylsulfonyl, sec-butylsulfonyl, tert-butylsulfonyl, pentylsulfonyl, isopentylsulfonyl, neopentylsulfonyl, 1-ethylpropylsulfonyl and hexylsulfonyl. Preferred is a $C_{1-3}$ alkylsulfonyl group.

In the present specification, examples of the "$C_{1-3}$ alkylsulfonyl group" include methylsulfonyl, ethylsulfonyl, propylsulfonyl and isopropylsulfonyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy. Preferred is a $C_{1-3}$ alkoxy group.

In the present specification, examples of the "$C_{1-3}$ alkoxy group" include methoxy, ethoxy, propoxy and isopropoxy.

In the present specification, examples of the "5- or 6-membered monocyclic aromatic heterocyclic group" include thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like. Preferred is a 5- or 6-membered monocyclic nitrogen-containing aromatic heterocyclic group.

In the present specification, examples of the "5- or 6-membered monocyclic nitrogen-containing aromatic heterocyclic group" include pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like.

In the present specification, examples of the "3- to 8-membered monocyclic non-aromatic heterocyclic group" include aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like. Preferred is a 3- to 6-membered monocyclic oxygen-containing non-aromatic heterocyclic group.

In the present specification, examples of the "3- to 6-membered monocyclic oxygen-containing non-aromatic heterocyclic group" include oxiranyl, oxetanyl, tetrahydrofuranyl, tetrahydropyranyl and the like.

In the present specification, examples of the "bridged morpholinyl group" include 3-oxa-8-azabicyclo[3.2.1]octan-8-yl.

In the present specification, examples of the "$C_{1-6}$ alkylene group" include —$CH_2$—, —$(CH_2)_2$—, —$(CH_2)_3$—, —$(CH_2)_4$—, —$(CH_2)_5$—, —$(CH_2)_6$—, —CH($CH_3$)—, —C($CH_3$)$_2$—, —CH($C_2H_5$)—, —CH($C_3H_7$)—, —CH(CH($CH_3$)$_2$)—, —(CH($CH_3$))$_2$—, —$CH_2$—CH($CH_3$)—, —CH($CH_3$)—$CH_2$—, —$CH_2$—C($CH_3$)$_2$—, —$CH_2$—$CH_2$—C($CH_3$)$_2$—, —C($CH_3$)$_2$—$CH_2$—$CH_2$—, —$CH_2$—$CH_2$—$CH_2$—C($CH_3$)$_2$— and —C($CH_3$)$_2$—$CH_2$—$CH_2$—$CH_2$—.

In the present specification, examples of the "$C_{1-3}$ alkylene group" include —$CH_2$—, —$(CH_2)_2$—, —$(CH_2)_3$—, —CH($CH_3$)—, —C($CH_3$)$_2$—, —CH($C_2H_5$)—, —$CH_2$—CH($CH_3$)—, —CH($CH_3$)—$CH_2$— and —$CH_2$—C($CH_3$)$_2$—.

The definition of each symbol in the formula (I) is explained in detail in the following.

A is CH or N.

$R^1$ is a $C_{1-3}$ alkyl group (e.g., methyl).

$R^1$ is preferably a methyl group.

$R^2$ is (1) a group represented by the formula: —O—[$X^1$—$X^2$—O]$_m$—Y:

wherein each of $X^1$ is independently a $C_{1-6}$ alkylene group (e.g., —$CH_2$—, —$(CH_2)_2$—, —$(CH_2)_3$—, —$(CH_2)_4$—, *—CH($CH_3$)—$CH_2$—$CH_2$—**, —$CH_2$—CH($CH_3$)—$CH_2$—, *—$CH_2$—$CH_2$—CH($CH_3$)—**, *—$CH_2$—C($CH_3$)$_2$—**, —$CH_2$—C($CH_3$)$_2$—$CH_2$—, *—$CH_2$—$CH_2$—C($CH_3$)$_2$—**, wherein * is the bonding site to the oxygen atom, and ** is the bonding site to $X^2$) optionally substituted by 1 to 4 halogen atoms (e.g., a fluorine atom), each of $X^2$ is independently (i) a bond, or (ii) a group represented by the formula:

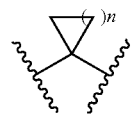

wherein n is an integer of 1 to 4, m is an integer of 0 to 8, and

Y is
(i) a hydrogen atom, or
(ii) a $C_{1-6}$ alkyl group (the $C_{1-6}$ alkyl group may be labeled with $^2H$ (e.g., methyl, ethyl, isopropyl, deuteromethyl)) optionally substituted by 1 to 3 halogen atoms (e.g., a fluorine atom), (2) a group represented by the formula: —O—$X^3$—$Z^1$:
wherein
$X^3$ is a $C_{1-6}$ alkylene group (e.g., —$CH_2$—, —$(CH_2)_2$—, —$(CH_2)_3$—) optionally substituted by 1 to 4 halogen atoms (e.g., a fluorine atom), and
$Z^1$ is
(i) a cyano group,
(ii) a $C_{1-6}$ alkylsulfonyl group (e.g., methylsulfonyl, ethylsulfonyl), or
(iii) a 3- to 8-membered monocyclic non-aromatic heterocyclic group (e.g., oxetanyl, tetrahydrofuryl, tetrahydropyranyl), or (3) a group represented by the formula: —O—$X^4$—$Z^2$:
wherein
$X^4$ is a bond or a $C_{1-6}$ alkylene group (e.g., —$CH_2$—, —$(CH_2)_2$—, —$(CH_2)_3$—) optionally substituted by 1 to 4 halogen atoms (e.g., a fluorine atom), and
$Z^2$ is a 5- or 6-membered monocyclic aromatic heterocyclic group (e.g., oxazolyl, thiazolyl, pyrazolyl, pyridyl, pyrimidinyl) optionally substituted by 1 to 3 $C_{1-6}$ alkyl groups (e.g., methyl).

$R^2$ is preferably
(1) a group represented by the formula: —O—[$X^1$—$X^2$—O]$_m$—Y:
wherein
each of $X^1$ is independently a $C_{1-6}$ alkylene group (e.g., —$CH_2$—, —$(CH_2)_2$—, —$(CH_2)_3$—, —$(CH_2)_4$—, *—$CH(CH_3)$—$CH_2$—$CH_2$—**, —$CH_2$—$CH(CH_3)$—$CH_2$—, *—$CH_2$—$CH_2$—$CH(CH_3)$—**, *—$CH_2$—$C(CH_3)_2$—**, —$CH_2$—$C(CH_3)_2$—$CH_2$—, *—$CH_2$—$CH_2$—$C(CH_3)_2$—**, wherein * is the bonding site to the oxygen atom, and ** is the bonding site to $X^2$) optionally substituted by 1 to 4 halogen atoms (e.g., a fluorine atom),
each of $X^2$ is independently
(i) a bond, or
(ii) a group represented by the formula:

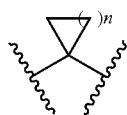

wherein n is an integer of 1 or 2,
m is an integer of 0 to 8, and
Y is
(i) a hydrogen atom, or
(ii) a $C_{1-3}$ alkyl group (the $C_{1-3}$ alkyl group may be labeled with $^2H$ (e.g., methyl, ethyl, isopropyl, deuteromethyl)) optionally substituted by 1 to 3 halogen atoms (e.g., a fluorine atom), (2) a group represented by the formula: —O—$X^3$—$Z^1$:
wherein
$X^3$ is a $C_{1-3}$ alkylene group (e.g., —$CH_2$—, —$(CH_2)_2$—, —$(CH_2)_3$—) optionally substituted by 1 to 4 halogen atoms (e.g., a fluorine atom), and
$Z^1$ is
(i) a cyano group,
(ii) a $C_{1-3}$ alkylsulfonyl group (e.g., methylsulfonyl, ethylsulfonyl), or
(iii) a 3- to 6-membered monocyclic oxygen-containing non-aromatic heterocyclic group (e.g., oxetanyl, tetrahydrofuryl, tetrahydropyranyl), or (3) a group represented by the formula: —O—$X^4$—$Z^2$:
wherein
$X^4$ is a bond or a $C_{1-3}$ alkylene group (e.g., —$CH_2$—, —$(CH_2)_2$—, —$(CH_2)_3$—) optionally substituted by 1 to 4 halogen atoms (e.g., a fluorine atom), and
$Z^2$ is a 5- or 6-membered monocyclic nitrogen-containing aromatic heterocyclic group (e.g., oxazolyl, thiazolyl, pyrazolyl, pyridyl, pyrimidinyl) optionally substituted by 1 to 3 $C_{1-3}$ alkyl groups (e.g., methyl).

As another embodiment, $R^2$ is preferably
(1) a group represented by the formula: —O—[$X^1$—$X^2$—O]$_m$—Y:
wherein
each of $X^1$ is independently a $C_{1-6}$ alkylene group (e.g., —$(CH_2)_2$—, —$(CH_2)_3$—, —$(CH_2)_4$—),
$X^2$ is a bond,
m is an integer of 0 to 2, and
Y is
(i) a hydrogen atom, or
(ii) a $C_{1-6}$ alkyl group (e.g., methyl, ethyl, isopropyl) optionally substituted by 1 to 3 halogen atoms (e.g., a fluorine atom), (2) a group represented by the formula: —O—$X^3$—$Z^1$:
wherein
$X^3$ is a $C_{1-6}$ alkylene group (e.g., —$(CH_2)_2$—, —$(CH_2)_3$—), and
$Z^1$ is a $C_{1-6}$ alkylsulfonyl group (e.g., methylsulfonyl), or (3) a group represented by the formula: —O—$X^4$—$Z^2$:
wherein
$X^4$ is a $C_{1-6}$ alkylene group (e.g., —$CH_2$—), and
$Z^2$ is a 5- or 6-membered monocyclic aromatic heterocyclic group (e.g., pyridyl).

In this embodiment, $R^2$ is more preferably
(1) a group represented by the formula: —O—[$X^1$—$X^2$—O]$_m$—Y:
wherein
each of $X^1$ is independently a $C_{1-6}$ alkylene group (e.g., —$(CH_2)_2$—, —$(CH_2)_3$—, —$(CH_2)_4$—),
$X^2$ is a bond,
m is an integer of 0 to 2, and
Y is
(i) a hydrogen atom, or
(ii) a $C_{1-3}$ alkyl group (e.g., methyl, ethyl, isopropyl) optionally substituted by 1 to 3 halogen atoms (e.g., a fluorine atom), (2) a group represented by the formula: —O—$X^3$—$Z^1$:
wherein
$X^3$ is a $C_{1-3}$ alkylene group (e.g., —$(CH_2)_2$—, —$(CH_2)_3$—), and
$Z^1$ is a $C_{1-3}$ alkylsulfonyl group (e.g., methylsulfonyl), or (3) a group represented by the formula: —O—$X^4$—$Z^2$:
wherein
$X^4$ is a $C_{1-3}$ alkylene group (e.g., —$CH_2$—), and
$Z^2$ is a 5- or 6-membered monocyclic nitrogen-containing aromatic heterocyclic group (e.g., pyridyl).

$R^2$
(1) a group represented by the formula: —O—[$X^1$—$X^2$—O]$_m$—Y:

wherein
each of X¹ is independently a $C_{1-6}$ alkylene group (e.g., —$CH_2$—, —$(CH_2)_2$—, —$(CH_2)_3$—, —$(CH_2)_4$—, *—$CH_2$—$CH(CH_3)$—**, *—$CH(CH_3)$—$CH_2$—$CH_2$—**, —$CH_2$—$CH(CH_3)$—$CH_2$—, *—$CH_2$—$CH_2$—$CH(CH_3)$—**, *—$CH_2$—$C(CH_3)_2$—**, —$CH_2$—$C(CH_3)_2$—$CH_2$—, *—$CH_2$—$CH_2$—$C(CH_3)_2$—**, wherein * is the bonding site to the oxygen atom, and ** is the bonding site to X²) optionally substituted by 1 to 4 halogen atoms (e.g., a fluorine atom), each of X² is independently
  (i) a bond, or
  (ii) a group represented by the formula:

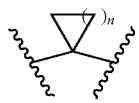

wherein n is an integer of 1 to 4,
m is an integer of 0 to 8 (preferably an integer of 1 to 8), and
Y is
  (i) a hydrogen atom, or
  (ii) a $C_{1-6}$ alkyl group (the $C_{1-6}$ alkyl group may be labeled with ²H (e.g., methyl, ethyl, isopropyl, deuteromethyl)) optionally substituted by 1 to 3 halogen atoms (e.g., a fluorine atom),
(2) a group represented by the formula: —O—X³—Z¹:
wherein
X³ is a $C_{1-6}$ alkylene group (e.g., —$CH_2$—, —$(CH_2)_2$—, —$(CH_2)_3$—) optionally substituted by 1 to 4 halogen atoms (e.g., a fluorine atom), and
Z¹ is
  (i) a cyano group,
  (ii) a $C_{1-6}$ alkylsulfonyl group (e.g., methylsulfonyl, ethylsulfonyl), or
  (iii) a 3- to 8-membered monocyclic non-aromatic heterocyclic group (e.g., oxetanyl, tetrahydrofuryl, tetrahydropyranyl), or
(3) a group represented by the formula: —O—X⁴—Z²:
wherein
X⁴ is a bond or a $C_{1-6}$ alkylene group (e.g., —$CH_2$—, —$(CH_2)_2$—, —$(CH_2)_3$—) optionally substituted by 1 to 4 halogen atoms (e.g., a fluorine atom), and
Z² is a 5- or 6-membered monocyclic aromatic heterocyclic group (e.g., oxazolyl, thiazolyl, pyrazolyl, triazolyl, imidazolyl, isoxazolyl, pyridyl, pyrimidinyl) optionally substituted by 1 to 3 $C_{1-6}$ alkyl groups (e.g., methyl).

R² is preferably
(1) a group represented by the formula: —O—[X¹—X²—O]$_m$—Y:
wherein
each of X¹ is independently a $C_{1-6}$ alkylene group (e.g., —$CH_2$—, —$(CH_2)_2$—, —$(CH_2)_3$—, —$(CH_2)_4$—, *—$CH_2$—$CH(CH_3)$—**, *—$CH(CH_3)$—$CH_2$—$CH_2$—**, —$CH_2$—$CH(CH_3)$—$CH_2$—, *—$CH_2$—$CH_2$—$CH(CH_3)$—**, *—$CH_2$—$C(CH_3)$ 2-**, —$CH_2$—$C(CH_3)_2$—$CH_2$—, *—$CH_2$—$CH_2$—$C(CH_3)$ 2-**,
wherein * is the bonding site to the oxygen atom, and ** is the bonding site to X²) optionally substituted by 1 to 4 halogen atoms (e.g., a fluorine atom), each of X² is independently
  (i) a bond, or
  (ii) a group represented by the formula:

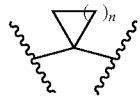

wherein n is an integer of 1 or 2,
m is an integer of 0 to 8 (preferably an integer of 1 to 8), and
Y is
  (i) a hydrogen atom, or
  (ii) a $C_{1-3}$ alkyl group (the $C_{1-3}$ alkyl group may be labeled with ²H (e.g., methyl, ethyl, isopropyl, deuteromethyl)) optionally substituted by 1 to 3 halogen atoms (e.g., a fluorine atom),
(2) a group represented by the formula: —O—X³—Z¹:
wherein
X³ is a $C_{1-3}$ alkylene group (e.g., —$CH_2$—, —$(CH_2)_2$—, —$(CH_2)_3$—) optionally substituted by 1 to 4 halogen atoms (e.g., a fluorine atom), and
Z¹ is
  (i) a cyano group,
  (ii) a $C_{1-3}$ alkylsulfonyl group (e.g., methylsulfonyl, ethylsulfonyl), or
  (iii) a 3- to 6-membered monocyclic non-aromatic heterocyclic group (preferably a 3- to 6-membered monocyclic oxygen-containing non-aromatic heterocyclic group) (e.g., oxetanyl, tetrahydrofuryl, tetrahydropyranyl), or
(3) a group represented by the formula: —O—X⁴—Z²:
wherein
X⁴ is a bond or a $C_{1-3}$ alkylene group (e.g., —$CH_2$—, —$(CH_2)_2$—, —$(CH_2)_3$—) optionally substituted by 1 to 4 halogen atoms (e.g., a fluorine atom), and
Z² is a 5- or 6-membered monocyclic aromatic heterocyclic group (preferably a 5- or 6-membered monocyclic nitrogen-containing aromatic heterocyclic group) (e.g., oxazolyl, thiazolyl, pyrazolyl, triazolyl, imidazolyl, isoxazolyl, pyridyl, pyrimidinyl) optionally substituted by 1 to 3 $C_{1-3}$ alkyl groups (e.g., methyl).

As another embodiment, R² is preferably
(1) a group represented by the formula: —O—[X¹—X²—O]$_m$—Y:
wherein
each of X¹ is independently a $C_{1-6}$ alkylene group (e.g., —$(CH_2)_2$—, —$(CH_2)_3$—, —$(CH_2)_4$—, *—$CH_2$—$CH(CH_3)$—**, *—$CH_2$—$CH_2$—$C(CH_3)_2$—**, wherein * is the bonding site to the oxygen atom, and ** is the bonding site to X²),
X² is a bond,
m is an integer of 0 to 2 (preferably an integer of 1 or 2), and
Y is
  (i) a hydrogen atom, or
  (ii) a $C_{1-6}$ alkyl group (the $C_{1-6}$ alkyl group may be labeled with ²H (e.g., methyl, ethyl, isopropyl, deuteromethyl)) optionally substituted by 1 to 3 halogen atoms (e.g., a fluorine atom),
(2) a group represented by the formula: —O—X³—Z¹:
wherein
X³ is a $C_{1-6}$ alkylene group (e.g., —$CH_2$—, —$(CH_2)_2$—, —$(CH_2)_3$—), and $Z^1$ is
(i) a cyano group,
(ii) a $C_{1-6}$ alkylsulfonyl group (e.g., methylsulfonyl), or
(iii) a 3- to 8-membered monocyclic non-aromatic heterocyclic group (e.g., oxetanyl, tetrahydrofuryl, tetrahydropyranyl), or
(3) a group represented by the formula: —O—$X^4$—$Z^2$:
wherein
$X^4$ is a $C_{1-6}$ alkylene group (e.g., —$CH_2$—, —$(CH_2)_2$—, —$(CH_2)_3$—), and
$Z^2$ is a 5- or 6-membered monocyclic aromatic heterocyclic group (e.g., oxazolyl, thiazolyl, pyrazolyl, triazolyl, imidazolyl, isoxazolyl, pyridyl) optionally substituted by 1 to 3 $C_{1-6}$ alkyl groups (e.g., methyl).

In this embodiment, $R^2$ is more preferably
(1) a group represented by the formula: —O—[$X^1$—$X^2$—O]$_m$—Y:
wherein
each of $X^1$ is independently a $C_{1-6}$ alkylene group (e.g., —$(CH_2)_2$—, —$(CH_2)_3$—, —$(CH_2)_4$—, *—$CH_2$—CH($CH_3$)—**, *—$CH_2$—$CH_2$—C($CH_3$)$_2$—**, wherein * is the bonding site to the oxygen atom, and ** is the bonding site to $X^2$),
$X^2$ is a bond,
m is an integer of 0 to 2 (preferably an integer of 1 or 2), and
Y is
(i) a hydrogen atom, or
(ii) a $C_{1-3}$ alkyl group (the $C_{1-3}$ alkyl group may be labeled with $^2$H (e.g., methyl, ethyl, isopropyl, deuteromethyl)) optionally substituted by 1 to 3 halogen atoms (e.g., a fluorine atom),
(2) a group represented by the formula: —O—$X^3$—$Z^1$:
wherein
$X^3$ is a $C_{1-3}$ alkylene group (e.g., —$CH_2$—, —$(CH_2)_2$—, —$(CH_2)_3$—), and
$Z^1$ is
(i) a cyano group,
(ii) a $C_{1-3}$ alkylsulfonyl group (e.g., methylsulfonyl), or
(iii) a 3- to 6-membered monocyclic non-aromatic heterocyclic group (preferably a 3- to 6-membered monocyclic oxygen-containing non-aromatic heterocyclic group) (e.g., oxetanyl, tetrahydrofuryl, tetrahydropyranyl), or
(3) a group represented by the formula: —O—$X^4$—$Z^2$:
wherein
$X^4$ is a $C_{1-3}$ alkylene group (e.g., —$CH_2$—, —$(CH_2)_2$—, —$(CH_2)_3$—), and
$Z^2$ is a 5- or 6-membered monocyclic aromatic heterocyclic group (preferably a 5- or 6-membered monocyclic nitrogen-containing aromatic heterocyclic group) (e.g., oxazolyl, thiazolyl, pyrazolyl, triazolyl, imidazolyl, isoxazolyl, pyridyl) optionally substituted by 1 to 3 $C_{1-3}$ alkyl groups (e.g., methyl).

As another embodiment, $R^2$ is more preferably
(1) a group represented by the formula: —O—[$X^1$—$X^2$—O]$_m$—Y:
wherein
each of $X^1$ is independently a $C_{1-6}$ alkylene group (e.g., —$(CH_2)_2$—, —$(CH_2)_3$—, *—$CH_2$—$CH_2$—C($CH_3$)$_2$—**, wherein * is the bonding site to the oxygen atom, and ** is the bonding site to $X^2$),
$X^2$ is a bond,
m is an integer of 1 or 2, and
Y is
(i) a hydrogen atom, or
(ii) a $C_{1-6}$ alkyl group (e.g., methyl, ethyl), or
(2) a group represented by the formula: —O—$X^3$—$Z^1$:
wherein
$X^3$ is a $C_{1-6}$ alkylene group (e.g., —$CH_2$—, —$(CH_2)_2$—), and
$Z^1$ is a 3- to 8-membered monocyclic non-aromatic heterocyclic group (e.g., oxetanyl, tetrahydropyranyl).

As another embodiment, $R^2$ is further more preferably
(1) a group represented by the formula: —O—[$X^1$—$X^2$—O]$_m$—Y:
wherein
each of $X^1$ is independently a $C_{1-6}$ alkylene group (e.g., —$(CH_2)_2$—, —$(CH_2)_3$—, *—$CH_2$—$CH_2$—C($CH_3$)$_2$—**, wherein * is the bonding site to the oxygen atom, and ** is the bonding site to $X^2$),
$X^2$ is a bond,
m is an integer of 1 or 2, and
Y is
(i) a hydrogen atom, or
(ii) a $C_{1-3}$ alkyl group (e.g., methyl, ethyl), or
(2) a group represented by the formula: —O—$X^3$—$Z^1$:
wherein
$X^3$ is a $C_{1-3}$ alkylene group (e.g., —$CH_2$—, —$(CH_2)_2$—), and
$Z^1$ is a 3- to 6-membered monocyclic non-aromatic heterocyclic group (preferably a 3- to 6-membered monocyclic oxygen-containing non-aromatic heterocyclic group) (e.g., oxetanyl, tetrahydropyranyl).

Furthermore, as another embodiment, $R^2$ is
(1) a group represented by the formula: —O—$X^1$—$X^2$—O—($CH_2$—$CH_2$—O)$_p$—Y:
wherein
$X^1$ is a $C_{1-6}$ alkylene group (e.g., —$CH_2$—, —$(CH_2)_2$—, —$(CH_2)_3$—, —$(CH_2)_4$—, *—CH($CH_3$)—$CH_2$—$CH_2$—**, —$CH_2$—CH($CH_3$)—$CH_2$—, *—$CH_2$—$CH_2$—CH($CH_3$)—**, *—$CH_2$—C($CH_3$)$_2$—**, —$CH_2$—C($CH_3$)$_2$—$CH_2$—, *—$CH_2$—$CH_2$—C($CH_3$)$_2$—**, wherein * is the bonding site to the oxygen atom, and ** is the bonding site to $X^2$) optionally substituted by 1 to 4 halogen atoms (e.g., a fluorine atom),
$X^2$ is
(i) a bond, or
(ii) a group represented by the formula:

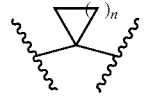

wherein n is an integer of 1 to 4,
p is an integer of 0 to 7, and
Y is
(i) a hydrogen atom, or
(ii) a $C_{1-6}$ alkyl group (the $C_{1-6}$ alkyl group may be labeled with $^2$H (e.g., methyl, ethyl, isopropyl, deuteromethyl)) optionally substituted by 1 to 3 halogen atoms (e.g., a fluorine atom),
(2) a group represented by the formula: —O—$X^3$—$Z^1$:
wherein
$X^3$ is a $C_{1-6}$ alkylene group (e.g., —$CH_2$—, —$(CH_2)_2$—, —$(CH_2)_3$—) optionally substituted by 1 to 4 halogen atoms (e.g., a fluorine atom), and $Z^1$ is
(i) a cyano group,
(ii) a $C_{1-6}$ alkylsulfonyl group (e.g., methylsulfonyl, ethylsulfonyl), or
(iii) a 3- to 8-membered monocyclic non-aromatic heterocyclic group (e.g., oxetanyl, tetrahydrofuryl, tetrahydropyranyl),
(3) a group represented by the formula: —O—$X^4$—$Z^2$:
wherein
$X^4$ is a bond or a $C_{1-6}$ alkylene group (e.g., —$CH_2$—, —$(CH_2)_2$—, —$(CH_2)_3$—) optionally substituted by 1 to 4 halogen atoms (e.g., a fluorine atom), and
$Z^2$ is a 5- or 6-membered monocyclic aromatic heterocyclic group (e.g., oxazolyl, thiazolyl, pyrazolyl, pyridyl, pyrimidinyl) optionally substituted by 1 to 3 $C_{1-6}$ alkyl groups (e.g., methyl), or
(4) a hydroxy group.
In this embodiment, $R^2$ is preferably
(1) a group represented by the formula: —O—$X^1$—$X^2$—O—$(CH_2$—$CH_2$—$O)_p$—Y:
wherein
$X^1$ is a $C_{1-6}$ alkylene group (e.g., —$CH_2$—, —$(CH_2)_2$—, —$(CH_2)_3$—, —$(CH_2)_4$—, *—CH($CH_3$)—$CH_2$—$CH_2$—**, —$CH_2$—CH($CH_3$)—$CH_2$—, *—$CH_2$—$CH_2$—CH($CH_3$)—**, *—$CH_2$—C($CH_3$)$_2$—**, —$CH_2$—C($CH_3$)$_2$—$CH_2$—, *—$CH_2$—$CH_2$—C($CH_3$)$_2$—**, wherein * is the bonding site to the oxygen atom, and ** is the bonding site to $X^2$) optionally substituted by 1 to 4 halogen atoms (e.g., a fluorine atom),
$X^2$ is
(i) a bond, or
(ii) a group represented by the formula:

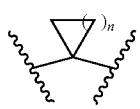

wherein n is an integer of 1 or 2,
p is an integer of 0 to 7, and
Y is
(i) a hydrogen atom, or
(ii) a $C_{1-3}$ alkyl group (the $C_{1-3}$ alkyl group may be labeled with $^2$H (e.g., methyl, ethyl, isopropyl, deuteromethyl)) optionally substituted by 1 to 3 halogen atoms (e.g., a fluorine atom),
(2) a group represented by the formula: —O—$X^3$—$Z^1$:
wherein
$X^3$ is a $C_{1-3}$ alkylene group (e.g., —$CH_2$—, —$(CH_2)_2$—, —$(CH_2)_3$—) optionally substituted by 1 to 4 halogen atoms (e.g., a fluorine atom), and
$Z^1$ is
(i) a cyano group,
(ii) a $C_{1-3}$ alkylsulfonyl group (e.g., methylsulfonyl, ethylsulfonyl), or
(iii) a 3- to 6-membered monocyclic oxygen-containing non-aromatic heterocyclic group (e.g., oxetanyl, tetrahydrofuryl, tetrahydropyranyl),
(3) a group represented by the formula: —O—$X^4$—$Z^2$:
wherein
$X^4$ is a bond or a $C_{1-3}$ alkylene group (e.g., —$CH_2$—, —$(CH_2)_2$—, —$(CH_2)_3$—) optionally substituted by 1 to 4 halogen atoms (e.g., a fluorine atom), and $Z^2$ is a 5- or 6-membered monocyclic nitrogen-containing aromatic heterocyclic group (e.g., oxazolyl, thiazolyl, pyrazolyl, pyridyl, pyrimidinyl) optionally substituted by 1 to 3 $C_{1-3}$ alkyl groups (e.g., methyl), or
(4) a hydroxy group.
Moreover, as another embodiment, $R^2$ is preferably
(1) a group represented by the formula: —O—$X^1$—$X^2$—O—$(CH_2$—$CH_2$—$O)_p$—Y:
wherein
$X^1$ is a $C_{1-6}$ alkylene group (e.g., —$(CH_2)_2$—, —$(CH_2)_3$—, —$(CH_2)_4$—),
$X^2$ is a bond,
p is an integer of 0 or 1, and
Y is
(i) a hydrogen atom, or
(ii) a $C_{1-6}$ alkyl group (e.g., methyl, ethyl, isopropyl) optionally substituted by 1 to 3 halogen atoms (e.g., a fluorine atom),
(2) a group represented by the formula: —O—$X^3$—$Z^1$:
wherein
$X^3$ is a $C_{1-6}$ alkylene group (e.g., —$(CH_2)_2$—, —$(CH_2)_3$—), and $Z^1$ is a $C_{1-6}$ alkylsulfonyl group (e.g., methylsulfonyl),
(3) a group represented by the formula: —O—$X^4$—$Z^2$:
wherein
$X^4$ is a $C_{1-6}$ alkylene group (e.g., —$CH_2$—), and
$Z^2$ is a 5- or 6-membered monocyclic aromatic heterocyclic group (e.g., pyridyl), or
(4) a hydroxy group.
In this embodiment, $R^2$ is more preferably
(1) a group represented by the formula: —O—$X^1$—$X^2$—O—$(CH_2$—$CH_2$—$O)_p$—Y:
wherein
$X^1$ is a $C_{1-6}$ alkylene group (e.g., —$(CH_2)_2$—, —$(CH_2)_3$—, —$(CH_2)_4$—),
$X^2$ is a bond,
p is an integer of 0 or 1, and
Y is
(i) a hydrogen atom, or
(ii) a $C_{1-3}$ alkyl group (e.g., methyl, ethyl, isopropyl) optionally substituted by 1 to 3 halogen atoms (e.g., a fluorine atom),
(2) a group represented by the formula: —O—$X^3$—$Z^1$:
wherein
$X^3$ is a $C_{1-3}$ alkylene group (e.g., —$(CH_2)_2$—, —$(CH_2)_3$—), and
$Z^1$ is a $C_{1-3}$ alkylsulfonyl group (e.g., methylsulfonyl),
(3) a group represented by the formula: —O—$X^4$—$Z^2$:
wherein
$X^4$ is a $C_{1-3}$ alkylene group (e.g., —$CH_2$—), and
$Z^2$ is a 5- or 6-membered monocyclic nitrogen-containing aromatic heterocyclic group (e.g., pyridyl), or
(4) a hydroxy group.
Furthermore, as another embodiment, $R^2$ is
(1) a group represented by the formula: —O—$X^1$—$X^2$—O—$(CH_2$—$CH_2$—$O)_p$—Y:
wherein
$X^1$ is a $C_{1-6}$ alkylene group (e.g., —$CH_2$—, —$(CH_2)_2$—, —$(CH_2)_3$—, —$(CH_2)_4$—, *—$CH_2$—CH($CH_3$)—**, *—CH($CH_3$)—$CH_2$—$CH_2$—**, —$CH_2$—CH($CH_3$)—$CH_2$—, *—$CH_2$—$CH_2$—CH($CH_3$)—**, *—$CH_2$—C($CH_3$)$_2$—**, —$CH_2$—C($CH_3$)$_2$—$CH_2$—, *—$CH_2$—$CH_2$—C($CH_3$)$_2$—**, wherein * is the bonding site to the oxygen atom, and ** is the bonding site to $X^2$) optionally substituted by 1 to 4 halogen atoms (e.g., a fluorine atom), $X^2$ is
(i) a bond, or
(ii) a group represented by the formula:

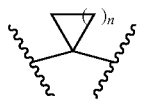

wherein n is an integer of 1 to 4,
p is an integer of 0 to 7, and
Y is
(i) a hydrogen atom, or
(ii) a $C_{1-6}$ alkyl group (the $C_{1-6}$ alkyl group may be labeled with $^2$H (e.g., methyl, ethyl, isopropyl, deuteromethyl)) optionally substituted by 1 to 3 halogen atoms (e.g., a fluorine atom),
(2) a group represented by the formula: —O—$X^3$—$Z^1$:
wherein
$X^3$ is a $C_{1-6}$ alkylene group (e.g., —CH$_2$—, —(CH$_2$)$_2$—, —(CH$_2$)$_3$—) optionally substituted by 1 to 4 halogen atoms (e.g., a fluorine atom), and
$Z^1$ is
(i) a cyano group,
(ii) a $C_{1-6}$ alkylsulfonyl group (e.g., methylsulfonyl, ethylsulfonyl), or
(iii) a 3- to 8-membered monocyclic non-aromatic heterocyclic group (e.g., oxetanyl, tetrahydrofuryl, tetrahydropyranyl),
(3) a group represented by the formula: —O—$X^4$—$Z^2$:
wherein
$X^4$ is a bond or a $C_{1-6}$ alkylene group (e.g., —CH$_2$—, —(CH$_2$)$_2$—, —(CH$_2$)$_3$—) optionally substituted by 1 to 4 halogen atoms (e.g., a fluorine atom), and
$Z^2$ is a 5- or 6-membered monocyclic aromatic heterocyclic group (e.g., oxazolyl, thiazolyl, pyrazolyl, triazolyl, imidazolyl, isoxazolyl, pyridyl, pyrimidinyl) optionally substituted by 1 to 3 $C_{1-6}$ alkyl groups (e.g., methyl), or
(4) a hydroxy group.
In this embodiment, $R^2$ is preferably
(1) a group represented by the formula: —O—$X^1$—$X^2$—O—(CH$_2$—CH$_2$—O)$_p$—Y:
wherein
$X^1$ is a $C_{1-6}$ alkylene group (e.g., —CH$_2$—, —(CH$_2$)$_2$—, —(CH$_2$)$_3$—, —(CH$_2$)$_4$—, *—CH$_2$—CH(CH$_3$)—**, *—CH(CH$_3$)—CH$_2$—CH$_2$—**, —CH$_2$—CH(CH$_3$)—CH$_2$—, *—CH$_2$—CH$_2$—CH(CH$_3$)—**, *—CH$_2$—C(CH$_3$)$_2$—**, —CH$_2$—C(CH$_3$) 2-CH$_2$—, *—CH$_2$—CH$_2$—C(CH$_3$)$_2$—**, wherein * is the bonding site to the oxygen atom, and ** is the bonding site to $X^2$) optionally substituted by 1 to 4 halogen atoms (e.g., a fluorine atom),
$X^2$ is
(i) a bond, or
(ii) a group represented by the formula:

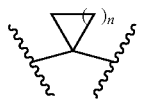

wherein n is an integer of 1 or 2,
p is an integer of 0 to 7, and
Y is
(i) a hydrogen atom, or
(ii) a $C_{1-3}$ alkyl group (the $C_{1-3}$ alkyl group may be labeled with $^2$H (e.g., methyl, ethyl, isopropyl, deuteromethyl)) optionally substituted by 1 to 3 halogen atoms (e.g., a fluorine atom),
(2) a group represented by the formula: —O—$X^3$—$Z^1$:
wherein
$X^3$ is a $C_{1-3}$ alkylene group (e.g., —CH$_2$—, —(CH$_2$)$_2$—, —(CH$_2$)$_3$—) optionally substituted by 1 to 4 halogen atoms (e.g., a fluorine atom), and
$Z^1$ is
(i) a cyano group,
(ii) a $C_{1-3}$ alkylsulfonyl group (e.g., methylsulfonyl, ethylsulfonyl), or
(iii) a 3- to 6-membered monocyclic non-aromatic heterocyclic group (preferably a 3- to 6-membered monocyclic oxygen-containing non-aromatic heterocyclic group) (e.g., oxetanyl, tetrahydrofuryl, tetrahydropyranyl),
(3) a group represented by the formula: —O—$X^4$—$Z^2$:
wherein
$X^4$ is a bond or a $C_{1-3}$ alkylene group (e.g., —CH$_2$—, —(CH$_2$)$_2$—, —(CH$_2$)$_3$—) optionally substituted by 1 to 4 halogen atoms (e.g., a fluorine atom), and
$Z^2$ is a 5- or 6-membered monocyclic aromatic heterocyclic group (preferably a 5- or 6-membered monocyclic nitrogen-containing aromatic heterocyclic group) (e.g., oxazolyl, thiazolyl, pyrazolyl, triazolyl, imidazolyl, isoxazolyl, pyridyl, pyrimidinyl) optionally substituted by 1 to 3 $C_{1-3}$ alkyl groups (e.g., methyl), or
(4) a hydroxy group.
Moreover, as another embodiment, $R^2$ is preferably
(1) a group represented by the formula: —O—$X^1$—$X^2$—O—(CH$_2$—CH$_2$—O)$_p$—Y:
wherein
$X^1$ is a $C_{1-6}$ alkylene group (e.g., —(CH$_2$)$_2$—, —(CH$_2$)$_3$—, —(CH$_2$)$_4$—, *—CH$_2$—CH(CH$_3$)—**, *—CH$_2$—CH$_2$—C(CH$_3$)$_2$—**, wherein * is the bonding site to the oxygen atom, and ** is the bonding site to $X^2$),
$X^2$ is a bond,
p is an integer of 0 or 1, and
Y is
(i) a hydrogen atom, or
(ii) a $C_{1-6}$ alkyl group (the $C_{1-6}$ alkyl group may be labeled with $^2$H (e.g., methyl, ethyl, isopropyl, deuteromethyl)) optionally substituted by 1 to 3 halogen atoms (e.g., a fluorine atom),
(2) a group represented by the formula: —O—$X^3$—$Z^1$:
wherein
$X^3$ is a $C_{1-6}$ alkylene group (e.g., —CH$_2$—, —(CH$_2$)$_2$—, —(CH$_2$)$_3$—), and
$Z^1$ is
(i) a cyano group,
(ii) a $C_{1-6}$ alkylsulfonyl group (e.g., methylsulfonyl), or
(iii) a 3- to 8-membered monocyclic non-aromatic heterocyclic group (e.g., oxetanyl, tetrahydrofuryl, tetrahydropyranyl),
(3) a group represented by the formula: —O—$X^4$—$Z^2$:
wherein
$X^4$ is a $C_{1-6}$ alkylene group (e.g., —CH$_2$—, —(CH$_2$)$_2$—, —(CH$_2$)$_3$—), and
$Z^2$ is a 5- or 6-membered monocyclic aromatic heterocyclic group (e.g., oxazolyl, thiazolyl, pyrazolyl, triazolyl, imidazolyl, isoxazolyl, pyridyl) optionally substituted by 1 to 3 $C_{1-6}$ alkyl groups (e.g., methyl), or (4) a hydroxy group.

In this embodiment, $R^2$ is more preferably (1) a group represented by the formula: —O—$X^1$—$X^2$—O—($CH_2$—$CH_2$—O)$_p$—Y:

wherein $X^1$ is a $C_{1-6}$ alkylene group (e.g., —($CH_2$)$_2$—, —($CH_2$)$_3$—, —($CH_2$)$_4$—, *—$CH_2$—CH($CH_3$)—**, *—$CH_2$—$CH_2$—C($CH_3$)$_2$—**, wherein * is the bonding site to the oxygen atom, and ** is the bonding site to $X^2$), $X^2$ is a bond, p is an integer of 0 or 1, and Y is (i) a hydrogen atom, or (ii) a $C_{1-3}$ alkyl group (the $C_{1-3}$ alkyl group may be labeled with $^2H$ (e.g., methyl, ethyl, isopropyl, deuteromethyl)) optionally substituted by 1 to 3 halogen atoms (e.g., a fluorine atom), (2) a group represented by the formula: —O—$X^3$—$Z^1$:

wherein $X^3$ is a $C_{1-3}$ alkylene group (e.g., —$CH_2$—, —($CH_2$)$_2$—, —($CH_2$)$_3$—), and $Z^1$ is (i) a cyano group, (ii) a $C_{1-3}$ alkylsulfonyl group (e.g., methylsulfonyl), or (iii) a 3- to 6-membered monocyclic non-aromatic heterocyclic group (preferably a 3- to 6-membered monocyclic oxygen-containing non-aromatic heterocyclic group) (e.g., oxetanyl, tetrahydrofuryl, tetrahydropyranyl), (3) a group represented by the formula: —O—$X^4$—$Z^2$:

wherein $X^4$ is a $C_{1-3}$ alkylene group (e.g., —$CH_2$—, —($CH_2$)$_2$—, —($CH_2$)$_3$—), and $Z^2$ is a 5- or 6-membered monocyclic aromatic heterocyclic group (preferably a 5- or 6-membered monocyclic nitrogen-containing aromatic heterocyclic group) (e.g., oxazolyl, thiazolyl, pyrazolyl, triazolyl, imidazolyl, isoxazolyl, pyridyl) optionally substituted by 1 to 3 $C_{1-3}$ alkyl groups (e.g., methyl), or (4) a hydroxy group.

Moreover, as another embodiment, $R^2$ is more preferably (1) a group represented by the formula: —O—$X^1$—$X^2$—O—($CH_2$—$CH_2$—O)$_p$—Y:

wherein $X^1$ is a $C_{1-6}$ alkylene group (e.g., —($CH_2$)$_2$—, —($CH_2$)$_3$—, *—$CH_2$—$CH_2$—C($CH_3$)$_2$—**, wherein * is the bonding site to the oxygen atom, and ** is the bonding site to $X^2$), $X^2$ is a bond, p is an integer of 0 or 1, and Y is (i) a hydrogen atom, or (ii) a $C_{1-6}$ alkyl group (e.g., methyl, ethyl), or (2) a group represented by the formula: —O—$X^3$—$Z^1$:

wherein $X^3$ is a $C_{1-6}$ alkylene group (e.g., —$CH_2$—, —($CH_2$)$_2$—), and $Z^1$ is a 3- to 8-membered monocyclic non-aromatic heterocyclic group (e.g., oxetanyl, tetrahydropyranyl).

Moreover, as another embodiment, $R^2$ is further more preferably (1) a group represented by the formula: —O—$X^1$—$X^2$—O—($CH_2$—$CH_2$—O)$_p$—Y:

wherein $X^1$ is a $C_{1-6}$ alkylene group (e.g., —($CH_2$)$_2$—, —($CH_2$)$_3$—, *—$CH_2$—$CH_2$—C($CH_3$)$_2$—**, wherein * is the bonding site to the oxygen atom, and ** is the bonding site to $X^2$), $X^2$ is a bond, p is an integer of 0 or 1, and Y is (i) a hydrogen atom, or (ii) a $C_{1-3}$ alkyl group (e.g., methyl, ethyl), or (2) a group represented by the formula: —O—$X^3$—$Z^1$:

wherein $X^3$ is a $C_{1-3}$ alkylene group (e.g., —$CH_2$—, —($CH_2$)$_2$—), and $Z^1$ is a 3- to 6-membered monocyclic non-aromatic heterocyclic group (preferably a 3- to 6-membered monocyclic oxygen-containing non-aromatic heterocyclic group) (e.g., oxetanyl, tetrahydropyranyl).

Moreover, as another embodiment, $R^2$ is still more preferably (1) a group represented by the formula: —O—$X^1$—$X^2$—O—($CH_2$—$CH_2$—O)$_p$—Y:

wherein $X^1$ is —($CH_2$)$_2$—, —($CH_2$)$_3$— or *—$CH_2$—$CH_2$—C($CH_3$)$_2$—**, wherein * is the bonding site to the oxygen atom, and ** is the bonding site to $X^2$, $X^2$ is a bond, p is an integer of 0 or 1, and Y is a hydrogen atom, a methyl group or an ethyl group, or (2) a group represented by the formula: —O—$X^3$—$Z^1$:

wherein $X^3$ is —$CH_2$— or —($CH_2$)$_2$—, and $Z^1$ is an oxetanyl group or a tetrahydropyranyl group.

$R^3$ is a cyano group or a halogen atom (e.g., a chlorine atom).

$R^3$ is preferably a cyano group or a chlorine atom.

$R^4$ is a morpholinyl group (e.g., morpholino) or a bridged morpholinyl group (e.g., 3-oxa-8-azabicyclo[3.2.1]octan-8-yl), each optionally substituted by 1 to 3 $C_{1-6}$ alkyl groups (e.g., methyl).

$R^4$ is preferably a morpholino group or a 3-oxa-8-azabicyclo[3.2.1]octan-8-yl group, each optionally substituted by 1 to 3 $C_{1-6}$ alkyl groups (e.g., methyl).

$R^4$ is more preferably a morpholino group, a morpholino group substituted by 1 or 2 $C_{1-6}$ alkyl groups (e.g., methyl), or a 3-oxa-8-azabicyclo[3.2.1]octan-8-yl group.

In the formula (I), when m is 0, then Y is a hydrogen atom.

Compound (I) is preferably a compound represented by the formula (Ia):

(Ia)

or a salt thereof (hereinafter sometimes to be referred to as "compound (Ia)").

Preferable examples of compound (I) and compound (Ia) include the following compounds.

Compound (I) or compound (Ia) wherein
$R^2$ is
(1) a group represented by the formula: —O—[$X^1$—$X^2$—O]$_m$—Y:
wherein
each of $X^1$ is independently a $C_{1-6}$ alkylene group (e.g., —CH$_2$—, —(CH$_2$)$_2$—, —(CH$_2$)$_3$—, —(CH$_2$)$_4$—, *—CH(CH$_3$)—CH$_2$—CH$_2$—**, —CH$_2$—CH(CH$_3$)—CH$_2$—, *—CH$_2$—CH$_2$—CH(CH$_3$)—**, *—CH$_2$—C(CH$_3$)$_2$—**, —CH$_2$—C(CH$_3$)$_2$—CH$_2$—, *—CH$_2$—CH$_2$—C(CH$_3$)$_2$—**, wherein * is the bonding site to the oxygen atom, and ** is the bonding site to $X^2$) optionally substituted by 1 to 4 halogen atoms (e.g., a fluorine atom),
each of $X^2$ is independently
(i) a bond, or
(ii) a group represented by the formula:

wherein n is an integer of 1 or 2,
m is an integer of 0 to 8, and
Y is
(i) a hydrogen atom, or
(ii) a $C_{1-3}$ alkyl group (the $C_{1-3}$ alkyl group may be labeled with $^2$H (e.g., methyl, ethyl, isopropyl, deuteromethyl)) optionally substituted by 1 to 3 halogen atoms (e.g., a fluorine atom),
(2) a group represented by the formula: —O—$X^3$—$Z^1$:
wherein
$X^3$ is a $C_{1-3}$ alkylene group (e.g., —CH$_2$—, —(CH$_2$)$_2$—, —(CH$_2$)$_3$—) optionally substituted by 1 to 4 halogen atoms (e.g., a fluorine atom), and
$Z^1$ is
(i) a cyano group,
(ii) a $C_{1-3}$ alkylsulfonyl group (e.g., methylsulfonyl, ethylsulfonyl), or
(iii) a 3- to 6-membered monocyclic oxygen-containing non-aromatic heterocyclic group (e.g., oxetanyl, tetrahydrofuryl, tetrahydropyranyl), or
(3) a group represented by the formula: —O—$X^4$—$Z^2$:
wherein
$X^4$ is a bond or a $C_{1-3}$ alkylene group (e.g., —CH$_2$—, —(CH$_2$)$_2$—, —(CH$_2$)$_3$—) optionally substituted by 1 to 4 halogen atoms (e.g., a fluorine atom), and
$Z^2$ is a 5- or 6-membered monocyclic nitrogen-containing aromatic heterocyclic group (e.g., oxazolyl, thiazolyl, pyrazolyl, pyridyl, pyrimidinyl) optionally substituted by 1 to 3 $C_{1-3}$ alkyl groups (e.g., methyl).

Compound (I) or compound (Ia) wherein
$R^1$ is a methyl group;
$R^2$ is
(1) a group represented by the formula: —O—[$X^1$—$X^2$—O]$_m$—Y:
wherein
each of $X^1$ is independently a $C_{1-6}$ alkylene group (e.g., —CH$_2$—, —(CH$_2$)$_2$—, —(CH$_2$)$_3$—, —(CH$_2$)$_4$—, *—CH(CH$_3$)—CH$_2$—CH$_2$—**, —CH$_2$—CH(CH$_3$)—CH$_2$—, *—CH$_2$—CH$_2$—CH(CH$_3$)—**, *—CH$_2$—C(CH$_3$)$_2$—**, —CH$_2$—C(CH$_3$)$_2$—CH$_2$—, *—CH$_2$—CH$_2$—C(CH$_3$)$_2$—**, wherein * is the bonding site to the oxygen atom, and ** is the bonding site to $X^2$) optionally substituted by 1 to 4 halogen atoms (e.g., a fluorine atom),
each of $X^2$ is independently
(i) a bond, or
(ii) a group represented by the formula:

wherein n is an integer of 1 or 2,
m is an integer of 0 to 8, and
Y is
(i) a hydrogen atom, or
(ii) a $C_{1-3}$ alkyl group (the $C_{1-3}$ alkyl group may be labeled with $^2$H (e.g., methyl, ethyl, isopropyl, deuteromethyl)) optionally substituted by 1 to 3 halogen atoms (e.g., a fluorine atom),
(2) a group represented by the formula: —O—$X^3$—$Z^1$:
wherein
$X^3$ is a $C_{1-3}$ alkylene group (e.g., —CH$_2$—, —(CH$_2$)$_2$—, —(CH$_2$)$_3$—) optionally substituted by 1 to 4 halogen atoms (e.g., a fluorine atom), and
$Z^1$ is
(i) a cyano group,
(ii) a $C_{1-3}$ alkylsulfonyl group (e.g., methylsulfonyl, ethylsulfonyl), or
(iii) a 3- to 6-membered monocyclic oxygen-containing non-aromatic heterocyclic group (e.g., oxetanyl, tetrahydrofuryl, tetrahydropyranyl), or
(3) a group represented by the formula: —O—$X^4$—$Z^2$:
wherein
$X^4$ is a bond or a $C_{1-3}$ alkylene group (e.g., —CH$_2$—, —(CH$_2$)$_2$—, —(CH$_2$)$_3$—) optionally substituted by 1 to 4 halogen atoms (e.g., a fluorine atom), and
$Z^2$ is a 5- or 6-membered monocyclic nitrogen-containing aromatic heterocyclic group (e.g., oxazolyl, thiazolyl, pyrazolyl, pyridyl, pyrimidinyl) optionally substituted by 1 to 3 $C_{1-3}$ alkyl groups (e.g., methyl);

R³ is a cyano group or a chlorine atom; and
R⁴ is a morpholino group or a 3-oxa-8-azabicyclo[3.2.1]
  octan-8-yl group, each optionally substituted by 1 to 3
  $C_{1-6}$ alkyl groups (e.g., methyl).
Compound (I) or compound (Ia) wherein
R² is
(1) a group represented by the formula: —O—[X¹—X²—
  O]$_m$—Y:
  wherein
  each of X¹ is independently a $C_{1-6}$ alkylene group (e.g.,
    —(CH₂)₂—, —(CH₂)₃—, —(CH₂)₄—),
  X² is a bond,
  m is an integer of 0 to 2, and
  Y is
    (i) a hydrogen atom, or
    (ii) a $C_{1-6}$ alkyl group (e.g., methyl, ethyl, isopropyl)
      optionally substituted by 1 to 3 halogen atoms
      (e.g., a fluorine atom),
(2) a group represented by the formula: —O—X³—Z¹:
  wherein
  X³ is a $C_{1-6}$ alkylene group (e.g., —(CH₂)₂—,
    —(CH₂)₃—), and
  Z¹ is a $C_{1-6}$ alkylsulfonyl group (e.g., methylsulfonyl),
    or
(3) a group represented by the formula: —O—X⁴—Z²:
  wherein
  X⁴ is a $C_{1-6}$ alkylene group (e.g., —CH₂—), and
  Z² is a 5- or 6-membered monocyclic aromatic heterocyclic group (e.g., pyridyl).
Compound (I) or compound (Ia) wherein
R² is
(1) a group represented by the formula: —O—[X¹—X²—
  O]$_m$—Y:
  wherein
  each of X¹ is independently a $C_{1-6}$ alkylene group (e.g.,
    —(CH₂)₂—, —(CH₂)₃—, —(CH₂)₄—), X² is a
    bond,
  m is an integer of 0 to 2, and
  Y is
    (i) a hydrogen atom, or
    (ii) a $C_{1-3}$ alkyl group (e.g., methyl, ethyl, isopropyl)
      optionally substituted by 1 to 3 halogen atoms
      (e.g., a fluorine atom),
(2) a group represented by the formula: —O—X³—Z¹:
  wherein
  X³ is a $C_{1-3}$ alkylene group (e.g., —(CH₂)₂—,
    —(CH₂)₃—), and
  Z¹ is a $C_{1-3}$ alkylsulfonyl group (e.g., methylsulfonyl),
    or
(3) a group represented by the formula: —O—X⁴—Z²:
  wherein
  X⁴ is a $C_{1-3}$ alkylene group (e.g., —CH₂—), and
  Z² is a 5- or 6-membered monocyclic nitrogen-containing aromatic heterocyclic group (e.g., pyridyl).
Compound (I) or compound (Ia) wherein
R¹ is a methyl group;
R² is
(1) a group represented by the formula: —O—[X¹—X²—
  O]$_m$—Y:
  wherein
  each of X¹ is independently a $C_{1-6}$ alkylene group (e.g.,
    —(CH₂)₂—, —(CH₂)₃—, —(CH₂)₄—),
  X² is a bond,
  m is an integer of 0 to 2, and
  Y is
    (i) a hydrogen atom, or
    (ii) a $C_{1-3}$ alkyl group (e.g., methyl, ethyl, isopropyl)
      optionally substituted by 1 to 3 halogen atoms
      (e.g., a fluorine atom),
(2) a group represented by the formula: —O—X³—Z¹:
  wherein
  X³ is a $C_{1-3}$ alkylene group (e.g., —(CH₂)₂—,
    —(CH₂)₃—), and
  Z¹ is a $C_{1-3}$ alkylsulfonyl group (e.g., methylsulfonyl),
    or
(3) a group represented by the formula: —O—X⁴—Z²:
  wherein
  X⁴ is a $C_{1-3}$ alkylene group (e.g., —CH₂—), and
  Z² is a 5- or 6-membered monocyclic nitrogen-containing aromatic heterocyclic group (e.g., pyridyl);
R³ is a cyano group or a chlorine atom; and
R⁴ is a morpholino group or a 3-oxa-8-azabicyclo[3.2.1]
  octan-8-yl group, each optionally substituted by 1 to 3
  $C_{1-6}$ alkyl groups (e.g., methyl).
Compound (I) or compound (Ia) wherein
R² is
(1) a group represented by the formula: —O—[X¹—X²—
  O]$_m$—Y:
  wherein
  each of X¹ is independently a $C_{1-6}$ alkylene group (e.g.,
    —CH₂—, —(CH₂)₂—, —(CH₂)₃—, —(CH₂)₄—,
    *—CH₂—CH(CH₃)—**, *—CH(CH₃)—CH₂—
    CH₂—**, —CH₂—CH(CH₃)—CH₂—, *—CH₂—
    CH₂—CH(CH₃)—**, *—CH₂—C(CH₃) 2-**,
    —CH₂—C(CH₃)₂—CH₂—, *—CH₂—CH₂—C
    (CH₃) 2-**,
  wherein * is the bonding site to the oxygen atom, and
    ** is the bonding site to X²) optionally substituted by
    1 to 4 halogen atoms (e.g., a fluorine atom),
  each of X² is independently
    (i) a bond, or
    (ii) a group represented by the formula:

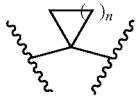

wherein n is an integer of 1 or 2,
  m is an integer of 0 to 8 (preferably an integer of 1 to
    8), and
  Y is
    (i) a hydrogen atom, or
    (ii) a $C_{1-3}$ alkyl group (the $C_{1-3}$ alkyl group may be
      labeled with ²H (e.g., methyl, ethyl, isopropyl,
      deuteromethyl)) optionally substituted by 1 to 3
      halogen atoms (e.g., a fluorine atom),
(2) a group represented by the formula: —O—X³—Z¹:
  wherein
  X³ is a $C_{1-3}$ alkylene group (e.g., —CH₂—,
    —(CH₂)₂—, —(CH₂)₃—) optionally substituted by
    1 to 4 halogen atoms (e.g., a fluorine atom), and
  Z¹ is
    (i) a cyano group,
    (ii) a $C_{1-3}$ alkylsulfonyl group (e.g., methylsulfonyl,
      ethylsulfonyl), or
    (iii) a 3- to 6-membered monocyclic non-aromatic
      heterocyclic group (preferably a 3- to 6-membered
      monocyclic oxygen-containing non-aromatic heterocyclic group) (e.g., oxetanyl, tetrahydrofuryl,
      tetrahydropyranyl), or (3) a group represented by the formula: —O—$X^4$—$Z^2$:
wherein
$X^4$ is a bond or a $C_{1-3}$ alkylene group (e.g., —$CH_2$—, —$(CH_2)_2$—, —$(CH_2)_3$—) optionally substituted by 1 to 4 halogen atoms (e.g., a fluorine atom), and
$Z^2$ is a 5- or 6-membered monocyclic aromatic heterocyclic group (preferably a 5- or 6-membered monocyclic nitrogen-containing aromatic heterocyclic group) (e.g., oxazolyl, thiazolyl, pyrazolyl, triazolyl, imidazolyl, isoxazolyl, pyridyl, pyrimidinyl) optionally substituted by 1 to 3 $C_{1-3}$ alkyl groups (e.g., methyl).

Compound (I) or compound (Ia) wherein
$R^1$ is a methyl group;
$R^2$ is
(1) a group represented by the formula: —O—[$X^1$—$X^2$—O]$_m$—Y:
wherein
each of $X^1$ is independently a $C_{1-6}$ alkylene group (e.g., —$CH_2$—, —$(CH_2)_2$—, —$(CH_2)_3$—, —$(CH_2)_4$—, *—$CH_2$—CH($CH_3$)—**, *—CH($CH_3$)—$CH_2$—**, —$CH_2$—CH($CH_3$)—$CH_2$—, *—$CH_2$—$CH_2$—CH($CH_3$)—**, *—$CH_2$—C($CH_3$)2-**, —$CH_2$—C($CH_3$)$_2$—$CH_2$—, *—$CH_2$—$CH_2$—C($CH_3$)2-**,
wherein * is the bonding site to the oxygen atom, and ** is the bonding site to $X^2$) optionally substituted by 1 to 4 halogen atoms (e.g., a fluorine atom),
each of $X^2$ is independently
(i) a bond, or
(ii) a group represented by the formula:

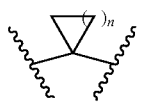

wherein n is an integer of 1 or 2,
m is an integer of 0 to 8 (preferably an integer of 1 to 8), and
Y is
(i) a hydrogen atom, or
(ii) a $C_{1-3}$ alkyl group (the $C_{1-3}$ alkyl group may be labeled with $^2H$ (e.g., methyl, ethyl, isopropyl, deuteromethyl)) optionally substituted by 1 to 3 halogen atoms (e.g., a fluorine atom),
(2) a group represented by the formula: —O—$X^3$—$Z^1$:
wherein
$X^3$ is a $C_{1-3}$ alkylene group (e.g., —$CH_2$—, —$(CH_2)_2$—, —$(CH_2)_3$—) optionally substituted by 1 to 4 halogen atoms (e.g., a fluorine atom), and
$Z^1$ is
(i) a cyano group,
(ii) a $C_{1-3}$ alkylsulfonyl group (e.g., methylsulfonyl, ethylsulfonyl), or
(iii) a 3- to 6-membered monocyclic non-aromatic heterocyclic group (preferably a 3- to 6-membered monocyclic oxygen-containing non-aromatic heterocyclic group) (e.g., oxetanyl, tetrahydrofuryl, tetrahydropyranyl), or
(3) a group represented by the formula: —O—$X^4$—$Z^2$:
wherein
$X^4$ is a bond or a $C_{1-3}$ alkylene group (e.g., —$CH_2$—, —$(CH_2)_2$—, —$(CH_2)_3$—) optionally substituted by 1 to 4 halogen atoms (e.g., a fluorine atom), and
$Z^2$ is a 5- or 6-membered monocyclic aromatic heterocyclic group (preferably a 5- or 6-membered monocyclic nitrogen-containing aromatic heterocyclic group) (e.g., oxazolyl, thiazolyl, pyrazolyl, triazolyl, imidazolyl, isoxazolyl, pyridyl, pyrimidinyl) optionally substituted by 1 to 3 $C_{1-3}$ alkyl groups (e.g., methyl);
$R^3$ is a cyano group or a chlorine atom; and
$R^4$ is a morpholino group or a 3-oxa-8-azabicyclo[3.2.1]octan-8-yl group, each optionally substituted by 1 to 3 $C_{1-6}$ alkyl groups (e.g., methyl).

Compound (I) or compound (Ia) wherein
$R^1$ is a methyl group;
$R^2$ is
(1) a group represented by the formula: —O—$X^1$—$X^2$—O—($CH_2$—$CH_2$—O)$_p$—Y:
wherein
$X^1$ is a $C_{1-6}$ alkylene group (e.g., —$CH_2$—, —$(CH_2)_2$—, —$(CH_2)_3$—, —$(CH_2)_4$—, *—$CH_2$—CH($CH_3$)—**, *—CH($CH_3$)—$CH_2$—$CH_2$—**, —$CH_2$—CH($CH_3$)—$CH_2$—, *—$CH_2$—$CH_2$—CH($CH_3$)—**, *—$CH_2$—C($CH_3$)$_2$—**, —$CH_2$—C($CH_3$)$_2$—$CH_2$—, *—$CH_2$—$CH_2$—C($CH_3$)$_2$—**,
wherein * is the bonding site to the oxygen atom, and ** is the bonding site to $X^2$) optionally substituted by 1 to 4 halogen atoms (e.g., a fluorine atom),
$X^2$ is
(i) a bond, or
(ii) a group represented by the formula:

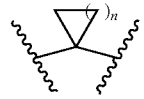

wherein n is an integer of 1 or 2,
p is an integer of 0 to 7, and
Y is
(i) a hydrogen atom, or
(ii) a $C_{1-3}$ alkyl group (the $C_{1-3}$ alkyl group may be labeled with $^2H$ (e.g., methyl, ethyl, isopropyl, deuteromethyl)) optionally substituted by 1 to 3 halogen atoms (e.g., a fluorine atom),
(2) a group represented by the formula: —O—$X^3$—$Z^1$:
wherein
$X^3$ is a $C_{1-3}$ alkylene group (e.g., —$CH_2$—, —$(CH_2)_2$—, —$(CH_2)_3$—) optionally substituted by 1 to 4 halogen atoms (e.g., a fluorine atom), and
$Z^1$ is
(i) a cyano group,
(ii) a $C_{1-3}$ alkylsulfonyl group (e.g., methylsulfonyl, ethylsulfonyl), or
(iii) a 3- to 6-membered monocyclic non-aromatic heterocyclic group (preferably a 3- to 6-membered monocyclic oxygen-containing non-aromatic heterocyclic group) (e.g., oxetanyl, tetrahydrofuryl, tetrahydropyranyl),
(3) a group represented by the formula: —O—$X^4$—$Z^2$:
wherein
$X^4$ is a bond or a $C_{1-3}$ alkylene group (e.g., —$CH_2$—, —$(CH_2)_2$—, —$(CH_2)_3$—) optionally substituted by 1 to 4 halogen atoms (e.g., a fluorine atom), and
$Z^2$ is a 5- or 6-membered monocyclic aromatic heterocyclic group (preferably a 5- or 6-membered monocyclic nitrogen-containing aromatic heterocyclic group) (e.g., oxazolyl, thiazolyl, pyrazolyl, triazolyl, imidazolyl, isoxazolyl, pyridyl, pyrimidinyl) optionally substituted by 1 to 3 $C_{1-3}$ alkyl groups (e.g., methyl), or
(4) a hydroxy group;
$R^3$ is a cyano group or a chlorine atom; and
$R^4$ is a morpholino group or a 3-oxa-8-azabicyclo[3.2.1]octan-8-yl group, each optionally substituted by 1 to 3 $C_{1-6}$ alkyl groups (e.g., methyl).

Compound (I) or compound (Ia) wherein
$R^2$ is
(1) a group represented by the formula: —O—[$X^1$—$X^2$—O]$_m$—Y:
wherein
each of $X^1$ is independently a $C_{1-6}$ alkylene group (e.g., —(CH$_2$)$_2$—, —(CH$_2$)$_3$—, —(CH$_2$)$_4$—, *—CH$_2$—CH(CH$_3$)—**, *—CH$_2$—CH$_2$—C(CH$_3$)$_2$—**, wherein * is the bonding site to the oxygen atom, and ** is the bonding site to $X^2$),
$X^2$ is a bond,
m is an integer of 0 to 2 (preferably an integer of 1 or 2), and
Y is
(i) a hydrogen atom, or
(ii) a $C_{1-6}$ alkyl group (the $C_{1-6}$ alkyl group may be labeled with $^2$H (e.g., methyl, ethyl, isopropyl, deuteromethyl)) optionally substituted by 1 to 3 halogen atoms (e.g., a fluorine atom),
(2) a group represented by the formula: —O—$X^3$—$Z^1$:
wherein
$X^3$ is a $C_{1-6}$ alkylene group (e.g., —CH$_2$—, —(CH$_2$)$_2$—, —(CH$_2$)$_3$—), and
$Z^1$ is
(i) a cyano group,
(ii) a $C_{1-6}$ alkylsulfonyl group (e.g., methylsulfonyl), or
(iii) a 3- to 8-membered monocyclic non-aromatic heterocyclic group (e.g., oxetanyl, tetrahydrofuryl, tetrahydropyranyl), or
(3) a group represented by the formula: —O—$X^4$—$Z^2$:
wherein
$X^4$ is a $C_{1-6}$ alkylene group (e.g., —CH$_2$—, —(CH$_2$)$_2$—, —(CH$_2$)$_3$—), and
$Z^2$ is a 5- or 6-membered monocyclic aromatic heterocyclic group (e.g., oxazolyl, thiazolyl, pyrazolyl, triazolyl, imidazolyl, isoxazolyl, pyridyl) optionally substituted by 1 to 3 $C_{1-6}$ alkyl groups (e.g., methyl).

Compound (I) or compound (Ia) wherein
$R^2$ is
(1) a group represented by the formula: —O—[$X^1$—$X^2$—O]$_m$—Y:
wherein
each of $X^1$ is independently a $C_{1-6}$ alkylene group (e.g., —(CH$_2$)$_2$—, —(CH$_2$)$_3$—, —(CH$_2$)$_4$—, *—CH$_2$—CH(CH$_3$)—**, *—CH$_2$—CH$_2$—C(CH$_3$)$_2$—**, wherein * is the bonding site to the oxygen atom, and ** is the bonding site to $X^2$),
$X^2$ is a bond,
m is an integer of 0 to 2 (preferably an integer of 1 or 2), and
Y is
(i) a hydrogen atom, or
(ii) a $C_{1-3}$ alkyl group (the $C_{1-3}$ alkyl group may be labeled with $^2$H (e.g., methyl, ethyl, isopropyl, deuteromethyl)) optionally substituted by 1 to 3 halogen atoms (e.g., a fluorine atom),
(2) a group represented by the formula: —O—$X^3$—$Z^1$:
wherein
$X^3$ is a $C_{1-3}$ alkylene group (e.g., —CH$_2$—, —(CH$_2$)$_2$—, —(CH$_2$)$_3$—), and
$Z^1$ is
(i) a cyano group,
(ii) a $C_{1-3}$ alkylsulfonyl group (e.g., methylsulfonyl), or
(iii) a 3- to 6-membered monocyclic non-aromatic heterocyclic group (preferably a 3- to 6-membered monocyclic oxygen-containing non-aromatic heterocyclic group) (e.g., oxetanyl, tetrahydrofuryl, tetrahydropyranyl), or
(3) a group represented by the formula: —O—$X^4$—$Z^2$:
wherein
$X^4$ is a $C_{1-3}$ alkylene group (e.g., —CH$_2$—, —(CH$_2$)$_2$—, —(CH$_2$)$_3$—), and
$Z^2$ is a 5- or 6-membered monocyclic aromatic heterocyclic group (preferably a 5- or 6-membered monocyclic nitrogen-containing aromatic heterocyclic group) (e.g., oxazolyl, thiazolyl, pyrazolyl, triazolyl, imidazolyl, isoxazolyl, pyridyl) optionally substituted by 1 to 3 $C_{1-3}$ alkyl groups (e.g., methyl).

Compound (I) or compound (Ia) wherein
$R^1$ is a methyl group;
$R^2$ is
(1) a group represented by the formula: —O—[$X^1$—$X^2$—O]$_m$—Y:
wherein
each of $X^1$ is independently a $C_{1-6}$ alkylene group (e.g., —(CH$_2$)$_2$—, —(CH$_2$)$_3$—, —(CH$_2$)$_4$—, *—CH$_2$—CH(CH$_3$)—**, *—CH$_2$—CH$_2$—C(CH$_3$)$_2$—**, wherein * is the bonding site to the oxygen atom, and ** is the bonding site to $X^2$),
$X^2$ is a bond,
m is an integer of 0 to 2 (preferably an integer of 1 or 2), and
Y is
(i) a hydrogen atom, or
(ii) a $C_{1-3}$ alkyl group (the $C_{1-3}$ alkyl group may be labeled with $^2$H (e.g., methyl, ethyl, isopropyl, deuteromethyl)) optionally substituted by 1 to 3 halogen atoms (e.g., a fluorine atom),
(2) a group represented by the formula: —O—$X^3$—$Z^1$:
wherein
$X^3$ is a $C_{1-3}$ alkylene group (e.g., —CH$_2$—, —(CH$_2$)$_2$—, —(CH$_2$)$_3$—), and
$Z^1$ is
(i) a cyano group,
(ii) a $C_{1-3}$ alkylsulfonyl group (e.g., methylsulfonyl), or
(iii) a 3- to 6-membered monocyclic non-aromatic heterocyclic group (preferably a 3- to 6-membered monocyclic oxygen-containing non-aromatic heterocyclic group) (e.g., oxetanyl, tetrahydrofuryl, tetrahydropyranyl), or
(3) a group represented by the formula: —O—$X^4$—$Z^2$:
wherein
$X^4$ is a $C_{1-3}$ alkylene group (e.g., —CH$_2$—, —(CH$_2$)$_2$—, —(CH$_2$)$_3$—), and
$Z^2$ is a 5- or 6-membered monocyclic aromatic heterocyclic group (preferably a 5- or 6-membered monocyclic nitrogen-containing aromatic heterocyclic group) (e.g., oxazolyl, thiazolyl, pyrazolyl, triazolyl, imidazolyl, isoxazolyl, pyridyl) optionally substituted by 1 to 3 $C_{1-3}$ alkyl groups (e.g., methyl);
$R^3$ is a cyano group or a chlorine atom; and $R^4$ is a morpholino group or a 3-oxa-8-azabicyclo[3.2.1]octan-8-yl group, each optionally substituted by 1 to 3 $C_{1-6}$ alkyl groups (e.g., methyl).

Compound (I) or compound (Ia) wherein
$R^1$ is a methyl group;
$R^2$ is
(1) a group represented by the formula: —O—$X^1$—$X^2$—O—$(CH_2$—$CH_2$—$O)_p$—Y:
wherein
$X^1$ is a $C_{1-6}$ alkylene group (e.g., —$(CH_2)_2$—, —$(CH_2)_3$—, —$(CH_2)_4$—, *—$CH_2$—$CH(CH_3)$—**, *—$CH_2$—$CH_2$—$C(CH_3)$ 2-**, wherein * is the bonding site to the oxygen atom, and ** is the bonding site to $X^2$),
$X^2$ is a bond,
p is an integer of 0 or 1, and
Y is
  (i) a hydrogen atom, or
  (ii) a $C_{1-3}$ alkyl group (the $C_{1-3}$ alkyl group may be labeled with $^2H$ (e.g., methyl, ethyl, isopropyl, deuteromethyl)) optionally substituted by 1 to 3 halogen atoms (e.g., a fluorine atom),
(2) a group represented by the formula: —O—$X^3$—$Z^1$:
wherein
$X^3$ is a $C_{1-3}$ alkylene group (e.g., —$CH_2$—, —$(CH_2)_2$—, —$(CH_2)_3$—), and
$Z^1$ is
  (i) a cyano group,
  (ii) a $C_{1-3}$ alkylsulfonyl group (e.g., methylsulfonyl), or
  (iii) a 3- to 6-membered monocyclic non-aromatic heterocyclic group (preferably a 3- to 6-membered monocyclic oxygen-containing non-aromatic heterocyclic group) (e.g., oxetanyl, tetrahydrofuryl, tetrahydropyranyl),
(3) a group represented by the formula: —O—$X^4$—$Z^2$:
wherein
$X^4$ is a $C_{1-3}$ alkylene group (e.g., —$CH_2$—, —$(CH_2)_2$—, —$(CH_2)_3$—), and
$Z^2$ is a 5- or 6-membered monocyclic aromatic heterocyclic group (preferably a 5- or 6-membered monocyclic nitrogen-containing aromatic heterocyclic group) (e.g., oxazolyl, thiazolyl, pyrazolyl, triazolyl, imidazolyl, isoxazolyl, pyridyl) optionally substituted by 1 to 3 $C_{1-3}$ alkyl groups (e.g., methyl), or
(4) a hydroxy group;
$R^3$ is a cyano group or a chlorine atom; and
$R^4$ is a morpholino group or a 3-oxa-8-azabicyclo[3.2.1]octan-8-yl group, each optionally substituted by 1 to 3 $C_{1-6}$ alkyl groups (e.g., methyl).

Compound (I) or compound (Ia) wherein
$R^2$ is
(1) a group represented by the formula: —O—[$X^1$—$X^2$—O]$_m$—Y:
wherein
each of $X^1$ is independently a $C_{1-6}$ alkylene group (e.g., —$(CH_2)_2$—, —$(CH_2)_3$—, *—$CH_2$—$CH_2$—$C(CH_3)_2$—** wherein * is the bonding site to the oxygen atom, and ** is the bonding site to $X^2$),
$X^2$ is a bond,
m is an integer of 1 or 2, and
Y is
  (i) a hydrogen atom, or
  (ii) a $C_{1-6}$ alkyl group (e.g., methyl, ethyl), or
(2) a group represented by the formula: —O—$X^3$—$Z^1$:
wherein
$X^3$ is a $C_{1-6}$ alkylene group (e.g., —$CH_2$—, —$(CH_2)_2$—), and
$Z^1$ is a 3- to 8-membered monocyclic non-aromatic heterocyclic group (e.g., oxetanyl, tetrahydropyranyl).

Compound (I) or compound (Ia) wherein
$R^2$ is
(1) a group represented by the formula: —O—[$X^1$—$X^2$—O]$_m$—Y:
wherein
each of $X^1$ is independently a $C_{1-6}$ alkylene group (e.g., —$(CH_2)_2$—, —$(CH_2)_3$—, *—$CH_2$—$CH_2$—$C(CH_3)_2$—**, wherein * is the bonding site to the oxygen atom, and ** is the bonding site to $X^2$),
$X^2$ is a bond,
m is an integer of 1 or 2, and
Y is
  (i) a hydrogen atom, or
  (ii) a $C_{1-3}$ alkyl group (e.g., methyl, ethyl), or
(2) a group represented by the formula: —O—$X^3$—$Z^1$:
wherein
$X^3$ is a $C_{1-3}$ alkylene group (e.g., —$CH_2$—, —$(CH_2)_2$—), and
$Z^1$ is a 3- to 6-membered monocyclic non-aromatic heterocyclic group (preferably a 3- to 6-membered monocyclic oxygen-containing non-aromatic heterocyclic group) (e.g., oxetanyl, tetrahydropyranyl).

Compound (I) or compound (Ia) wherein
$R^1$ is a methyl group;
$R^2$ is
(1) a group represented by the formula: —O—[$X^1$—$X^2$—O]$_m$—Y:
wherein
each of $X^1$ is independently a $C_{1-6}$ alkylene group (e.g., —$(CH_2)_2$—, —$(CH_2)_3$—, *—$CH_2$—$CH_2$—$C(CH_3)_2$—**, wherein * is the bonding site to the oxygen atom, and ** is the bonding site to $X^2$),
$X^2$ is a bond,
m is an integer of 1 or 2, and
Y is
  (i) a hydrogen atom, or
  (ii) a $C_{1-3}$ alkyl group (e.g., methyl, ethyl), or
(2) a group represented by the formula: —O—$X^3$—$Z^1$:
wherein
$X^3$ is a $C_{1-3}$ alkylene group (e.g., —$CH_2$—, —$(CH_2)_2$—), and
$Z^1$ is a 3- to 6-membered monocyclic non-aromatic heterocyclic group (preferably a 3- to 6-membered monocyclic oxygen-containing non-aromatic heterocyclic group) (e.g., oxetanyl, tetrahydropyranyl);
$R^3$ is a cyano group or a chlorine atom; and
$R^4$ is a morpholino group, a morpholino group substituted by 1 or 2 $C_{1-6}$ alkyl groups (e.g., methyl), or a 3-oxa-8-azabicyclo[3.2.1]octan-8-yl group.

Compound (I) or compound (Ia) wherein
$R^1$ is a methyl group;
$R^2$ is
(1) a group represented by the formula: —O—$X^1$—$X^2$—O—$(CH_2$—$CH_2$—$O)_p$—Y:
wherein
$X^1$ is a $C_{1-6}$ alkylene group (e.g., —$(CH_2)_2$—, —$(CH_2)_3$—, *—$CH_2$—$CH_2$—$C(CH_3)_2$—**, wherein * is the bonding site to the oxygen atom, and ** is the bonding site to $X^2$),
$X^2$ is a bond,
p is an integer of 0 or 1, and Y is
(i) a hydrogen atom, or
(ii) a $C_{1-3}$ alkyl group (e.g., methyl, ethyl), or
(2) a group represented by the formula: —O—$X^3$—$Z^1$:
wherein
$X^3$ is a $C_{1-3}$ alkylene group (e.g., —CH$_2$—, —(CH$_2$)$_2$—), and
$Z^1$ is a 3- to 6-membered monocyclic non-aromatic heterocyclic group (preferably a 3- to 6-membered monocyclic oxygen-containing non-aromatic heterocyclic group) (e.g., oxetanyl, tetrahydropyranyl);
$R^3$ is a cyano group or a chlorine atom; and
$R^4$ is a morpholino group, a morpholino group substituted by 1 or 2 $C_{1-6}$ alkyl groups (e.g., methyl), or a 3-oxa-8-azabicyclo[3.2.1]octan-8-yl group.

Compound (I) or compound (Ia), which is v selected from
2-(((S)-1-(1H-tetrazol-1-yl)propan-2-yl)oxy)-4-(2-((1-((1r,4r)-4-((1R,5S)-3-oxa-8-azabicyclo[3.2.1]octan-8-yl)cyclohexyl)-3-(2-ethoxyethoxy)-1H-pyrazol-4-yl)amino)pyrimidin-5-yl)benzonitrile,
2-(((S)-1-(1H-tetrazol-1-yl)propan-2-yl)oxy)-4-(2-((3-(3-methoxypropoxy)-1-((r,4r)-4-morpholinocyclohexyl)-1H-pyrazol-4-yl)amino)pyrimidin-5-yl)benzonitrile,
2-(((S)-1-(1H-tetrazol-1-yl)propan-2-yl)oxy)-4-(2-((1r,4r)-4-((1R,5S)-3-oxa-8-azabicyclo[3.2.1]octan-8-yl)cyclohexyl)-3-(3-methoxypropoxy)-1H-pyrazol-4-yl)amino)pyrimidin-5-yl)benzonitrile,
2-(((S)-1-(1H-tetrazol-1-yl)propan-2-yl)oxy)-4-(2-((3-(3-ethoxypropoxy)-1-((1r,4r)-4-morpholinocyclohexyl)-1H-pyrazol-4-yl)amino)pyrimidin-5-yl)benzonitrile,
2-(((S)-1-(1H-tetrazol-1-yl)propan-2-yl)oxy)-4-(2-((1r,4r)-4-((1R,5S)-3-oxa-8-azabicyclo[3.2.1]octan-8-yl)cyclohexyl)-3-(3-ethoxypropoxy)-1H-pyrazol-4-yl)amino)pyrimidin-5-yl)benzonitrile,
2-(((S)-1-(1H-tetrazol-1-yl)propan-2-yl)oxy)-4-(2-((1r,4r)-4-((2S,6R)-2,6-dimethylmorpholino)cyclohexyl)-3-(3-methoxypropoxy)-1H-pyrazol-4-yl)amino)pyrimidin-5-yl)benzonitrile,
2-(((S)-1-(1H-tetrazol-1-yl)propan-2-yl)oxy)-4-(2-((1r,4r)-4-((2S,6R)-2,6-dimethylmorpholino)cyclohexyl)-3-(2-(2-methoxyethoxy)ethoxy)-1H-pyrazol-4-yl)amino)pyrimidin-5-yl)benzonitrile hydrochloride,
2-(3-((4-((5-(3-(((S)-1-(1H-tetrazol-1-yl) propan-2-yl)oxy)-4-chlorophenyl)pyrimidin-2-yl)amino)-1-((1r,4r)-4-((2S,6R)-2,6-dimethylmorpholino)cyclohexyl)-1H-pyrazol-3-yl)oxy)propoxy)ethan-1-ol,
2-(((S)-1-(1H-tetrazol-1-yl)propan-2-yl)oxy)-4-(2-((1r,4r)-4-((2S,6R)-2,6-dimethylmorpholino)cyclohexyl)-3-(2-(oxetan-3-yl)ethoxy)-1H-pyrazol-4-yl)amino)pyrimidin-5-yl)benzonitrile,
2-(((S)-1-(1H-tetrazol-1-yl)propan-2-yl)oxy)-4-(2-((1r,4r)-4-((2S,6R)-2,6-dimethylmorpholino)cyclohexyl)-3-(oxetan-3-ylmethoxy)-1H-pyrazol-4-yl)amino)pyrimidin-5-yl)benzonitrile,
2-(((S)-1-(1H-tetrazol-1-yl)propan-2-yl)oxy)-4-(2-((1r,4r)-4-((2S,6R)-2,6-dimethylmorpholino)cyclohexyl)-3-((tetrahydro-2H-pyran-4-yl)methoxy)-1H-pyrazol-4-yl)amino)pyrimidin-5-yl)benzonitrile,
2-(((S)-1-(1H-tetrazol-1-yl)propan-2-yl)oxy)-4-(2-((1-((1r,4r)-4-((2S,6R)-2,6-dimethylmorpholino)cyclohexyl)-3-(3-hydroxy-3-methylbutoxy)-1H-pyrazol-4-yl)amino)pyrimidin-5-yl)benzonitrile,
4-((4-((5-(3-(((S)-1-(1H-tetrazol-1-yl)propan-2-yl)oxy)-4-chlorophenyl)pyrimidin-2-yl)amino)-1-((1r,4r)-4-((2S,6R)-2,6-dimethylmorpholino)cyclohexyl)-1H-pyrazol-3-yl)oxy)-2-methylbutan-2-ol,
5-(3-(((S)-1-(1H-tetrazol-1-yl)propan-2-yl)oxy)-4-chlorophenyl)-N-(1-((1r,4r)-4-((2S,6R)-2,6-dimethylmorpholino)cyclohexyl)-3-(2-methoxyethoxy)propoxy)-1H-pyrazol-4-yl)pyrimidin-2-amine,
2-(((S)-1-(1H-tetrazol-1-yl)propan-2-yl)oxy)-4-(2-((1-((1r,4r)-4-((2S,6R)-2,6-dimethylmorpholino)cyclohexyl)-3-(3-(2-methoxyethoxy)propoxy)-1H-pyrazol-4-yl)amino)pyrimidin-5-yl)benzonitrile, and
5-(3-(((S)-1-(1H-tetrazol-1-yl)propan-2-yl)oxy)-4-chlorophenyl)-N-(1-((1r,4r)-4-((2S,6R)-2,6-dimethylmorpholino)cyclohexyl)-3-(3-methoxypropoxy)-1H-pyrazol-4-yl)pyrimidin-2-amine,
or a salt thereof.

Specific examples of compound (I) include the compounds of Examples 1 to 194, 196 to 483 and 485-513.

When compound (I) is a salt, examples of the salt include metal salts, ammonium salts, salts with organic base, salts with inorganic acid, salts with organic acid, and salts with basic or acidic amino acid. Preferable examples of the metal salt include alkali metal salts such as sodium salts, potassium salts and the like; alkali earth metal salts such as calcium salts, magnesium salts, barium salts and the like; and aluminum salts. Preferable examples of the salt with organic base include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of the salt with inorganic acid include salts with hydrochloric acid, hydrobromic acid, nitric acid, sulfuric acid, phosphoric acid and the like. Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of the salts with basic amino acid include salts with arginine, lysine, ornithine and the like. Preferable examples of the salt with acidic amino acid include salts with aspartic acid, glutamic acid and the like. Among them, a pharmaceutically acceptable salt is preferable. For example, when a compound has an acidic functional group, examples of the salt include inorganic salts such as alkali metal salts (e.g., sodium salt, potassium salt etc.), alkaline earth metal salts (e.g., calcium salt, magnesium salt etc.) and the like, ammonium salt etc., and when a compound has a basic functional group, examples of the salt include salts with inorganic acid such as hydrochloric acid, hydrobromic acid, nitric acid, sulfuric acid, phosphoric acid and the like, and salts with organic acid such as acetic acid, phthalic acid, fumaric acid, oxalic acid, tartaric acid, maleic acid, citric acid, succinic acid, methanesulfonic acid, benzenesulfonic acid, p-toluenesulfonic acid and the like.

When compound (I) contains isomers such as tautomers, optical isomers, stereoisomers, position isomers and rotational isomers, any of isomers or mixture are also encompassed in the compound of the present invention. Further, when compound (I) contains an optical isomer, the optical isomer separated from the racemate is encompassed in compound (I).

Compound (I) can be obtained in the crystal form. Either single crystalline form or crystalline mixture can be encompassed in compound (I).

Compound (I) can be a pharmaceutically acceptable co-crystal or a co-crystal salt. The co-crystal or co-crystal salt as used herein means a crystalline material composed of two or more unique solids at room temperature, each of which has distinctive physical characteristics such as structure, melting point, and heats of fusion, hygroscopicity, solubility, and stability. A co-crystal or a co-crystal salt can be produced according to co-crystallization method known per se.

Compound (I) may be a solvate (e.g., a hydrate) or a non-solvate and both are encompassed in compound (I).

Compounds labeled with or substituted by isotopes (e.g., $^2$H, $^3$H, $^{11}$C, $^{14}$C, $^{18}$F, $^{35}$S, $^{125}$I, etc.) are also encompassed in compound (I). The compound labeled with or substituted by isotopes can be used as, for example, a tracer used for Positron Emission Tomography (PET) (PET tracer), and are expected to be useful in the field of medical diagnosis and the like.

The production method of the compound of the present invention is explained below.

The raw material compound and reagent used and the compound obtained in each step in the following production method may be each in a form of a salt, and examples of such salt include those similar to the salts of the compound of the present invention and the like.

When the compound obtained in each step is a free form, it can be converted to the objective salt according to a method known per se. When the compound obtained in each step is a salt, it can be converted to the objective free form or the other salt according to a method known per se.

The compound obtained in each step can be used directly as the reaction mixture or as a crude product for the next reaction. Alternatively, the compound obtained in each step can be isolated and purified from a reaction mixture according to a method known per se, for example, a separation means such as concentration, crystallization, recrystallization, distillation, solvent extraction, fractional distillation, column chromatography and the like.

When the raw material compound and reagent used in each step are commercially available, the commercially available product can also be used directly.

In the reaction in each step, while the reaction time varies depending on the kind of the reagent and solvent to be used, it is generally 1 min-48 hr, preferably 10 min-8 hr, unless otherwise specified.

In the reaction in each step, while the reaction temperature varies depending on the kind of the reagent and solvent to be used, it is generally −78° C.-300° C., preferably −78° C.-150° C., unless otherwise specified.

In the reaction in each step, while the pressure varies depending on the kind of the reagent and solvent to be used, it is generally 1 atm-20 atm, preferably 1 atm-3 atm, unless otherwise specified.

Microwave synthesizer such as Initiator manufactured by Biotage and the like may be used for the reaction in each step. While the reaction temperature varies depending on the kind of the reagent and solvent to be used, it is generally room temperature-300° C., preferably 50° C.-250° C., unless otherwise specified. While the reaction time varies depending on the kind of the reagent and solvent to be used, it is generally 1 min-48 hr, preferably 1 min-8 hr, unless otherwise specified.

In the reaction in each step, the reagent is used in an amount of 0.5 equivalents-20 equivalents, preferably 0.8 equivalents-5 equivalents, relative to the substrate, unless otherwise specified. When the reagent is used as a catalyst, the reagent is used in an amount of 0.001 equivalent-1 equivalent, preferably 0.01 equivalent-0.2 equivalent, relative to the substrate. When the reagent is used as a ligand, the reagent is used in an amount of 0.001 equivalent-1 equivalent, preferably 0.01 equivalent-0.2 equivalent, relative to the substrate. When the reagent is used as a reaction solvent, the reagent is used in a solvent amount.

Unless otherwise specified, the reaction in each step is carried out without solvent, or by dissolving or suspending the raw material compound in a suitable solvent. Examples of the solvent include those described in Examples and the following solvents.

alcohols: methanol, ethanol, tert-butyl alcohol, 2-methoxyethanol, benzyl alcohol and the like;
ethers: diethyl ether, diphenyl ether, tetrahydrofuran, 1,2-dimethoxyethane and the like;
aromatic hydrocarbons: chlorobenzene, toluene, xylene and the like;
saturated hydrocarbons: cyclohexane, hexane and the like;
amides: N,N-dimethylformamide, N-methylpyrrolidone and the like;
halogenated hydrocarbons: dichloromethane, carbon tetrachloride and the like;
nitriles: acetonitrile and the like;
sulfoxides: dimethyl sulfoxide and the like;
aromatic organic bases: pyridine and the like;
anhydrides: acetic anhydride and the like;
organic acids: formic acid, acetic acid, trifluoroacetic acid and the like;
inorganic acids: hydrochloric acid, sulfuric acid and the like;
esters: ethyl acetate and the like;
ketones: acetone, methyl ethyl ketone and the like;
water.

The above-mentioned solvent can be used in a mixture of two or more kinds thereof in an appropriate ratio.

When a base is used for the reaction in each step, examples thereof include those described in Examples and the following bases.

inorganic bases: sodium hydroxide, magnesium hydroxide, sodium carbonate, calcium carbonate, sodium hydrogen carbonate and the like;
organic bases: triethylamine, diethylamine, pyridine, 4-dimethylaminopyridine, N,N-dimethylaniline, 1,4-diazabicyclo[2.2.2]octane, 1,8-diazabicyclo[5.4.0]-7-undecene, imidazole, piperidine and the like;
metal alkoxides: sodium ethoxide, potassium tert-butoxide and the like;
alkali metal hydrides: sodium hydride and the like;
metal amides: sodium amide, lithium diisopropylamide, lithium hexamethyldisilazide and the like;
organic lithiums: n-butyllithium and the like.

When an acid or an acid catalyst is used for the reaction in each step, examples thereof include those described in Examples and the following acids and acid catalysts.
inorganic acids: hydrochloric acid, sulfuric acid, nitric acid, hydrobromic acid, phosphoric acid and the like;
organic acids: acetic acid, trifluoroacetic acid, citric acid, p-toluenesulfonic acid, 10-camphorsulfonic acid and the like;
Lewis acid: boron trifluoride diethyl ether complex, zinc iodide, anhydrous aluminum chloride, anhydrous zinc chloride, anhydrous iron chloride and the like.

Unless otherwise specified, the reaction in each step is carried out according to a method known per se, for example, the method described in Jikken Kagaku Kouza, 5th Edition, vol. 13-19 (the Chemical Society of Japan ed.); Shin Jikken Kagaku Kouza, vol. 14-15 (the Chemical Society of Japan ed.); Fine Organic Chemistry, Revised 2nd Edition (L. F. Tietze, Th. Eicher, Nankodo); Organic Name Reactions, the Reaction Mechanism and Essence, Revised Edition (Hideo Togo, Kodansha); ORGANIC SYNTHESES Collective Volume I-VII (John Wiley & Sons Inc.); Modern Organic Synthesis in the Laboratory A Collection of Standard Experimental Procedures (Jie Jack Li, OXFORD UNI- VERSITY); Comprehensive Heterocyclic Chemistry III, Vol. 1-Vol. 14 (Elsevier Japan); Strategic Applications of Named Reactions in Organic Synthesis (translated by Kiyoshi Tomioka, Kagakudojin); Comprehensive Organic Transformations (VCH Publishers Inc.), 1989, or the like, or the method described in Examples.

In each step, the protection or deprotection reaction of a functional group is carried out according to a method known per se, for example, the method described in "Protective Groups in Organic Synthesis, 4th Ed", Wiley-Interscience, Inc., 2007 (Theodora W. Greene, Peter G. M. Wuts); "Protecting Groups 3rd Ed." Thieme, 2004 (P. J. Kocienski), or the like, or the method described in Examples.

Examples of the protecting group for a hydroxy group of an alcohol and the like and a phenolic hydroxy group include ether-type protecting groups such as methoxymethyl ether, benzyl ether, tert-butyldimethylsilyl ether, tetrahydropyranyl ether and the like; carboxylate ester-type protecting groups such as acetate ester and the like; sulfonate ester-type protecting groups such as methanesulfonate ester and the like; carbonate ester-type protecting groups such as tert-butylcarbonate and the like, and the like.

Examples of the protecting group for a carbonyl group of an aldehyde include acetal-type protecting groups such as dimethylacetal and the like; cyclic acetal-type protecting groups such as 1,3-dioxane and the like, and the like.

Examples of the protecting group for a carbonyl group of a ketone include ketal-type protecting groups such as dimethylketal and the like; cyclic ketal-type protecting groups such as 1,3-dioxane and the like; oxime-type protecting groups such as O-methyloxime and the like; hydrazone-type protecting groups such as N,N-dimethylhydrazone and the like, and the like.

Examples of the protecting group for a carboxyl group include ester-type protecting groups such as methyl ester and the like; amide-type protecting groups such as N,N-dimethylamide and the like, and the like.

Examples of the protecting group for a thiol include ether-type protecting groups such as benzyl thioether and the like; ester-type protecting groups such as thioacetate ester, thiocarbonate, thiocarbamate and the like, and the like.

Examples of the protecting group for an amino group and an aromatic heterocycle such as imidazole, pyrrole, indole and the like include carbamate-type protecting groups such as benzyl carbamate and the like; amide-type protecting groups such as acetamide and the like; alkyl amine-type protecting groups such as N-triphenylmethylamine and the like; sulfonamide-type protecting groups such as methanesulfonamide and the like, and the like.

The protecting groups can be removed according to a method known per se, for example, by employing a method using acid, base, ultraviolet rays, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide) and the like, a reduction method, and the like.

When reduction reaction is carried out in each step, examples of the reducing agent to be used include metal hydrides such as lithium aluminum hydride, sodium triacetoxyborohydride, sodium cyanoborohydride, diisobutylaluminum hydride (DIBAL-H), sodium borohydride, tetramethylammonium triacetoxyborohydride and the like; boranes such as borane tetrahydrofuran complex and the like; Raney nickel; Raney cobalt; hydrogen; formic acid; triethylsilane and the like. When carbon-carbon double bond or triple bond or a nitro group or a benzyloxycarbonyl group is reduced, a method using a catalyst such as palladium-carbon, Lindlar's catalyst and the like may be employed.

When oxidation reaction is carried out in each step, examples of the oxidizing agent to be used include peroxides such as m-chloroperbenzoic acid (mCPBA), hydrogen peroxide, tert-butylhydroperoxide and the like; perchlorates such as tetrabutylammonium perchlorate and the like; chlorates such as sodium chlorate and the like; chlorites such as sodium chlorite and the like; periodates such as sodium periodate and the like; hypervalent iodine reagents such as iodosylbenzene and the like; reagents containing manganese such as manganese dioxide, potassium permanganate and the like; leads such as lead tetraacetate and the like; reagents containing chromium such as pyridinium chlorochromate (PCC), pyridinium dichromate (PDC), Jones reagent and the like; halogen compounds such as N-bromosuccinimide (NBS) and the like; oxygen; ozone; sulfur trioxide-pyridine complex; osmium tetroxide; selenium dioxide; 2,3-dichloro-5,6-dicyano-1,4-benzoquinone (DDQ), oxone and the like.

When radical cyclization reaction is carried out in each step, examples of the radical initiator to be used include azo compounds such as azobisisobutyronitrile (AIBN) and the like; water-soluble radical initiators such as 4-4'-azobis-4-cyanopentanoic acid (ACPA) and the like; triethylboron in the presence of air or oxygen; benzoyl peroxide and the like. Examples of the radical reagent to be used include tributylstannane, tristrimethylsilylsilane, 1,1,2,2-tetraphenyldisilane, diphenylsilane, samarium iodide and the like.

When Wittig reaction is carried out in each step, examples of the Wittig reagent to be used include alkylidene phosphoranes and the like. The alkylidene phosphoranes can be prepared according to a method known per se, for example, by reacting a phosphonium salt with a strong base.

When Horner-Emmons reaction is carried out in each step, examples of the reagent to be used include phosphonoacetates such as methyl dimethylphosphonoacetate, ethyl diethylphosphonoacetate and the like; and bases such as alkali metal hydrides, organic lithiums and the like.

When Friedel-Crafts reaction is carried out in each step, a combination of a Lewis acid and an acid chloride or a combination of a Lewis acid and an alkylating agent (e.g., an alkyl halide, an alcohol, an olefin etc.) is used as a reagent. Alternatively, an organic acid or an inorganic acid can also be used instead of a Lewis acid, and an anhydride such as acetic anhydride and the like can also be used instead of an acid chloride.

When aromatic nucleophilic substitution reaction is carried out in each step, a combination of a nucleophile (e.g., a hydroxy, an amine, imidazole etc.) and a base (e.g., an organic base etc.), or a combination of a nucleophile and an acid (e.g., an organic acid etc.) is used as a reagent.

When nucleophilic addition reaction by a carbo anion, nucleophilic 1,4-addition reaction (Michael addition reaction) by a carbo anion or nucleophilic substitution reaction by a carbo anion is carried out in each step, and examples of the base to be used for generation of the carbo anion include organic lithiums, metal alkoxides, inorganic bases, organic bases and the like.

When Grignard reaction is carried out in each step, examples of the Grignard reagent to be used include arylmagnesium halides such as phenylmagnesium bromide and the like; and alkylmagnesium halides such as methylmagnesium bromide and the like. The Grignard reagent can be prepared according to a method known per se, for example, by reacting an alkyl halide or an aryl halide with a metal magnesium in an ether or tetrahydrofuran as a solvent.

When Knoevenagel condensation reaction is carried out in each step, a compound having an activated methylene group with two electron withdrawing groups (e.g., malonic acid, diethyl malonate, malononitrile etc.) and a base (e.g., an organic base, a metal alkoxide, an inorganic base) are used as a reagent.

When Vilsmeier-Haack reaction is carried out in each step, phosphoryl chloride and an amide derivative (e.g., N,N-dimethylformamide etc.) are used as a reagent.

When azidation reaction of an alcohol, an alkyl halide or a sulfonate is carried out in each step, examples of the azidating agent to be used include diphenylphosphorylazide (DPPA), trimethylsilylazide, sodium azide and the like. For example, for the azidation reaction of an alcohol, a method using diphenylphosphorylazide and 1,8-diazabicyclo[5.4.0]undec-7-ene (DBU), a method using trimethylsilylazide and a Lewis acid, and the like are employed.

When reductive amination reaction is carried out in each step, examples of the reducing agent to be used include sodium triacetoxyborohydride, sodium cyanoborohydride, borane-2-methylpyridine complex, hydrogen, formic acid and the like. When the substrate is an amine compound, examples of the carbonyl compound to be used include paraformaldehyde, aldehydes such as acetaldehyde and the like, and ketones such as cyclohexanone and the like. When the substrate is a carbonyl compound, examples of the amine to be used include ammonia, primary amines such as methylamine and the like; secondary amines such as dimethylamine and the like, and the like.

When Mitsunobu reaction is carried out in each step, a combination of an azodicarboxylate (e.g., diethyl azodicarboxylate (DEAD), diisopropyl azodicarboxylate (DIAD) etc.) and triphenylphosphine, or a phosphorane reagent (e.g., cyanomethylenetributylphosphorane (Tsunoda reagent) is used as a reagent.

When esterification reaction, amidation reaction or urea formation reaction is carried out in each step, examples of the reagent to be used include acyl halides such as acid chlorides, acid bromides and the like; activated carboxylic acids such as anhydrides, activated esters, sulfates and the like. Examples of the activating agent of the carboxylic acid include carbodiimide condensing agents such as 1-ethyl-3-(3-dimethylaminopropyl)carbodiimide hydrochloride (WSCD) and the like; triazine condensing agents such as 4-(4,6-dimethoxy-1,3,5-triazin-2-yl)-4-methylmorpholinium chloride n-hydrate (DMT-MM) and the like; carbonate condensing agents such as 1,1-carbonyldiimidazole (CDI) and the like; diphenylphosphoryl azide (DPPA); benzotriazol-1-yloxy-trisdimethylaminophosphonium salt (BOP reagent); 2-chloro-1-methyl-pyridinium iodide (Mukaiyama reagent); thionyl chloride; lower alkyl haloformates such as ethyl chloroformate and the like; O-(7-azabenzotriazol-1-yl)-N,N,N',N'-tetramethyluronium hexafluorophosphorate (HATU); sulfuric acid; combinations thereof and the like. When carbodiimide condensing agent is used, an additive such as 1-hydroxybenzotriazole (HOBt), N-hydroxysuccinimide (HOSu), dimethylaminopyridine (DMAP) and the like may be added to the reaction system.

When coupling reaction is carried out in each step, examples of the metal catalyst to be used include palladium compounds such as palladium(II) acetate, tetrakis(triphenylphosphine)palladium(0), dichlorobis(triphenylphosphine)palladium(II), dichlorobis(triethylphosphine)palladium(II), tris(dibenzylideneacetone)dipalladium(0), 1,1'-bis(diphenylphosphino)ferrocene palladium(II) chloride, (tri-tert-butylphosphine)palladium(0) and the like; nickel compounds such as tetrakis(triphenylphosphine)nickel(0) and the like; rhodium compounds such as tris(triphenylphosphine)rhodium(III) chloride and the like; cobalt compounds; copper compounds such as copper oxide, copper(I) iodide, copper(II) diacetate and the like; platinum compounds and the like. In addition, a base can be added to the reaction system, and examples thereof include organic bases (e.g., 1,8-diazabicyclo[5.4.0]undec-7-ene, N,N-diisopropylethylamine), inorganic bases and the like. Moreover, a ligand can be added to the reaction system, and examples thereof include organic amines such as N,N'-dimethylethylenediamine, N,N'-dimethyl-cyclohexane-1,2-diamine, 2,2-bipyridyl and the like; organophosphorus compounds such as triphenylphosphine, tri-tert-butylphosphine, tricyclohexylphosphine, BINAP (2,2'-bis(diphenylphosphino)-1,1-binaphthyl) and the like, and the like.

When thiocarbonylation reaction is carried out in each step, phosphorus pentasulfide is typically used as the thiocarbonylating agent. Alternatively, a reagent having a 1,3,2,4-dithiadiphosphetane-2,4-disulfide structure (e.g., 2,4-bis(4-methoxyphenyl)-1,3,2,4-dithiadiphosphetane-2,4-disulfide (Lawesson reagent) etc.) can also be used instead of phosphorus pentasulfide.

When Wohl-Ziegler reaction is carried out in each step, examples of the halogenating agent to be used include N-iodosuccinimide, N-bromosuccinimide (NBS), N-chlorosuccinimide (NCS), bromine, sulfuryl chloride and the like. In addition, the reaction can be accelerated by subjecting a radical initiator such as heat, light, benzoyl peroxide, azobisisobutyronitrile and the like to the reaction system reaction.

When halogenation reaction of a hydroxy group is carried out in each step, examples of the halogenating agent to be used include hydrohalic acids and acid halides of inorganic acids, specifically, hydrochloric acid, thionyl chloride, phosphorus oxychloride and the like for chlorination, 48% hydrobromic acid and the like for bromination. In addition, a method of producing an alkyl halide by reacting an alcohol with triphenylphosphine and carbon tetrachloride or carbon tetrabromide or the like can be employed. Alternatively, a method of producing an alkyl halide via two steps comprising converting an alcohol to the corresponding sulfonate, and then reacting the sulfonate with lithium bromide, lithium chloride or sodium iodide can also be employed.

When Arbuzov reaction is carried out in each step, examples of the reagent to be used include alkyl halides such as ethyl bromoacetate and the like; and phosphites such as triethyl phosphite, tri(isopropyl)phosphite and the like.

When sulfonate esterification reaction is carried out in each step, examples of the sulfonating agent to be used include methanesulfonyl chloride, p-toluenesulfonyl chloride, methanesulfonic anhydride, p-toluenesulfonic anhydride and the like.

When hydrolysis reaction is carried out in each step, an acid or a base is used as a reagent. For acid hydrolysis reaction of tert-butyl ester, formic acid, triethylsilane and the like may be added to reductively-trap tert-butyl cation which is by-produced.

When dehydration reaction is carried out in each step, examples of the dehydrating agent to be used include sulfuric acid, diphosphorus pentaoxide, phosphorus oxychloride, N,N'-dicyclohexylcarbodiimide, alumina, polyphosphoric acid and the like.

When Curtius reaction is carried out in each step, a combination of an azidating agent (e.g., diphenylphosphorylazide (DPPA) and sodium azide etc.) and water or alcohols and base (e.g., triethylamine) is used as a reagent.

When Strecker reaction is carried out in each step, examples of the cyanation agent to be used include sodium cyanide, cyanotrimethylsilane and the like.

When Bruylants reaction is carried out in each step, examples of the alkylation agent to be used include arylmagnesium halides such as phenylmagnesium bromide and the like; and alkylmagnesium halides such as methylmagnesium bromide and the like.

When Corey-Chaykovsky reaction is carried out in each step, examples of the epoxydation agent to be used include trialkylsulfonium salt, trialkylsulfoxonium salt and the like. In addition, a base can be added to the reaction system, and examples thereof include metal alkoxides (e.g., potassium tert-butoxide) or alkali metal hydrides (e.g., sodium hydride) and the like.

When cyanation reaction is carried out in each step, examples of the metal catalyst to be used include palladium compounds such as chloro(2-dicyclohexylphosphino-2',4',6'-tri-i-propyl-1,1'-biphenyl)(2'-amino-1,1'-biphenyl-2-yl)palladium(II), palladium(II) acetate, tetrakis(triphenylphosphine)palladium(0), dichlorobis(triphenylphosphine)palladium(II), tris(dibenzylideneacetone)dipalladium(0), 1,1'-bis(diphenylphosphino)ferrocene palladium(II) chloride, (tri-tert-butylphosphine)palladium(0) and the like; nickel compounds such as tetrakis(triphenylphosphine)nickel(0) and the like; rhodium compounds such as tris(triphenylphosphine)rhodium(III) chloride and the like; cobalt compounds; copper compounds such as copper oxide, copper(I) iodide, copper(II) diacetate and the like; platinum compounds and the like. Examples of the cyano compound to be used include potassium hexacyanoferrate(II) trihydrate, copper(I) cyanide, zinc cyanide, potassium cyanide, sodium cyanide and the like. In addition, a base can be added to the reaction system, and examples thereof include organic bases, inorganic bases and the like. Moreover, a ligand can be added to the reaction system, and examples thereof include organic amines such as N,N'-dimethylethylenediamine, N,N'-dimethyl-cyclohexane-1,2-diamine, 2,2-bipyridyl and the like; organophosphorus compounds such as 2-dicyclohexylphosphino-2',4',6'-triisopropylbiphenyl, triphenylphosphine, tri-tert-butylphosphine, tricyclohexylphosphine, BINAP (2,2'-bis(diphenylphosphino)-1,1-binaphthyl) and the like.

When nitration reaction is carried out in each step, examples of the nitrating agent to be used include mineral acids such as mixed acid, nitric acid and the like; nitrates such as potassium nitrate, sodium nitrate, tetramethylammonium nitrate, silver nitrate and the like.

When nucleophilic substitution reaction is carried out in each step, examples of the base to be used include organic lithiums (e.g., lithium bis(trimethylsilyl)amide), metal alkoxides (e.g., potassium tert-butoxide), alkali metal hydrides (e.g., sodium hydride), inorganic bases, organic bases and the like.

When O-alkylation reaction or N-alkylation reaction is carried out in each step, a combination of an alkylating agent (e.g., an alkyl halide, an alkyl sulfonate ester etc.) and a base (e.g., an organic base, an inorganic base, alkali metal hydrides etc.) is used as a reagent.

Compound (I) of the present invention can be produced according to the methods explained below.

$R^1$, $R^2$, $R^3$, $R^4$ and A in the following schemes are as defined above.

Compound (I) can be produced from compound (2) according to the method shown in Scheme 1-1.

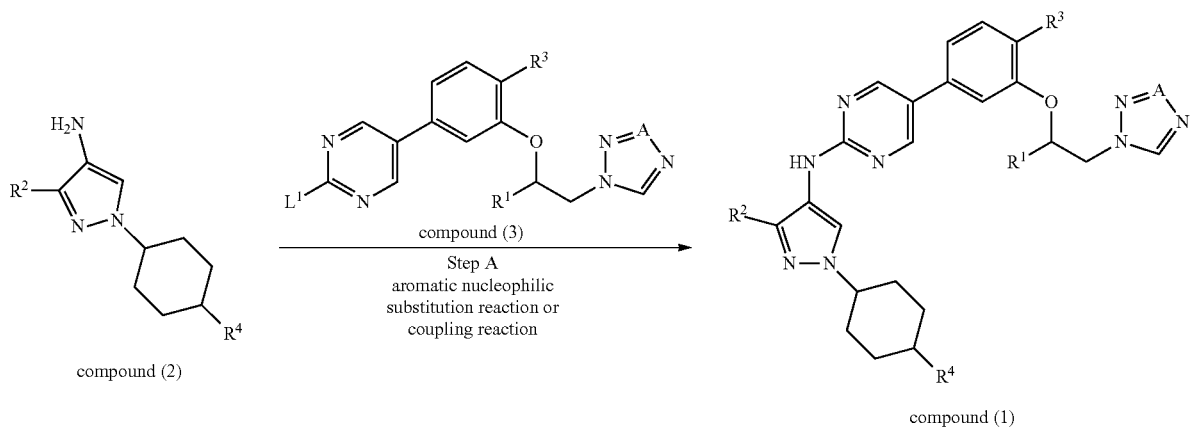

[Scheme 1-1]

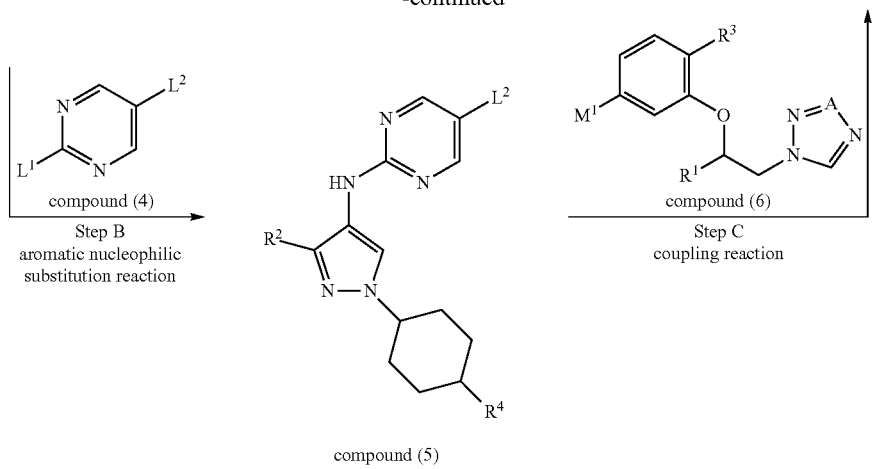

wherein $L^1$ and $L^2$ are each independently a leaving group, $M^1$ is a boronic acid group (—B(OH)$_2$), or a boronate ester group (—B(OR)$_2$; R is a $C_{1-6}$ alkyl group) or a cyclic group thereof (e.g., a 4,4,5,5-tetramethyl-1,3,2-dioxaborolan-2-yl, etc.), and the other symbols are as defined above.

Examples of the "leaving group" for $L^1$ or $L^2$ include a halogen atom (e.g., a fluorine atom, a chlorine atom, a bromine atom, an iodine atom etc.), an optionally halogenated $C_{1-6}$ alkylsulfonyloxy group (e.g., methanesulfonyloxy, ethanesulfonyloxy, trifluoromethanesulfonyloxy etc.), an optionally substituted $C_{6-14}$ arylsulfonyloxy group [e.g., a $C_{6-14}$ arylsulfonyloxy group optionally having 1 to 3 substituents selected from a $C_{1-6}$ alkyl group (e.g., methyl, etc.)], an optionally halogenated $C_{1-6}$ alkylsulfide group, an optionally substituted $C_{6-14}$ arylsulfide group, a $C_{1-6}$ alkoxy group (e.g., methoxy, etc.), a nitro group, m-nitrobenzenesulfonyloxy and naphthylsulfonyloxy and the like.

Compounds (3), (4) and (6) may be a commercially available product, or can be produced according to a method known per se.

Compound (I) wherein $R^3$ is a cyano group, can also be produced from compound (2) according to the method shown in Scheme 1-2.

[Scheme 1-2]

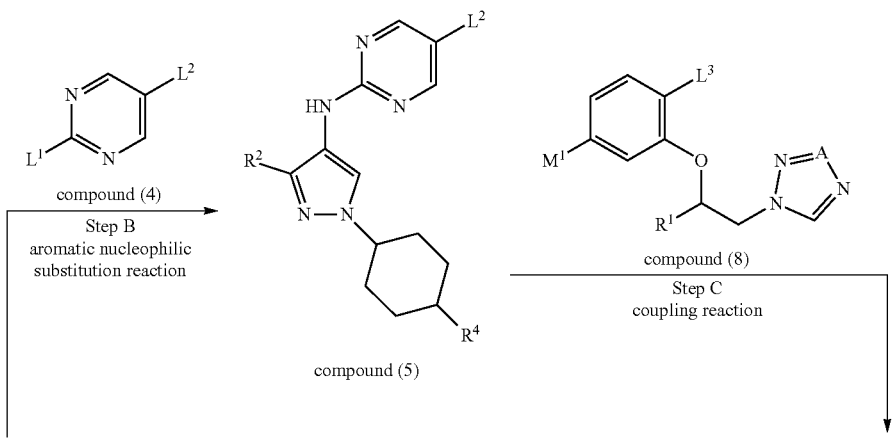

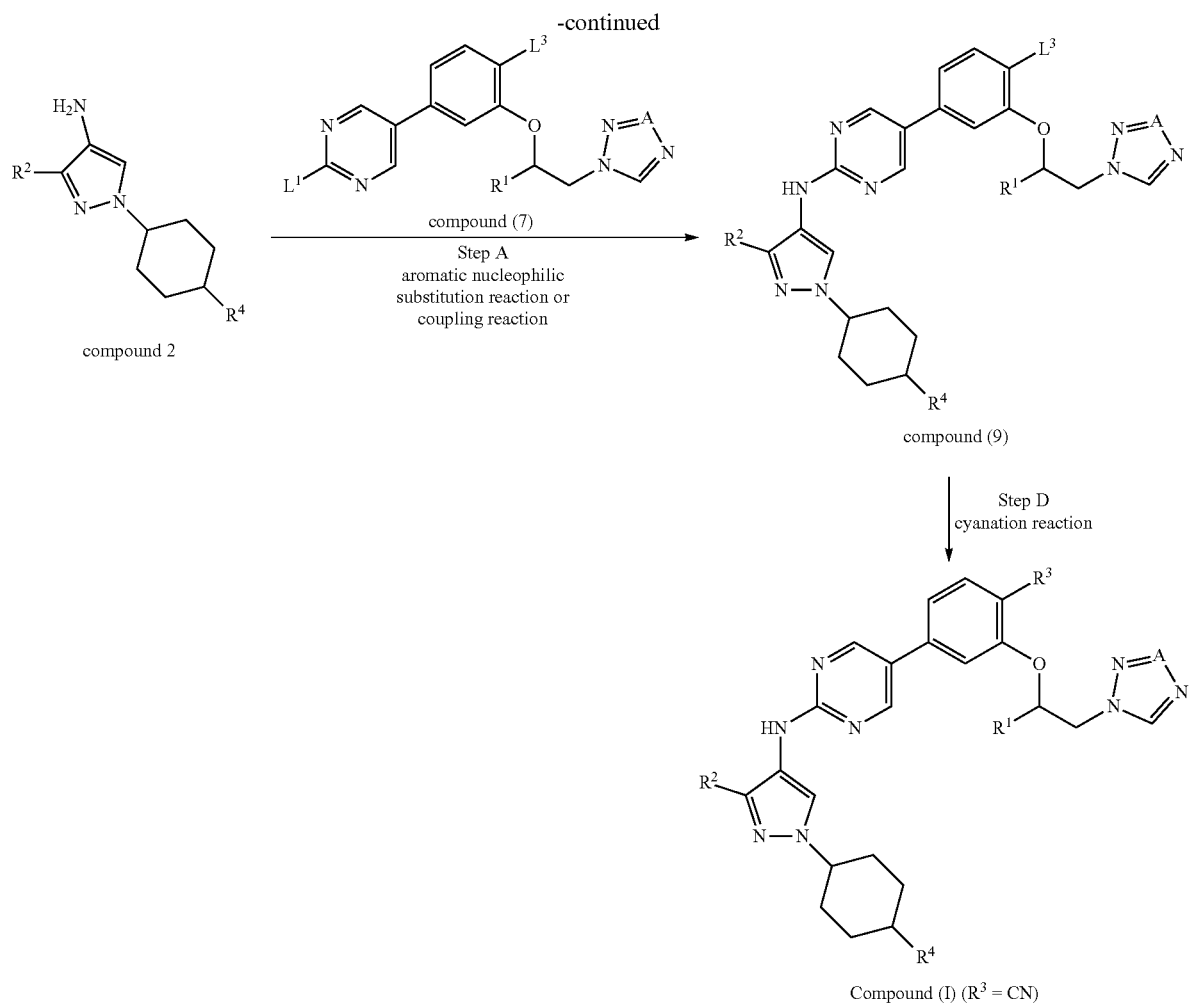

wherein $L^3$ is a leaving group, and the other symbols are as defined above.

Examples of the "leaving group" for $L^3$ include those exemplified as the "leaving group" for $L^1$ or $L^2$.

Compounds (7) and (8) may be a commercially available product, or can be produced according to a method known per se.

Compound (I) can also be produced from compound (10) according to the method shown in Scheme 1-3.

[Scheme 1-3]

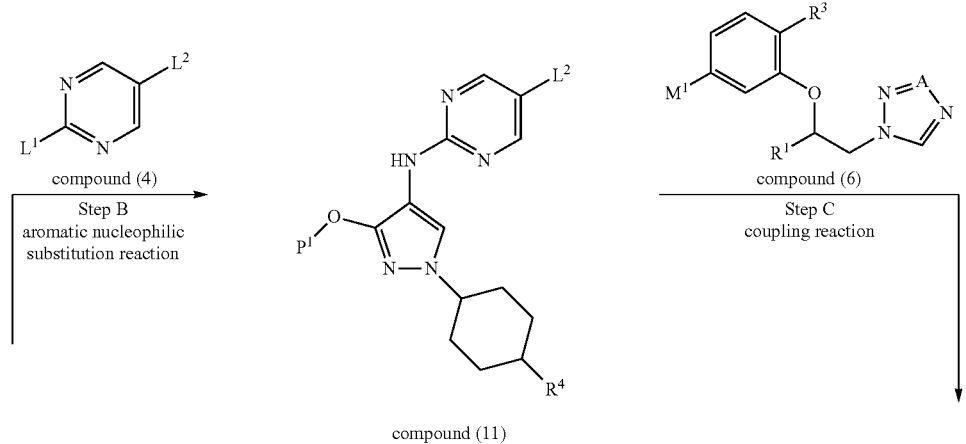

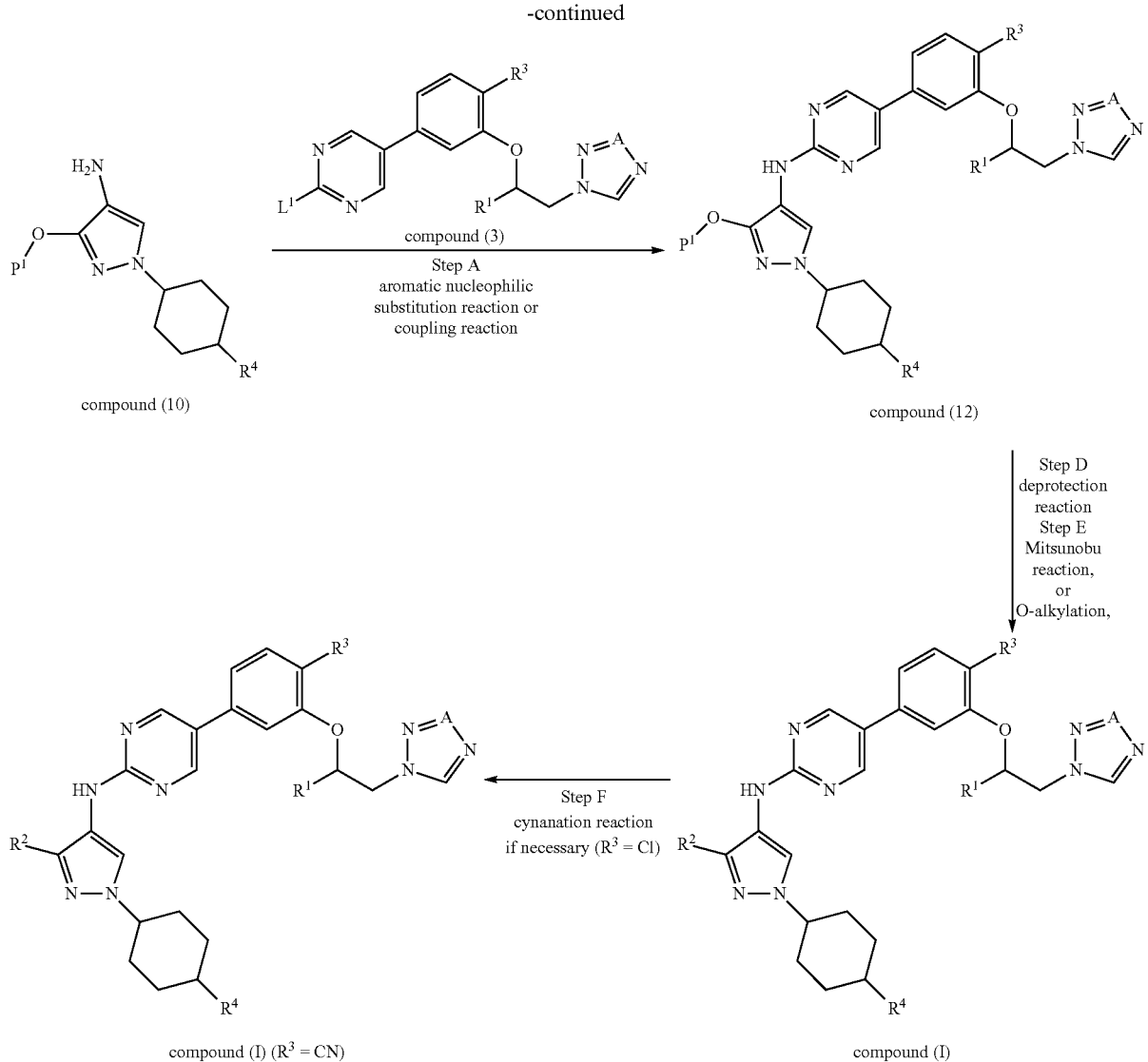

compound (10)  compound (12)  
compound (I) (R³ = CN)  compound (I)

Step A: aromatic nucleophilic substitution reaction or coupling reaction
Step D: deprotection reaction
Step E: Mitsunobu reaction, or O-alkylation,
Step F: cyanation reaction if necessary (R³ = Cl)

wherein $P^1$ is a hydrogen atom or a protecting group for a hydroxy group, and the other symbols are as defined above.

When $R^3$ is a chloro atom, $R^3$ of compound (I) can be changed to a cyano group by cyanation (Step F).

Compounds (10) may be a commercially available product, or can be produced according to a method known per se.

Compound (3), compound (6), compound (7) and compound (8) can be produced from compound (13) according to the method shown in Scheme 2-1, respectively.

[Scheme 2-1]

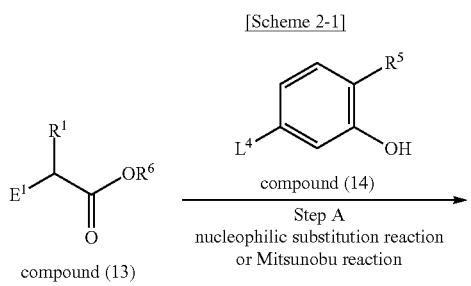

compound (13)

compound (14)

Step A
nucleophilic substitution reaction or Mitsunobu reaction

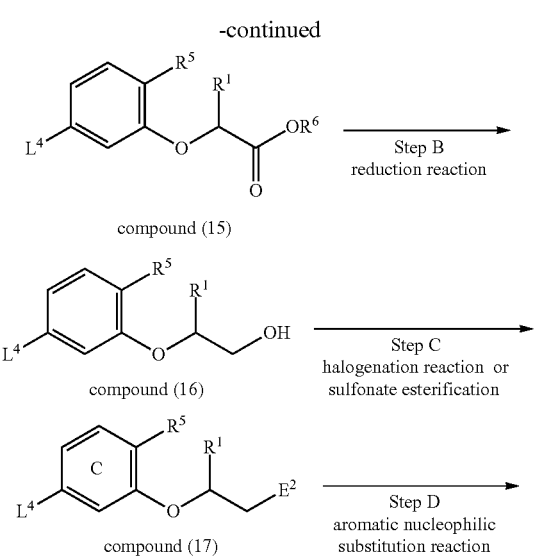

compound (15)

Step B
reduction reaction compound (16)

Step C
halogenation reaction or sulfonate esterification compound (17)

Step D
aromatic nucleophilic substitution reaction

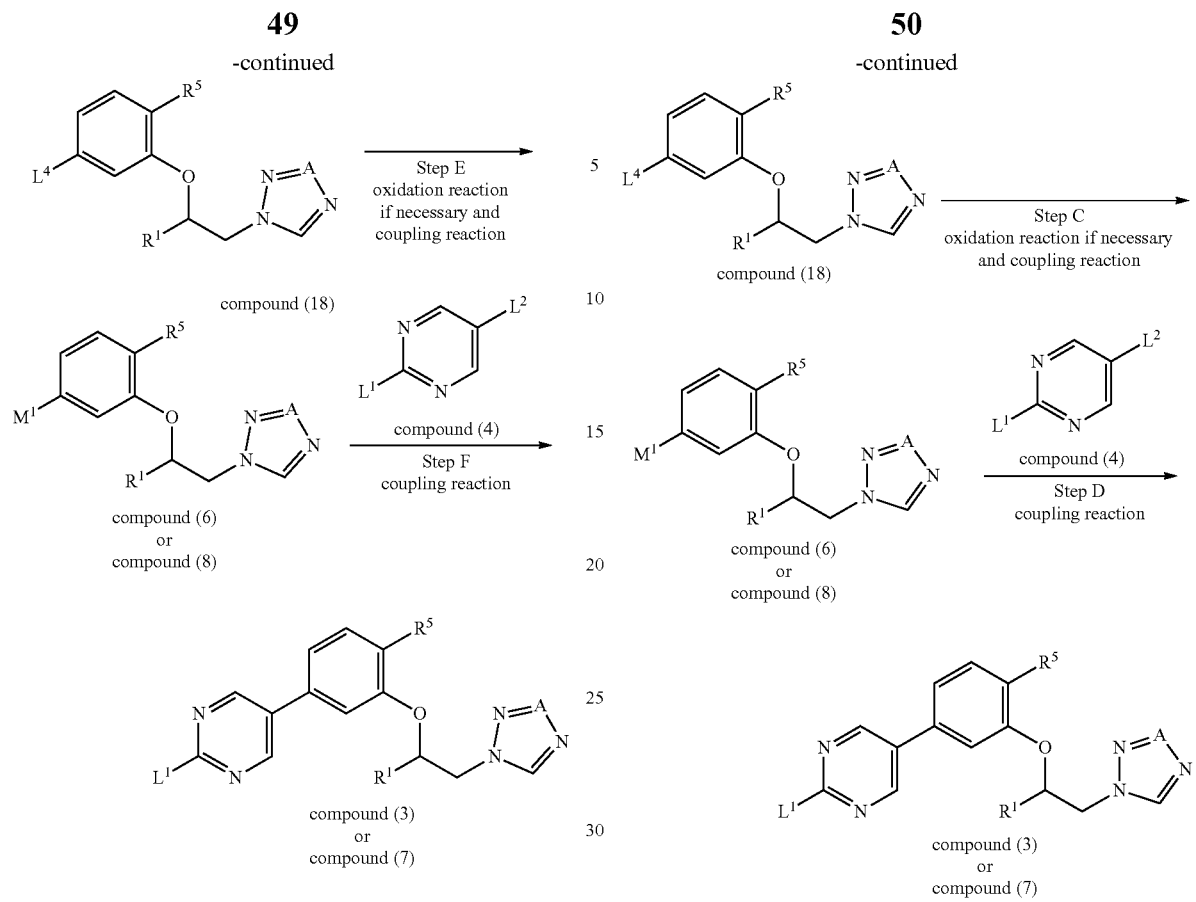

wherein $E^1$ is a hydroxyl group or a leaving group, $E^2$ and $L^4$ are each independently a leaving group, $R^5$ is a cyano group or a leaving group, $R^6$ is an optionally substituted $C_{1-6}$ alkyl group, and the other symbols are as defined above.

Examples of the "leaving group" for $E^1$, $E^2$, $L^4$ and $R^5$ include those exemplified as the "leaving group" for $L^1$ or $L^2$.

Compounds (13) and (14) may be a commercially available product, or can be produced according to a method known per se.

Compound (3), compound (6), compound (7) and compound (8) can also be produced from compound (19) according to the method shown in Scheme 2-2, respectively.

wherein $L^5$ is a leaving group, and the other symbols are as defined above.

Examples of the "leaving group" for $L^5$ include those exemplified as the "leaving group" for $L^1$ or $L^2$.

Compound (19) and (21) may be a commercially available product, or can be produced according to a method known per se.

Compound (2) can be produced from compound (22) according to the method shown in Scheme 3-1.

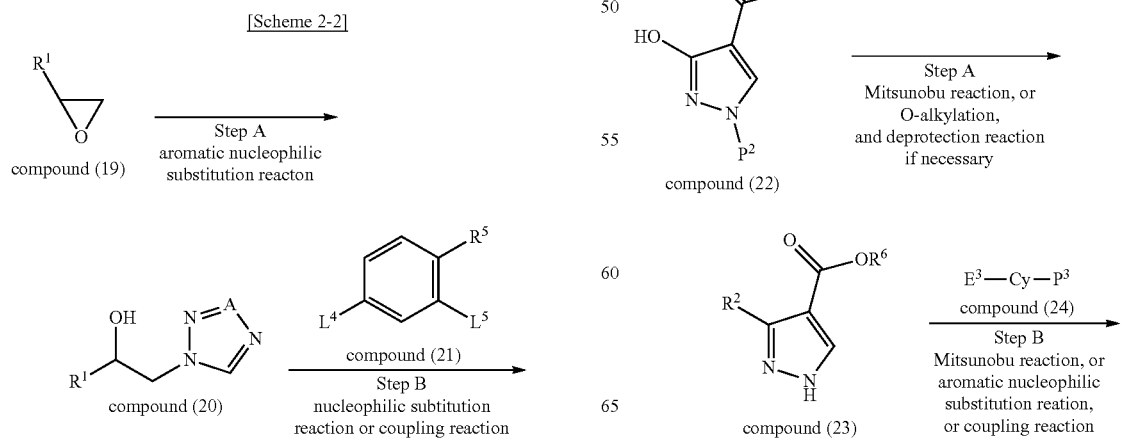

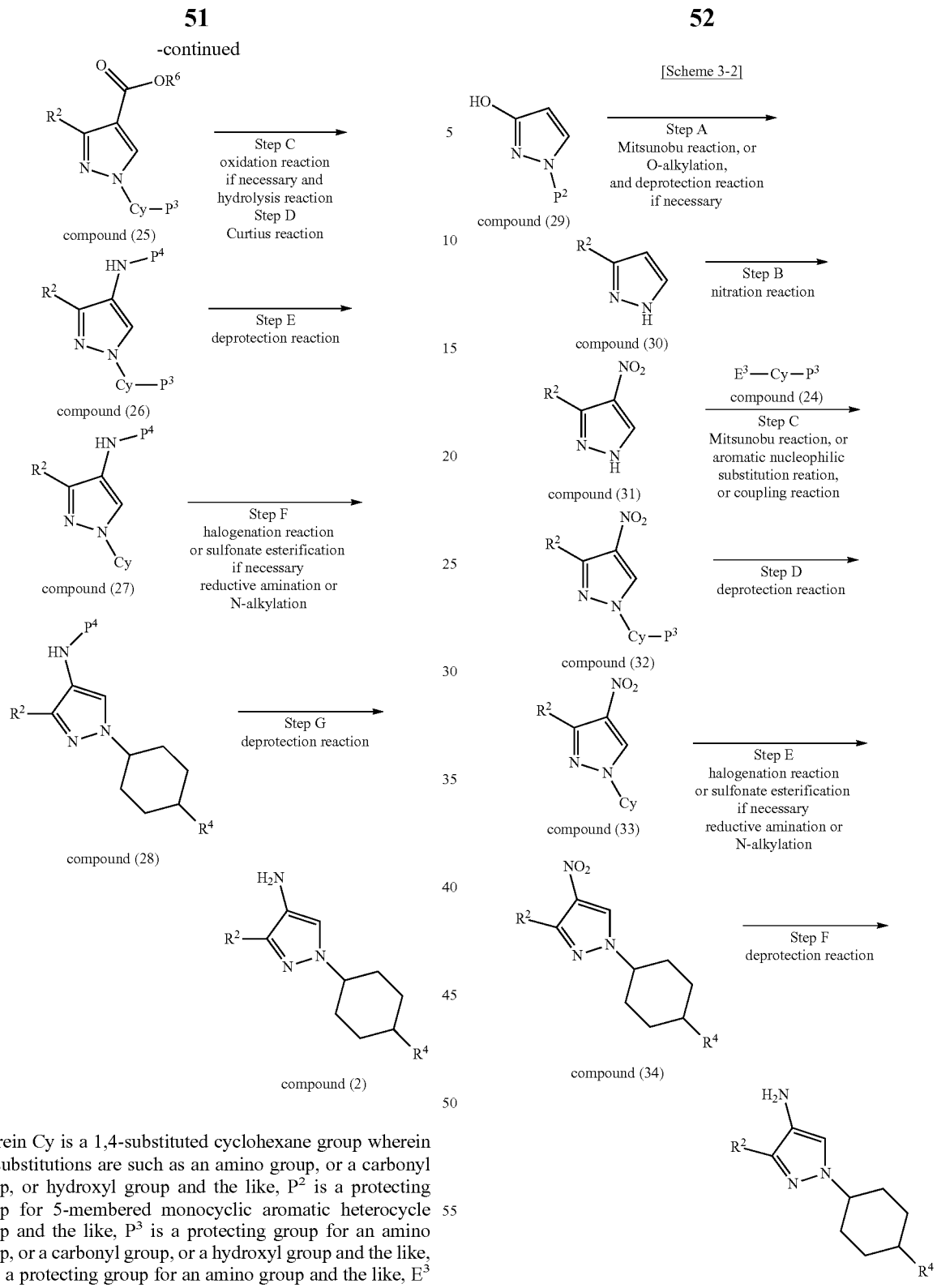

wherein Cy is a 1,4-substituted cyclohexane group wherein the substitutions are such as an amino group, or a carbonyl group, or hydroxyl group and the like, $P^2$ is a protecting group for 5-membered monocyclic aromatic heterocycle group and the like, $P^3$ is a protecting group for an amino group, or a carbonyl group, or a hydroxyl group and the like, $P^4$ is a protecting group for an amino group and the like, $E^3$ is a hydroxyl group or a leaving group, and the other symbols are as defined above.

Examples of the "leaving group" for $E^3$ include those exemplified as the "leaving group" for $L^1$ or $L^2$.

Compound (22) and compound (24) may be a commercially available product, or can be produced according to a method known per se.

Compound (2) can also be produced from compound (29) according to the method shown in Scheme 3-2.

wherein each symbol is as defined above.

Compound (29) may be a commercially available product, or can be produced according to a method known per se.

Compound (10) can be produced from compound (22) according to the method shown in Scheme 3-3.

[Scheme 3-3]

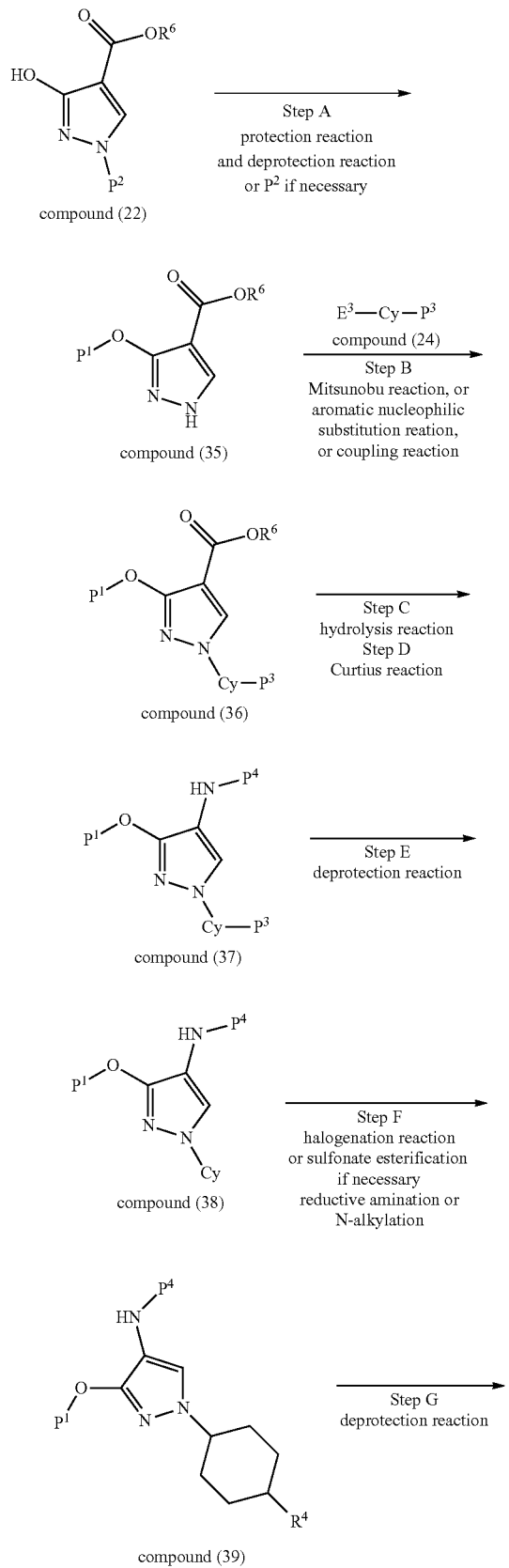

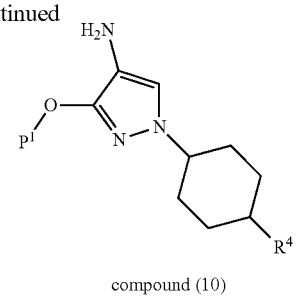

compound (10)

wherein each symbol is as defined above.

The starting compound and/or production intermediate for compound (I) may form a salt. While the salt is not particularly limited as long as the reaction can be performed, examples thereof include those similar to the salts optionally formed by compound (I) and the like, and the like.

As for the configurational isomers (E, Z forms) of compound (I), they can be isolated and purified when isomerization occurs, for example, according to a conventional separation means such as extraction, recrystallization, distillation, chromatography and the like to obtain a pure compound. In addition, the corresponding pure isomer can also be obtained by isomerizing a double bond using heating, an acid catalyst, a transition metal complex, a metal catalyst, a radical catalyst, light irradiation, a strong base catalyst and the like, according to the method described in Shin Jikken Kagaku Kouza 14 (The Chemical Society of Japan ed.), pages 251 to 253, 4th Edition Jikken Kagaku Kouza 19 (The Chemical Society of Japan ed.), pages 273 to 274 or a method analogous thereto.

Compound (I) contains a stereoisomer depending on the kind of a substituent, and each stereoisomer and a mixture thereof are encompassed in the present invention.

Compound (I) may be a hydrate or a non-hydrate.

When desired, compound (I) can be synthesized by performing deprotection reaction, acylation reaction, alkylation reaction, hydrogenation reaction, oxidation reaction, reduction reaction, reaction of carbon chain extension, halogenation reaction, substituent exchange reaction, coupling reaction, reductive amination, nucleophilic addition reaction by a carbo anion, Grignard reagent and deoxofluorination reaction singly or two or more thereof in combination.

When the objective product is obtained as a free form by the above-mentioned reaction, it can be converted to a salt according to a conventional method, or when the objective product is obtained as a salt, it can be converted to a free form or other salt according to a conventional method. The thus-obtained compound (I) can also be isolated and purified from a reaction mixture according to a known method such as phase transfer, concentration, solvent extraction, distillation, crystallization, recrystallization, chromatography and the like.

When compound (I) contains a configurational isomer, a diastereomer, a conformer and the like, each can be isolated according to the above-mentioned separation and purification methods, if desired. In addition, when compound (I) is racemic, d-form and l-form can be isolated according to a conventional optical resolution.

The thus-obtained compound (I), other reaction intermediate therefor and starting compounds thereof can be isolated and purified from a reaction mixture according to a method known per se, for example, extraction, concentration, neutralization, filtration, distillation, recrystallization, column chromatography, thin layer chromatography, preparative high performance liquid chromatography (preparative HPLC), moderate-pressure preparative liquid chromatography (moderate-pressure preparative LC) and the like.

A salt of compound (I) can be produced according to a method known per se. For example, when compound (I) is a basic compound, it can be produced by adding an inorganic acid or organic acid, or when compound (I) is an acidic compound, by adding an organic base or inorganic base.

When compound (I) contains an optical isomer, each optical isomer and a mixture thereof are encompassed in the scope of the present invention, and these isomers can be subjected to optical resolution or can be produced respectively, according to a method known per se, if desired.

When compound (I) contains a configurational isomer, a diastereomer, a conformer and the like, each can be isolated according to the above-mentioned separation and purification methods, if desired. In addition, when compound (I) is racemic, S-form and R-form can be isolated according to a conventional optical resolution.

When compound (I) contains a stereoisomer, each isomer and a mixture thereof are encompassed in the present invention.

Compound (I) may be a prodrug. A prodrug of compound (I) means a compound which is converted to compound (I) with a reaction due to an enzyme, an gastric acid, etc. under the physiological condition in the living body, that is, a compound which is converted to compound (I) with oxidation, reduction, hydrolysis, etc. according to an enzyme; a compound which is converted to compound (I) by hydrolysis etc. due to gastric acid, etc.

A prodrug for compound (I) may be a compound obtained by subjecting an amino group in compound (I) to an acylation, alkylation or phosphorylation (e.g., a compound obtained by subjecting an amino group in compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation or tert-butylation, etc.); a compound obtained by subjecting a hydroxy group in compound (I) to an acylation, alkylation, phosphorylation or boration (e.g., a compound obtained by subjecting an hydroxy group in compound (I) to an acetylation, palmitoylation, propanoylation, pivaloylation, succinylation, fumarylation, alanylation or dimethylaminomethylcarbonylation, etc.); a compound obtained by subjecting a carboxyl group in compound (I) to an esterification or amidation (e.g., a compound obtained by subjecting a carboxyl group in compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation, etc.) and the like. Any of these compounds can be produced from compound (I) by a method known per se. The prodrug of compound (I) may be a compound that converts to compound (I) under physiological conditions as described in Development of Pharmaceutical Products, vol. 7, Molecule Design, 163-198, Hirokawa Shoten (1990).

Compound (I) or a prodrug thereof (to be abbreviated as the compound of the present invention) is superior in vivo kinetics (e.g., plasma drug half-life, intracerebral transferability, metabolic stability), shows low toxicity (e.g., more superior as a medicament in terms of liver/hepatotoxicity, acute toxicity, chronic toxicity, genetic toxicity, reproductive toxicity, cardiotoxicity, cytotoxicity, drug interaction, carcinogenicity etc.; especially cytotoxicity, liver/hepatotoxicity). The compound of the present invention is extremely useful as a medicament in terms of improved cytotoxicity. The compound of the present invention is directly used as a medicament or a pharmaceutical composition mixed with a pharmaceutically acceptable carrier or the like to be orally or parenterally administered to mammals (e.g., humans, monkeys, cows, horses, pigs, mice, rats, hamsters, rabbits, cats, dogs, sheep and goats) in safety. Examples of the "parenteral" include intravenous, intramuscular, subcutaneous, intra-organ, intranasal, intradermal, instillation, intracerebral, intrarectal, intravaginal, intraperitoneal and intratumor administrations, administration to the vicinity of tumor etc. and direct administration to the lesion.

Since the compound of the present invention has a superior CaMKII inhibitory action, it is expected to be useful for the prophylaxis or treatment of, for example, cardiac diseases (cardiac hypertrophy, acute heart failure and chronic heart failure including congestive heart failure, cardiomyopathy, angina, myocarditis, atrial/ventricular arrhythmia, tachycardia, myocardial infarction, etc.), myocardial ischemia, venous insufficiency, post-myocardial infarction transition to heart failure, hypertension, corpulmonale, arteriosclerosis including atherosclerosis (aneurysm, coronary arterial sclerosis, cerebral arterial sclerosis, peripheral arterial sclerosis, etc.), vascular thickening, vascular thickening/occlusion and organ damages after intervention (percutaneous coronary angioplasty, stent placement, coronary angioscopy, intravascular ultrasound, coronary thrombolytic therapy, etc.), vascular reocclusion/restenosis after bypass surgery, cardiac hypofunction after artificial heart lung surgery, respiratory diseases (cold syndrome, pneumonia, asthma, pulmonary hypertension, pulmonary thrombus/pulmonary embolism, etc.), bone disorders (nonmetabolic bone disorders such as bone fracture, refracture, bone malformation/spondylosis deformans, osteosarcoma, myeloma, dysostosis and scoliosis, bone defect, osteoporosis, osteomalacia, rickets, osteitis fibrosis, renal osteodystrophy, Paget's disease of bone, myelitis with rigidity, chronic rheumatoid arthritis, gonarthrosis and articular tissue destruction in similar disorders thereof, etc.), inflammatory diseases (diabetic complication such as retinopathy, nephropathy, nerve damage, macroangiopathy etc.; arthritis such as chronic rheumatoid arthritis, osteoarthritis, rheumatoid myelitis, periostitis etc.; inflammation after surgery/trauma; reduction of swelling; pharyngitis; cystitis; pneumonia; atopic dermatitis; inflammatory enteric diseases such as Crohn's disease, ulcerative colitis etc.; meningitis; inflammatory eye diseases; inflammatory pulmonary diseases such as pneumonia, silicosis, pulmonary sarcoidosis, pulmonary tuberculosis etc, and the like), allergic diseases (allergic rhinitis, conjunctivitis, gastrointestinal allergy, pollen allergy, anaphylaxis, etc.), drug dependence, neurodegenerative diseases (Alzheimer's disease, Parkinson's disease, amyotrophic lateral sclerosis, AIDS encephalopathy, etc.), central nervous system damage (disorders such as cerebral hemorrhage and cerebral infarction and aftereffects and complications thereof, head injury, spinal damage, cerebral edema, sensory dysfunction, sensory abnormality, autonomic dysfunction, abnormal autonomic function, multiple sclerosis etc.), dementia, disturbed memory, disturbed consciousness, amnesia, anxiety symptoms, nervous symptoms, unpleasant condition, mental disorders (depression, epilepsy, alcohol dependency, etc.), ischemic peripheral circulatory disorder, deep-vein thrombosis, occlusive peripheral circulatory disorder, arteriosclerosis obliterans (ASO), occlusive thromboangiitis, diabetes (type 1 diabetes, type 2 diabetes, pregnancy diabetes etc.), diabetic complications (nerve damage, nephropathy, retinopathy, cataract, macroangiopathy, osteopenia, diabetic hyperosmolar diabetic coma, infectious diseases, diabetic gangrene, xerostomia, deterioration in hearing, cerebrovascular damage, peripheral circulatory disorder, etc.), urinary incontinence, metabolic/nutritional disorders (obesity, hyperlipidemia, hypercholesterolemia, diabetes, impaired glucose tolerance, hyperuricemia, hyperkalemia, hypernatremia etc.), metabolic syndrome, vesceral obesity syndrome, male or female sexual dysfunction and the like, and for the prophylaxis or treatment of dysgeusia, smell disturbance, abnormal circadian rhythm of blood pressure, cerebrovascular damage (asymptomatic cerebrovascular damage, transient cerebral ischemia attack, stroke, cerebrovascular dementia, hypertensive encephalopathy, cerebral infarction, etc.), cerebral edema, cerebral circulatory disturbance, recurrence and aftereffects of cerebrovascular damages (neurological symptoms, mental symptoms, subjective symptoms, impairment of activities of daily living, etc.), kidney diseases (nephritis, glomerulonephritis, glomerulosclerosis, renal failure, thrombotic microangiopathy, diabetic nephropathy, nephrotic syndrome, hypertensive nephrosclerosis, complications of dialysis, organ damage including nephropathy by irradiation, etc.), erythrocytosis/hypertension/organ damage/vascular thickening after transplantation, rejection after transplantation, ocular disorders (glaucoma, ocular hypertension, etc.), thrombosis, multiple organ failure, endothelial dysfunction, hypertensive tinnitus, other circulatory diseases (ischemic cerebral circulatory disturbance, Raynaud's disease, Buerger's disease, etc.), chronic occlusive pulmonary diseases, interstitial pneumonia, carinii pneumonia, connective tissue disorders (e.g., systemic erythematosus, scleroderma, polyarteritis, etc.), liver disorders (hepatitis and cirrhosis including chronic types, etc.), portal hypertension, digestive disorders (gastritis, gastric ulcer, gastric cancer, disorder after gastric surgery, poor digestion, esophageal ulcer, pancreatitis, colon polyp, cholelithiasis, hemorrhoidal problem, esophageal and gastric variceal rupture, etc.), hematological/hematopoietic disorders (erythrocytosis, vascular purpura, autoimmune hemolytic anemia, disseminated intravascular coagulation syndrome, multiple myelosis, etc.), solid tumor, tumors (malignant melanoma, malignant lymphoma, digestive organs (e.g., stomach, intestine, etc.) cancers, etc.), cancers and cachexia associated therewith, cancer metastases, endocrine disorders (Addison's disease, Cushing's syndrome, pheochromocytoma, primary aldosteronism, etc.), Creutzfeldt-Jakob disease, urological/male genital diseases (cystitis, prostatic enlargement, prostate cancer, sexually transmitted diseases, etc.), gynecological disorders (menopausal disorders, pregnancy toxemia, endometriosis, uterine fibroid, ovarian diseases, mammary gland diseases, sexually transmitted diseases, etc.), diseases caused by environmental/occupational factor (e.g., radiation damage, damage from ultraviolet/infrared/laser beam, altitude sickness etc.), infectious diseases (viral infectious diseases of, for example, cytomegalovirus, influenza virus and herpesvirus, rickettsial infectious diseases, bacterial infectious diseases, etc.), toxemia (septicemia, septic shock, endotoxic shock, gram-negative septicemia, toxin shock syndrome, etc.), ear nose throat diseases (Ménière's disease, tinnitus, dysgeusia, vertigo, balance disorder, deglutition disorder etc.), cutaneous diseases (keloid, hemangioma, psoriasis, etc.), dialysis hypotension, myasthenia gravis, systemic diseases such as chronic fatigue syndrome, and the like, particularly cardiac diseases (particularly catecholaminergic polymorphic ventricular tachycardia, postoperative atrial fibrillation, heart failure, fatal arrhythmia) and the like, in animals, particularly mammals (e.g., humans, monkeys, cats, pigs, horses, bovines, mice, rats, guinea pigs, dogs, rabbits etc.).

Herein, the concept of prophylaxis of cardiac diseases include treatment of prognosis of myocardial infarction, angina attack, cardiac bypass surgery, thrombolytic therapy, coronary revascularization and the like, and the concept of treatment of cardiac diseases include suppress of progress or severity of heart failure (including both contractile failure HFrEF, and heart failure HFpEF with maintained ejection fraction), and maintenance of cardiac function when performing non-drug therapies (e.g., an implantable defibrillator, resection of cardiac sympathetic nerve, catheter ablation, cardiac pacemaker, intra aortic balloon pumping, auxiliary artificial heart, Batista operation, cell transplantation, gene therapy, heart transplantation and the like) for severe heart failure/arrhythmia, and the like. When the compound of the present invention is applied to prophylaxis or treatment of heart failure, improvement of heart contractility or atonicity is expected to be achieved by short-time administration, without side effects such as pressure decrease, tachycardia, reduced renal blood flow and the like, regardless of differences in causative diseases such as ischemic cardiac disease, cardiomyopathy, hypertension and the like and symptoms such as contractile failure, diastolic failure and the like. Moreover, long-term improvement of prognosis (survival rate, readmission rate, cardiac event rate etc.) is expected to be achieved, in addition to short-term improvement of cardiac function. When the compound of the present invention is applied to prophylaxis or treatment of arrhythmia, improvement or remission of the symptom is expected to be achieved, regardless of differences in etiology and atrial/ventricular. In addition, long-term improvement of prognosis (survival rate, readmission rate, cardiac event rate etc.) is expected to be achieved.

While the dose of the compound of the present invention varies depending on the administration route, symptom and the like, when, for example, the compound is orally administered to a patient with cardiac disease (adult, body weight 40-80 kg, for example, 60 kg), it is, for example, 0.001-1000 mg/kg body weight/day, preferably 0.01-100 mg/kg body weight/day, more preferably 0.1-10 mg/kg body weight/day. This amount can be administered in 1 to 3 portions per day.

A medicament containing the compound of the present invention can be used alone or as a pharmaceutical composition containing the compound of the present invention and a pharmaceutically acceptable carrier according to a method known per se as a production method of a pharmaceutical preparation (e.g., the method described in the Japanese Pharmacopoeia etc.). A medicament containing the compound of the present invention can be safely administered in the form of, for example, tablet (including sugar-coated tablet, film-coated tablet, sublingual tablet, orally disintegrating tablet, buccal and the like), pill, powder, granule, capsule (including soft capsule, microcapsule), troche, syrup, liquid, emulsion, suspension, release control preparation (e.g., immediate-release preparation, sustained-release preparation, sustained-release microcapsule), aerosol, film (e.g., orally disintegrating film, oral mucosa-adhesive film), injection (e.g., subcutaneous injection, intravenous injection, intramuscular injection, intraperitoneal injection), drip infusion, transdermal absorption type preparation, ointment, lotion, adhesive preparation, suppository (e.g., rectal suppository, vaginal suppository), pellet, nasal preparation, pulmonary preparation (inhalant), eye drop and the like, orally or parenterally (e.g., intravenous, intramuscular, subcutaneous, intraorgan, intranasal, intradermal, instillation, intracerebral, intrarectal, intravaginal, intraperitoneal administrations, and administration to the lesion).

As the aforementioned "pharmaceutically acceptable carrier", various organic or inorganic carriers conventionally used as preparation materials (starting materials) can be used. For example, excipient, lubricant, binder, disintegrant and the like are used for solid preparations, and solvent, solubilizing agent, suspending agent, isotonicity agent, buffer, soothing agent and the like are used for liquid preparations. Where necessary, preparation additives such as preservative, antioxidant, colorant, sweetening agent and the like can also be used.

Examples of the excipient include lactose, sucrose, D-mannitol, starch, corn starch, crystalline cellulose, light anhydrous silicic acid and the like.

Examples of the lubricant include magnesium stearate, calcium stearate, talc, colloidal silica and the like.

Examples of the binding agent include crystalline cellulose, white sugar, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

Examples of the disintegrant include starch, carboxymethylcellulose, carboxymethylcellulose calcium, sodium carboxymethyl starch, L-hydroxypropylcellulose and the like.

Examples of the solvent include water for injection, alcohol, propylene glycol, Macrogol, sesame oil, corn oil, olive oil and the like.

Examples of the solubilizing agent include polyethylene glycol, propylene glycol, D-mannitol, benzyl benzoate, ethanol, trisaminomethane, cholesterol, triethanolamine, sodium carbonate, sodium citrate and the like. Examples of the suspending agent include surfactants such as stearyl triethanolamine, sodium lauryl sulfate, laurylaminopropionic acid, lecithin, benzalkonium chloride, benzetonium chloride, glycerin monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like; and the like.

Examples of the isotonic agent include glucose, D-sorbitol, sodium chloride, glycerin, D-mannitol and the like.

Examples of the buffering agent include buffer solutions such as phosphates, acetates, carbonates, citrates and the like.

Examples of the soothing agent include benzyl alcohol and the like.

Examples of the preservative include p-oxybenzoates, chlorobutanol, benzyl alcohol, phenylethyl alcohol, dehydroacetic acid, sorbic acid and the like.

Examples of the antioxidant include sulfite, ascorbic acid, α-tocopherol and the like.

While the pharmaceutical composition varies according to the dosage form, administration method, carrier and the like, it can be produced according to a conventional method by adding the compound of the present invention in a proportion of generally 0.01-100% (w/w), preferably 0.1-95% (w/w), of the total amount of the preparation.

When the compound of the present invention is applied to each of the above-mentioned diseases, it can be used in appropriate combination with a pharmaceutical agent (hereinafter to be abbreviated as a concomitant drug) or a treatment method generally employed for such diseases. For heart failure, for example, it can be used concurrently with angiotensin converting enzyme (ACE) inhibitors (e.g., alacepril, captopril, cilazapril, delapril, enalapril, lisinopril, temocapril, trandolapril, quinapril, imidapril, benazepril, perendopril and the like), angiotensin II receptor antagonists (e.g., losartan, candesartan cillexetil, valsartan, termisartan, irbesartan, forasartan and the like), angiotensin II receptor antagonist/NEP inhibitor combination agent (entresto), β receptor antagonists (e.g., propranolol, nadolol, timolol, nipradilol, bunitorolol, indenolol, penbutolol, carteolol, carvedilol, pindolol, acebutolol, atenolol, bisoprolol, metoprolol, labetalol, amosulalol, arotinolol and the like), Ca antagonists (e.g., manidipine, nicardipine, nilvadipine, nisoldipine, nitrendipine, benidipine, amlodipine, aranidipine and the like), diuretics (e.g., thiazide diuretics such as benzylhydrochlorothiazide, cyclopentiazide, ethiazide, hydrochlorothiazide, hydroflumethiazide, methyclothiazide, penfluthiazide, polythiazide, trichlormethiazide and the like; loop diuretics such as chlorthalidone, clofenamide, indapamide, mefruside, meticrane, sotolazone, tribamide, quinetazone, metolazone, furosemide, mefruside and the like; potassium retention diuretics such as spironolactone, triamterene and the like; and the like), digitalis preparations (e.g., digitoxin, digoxin, methyldigoxin, lanatoside C, proscillaridin and the like), ANP or BNP preparations, Ca sensitizers (e.g., pimobendan and the like), anticoagulants (e.g., warfarin, sodium citrate, activated protein C, tissue factor pathway inhibitor, antithrombin III, dalteparin sodium, aragatroban, gabexate, sodium ozagrel, ethyl icosapentate, beraprost sodium, alprostadil, pentoxifyline, tisokinase, streptokinase and the like), antiarrhythmic drugs (e.g., sodium channel blockers such as quinidine, procainamide, disopyramide, ajmaline, cibenzoline, lidocain, diphenylhydantoin, mexiletine, propafenone, flecainide, pilsicainide, phenytoin and the like; potassium channel blockers such as amiodarone and the like; calcium channel blockers such as verapamil, diltiazem and the like; and the like), PDE inhibitors (e.g., amrinone, milrinone, olprinone hydrochloride and the like), therapeutic drugs for diabetes (e.g., sulfonylureas such as tolbutamide, chlorpropamide, glyclopyramide, acetohexamide, tolazamide, glibenclamide, glybuzole and the like; biguanides such as metformin hydrochloride, buformin hydrochloride and the like; α-glucosidase inhibitors such as voglibose, acarbose and the like, insulin sensitizers such as pioglitazone, troglitazone and the like; SGLT2 inhibitors such as ipragliflozin, dapagliflozin, ruseogurifurojin, tofogliflozin, canagliflozin, empagliflozin and the like; insulin, glucagon; therapeutic drugs for diabetic complications such as epalrestat and the like; and the like), anti-obesity drugs and the like, and is also applicable when an implantable artificial heart, an implantable defibrillator, a ventricular pacing, Batista operation, heart transplantation or cell transplantation is performed. In addition, for arrhythmia, for example, it can be used concurrently with other antiarrhythmic drugs (e.g., sodium channel blockers such as flecainide, quinidine, procainamide, disopyramide, ajmaline, cibenzoline, lidocain, diphenylhydantoin, mexiletine, propafenone, pilsicainide, phenytoin and the like; potassium channel blockers such as amiodarone and the like; calcium channel blockers such as verapamil, diltiazem and the like, and the like) and β receptor antagonists, non-drug therapies (e.g., an implantable defibrillator, resection of cardiac sympathetic nerve, catheter ablation, cardiac pacemaker and the like). In addition, after acute myocardial infarction or during myocardial infarction prognosis, for example, the compound can be used in combination with antithrombotics (e.g., anticoagulants such as heparin sodium, heparin calcium, warfarin and the like; thrombolytic agents such as urokinase and the like; anti-platelet drugs such as aspirin, sulfinpyrazone (anturan), dipyridamole (persantin), ticropidine (panaldine), cilostazol (pletal), clopidogrel and the like; and the like), angiotensin converting enzyme inhibitors, angiotensin II receptor antagonists, 3 receptor antagonists, therapeutic drugs for diabetes, therapeutic drugs for hyperlipidemia (e.g., HMG-CoA reductase inhibitors such as pravastatine, fluvastatine, cerivastatine, atorvastatine and the like; fibrate drugs such as sinfibrate, clofibrate aluminum, clinofibrate, fenofibrate and the like; and the like), coronary vessel reconstructive surgery such as PTCA, CABG and the like; and the like. Furthermore, in chronic rheumatoid arthritis, for example, the compound can be used in combination with non-steroidal antiinflammatory agents (e.g., acetaminophen, phenacetin, ethenzamide, sulpyrine, antipyrine, migrenine, aspirin, mefenamic acid, flufenamic acid, diclofenac sodium, loxoprofen sodium, phenylbutazone, indomethacin, ibuprofen, ketoprofen, naproxen, oxaprozin, flurbiprofen, fenbufen, pranoprofen, floctafenine, epirizole, tiaramide hydrochloride, zaltoprofen, gabexate mesilate, camostat mesilate, ulinastatine, colchicine, probenecid, sulfinpyrazone, benzbromarone, allopurinol, sodium aurothiomalate, sodium hyaluronate, sodium salicylate, morphine hydrochloride, salicylic acid, atropine, scopolamine, morphine, pethidine, levorphanol, ketoprofen, naproxen, oxymorphone or a salt thereof and the like), immunomodulators or immunosuppressants (e.g., methotrexate, cyclosporine, tacrolimus, gusperimus, azathioprine, antilymphocyte serum, dried sulfonated immunoglobulin, erythropoietin, colony stimulating factor, interleukin, interferon and the like), steroids (e.g., dexamethasone, hexestrol, methimazole, betamethasone, triamcinolone, triamcinoloneacetonide, fluocinonide, fluocinoloneacetonide, prednisolone, methylprednisolone, cortisone acetate, hydrocortisone, fluorometholone, beclometasone dipropionate, estriol and the like), p38 MAP kinase inhibitors, anti-TNF-α drugs (e.g., etanercept, infliximab, D2E7, CDP-571, PASS TNF-α, soluble TNF-α receptor, TNF-α binding protein, anti-TNF-α antibody and the like), cyclooxygenase inhibitors (e.g., salicylic acid derivatives such as celecoxib, rofecoxib, aspirin and the like, MK-663, valdecoxib, SC-57666, tiracoxib, S-2474, diclofenac, indomethacin, loxoprofen and the like) and the like.

Moreover, it is possible to use the compound of the present invention in combination with biological products (e.g.: antibody, vaccine preparation and the like) when applying to the above-mentioned respective diseases, and it is also possible to apply the compound in combination with a gene therapy and the like as a combination therapy. As antibody and vaccine preparation, for example, vaccine preparation to angiotensin II, vaccine preparation to CETP, CETP antibody, TNF α antibody, antibody to other cytokine, amiloid β vaccine preparation, type 1 diabetes vaccine (DIAPEP-277 of Peptor Ltd. and the like), anti-HIV antibody, HIV vaccine preparation and the like, antibody and vaccine preparation to cytokine, renin-angiotensin enzyme and products thereof, antibody and vaccine preparation to enzyme and protein involved in blood lipid metabolism, antibody and vaccine preparation to enzyme and protein involved in blood coagulation-fibrinolytic system, antibody and vaccine preparation to protein involved in glucose metabolism and insulin resistance and the like can be mentioned. In addition, a combined use with biological products involved in growth factors such as GH, IGF and the like is possible. As a gene therapy, for example, a treatment method using a gene relating to cytokine, renin-angiotensin enzyme and products thereof, G protein, G protein-coupled receptor and phosphorylation enzyme thereof, a therapeutic method using a DNA decoy such as NFκB decoy and the like, a therapeutic method using antisense, a therapeutic method using a gene relating to enzyme and protein involved in blood lipid metabolism (e.g., gene relating to metabolism, excretion and absorption of cholesterol or triglyceride or HDL-cholesterol or blood phospholipid, and the like), a therapeutic method using a gene relating to enzyme and protein (e.g., growth factors such as HGF, VEGF and the like, and the like) involved in angiogenetic therapy aiming at obstruction of peripheral vessel and the like, a therapeutic method using a gene relating protein involved in glucose metabolism and insulin resistance, antisense to cytokine such as TNF-α and the like, and the like can be mentioned. In addition, it is possible to use the compound in combination with various organ regeneration methods such as heart regeneration, kidney regeneration, pancreas regeneration, blood vessel regeneration and the like, cell transplantation therapy using bone marrow cells (bone marrow mononuclear cell, bone marrow mesenchymal stem cell and the like), and artificial organs (artificial blood vessels and cardiac muscle cell sheet) using tissue engineering.

By combining the compound of the present invention and a concomitant drug, a superior effect such as (1) the dose can be reduced as compared to single administration of the compound of the present invention or a concomitant drug, (2) the drug to be combined with the compound of the present invention can be selected according to the condition of patients (mild case, severe case and the like), (3) the period of treatment can be set longer by selecting a concomitant drug having different action and mechanism from the compound of the present invention, (4) a sustained treatment effect can be designed by selecting a concomitant drug having different action and mechanism from the compound of the present invention, (5) a synergistic effect can be afforded by a combined use of the compound of the present invention and a concomitant drug, and the like, can be achieved.

Hereinafter the compound of the present invention and a concomitant drug used in combination are referred to as the "combination agent of the present invention".

When using the combination agent of the present invention, the administration time of the compound of the present invention and the concomitant drug is not restricted, and the compound of the present invention or a pharmaceutical composition thereof and the concomitant drug or a pharmaceutical composition thereof can be administered to an administration subject simultaneously, or may be administered at different times. The dosage of the concomitant drug may be determined according to the dose clinically used, and can be appropriately selected depending on an administration subject, administration route, disease, combination and the like. The administration mode of the concomitant drug of the present invention is not particularly restricted, and it is sufficient that the compound of the present invention and the concomitant drug are combined in administration. Examples of such administration mode include the following methods: (1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (for example, administration in the order of the compound of the present invention and the concomitant drug, or in the reverse order) and the like.

The combination agent of the present invention exhibits low toxicity. For example, the compound of the present invention or(and) the aforementioned concomitant drug can be combined with a pharmacologically acceptable carrier according to the known method to prepare a pharmaceutical composition such as tablets (including sugar-coated tablet and film-coated tablet), powders, granules, capsules (including soft capsule), liquids, injections, suppositories, sustained-release agents, etc. These compositions can be administered safely orally or non-orally (e.g., topical, rectal, intravenous administration etc.). Injection can be administered intravenously, intramuscularly, subcutaneously, or by intraorgan administration or directly to the lesion.

Examples of the pharmacologically acceptable carriers usable for the production of a combination agent of the present invention, various organic or inorganic carrier substances conventionally used as preparation materials can be mentioned. For solid preparations, for example, excipient, lubricant, binder and disintegrant can be used. For liquid preparations, for example, solvent, solubilizing agent, suspending agent, isotonic agent, buffering agent, soothing agent and the like can be used. Where necessary, an appropriate amount of conventional preservative, antioxidant, colorant, sweetening agent, adsorbent, wetting agent and the like can be used as appropriate.

Examples of the excipient include lactose, sucrose, D-mannitol, starch, corn starch, crystalline cellulose, light anhydrous silicic acid and the like.

Examples of the lubricant include magnesium stearate, calcium stearate, talc, colloidal silica and the like.

Examples of the binding agent include crystalline cellulose, white sugar, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

Examples of the disintegrant include starch, carboxymethylcellulose, carboxymethylcellulose calcium, sodium carboxymethyl starch, L-hydroxypropylcellulose and the like.

Examples of the solvent include water for injection, alcohol, propylene glycol, Macrogol, sesame oil, corn oil, olive oil and the like.

Examples of the solubilizing agent include polyethylene glycol, propylene glycol, D-mannitol, benzyl benzoate, ethanol, trisaminomethane, cholesterol, triethanolamine, sodium carbonate, sodium citrate and the like.

Examples of the suspending agent include surfactants such as stearyl triethanolamine, sodium lauryl sulfate, laurylaminopropionic acid, lecithin, benzalkonium chloride, benzetonium chloride, glycerin monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like; and the like.

Examples of the isotonic agent include glucose, D-sorbitol, sodium chloride, glycerin, D-mannitol and the like.

Examples of the buffering agent include buffer solutions such as phosphates, acetates, carbonates, citrates and the like.

Examples of the soothing agent include benzyl alcohol and the like.

Examples of the preservative include p-oxybenzoates, chlorobutanol, benzyl alcohol, phenylethyl alcohol, dehydroacetic acid, sorbic acid and the like.

Examples of the antioxidant include sulfite, ascorbic acid, α-tocopherol and the like.

The mixing ratio of the compound of the present invention to the concomitant drug in the combination agent of the present invention can be appropriately selected depending on an administration subject, administration route, diseases and the like.

For example, the content of the compound of the present invention in the combination agent of the present invention differs depending on the form of a preparation, and usually from about 0.01 to about 100 wt %, preferably from about 0.1 to about 50 wt %, further preferably from about 0.5 to about 20 wt %, based on the preparation.

The content of the concomitant drug in the combination agent of the present invention differs depending on the form of a preparation, and usually from about 0.01 to about 100 wt %, preferably from about 0.1 to about 50 wt %, further preferably from about 0.5 to about 20 wt %, based on the preparation.

The content of additives such as a carrier and the like in the combination agent of the present invention differs depending on the form of a preparation, and usually from about 1 to about 99.99 wt %, preferably from about 10 to about 90 wt %, based on the preparation.

When the compound of the present invention and a concomitant drug are separately formulated into preparations, the contents thereof are similar to the above.

EXAMPLES

The present invention is explained in detail in the following by referring to Examples, Experimental Examples and Formulation Examples, which are not to be construed as limitative, and the invention may be changed within the scope of the present invention.

In the following Examples, the "room temperature" generally means about 10° C. to about 35° C. The ratios indicated for mixed solvents are volume mixing ratios, unless otherwise specified. % means wt %, unless otherwise specified.

Unless particularly specified, the elution in column chromatography in Example was performed under observation by TLC (Thin Layer Chromatography). For TLC observation, 60F$_{254}$ manufactured by Merck was used as a TLC plate, and the solvent used as an elution solvent for column chromatography was used as a developing solvent. For detection, a UV detector was adopted. In silica gel column chromatography, NH means use of aminopropylsilane-bonded silica gel, and Diol means use of 3-(2,3-dihydroxypropoxy)propylsilane-bonded silica gel. In preparative HPLC (high performance liquid chromatography), C18 means use of octadecyl-bonded silica gel. The ratios indicated for elution solvents are volume mixing ratios, unless otherwise specified.

For $^1$H NMR analysis, ACD/SpecManager (trade name) software and the like were used. Peaks of a hydroxy group, an amino group and the like, which having very mild protons, may not be described.

MS was measured by LC/MS. As ionization method, ESI method or APCI method was used. The data indicates actual measured value (found). Generally, molecular ion peaks are observed, and may be observed as a fragment ion. In the case of a salt, a molecular ion peak or fragment ion peak of free form is generally observed.

The unit of sample concentration (c) for optical rotation ($[\alpha]_D$) is g/100 mL.

Elemental analysis value (Anal.) was described as calculated value (Calcd) and actual measured value (Found).

The peak by powder X-RAY diffraction in Example means the peak measured using Cu Kα-ray as a source by Ultima IV(Rigaku Corporation, Japan) at room temperature. The measurement conditions are as follows.

Electric pressure/Electric current: 40 kV/50 mA
Scan speed: 6 degree/min
Scan range of 2 Theta: 2-35 degree The crystallinity by powder X-RAY diffraction in Example was calculated by Hermans method.

In Examples, the following abbreviations are used.
mp: melting point
MS: mass spectrum
M: mol concentration
N: normality
$CDCl_3$: deuterochloroform
DMSO-$d_6$: deuterodimethyl sulfoxide
$^1$H NMR: proton nuclear magnetic resonance
LC/MS: liquid chromatograph mass spectrometer
ESI: electrospray ionization, Electron Spray Ionization
APCI: atmospheric pressure chemical ionization, atmospheric pressure chemical ionization
AcOH: acetic acid
Boc: tert-butoxycarbonyl
n-BuOH: normal butanol
$CH_3CN$: acetonitrile
CPME: cyclopentyl methyl ether
DIAD: diisopropyl azodicarboxylate
DMA: N,N-dimethylacetamide
DMF: N,N-dimethylformamide
DME: 1,2-dimethoxyethane
DMSO: dimethyl sulfoxide
DPPA: diphenylphosphoryl azide
EtOH: ethanol
IPE: diisopropyl ether
MeOH: methanol
NMP: N-methylpyrrolidone
Pd(dppf)$Cl_2$: dichloro[1,1'-bis(diphenylphosphino) ferrocene]palladium(II)
Pd(PPh$_3$)$_4$: tetrakis(triphenylphosphine)palladium(0)
TFA: trifluoroacetic acid
THF: tetrahydrofuran
XPhos: 2-dicyclohexylphosphino-2',4',6'-triisopropylbiphenyl
XPhos Pd G2: chloro(2-dicyclohexylphosphino-2',4',6'-tri-1-propyl-1,1'-biphenyl)(2'-amino-1,1'-biphenyl-2-yl)palladium(II)

Example 1

2-(((S)-1-(1H-tetrazol-1-yl)propan-2-yl)oxy)-4-(2-((3-(2-methoxyethoxy)-1-((1r,4r)-4-morpholinocyclohexyl)-1H-pyrazol-4-yl)amino)pyrimidin-5-yl)benzonitrile A)
methyl(2S)-2-(5-bromo-2-cyanophenoxy)propanoate To a mixture of 4-bromo-2-hydroxybenzonitrile (14.5 g), methyl(2R)-2-hydroxypropanoate (15.3 g), triphenylphosphine (57.6 g) and THF (dry) (150 mL) was added 2.2M diethyl(E)-diazene-1,2-dicarboxylate toluene solution (116 mL) at 0° C. The mixture was stirred at room temperature overnight under nitrogen atmosphere. To the mixture was added water at room temperature, and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane) to give the title compound (20.0 g).

$^1$H NMR (300 MHz, DMSO-$d_6$) δ 7.72 (d, J=8.3 Hz, 1H), 7.47 (d, J=1.6 Hz, 1H), 7.35 (dd, J=8.3, 1.7 Hz, 1H), 5.40 (q, J=6.8 Hz, 1H), 3.71 (s, 3H), 1.57 (d, J=6.8 Hz, 3H).

B) 4-bromo-2-(((2S)-1-hydroxypropan-2-yl)oxy)benzonitrile

To a mixture of methyl(2S)-2-(5-bromo-2-cyanophenoxy)propanoate (20.0 g), THF (dry) (100 mL) and MeOH (170 mL) was added sodium tetrahydroborate (2.66 g) at 0° C., and the mixture was stirred at room temperature under nitrogen atmosphere. After being stirred for 3 hr, additional sodium tetrahydroborate (2.13 g) was added to the mixture at 0° C., and the mixture was stirred at room temperature overnight. To the mixture was added saturated aqueous ammonium chloride solution at 0° C., and the mixture was concentrated under reduced pressure, and the residue was extracted with ethyl acetate. The organic layer was separated, washed with water and saturated brine, dried over anhydrous magnesium sulfate, and concentrated under reduced pressure to give the title compound (18.0 g). This product was subjected to the next reaction without further purification.

$^1$H NMR (300 MHz, DMSO-$d_6$) δ 7.66 (d, J=8.3 Hz, 1H), 7.60 (d, J=1.7 Hz, 1H), 7.28 (dd, J=8.3, 1.7 Hz, 1H), 4.97 (t, J=5.5 Hz, 1H), 4.71 (sxt, J=5.7 Hz, 1H), 3.50-3.57 (m, 2H), 1.23 (d, J=6.1 Hz, 3H).

C) (2S)-2-(5-bromo-2-cyanophenoxy)propyl methanesulfonate

To a mixture of 4-bromo-2-(((2S)-1-hydroxypropan-2-yl)oxy)benzonitrile (32.6 g), triethylamine (25.8 g) and THF (dry) (300 mL) was added methanesulfonyl chloride (20.4 g) at 0° C. The mixture was stirred at room temperature for 2 hr under nitrogen atmosphere. To the mixture was added water at room temperature, and the mixture was extracted with ethyl acetate. The organic layer was separated, washed with water and saturated brine, dried over anhydrous magnesium sulfate, and concentrated under reduced pressure. The residue was purified by silica gel column chromatography (NH, ethyl acetate) to give the title compound (42.5 g).

$^1$H NMR (300 MHz, DMSO-$d_6$) δ 7.71 (d, J=8.3 Hz, 1H), 7.66 (d, J=1.6 Hz, 1H), 7.34 (dd, J=8.3, 1.7 Hz, 1H), 5.07 (quind, J=6.2, 3.0 Hz, 1H), 4.42-4.49 (m, 1H), 4.31-4.40 (m, 1H), 3.21-3.25 (m, 3H), 1.33 (d, J=6.2 Hz, 3H); MS m/z 334.1 [M+H]$^+$.

D) 4-bromo-2-(((2S)-1-(1H-tetrazol-1-yl)propan-2-yl)oxy)benzonitrile

To a mixture of (2S)-2-(5-bromo-2-cyanophenoxy)propyl methanesulfonate (25.0 g), 1H-tetrazole (10.5 g) and DMF (dry) (100 mL) was added potassium carbonate (20.7 g) at room temperature, and the mixture was stirred at 80° C. overnight. To the mixture was added water at room temperature, and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane) to give the title compound (10.3 g).

$^1$H NMR (300 MHz, CDCl$_3$) δ 8.88-9.02 (m, 1H), 7.42 (d, J=8.2 Hz, 1H), 7.21 (dd, J=8.3, 1.7 Hz, 1H), 7.01 (d, J=1.6 Hz, 1H), 4.79-4.89 (m, 2H), 4.64-4.77 (m, 1H), 1.44-1.51 (m, 3H); MS m/z 308.2 [M+H]$^+$.

E) 4-(4,4,5,5-tetramethyl-1,3,2-dioxaborolan-2-yl)-2-(((2S)-1-(1H-tetrazol-1-yl)propan-2-yl)oxy)benzonitrile To a mixture of 4-bromo-2-(((2S)-1-(1H-tetrazol-1-yl)propan-2-yl)oxy)benzonitrile (6.30 g) and DMSO (120 mL) were added 4,4,4',4',5,5,5',5'-octamethyl-2,2'-bi-1,3,2-dioxaborolane (7.79 g) and Pd(dppf)Cl$_2$ dichloromethane adduct (1.67 g) at room temperature, and the mixture was stirred at 100° C. for 3 hr under nitrogen atmosphere. To the reaction solution was added water at room temperature, and the insoluble material was removed by filtration. The filtrate was partitioned with ethyl acetate-water, and the organic layer was washed with water and saturated brine, dried over anhydrous magnesium sulfate, and concentrated under reduced pressure to give the title compound. The obtained title compound was used in the next reaction without purification.

MS m/z 356.3 [M+H]$^+$.

F) (S)-2-((1-(1H-tetrazol-1-yl) propan-2-yl)oxy)-4-(2-chloropyrimidin-5-yl)benzonitrile A mixture of 4-(4,4,5,5-tetramethyl-1,3,2-dioxaborolan-2-yl)-2-(((2S)-1-(1H-tetrazol-1-yl)propan-2-yl)oxy)benzonitrile (7.26 g), 5-bromo-2-chloropyrimidine (5.93 g), Pd(dppf)Cl$_2$ dichloromethane adduct (1.67 g) and cesium carbonate (20.0 g) in DME (80 mL) and water (20 mL) was stirred at 100° C. under nitrogen atmosphere for 5 hr. The mixture was quenched with water. The insoluble material was removed by filtration, and the filtrate was extracted with ethyl acetate. The organic layer was separated, dried over anhydrous magnesium sulfate and concentrated under reduced pressure. The residue was purified by silica gel column chromatography (ethyl acetate/hexane) and crystallized from ethyl acetate/IPE to give the title compound (2.00 g).

$^1$H NMR (300 MHz, DMSO-d$_6$) δ 9.35 (s, 1H), 9.14-9.24 (m, 2H), 7.89 (d, J=8.0 Hz, 1H), 7.66 (s, 1H), 7.55 (d, J=8.3 Hz, 1H), 5.28-5.45 (m, 1H), 4.79-5.03 (m, 2H), 1.37 (d, J=6.0 Hz, 3H); MS m/z 342.1[M+1]$^+$.

G) 1-[3-(2-methoxyethoxy)-1H-pyrazol-1-yl]ethan-1-one

Potassium carbonate (4.90 g) was added to a mixture of 1-acetyl-2,3-dihydro-1H-pyrazol-3-one (3.00 g) and 1-bromo-2-methoxyethane (3.44 g) in DMF (20 mL) at 80° C., and the mixture was stirred for 1 hr. The mixture was poured into water and extracted with ethyl acetate. The organic layer was separated, washed with saturated brine, dried over anhydrous magnesium sulfate and concentrated under reduced pressure to give the title compound (3.22 g). This product was subjected to the next reaction without further purification.

MS m/z 143.2 [M+H-Ac].

H) 3-(2-methoxyethoxy)-1H-pyrazole

8 M Aqueous sodium hydroxide solution (6.5 mL) was added to a solution of 1-[3-(2-methoxyethoxy)-1H-pyrazol-1-yl]ethan-1-one (3.22 g) in MeOH (20 mL) at room temperature, and the mixture was stirred at 50° C. for 1 hr. The mixture was neutralized with 1 M aqueous hydrogen chloride solution and extracted with ethyl acetate. The organic layer was separated, washed with saturated brine, dried over anhydrous magnesium sulfate and concentrated under reduced pressure to give the title compound (2.50 g). This product was subjected to the next reaction without further purification.

MS m/z 143.2 [M+H]+.

I) 3-(2-methoxyethoxy)-4-nitro-1H-pyrazole

Nitric acid (fuming) (2.82 g) was added to a mixture of 3-(2-methoxyethoxy)-1H-pyrazole (2.50 g) and sulfuric acid (10 mL) at room temperature, and the mixture was stirred at 50° C. for 15 hr. The mixture was poured into water and extracted with ethyl acetate. The organic layer was separated, washed with saturated brine, dried over anhydrous magnesium sulfate and concentrated under reduced pressure. The residue was purified by silica gel column chromatography (ethyl acetate/hexane) to give the title compound (590 mg).

MS m/z 188.2 [M+H]+.

J) tert-butyl N-[(r,4r)-4-[3-(2-methoxyethoxy)-4-nitro-1H-pyrazol-1-yl]cyclohexyl]carbamate Potassium carbonate (1.30 g) was added to a mixture of 3-(2-methoxyethoxy)-4-nitro-1H-pyrazole (590 mg) and tert-butyl N-[(1s,4s)-4-(methanesulfonyloxy)cyclohexyl]carbamate (1.84 g) in DMA (10 mL) at 120° C., and the mixture was stirred for 3 hr. The mixture was poured into water and extracted with ethyl acetate. The organic layer was separated, washed with saturated brine, dried over anhydrous magnesium sulfate and concentrated under reduced pressure. The residue was purified by silica gel column chromatography (ethyl acetate/hexane) to give the title compound (840 mg).

MS m/z 407.2 [M+Na]+.

K) (1r,4r)-4-[3-(2-methoxyethoxy)-4-nitro-1H-pyrazol-1-yl]cyclohexan-1-amine hydrochloride 4 M Hydrogen chloride-ethyl acetate (1.6 mL) was added to a solution of tert-butyl N-[(1r,4r)-4-[3-(2-methoxyethoxy)-4-nitro-1H-pyrazol-1-yl]cyclohexyl]carbamate (820 mg) in THF (10 mL) at room temperature, and the mixture was stirred at 50° C. for 2 hr. The reaction mixture was concentrated under reduced pressure and the precipitate was collected by filtration, washed with IPE and dried under reduced pressure to give the title compound (690 mg).

MS m/z 285.2 [M+H]+.

L) 4-[(1r,4r)-4-[3-(2-methoxyethoxy)-4-nitro-1H-pyrazol-1-yl]cyclohexyl]morpholine 1-Chloro-2-(2-chloroethoxy)ethane (307 mg) was added to a mixture of (1r,4r)-4-[3-(2-methoxyethoxy)-4-nitro-1H-pyrazol-1-yl]cyclohexan-1-amine hydrochloride (690 mg), sodium iodide (482 mg) and potassium carbonate (1.18 g) in DMA (10 mL) at 100° C., and the mixture was stirred for 3 hr. The mixture was poured into water and extracted with ethyl acetate. The organic layer was separated, washed with saturated brine, dried over anhydrous magnesium sulfate and concentrated under reduced pressure. The residue was purified by silica gel column chromatography (NH, ethyl acetate/hexane) to give the title compound (514 mg).

MS m/z 355.3 [M+H]+.

M) 3-(2-methoxyethoxy)-1-[(r,4r)-4-(morpholin-4-yl)cyclohexyl]-1H-pyrazol-4-amine hydrochloride A mixture of 4-[(1r,4r)-4-[3-(2-methoxyethoxy)-4-nitro-1H-pyrazol-1-yl]cyclohexyl]morpholine (514 mg) and 10% palladium-carbon (50 mg) in EtOH (10 mL) was stirred at 50° C. for 15 hr under normal pressure of hydrogen atmosphere. The catalyst was removed by filtration, and the filtrate was concentrated under reduced pressure. The residue was purified by silica gel column chromatography (NH, ethyl acetate/hexane) to give a brown oil. To the obtained brown oil was added 4 M hydrogen chloride-ethyl acetate (1.0 mL), and the mixture was concentrated under reduced pressure to give the title compound (390 mg).

MS m/z 325.3 [M+H]+.

N) 2-(((S)-1-(1H-tetrazol-1-yl)propan-2-yl)oxy)-4-(2-((3-(2-methoxyethoxy)-1-((1r,4r)-4-morpholinocyclohexyl)-1H-pyrazol-4-yl)amino)pyrimidin-5-yl)benzonitrile To a solution of 3-(2-methoxyethoxy)-1-[(1r,4r)-4-(morpholin-4-yl)cyclohexyl]-1H-pyrazol-4-amine hydrochloride (190 mg) in NMP (0.50 mL) was added (S)-2-((1-(1H-tetrazol-1-yl)propan-2-yl)oxy)-4-(2-chloropyrimidin-5-yl)benzonitrile (179 mg) at room temperature, and the mixture was stirred at 110° C. for 5 hr. The mixture was quenched with 1 M aqueous hydrogen chloride solution and washed with ethyl acetate. The aqueous layer was neutralized with 2 M aqueous sodium hydroxide solution and extracted with ethyl acetate. The organic layer was separated, washed with saturated brine, dried over anhydrous magnesium sulfate and concentrated under reduced pressure. The residue was purified by silica gel column chromatography (NH, ethyl acetate/hexane) and silica gel column chromatography (MeOH/ethyl acetate) to give the title compound (154 mg).

$^1$H NMR (300 MHz, DMSO-d$_6$) δ 9.35 (s, 1H), 8.79 (s, 2H), 8.72 (s, 1H), 7.76 (s, 1H), 7.74 (s, 1H), 7.47 (s, 1H), 7.37-7.43 (m, 1H), 5.28-5.39 (m, 1H), 4.79-5.00 (m, 2H), 4.17-4.24 (m, 2H), 3.83-3.95 (m, 1H), 3.53-3.64 (m, 6H), 3.26 (s, 3H), 2.45-2.50 (m, 4H), 2.22-2.34 (m, 1H), 2.02-2.11 (m, 2H), 1.88-1.98 (m, 2H), 1.58-1.78 (m, 2H), δ 1.29-1.45 (m, 5H); MS m/z 630.27 [M+1]$^+$.

Example 2

5-(3-(((S)-1-(1H-tetrazol-1-yl) propan-2-yl)oxy)-4-chlorophenyl)-N-(3-(2-methoxyethoxy)-1-((1r,4r)-4-morpholinocyclohexyl)-1H-pyrazol-4-yl)pyrimidin-2-amine

A) methyl(2S)-2-(5-bromo-2-chlorophenoxy)propanoate

To a mixture of 5-bromo-2-chlorophenol (31.0 g), methyl (2R)-2-hydroxypropanoate (31.1 g), triphenylphosphine (118 g) and THF (dry) (250 mL) was added 2.2M diethyl (E)-diazene-1,2-dicarboxylate toluene solution (238 mL) at 0° C., and the mixture was stirred at room temperature overnight under nitrogen atmosphere. To the mixture was added water at room temperature, and the mixture was extracted with ethyl acetate. The organic layer was separated, washed with water and saturated brine, dried over anhydrous magnesium sulfate, and concentrated under reduced pressure. To the obtained residue were added hexane and IPE (1:1, 200 mL), the mixture was stirred at 0° C. for 20 min, and the reaction solution was concentrated. To the obtained solid were added IPE and ethyl acetate (2:1, 400 mL) and the mixture was stirred at 0° C. for 30 min. The insoluble material was removed by filtration, and the filtrate was concentrated under reduced pressure. The residue was purified by silica gel column chromatography (ethyl acetate/hexane) to give the title compound (43.9 g).

$^1$H NMR (300 MHz, DMSO-d$_6$) δ 7.41 (d, J=8.4 Hz, 1H), 7.26 (d, J=2.1 Hz, 1H), 7.18 (dd, J=8.4, 2.1 Hz, 1H), 5.24 (q, J=6.8 Hz, 1H), 3.70 (s, 3H), 1.54 (d, J=6.7 Hz, 3H).

B) (2S)-2-(5-bromo-2-chlorophenoxy)propan-1-ol

To a solution of methyl(2S)-2-(5-bromo-2-chlorophenoxy)propanoate (43.9 g) in MeOH (204 mL) and THF (dry) (120 mL) was added sodium tetrahydroborate (5.66 g) at 0° C. The mixture was stirred at room temperature overnight. To the mixture was added saturated aqueous ammonium chloride solution at 0° C., and the mixture was concentrated under reduced pressure. The obtained residue was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane) to give the title compound (40.4 g).

$^1$H NMR (300 MHz, DMSO-d$_6$) δ 7.43 (d, J=2.2 Hz, 1H), 7.37 (d, J=8.4 Hz, 1H), 7.12 (dd, J=8.4, 2.2 Hz, 1H), 4.91 (t, J=5.6 Hz, 1H), 4.47-4.62 (m, 1H), 3.44-3.62 (m, 2H), 1.22 (d, J=6.2 Hz, 3H).

C) (2S)-2-(5-bromo-2-chlorophenoxy)propyl methanesulfonate

To a mixture of (2S)-2-(5-bromo-2-chlorophenoxy)propan-1-ol (40.4 g) and triethylamine (30.8 g) in THF (dry) (200 mL) was added methanesulfonyl chloride (24.4 g) at 0° C. The mixture was stirred at room temperature for 1 hr under nitrogen atmosphere. To the mixture was added water at room temperature, and the mixture was extracted with ethyl acetate. The organic layer was separated, washed with water and saturated brine, dried over anhydrous magnesium sulfate, and concentrated under reduced pressure. The residue was purified by silica gel column chromatography (NH, ethyl acetate) to give the title compound (52.0 g).

$^1$H NMR (300 MHz, DMSO-d$_6$) δ 7.49 (s, 1H), 7.40 (d, J=8.4 Hz, 1H), 7.18 (d, J=8.4 Hz, 1H), 4.85-5.02 (m, 1H), 4.37-4.46 (m, 1H), 4.27-4.37 (m, 1H), 3.21 (s, 3H), 1.30 (d, J=6.2 Hz, 3H).

D) 1-((2S)-2-(5-bromo-2-chlorophenoxy)propyl)-1H-tetrazole

To a mixture of (2S)-2-(5-bromo-2-chlorophenoxy)propyl methanesulfonate (52.0 g), potassium carbonate (41.8 g) and DMF (dry) (100 mL) was added 1H-tetrazole (21.2 g) at room temperature. The mixture was stirred at 80° C. overnight. To the mixture was added water at room temperature, and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane) to give the title compound (26.0 g).

$^1$H NMR (300 MHz, CDCl$_3$) δ 8.92 (s, 1H), 7.09 (d, J=8.5 Hz, 1H), 6.97 (s, 1H), 4.64-4.87 (m, 3H), 1.40 (d, J=5.9 Hz, 3H); MS m/z 317.0 [M+H]$^+$.

E) 1-((2S)-2-(2-chloro-5-(4,4,5,5-tetramethyl-1,3,2-dioxaborolan-2-yl)phenoxy)propyl)-1H-tetrazole To a mixture of 4,4,4',4',5,5,5',5'-octamethyl-2,2'-bi-1,3,2-dioxaborolane (12.0 g), 1-((2S)-2-(5-bromo-2-chlorophenoxy)propyl)-1H-tetrazole (10.0 g), potassium acetate (9.27 g) and DMSO (100 mL) was added Pd(dppf)Cl$_2$ dichloromethane adduct (2.57 g) at room temperature. The mixture was stirred at 100° C. for 2 hr under nitrogen atmosphere. To the mixture were added water and ethyl acetate at room temperature, the insoluble material was removed by filtration through celite, and the filtrate was extracted with ethyl acetate. The organic layer was separated, washed with water and saturated brine, dried over anhydrous magnesium sulfate, and concentrated under reduced pressure to give the title compound (16.9 g). This product was subjected to the next reaction without further purification.

MS m/z 365.2 [M+H]$^+$.

F) 2-chloro-5-(4-chloro-3-(((2S)-1-(1H-tetrazol-1-yl)propan-2-yl)oxy)phenyl)pyrimidine To a mixture of 1-((2S)-2-(2-chloro-5-(4,4,5,5-tetramethyl-1,3,2-dioxaborolan-2-yl)phenoxy)propyl)-1H-tetrazole (12.3 g), 5-bromo-2-chloropyrimidine (9.82 g) and cesium carbonate (33.1 g) in DME (100 mL) and water (25 mL) was added Pd(dppf)Cl$_2$ (2.76 g) at room temperature. The mixture was stirred at 100° C. for 5 hr under nitrogen atmosphere. To the reaction solution were added ethyl acetate and water at room temperature, and the insoluble material was removed by filtration. The filtrate was partitioned with ethyl acetate-water, and the organic layer was washed with saturated brine, dried over anhydrous magnesium sulfate, and concentrated under reduced pressure. The residue was purified by silica gel column chromatography (ethyl acetate/hexane) to give the title compound (3.18 g).

$^1$H NMR (300 MHz, DMSO-d$_6$) δ 9.33-9.40 (m, 1H), 7.51-7.61 (m, 2H), 7.37-7.44 (m, 1H), 5.21 (td, J=6.6, 3.6 Hz, 1H), 4.76-5.00 (m, 2H), 1.34 (d, J=6.3 Hz, 3H); MS m/z 351.1 [M+H]$^+$.

G) 5-(3-(((S)-1-(1H-tetrazol-1-yl)propan-2-yl)oxy)-4-chlorophenyl)-N-(3-(2-methoxyethoxy)-1-((1r,4r)-4-morpholinocyclohexyl)-1H-pyrazol-4-yl)pyrimidin-2-amine To a solution of 3-(2-methoxyethoxy)-1-[(1r,4r)-4-(morpholin-4-yl)cyclohexyl]-1H-pyrazol-4-amine hydrochloride (190 mg) in NMP (0.50 mL) was added 2-chloro-5-(4-chloro-3-{[(2S)-1-(1H-tetrazol-1-yl)propan-2-yl]oxy}phenyl)pyrimidine (184 mg) at room temperature, and the mixture was stirred at 110° C. for 5 hr. The mixture was quenched with 1 M aqueous hydrogen chloride solution and washed with ethyl acetate. The aqueous layer was neutralized with 2 M aqueous sodium hydroxide solution and extracted with ethyl acetate. The organic layer was separated, washed with saturated brine, dried over anhydrous magnesium sulfate and concentrated under reduced pressure. The residue was purified by silica gel column chromatography (NH, ethyl acetate/hexane) and silica gel column chromatography (MeOH/ethyl acetate) to give the title compound (123 mg).

$^1$H NMR (300 MHz, DMSO-d$_6$) δ 9.37 (s, 1H), 8.70 (s, 2H), 8.53 (s, 1H), 7.73 (s, 1H), 7.43-7.46 (m, 1H), 7.37 (s, 1H), 7.23-7.26 (m, 1H), 5.14-5.21 (m, 1H), 4.76-4.94 (m, 2H), 4.19-4.22 (m, 2H), 3.84-3.94 (m, 1H), 3.52-3.62 (m, 6H), 3.26 (s, 3H), 2.45-2.50 (m, 4H), 2.22-2.33 (m, 1H), 2.02-2.10 (m, 2H), 1.88-1.95 (m, 2H), 1.62-1.75 (m, 2H), 1.29-1.45 (m, 5H); MS m/z 639.27 [M+1]$^+$.

Example 8

2-(((S)-1-(1H-tetrazol-1-yl)propan-2-yl)oxy)-4-(2-((3-(2-ethoxyethoxy)-1-((1r,4r)-4-morpholinocyclohexyl)-1H-pyrazol-4-yl)amino)pyrimidin-5-yl)benzonitrile

A) ethyl 1-acetyl-3-(2-ethoxyethoxy)-1H-pyrazole-4-carboxylate

To a mixture of ethyl 1-acetyl-3-hydroxy-1H-pyrazole-4-carboxylate (5.15 g), 2-ethoxyethan-1-ol (3.02 g), triphenylphosphane (8.13 g) and toluene (80 mL) was added DIAD (6.26 g). After being stirred at 60° C. for 15 hr, magnesium chloride (20.0 g) was added thereto, and the mixture was stirred for 30 min. The insoluble materials were removed by filtration to give the title compound (7.00 g). This product was subjected to the next reaction without further purification.

MS m/z 271.1 [M+H]$^+$.

B) ethyl 3-(2-ethoxyethoxy)-1H-pyrazole-4-carboxylate

To a solution of ethyl 1-acetyl-3-(2-ethoxyethoxy)-1H-pyrazole-4-carboxylate (7.00 g) in DMF (50 mL) was added potassium carbonate (17.8 g) at 100° C., and the mixture was stirred for 3 hr. The mixture was poured into water and extracted with ethyl acetate. The organic layer was separated, washed with saturated brine, dried over anhydrous magnesium sulfate and concentrated under reduced pressure. The residue was purified by silica gel column chromatography (ethyl acetate/hexane) to give the title compound (4.15 g).

MS m/z 229.2 [M+H]$^+$.

C) ethyl 3-(2-ethoxyethoxy)-1-[(1r,4r)-4-{[(tert-butoxy)carbonyl]amino}cyclohexyl]-1H-pyrazole-4-carboxylate Potassium carbonate (8.33 g) was added to a mixture of ethyl 3-(2-ethoxyethoxy)-1H-pyrazole-4-carboxylate (4.60 g) and tert-butyl N-[(1s,4s)-4-(methanesulfonyloxy)cyclohexyl]carbamate (10.0 g) in DMF (50 mL) at 120° C., and the mixture was stirred for 3 hr. The mixture was poured into water and extracted with ethyl acetate. The organic layer was separated, washed with saturated brine, dried over anhydrous magnesium sulfate and concentrated under reduced pressure. The residue was purified by silica gel column chromatography (ethyl acetate/hexane) to give the title compound (3.37 g).

MS m/z 426.3 [M+H]+.

D) 3-(2-ethoxyethoxy)-1-[(1r,4r)-4-{[(tert-butoxy) carbonyl]amino}cyclohexyl]-1H-pyrazole-4-carboxylic acid 2 M Aqueous sodium hydroxide solution (12 mL) was added to a solution of ethyl 3-(2-ethoxyethoxy)-1-[(1r,4r)-4-{[(tert-butoxy)carbonyl]amino}cyclohexyl]-1H-pyrazole-4-carboxylate (3.37 g) in EtOH (30 mL) at 50° C., and the mixture was stirred for 15 hr. The mixture was neutralized with 1 M aqueous hydrogen chloride solution and extracted with ethyl acetate. The organic layer was separated, washed with saturated brine, dried over anhydrous magnesium sulfate and concentrated under reduced pressure to give the title compound (3.10 g).
MS m/z 398.2 [M+H]+.

E) benzyl N-[3-(2-ethoxyethoxy)-1-[(1r,4r)-4-{[(tert-butoxy)carbonyl]amino}cyclohexyl]-1H-pyrazol-4-yl]carbamate DPPA (2.27 g) was added to a mixture of 3-(2-ethoxyethoxy)-1-[(1r,4r)-4-{[(tert-butoxy)carbonyl]amino}cyclohexyl]-1H-pyrazole-4-carboxylic acid (3.10 g), benzyl alcohol (1.67 g) and triethylamine (1.17 g) in toluene (30 mL) at 100° C., and the mixture was stirred for 3 hr. The mixture was poured into water and extracted with ethyl acetate. The organic layer was separated, washed with saturated brine, dried over anhydrous magnesium sulfate and concentrated under reduced pressure. The residue was purified by silica gel column chromatography (ethyl acetate/hexane) to give the title compound (2.49 g).
MS m/z 503.4 [M+H]+.

F) benzyl N-[3-(2-ethoxyethoxy)-1-[(1r,4r)-4-aminocyclohexyl]-1H-pyrazol-4-yl]carbamate trifluoroacetate A solution of benzyl N-[3-(2-ethoxyethoxy)-1-[(1r,4r)-4-{[(tert-butoxy)carbonyl]amino}cyclohexyl]-1H-pyrazol-4-yl]carbamate (2.49 g) in TFA (10 mL) was stirred at 50° C. for 2 hr. The reaction mixture was concentrated under reduced pressure to give the title compound (2.60 g). This product was subjected to the next reaction without further purification.
MS m/z 402.3 [M+H]+.

G) benzyl N-[3-(2-ethoxyethoxy)-1-[(1r,4r)-4-(morpholin-4-yl)cyclohexyl]-1H-pyrazol-4-yl]carbamate 1-Chloro-2-(2-chloroethoxy)ethane (709 mg) was added to a mixture of benzyl N-[3-(2-ethoxyethoxy)-1-[(1r,4r)-4-aminocyclohexyl]-1H-pyrazol-4-yl]carbamate trifluoroacetate (2.60 g), sodium iodide (1.11 g) and potassium carbonate (3.41 g) in DMA (20 mL) at 100° C., and the mixture was stirred for 2 hr. The mixture was poured into water and extracted with ethyl acetate. The organic layer was separated, washed with saturated brine, dried over anhydrous magnesium sulfate and concentrated under reduced pressure. The residue was purified by silica gel column chromatography (NH, ethyl acetate/hexane) to give the title compound (680 mg).
MS m/z 473.3 [M+H]+.

H) 3-(2-ethoxyethoxy)-1-[(1r,4r)-4-(morpholin-4-yl) cyclohexyl]-1H-pyrazol-4-amine hydrochloride A mixture of benzyl N-[3-(2-ethoxyethoxy)-1-[(1r,4r)-4-(morpholin-4-yl)cyclohexyl]-1H-pyrazol-4-yl]carbamate (680 mg) and 10% palladium-carbon (60.0 mg) in EtOH (20 mL) was stirred under normal pressure of hydrogen atmosphere at room temperature for 14 hr. The catalyst was removed by filtration, and the filtrate was concentrated under reduced pressure. The residue was purified by silica gel column chromatography (NH, ethyl acetate/hexane) to give a brown oil. To the obtained brown oil was added 4 M hydrogen chloride-ethyl acetate (1.0 mL), and the mixture was concentrated under reduced pressure to give the title compound (520 mg).
MS m/z 339.3 [M+H]+.

I) 2-(((S)-1-(1H-tetrazol-1-yl)propan-2-yl)oxy)-4-(2-((3-(2-ethoxyethoxy)-1-((1r,4r)-4-morpholinocyclohexyl)-1H-pyrazol-4-yl)amino)pyrimidin-5-yl)benzonitrile To a solution of 3-(2-ethoxyethoxy)-1-[(1r,4r)-4-(morpholin-4-yl)cyclohexyl]-1H-pyrazol-4-amine hydrochloride (250 mg) in NMP (1.0 mL) was added (S)-2-((1-(1H-tetrazol-1-yl)propan-2-yl)oxy)-4-(2-chloropyrimidin-5-yl) benzonitrile (273 mg) at room temperature, and the mixture was stirred at 110° C. for 5 hr. The mixture was quenched with 1 M aqueous hydrogen chloride solution and washed with ethyl acetate. The aqueous layer was neutralized with 2 M aqueous sodium hydroxide solution and extracted with ethyl acetate. The organic layer was separated, washed with saturated brine, dried over anhydrous magnesium sulfate and concentrated under reduced pressure. The residue was purified by silica gel column chromatography (NH, ethyl acetate/hexane). The residue was purified by preparative HPLC (water/CH$_3$CN containing 0.1% TFA) The desired fraction was neutralized with saturated aqueous sodium hydrogencarbonate solution and extracted with ethyl acetate. The organic layer was separated, dried over anhydrous magnesium sulfate and concentrated under reduced pressure to give the title compound (207 mg).
$^1$H NMR (300 MHz, DMSO-d$_6$) δ 9.35 (s, 1H), 8.79 (s, 2H), 8.71 (s, 1H), 7.72-7.76 (m, 2H), 7.46 (s, 1H), 7.38-7.41 (m, 1H), 5.29-5.41 (m, 1H), 4.80-4.97 (m, 2H), 4.18-4.21 (m, 2H), 3.82-3.95 (m, 1H), 3.62-3.66 (m, 2H), 3.52-3.60 (m, 4H), 3.45 (q, J=7.2 Hz, 2H), 2.45-2.50 (m, 4H), 2.22-2.33 (m, 1H), 2.01-2.10 (m, 2H), 1.87-1.97 (m, 2H), 1.62-1.75 (m, 2H), 1.30-1.44 (m, 5H), 1.08 (t, J=7.2 Hz, 3H); MS m/z 644.37 [M+1]$^+$.

Example 9

5-(3-(((S)-1-(1H-tetrazol-1-yl) propan-2-yl)oxy)-4-chlorophenyl)-N-(3-(2-ethoxyethoxy)-1-((1r,4r)-4-morpholinocyclohexyl)-1H-pyrazol-4-yl)pyrimidin-2-amine To a solution of 3-(2-ethoxyethoxy)-1-[(1r,4r)-4-(morpholin-4-yl)cyclohexyl]-1H-pyrazol-4-amine hydrochloride (250 mg) in NMP (1.0 mL) was added 2-chloro-5-(4-chloro-3-{[(2S)-1-(1H-tetrazol-1-yl)propan-2-yl]oxy}phenyl)pyrimidine (280 mg) at room temperature, and the mixture was stirred at 110° C. for 5 hr. The mixture was quenched with 1 M aqueous hydrogen chloride solution and washed with ethyl acetate. The aqueous layer was neutralized with 2 M aqueous sodium hydroxide solution and extracted with ethyl acetate. The organic layer was separated, washed with saturated brine, dried over anhydrous magnesium sulfate and concentrated under reduced pressure. The residue was purified by silica gel column chromatography (NH, ethyl acetate/hexane) and silica gel column chromatography (MeOH/ethyl acetate) to give the title compound (212 mg).

$^1$H NMR (300 MHz, DMSO-$d_6$) δ 9.37 (s, 1H), 8.70 (s, 2H), 8.53 (s, 1H), 7.73 (s, 1H), 7.42-7.43 (m, 1H), 7.37 (s, 1H), 7.21-7.26 (m, 1H), 5.12-5.22 (m, 1H), 4.77-4.94 (m, 2H), 4.18-4.21 (m, 2H), 3.84-3.95 (m, 1H), 3.61-3.67 (m, 2H), 3.53-3.60 (m, 4H), 3.44 (q, J=7.2 Hz, 2H), 2.45-2.50 (m, 4H), 2.21-2.33 (m, 1H), 2.01-2.10 (m, 2H), 1.88-1.99 (m, 2H), 1.60-1.75 (m, 2H), 1.29-1.45 (m, 5H), 1.08 (t, J=7.2 Hz, 3H); MS m/z 653.33 [M+1]$^+$.

Example 12

2-(((S)-1-(1H-tetrazol-1-yl)propan-2-yl)oxy)-4-(2-((1-((1r,4r)-4-((1R,5S)-3-oxa-8-azabicyclo[3.2.1]octan-8-yl)cyclohexyl)-3-(2-ethoxyethoxy)-1H-pyrazol-4-yl)amino)pyrimidin-5-yl)benzonitrile A) ethyl 1-{1,4-dioxaspiro[4.5]decan-8-yl}-3-(2-ethoxyethoxy)-1H-pyrazole-4-carboxylate A mixture of ethyl 3-(2-ethoxyethoxy)-1H-pyrazole-4-carboxylate (4.10 g), 1,4-dioxaspiro[4.5]decan-8-yl methanesulfonate (5.90 g) and cesium carbonate (7.55 g) in DMF (100 mL) was stirred at 100° C. for 12 hr. The mixture was poured into water and extracted with ethyl acetate. The organic layer was separated, washed with saturated brine, dried over anhydrous magnesium sulfate and concentrated under reduced pressure. The residue was purified by silica gel column chromatography (NH, ethyl acetate/hexane) to give the title compound (5.52 g).

MS m/z 369.2 [M+H]$^+$.

B) 1-{1,4-dioxaspiro[4.5]decan-8-yl}-3-(2-ethoxyethoxy)-1H-pyrazole-4-carboxylic acid To a mixture of ethyl 1-{1,4-dioxaspiro[4.5]decan-8-yl}-3-(2-ethoxyethoxy)-1H-pyrazole-4-carboxylate (4.71 g) and EtOH (30 mL) was added 2 M aqueous sodium hydroxide solution (20 mL). After being stirred at 80° C. for 1 hr, the mixture was neutralized with 1 M aqueous hydrogen chloride solution at room temperature and extracted with ethyl acetate. The organic layer was washed with saturated brine, dried over anhydrous magnesium sulfate and concentrated under reduced pressure to give the title compound (4.35 g). This product was subjected to the next reaction without further purification.

MS m/z 341.2 [M+H]$^+$.

C) benzyl N-[3-(2-ethoxyethoxy)-1-(4-oxocyclohexyl)-1H-pyrazol-4-yl]carbamate

To a mixture of 1-{1,4-dioxaspiro[4.5]decan-8-yl}-3-(2-ethoxyethoxy)-1H-pyrazole-4-carboxylic acid (4.35 g), triethylamine (2.06 g) and benzyl alcohol (2.07 g) in toluene (100 mL) was added DPPA (5.28 g). After being stirred at room temperature for 1 hr and at 100° C. for 2 hr, the mixture was concentrated. The residue was purified by silica gel column chromatography (ethyl acetate/hexane) to give a colorless oil. To a solution of the obtained oil in THF (20 mL) was added 1 M aqueous hydrogen chloride solution (20 mL) at room temperature, and the mixture was stirred at 60° C. for 2 hr. The mixture was poured into water and extracted with ethyl acetate. The organic layer was separated, washed with saturated brine, dried over anhydrous magnesium sulfate and concentrated under reduced pressure to give the title compound (2.85 g).

MS m/z 402.2 [M+H]$^+$.

D) benzyl N-[3-(2-ethoxyethoxy)-1-[(1r,4r)-4-[(1R,5S)-3-oxa-8-azabicyclo[3.2.1]octan-8-yl]cyclohexyl]-1H-pyrazol-4-yl]carbamate 2-Methylpyridine-borane (744 mg) was added to a mixture of benzyl N-[3-(2-ethoxyethoxy)-1-(4-oxocyclohexyl)-1H-pyrazol-4-yl]carbamate (1.40 g), (1R,5S)-3-oxa-8-azabicyclo[3.2.1]octane hydrochloride (781 mg) and triethylamine (528 mg) in MeOH (30 mL) and AcOH (1.0 mL) at 50° C., and the mixture was stirred for 1 hr. The mixture was neutralized with saturated aqueous sodium hydrogencarbonate solution and extracted with ethyl acetate. The organic layer was separated, washed with saturated brine, dried over anhydrous magnesium sulfate and concentrated under reduced pressure. The residue was purified by silica gel column chromatography (NH, ethyl acetate/hexane) to give the title compound (580 mg).

MS m/z 499.3 [M+H]+.

E) 3-(2-ethoxyethoxy)-1-[(1r,4r)-4-[(1R,5S)-3-oxa-8-azabicyclo[3.2.1]octan-8-yl]cyclohexyl]-1H-pyrazol-4-amine A mixture of benzyl N-[3-(2-ethoxyethoxy)-1-[(1r,4r)-4-[(1R,5S)-3-oxa-8-azabicyclo[3.2.1]octan-8-yl]cyclohexyl]-1H-pyrazol-4-yl]carbamate (580 mg) and 10% palladium-carbon (50 mg) in EtOH (20 mL) was stirred under normal pressure of hydrogen atmosphere at 50° C. for 14 hr. The catalyst was removed by filtration, and the filtrate was concentrated under reduced pressure. The residue was purified by silica gel column chromatography (NH, ethyl acetate/hexane) to give the title compound (353 mg).

MS m/z 365.2 [M+H]+.

F) 5-bromo-N-[3-(2-ethoxyethoxy)-1-[(1r,4r)-4-[(1R,5S)-3-oxa-8-azabicyclo[3.2.1]octan-8-yl]cyclohexyl]-1H-pyrazol-4-yl]pyrimidin-2-amine To a solution of 3-(2-ethoxyethoxy)-1-[(1r,4r)-4-[(1R,5S)-3-oxa-8-azabicyclo[3.2.1]octan-8-yl]cyclohexyl]-1H-pyrazol-4-amine (353 mg) in NMP (3.0 mL) were added 5-bromo-2-chloropyrimidine (224 mg) and methanesulfonic acid (278 mg) at room temperature, and the mixture was stirred at 110° C. for 6 hr. The mixture was poured into saturated aqueous sodium hydrogencarbonate solution and extracted with ethyl acetate. The organic layer was separated, washed with saturated brine, dried over anhydrous magnesium sulfate and concentrated under reduced pressure. The residue was purified by silica gel column chromatography (NH, ethyl acetate/hexane) to give the title compound (224 mg).

MS m/z 521.2, 523.2 [M+H]+.

G) 2-(((S)-1-(1H-tetrazol-1-yl)propan-2-yl)oxy)-4-(2-((1-((1r,4r)-4-((1R,5S)-3-oxa-8-azabicyclo[3.2.1]octan-8-yl)cyclohexyl)-3-(2-ethoxyethoxy)-1H-pyrazol-4-yl)amino)pyrimidin-5-yl)benzonitrile To a mixture of 4-(4,4,5,5-tetramethyl-1,3,2-dioxaborolan-2-yl)-2-{[(2S)-1-(1H-tetrazol-1-yl)propan-2-yl]oxy}benzonitrile (184 mg), 5-bromo-N-[3-(2-ethoxyethoxy)-1-[(1r,4r)-4-[(1R,5S)-3-oxa-8-azabicyclo[3.2.1]octan-8-yl]cyclohexyl]-1H-pyrazol-4-yl]pyrimidin-2-amine (226 mg) and 2 M aqueous sodium carbonate solution (0.45 mL) in DME (5.0 mL) was added Pd(dppf)Cl$_2$ dichloromethane adduct (15.8 mg), and the mixture was stirred under nitrogen atmosphere at 90° C. for 1 hr. The mixture was poured into water and extracted with ethyl acetate. The organic layer was separated, washed with saturated brine, dried over anhydrous anhydrous magnesium sulfate and concentrated under reduced pressure. The residue was purified by silica gel column chromatography (NH, ethyl acetate/hexane) and silica gel column chromatography (MeOH/ethyl acetate) to give the title compound (154 mg).

$^1$H NMR (300 MHz, DMSO-$d_6$) δ 9.35 (s, 1H), 8.79 (s, 2H), 8.72 (s, 1H), 7.72-7.76 (m, 2H), 7.46 (s, 1H), 7.36-7.42 (m, 1H), 5.28-5.39 (m, 1H), 4.80-4.98 (m, 2H), 4.15-4.23 (m, 2H), 3.84-3.95 (m, 1H), 3.61-3.67 (m, 2H), 3.37-3.66 (m, 6H), 3.26-3.28 (m, 2H), 1.96-2.17 (m, 5H), 1.62-1.83 (m, 6H), 1.35 (d, J=6.0 Hz, 3H), 1.12-1.24 (m, 2H), 1.08 (t, J=7.2 Hz, 3H); MS m/z 670.41 [M+1]$^+$.

Example 14

2-(((S)-1-(1H-tetrazol-1-yl)propan-2-yl)oxy)-4-(2-((3-(2-isopropoxyethoxy)-1-((1r,4r)-4-morpholinocyclohexyl)-1H-pyrazol-4-yl)amino)pyrimidin-5-yl)benzonitrile A) ethyl 1-acetyl-3-[2-(propan-2-yloxy)ethoxy]-1H-pyrazole-4-carboxylate To a mixture of ethyl 1-acetyl-3-hydroxy-1H-pyrazole-4-carboxylate (2.20 g), 2-(propan-2-yloxy)ethan-1-ol (1.49 g), triphenylphosphine (3.48 g) and toluene (30 mL) was added DIAD (2.6 mL). After being stirred at 60° C. for 1 hr, the mixture was concentrated. The residue was purified by silica gel column chromatography (ethyl acetate) to give the title compound (3.08 g).

$^1$H NMR (300 MHz, CDCl$_3$) δ 8.54 (s, 1H), 4.45 (s, 2H), 4.30 (d, J=7.15 Hz, 2H), 3.80-3.88 (m, 2H), 3.64-3.77 (m, 1H), 2.61 (s, 3H), 1.34 (t, J=7.11 Hz, 3H), 1.20 (d, J=6.14 Hz, 6H).

B) ethyl 3-[2-(propan-2-yloxy)ethoxy]-1H-pyrazole-4-carboxylate

To a solution of ethyl 1-acetyl-3-[2-(propan-2-yloxy)ethoxy]-1H-pyrazole-4-carboxylate (3.05 g) in EtOH (50 mL) was added sodium ethanolate (871 mg) at room temperature. The mixture was stirred at 40° C. under nitrogen atmosphere for 1 hr. After cooling, the mixture was neutralized with 2 M aqueous hydrogen chloride solution at 0° C. and extracted with ethyl acetate. The organic layer was separated, washed with water and saturated brine, dried over anhydrous magnesium sulfate and concentrated under reduced pressure. The residue was purified by silica gel column chromatography (ethyl acetate/hexane) to give the title compound (2.72 g).

$^1$H NMR (300 MHz, CDCl$_3$) δ 7.88 (s, 1H), 4.36-4.44 (m, 2H), 4.28 (d, J=7.06 Hz, 2H), 3.82 (s, 2H), 3.64-3.77 (m, 1H), 1.33 (s, 3H), 1.17-1.22 (m, 6H)(NH peak was omitted).

C) ethyl 3-[2-(propan-2-yloxy)ethoxy]-1-[(1r,4r)-4-{[(tert-butoxy)carbonyl]amino}cyclohexyl]-1H-pyrazole-4-carboxylate To a solution of ethyl 3-[2-(propan-2-yloxy)ethoxy]-1H-pyrazole-4-carboxylate (2.72 g) and cesium carbonate (10.9 g) in DMA (6.0 mL) was added tert-butyl N-[(1s,4s)-4-(methanesulfonyloxy)cyclohexyl]carbamate (4.89 g) at room temperature. The mixture was stirred at 80° C. under nitrogen atmosphere for 14 hr. Additional tert-butyl N-[(1s,4s)-4-(methanesulfonyloxy)cyclohexyl]carbamate (1.64 g) and DMA (5.0 mL) were added to the mixture, and the mixture was stirred at 80° C. for 3 hr. Additional tert-butyl N-[(1s,4s)-4-(methanesulfonyloxy)cyclohexyl]carbamate (1.64 g) and DMA (5.0 mL) were added to the mixture, and the mixture was stirred at 80° C. for 3 hr. The mixture was poured into water and extracted with ethyl acetate. The organic layer was separated, washed with water and saturated brine, dried over anhydrous magnesium sulfate and concentrated under reduced pressure. The residue was purified by silica gel column chromatography (NH, ethyl acetate/hexane) to give the crude title compound (2.22 g).

$^1$H NMR (300 MHz, CDCl$_3$) δ 7.68-7.71 (m, 1H), 4.39-4.57 (m, 1H), 4.31-4.39 (m, 2H), 4.19-4.31 (m, 2H), 3.84-3.94 (m, 1H), 3.77-3.83 (m, 2H), 3.65-3.76 (m, 1H), 3.40-3.60 (m, 1H), 2.12-2.24 (m, 4H), 1.65-1.85 (m, 2H), 1.45 (s, 9H), 1.22-1.36 (m, 5H), 1.18 (d, J=6.05 Hz, 6H).

D) 3-[2-(propan-2-yloxy)ethoxy]-1-[(1r,4r)-4-{[(tert-butoxy)carbonyl]amino}cyclohexyl]-1H-pyrazole-4-carboxylic acid To a solution of the crude ethyl 3-[2-(propan-2-yloxy)ethoxy]-1-[(1r,4r)-4-{[(tert-butoxy)carbonyl]amino}cyclohexyl]-1H-pyrazole-4-carboxylate (3.84 g) in EtOH (30 mL) was added 2 M aqueous sodium hydroxide solution (12 mL), and the mixture was stirred at 50° C. for 14 hr. After cooling, the reaction mixture was diluted with water (20 mL) and washed with IPE (20 mL×2). The aqueous phase was acidified with 2 M aqueous hydrogen chloride solution (13 mL) and extracted with ethyl acetate. The organic layer was separated, washed with saturated brine, dried over anhydrous magnesium sulfate and concentrated under reduced pressure to give the crude title compound (2.77 g).

$^1$H NMR (300 MHz, CDCl$_3$) δ 7.78 (s, 1H), 4.39-4.48 (m, 3H), 3.84-3.96 (m, 1H), 3.75-3.81 (m, 2H), 3.62-3.73 (m, 1H), 3.43-3.61 (m, 1H), 2.12-2.24 (m, 4H), 1.70-1.87 (m, 2H), 1.45 (s, 9H), 1.23-1.38 (m, 2H), 1.18 (d, J=6.05 Hz, 6H) CO$_2$H peak was omitted.

E) benzyl N-{3-[2-(propan-2-yloxy)ethoxy]-1-[(1r,4r)-4-{[(tert-butoxy)carbonyl]amino}cyclohexyl]-1H-pyrazol-4-yl}carbamate To a mixture of 3-[2-(propan-2-yloxy)ethoxy]-1-[(1r,4r)-4-{[(tert-butoxy)carbonyl]amino}cyclohexyl]-1H-pyrazole-4-carboxylic acid (2.25 g), benzyl alcohol (1.76 g) and triethylamine (828 mg) in toluene (50 mL) was added DPPA (2.65 g) at room temperature. The mixture was stirred at 100° C. under nitrogen atmosphere for 3 hr. The mixture was poured into water and extracted with ethyl acetate. The organic layer was separated, washed with saturated brine, dried over anhydrous magnesium sulfate and concentrated under reduced pressure. The residue was purified by silica gel column chromatography (ethyl acetate/hexane) to give the crude title compound (3.12 g). This product was subjected to the next reaction without further purification.

$^1$H NMR (300 MHz, CDCl$_3$) δ 7.57-7.63 (m, 1H), 7.32-7.42 (m, 5H), 6.90-7.00 (m, 1H), 5.17 (s, 2H), 4.23-4.29 (m, 2H), 3.76-3.90 (m, 1H), 3.67-3.72 (m, 2H), 3.57-3.66 (m,

1H), 2.06-2.20 (m, 4H), 1.68-1.87 (m, 2H), 1.45 (s, 9H), 1.24-1.33 (m, 4H), 1.17 (d, J=6.05 Hz, 6H).

F) benzyl N-{3-[2-(propan-2-yloxy)ethoxy]-1-[(1r, 4r)-4-aminocyclohexyl]-1H-pyrazol-4-yl}carbamate hydrochloride A solution of benzyl N-{3-[2-(propan-2-yloxy)ethoxy]-1-[(r,4r)-4-{[(tert-butoxy)carbonyl]amino}cyclohexyl]-1H-pyrazol-4-yl}carbamate (3.02 g) in 4 M hydrogen chloride-cyclopentyl methyl ether (20 mL) and ethyl acetate (10 mL) was stirred at room temperature for 14 hr. The reaction mixture was concentrated under reduced pressure. The precipitate was collected by filtration, washed with ethyl acetate and dried in reduced pressure to give the title compound (2.03 g).
$^1$H NMR (300 MHz, DMSO-$d_6$) δ 8.63-8.71 (m, 1H), 7.96-8.09 (m, 3H), 7.58-7.62 (m, 1H), 7.28-7.44 (m, 5H), 5.04-5.11 (m, 2H), 4.09-4.17 (m, 2H), 3.84-3.96 (m, 1H), 3.57-3.67 (m, 3H), 1.95-2.11 (m, 4H), 1.65-1.83 (m, 2H), 1.37-1.59 (m, 3H), 1.08 (d, J=6.05 Hz, 6H).

G) benzyl N-{3-[2-(propan-2-yloxy)ethoxy]-1-[(1r, 4r)-4-(morpholin-4-yl)cyclohexyl]-1H-pyrazol-4-yl}carbamate To a mixture of benzyl N-{3-[2-(propan-2-yloxy)ethoxy]-1-[(1r,4r)-4-aminocyclohexyl]-1H-pyrazol-4-yl}carbamate hydrochloride (2.01 g) and potassium carbonate (2.44 g) in DMA (20 mL) was added 1-chloro-2-(2-chloroethoxy)ethane (759 mg) at room temperature. The mixture was stirred at 90° C. under argon atmosphere for 4 hr. The mixture was concentrated under reduced pressure, and the residue was poured into water and extracted with ethyl acetate. The organic layer was separated, washed with saturated aqueous ammonium chloride solution and saturated brine, dried over anhydrous magnesium sulfate and concentrated under reduced pressure. The residue was purified by silica gel column chromatography (NH, ethyl acetate/hexane) to give the crude title compound (1.93 g).
$^1$H NMR (300 MHz, CDCl$_3$) δ 7.57-7.65 (m, 1H), 7.31-7.47 (m, 5H), 6.94-7.02 (m, 1H), 5.17 (s, 2H), 4.22-4.30 (m, 2H), 3.58-3.88 (m, 9H), 2.52-2.62 (m, 4H), 2.18-2.34 (m, 2H), 1.97-2.04 (m, 2H), 1.66 (brs, 2H), 1.32-1.47 (m, 2H), 1.12-1.19 (m, 6H).

H) 3-[2-(propan-2-yloxy)ethoxy]-1-[(1r,4r)-4-(morpholin-4-yl)cyclohexyl]-1H-pyrazol-4-amine dihydrochloride A mixture of benzyl N-{3-[2-(propan-2-yloxy)ethoxy]-1-[(1r,4r)-4-(morpholin-4-yl)cyclohexyl]-1H-pyrazol-4-yl}carbamate (1.39 g), 10% palladium-carbon (606 mg) and 4 M hydrogen chloride-ethyl acetate (2.9 mL) in EtOH (50 mL) was stirred under normal pressure of hydrogen atmosphere at room temperature for 2 hr. The catalyst was removed by filtration, and the filtrate was concentrated under reduced pressure to give the crude title compound (1.10 g). This product was subjected to the next reaction without further purification.
$^1$H NMR (300 MHz, DMSO-$d_6$) δ 11.09-11.76 (m, 1H), 9.87-10.40 (m, 3H), 7.76-7.81 (m, 1H), 4.21-4.27 (m, 2H), 3.95 (brs, 5H), 3.66-3.72 (m, 2H), 3.21-3.42 (m, 4H), 3.01-3.17 (m, 2H), 2.22-2.35 (m, 2H), 2.04-2.16 (m, 2H), 1.61-1.83 (m, 4H), 1.10 (d, J=6.05 Hz, 6H).

I) 5-bromo-N-{3-[2-(propan-2-yloxy)ethoxy]-1-[(1r, 4r)-4-(morpholin-4-yl)cyclohexyl]-1H-pyrazol-4-yl}pyrimidin-2-amine To a solution of 3-[2-(propan-2-yloxy)ethoxy]-1-[(1r,4r)-4-(morpholin-4-yl)cyclohexyl]-1H-pyrazol-4-amine dihydrochloride (1.05 g) in NMP (15 mL) was added 5-bromo-2-chloropyrimidine (617 mg) at room temperature. The mixture was stirred at 120° C. under argon atmosphere for 14 hr. The mixture was poured into water, basified with sodium hydrogencarbonate and extracted with ethyl acetate. The organic layer was extracted with 2 M aqueous hydrogen chloride solution. The aqueous layer was washed with ethyl acetate and basified with 8 M aqueous sodium hydroxide solution. The aqueous solution was extracted with ethyl acetate, and the organic layer was washed with saturated brine, dried over anhydrous magnesium sulfate and concentrated under reduced pressure. The residue was purified by silica gel column chromatography (NH, ethyl acetate/hexane) to give the title compound (1.01 g).
$^1$H NMR (300 MHz, CDCl$_3$) δ 8.36 (s, 2H), 7.80 (s, 1H), 7.08-7.16 (m, 1H), 4.30-4.39 (m, 2H), 3.80-3.95 (m, 1H), 3.70-3.79 (m, 7H), 2.58 (brs, 4H), 2.27-2.37 (m, 1H), 2.04-2.25 (m, 4H), 1.67-1.83 (m, 2H), 1.31-1.48 (m, 2H), 1.21 (d, J=6.14 Hz, 6H).

J) 2-(((S)-1-(1H-tetrazol-1-yl)propan-2-yl)oxy)-4-(2-((3-(2-isopropoxyethoxy)-1-((1r,4r)-4-morpholinocyclohexyl)-1H-pyrazol-4-yl)amino)pyrimidin-5-yl)benzonitrile To a mixture of 5-bromo-N-{3-[2-(propan-2-yloxy)ethoxy]-1-[(1r,4r)-4-(morpholin-4-yl)cyclohexyl]-1H-pyrazol-4-yl}pyrimidin-2-amine (113 mg), 4,4,5,5-tetramethyl-2-(4,4,5,5-tetramethyl-1,3,2-dioxaborolan-2-yl)-1,3,2-dioxaborolane (67.5 mg) and potassium acetate (65.3 mg) in DME (4.0 mL) was added Pd(dppf)Cl$_2$ (8.13 mg) at room temperature. The mixture was stirred at 85° C. under argon atmosphere for 14 hr. After cooling to room temperature, DME (4.0 mL), 2 M aqueous sodium carbonate solution (332 uL), 4-bromo-2-{[(2S)-1-(1H-tetrazol-1-yl)propan-2-yl]oxy}benzonitrile (61.5 mg) and Pd(dppf)Cl$_2$ (8.13 mg) were added to the mixture. The mixture was stirred at 85° C. under argon atmosphere for 7 hr. The mixture was poured into water and extracted with ethyl acetate. The organic layer was separated, washed with saturated brine, dried over anhydrous magnesium sulfate and concentrated under reduced pressure. The residue was purified by silica gel column chromatography (NH, ethyl acetate/hexane) to give the title compound (101 mg).
$^1$H NMR (300 MHz, CDCl$_3$) δ 8.97-9.02 (m, 1H), 8.56 (s, 2H), 7.92 (s, 1H), 7.61 (d, J=8.07 Hz, 1H), 7.43-7.48 (m, 1H), 7.13-7.21 (m, 1H), 6.88-6.93 (m, 1H), 4.94-5.04 (m, 1H), 4.83-4.93 (m, 1H), 4.68-4.79 (m, 1H), 4.32-4.41 (m, 2H), 3.82-3.95 (m, 1H), 3.63-3.79 (m, 7H), 2.54-2.65 (m, 4H), 2.20-2.38 (m, 3H), 2.06-2.17 (m, 2H), 1.68-1.86 (m, 2H), 1.52 (d, J=6.14 Hz, 3H), 1.32-1.48 (m, 2H), 1.21 (d, J=6.14 Hz, 6H); MS m/z 658.44 [M+1]+.

Example 16

2-(((S)-1-(1H-1,2,4-triazol-1-yl)propan-2-yl)oxy)-4-(2-((3-(2-isopropoxyethoxy)-1-((1r,4r)-4-morpholinocyclohexyl)-1H-pyrazol-4-yl)amino)pyrimidin-5-yl)benzonitrile

A) 4-bromo-2-(((2S)-1-(1H-1,2,4-triazol-1-yl)propan-2-yl)oxy)benzonitrile

To a mixture of (2S)-1-(1H-1,2,4-triazol-1-yl)propan-2-ol (6.79 g) and DMF (120 ml) was added 60% sodium hydride (2.56 g) at 0° C. The mixture was stirred at 0° C. for 15 min, 4-bromo-2-fluorobenzonitrile (11.8 g) was added to the mixture, and the mixture was stirred at room temperature for 2 days. To the mixture was added water at 0° C., and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane). A mixture of the obtained solid and IPE was stirred at room temperature for 1 hr, and the precipitated solid was collected by filtration to give the title compound (9.60 g).

$^1$H NMR (300 MHz, DMSO-d$_6$) δ 8.46 (s, 1H), 7.95 (s, 1H), 7.64 (d, J=8.2 Hz, 1H), 7.45 (d, J=1.5 Hz, 1H), 7.28 (dd, J=8.3, 1.7 Hz, 1H), 5.05-5.19 (m, 1H), 4.52 (d, J=5.6 Hz, 2H), 1.32 (d, J=6.1 Hz, 3H); MS m/z 306.9 [M+H]$^+$.

B) 2-(((S)-1-(1H-1,2,4-triazol-1-yl)propan-2-yl) oxy)-4-(2-((3-(2-isopropoxyethoxy)-1-((1r,4r)-4-morpholinocyclohexyl)-1H-pyrazol-4-yl)amino) pyrimidin-5-yl)benzonitrile To a mixture of 4-bromo-2-{[(2S)-1-(1H-1,2,4-triazol-1-yl)propan-2-yl]oxy}benzonitrile (361 mg), 4,4,5,5-tetramethyl-2-(4,4,5,5-tetramethyl-1,3,2-dioxaborolan-2-yl)-1,3,2-dioxaborolane (358 mg) and potassium acetate (230 mg) in DME (10 mL) was added Pd(dppf)Cl$_2$ (48.1 mg) at room temperature. The mixture was stirred at 80° C. under nitrogen atmosphere for 14 hr. After cooling to room temperature, DME (5.0 mL), 2 M aqueous sodium carbonate solution (3.0 mL), 5-bromo-N-{3-[2-(propan-2-yloxy)ethoxy]-1-[(1r,4r)-4-(morpholin-4-yl)cyclohexyl]-1H-pyrazol-4-yl}pyrimidin-2-amine (220 mg) and Pd(dppf)Cl$_2$ (48.1 mg) were added to the mixture. The mixture was stirred at 80° C. under nitrogen atmosphere for 2 hr. The mixture was poured into water and extracted with ethyl acetate. The organic layer was separated, washed with saturated brine, dried over anhydrous magnesium sulfate and concentrated under reduced pressure. The residue was purified by silica gel column chromatography (NH, ethyl acetate/hexane) and silica gel column chromatography (MeOH/ethyl acetate) to give the title compound (200 mg).

$^1$H NMR (300 MHz, CDCl$_3$) δ 8.55 (s, 2H), 8.29 (s, 1H), 7.93 (d, J=8.5 Hz, 2H), 7.59 (d, J=8.1 Hz, 1H), 7.29-7.41 (m, 1H), 7.12 (d, J=8.1 Hz, 1H), 6.84 (s, 1H), 4.92-5.04 (m, 1H), 4.42-4.56 (m, 2H), 4.31-4.41 (m, 2H), 3.82-3.99 (m, 1H), 3.65-3.81 (m, 7H), 2.60 (brs, 4H), 2.30-2.47 (m, 1H), 2.24 (br d, J=11.6 Hz, 2H), 2.10 (d, J=12.0 Hz, 2H), 1.67-1.96 (m, 5H), 1.35-1.47 (m, 2H), 1.22 (d, J=6.2 Hz, 6H); MS m/z 657.37 [M+1]$^+$.

Example 26

2-(((S)-1-(1H-tetrazol-1-yl)propan-2-yl)oxy)-4-(2-((3-(3-methoxypropoxy)-1-((1r,4r)-4-morpholinocyclohexyl)-1H-pyrazol-4-yl)amino)pyrimidin-5-yl) benzonitrile A) ethyl 1-acetyl-3-(3-methoxypropoxy)-1H-pyrazole-4-carboxylate To a mixture of ethyl 1-acetyl-3-hydroxy-1H-pyrazole-4-carboxylate (2.20 g), 3-methoxypropan-1-ol (1.29 g), triphenylphosphine (3.48 g) and toluene (50 mL) was added DIAD (2.68 g). After being stirred at 60° C. for 1 hr, the mixture was concentrated. The residue was purified by silica gel column chromatography (ethyl acetate/hexane) to give the title compound (3.04 g).

$^1$H NMR (300 MHz, CDCl$_3$) δ 8.54 (s, 1H), 4.41 (t, J=6.33 Hz, 2H), 4.30 (d, J=7.06 Hz, 2H), 3.58 (t, J=6.14 Hz, 2H), 3.36 (s, 3H), 2.61 (s, 3H), 2.11 (t, J=6.28 Hz, 2H), 1.34 (t, J=7.11 Hz, 3H).

B) ethyl 3-(3-methoxypropoxy)-1H-pyrazole-4-carboxylate

To a solution of ethyl 1-acetyl-3-(3-methoxypropoxy)-1H-pyrazole-4-carboxylate (3.04 g) in EtOH (30 mL) was added sodium ethanolate (837 mg) at room temperature. The mixture was stirred at 40° C. under nitrogen atmosphere for 1 hr. After cooling, the mixture was neutralized with 2 M aqueous hydrogen chloride solution at 0° C. and extracted with ethyl acetate. The organic layer was separated, washed with water and saturated brine, dried over anhydrous magnesium sulfate and concentrated under reduced pressure. The residue was purified by silica gel column chromatography (ethyl acetate/hexane) to give the title compound (2.50 g).

$^1$H NMR (300 MHz, CDCl$_3$) δ 7.85-7.92 (m, 1H), 4.36 (s, 2H), 4.23-4.33 (m, 2H), 3.53-3.62 (m, 2H), 3.36 (s, 3H), 2.10 (t, J=6.37 Hz, 2H), 1.34 (s, 3H), NH proton was not detected.

C) ethyl 3-(3-methoxypropoxy)-1-[(1r,4r)-4-{[(tert-butoxy)carbonyl]amino}cyclohexyl]-1H-pyrazole-4-carboxylate To a solution of ethyl 3-(3-methoxypropoxy)-1H-pyrazole-4-carboxylate (1.00 g) and cesium carbonate (4.26 g) in DMA (6.0 mL) was added tert-butyl N-[(1s,4s)-4-(methanesulfonyloxy)cyclohexyl]carbamate (1.92 g) at room temperature. The mixture was stirred at 80° C. under nitrogen atmosphere for 14 hr. Additional tert-butyl N-[(1s,4s)-4-(methanesulfonyloxy)cyclohexyl]carbamate (642 mg) and DMA (5.0 mL) were added to the mixture, and the mixture was stirred at 80° C. for 3 hr. Additional tert-butyl N-[(1s,4s)-4-(methanesulfonyloxy)cyclohexyl]carbamate (642 mg) and DMA (5.0 mL) were added to the mixture, and the mixture was stirred at 80° C. for 3 hr. The mixture was poured into water and extracted with ethyl acetate. The organic layer was separated, washed with water and saturated brine, dried over anhydrous magnesium sulfate and concentrated under reduced pressure. The residue was purified by silica gel column chromatography (ethyl acetate/hexane) to give the crude title compound (2.21 g). This product was subjected to the next reaction without further purification.

$^1$H NMR (300 MHz, CDCl$_3$) δ 7.67-7.71 (m, 1H), 4.38-4.55 (m, 1H), 4.21-4.35 (m, 4H), 3.78-3.98 (m, 1H), 3.57 (t, J=6.37 Hz, 2H), 3.35 (s, 3H), 2.09-2.25 (m, 4H), 1.74 (d, J=4.49 Hz, 4H), 1.45 (s, 9H), 1.21-1.37 (m, 6H).

D) 3-(3-methoxypropoxy)-1-[(1r,4r)-4-{[(tert-butoxy)carbonyl]amino}cyclohexyl]-1H-pyrazole-4-carboxylic acid To a solution of ethyl 3-(3-methoxypropoxy)-1-[(1r,4r)-4-{[(tert-butoxy)carbonyl]amino}cyclohexyl]-1H-pyrazole-4-carboxylate (2.21 g) in EtOH (30 mL) was added 2 M aqueous sodium hydroxide solution (7.8 mL). The mixture was stirred at 50° C. for 14 hr. After cooling, the reaction mixture was diluted with water and washed with IPE. The aqueous phase was acidified with 2 M aqueous hydrogen chloride solution and extracted with ethyl acetate. The organic layer was separated, washed with saturated brine, dried over anhydrous magnesium sulfate and concentrated under reduced pressure to give the title compound (1.23 g).

$^1$H NMR (300 MHz, CDCl$_3$) δ 7.76-7.80 (m, 1H), 4.39 (s, 2H), 3.82-3.97 (m, 1H), 3.52-3.60 (m, 2H), 3.35 (s, 3H), 2.13-2.26 (m, 4H), 2.04-2.12 (m, 3H), 1.66-1.88 (m, 2H), 1.45 (s, 9H), 1.18-1.36 (m, 3H), CO$_2$H proton was not detected.

E) benzyl N-[3-(3-methoxypropoxy)-1-[(1r,4r)-4-{[(tert-butoxy)carbonyl]amino}cyclohexyl]-1H-pyrazol-4-yl]carbamate To a mixture of 3-(3-methoxypropoxy)-1-[(1r,4r)-4-{[(tert-butoxy)carbonyl]amino}cyclohexyl]-1H-pyrazole-4-carboxylic acid (1.23 g), benzyl alcohol (1.00 g) and triethylamine (468 mg) in toluene (30 mL) was added DPPA (1.50 g) at room temperature. The mixture was stirred at 100° C. under nitrogen atmosphere for 3 hr. The mixture was poured into water and extracted with ethyl acetate. The organic layer was separated, washed with saturated brine, dried over anhydrous magnesium sulfate and concentrated under reduced pressure. The residue was purified by silica gel column chromatography (ethyl acetate/hexane) to give the title compound (1.07 g).

$^1$H NMR (300 MHz, CDCl$_3$) δ 7.55-7.60 (m, 1H), 7.37 (brs, 5H), 6.45-6.54 (m, 1H), 5.17 (s, 2H), 4.23 (s, 2H), 3.73-3.95 (m, 1H), 3.49-3.55 (m, 2H), 3.34 (s, 3H), 2.08-2.20 (m, 4H), 1.66-1.86 (m, 2H), 1.45 (s, 9H), 1.26 (s, 6H).

F) benzyl N-[3-(3-methoxypropoxy)-1-[(1r,4r)-4-aminocyclohexyl]-1H-pyrazol-4-yl]carbamate hydrochloride To a solution of benzyl N-[3-(3-methoxypropoxy)-1-[(1r,4r)-4-{[(tert-butoxy)carbonyl]amino}cyclohexyl]-1H-pyrazol-4-yl]carbamate (1.05 g) in EtOH (5.0 mL) was added 4 M hydrogen chloride-ethyl acetate (5.1 mL) at room temperature. The mixture was stirred at room temperature for 14 hr. The mixture was concentrated under reduced pressure to give the crude title compound (920 mg). This product was subjected to the next reaction without further purification.

MS m/z 403.3 [M+H]+.

G) benzyl N-[3-(3-methoxypropoxy)-1-[(1r,4r)-4-(morpholin-4-yl)cyclohexyl]-1H-pyrazol-4-yl]carbamate To a mixture of benzyl N-[3-(3-methoxypropoxy)-1-[(1r,4r)-4-aminocyclohexyl]-1H-pyrazol-4-yl]carbamate hydrochloride (915 mg), 1-chloro-2-(2-chloroethoxy)ethane (356 mg) and potassium carbonate (1.14 g) in DMA (10 mL) was added sodium iodide (0.935 g) at room temperature. The mixture was stirred at 90° C. under argon atmosphere for 2 hr. The mixture was concentrated under reduced pressure, and the residue was poured into water and extracted with ethyl acetate. The organic layer was separated, washed with saturated aqueous ammonium chloride solution and saturated brine, dried over anhydrous magnesium sulfate and concentrated under reduced pressure. The residue was purified by silica gel column chromatography (NH, ethyl acetate/hexane) to give the title compound (791 mg).

$^1$H NMR (300 MHz, CDCl$_3$) δ 7.59 (s, 1H), 7.38 (dd, J=1.47, 3.48 Hz, 6H), 6.47-6.55 (m, 1H), 5.17 (s, 2H), 4.24 (s, 2H), 3.77-3.89 (m, 1H), 3.68-3.76 (m, 4H), 3.52 (s, 2H), 3.34 (s, 3H), 2.52-2.62 (m, 4H), 2.10-2.31 (m, 3H), 1.94-2.03 (m, 2H), 1.66 (s, 2H), 1.32-1.48 (m, 2H)(NH peak was omitted).

H) 3-(3-methoxypropoxy)-1-[(1r,4r)-4-(morpholin-4-yl)cyclohexyl]-1H-pyrazol-4-amine dihydrochloride A mixture of benzyl N-[3-(3-methoxypropoxy)-1-[(1r,4r)-4-(morpholin-4-yl)cyclohexyl]-1H-pyrazol-4-yl]carbamate (790 mg), 10% palladium-carbon (354 mg) and 4 M hydrogen chloride-ethyl acetate (1.7 mL) in EtOH (20 mL) was stirred under normal pressure of hydrogen atmosphere at room temperature for 14 hr. The catalyst was removed by filtration, and then the filtrate was concentrated under reduced pressure to give the crude title compound (669 mg). This product was subjected to the next reaction without further purification.

MS m/z 339.3 [M+H]+.

I) 2-(((S)-1-(1H-tetrazol-1-yl)propan-2-yl)oxy)-4-(2-((3-(3-methoxypropoxy)-1-((1r,4r)-4-morpholinocyclohexyl)-1H-pyrazol-4-yl)amino)pyrimidin-5-yl)benzonitrile To a solution of 3-(3-methoxypropoxy)-1-[(1r,4r)-4-(morpholin-4-yl)cyclohexyl]-1H-pyrazol-4-amine dihydrochloride (173 mg) in NMP (1.0 mL) was added (S)-2-((1-(1H-tetrazol-1-yl)propan-2-yl)oxy)-4-(2-chloropyrimidin-5-yl)benzonitrile (143 mg) at room temperature, and the mixture was stirred at 110° C. for 15 hr. The mixture was quenched with 1 M aqueous hydrogen chloride solution and washed with ethyl acetate. The aqueous layer was basified with 2 M aqueous sodium hydroxide solution and extracted with ethyl acetate. The organic layer was separated, washed with saturated brine, dried over anhydrous magnesium sulfate and concentrated under reduced pressure. The residue was purified by preparative HPLC (water/CH$_3$CN containing 0.1% TFA). The desired fraction was neutralized with saturated aqueous sodium hydrogencarbonate solution and extracted with ethyl acetate. The organic layer was separated, dried over anhydrous magnesium sulfate and concentrated under reduced pressure to give the title compound (105 mg). The obtained title compound (67.0 mg) was crystallized from MeOH to give the title compound (47.0 mg) as pale yellow crystals.

$^1$H NMR (300 MHz, DMSO-d$_6$) δ 9.32-9.39 (m, 1H), 8.78-8.83 (m, 2H), 8.74-8.77 (m, 1H), 7.71-7.78 (m, 2H), 7.45-7.49 (m, 1H), 7.35-7.42 (m, 1H), 5.24-5.42 (m, 1H), 4.90-5.00 (m, 1H), 4.78-4.88 (m, 1H), 4.13 (s, 2H), 3.83-3.96 (m, 1H), 3.53-3.64 (m, 4H), 3.37-3.47 (m, 2H), 3.21 (s, 3H), 2.45-2.50 (m, 4H), 2.20-2.34 (m, 1H), 2.01-2.11 (m, 2H), 1.83-1.97 (m, 4H), 1.58-1.76 (m, 2H), 1.29-1.45 (m, 5H); MS m/z 644.41 [M+1]$^+$.

Example 27

5-(3-(((S)-1-(1H-tetrazol-1-yl)propan-2-yl)oxy)-4-chlorophenyl)-N-(3-(3-methoxypropoxy)-1-((1r,4r)-4-morpholinocyclohexyl)-1H-pyrazol-4-yl)pyrimidin-2-amine To a solution of 3-(3-methoxypropoxy)-1-[(1r,4r)-4-(morpholin-4-yl)cyclohexyl]-1H-pyrazol-4-amine dihydrochloride (175 mg) in NMP (1.0 mL) was added 2-chloro-5-(4-chloro-3-{[(2S)-1-(1H-tetrazol-1-yl)propan-2-yl]oxy}phenyl)pyrimidine (149 mg) at room temperature, and the mixture was stirred at 110° C. for 15 hr. The mixture was quenched with 1 M aqueous hydrogen chloride solution and washed with ethyl acetate. The aqueous layer was basified with 2 M aqueous sodium hydroxide solution and extracted with ethyl acetate. The organic layer was separated, washed with saturated brine, dried over anhydrous magnesium sulfate and concentrated under reduced pressure. The residue was purified by silica gel column chromatography (NH, MeOH/ethyl acetate) and silica gel column chromatography (MeOH/ethyl acetate) to give the title compound (128 mg).

$^1$H NMR (300 MHz, DMSO-d$_6$) δ 9.37 (s, 1H), 8.70 (s, 2H), 8.58 (s, 1H), 7.73 (s, 1H), 7.41-7.48 (m, 1H), 7.33-7.39 (m, 1H), 7.20-7.27 (m, 1H), 5.08-5.27 (m, 1H), 4.86-4.95 (m, 1H), 4.73-4.84 (m, 1H), 4.12 (t, J=6.42 Hz, 2H), 3.82-3.96 (m, 1H), 3.52-3.63 (m, 4H), 3.42 (t, J=6.33 Hz, 2H), 3.21 (s, 3H), 2.49 (brs, 4H), 2.19-2.36 (m, 1H), 2.01-2.12 (m, 2H), 1.89 (d, J=6.42 Hz, 4H), 1.58-1.78 (m, 2H), 1.33 (d, J=6.14 Hz, 5H); MS m/z 653.36 [M+1]$^+$.

Example 28

2-(((S)-1-(1H-1,2,4-triazol-1-yl)propan-2-yl)oxy)-4-(2-((3-(3-methoxypropoxy)-1-((1r,4r)-4-morpholinocyclohexyl)-1H-pyrazol-4-yl)amino)pyrimidin-5-yl)benzonitrile A) 5-bromo-N-[3-(3-methoxypropoxy)-1-[(1r,4r)-4-(morpholin-4-yl)cyclohexyl]-1H-pyrazol-4-yl]pyrimidin-2-amine A mixture of 3-(3-methoxypropoxy)-1-[(1r,4r)-4-(morpholin-4-yl)cyclohexyl]-1H-pyrazol-4-amine dihydrochloride (320 mg) and 5-bromo-2-chloropyrimidine (195 mg) in NMP (15 mL) was stirred at 120° C. for 7 hr. The mixture was neutralized with saturated aqueous sodium hydrogencarbonate solution at room temperature and extracted with ethyl acetate. The organic layer was separated, washed with saturated brine, dried over anhydrous magnesium sulfate and concentrated under reduced pressure. The residue was purified by silica gel column chromatography (NH, ethyl acetate/hexane) to give the title compound (150 mg).

$^1$H NMR (300 MHz, CDCl$_3$) δ 8.37 (s, 2H), 7.77-7.79 (m, 1H), 6.91-6.97 (m, 1H), 4.30 (s, 2H), 3.80-3.93 (m, 1H), 3.70-3.77 (m, 4H), 3.49-3.58 (m, 2H), 3.36 (s, 3H), 2.55-2.62 (m, 4H), 2.17-2.32 (m, 3H), 2.01-2.13 (m, 4H), 1.66-1.79 (m, 2H), 1.35-1.48 (m, 2H).

B) 2-(((S)-1-(1H-1,2,4-triazol-1-yl)propan-2-yl)oxy)-4-(2-((3-(3-methoxypropoxy)-1-((1r,4r)-4-morpholinocyclohexyl)-1H-pyrazol-4-yl)amino)pyrimidin-5-yl)benzonitrile To a mixture of 5-bromo-N-[3-(3-methoxypropoxy)-1-[(1r,4r)-4-(morpholin-4-yl)cyclohexyl]-1H-pyrazol-4-yl]pyrimidin-2-amine (140 mg), 4,4,5,5-tetramethyl-2-(4,4,5,5-tetramethyl-1,3,2-dioxaborolan-2-yl)-1,3,2-dioxaborolane (86.0 mg) and potassium acetate (83.1 mg) in DME (4.0 mL) was added Pd(dppf)Cl$_2$ (10.3 mg) at room temperature. The mixture was stirred at 85° C. under argon atmosphere for 14 hr. After cooling to room temperature, DME (4.0 mL), 2 M aqueous sodium carbonate solution (423 uL), 4-bromo-2-{[(2S)-1-(1H-1,2,4-triazol-1-yl)propan-2-yl]oxy}benzonitrile (78.0 mg) and Pd(dppf)Cl$_2$ (10.3 mg) were added to the mixture. The mixture was stirred at 85° C. under argon for 7 hr. The mixture was poured into water and extracted with ethyl acetate. The organic layer was separated, washed with saturated brine, dried over anhydrous magnesium sulfate and concentrated under reduced pressure. The residue was purified by silica gel column chromatography (NH, ethyl acetate/hexane) and purified by preparative HPLC (water/CH$_3$CN containing 0.1% TFA). The desired fraction was neutralized with saturated aqueous sodium hydrogencarbonate solution and extracted with ethyl acetate. The organic layer was separated, dried over anhydrous magnesium sulfate and concentrated under reduced pressure to give the title compound (61.0 mg).

$^1$H NMR (300 MHz, CDCl$_3$) δ 8.55 (s, 2H), 8.28 (s, 1H), 7.86-7.98 (m, 2H), 7.56-7.62 (m, 1H), 7.10-7.16 (m, 1H), 7.04-7.09 (m, 1H), 6.81-6.86 (m, 1H), 4.91-5.06 (m, 1H), 4.49-4.52 (m, 1H), 4.48 (s, 1H), 4.32 (t, J=6.28 Hz, 2H), 3.84-3.97 (m, 1H), 3.70-3.77 (m, 4H), 3.56 (t, J=6.33 Hz, 2H), 3.37 (s, 3H), 2.55-2.65 (m, 4H), 2.30-2.39 (m, 1H), 2.18-2.30 (m, 2H), 2.06 (d, J=6.33 Hz, 4H), 1.76-1.85 (m, 2H), 1.50 (d, J=6.24 Hz, 3H), 1.34-1.47 (m, 2H); MS m/z 643.42 [M+1]$^+$.

Example 30

2-(((S)-1-(1H-tetrazol-1-yl)propan-2-yl)oxy)-4-(2-((1-((1r,4r)-4-((1R,5S)-3-oxa-8-azabicyclo[3.2.1]octan-8-yl)cyclohexyl)-3-(3-methoxypropoxy)-1H-pyrazol-4-yl)amino)pyrimidin-5-yl)benzonitrile A) ethyl 1-{1,4-dioxaspiro[4.5]decan-8-yl}-3-(3-methoxypropoxy)-1H-pyrazole-4-carboxylate To a mixture of ethyl 3-(3-methoxypropoxy)-1H-pyrazole-4-carboxylate (1.45 g) and 1,4-dioxaspiro[4.5]decan-8-yl methanesulfonate (2.24 g) in DMF (25 mL) was added cesium carbonate (6.19 g) at room temperature. The mixture was stirred at 90° C. under argon atmosphere for 14 hr. Additional 1,4-dioxaspiro[4.5]decan-8-yl methanesulfonate (749 mg) was added to the mixture, and the mixture was stirred at 90° C. under argon atmosphere for 4 hr. To remove remaining 1,4-dioxaspiro[4.5]decan-8-yl methanesulfonate, the mixture was stirred at 120° C. for 1 hr. The mixture was poured into water and extracted with ethyl acetate. The organic layer was separated, washed with saturated brine, dried over anhydrous magnesium sulfate and concentrated under reduced pressure. The residue was purified by silica gel column chromatography (ethyl acetate/hexane) to give the crude title compound (2.29 g).

$^1$H NMR (300 MHz, CDCl$_3$) δ 7.74 (s, 1H), 4.79-4.91 (m, 1H), 4.30-4.36 (m, 2H), 4.20-4.29 (m, 2H), 3.97 (s, 4H), 3.57 (s, 2H), 3.35 (s, 3H), 1.96-2.03 (m, 4H), 1.80-1.92 (m, 4H), 1.66-1.77 (m, 2H), 1.32 (t, J=7.15 Hz, 3H).

B) 1-{1,4-dioxaspiro[4.5]decan-8-yl}-3-(3-methoxypropoxy)-1H-pyrazole-4-carboxylic acid 2 M aqueous sodium hydroxide solution (10 mL) was added to a solution of ethyl 1-{1,4-dioxaspiro[4.5]decan-8-yl}-3-(3-methoxypropoxy)-1H-pyrazole-4-carboxylate (2.00 g) in EtOH (20 mL) at room temperature, and the mixture was stirred for 15 h. The mixture was neutralized with 1 M aqueous hydrogen chloride solution and extracted with ethyl acetate. The organic layer was separated, washed with saturated brine, dried over anhydrous magnesium sulfate and concentrated under reduced pressure to give the title compound (1.80 g). This product was subjected to the next reaction without further purification.

MS m/z 341.2 [M+H]+.

C) benzyl N-(1-{1,4-dioxaspiro[4.5]decan-8-yl}-3-(3-methoxypropoxy)-1H-pyrazol-4-yl)carbamate DPPA (1.53 g) was added to a mixture of 1-{1,4-dioxaspiro[4.5]decan-8-yl}-3-(3-methoxypropoxy)-1H-pyrazole-4-carboxylic acid (1.80 g), benzyl alcohol (1.13 g) and triethylamine (801 mg) in toluene (20 mL) at 100° C., and the mixture was stirred for 3 hr. The mixture was poured into water and extracted with ethyl acetate. The organic layer was separated, washed with saturated brine, dried over anhydrous magnesium sulfate and concentrated under reduced pressure. The residue was purified by silica gel column chromatography (ethyl acetate/hexane) to give the title compound (1.58 g).

MS m/z 446.3 [M+H]+

D) benzyl N-[3-(3-methoxypropoxy)-1-(4-oxocyclohexyl)-1H-pyrazol-4-yl]carbamate 1 M Aqueous hydrogen chloride solution (10 mL) was added to a solution of benzyl N-(1-{1,4-dioxaspiro[4.5]decan-8-yl}-3-(3-methoxypropoxy)-1H-pyrazol-4-yl)carbamate (1.58 g) in THF (10 mL) at 50° C., and the mixture was stirred for 2 h. The mixture was neutralized with saturated aqueous sodium hydrogencarbonate solution and extracted with ethyl acetate. The organic layer was separated, washed with saturated brine, dried over anhydrous magnesium sulfate and concentrated under reduced pressure to give the title compound (1.45 g). This product was subjected to the next reaction without further purification.

MS m/z 402.2 [M+H]+.

E) benzyl N-[3-(3-methoxypropoxy)-1-[(1r,4r)-4-[(1R,5S)-3-oxa-8-azabicyclo[3.2.1]octan-8-yl]cyclohexyl]-1H-pyrazol-4-yl]carbamate 2-Methylpyridine-borane (755 mg) was added to a mixture of benzyl N-[3-(3-methoxypropoxy)-1-(4-oxocyclohexyl)-1H-pyrazol-4-yl]carbamate (1.42 g), (1R,5S)-3-oxa-8-azabicyclo[3.2.1]octane hydrochloride (791 mg) and triethylamine (1.06 g) in MeOH (30 mL) and AcOH (1.0 mL) at 50° C., and the mixture was stirred for 1 h. The mixture was neutralized with saturated aqueous sodium hydrogencarbonate solution and extracted with ethyl acetate. The organic layer was separated, washed with saturated brine, dried over anhydrous magnesium sulfate and concentrated under reduced pressure. The residue was purified by silica gel column chromatography (NH, ethyl acetate/hexane) to give the title compound (583 mg).

MS m/z 499.3 [M+H]+.

F) 3-(3-methoxypropoxy)-1-[(1r,4r)-4-[(1R,5S)-3-oxa-8-azabicyclo[3.2.1]octan-8-yl]cyclohexyl]-1H-pyrazol-4-amine A mixture of benzyl N-[3-(3-methoxypropoxy)-1-[(1r,4r)-4-[(1R,5S)-3-oxa-8-azabicyclo[3.2.1]octan-8-yl]cyclohexyl]-1H-pyrazol-4-yl]carbamate (583 mg) and 10% palladium-carbon (50.0 mg) in EtOH (10 mL) was stirred under normal pressure of hydrogen atmosphere at 50° C. for 14 hr. The catalyst was removed by filtration, and then the filtrate was concentrated under reduced pressure. The residue was purified by silica gel column chromatography (NH, ethyl acetate/hexane) to give the title compound (421 mg).

MS m/z 365.2 [M+H]+.

G) 5-bromo-N-[3-(3-methoxypropoxy)-1-[(1r,4r)-4-[(1R,5S)-3-oxa-8-azabicyclo[3.2.1]octan-8-yl]cyclohexyl]-1H-pyrazol-4-yl]pyrimidin-2-amine To a solution of 3-(3-methoxypropoxy)-1-[(1r,4r)-4-[(1R,5S)-3-oxa-8-azabicyclo[3.2.1]octan-8-yl]cyclohexyl]-1H-pyrazol-4-amine (421 mg) in NMP (3.0 mL) were added 5-bromo-2-chloropyrimidine (332 mg) and methanesulfonic acid (330 mg) at room temperature, and the mixture was stirred at 110° C. for 6 hr. The mixture was poured into saturated aqueous sodium hydrogencarbonate solution and extracted with ethyl acetate. The organic layer was separated, washed with saturated brine, dried over anhydrous magnesium sulfate and concentrated under reduced pressure. The residue was purified by silica gel column chromatography (NH, ethyl acetate/hexane) to give the title compound (434 mg).

MS m/z 521.2, 523.2 [M+H]+.

H) 2-(((S)-1-(1H-tetrazol-1-yl)propan-2-yl)oxy)-4-(2-((1-((1r,4r)-4-((1R,5S)-3-oxa-8-azabicyclo[3.2.1]octan-8-yl)cyclohexyl)-3-(3-methoxypropoxy)-1H-pyrazol-4-yl)amino)pyrimidin-5-yl)benzonitrile To a mixture of 4-(4,4,5,5-tetramethyl-1,3,2-dioxaborolan-2-yl)-2-{[(2S)-1-(1H-tetrazol-1-yl)propan-2-yl]oxy}benzonitrile (440 mg), 5-bromo-N-[3-(3-methoxypropoxy)-1-[(1r,4r)-4-[(1R,5S)-3-oxa-8-azabicyclo[3.2.1]octan-8-yl]cyclohexyl]-1H-pyrazol-4-yl]pyrimidin-2-amine (432 mg) and 2 M aqueous sodium carbonate solution (1.0 mL) in DME (10 mL) was added Pd(dppf)Cl$_2$ dichloromethane adduct (30.3 mg) at room temperature. The mixture was stirred under nitrogen atmosphere at 90° C. for 14 hr. The mixture was poured into water and extracted with ethyl acetate. The organic layer was separated, washed with saturated brine, dried over anhydrous magnesium sulfate and concentrated under reduced pressure. The residue was purified by silica gel column chromatography (NH, ethyl acetate/hexane) and silica gel column chromatography (MeOH/ethyl acetate) to give the title compound (331 mg).

$^1$H NMR (300 MHz, DMSO-d$_6$) δ 9.35 (s, 1H), 8.80 (s, 2H), 8.77 (s, 1H), 7.72-7.77 (m, 2H), 7.46 (s, 1H), 7.38-7.41 (m, 1H), 5.28-5.39 (m, 1H), 4.80-4.97 (m, 2H), 4.10-4.14 (m, 2H), 3.86-3.95 (m, 1H), 3.48-3.55 (m, 2H), 3.37-3.44 (m, 4H), 3.25-3.34 (m, 3H), 3.21 (s, 3H), 1.96-2.20 (m, 4H), 1.84-1.94 (m, 2H), 1.58-1.64 (m, 6H), 1.34 (d, J=6.0 Hz, 3H), 1.09-1.24 (m, 2H); MS m/z 670.39 [M+1]$^+$.

Example 33

2-(((S)-1-(1H-tetrazol-1-yl)propan-2-yl)oxy)-4-(2-((3-(3-ethoxypropoxy)-1-((1r,4r)-4-morpholinocyclohexyl)-1H-pyrazol-4-yl)amino)pyrimidin-5-yl)benzonitrile To a mixture of 5-(3-(((S)-1-(1H-tetrazol-1-yl)propan-2-yl)oxy)-4-chlorophenyl)-N-(3-(3-ethoxypropoxy)-1-((1r,4r)-4-morpholinocyclohexyl)-1H-pyrazol-4-yl)pyrimidin-2-amine (310 mg), potassium hexacyanoferrate(II) trihydrate (391 mg), XPhos (44.2 mg) and potassium acetate (136 mg) in CPME (15 mL) and water (15 mL) was added XPhos Pd G2 (36.5 mg) at room temperature. The mixture was stirred at 100° C. under nitrogen atmosphere for 14 hr. The mixture was quenched with water at room temperature and extracted with ethyl acetate. The organic layer was separated, washed with saturated brine, dried over anhydrous magnesium sulfate and concentrated under reduced pressure. The residue was purified by silica gel column chromatography (NH, ethyl acetate/hexane) and crystallized from ethyl acetate/hexane to give the title compound (212 mg).

$^1$H NMR (300 MHz, DMSO-$d_6$) δ 9.35 (s, 1H), 8.72-8.84 (m, 3H), 7.70-7.78 (m, 2H), 7.47 (s, 1H), 7.39 (dd, J=1.24, 8.12 Hz, 1H), 5.34 (dt, J=3.81, 6.35 Hz, 1H), 4.77-5.01 (m, 2H), 4.13 (t, J=6.42 Hz, 2H), 3.89 (tt, J=3.79, 11.70 Hz, 1H), 3.52-3.63 (m, 4H), 3.27-3.48 (m, 8H), 2.19-2.34 (m, 1H), 1.99-2.11 (m, 2H), 1.81-1.98 (m, 4H), 1.59-1.77 (m, 2H), 1.27-1.46 (m, 5H), 1.07 (t, J=7.01 Hz, 3H); MS m/z 658.40 [M+1]$^+$.

Example 34

5-(3-(((S)-1-(1H-tetrazol-1-yl) propan-2-yl)oxy)-4-chlorophenyl)-N-(3-(3-ethoxypropoxy)-1-((1r,4r)-4-morpholinocyclohexyl)-1H-pyrazol-4-yl)pyrimidin-2-amine A) ethyl 1-acetyl-3-(3-ethoxypropoxy)-1H-pyrazole-4-carboxylate To a mixture of ethyl 1-acetyl-3-hydroxy-1H-pyrazole-4-carboxylate (5.00 g), triphenylphosphane (7.92 g) and 3-ethoxypropan-1-ol (3.40 g) in toluene (100 mL) was added (Z)-N-{[(propan-2-yloxy)carbonyl]imino}(propan-2-yloxy)formamide (6.10 g). The mixture was stirred at 60° C. for 2 hr. The mixture was concentrated under reduced pressure. The residue was purified by silica gel column chromatography (ethyl acetate/hexane) to give the title compound (6.10 g).

MS m/z 285.2 [M+H]$^+$.

B) ethyl 3-(3-ethoxypropoxy)-1H-pyrazole-4-carboxylate

To a solution of ethyl 1-acetyl-3-(3-ethoxypropoxy)-1H-pyrazole-4-carboxylate (6.10 g) in EtOH (70 mL) was added sodium ethanolate (1.59 g) at room temperature. The mixture was stirred at 40° C. under nitrogen atmosphere for 1 hr. After cooled, the mixture was neutralized with 2 M aqueous hydrogen chloride solution at 0° C. and extracted with ethyl acetate. The organic layer was separated, washed with water and saturated brine, dried over anhydrous magnesium sulfate and concentrated under reduced pressure to give the title compound (2.50 g).

MS m/z 243.2 [M+H]$^+$.

C) ethyl 1-{1,4-dioxaspiro[4.5]decan-8-yl}-3-(3-ethoxypropoxy)-1H-pyrazole-4-carboxylate To a mixture of ethyl 3-(3-ethoxypropoxy)-1H-pyrazole-4-carboxylate (3.04 g) and cesium carbonate (12.2 g) in DMF (35 mL) was added 1,4-dioxaspiro[4.5]decan-8-yl methanesulfonate (4.41 g) at room temperature. The mixture was stirred at 100° C. for 4 hr. The mixture was poured into water and extracted with ethyl acetate. The organic layer was separated, washed with saturated brine, dried over anhydrous magnesium sulfate and concentrated under reduced pressure. The residue was purified by silica gel column chromatography (NH, ethyl acetate/hexane) to give the title compound (4.78 g).

MS m/z 383.2 [M+H]$^+$.

D) 1-{1,4-dioxaspiro[4.5]decan-8-yl}-3-(3-ethoxypropoxy)-1H-pyrazole-4-carboxylic acid 1 M aqueous sodium hydroxide solution (25 ml) was added to a solution of ethyl 1-{1,4-dioxaspiro[4.5]decan-8-yl}-3-(3-ethoxypropoxy)-1H-pyrazole-4-carboxylate (4.78 g) in EtOH (50 ml) at room temperature, and the mixture was stirred at room temperature for 15 hr. 2 M aqueous sodium hydroxide solution (25 mL) was added to the mixture, and the mixture was stirred at 60° C. for 2 hr. The mixture was evaporated under reduced pressure to reduce the amount of EtOH, neutralized with 2 M aqueous hydrogen chloride solution and extracted with ethyl acetate. The organic layer was separated, washed with saturated brine, dried over anhydrous magnesium sulfate and concentrated under reduced pressure to give the title compound (4.16 g). This product was subjected to the next reaction without further purification.

MS m/z 355.2 [M+H]$^+$.

E) benzyl N-(1-{1,4-dioxaspiro[4.5]decan-8-yl}-3-(3-ethoxypropoxy)-1H-pyrazol-4-yl)carbamate DPPA (3.40 g) was added to a mixture of 1-{1,4-dioxaspiro[4.5]decan-8-yl}-3-(3-ethoxypropoxy)-1H-pyrazole-4-carboxylic acid (4.16 g), benzyl alcohol (2.53 g) and triethylamine (1.77 g) in toluene (50 ml) at room temperature, and the mixture was stirred at 100° C. under nitrogen atmosphere for 2 hr. The mixture was poured into water and extracted with ethyl acetate. The organic layer was separated, washed with saturated brine, dried over anhydrous magnesium sulfate and concentrated under reduced pressure. The residue was purified by silica gel column chromatography (NH, ethyl acetate/hexane) and silica gel column chromatography (ethyl acetate/hexane) to give the title compound (4.79 g).

MS m/z 460.3 [M+H]$^+$.

F) benzyl N-[3-(3-ethoxypropoxy)-1-(4-oxocyclohexyl)-1H-pyrazol-4-yl]carbamate

To a solution of benzyl N-(1-{1,4-dioxaspiro[4.5]decan-8-yl}-3-(3-ethoxypropoxy)-1H-pyrazol-4-yl)carbamate (3.41 g) in THF (35 mL) was added 1 M aqueous hydrogen chloride solution (22 mL) at room temperature. The mixture was stirred at 50° C. for 2 hr. The mixture was neutralized with aqueous sodium hydrogencarbonate solution and extracted with ethyl acetate. The organic layer was separated, washed with saturated brine, dried over anhydrous magnesium sulfate and concentrated under reduced pressure. The residue was purified by silica gel column chromatography (ethyl acetate/hexane) to give the title compound (1.40 g).

MS m/z 416.2 [M+H]$^+$.

G) benzyl N-[3-(3-ethoxypropoxy)-1-[(1r,4r)-4-(morpholin-4-yl)cyclohexyl]-1H-pyrazol-4-yl]carbamate To a mixture of benzyl N-[3-(3-ethoxypropoxy)-1-(4-oxocyclohexyl)-1H-pyrazol-4-yl]carbamate (1.24 g) and morpholine (389 mg) in MeOH (20 mL) and AcOH (1.0 mL) was added 2-methylpyridine-borane (637 mg) at room temperature. The mixture was stirred at room temperature for 14 hr. The mixture was neutralized with saturated aqueous sodium hydrogencarbonate solution at 0° C. and extracted with ethyl acetate. The organic layer was separated, washed with saturated brine, dried over anhydrous magnesium sulfate and concentrated under reduced pressure. The residue was purified by silica gel column chromatography (NH, ethyl acetate/hexane) to give the title compound (650 mg).

MS m/z 487.2 [M+H]$^+$.

H) 3-(3-ethoxypropoxy)-1-[(r,4r)-4-(morpholin-4-yl) cyclohexyl]-1H-pyrazol-4-amine A mixture of benzyl N-[3-(3-ethoxypropoxy)-1-[(1r,4r)-4-(morpholin-4-yl)cyclohexyl]-1H-pyrazol-4-yl]carbamate (650 mg) and 10% palladium-carbon (140 mg) in EtOH (20 mL) was stirred under normal pressure of hydrogen atmosphere at room temperature for 2 hr. The catalyst was removed by filtration, and then the filtrate was concentrated under reduced pressure to give the title compound (468 mg). This product was subjected to the next reaction without further purification.

MS m/z 353.3 [M+H]$^+$.

I) 5-(3-(((S)-1-(1H-tetrazol-1-yl)propan-2-yl)oxy)-4-chlorophenyl)-N-(3-(3-ethoxypropoxy)-1-((1r,4r)-4-morpholinocyclohexyl)-1H-pyrazol-4-yl)pyrimidin-2-amine To a mixture of 3-(3-ethoxypropoxy)-1-[(1r,4r)-4-(morpholin-4-yl)cyclohexyl]-1H-pyrazol-4-amine (410 mg) and 2-chloro-5-(4-chloro-3-{[(2S)-1-(1H-tetrazol-1-yl)propan-2-yl]oxy}phenyl)pyrimidine (611 mg) in NMP (4.0 mL) was added methanesulfonic acid (334 mg) at room temperature, and the mixture was stirred at 110° C. for 14 h. The mixture was neutralized with saturated aqueous sodium hydrogencarbonate solution at 0° C. and extracted with ethyl acetate. The organic layer was separated, washed with saturated brine, dried over anhydrous magnesium sulfate and concentrated under reduced pressure. The residue was purified by silica gel column chromatography (NH, ethyl acetate/hexane) to give the title compound (510 mg).

$^1$H NMR (300 MHz, DMSO-d$_6$) δ 9.37 (s, 1H), 8.70 (s, 2H), 8.57 (s, 1H), 7.73 (s, 1H), 7.45 (d, J=8.34 Hz, 1H), 7.36 (d, J=1.83 Hz, 1H), 7.24 (dd, J=1.93, 8.25 Hz, 1H), 5.09-5.26 (m, 1H), 4.73-4.97 (m, 2H), 4.13 (t, J=6.42 Hz, 2H), 3.88 (tt, J=3.69, 11.58 Hz, 1H), 3.52-3.63 (m, 4H), 3.24-3.50 (m, 8H), 2.19-2.35 (m, 1H), 2.05 (d, J=11.46 Hz, 2H), 1.82-1.97 (m, 4H), 1.59-1.76 (m, 2H), 1.26-1.46 (m, 5H), 1.07 (t, J=7.01 Hz, 3H); MS m/z 667.35 [M+1]$^+$.

Example 36

2-(((S)-1-(1H-tetrazol-1-yl)propan-2-yl)oxy)-4-(2-((1-((1r,4r)-4-((1R,5S)-3-oxa-8-azabicyclo[3.2.1]octan-8-yl)cyclohexyl)-3-(3-ethoxypropoxy)-1H-pyrazol-4-yl)amino)pyrimidin-5-yl)benzonitrile To a mixture of 5-(3-(((S)-1-(1H-tetrazol-1-yl)propan-2-yl)oxy)-4-chlorophenyl)-N-(1-((1r,4r)-4-((R, 5S)-3-oxa-8-azabicyclo[3.2.1]octan-8-yl)cyclohexyl)-3-(3-ethoxypropoxy)-1H-pyrazol-4-yl)pyrimidin-2-amine (300 mg), potassium hexacyanoferrate(II) trihydrate (364 mg), XPhos (41.1 mg) and potassium acetate (126 mg) in CPME (15 mL) and water (15 mL) was added XPhos Pd G2 (33.9 mg) at room temperature. The mixture was stirred at 100° C. under nitrogen atmosphere for 14 hr. The mixture was quenched with water at room temperature and extracted with ethyl acetate. The organic layer was separated, washed with saturated brine, dried over anhydrous magnesium sulfate and concentrated under reduced pressure. The residue was purified by silica gel column chromatography (NH, ethyl acetate/hexane) and crystallized from ethyl acetate/hexane to give the title compound (214 mg).

$^1$H NMR (300 MHz, DMSO-d$_6$) δ 9.35 (s, 1H), 8.73-8.84 (m, 3H), 7.70-7.79 (m, 2H), 7.46 (s, 1H), 7.39 (dd, J=1.28, 8.16 Hz, 1H), 5.34 (dt, J=3.85, 6.28 Hz, 1H), 4.77-5.01 (m, 2H), 4.13 (t, J=6.37 Hz, 2H), 3.83-3.98 (m, 1H), 3.25-3.56 (m, 10H), 1.95-2.23 (m, 5H), 1.59-1.93 (m, 8H), 1.35 (d, J=6.24 Hz, 3H), 1.13-1.27 (m, 2H), 1.07 (t, J=6.97 Hz, 3H); MS m/z 684.40 [M+1]$^+$.

Example 46

2-(((S)-1-(1H-tetrazol-1-yl)propan-2-yl)oxy)-4-(2-((3-(3-(2,2-difluoroethoxy)propoxy)-1-((1r,4r)-4-morpholinocyclohexyl)-1H-pyrazol-4-yl)amino) pyrimidin-5-yl)benzonitrile To a mixture of 5-(3-(((S)-1-(1H-tetrazol-1-yl)propan-2-yl)oxy)-4-chlorophenyl)-N-(3-(3-(2,2-difluoroethoxy)propoxy)-1-((1r,4r)-4-morpholinocyclohexyl)-1H-pyrazol-4-yl)pyrimidin-2-amine (105 mg), potassium hexacyanoferrate(II) trihydrate (110 mg) and potassium acetate (44 mg) in water (5.0 mL) and CPME (5.0 mL) were added XPhos Pd G2 (12 mg) and XPhos (14 mg). After being stirred under nitrogen atmosphere at 100° C. for 14 hr, the mixture was poured into water and extracted with ethyl acetate. The organic layer was separated, washed with saturated brine, dried over anhydrous sodium sulfate and concentrated under reduced pressure. The residue was purified by silica gel column chromatography (NH, ethyl acetate/hexane) to give the title compound (80.0 mg).

$^1$H NMR (300 MHz, DMSO-d$_6$) δ 9.35 (s, 1H), 8.76-8.82 (m, 3H), 7.72-7.78 (m, 2H), 7.46 (s, 1H), 7.40 (dd, J=1.24, 8.12 Hz, 1H), 6.11 (tt, J=3.76, 55.02 Hz, 1H), 5.28-5.41 (m, 1H), 4.90-4.99 (m, 1H), 4.79-4.89 (m, 1H), 4.14 (t, J=6.37 Hz, 2H), 3.83-3.96 (m, 1H), 3.61-3.71 (m, 3H), 3.53-3.61 (m, 5H), 2.43-2.49 (m, 4H), 2.21-2.34 (m, 1H), 2.00-2.12 (m, 2H), 1.86-1.98 (m, 4H), 1.59-1.77 (m, 2H), 1.28-1.45 (m, 5H); MS m/z 694.40 [M+1]$^+$.

Example 47

5-(3-(((S)-1-(1H-tetrazol-1-yl) propan-2-yl)oxy)-4-chlorophenyl)-N-(3-(3-(2,2-difluoroethoxy) propoxy)-1-((1r,4r)-4-morpholinocyclohexyl)-1H-pyrazol-4-yl)pyrimidin-2-amine To a mixture of 4-((5-(3-(((S)-1-(1H-tetrazol-1-yl)propan-2-yl)oxy)-4-chlorophenyl)pyrimidin-2-yl)amino)-1-((1r,4r)-4-morpholinocyclohexyl)-1H-pyrazol-3-ol (200 mg) and 3-(2,2-difluoroethoxy)propan-1-ol (57 mg) in toluene (5.0 mL) was added cyanomethylenetributylphosphorane (92.0 mg). After being stirred at 100° C. for 2 hr, additional 3-(2,2-difluoroethoxy)propan-1-ol (57 mg) and cyanomethylenetributylphosphorane (92.0 mg) were added to the mixture. After being stirred at 100° C. for 1 hr, the mixture was concentrated in vacuo. The residue was purified by silica gel column chromatography (NH, ethyl acetate/hexane) and silica gel column chromatography (MeOH/ethyl acetate). The obtained product was purified by preparative HPLC (water/CH$_3$CN containing 0.1% TFA). The desired fraction was neutralized with saturated aqueous sodium hydrogencarbonate solution and extracted with ethyl acetate. The organic layer was separated, dried over anhydrous magnesium sulfate and concentrated under reduced pressure to give the title compound (114 mg).

$^1$H NMR (300 MHz, DMSO-d$_6$) δ 9.37 (s, 1H), 8.70 (s, 2H), 8.60 (s, 1H), 7.74 (s, 1H), 7.45 (d, J=8.25 Hz, 1H), 7.36 (d, J=1.83 Hz, 1H), 7.24 (dd, J=1.93, 8.34 Hz, 1H), 6.12 (tt,

J=3.85, 55.02 Hz, 1H), 5.11-5.24 (m, 1H), 4.86-4.95 (m, 1H), 4.75-4.85 (m, 1H), 4.14 (t, J=6.33 Hz, 2H), 3.82-3.96 (m, 1H), 3.61-3.71 (m, 3H), 3.52-3.61 (m, 5H), 2.44-2.49 (m, 4H), 2.22-2.33 (m, 1H), 1.99-2.11 (m, 2H), 1.86-1.98 (m, 4H), 1.59-1.77 (m, 2H), 1.28-1.45 (m, 5H); MS m/z 703.40 [M+1]$^+$.

Example 48

2-(((S)-1-(1H-tetrazol-1-yl)propan-2-yl)oxy)-4-(2-((3-(2-(2-methoxyethoxy)ethoxy)-1-((1r,4r)-4-morpholinocyclohexyl)-1H-pyrazol-4-yl)amino)pyrimidin-5-yl)benzonitrile hydrochloride A) 2-(((S)-1-(1H-tetrazol-1-yl)propan-2-yl)oxy)-4-(2-((3-(2-(2-methoxyethoxy)ethoxy)-1-((1r,4r)-4-morpholinocyclohexyl)-1H-pyrazol-4-yl)amino) pyrimidin-5-yl)benzonitrile A mixture of 5-(3-(((S)-1-(1H-tetrazol-1-yl)propan-2-yl)oxy)-4-chlorophenyl)-N-(3-(2-(2-methoxyethoxy)ethoxy)-1-((1r,4r)-4-morpholinocyclohexyl)-1H-pyrazol-4-yl)pyrimidin-2-amine (135 mg), potassium hexacyanoferrate(II) trihydrate (166 mg), XPhos Pd G2 (15.5 mg), XPhos (19.1 mg) and potassium acetate (58.1 mg) in CPME (6.0 mL) and water (6.0 mL) was stirred at 110° C. for 14.5 hr under argon atmosphere. The residue was partitioned between ethyl acetate and water. The organic layer was washed with saturated brine, dried over anhydrous sodium sulfate and concentrated under reduced pressure. The residue was purified by silica gel column chromatography (NH, ethyl acetate/hexane) to give the title compound (117 mg).

$^1$H NMR (300 MHz, CDCl$_3$) δ 8.96 (s, 1H), 8.54 (s, 2H), 7.90 (s, 1H), 7.62 (d, J=8.07 Hz, 1H), 7.29 (s, 1H), 7.17 (dd, J=1.42, 8.02 Hz, 1H), 6.85 (d, J=1.19 Hz, 1H), 4.90-5.01 (m, 1H), 4.82-4.89 (m, 1H), 4.68-4.77 (m, 1H), 4.38-4.43 (m, 2H), 3.83-3.94 (m, 3H), 3.70-3.76 (m, 6H), 3.59-3.63 (m, 2H), 3.40 (s, 3H), 2.56-2.61 (m, 4H), 2.20-2.38 (m, 3H), 2.05-2.14 (m, 2H), 1.77 (dq, J=2.52, 12.64 Hz, 2H), 1.52 (d, J=6.24 Hz, 3H), 1.34-1.48 (m, 2H).

B) 2-(((S)-1-(1H-tetrazol-1-yl)propan-2-yl)oxy)-4-(2-((3-(2-(2-methoxyethoxy)ethoxy)-1-((1r,4r)-4-morpholinocyclohexyl)-1H-pyrazol-4-yl)amino) pyrimidin-5-yl)benzonitrile hydrochloride 4 M Hydrogen chloride in ethyl acetate (42 uL) was added to a solution of 2-(((S)-1-(1H-tetrazol-1-yl)propan-2-yl)oxy)-4-(2-((3-(2-(2-methoxyethoxy) ethoxy)-1-((1r,4r)-4-morpholinocyclohexyl)-1H-pyrazol-4-yl)amino)pyrimidin-5-yl)benzonitrile (112 mg) in ethyl acetate (3.0 mL) at room temperature. EtOH (0.30 mL) was added at room temperature. The mixture was stirred at room temperature for 16 hr. The reaction mixture was concentrated with hexane under reduced pressure to give the title compound (81 mg).

$^1$H NMR (300 MHz, DMSO-d$_6$) δ 9.35 (s, 1H), 8.79 (s, 2H), 8.71 (brs, 1H), 7.71-7.78 (m, 2H), 7.46 (s, 1H), 7.39 (dd, J=1.28, 8.16 Hz, 1H), 5.29-5.39 (m, 1H), 4.90-4.98 (m, 1H), 4.80-4.88 (m, 1H), 4.20 (dd, J=3.94, 5.50 Hz, 2H), 3.73-4.10 (m, 2H), 3.68 (dd, J=3.99, 5.46 Hz, 2H), 3.51-3.64 (m, 5H), 3.38-3.42 (m, 2H), 3.29 (brs, 1H), 3.20 (s, 3H), 1.86-2.16 (m, 4H), 1.48-1.83 (m, 3H), 1.37-1.47 (m, 1H), 1.35 (d, J=6.14 Hz, 3H). 4H were hidden by DMSO, HCl protons weren't detected; MS m/z 674.40 [M+1]+.

Example 49

5-(3-(((S)-1-(1H-tetrazol-1-yl)propan-2-yl)oxy)-4-chlorophenyl)-N-(3-(2-(2-methoxyethoxy) ethoxy)-1-((1r,4r)-4-morpholinocyclohexyl)-1H-pyrazol-4-yl)pyrimidin-2-amine hydrochloride A) ethyl 1-acetyl-3-[2-(2-methoxyethoxy)ethoxy]-1H-pyrazole-4-carboxylate To a mixture of ethyl 1-acetyl-3-hydroxy-1H-pyrazole-4-carboxylate (3.33 g), DIAD (4.06 g) and triphenylphosphine (5.27 g) in toluene (50 mL) was added 2-(2-methoxyethoxy) ethan-1-ol (2.61 g) at room temperature. After being stirred at 60° C. for 2 hr, the mixture was concentrated. The residue was purified by silica gel column chromatography (ethyl acetate/hexane) to give the title compound (4.57 g).

$^1$H NMR (300 MHz, CDCl$_3$) δ 8.54 (s, 1H), 4.50 (dd, J=4.40, 5.59 Hz, 2H), 4.29 (d, J=7.15 Hz, 2H), 3.86-3.96 (m, 2H), 3.72-3.79 (m, 2H), 3.54-3.62 (m, 2H), 3.39 (s, 3H), 2.60 (s, 3H), 1.34 (t, J=7.11 Hz, 3H)

B) ethyl 3-[2-(2-methoxyethoxy)ethoxy]-1H-pyrazole-4-carboxylate

To a solution of ethyl 1-acetyl-3-[2-(2-methoxyethoxy)ethoxy]-1H-pyrazole-4-carboxylate (4.50 g) in EtOH (40 mL) was added sodium ethanolate (1.10 g) at room temperature. The mixture was stirred at 50° C. for 2 hr. The mixture was neutralized with 1 M aqueous hydrogen chloride solution at 0° C. and extracted with ethyl acetate. The organic layer was separated, washed with saturated brine, dried over anhydrous magnesium sulfate and concentrated under reduced pressure. The residue was purified by silica gel column chromatography (ethyl acetate/hexane) to give the title compound (3.81 g).

$^1$H NMR (300 MHz, CDCl$_3$) δ 7.86 (s, 1H), 4.38-4.50 (m, 2H), 4.21-4.35 (m, 2H), 3.87-3.95 (m, 2H), 3.72-3.80 (m, 2H), 3.53-3.63 (m, 2H), 3.40 (s, 3H), 1.33 (t, J=7.15 Hz, 3H), NH proton was not detected.

C) ethyl 1-{1,4-dioxaspiro[4.5]decan-8-yl}-3-[2-(2-methoxyethoxy)ethoxy]-1H-pyrazole-4-carboxylate A mixture of ethyl 3-[2-(2-methoxyethoxy)ethoxy]-1H-pyrazole-4-carboxylate (3.81 g), 1,4-dioxaspiro[4.5]decan-8-yl methanesulfonate (6.94 g) and cesium carbonate (9.57 g) in DMA (70 mL) was stirred at 100° C. for 17.5 hr. The reaction mixture was partitioned between ethyl acetate and water. The organic layer was separated, washed with saturated brine, dried over anhydrous sodium sulfate and concentrated under reduced pressure. The residue was purified by silica gel column chromatography (ethyl acetate/hexane) to give the title compound (3.94 g) as colorless oil.

MS m/z 399.2 [M+H]+.

D) 1-{1,4-dioxaspiro[4.5]decan-8-yl}-3-[2-(2-methoxyethoxy)ethoxy]-1H-pyrazole-4-carboxylic acid A mixture of ethyl 1-{1,4-dioxaspiro[4.5]decan-8-yl}-3-[2-(2-methoxyethoxy)ethoxy]-1H-pyrazole-4-carboxylate (3.93 g) and 2 M aqueous sodium hydroxide solution (25 mL) was stirred at 50° C. for 3 hr. The reaction mixture was concentrated under reduced pressure. The residue was partitioned between ethyl acetate and 1 M aqueous hydrogen chloride solution. The organic layer was washed with saturated brine, dried over anhydrous sodium sulfate and concentrated under reduced pressure to give the title compound (3.65 g).
MS m/z 371.2 [M+H]+.

E) benzyl N-(1-{1,4-dioxaspiro[4.5]decan-8-yl}-3-[2-(2-methoxyethoxy)ethoxy]-1H-pyrazol-4-yl)carbamate A mixture of 1-{1,4-dioxaspiro[4.5]decan-8-yl}-3-[2-(2-methoxyethoxy)ethoxy]-1H-pyrazole-4-carboxylic acid (3.65 g), triethylamine (1.99 g), phenylmethanol (3.19 g) and DPPA (3.24 g) in toluene (40 mL) was stirred at 100° C. for 2 hr. The reaction mixture was cool to room temperature. The resulting mixture was partitioned between ethyl acetate and aqueous sodium hydrogen carbonate. The organic layer was washed with saturated brine, dried over anhydrous sodium sulfate and concentrated under reduced pressure. The residue was purified by silica gel column chromatography (NH, ethyl acetate/hexane) to give the title compound (3.61 g).
MS m/z 476.3 [M+H]+.

F) benzyl N-{3-[2-(2-methoxyethoxy)ethoxy]-1-(4-oxocyclohexyl)-1H-pyrazol-4-yl}carbamate A mixture of benzyl N-(1-{1,4-dioxaspiro[4.5]decan-8-yl}-3-[2-(2-methoxyethoxy)ethoxy]-1H-pyrazol-4-yl)carbamate (2.04 g) and 1 M aqueous hydrogen chloride solution (21 mL) was stirred at 50° C. for 2.5 hr. The reaction mixture was partitioned between ethyl acetate and aqueous sodium hydrogen carbonate. The organic layer was washed with saturated brine, dried over anhydrous sodium sulfate and concentrated under reduced pressure to give the title compound (1.80 g).
MS m/z 432.2 [M+H]+.

G) benzyl N-{3-[2-(2-methoxyethoxy)ethoxy]-1-[(1r,4r)-4-(morpholin-4-yl)cyclohexyl]-1H-pyrazol-4-yl}carbamate A mixture of benzyl N-{3-[2-(2-methoxyethoxy)ethoxy]-1-(4-oxocyclohexyl)-1H-pyrazol-4-yl}carbamate (900 mg), morpholine (543 mg) and 2-methylpyridine-borane (654 mg) in MeOH (10 mL) and acetic acid (1.0 mL) was stirred at 60° C. for 1 hr under argon atmosphere. The reaction mixture was concentrated under reduced pressure. The residue was partitioned between ethyl acetate and aqueous sodium hydrogen carbonate. The organic layer was washed with saturated brine, dried over anhydrous sodium sulfate and concentrated under reduced pressure. The residue was purified by silica gel column chromatography (NH, ethyl acetate/hexane) to give the title compound (450 mg).
MS m/z 503.3 [M+H]+.

H) 3-[2-(2-methoxyethoxy)ethoxy]-1-[(1r,4r)-4-(morpholin-4-yl)cyclohexyl]-1H-pyrazol-4-amine dihydrochloride A mixture of benzyl N-{3-[2-(2-methoxyethoxy)ethoxy]-1-[(1r,4r)-4-(morpholin-4-yl)cyclohexyl]-1H-pyrazol-4-yl}carbamate (447 mg) and 10% palladium-carbon (86.0 mg) in 4 M hydrogen chloride-ethyl acetate (2.2 mL) and MeOH (10 mL) was stirred at room temperature for 1.5 hr under normal pressure of hydrogen atmosphere. The reaction mixture was filtered. The filtrate was concentrated under reduced pressure to give the title compound. This product was subjected to the next reaction without further purification.
MS m/z 369.3 [M+H]+.

I) 5-(3-(((S)-1-(1H-tetrazol-1-yl)propan-2-yl)oxy)-4-chlorophenyl)-N-(3-(2-(2-methoxyethoxy) ethoxy)-1-((1r,4r)-4-morpholinocyclohexyl)-1H-pyrazol-4-yl)pyrimidin-2-amine A mixture of 3-[2-(2-methoxyethoxy)ethoxy]-1-[(1r,4r)-4-(morpholin-4-yl)cyclohexyl]-1H-pyrazol-4-amine dihydrochloride (392 mg) and 2-chloro-5-(4-chloro-3-{[(2S)-1-(1H-tetrazol-1-yl)propan-2-yl]oxy}phenyl)pyrimidine (467 mg) in NMP (3.0 mL) was stirred at 120° C. for 16 hr. The residue was partitioned between ethyl acetate and aqueous sodium hydrogen carbonate. The organic layer was washed with saturated brine, dried over anhydrous sodium sulfate and concentrated under reduced pressure. The residue was purified by silica gel column chromatography (NH, ethyl acetate/hexane) to give the title compound (368 mg).
$^1$H NMR (300 MHz, DMSO-d$_6$) δ 9.37 (s, 1H), 8.70 (s, 2H), 8.52 (s, 1H), 7.73 (s, 1H), 7.45 (d, J=8.25 Hz, 1H), 7.36 (d, J=1.83 Hz, 1H), 7.24 (dd, J=1.88, 8.30 Hz, 1H), 5.17 (dt, J=3.99, 6.53 Hz, 1H), 4.87-4.95 (m, 1H), 4.75-4.84 (m, 1H), 4.19 (dd, J=3.94, 5.50 Hz, 2H), 3.83-3.96 (m, 1H), 3.65-3.71 (m, 2H), 3.51-3.60 (m, 6H), 3.39-3.44 (m, 2H), 3.20 (s, 3H), 2.47 (brs, 4H), 2.22-2.33 (m, 1H), 2.00-2.10 (m, 2H), 1.88-1.96 (m, 2H), 1.61-1.75 (m, 2H), 1.34-1.46 (m, 2H), 1.33 (d, J=6.14 Hz, 3H).

J) 5-(3-(((S)-1-(1H-tetrazol-1-yl)propan-2-yl)oxy)-4-chlorophenyl)-N-(3-(2-(2-methoxyethoxy) ethoxy)-1-((1r,4r)-4-morpholinocyclohexyl)-1H-pyrazol-4-yl)pyrimidin-2-amine hydrochloride 4 M Hydrogen chloride-ethyl acetate (68 uL) was added to a solution of 5-(3-(((S)-1-(1H-tetrazol-1-yl)propan-2-yl)oxy)-4-chlorophenyl)-N-(3-(2-(2-methoxyethoxy)ethoxy)-1-((r,4r)-4-morpholinocyclohexyl)-1H-pyrazol-4-yl)pyrimidin-2-amine (187 mg) in ethyl acetate (5.0 mL) at room temperature. EtOH (1.0 mL) was added at room temperature. The mixture was stirred at room temperature for 16 hr. The reaction mixture was concentrated with hexane under reduced pressure to give the title compound (176 mg).
$^1$H NMR (300 MHz, DMSO-d$_6$) δ 10.21-10.39 (m, 1H), 9.37 (s, 1H), 8.70 (s, 2H), 8.57 (s, 1H), 7.77 (s, 1H), 7.45 (d, J=8.25 Hz, 1H), 7.35 (d, J=1.47 Hz, 1H), 7.24 (dd, J=1.88, 8.30 Hz, 1H), 5.12-5.22 (m, 1H), 4.87-4.94 (m, 1H), 4.76-4.84 (m, 1H), 4.20 (dd, J=3.99, 5.46 Hz, 2H), 3.95-4.03 (m, 2H), 3.78 (t, J=12.38 Hz, 2H), 3.69 (dd, J=3.99, 5.46 Hz, 2H), 3.52-3.56 (m, 2H), 3.37-3.49 (m, 4H), 3.20 (s, 3H), 3.02-3.19 (m, 2H), 2.06-2.34 (m, 4H), 1.54-1.89 (m, 4H), 1.33 (d, J=6.14 Hz, 3H), 2H were hidden by DMSO; MS m/z 683.37 [M+1]+.

Example 86

5-(3-(((S)-1-(1H-tetrazol-1-yl) propan-2-yl)oxy)-4-chlorophenyl)-N-(1-((1r,4r)-4-((1R,5S)-3-oxa-8-azabicyclo[3.2.1]octan-8-yl)cyclohexyl)-3-(2-(methylsulfonyl)ethoxy)-1H-pyrazol-4-yl)pyrimidin-2-amine

A) ethyl 3-(2-methanesulfonylethoxy)-1H-pyrazole-4-carboxylate

To a mixture of ethyl 1-acetyl-3-hydroxy-1H-pyrazole-4-carboxylate (6.00 g), triphenylphosphane (11.8 g), 2-methanesulfonylethan-1-ol (5.62 g) and toluene (100 mL) was added DIAD (9.16 g), and the mixture was stirred at 70° C. for 15 hr. The mixture was concentrated under reduced pressure. The residue was purified by silica gel column chromatography (ethyl acetate/hexane) to give the title compound (2.80 g).

MS m/z 262.9 [M+H]+.

B) ethyl 1-{1,4-dioxaspiro[4.5]decan-8-yl}-3-(2-methanesulfonylethoxy)-1H-pyrazole-4-carboxylate 1,4-Dioxaspiro[4.5]decan-8-yl methanesulfonate (4.04 g) was added to a mixture of ethyl 3-(2-methanesulfonylethoxy)-1H-pyrazole-4-carboxylate (2.65 g) and potassium carbonate (4.18 g) in DMF (20 mL) at 100° C., and the mixture was stirred for 2 hr. The mixture was poured into water and extracted with ethyl acetate. The organic layer was separated, washed with saturated brine, dried over anhydrous magnesium sulfate and concentrated under reduced pressure. The residue was purified by silica gel column chromatography (NH, ethyl acetate/hexane) to give the title compound (2.34 g).

MS m/z 403.0 [M+H]+.

C) 1-{1,4-dioxaspiro[4.5]decan-8-yl}-3-(2-methanesulfonylethoxy)-1H-pyrazole-4-carboxylic acid 1 M Aqueous sodium hydroxide solution (11 ml) was added to a solution of ethyl 1-{1,4-dioxaspiro[4.5]decan-8-yl}-3-(2-methanesulfonylethoxy)-1H-pyrazole-4-carboxylate (2.34 g) in EtOH (20 mL) at 50° C., and the mixture was stirred for 15 hr. The mixture was poured into water and washed with ethyl acetate. The aqueous layer was neutralized with 1 M aqueous hydrogen chloride solution and extracted with ethyl acetate. The organic layer was separated, washed with saturated brine, dried over anhydrous magnesium sulfate and concentrated under reduced pressure to give the title compound (2.00 g). This product was subjected to the next reaction without further purification.

MS m/z 375.0 [M+H]+.

D) benzyl N-(1-{1,4-dioxaspiro[4.5]decan-8-yl}-3-(2-methanesulfonylethoxy)-1H-pyrazol-4-yl)carbamate DPPA (1.55 g) was added to a mixture of 1-{1,4-dioxaspiro[4.5]decan-8-yl}-3-(2-methanesulfonylethoxy)-1H-pyrazole-4-carboxylic acid (2.00 g), benzyl alcohol (1.14 g) and triethylamine (810 mg) in toluene (20 mL) at 100° C., and the mixture was stirred for 15 hr. The mixture was poured into water and extracted with ethyl acetate. The organic layer was separated, washed with saturated brine, dried over anhydrous magnesium sulfate and concentrated under reduced pressure. The residue was purified by silica gel column chromatography (ethyl acetate/hexane) to give the title compound (1.25 g).

MS m/z 480.1 [M+H]+.

E) benzyl N-[3-(2-methanesulfonylethoxy)-1-(4-oxocyclohexyl)-1H-pyrazol-4-yl]carbamate 1 M Aqueous hydrogen chloride solution (10 ml) was added to a solution of benzyl N-(1-{1,4-dioxaspiro[4.5] decan-8-yl}-3-(2-methanesulfonylethoxy)-1H-pyrazol-4-yl) carbamate (1.25 g) in THF (10 ml) at 50° C., and the mixture was stirred for 2 hr. The mixture was neutralized with saturated aqueous sodium hydrogencarbonate solution and extracted with ethyl acetate. The organic layer was separated, washed with saturated brine, dried over anhydrous magnesium sulfate and concentrated under reduced pressure to give the title compound (1.10 g). This product was subjected to the next reaction without further purification.

MS m/z 436.1 [M+H]+.

F) benzyl N-[3-(2-methanesulfonylethoxy)-1-[(1r,4r)-4-[(1R,5S)-3-oxa-8-azabicyclo[3.2.1]octan-8-yl] cyclohexyl]-1H-pyrazol-4-yl]carbamate 2-Methylpyridine-borane (539 mg) was added to a mixture of benzyl N-[3-(2-methanesulfonylethoxy)-1-(4-oxocyclohexyl)-1H-pyrazol-4-yl]carbamate (1.10 g), (1R,5S)-3-oxa-8-azabicyclo[3.2.1]octane hydrochloride (565 mg) and triethylamine (765 mg) in MeOH (10 mL) and AcOH (0.50 mL) at 50° C., and the mixture was stirred for 1 hr. The mixture was neutralized with saturated aqueous sodium hydrogencarbonate solution and extracted with ethyl acetate. The organic layer was separated, washed with saturated brine, dried over anhydrous magnesium sulfate and concentrated under reduced pressure. The residue was purified by silica gel column chromatography (NH, ethyl acetate/hexane) to give the title compound (445 mg).

MS m/z 533.2 [M+H]+.

G) 3-(2-methanesulfonylethoxy)-1-[(1r,4r)-4-[(1R,5S)-3-oxa-8-azabicyclo[3.2.1]octan-8-yl]cyclohexyl]-1H-pyrazol-4-amine A mixture of benzyl N-[3-(2-methanesulfonylethoxy)-1-[(1r,4r)-4-[(1R,5S)-3-oxa-8-azabicyclo[3.2.1]octan-8-yl]cyclohexyl]-1H-pyrazol-4-yl]carbamate (445 mg) and 10% palladium-carbon (50.0 mg) in EtOH (10 mL) was stirred under normal pressure of hydrogen atmosphere at 50° C. for 1 hr. The catalyst was removed by filtration, and then the filtrate was concentrated under reduced pressure to give the title compound (327 mg).

MS m/z 399.1 [M+H]+.

H) 5-(3-(((S)-1-(1H-tetrazol-1-yl)propan-2-yl)oxy)-4-chlorophenyl)-N-(1-((1r,4r)-4-((1R,5S)-3-oxa-8-azabicyclo[3.2.1]octan-8-yl)cyclohexyl)-3-(2-(methylsulfonyl) ethoxy)-1H-pyrazol-4-yl)pyrimidin-2-amine To a solution of 3-(2-methanesulfonylethoxy)-1-[(1r,4r)-4-[(1R,5S)-3-oxa-8-azabicyclo[3.2.1]octan-8-yl]cyclohexyl]-1H-pyrazol-4-amine (320 mg) in NMP (3.0 mL) were added 2-chloro-5-(4-chloro-3-{[(2S)-1-(1H-tetrazol-1-yl)propan-2-yl]oxy}phenyl)pyrimidine (421 mg) and methanesulfonic acid (330 mg) at room temperature, and the mixture was stirred at 110° C. for 6 hr. The mixture was poured into saturated aqueous sodium hydrogencarbonate solution and extracted with ethyl acetate. The organic layer was separated, washed with saturated brine, dried over anhydrous magnesium sulfate and concentrated under reduced pressure. The residue was purified by silica gel column chromatography (NH, ethyl acetate/hexane) to give the title compound (345 mg).

$^1$H NMR (300 MHz, DMSO-$d_6$) δ 9.37 (s, 1H), 8.71 (s, 2H), 8.59 (s, 1H), 7.84 (s, 1H), 7.44-7.47 (m, 1H), 7.36 (s, 1H), 7.23-7.26 (m, 1H), 5.13-5.22 (m, 1H), 4.76-4.94 (m, 2H), 4.33-4.48 (m, 3H), 3.58-3.65 (m, 2H), 3.47-3.54 (m, 2H), 3.36-3.43 (m, 2H), 3.18-3.28 (m, 2H), 2.91 (s, 3H), 2.05-2.16 (m, 3H), 1.85-1.96 (m, 2H), 1.65-1.77 (m, 4H), 1.29-1.47 (m, 5H), 1.06-1.21 (m, 2H); MS m/z 713.23 [M+1]+.

Example 129

2-(((S)-1-(1H-tetrazol-1-yl)propan-2-yl)oxy)-4-(2-((1-((1r,4r)-4-morpholinocyclohexyl)-3-(pyridin-2-ylmethoxy)-1H-pyrazol-4-yl)amino)pyrimidin-5-yl)benzonitrile A mixture of 5-(3-(((S)-1-(1H-tetrazol-1-yl)propan-2-yl)oxy)-4-chlorophenyl)-N-(1-((1r,4r)-4-morpholinocyclohexyl)-3-(pyridin-2-ylmethoxy)-1H-pyrazol-4-yl)pyrimidin-2-amine (42.0 mg), potassium hexacyanoferrate(II) trihydrate (46.0 mg), XPhos Pd G2 (5.00 mg), XPhos (6.00 mg), potassium acetate (18.0 mg), CPME (2.0 mL) and water (2.0 mL) was stirred under nitrogen atmosphere at 100° C. for 24 hr. After being cooled to room temperature, the mixture was poured into water and extracted with ethyl acetate. The organic layer was separated, washed with saturated brine, dried over anhydrous sodium sulfate and concentrated under reduced pressure. The residue was purified by preparative HPLC (water/CH$_3$CN containing 0.1% TFA). The desired fraction was neutralized with saturated aqueous sodium hydrogencarbonate solution and extracted with ethyl acetate. The organic layer was separated, dried over anhydrous sodium sulfate and concentrated under reduced pressure to give the title compound (10.0 mg).

$^1$H NMR (300 MHz, DMSO-d$_6$) δ 9.35 (s, 1H), 9.05 (s, 1H), 8.82 (s, 2H), 8.51-8.56 (m, 1H), 7.73-7.84 (m, 3H), 7.62 (d, J=7.79 Hz, 1H), 7.47 (s, 1H), 7.40 (dd, J=1.10, 8.16 Hz, 1H), 7.28-7.34 (m, 1H), 5.29-5.40 (m, 1H), 5.25 (s, 2H), 4.90-4.99 (m, 1H), 4.80-4.89 (m, 1H), 3.84-3.98 (m, 1H), 3.52-3.60 (m, 4H), 2.42-2.49 (m, 4H), 2.20-2.34 (m, 1H), 2.00-2.11 (m, 2H), 1.87-1.97 (m, 2H), 1.59-1.76 (m, 2H), 1.31-1.45 (m, 5H); MS m/z 663.34 [M+1]+.

Example 130

5-(3-(((S)-1-(1H-tetrazol-1-yl) propan-2-yl)oxy)-4-chlorophenyl)-N-(1-((1r,4r)-4-morpholinocyclohexyl)-3-(pyridin-2-ylmethoxy)-1H-pyrazol-4-yl)pyrimidin-2-amine A) ethyl 1-acetyl-3-[(pyridin-2-yl)methoxy]-1H-pyrazole-4-carboxylate To a mixture of ethyl 1-acetyl-3-hydroxy-1H-pyrazole-4-carboxylate (5.03 g), 2-pyridinemethanol (4.18 g) and triphenylphosphine (10.1 g) in toluene (100 mL) was added DIAD (7.6 mL). After being stirred at 80° C. for 14 hr, the mixture was concentrated under reduced pressure. The residue was purified by silica gel column chromatography (ethyl acetate/hexane) and subjected to the next reaction without further purification.

MS m/z 290.2 [M+H]+.

B) ethyl 1-{1,4-dioxaspiro[4.5]decan-8-yl}-3-[(pyridin-2-yl)methoxy]-1H-pyrazole-4-carboxylate To a mixture of ethyl 1-acetyl-3-[(pyridin-2-yl)methoxy]-1H-pyrazole-4-carboxylate (7.31 g), 1,4-dioxaspiro[4.5]decan-8-yl methanesulfonate (11.4 g) and DMF (80 mL) was added potassium carbonate (10.5 g). After being stirred at 100° C. for 4 hr, the mixture was poured into water and extracted with ethyl acetate. The organic layer was separated, washed with saturated brine, dried over anhydrous sodium sulfate and concentrated under reduced pressure. The residue was dissolved in toluene, and the solution was passed through NH silica gel pad (ethyl acetate/hexane) and concentrated under reduced pressure. The residue was subjected to the next reaction without further purification.

MS m/z 388.2 [M+H]+.

C) 1-{1,4-dioxaspiro[4.5]decan-8-yl}-3-[(pyridin-2-yl)methoxy]-1H-pyrazole-4-carboxylic acid To a mixture of ethyl 1-{1,4-dioxaspiro[4.5]decan-8-yl}-3-[(pyridin-2-yl)methoxy]-1H-pyrazole-4-carboxylate (9.76 g) and EtOH (80 mL) was added 2 M aqueous sodium hydroxide solution (25 mL). After being stirred at room temperature for 14 hr and at 80° C. for 1 hr, the mixture was diluted with ethyl acetate and extracted with water. The aqueous layer was separated, acidified with 6 M aqueous hydrogen chloride solution (ca. pH4) and extracted with ethyl acetate. The organic layer was separated, washed with saturated brine, dried over anhydrous sodium sulfate and concentrated under reduced pressure to give the title compound (4.74 g).

MS m/z 360.2 [M+H]+.

D) benzyl N-(1-{1,4-dioxaspiro[4.5]decan-8-yl}-3-[(pyridin-2-yl)methoxy]-1H-pyrazol-4-yl)carbamate To a mixture of 1-{1,4-dioxaspiro[4.5]decan-8-yl}-3-[(pyridin-2-yl)methoxy]-1H-pyrazole-4-carboxylic acid (4.74 g) and triethylamine (2.7 mL) in toluene (50 mL) was added DPPA (3.2 mL). After being stirred at room temperature for 5 min, benzyl alcohol (4.0 mL) was added to the mixture. After being stirred at 100° C. for 1 hr, the mixture was concentrated under reduced pressure. The residue was purified by silica gel column chromatography (ethyl acetate/hexane) to give the title compound (4.16 g).

MS m/z 465.3 [M+H]+.

E) benzyl N-[1-(4-oxocyclohexyl)-3-[(pyridin-2-yl)methoxy]-1H-pyrazol-4-yl]carbamate To a solution of benzyl N-(1-{1,4-dioxaspiro[4.5]decan-8-yl}-3-[(pyridin-2-yl)methoxy]-1H-pyrazol-4-yl)carbamate (1.18 g) in THF (20 mL) was added 2 M aqueous hydrogen chloride solution (3.0 mL). After being stirred at 60° C. for 2 hr, the mixture was neutralized with saturated aqueous sodium hydrogencarbonate solution at room temperature and extracted with ethyl acetate. The organic layer was separated, washed with saturated brine, dried over anhydrous sodium sulfate and concentrated under reduced pressure. The residue was subjected to the next reaction without further purification.

MS m/z 421.2 [M+H]+.

F) benzyl N-{3-[(pyridin-2-yl)methoxy]-1-[(1r,4r)-4-(morpholin-4-yl)cyclohexyl]-1H-pyrazol-4-yl}carbamate To a mixture of benzyl N-[1-(4-oxocyclohexyl)-3-[(pyridin-2-yl)methoxy]-1H-pyrazol-4-yl]carbamate (1.06 g), MeOH (10 mL) and AcOH (1.0 mL) was added morpholine (0.45 mL). After being stirred at room temperature for 5 min, 2-methylpyridine-borane (540 mg) was added to the mixture. After being stirred at room temperature for 1 hr, the mixture was neutralized with saturated aqueous sodium hydrogencarbonate solution and extracted with ethyl acetate.

The organic layer was separated, washed with saturated brine, dried over anhydrous sodium sulfate and concentrated under reduced pressure. The residue was purified by silica gel column chromatography (NH, ethyl acetate/hexane) to give the title compound (380 mg).

MS m/z 492.3 [M+H]+.

G) 5-(3-(((S)-1-(1H-tetrazol-1-yl)propan-2-yl)oxy)-4-chlorophenyl)-N-(1-((1r,4r)-4-morpholinocyclohexyl)-3-(pyridin-2-ylmethoxy)-1H-pyrazol-4-yl)pyrimidin-2-amine To a mixture of benzyl N-{3-[(pyridin-2-yl)methoxy]-1-[(1r,4r)-4-(morpholin-4-yl)cyclohexyl]-1H-pyrazol-4-yl}carbamate (380 mg), 10% palladium-carbon (83.0 mg) and MeOH (10 mL) was added methanesulfonic acid (60 µL). After being stirred under hydrogen atmosphere at room temperature for 1 hr, the insoluble material was removed by filtration, and the filtrate was concentrated under reduced pressure. The residue was dissolved in NMP (1.0 mL), and 2-chloro-5-(4-chloro-3-{[(2S)-1-(1H-tetrazol-1-yl)propan-2-yl]oxy}phenyl)pyrimidine (329 mg) was added to the mixture. After being stirred at 110° C. for 4 hr, the mixture was cooled to room temperature. The mixture was purified by silica gel column chromatography (NH, ethyl acetate/hexane) and by silica gel column chromatography (diol, ethyl acetate/hexane) to give the title compound (53.0 mg) and 4-{[5-(4-chloro-3-{[(2S)-1-(1H-tetrazol-1-yl)propan-2-yl]oxy}phenyl)pyrimidin-2-yl]amino}-1-[(r,4r)-4-(morpholin-4-yl)cyclohexyl]-1H-pyrazol-3-ol (140 mg).

Data for the Title Compound
¹H NMR (300 MHz, DMSO-d₆) δ 9.37 (s, 1H), 8.87 (s, 1H), 8.72 (s, 2H), 8.51-8.56 (m, 1H), 7.75-7.88 (m, 2H), 7.62 (d, J=7.70 Hz, 1H), 7.45 (d, J=8.25 Hz, 1H), 7.37 (d, J=1.74 Hz, 1H), 7.28-7.34 (m, 1H), 7.24 (dd, J=1.88, 8.30 Hz, 1H), 5.25 (s, 2H), 5.13-5.21 (m, 1H), 4.86-4.95 (m, 1H), 4.75-4.85 (m, 1H), 3.82-3.98 (m, 1H), 3.51-3.61 (m, 4H), 2.40-2.48 (m, 4H), 2.22-2.32 (m, 1H), 1.99-2.12 (m, 2H), 1.84-1.98 (m, 2H), 1.57-1.78 (m, 2H), 1.28-1.47 (m, 5H); MS m/z 672.38 [M+1]+.

Data for the Other Compound
¹H NMR (300 MHz, DMSO-d₆) δ 9.94 (brs, 1H), 9.37 (s, 1H), 8.81 (s, 1H), 8.73 (s, 2H), 7.60 (s, 1H), 7.45 (d, J=8.34 Hz, 1H), 7.38 (d, J=1.83 Hz, 1H), 7.25 (dd, J=1.88, 8.30 Hz, 1H), 5.11-5.24 (m, 1H), 4.87-4.95 (m, 1H), 4.75-4.85 (m, 1H), 3.75-3.92 (m, 1H), 3.52-3.62 (m, 4H), 2.42-2.49 (m, 4H), 2.19-2.32 (m, 1H), 1.98-2.07 (m, 2H), 1.86-1.96 (m, 2H), 1.57-1.74 (m, 2H), 1.26-1.43 (m, 5H); m/z 571.3 [M+H]+.

Example 142

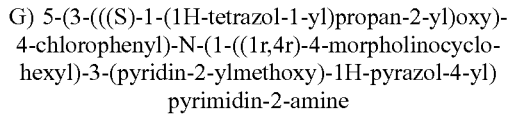

5-(3-(((S)-1-(1H-tetrazol-1-yl)propan-2-yl)oxy)-4-chlorophenyl)-N-(1-((1r,4r)-4-((1R,5S)-3-oxa-8-azabicyclo[3.2.1]octan-8-yl)cyclohexyl)-3-(3-(methylsulfonyl)propoxy)-1H-pyrazol-4-yl)pyrimidin-2-amine A) ethyl 1-acetyl-3-[3-(methylsulfanyl)propoxy]-1H-pyrazole-4-carboxylate To a mixture of ethyl 1-acetyl-3-hydroxy-1H-pyrazole-4-carboxylate (6.00 g), triphenylphosphane (11.8 g) and 3-(methylsulfanyl)propan-1-ol (4.80 g) in toluene (100 mL) was added DIAD (9.16 g) stirred at 70° C. for 15 hr. The mixture was concentrated under reduced pressure. The residue was purified by silica gel column chromatography (ethyl acetate/hexane) to give the title compound (1.97 g).

MS m/z 287.2 [M+H]+.

B) ethyl 1-{1,4-dioxaspiro[4.5]decan-8-yl}-3-[3-(methylsulfanyl)propoxy]-1H-pyrazole-4-carboxylate Cesium carbonate (6.71 g) was added to a solution of ethyl 1-acetyl-3-[3-(methylsulfanyl)propoxy]-1H-pyrazole-4-carboxylate (1.97 g) in DMF (30 mL) at 100° C., and the mixture was stirred for 1 hr. To the mixture was added 1,4-dioxaspiro[4.5]decan-8-yl methanesulfonate (2.74 g), and the mixture was stirred at 100° C. for 2 hr. The mixture was poured into water and extracted with ethyl acetate. The organic layer was separated, washed with saturated brine, dried over anhydrous magnesium sulfate and concentrated under reduced pressure. The residue was purified by silica gel column chromatography (ethyl acetate/hexane) to give the title compound (2.54 g).

MS m/z 385.2 [M+H]+.

C) ethyl 1-{1,4-dioxaspiro[4.5]decan-8-yl}-3-(3-methanesulfonylpropoxy)-1H-pyrazole-4-carboxylate A solution of ethyl 1-{1,4-dioxaspiro[4.5]decan-8-yl}-3-[3-(methylsulfanyl)propoxy]-1H-pyrazole-4-carboxylate (2.54 g) in MeOH (30 ml) was added dropwise to a solution of oxone (10.1 g) in water (30 mL) at 0° C., and the mixture was stirred for 1 hr. The mixture was poured into saturated aqueous sodium hydrogencarbonate solution and extracted with ethyl acetate. The organic layer was separated, washed with saturated brine, dried over anhydrous magnesium sulfate and concentrated under reduced pressure to give the title compound (2.90 g). This product was subjected to the next reaction without further purification.

MS m/z 417.2 [M+H]+.

D) 1-{1,4-dioxaspiro[4.5]decan-8-yl}-3-(3-methanesulfonylpropoxy)-1H-pyrazole-4-carboxylic acid 1 M Aqueous sodium hydroxide solution (14 mL) was added to a solution of ethyl 1-{1,4-dioxaspiro[4.5]decan-8-yl}-3-(3-methanesulfonylpropoxy)-1H-pyrazole-4-carboxylate (2.90 g) in EtOH (20 mL) at room temperature, and the mixture was stirred for 3 days. The mixture was poured into water and washed with ethyl acetate. The aqueous layer was neutralized with 1 M aqueous hydrogen chloride solution and extracted with ethyl acetate. The organic layer was separated, washed with saturated brine, dried over anhydrous magnesium sulfate and concentrated under reduced pressure to give the title compound (2.70 g). This product was subjected to the next reaction without further purification.

MS m/z 389.2 [M+H]+.

E) benzyl N-(1-{1,4-dioxaspiro[4.5]decan-8-yl}-3-(3-methanesulfonylpropoxy)-1H-pyrazol-4-yl)carbamate DPPA (3.57 g) was added to a mixture of 1-{1,4-dioxaspiro[4.5]decan-8-yl}-3-(3-methanesulfonylpropoxy)-1H-pyrazole-4-carboxylic acid (4.80 g), benzyl alcohol (2.66 g) and triethylamine (1.86 g) in toluene (50 mL) at 100° C., and the mixture was stirred for 1 hr. The mixture was poured into water and extracted with ethyl acetate. The organic layer was separated, washed with saturated brine, dried over anhydrous magnesium sulfate and concentrated under reduced pressure. The residue was purified by silica gel column chromatography (NH, ethyl acetate/hexane) to give the title compound (4.40 g).

MS m/z 494.2 [M+H]+.

F) benzyl N-[3-(3-methanesulfonylpropoxy)-1-(4-oxocyclohexyl)-1H-pyrazol-4-yl]carbamate 1 M Aqueous hydrogen chloride solution (6.0 mL) was added to a solution of benzyl N-(1-{1,4-dioxaspiro[4.5]decan-8-yl}-3-(3-methanesulfonylpropoxy)-1H-pyrazol-4-yl)carbamate (1.54 g) in THF (10 mL) at 50° C., and the mixture was stirred for 2 hr. The mixture was neutralized with saturated aqueous sodium hydrogencarbonate solution and extracted with ethyl acetate. The organic layer was separated, washed with saturated brine, dried over anhydrous magnesium sulfate and concentrated under reduced pressure to give the title compound (1.40 g). This product was subjected to the next reaction without further purification.

MS m/z 450.2 [M+H]+.

G) benzyl N-[3-(3-methanesulfonylpropoxy)-1-[(1r,4r)-4-[(1R,5S)-3-oxa-8-azabicyclo[3.2.1]octan-8-yl]cyclohexyl]-1H-pyrazol-4-yl]carbamate 2-Methylpyridine-borane (665 mg) was added to a mixture of benzyl N-[3-(3-methanesulfonylpropoxy)-1-(4-oxocyclohexyl)-1H-pyrazol-4-yl]carbamate (1.40 g), (1R,5S)-3-oxa-8-azabicyclo[3.2.1]octane hydrochloride (697 mg) and triethylamine (944 mg) in MeOH (10 mL) and AcOH (0.50 mL) at 50° C., and the mixture was stirred for 15 hr. The mixture was neutralized with saturated aqueous sodium hydrogencarbonate solution and extracted with ethyl acetate. The organic layer was separated, washed with saturated brine, dried over anhydrous magnesium sulfate and concentrated under reduced pressure. The residue was purified by silica gel column chromatography (NH, ethyl acetate/hexane) to give the title compound (720 mg).

MS m/z 547.3 [M+H]+.

H) 3-(3-methanesulfonylpropoxy)-1-[(r,4r)-4-[(1R,5S)-3-oxa-8-azabicyclo[3.2.1]octan-8-yl]cyclohexyl]-1H-pyrazol-4-amine A mixture of benzyl N-[3-(3-methanesulfonylpropoxy)-1-[(1r,4r)-4-[(1R,5S)-3-oxa-8-azabicyclo[3.2.1]octan-8-yl]cyclohexyl]-1H-pyrazol-4-yl]carbamate (610 mg) and 10% palladium-carbon (70 mg) in EtOH (20 mL) was stirred under normal pressure of hydrogen atmosphere at 50° C. for 1 hr. The catalyst was removed by filtration, and then the filtrate was concentrated under reduced pressure to give the title compound (445 mg).

MS m/z 413.3 [M+H]+.

I) 5-(3-(((S)-1-(1H-tetrazol-1-yl)propan-2-yl)oxy)-4-chlorophenyl)-N-(1-((1r,4r)-4-((1R,5S)-3-oxa-8-azabicyclo[3.2.1]octan-8-yl)cyclohexyl)-3-(3-(methylsulfonyl)propoxy)-1H-pyrazol-4-yl)pyrimidin-2-amine To a solution of 3-(3-methanesulfonylpropoxy)-1-[(1r,4r)-4-[(1R,5S)-3-oxa-8-azabicyclo[3.2.1]octan-8-yl]cyclohexyl]-1H-pyrazol-4-amine (425 mg) in NMP (3.0 mL) were added 2-chloro-5-(4-chloro-3-{[(2S)-1-(1H-tetrazol-1-yl)propan-2-yl]oxy}phenyl)pyrimidine (540 mg) and methanesulfonic acid (296 mg) at room temperature, and the mixture was stirred at 110° C. for 15 hr. The mixture was poured into saturated aqueous sodium hydrogencarbonate solution and extracted with ethyl acetate. The organic layer was separated, washed with saturated brine, dried over anhydrous magnesium sulfate and concentrated under reduced pressure. The residue was purified by silica gel column chromatography (NH, ethyl acetate/hexane) to give the title compound (375 mg).

$^1$H NMR (300 MHz, DMSO-$d_6$) δ 9.37 (s, 1H), 8.77 (s, 1H), 8.72 (s, 2H), 7.79 (s, 1H), 7.44-7.47 (m, 1H), 7.37 (s, 1H), 7.23-7.26 (m, 1H), 5.13-5.22 (m, 1H), 4.77-4.94 (m, 2H), 4.18-4.22 (m, 3H), 3.87-3.96 (m, 1H), 3.50-3.54 (m, 2H), 3.39-3.43 (m, 2H), 3.27-3.34 (m, 4H), 2.97 (s, 3H), 2.05-2.16 (m, 2H), 1.97-2.17 (m, 5H), 1.61-1.81 (m, 6H), 1.33 (d, J=6 Hz, 2H), 1.11-1.22 (m, 2H); MS m/z 727.33 [M+1]$^+$.

Example 143

2-(((S)-1-(1H-tetrazol-1-yl)propan-2-yl)oxy)-4-(2-((1-((1r,4r)-4-((2S,6R)-2,6-dimethylmorpholino)cyclohexyl)-3-(3-methoxypropoxy)-1H-pyrazol-4-yl)amino)pyrimidin-5-yl)benzonitrile A) benzyl N-[3-(3-methoxypropoxy)-1-[(1r,4r)-4-[(2R,6S)-2,6-dimethylmorpholin-4-yl]cyclohexyl]-1H-pyrazol-4-yl]carbamate To a mixture of benzyl N-[3-(3-methoxypropoxy)-1-(4-oxocyclohexyl)-1H-pyrazol-4-yl]carbamate (4.31 g), cis-2,6-dimethylmorpholine (2.46 g) and AcOH (3.0 mL) in MeOH (20 mL) and THF (20 mL) was added 2-methylpyridine-borane (3.42 g) at room temperature. The mixture was stirred at 60° C. for 2 hr. The mixture was neutralized with saturated aqueous sodium hydrogencarbonate solution at 0° C. and extracted with ethyl acetate. The organic layer was separated, washed with saturated brine, dried over anhydrous magnesium sulfate and concentrated under reduced pressure. The residue was purified by silica gel column chromatography (NH, ethyl acetate/hexane) to give the title compound (1.26 g).

MS m/z 501.3 [M+H]$^+$.

B) 3-(3-methoxypropoxy)-1-[(1r,4r)-4-[(2R,6S)-2,6-dimethylmorpholin-4-yl]cyclohexyl]-1H-pyrazol-4-amine dihydrochloride A mixture of benzyl N-[3-(3-methoxypropoxy)-1-[(1r,4r)-4-[(2R,6S)-2,6-dimethylmorpholin-4-yl]cyclohexyl]-1H-pyrazol-4-yl]carbamate (1.24 g), 4 M hydrogen chloride-ethyl acetate (10 mL) and 10% palladium-carbon (300 mg) in EtOH (50 mL) was stirred under normal pressure of hydrogen atmosphere at 80° C. for 2 hr. The catalyst was removed by filtration, and then the filtrate was concentrated under reduced pressure to give the title compound (850 mg). This product was subjected to the next reaction without further purification.

MS m/z 367.3 [M+H]+.

C) 5-bromo-N-[3-(3-methoxypropoxy)-1-[(1r,4r)-4-[(2R,6S)-2,6-dimethylmorpholin-4-yl]cyclohexyl]-1H-pyrazol-4-yl]pyrimidin-2-amine To a solution of 3-(3-methoxypropoxy)-1-[(1r,4r)-4-[(2R,6S)-2,6-dimethylmorpholin-4-yl]cyclohexyl]-1H-pyrazol- 4-amine dihydrochloride (840 mg) in NMP (30 mL) were added 5-bromo-2-chloropyrimidine (529 mg) and methanesulfonic acid (659 mg) at room temperature, and the mixture was stirred at 110° C. for 12 hr. The mixture was poured into saturated aqueous sodium hydrogencarbonate solution and extracted with ethyl acetate. The organic layer was separated, washed with saturated brine, dried over anhydrous magnesium sulfate and concentrated under reduced pressure. The residue was purified by silica gel column chromatography (NH, ethyl acetate/hexane) to give the title compound (730 mg).

MS m/z 523.22 [M+H]⁺.

D) 2-(((S)-1-(1H-tetrazol-1-yl)propan-2-yl)oxy)-4-(2-((1-((1r,4r)-4-((2S,6R)-2,6-dimethylmorpholino) cyclohexyl)-3-(3-methoxypropoxy)-1H-pyrazol-4-yl)amino)pyrimidin-5-yl)benzonitrile To a mixture of 4-(4,4,5,5-tetramethyl-1,3,2-dioxaborolan-2-yl)-2-{[(2S)-1-(1H-tetrazol-1-yl)propan-2-yl] oxy}benzonitrile (731 mg), 5-bromo-N-[3-(3-methoxypropoxy)-1-[(1r,4r)-4-[(2R,6S)-2,6-dimethylmorpholin-4-yl]cyclohexyl]-1H-pyrazol-4-yl]pyrimidin-2-amine (360 mg) and 2 M aqueous sodium carbonate solution (3.0 mL) in DME (5.0 mL) was added Pd(dppf)Cl₂ (75.8 mg). After being stirred under nitrogen atmosphere at 80° C. for 12 hr, the mixture was diluted with ethyl acetate and water, and passed through celite powder. The organic layer was separated, washed with saturated brine, dried over anhydrous magnesium sulfate and concentrated under reduced pressure. The residue was purified by silica gel column chromatography (NH, ethyl acetate/hexane) and silica gel column chromatography (MeOH/ethyl acetate) and crystallized from EtOH/IPE to give the title compound (110 mg).

¹H NMR (300 MHz, CDCl₃) δ 8.96 (s, 1H), 8.55 (s, 2H), 7.88 (s, 1H), 7.62 (d, J=8.1 Hz, 1H), 7.12-7.24 (m, 1H), 7.06 (s, 1H), 6.85 (s, 1H), 4.91-5.01 (m, 1H), 4.82-4.91 (m, 1H), 4.68-4.80 (m, 1H), 4.32 (t, J=6.2 Hz, 2H), 3.89 (t, J=11.8 Hz, 1H), 3.61-3.73 (m, 2H), 3.56 (t, J=6.2 Hz, 2H), 3.38 (s, 3H), 2.77 (d, J=10.7 Hz, 2H), 2.17-2.37 (m, 3H), 1.99-2.13 (m, 4H), 1.95 (t, J=10.6 Hz, 2H), 1.67-1.84 (m, 2H), 1.35-1.54 (m, 5H), 1.18 (d, J=6.2 Hz, 6H); MS m/z 672.45 [M+1]⁺.

Example 150

2-(((S)-1-(1H-tetrazol-1-yl)propan-2-yl)oxy)-4-(2-((3-(4-methoxybutoxy)-1-((1r,4r)-4-morpholinocyclohexyl)-1H-pyrazol-4-yl)amino)pyrimidin-5-yl)benzonitrile A mixture of 5-(3-(((S)-1-(1H-tetrazol-1-yl)propan-2-yl)oxy)-4-chlorophenyl)-N-(3-(4-methoxybutoxy)-1-((1r,4r)-4-morpholinocyclohexyl)-1H-pyrazol-4-yl)pyrimidin-2-amine (30.0 mg), potassium hexacyanoferrate(II) trihydrate (35.0 mg), XPhos Pd G2 (4.00 mg), XPhos (5.00 mg), potassium acetate (14.0 mg), CPME (2.0 mL) and water (2.0 mL) was stirred under nitrogen atmosphere at 100° C. for 14 hr. After being cooled to room temperature, the mixture was poured into water and extracted with ethyl acetate. The organic layer was separated, washed with saturated brine, dried over anhydrous sodium sulfate and concentrated under reduced pressure. The residue was purified by silica gel column chromatography (MeOH/ethyl acetate) and by silica gel column chromatography (NH, ethyl acetate/hexane). The obtained solid was crystallized from ethyl acetate/hexane to give the title compound (15.0 mg).

¹H NMR (300 MHz, DMSO-d₆) δ 9.35 (s, 1H), 8.72-8.82 (m, 3H), 7.70-7.78 (m, 2H), 7.46 (s, 1H), 7.39 (dd, J=1.28, 8.16 Hz, 1H), 5.28-5.43 (m, 1H), 4.90-4.98 (m, 1H), 4.79- 4.89 (m, 1H), 4.08 (t, J=6.19 Hz, 2H), 3.78-3.96 (m, 1H), 3.50-3.72 (m, 4H), 3.28-3.30 (m, 2H), 3.18 (s, 3H), 2.45-2.49 (m, 4H), 2.23-2.33 (m, 1H), 2.00-2.13 (m, 2H), 1.85-1.98 (m, 2H), 1.52-1.77 (m, 6H), 1.27-1.46 (m, 5H); MS m/z 658.42 [M+1]+.

Example 151

5-(3-(((S)-1-(1H-tetrazol-1-yl) propan-2-yl)oxy)-4-chlorophenyl)-N-(3-(4-methoxybutoxy)-1-((1r,4r)-4-morpholinocyclohexyl)-1H-pyrazol-4-yl)pyrimidin-2-amine To a mixture of 4-{[5-(4-chloro-3-{[(2S)-1-(1H-tetrazol-1-yl)propan-2-yl]oxy}phenyl)pyrimidin-2-yl]amino}-1-[(r,4r)-4-(morpholin-4-yl)cyclohexyl]-1H-pyrazol-3-ol (127 mg), 4-methoxybutan-1-ol (37 μL) and triphenylphosphine (85.0 mg) in THF (5.0 mL) was added DIAD (65 μL). After being stirred at 70° C. for 24 hr, the mixture was concentrated under reduced pressure. The residue was purified by silica gel column chromatography (NH, ethyl acetate/ hexane), by silica gel column chromatography (MeOH/ethyl acetate) and by preparative HPLC (water/CH₃CN containing 0.1% TFA). The desired fraction was neutralized with saturated aqueous sodium hydrogencarbonate solution and extracted with ethyl acetate. The organic layer was separated, dried over anhydrous sodium sulfate and concentrated under reduced pressure to give the title compound (35.0 mg).

¹H NMR (300 MHz, DMSO-d₆) δ 9.37 (s, 1H), 8.69 (s, 2H), 8.56 (s, 1H), 7.71 (s, 1H), 7.45 (d, J=8.44 Hz, 1H), 7.36 (d, J=1.83 Hz, 1H), 7.23 (dd, J=1.83, 8.25 Hz, 1H), 5.11-5.23 (m, 1H), 4.86-4.95 (m, 1H), 4.75-4.85 (m, 1H), 4.08 (t, J=6.14 Hz, 2H), 3.80-3.95 (m, 1H), 3.50-3.63 (m, 4H), 3.28-3.31 (m, 2H), 3.18 (s, 3H), 2.41-2.49 (m, 4H), 2.20-2.33 (m, 1H), 1.99-2.12 (m, 2H), 1.85-1.98 (m, 2H), 1.52-1.75 (m, 6H), 1.28-1.45 (m, 5H); MS m/z 667.35 [M+1]⁺.

Example 240

5-(3-(((S)-1-(1H-tetrazol-1-yl) propan-2-yl)oxy)-4-chlorophenyl)-N-(1-((1r,4r)-4-((2S,6R)-2,6-dimethylmorpholino)cyclohexyl)-3-(2-(2-methoxyethoxy) ethoxy)-1H-pyrazol-4-yl)pyrimidin-2-amine hydrochloride A) benzyl N-{3-[2-(2-methoxyethoxy)ethoxy]-1-[(1r,4r)-4-[(2R,6S)-2,6-dimethylmorpholin-4-yl] cyclohexyl]-1H-pyrazol-4-yl}carbamate A mixture of benzyl N-{3-[2-(2-methoxyethoxy)ethoxy]-1-(4-oxocyclohexyl)-1H-pyrazol-4-yl}carbamate (900 mg), cis-2,6-dimethylmorpholine (718 mg) and 2-methylpyridine-borane (654 mg) in MeOH (10 mL) and AcOH (1.0 mL) was stirred at 60° C. for 1.5 hr under argon atmosphere. The reaction mixture was concentrated under reduced pressure. The residue was partitioned between ethyl acetate and aqueous sodium hydrogen carbonate. The organic layer was washed with saturated brine, dried over anhydrous sodium sulfate and concentrated under reduced pressure. The residue was purified by silica gel column chromatography (NH, ethyl acetate/hexane) to give the title compound (425 mg).

MS m/z 531.4 [M+H]+.

B) 3-[2-(2-methoxyethoxy)ethoxy]-1-[(1r,4r)-4-[(2R,6S)-2,6-dimethylmorpholin-4-yl]cyclohexyl]-1H-pyrazol-4-amine dihydrochloride A mixture of benzyl N-{3-[2-(2-methoxyethoxy)ethoxy]-1-[(1r,4r)-4-[(2R,6S)-2,6-dimethylmorpholin-4-yl]cyclohexyl]-1H-pyrazol-4-yl}carbamate (422 mg) and 10% palladium-carbon (76.9 mg) in 4 M hydrogen chloride-ethyl acetate (2.0 mL) was stirred at 50° C. for 1 hr under normal pressure of hydrogen atmosphere. The reaction mixture was filtered. The filtrate was concentrated under reduced pressure to give the title compound. This product was subjected to the next reaction without further purification.

MS m/z 397.3 [M+H]+.

C) 5-(3-(((S)-1-(1H-tetrazol-1-yl)propan-2-yl)oxy)-4-chlorophenyl)-N-(1-((1r,4r)-4-((2S,6R)-2,6-dimethylmorpholino)cyclohexyl)-3-(2-(2-methoxyethoxy)ethoxy)-1H-pyrazol-4-yl)pyrimidin-2-amine A mixture of 3-[2-(2-methoxyethoxy)ethoxy]-1-[(1r,4r)-4-[(2R,6S)-2,6-dimethylmorpholin-4-yl]cyclohexyl]-1H-pyrazol-4-amine dihydrochloride (373 mg) and 2-chloro-5-(4-chloro-3-{[(2S)-1-(1H-tetrazol-1-yl)propan-2-yl]oxy}phenyl)pyrimidine (361 mg) in NMP (3.0 mL) was stirred at 120° C. for 13 hr. The reaction mixture was partitioned between ethyl acetate and aqueous sodium hydrogen carbonate. The organic layer was washed with saturated brine, dried over anhydrous sodium sulfate and concentrated under reduced pressure. The residue was purified by silica gel column chromatography (NH, ethyl acetate/hexane) to give the title compound (342 mg).

$^1$H NMR (300 MHz, DMSO-$d_6$) δ 9.37 (s, 1H), 8.70 (s, 2H), 8.52 (s, 1H), 7.73 (s, 1H), 7.45 (d, J=8.25 Hz, 1H), 7.36 (d, J=1.83 Hz, 1H), 7.24 (dd, J=1.83, 8.34 Hz, 1H), 5.17 (dt, J=3.71, 6.30 Hz, 1H), 4.87-4.95 (m, 1H), 4.75-4.85 (m, 1H), 4.17-4.23 (m, 2H), 3.82-3.94 (m, 1H), 3.68 (dd, J=3.85, 5.59 Hz, 2H), 3.47-3.57 (m, 4H), 3.39-3.43 (m, 2H), 3.20 (s, 3H), 2.69-2.74 (m, 2H), 2.23-2.31 (m, 1H), 2.01-2.10 (m, 2H), 1.81-1.94 (m, 4H), 1.60-1.74 (m, 2H), 1.34-1.46 (m, 2H), 1.33 (d, J=6.14 Hz, 3H), 1.04 (d, J=6.33 Hz, 6H).

D) 5-(3-(((S)-1-(1H-tetrazol-1-yl)propan-2-yl)oxy)-4-chlorophenyl)-N-(1-((1r,4r)-4-((2S,6R)-2,6-dimethylmorpholino)cyclohexyl)-3-(2-(2-methoxyethoxy)ethoxy)-1H-pyrazol-4-yl)pyrimidin-2-amine hydrochloride 4 M Hydrogen chloride-ethyl acetate (65 uL) was added to a solution of 5-(3-(((S)-1-(1H-tetrazol-1-yl)propan-2-yl)oxy)-4-chlorophenyl)-N-(1-((1r,4r)-4-((2S,6R)-2,6-dimethylmorpholino)cyclohexyl)-3-(2-(2-methoxyethoxy)ethoxy)-1H-pyrazol-4-yl)pyrimidin-2-amine (185 mg) in ethyl acetate (5.0 mL) and EtOH (1.0 mL). The mixture was stirred at room temperature for 16 hr. The reaction mixture was concentrated with hexane under reduced pressure to give the title compound (169 mg).

$^1$H NMR (300 MHz, DMSO-$d_6$) δ 10.30-10.52 (m, 1H), 9.38 (s, 1H), 8.70 (s, 2H), 8.57 (s, 1H), 7.77 (s, 1H), 7.45 (d, J=8.34 Hz, 1H), 7.35 (d, J=1.65 Hz, 1H), 7.24 (dd, J=1.83, 8.25 Hz, 1H), 5.10-5.23 (m, 1H), 4.86-4.94 (m, 1H), 4.76-4.85 (m, 1H), 4.20 (dd, J=3.94, 5.50 Hz, 2H), 3.87-4.05 (m, 3H), 3.66-3.72 (m, 2H), 3.52-3.56 (m, 2H), 3.46 (brs, 1H), 3.39-3.43 (m, 3H), 3.26 (dd, J=3.16, 4.26 Hz, 1H), 3.20 (s, 3H), 2.61-2.74 (m, 2H), 2.10-2.32 (m, 4H), 1.59-1.84 (m, 4H), 1.33 (d, J=6.14 Hz, 3H), 1.16 (d, J=5.87 Hz, 6H); MS m/z 711.35 [M+1]+.

Example 241

2-(((S)-1-(1H-tetrazol-1-yl)propan-2-yl)oxy)-4-(2-((1-((1r,4r)-4-((2S,6R)-2,6-dimethylmorpholino)cyclohexyl)-3-(2-(2-methoxyethoxy)ethoxy)-1H-pyrazol-4-yl)amino)pyrimidin-5-yl)benzonitrile hydrochloride A) 2-(((S)-1-(1H-tetrazol-1-yl)propan-2-yl)oxy)-4-(2-((1-((1r,4r)-4-((2S,6R)-2,6-dimethylmorpholino)cyclohexyl)-3-(2-(2-methoxyethoxy)ethoxy)-1H-pyrazol-4-yl)amino)pyrimidin-5-yl)benzonitrile A mixture of 5-(3-(((S)-1-(1H-tetrazol-1-yl)propan-2-yl)oxy)-4-chlorophenyl)-N-(1-((1r,4r)-4-((2S,6R)-2,6-dimethylmorpholino)cyclohexyl)-3-(2-(2-methoxyethoxy)ethoxy)-1H-pyrazol-4-yl)pyrimidin-2-amine (135 mg), potassium hexacyanoferrate(II) trihydrate (160 mg), XPhos Pd G2 (14.9 mg), XPhos (18.0 mg) and potassium acetate (55.8 mg) in CPME (6.0 mL) and water (6.0 mL) was stirred at 110° C. for 14.5 hr under argon atmosphere. The reaction mixture was partitioned between ethyl acetate and water. The organic layer was washed with saturated brine, dried over anhydrous sodium sulfate and concentrated under reduced pressure. The residue was purified by silica gel column chromatography (NH, ethyl acetate/hexane) to give the title compound (86.2 mg).

$^1$H NMR (300 MHz, CDCl$_3$) δ 8.96 (s, 1H), 8.54 (s, 2H), 7.89 (s, 1H), 7.62 (d, J=7.98 Hz, 1H), 7.29 (s, 1H), 7.17 (dd, J=1.47, 8.07 Hz, 1H), 6.85 (d, J=1.28 Hz, 1H), 4.91-5.01 (m, 1H), 4.83-4.90 (m, 1H), 4.68-4.76 (m, 1H), 4.38-4.42 (m, 2H), 3.83-3.93 (m, 3H), 3.71-3.75 (m, 2H), 3.64-3.70 (m, 2H), 3.59-3.63 (m, 2H), 3.40 (s, 3H), 2.77 (d, J=10.27 Hz, 2H), 2.21-2.37 (m, 3H), 2.05-2.12 (m, 2H), 1.95 (t, J=10.68 Hz, 2H), 1.68-1.83 (m, 2H), 1.52 (d, J=6.14 Hz, 3H), 1.34-1.47 (m, 2H), 1.18 (d, J=6.24 Hz, 6H).

B) 2-(((S)-1-(1H-tetrazol-1-yl)propan-2-yl)oxy)-4-(2-((1-((1r,4r)-4-((2S,6R)-2,6-dimethylmorpholino)cyclohexyl)-3-(2-(2-methoxyethoxy)ethoxy)-1H-pyrazol-4-yl)amino)pyrimidin-5-yl)benzonitrile hydrochloride 4 M Hydrogen chloride-ethyl acetate (29 uL) was added to a solution of 2-(((S)-1-(1H-tetrazol-1-yl)propan-2-yl)oxy)-4-(2-((1-((1r,4r)-4-((2S,6R)-2,6-dimethylmorpholino)cyclohexyl)-3-(2-(2-methoxyethoxy)ethoxy)-1H-pyrazol-4-yl)amino)pyrimidin-5-yl)benzonitrile (81.2 mg) in ethyl acetate (3.0 mL) and EtOH (0.30 mL). The mixture was stirred at room temperature for 16 hr. The reaction mixture was concentrated with hexane under reduced pressure to give the title compound (57.2 mg).

$^1$H NMR (300 MHz, DMSO-$d_6$) δ 9.35 (s, 1H), 8.79 (s, 2H), 8.69-8.76 (m, 1H), 7.75 (d, J=8.07 Hz, 2H), 7.46 (s, 1H), 7.39 (dd, J=1.24, 8.21 Hz, 1H), 5.30-5.39 (m, 1H), 4.91-4.98 (m, 1H), 4.80-4.89 (m, 1H), 4.20 (dd, J=3.90, 5.55 Hz, 2H), 3.82-4.05 (m, 2H), 3.68 (dd, J=3.94, 5.41 Hz, 2H), 3.51-3.56 (m, 3H), 3.37-3.45 (m, 3H), 3.20 (s, 3H), 2.65-2.77 (m, 2H), 2.14-2.38 (m, 2H), 2.00-2.13 (m, 2H), 1.81-1.96 (m, 3H), 1.57-1.79 (m, 3H), 1.35 (d, J=6.05 Hz, 3H), 0.95-1.13 (m, 6H); MS m/z 702.42 [M+1]$^+$.

Example 242

5-(3-(((S)-1-(1H-tetrazol-1-yl) propan-2-yl)oxy)-4-chlorophenyl)-N-(1-((1r,4r)-4-((1R,5S)-3-oxa-8-azabicyclo[3.2.1]octan-8-yl)cyclohexyl)-3-(3-ethoxypropoxy)-1H-pyrazol-4-yl)pyrimidin-2-amine A) benzyl N-[3-(3-ethoxypropoxy)-1-[(1r,4r)-4-[(1R,5S)-3-oxa-8-azabicyclo[3.2.1]octan-8-yl]cyclohexyl]-1H-pyrazol-4-yl]carbamate A mixture of (1R,5S)-3-oxa-8-azabicyclo[3.2.1]octane hydrochloride (1.00 g) and triethylamine (1.87 mL) in MeOH (20 mL) was stirred at room temperature for 10 min. Benzyl N-[3-(3-ethoxypropoxy)-1-(4-oxocyclohexyl)-1H-pyrazol-4-yl]carbamate (1.87 g), AcOH (1.0 mL) and 2-methylpyridine-borane (962 mg) were added to the mixture at room temperature. The mixture was stirred at 50° C. for 14 hr. The mixture was neutralized with saturated aqueous sodium hydrogencarbonate solution at 0° C. and extracted with ethyl acetate. The organic layer was separated, washed with saturated brine, dried over anhydrous magnesium sulfate and concentrated under reduced pressure. The residue was purified by silica gel column chromatography (NH, ethyl acetate/hexane) to give the title compound (900 mg).
MS m/z 513.3 [M+H]$^+$.

B) 3-(3-ethoxypropoxy)-1-[(1r,4r)-4-[(1R,5S)-3-oxa-8-azabicyclo[3.2.1]octan-8-yl]cyclohexyl]-1H-pyrazol-4-amine A mixture of benzyl N-[3-(3-ethoxypropoxy)-1-[(1r,4r)-4-[(1R,5S)-3-oxa-8-azabicyclo[3.2.1]octan-8-yl]cyclohexyl]-1H-pyrazol-4-yl]carbamate (900 mg) and 10% palladium-carbon (186 mg) in EtOH (30 mL) and THF (10 mL) was stirred under normal pressure of hydrogen atmosphere at room temperature for 2 hr. The catalyst was removed by filtration, and then the filtrate was concentrated under reduced pressure to give the title compound (662 mg). This product was subjected to the next reaction without further purification.
MS m/z 379.3 [M+H]$^+$.

C) 5-(3-(((S)-1-(1H-tetrazol-1-yl)propan-2-yl)oxy)-4-chlorophenyl)-N-(1-((1r,4r)-4-((1R,5S)-3-oxa-8-azabicyclo[3.2.1]octan-8-yl)cyclohexyl)-3-(3-ethoxypropoxy)-1H-pyrazol-4-yl)pyrimidin-2-amine To a mixture of 3-(3-ethoxypropoxy)-1-[(1r,4r)-4-[(1R,5S)-3-oxa-8-azabicyclo[3.2.1]octan-8-yl]cyclohexyl]-1H-pyrazol-4-amine (662 mg) and 2-chloro-5-(4-chloro-3-{[(2S)-1-(1H-tetrazol-1-yl)propan-2-yl]oxy}phenyl)pyrimidine (916 mg) in NMP (6.0 mL) was added methanesulfonic acid (501 mg) at room temperature, and the mixture was stirred at 110° C. for 15 h. The mixture was neutralized with saturated aqueous sodium hydrogencarbonate solution at 0° C. and extracted with ethyl acetate. The organic layer was separated, washed with saturated brine, dried over anhydrous magnesium sulfate and concentrated under reduced pressure. The residue was purified by silica gel column chromatography (NH, ethyl acetate/hexane) and crystallized from ethyl acetate/hexane to give the title compound (759 mg).
$^1$H NMR (300 MHz, DMSO-d$_6$) δ 9.37 (s, 1H), 8.70 (s, 2H), 8.58 (s, 1H), 7.73 (s, 1H), 7.45 (d, J=8.34 Hz, 1H), 7.36 (d, J=1.74 Hz, 1H), 7.24 (dd, J=1.88, 8.30 Hz, 1H), 5.09-5.26 (m, 1H), 4.73-4.97 (m, 2H), 4.12 (t, J=6.42 Hz, 2H), 3.82-3.99 (m, 1H), 3.23-3.57 (m, 10H), 1.95-2.24 (m, 5H), 1.58-1.93 (m, 8H), 1.33 (d, J=6.14 Hz, 3H), 1.13-1.26 (m, 2H), 1.07 (t, J=6.97 Hz, 3H); MS m/z 693.35 [M+1]$^+$.

Example 462

4-((5-(3-(((S)-1-(1H-tetrazol-1-yl)propan-2-yl)oxy)-4-chlorophenyl)pyrimidin-2-yl)amino)-1-((1r,4r)-4-morpholinocyclohexyl)-1H-pyrazol-3-ol A) ethyl 3-(benzyloxy)-1H-pyrazole-4-carboxylate To a mixture of ethyl 1-acetyl-3-hydroxy-1H-pyrazole-4-carboxylate (10.0 g), benzyl alcohol (6.53 g) and triphenylphosphine (19.8 g) in toluene (100 mL) was added dropwise DIAD (14.7 mL) at room temperature. The mixture was stirred at room temperature under nitrogen atmosphere for 2 hr. The mixture was concentrated in vacuo. To a solution of the residue in EtOH (100 mL) was added potassium carbonate (13.8 g) at 0° C. The mixture was stirred at room temperature for 1 hr. The mixture was concentrated in vacuo. The residue was diluted with water, and the mixture was extracted with ethyl acetate. The organic layer was separated, washed with water and saturated brine, dried over anhydrous magnesium sulfate and concentrated under reduced pressure. The residue was purified by silica gel column chromatography (ethyl acetate/hexane) to give the title compound containing DIAD derivative (18.0 g).
MS m/z 247.2 [M+H]$^+$.

B) ethyl 3-(benzyloxy)-1-[(1r,4r)-4-{[(tert-butoxy)carbonyl]amino}cyclohexyl]-1H-pyrazole-4-carboxylate To a mixture of ethyl 3-(benzyloxy)-1H-pyrazole-4-carboxylate (13.0 g) and tert-butyl N-[(1s,4s)-4-[(4-methylbenzenesulfonyl)oxy]cyclohexyl]carbamate (29.1 g) in DMF (100 mL) was added cesium carbonate (34.2 g) at room temperature. The mixture was stirred at 90° C. under nitrogen atmosphere overnight. The mixture was quenched with water at room temperature and extracted with ethyl acetate. The organic layer was separated, washed with water and saturated brine, dried over anhydrous magnesium sulfate and concentrated under reduced pressure. The residue was purified by silica gel column chromatography (NH, ethyl acetate/hexane) to give the title compound (17.0 g).
MS m/z 444.3 [M+H]$^+$.

C) 3-(benzyloxy)-1-[(1r,4r)-4-{[(tert-butoxy)carbonyl]amino}cyclohexyl]-1H-pyrazole-4-carboxylic acid To a solution of ethyl 3-(benzyloxy)-1-[(1r,4r)-4-{[(tert-butoxy)carbonyl]amino}cyclohexyl]-1H-pyrazole-4-carboxylate (17.0 g) in EtOH (100 mL) and THF (100 mL) was added 8 M aqueous sodium hydroxide solution (11.9 mL) at room temperature. The mixture was stirred at room temperature for 14 hr. Additional 8 M aqueous sodium hydroxide solution (10 mL) was added to the mixture. The mixture was stirred at 40° C. for 4 hr. The mixture was acidified with 6 M aqueous hydrogen chloride solution (ca. pH2-3) and concentrated in reduced pressure. The residue was extracted with ethyl acetate. The organic layer was separated, washed with water and saturated brine, dried over anhydrous magnesium sulfate and concentrated under reduced pressure. The residue was purified by silica gel column chromatography (ethyl acetate/hexane) to give the title compound (10.0 g).
MS m/z 416.3 [M+H]$^+$.

D) benzyl N-[3-(benzyloxy)-1-[(1r,4r)-4-{[(tert-butoxy)carbonyl]amino}cyclohexyl]-1H-pyrazol-4-yl]carbamate To a mixture of 3-(benzyloxy)-1-[(1r,4r)-4-{[(tert-butoxy)carbonyl]amino}cyclohexyl]-1H-pyrazole-4-carboxylic acid (10.0 g) and triethylamine (3.84 g) in toluene (200 mL) was added DPPA (9.76 g) at room temperature. After being stirred at room temperature for 3 hr, benzyl alcohol (3.91 g) was added to the reaction mixture. The mixture was stirred at 90° C. under nitrogen atmosphere for 14 hr. The mixture was quenched with water at room temperature and extracted with ethyl acetate. The organic layer was separated, washed with water and saturated brine, dried over anhydrous magnesium sulfate and concentrated under reduced pressure. The residue was purified by silica gel column chromatography (ethyl acetate/hexane) to give the title compound (12.0 g).
MS m/z 521.3 [M+H]$^+$.

E) benzyl N-[3-(benzyloxy)-1-[(1r,4r)-4-(morpholin-4-yl)cyclohexyl]-1H-pyrazol-4-yl]carbamate A solution of benzyl N-[3-(benzyloxy)-1-[(1r,4r)-4-{[(tert-butoxy)carbonyl]amino}cyclohexyl]-1H-pyrazol-4-yl]carbamate (12 g) in 4 M hydrogen chloride-ethyl acetate (6.70 g) was stirred at room temperature under nitrogen atmosphere for 2 hr. The mixture was concentrated under reduced pressure. To a mixture of the residue, sodium iodide (10.2 g) and potassium carbonate (3.21 g) in DMA (150 mL) was added 1-chloro-2-(2-chloroethoxy)ethane (3.27 g) at room temperature. The mixture was stirred at 90° C. under nitrogen atmosphere for 2 hr. The mixture was quenched with water at 60° C. After being stirred at 60° C. for 1 hr, additional water was added to the reaction mixture. The mixture was stirred at room temperature for 30 min and extracted with ethyl acetate. The organic layer was separated, washed with water and saturated brine, dried over anhydrous magnesium sulfate and concentrated under reduced pressure. The residue was purified by silica gel column chromatography (MeOH/ethyl acetate) to give the title compound (7.73 g).
MS m/z 491.3 [M+H]$^+$.

F) 4-((5-(3-(((S)-1-(1H-tetrazol-1-yl)propan-2-yl)oxy)-4-chlorophenyl)pyrimidin-2-yl)amino)-1-((1r,4r)-4-morpholinocyclohexyl)-1H-pyrazol-3-ol A mixture of benzyl N-[3-(benzyloxy)-1-[(1r,4r)-4-(morpholin-4-yl)cyclohexyl]-1H-pyrazol-4-yl]carbamate (7.50 g), 10% palladium-carbon (322 mg) and methanesulfonic acid (2.92 g) in MeOH (100 mL) was stirred at normal pressure of hydrogen atmosphere at 50° C. for 3 hr. The catalyst was removed by filtration, and the filtrate was concentrated under reduced pressure. To a solution of the residue in NMP (24 mL) was added 2-chloro-5-(4-chloro-3-{[(2S)-1-(1H-tetrazol-1-yl)propan-2-yl]oxy}phenyl)pyrimidine (7.93 g) at room temperature. The mixture was stirred at 120° C. under nitrogen atmosphere for 14 hr. After cooled to room temperature, the reaction mixture were added 2 M aqueous hydrogen chloride solution and ethyl acetate. The organic layer was extracted with 2 M aqueous hydrogen chloride solution. The combined aqueous layer was basified with 8 M aqueous sodium hydroxide solution. The insoluble material was collected by filtration, washed with water and dried in vacuo to give the title compound (3.50 g).
$^1$H NMR (300 MHz, DMSO-$d_6$) δ 9.94 (s, 1H), 9.37 (s, 1H), 8.81 (s, 1H), 8.73 (s, 2H), 7.60 (s, 1H), 7.45 (d, J=8.25 Hz, 1H), 7.38 (d, J=1.56 Hz, 1H), 7.25 (dd, J=1.65, 8.25 Hz, 1H), 5.12-5.22 (m, 1H), 4.86-4.96 (m, 1H), 4.74-4.83 (m, 1H), 3.75-3.88 (m, 1H), 3.54-3.61 (m, 4H), 2.42-2.48 (m, 4H), 2.22-2.29 (m, 1H), 1.99-2.08 (m, 2H), 1.87-1.95 (m, 2H), 1.57-1.72 (m, 2H), 1.31-1.43 (m, 5H); MS m/z 581.22 [M+1]$^+$.

The compounds of Examples 243, 244 and 461 were produced according to the methods described in the above-mentioned Examples or methods analogous thereto. The compounds of Examples 1, 2, 8, 9, 12, 14, 16, 26, 27, 28, 30, 33, 34, 36, 46, 47, 48, 49, 86, 129, 130, 142, 143, 150, 151, 240, 241, 242, 243, 244, 461 and 462 are shown in the following Table 1. The activity (IC$_{50}$) in the table is calculated in Experimental Example 1 and classified according to the following three activity ranks;
A: less than 10 nM,
B: 10 nM or more and less than 100 nM,
C: 100 nM or more.

TABLE 1

| Ex. No. | IUPAC NAME | STRUCTURE | ACTIVITY |
|---|---|---|---|
| 1 | 2-(((S)-1-(1H-tetrazol-1-yl)propan-2-yl)oxy)-4-(2-((3-(2-methoxyethoxy)-1-((1r,4r)-4-morpholinocyclohexyl)-1H-pyrazol-4-yl)amino)pyrimidin-5-yl)benzonitrile | 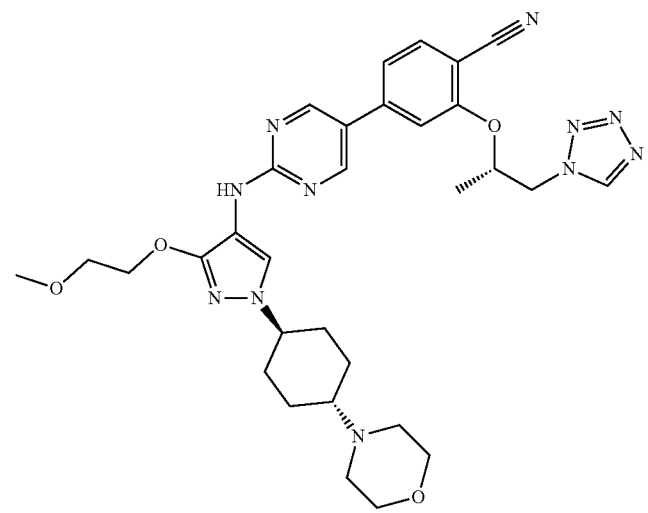 [SMILES: COCCOc1nn([C@H]2CC[C@H](N3CCOCC3)CC2)cc1Nc1ncc(-c2ccc(C#N)c(O[C@@H](C)Cn3cnnn3)c2)cn1] | A |

TABLE 1-continued

| Ex. No. | IUPAC NAME | STRUCTURE | ACTIVITY |
|---|---|---|---|
| 2 | 5-(3-(((S)-1-(1H-tetrazol-1-yl)propan-2-yl)oxy)-4-chlorophenyl)-N-(3-(2-methoxyethoxy)-1-((1r,4r)-4-morpholinocyclohexyl)-1H-pyrazol-4-yl)pyrimidin-2-amine | 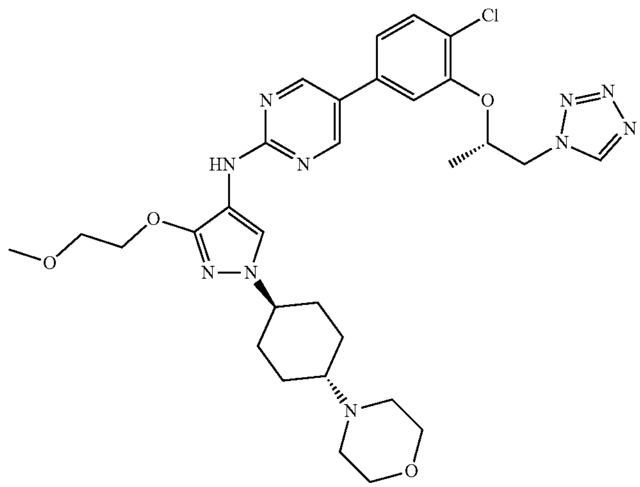 [SMILES: COCCOc1nn([C@H]2CC[C@H](N3CCOCC3)CC2)cc1Nc1ncc(-c2ccc(Cl)c(O[C@@H](C)Cn3cnnn3)c2)cn1] | A |
| 8 | 2-(((S)-1-(1H-tetrazol-1-yl)propan-2-yl)oxy)-4-(2-((3-(2-ethoxyethoxy)-1-((1r,4r)-4-morpholinocyclohexyl)-1H-pyrazol-4-yl)amino)pyrimidin-5-yl)benzonitrile | 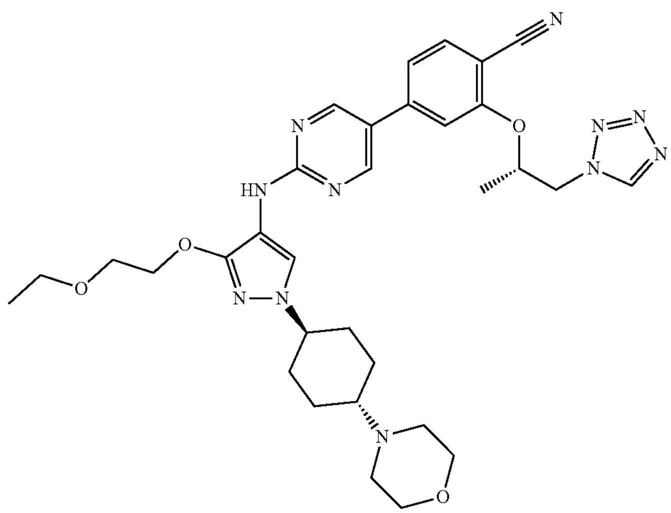 [SMILES: CCOCCOc1nn([C@H]2CC[C@H](N3CCOCC3)CC2)cc1Nc1ncc(-c2ccc(C#N)c(O[C@@H](C)Cn3cnnn3)c2)cn1] | A |
| 9 | 5-(3-(((S)-1-(1H-tetrazol-1-yl)propan-2-yl)oxy)-4-chlorophenyl)-N-(3-(2-ethoxyethoxy)-1-((1r,4r)-4-morpholinocyclohexyl)-1H-pyrazol-4-yl)pyrimidin-2-amine | 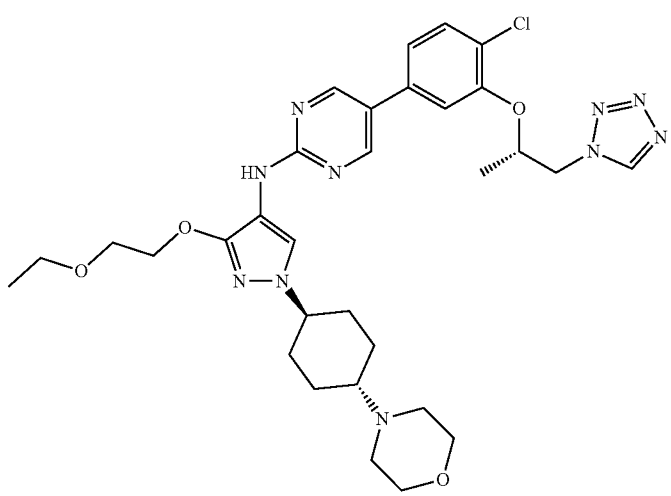 [SMILES: CCOCCOc1nn([C@H]2CC[C@H](N3CCOCC3)CC2)cc1Nc1ncc(-c2ccc(Cl)c(O[C@@H](C)Cn3cnnn3)c2)cn1] | A |

TABLE 1-continued

| Ex. No. | IUPAC NAME | STRUCTURE | ACTIVITY |
|---|---|---|---|
| 12 | 2-(((S)-1-(1H-tetrazol-1-yl)propan-2-yl)oxy)-4-(2-((1-((1r,4r)-4-((1R,5S)-3-oxa-8-azabicyclo[3.2.1]octan-8-yl)cyclohexyl)-3-(2-ethoxyethoxy)-1H-pyrazol-4-yl)amino)pyrimidin-5-yl)benzonitrile | 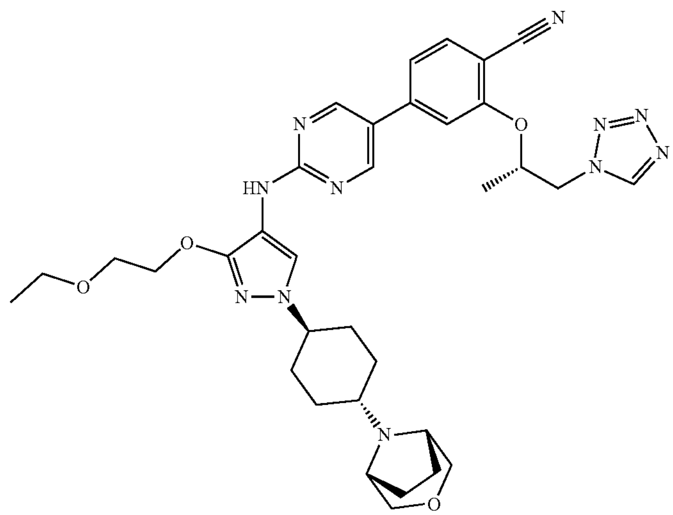 [SMILES: CCOCCOc1nn([C@H]2CC[C@H](N3[C@@H]4CC[C@H]3COC4)CC2)cc1Nc1ncc(-c2ccc(C#N)c(O[C@@H](C)Cn3cnnn3)c2)cn1] | A |
| 14 | 2-(((S)-1-(1H-tetrazol-1-yl)propan-2-yl)oxy)-4-(2-((3-(2-isopropoxyethoxy)-1-((1r,4r)-4-morpholinocyclohexyl)-1H-pyrazol-4-yl)amino)pyrimidin-5-yl)benzonitrile | 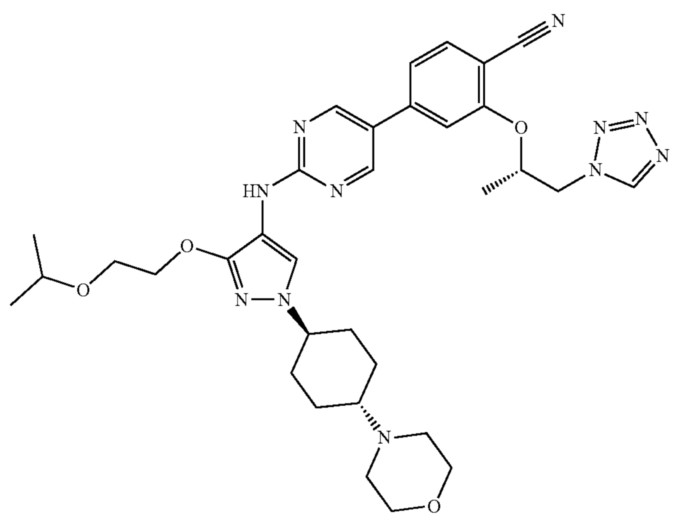 [SMILES: CC(C)OCCOc1nn([C@H]2CC[C@H](N3CCOCC3)CC2)cc1Nc1ncc(-c2ccc(C#N)c(O[C@@H](C)Cn3cnnn3)c2)cn1] | A |
| 16 | 2-(((S)-1-(1H-1,2,4-triazol-1-yl)propan-2-yl)oxy)-4-(2-((3-(2-isopropoxyethoxy)-1-((1r,4r)-4-morpholinocyclohexyl)-1H-pyrazol-4-yl)amino)pyrimidin-5-yl)benzonitrile | 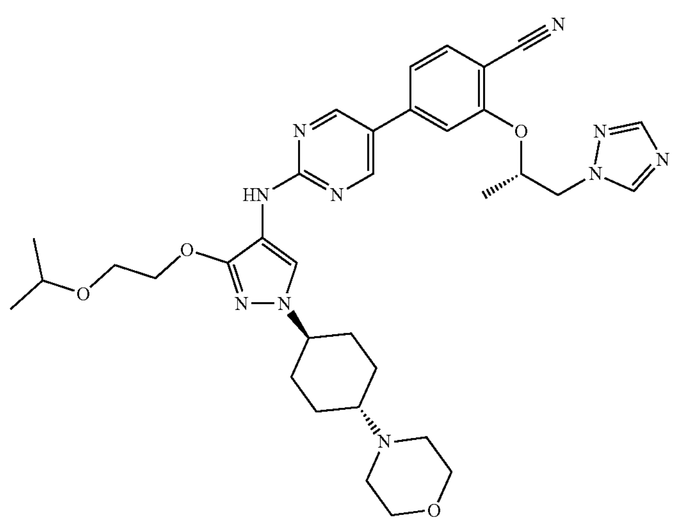 [SMILES: CC(C)OCCOc1nn([C@H]2CC[C@H](N3CCOCC3)CC2)cc1Nc1ncc(-c2ccc(C#N)c(O[C@@H](C)Cn3cncn3)c2)cn1] | A |

TABLE 1-continued

| Ex. No. | IUPAC NAME | STRUCTURE | ACTIVITY |
|---|---|---|---|
| 26 | 2-(((S)-1-(1H-tetrazol-1-yl)propan-2-yl)oxy)-4-(2-((3-(3-methoxypropoxy)-1-((1r,4r)-4-morpholinocyclohexyl)-1H-pyrazol-4-yl)amino)pyrimidin-5-yl)benzonitrile | 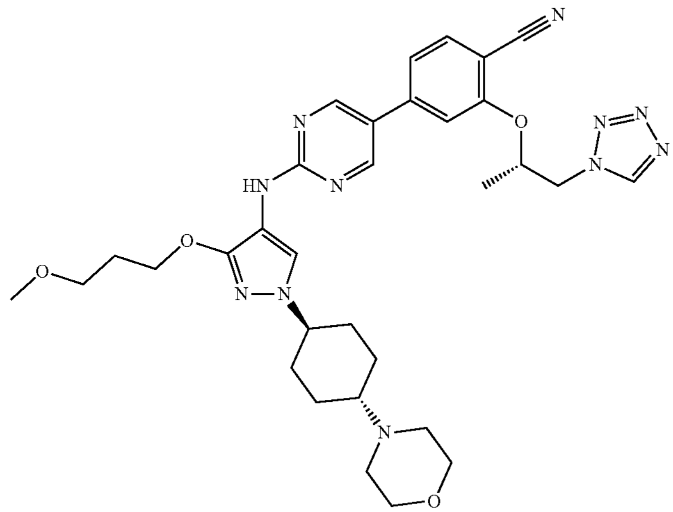 [SMILES: COCCCOc1nn([C@H]2CC[C@H](N3CCOCC3)CC2)cc1Nc1ncc(-c2ccc(C#N)c(O[C@@H](C)Cn3cnnn3)c2)cn1] | A |
| 27 | 5-(3-(((S)-1-(1H-tetrazol-1-yl)propan-2-yl)oxy)-4-chlorophenyl)-N-(3-(3-methoxypropoxy)-1-((1r,4r)-4-morpholinocyclohexyl)-1H-pyrazol-4-yl)pyrimidin-2-amine | 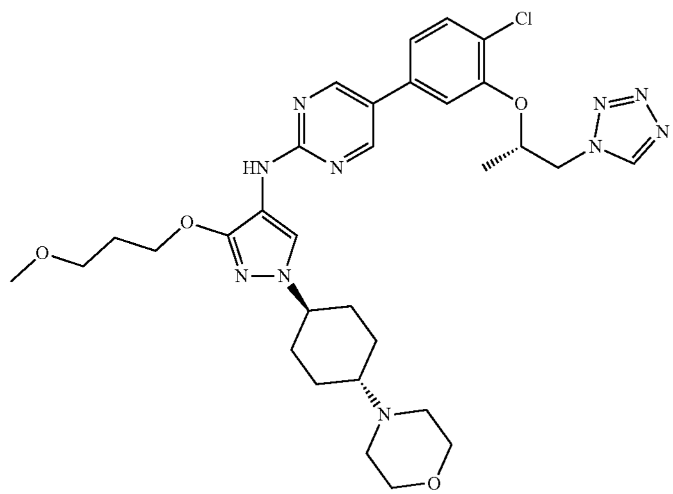 [SMILES: COCCCOc1nn([C@H]2CC[C@H](N3CCOCC3)CC2)cc1Nc1ncc(-c2ccc(Cl)c(O[C@@H](C)Cn3cnnn3)c2)cn1] | A |
| 28 | 2-(((S)-1-(1H-1,2,4-triazol-1-yl)propan-2-yl)oxy)-4-(2-((3-(3-methoxypropoxy)-1-((1r,4r)-4-morpholinocyclohexyl)-1H-pyrazol-4-yl)amino)pyrimidin-5-yl)benzonitrile | 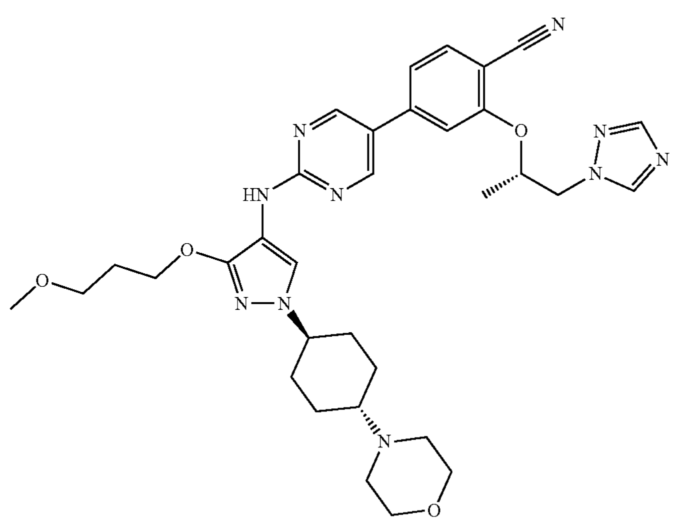 [SMILES: COCCCOc1nn([C@H]2CC[C@H](N3CCOCC3)CC2)cc1Nc1ncc(-c2ccc(C#N)c(O[C@@H](C)Cn3cncn3)c2)cn1] | A |

TABLE 1-continued

| Ex. No. | IUPAC NAME | STRUCTURE | ACTIVITY |
|---|---|---|---|
| 30 | 2-(((S)-1-(1H-tetrazol-1-yl)propan-2-yl)oxy)-4-(2-((1-((1r,4r)-4-((1R,5S)-3-oxa-8-azabicyclo[3.2.1]octan-8-yl)cyclohexyl)-3-(3-methoxypropoxy)-1H-pyrazol-4-yl)amino)pyrimidin-5-yl)benzonitrile | 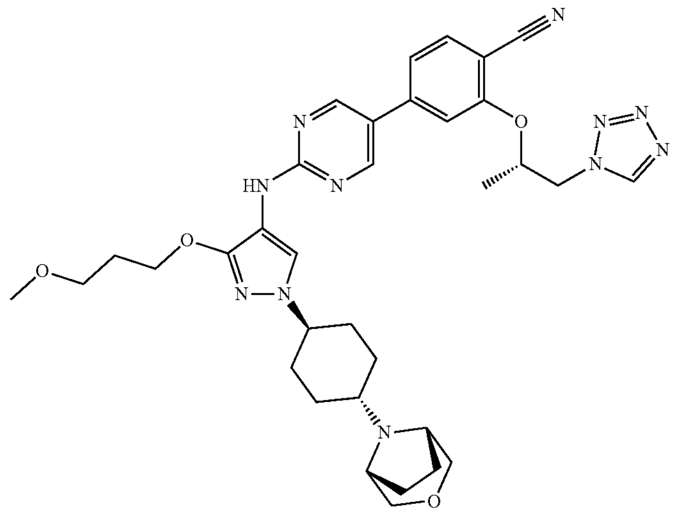 | A |
| 33 | 2-(((S)-1-(1H-tetrazol-1-yl)propan-2-yl)oxy)-4-(2-((3-(3-ethoxypropoxy)-1-((1r,4r)-4-morpholinocyclohexyl)-1H-pyrazol-4-yl)amino)pyrimidin-5-yl)benzonitrile | 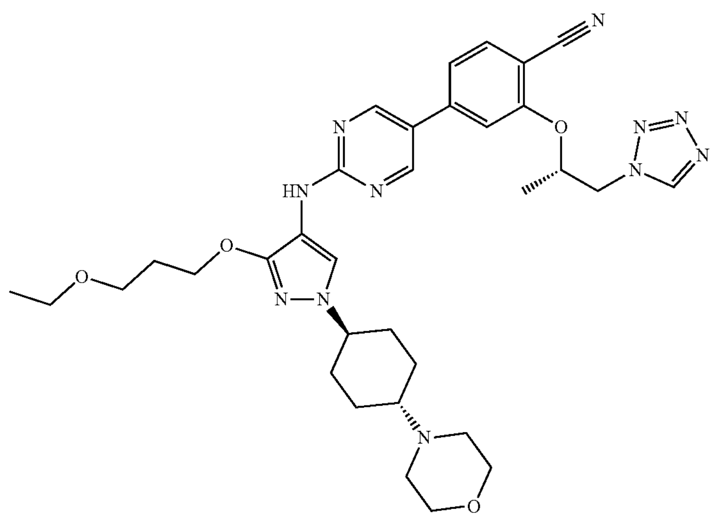 [SMILES: CCOCCCOc1nn([C@H]2CC[C@H](N3CCOCC3)CC2)cc1Nc1ncc(-c2ccc(C#N)c(O[C@@H](C)Cn3cnnn3)c2)cn1] | A |
| 34 | 5-(3-(((S)-1-(1H-tetrazol-1-yl)propan-2-yl)oxy)-4-chlorophenyl)-N-(3-(3-ethoxypropoxy)-1-((1r,4r)-4-morpholinocyclohexyl)-1H-pyrazol-4-yl)pyrimidin-2-amine | 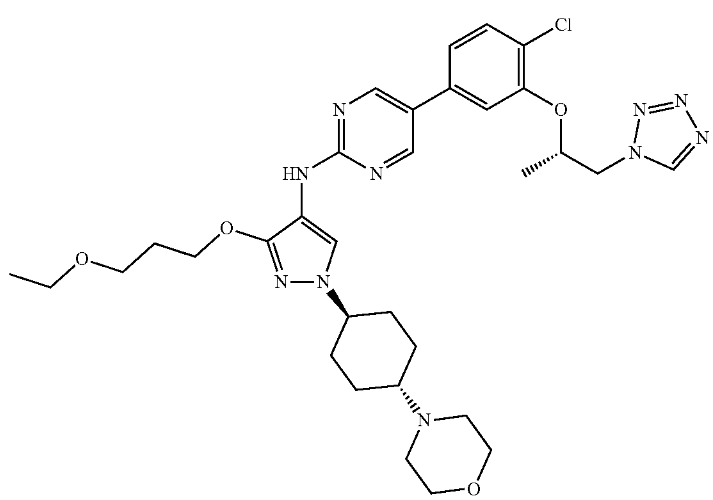 [SMILES: CCOCCCOc1nn([C@H]2CC[C@H](N3CCOCC3)CC2)cc1Nc1ncc(-c2ccc(Cl)c(O[C@@H](C)Cn3cnnn3)c2)cn1] | A |

TABLE 1-continued

| Ex. No. | IUPAC NAME | STRUCTURE | ACTIVITY |
|---|---|---|---|
| 36 | 2-(((S)-1-(1H-tetrazol-1-yl)propan-2-yl)oxy)-4-(2-((1-((1r,4r)-4-((1R,5S)-3-oxa-8-azabicyclo[3.2.1]octan-8-yl)cyclohexyl)-3-(3-ethoxypropoxy)-1H-pyrazol-4-yl)amino)pyrimidin-5-yl)benzonitrile | 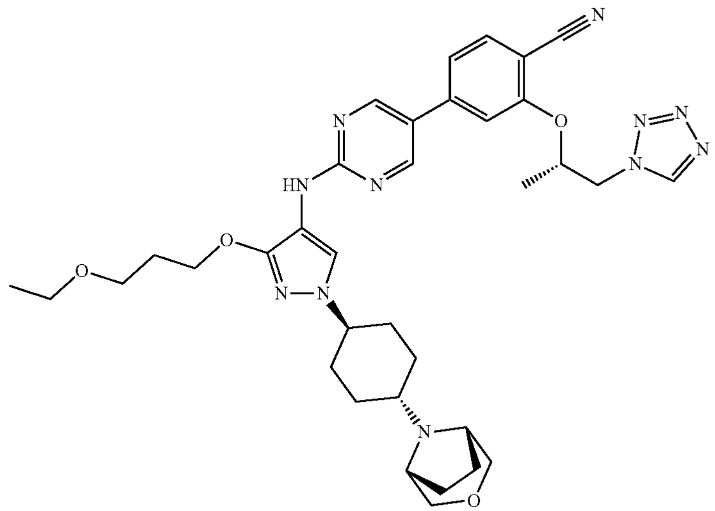 [SMILES: CCOCCCOc1nn([C@H]2CC[C@H](N3[C@@H]4CC[C@H]3COC4)CC2)cc1Nc1ncc(-c2ccc(C#N)c(O[C@@H](C)Cn3cnnn3)c2)cn1] | A |
| 46 | 2-(((S)-1-(1H-tetrazol-1-yl)propan-2-yl)oxy)-4-(2-((3-(3-(2,2-difluoroethoxy)propoxy)-1-((1r,4r)-4-morpholinocyclohexyl)-1H-pyrazol-4-yl)amino)pyrimidin-5-yl)benzonitrile | 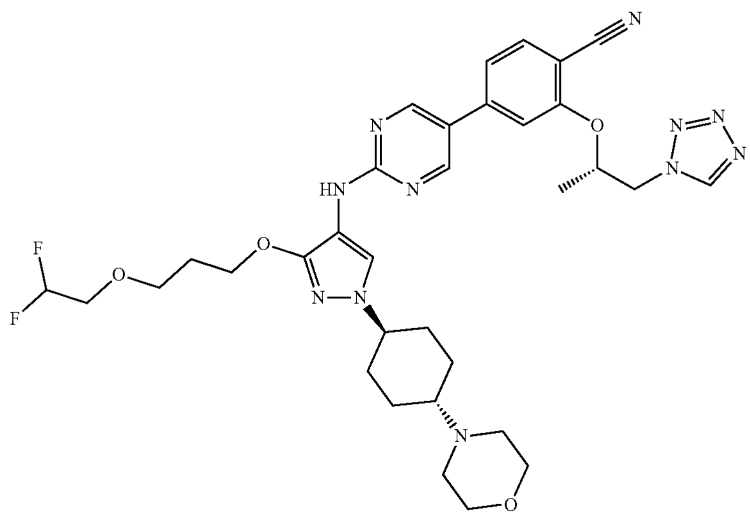 [SMILES: C[C@@H](Cn1cnnn1)Oc1cc(-c2cnc(Nc3cn([C@H]4CC[C@H](N5CCOCC5)CC4)nc3OCCCOCC(F)F)nc2)ccc1C#N] | A |
| 47 | 5-(3-((S)-1-(1H-tetrazol-1-yl)propan-2-yl)oxy)-4-chlorophenyl)-N-(3-(3-(2,2-difluoroethoxy)propoxy)-1-((1r,4r)-4-morpholinocyclohexyl)-1H-pyrazol-4-yl)pyrimidin-2-amine | 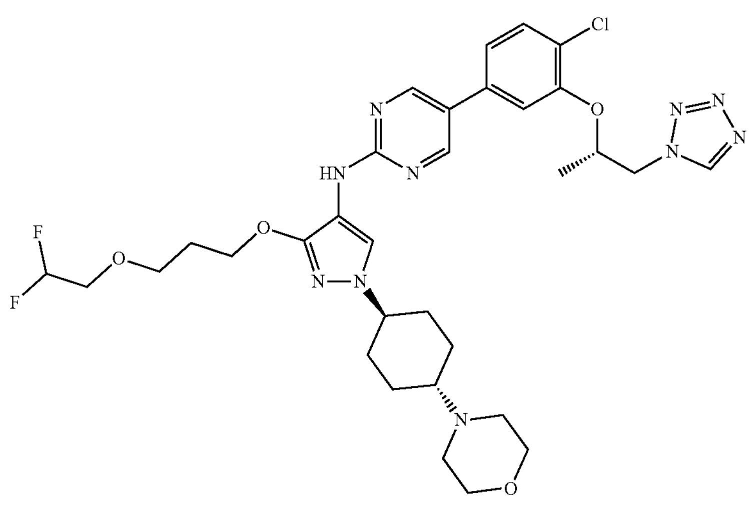 [SMILES: C[C@@H](Cn1cnnn1)Oc1cc(-c2cnc(Nc3cn([C@H]4CC[C@H](N5CCOCC5)CC4)nc3OCCCOCC(F)F)nc2)ccc1Cl] | A |

TABLE 1-continued

| Ex. No. | IUPAC NAME | STRUCTURE | ACTIVITY |
|---|---|---|---|
| 48 | 2-(((S)-1-(1H-tetrazol-1-yl)propan-2-yl)oxy)-4-(2-((3-(2-(2-methoxyethoxy)ethoxy)-1-((1r,4r)-4-morpholinocyclohexyl)-1H-pyrazol-4-yl)amino)pyrimidin-5-yl)benzonitrile hydrochloride | 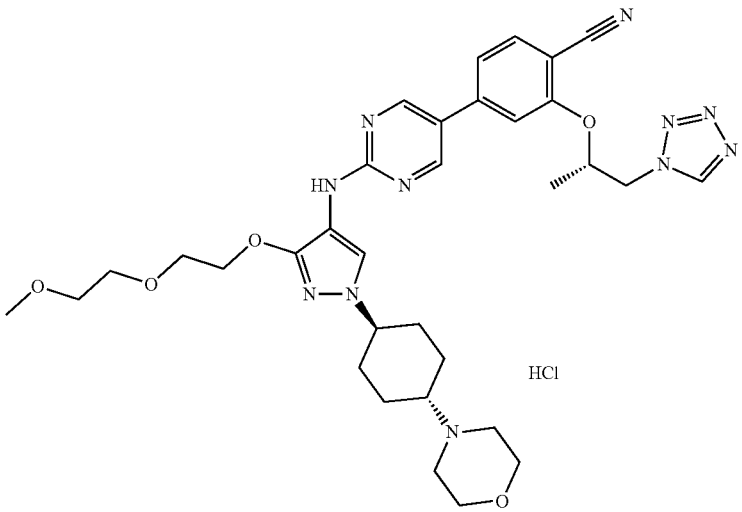 [SMILES: COCCOCCOc1nn([C@H]2CC[C@H](N3CCOCC3)CC2)cc1Nc1ncc(-c2ccc(C#N)c(O[C@@H](C)Cn3cnnn3)c2)cn1 ; Cl] | A |
| 49 | 5-(3-(((S)-1-(1H-tetrazol-1-yl)propan-2-yl)oxy)-4-chlorophenyl)-N-(3-(2-(2-methoxyethoxy)ethoxy)-1-((1r,4r)-4-morpholinocyclohexyl)-1H-pyrazol-4-yl)pyrimidin-2-amine hydrochloride | 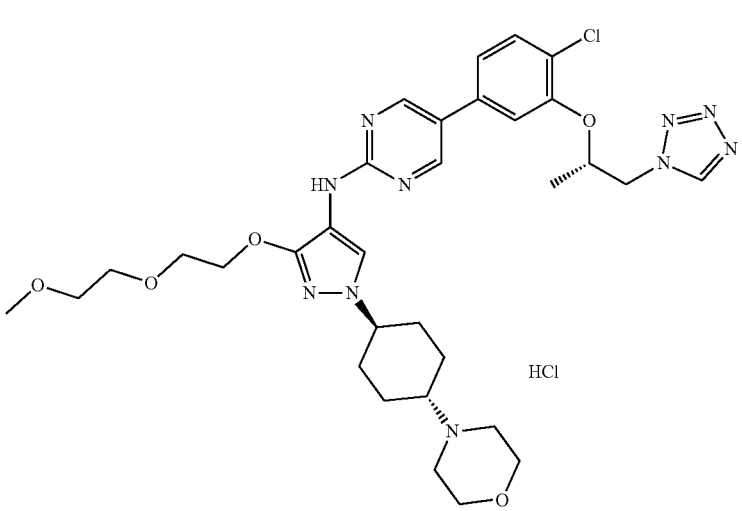 [SMILES: COCCOCCOc1nn([C@H]2CC[C@H](N3CCOCC3)CC2)cc1Nc1ncc(-c2ccc(Cl)c(O[C@@H](C)Cn3cnnn3)c2)cn1 ; Cl] | A |
| 86 | 5-(3-(((S)-1-(1H-tetrazol-1-yl)propan-2-yl)oxy)-4-chlorophenyl)-N-(1-((1r,4r)-4-((1R,5S)-3-oxa-8-azabicyclo[3.2.1]octan-8-yl)cyclohexyl)-3-(2-(methylsulfonyl)ethoxy)-1H-pyrazol-4-yl)pyrimidin-2-amine | 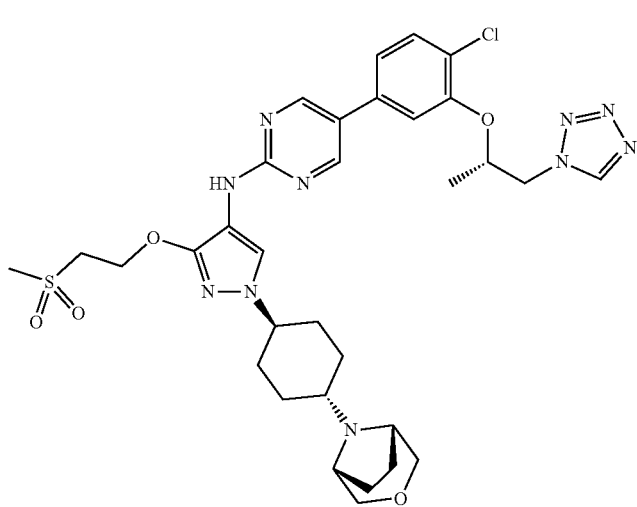 [SMILES: C[C@@H](Cn1cnnn1)Oc1cc(-c2cnc(Nc3cn([C@H]4CC[C@H](N5[C@@H]6CC[C@H]5COC6)CC4)nc3OCCS(C)(=O)=O)nc2)ccc1Cl] | A |

TABLE 1-continued

| Ex. No. | IUPAC NAME | STRUCTURE | ACTIVITY |
|---|---|---|---|
| 129 | 2-(((S)-1-(1H-tetrazol-1-yl)propan-2-yl)oxy)-4-(2-((1-((1r,4r)-4-morpholinocyclohexyl)-3-(pyridin-2-ylmethoxy)-1H-pyrazol-4-yl)amino)pyrimidin-5-yl)benzonitrile | 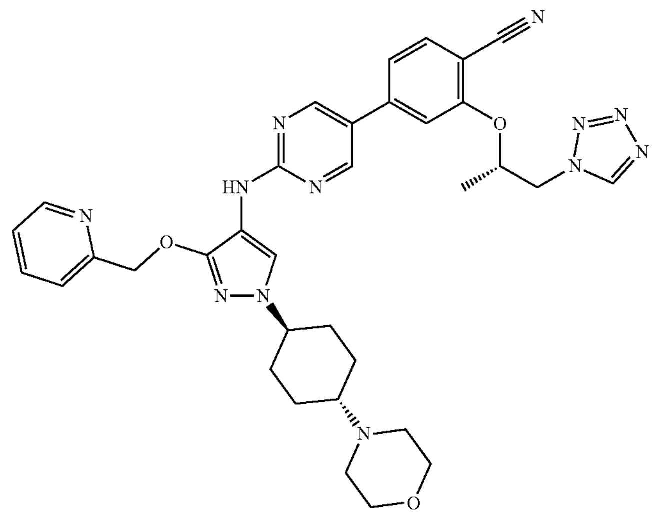 [SMILES: C[C@@H](Cn1cnnn1)Oc1cc(-c2cnc(Nc3cn([C@H]4CC[C@H](N5CCOCC5)CC4)nc3OCc3ccccn3)nc2)ccc1C#N] | A |
| 130 | 5-(3-(((S)-1-(1H-tetrazol-1-yl)propan-2-yl)oxy)-4-chlorophenyl)-N-(1-((1r,4r)-4-morpholinocyclohexyl)-3-(pyridin-2-ylmethoxy)-1H-pyrazol-4-yl)pyrimidin-2-amine | 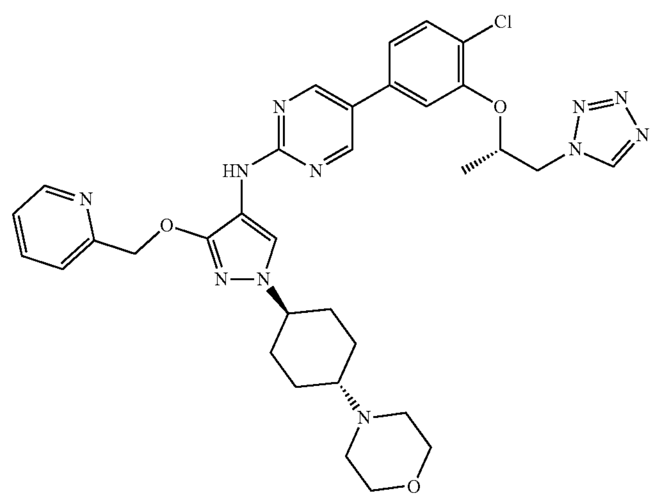 [SMILES: C[C@@H](Cn1cnnn1)Oc1cc(-c2cnc(Nc3cn([C@H]4CC[C@H](N5CCOCC5)CC4)nc3OCc3ccccn3)nc2)ccc1Cl] | A |
| 142 | 5-(3-(((S)-1-(1H-tetrazol-1-yl)propan-2-yl)oxy)-4-chlorophenyl)-N-(1-((1r,4r)-4-((1R,5S)-3-oxa-8-azabicyclo[3.2.1]octan-8-yl)cyclohexyl)-3-(3-(methylsulfonyl)propoxy)-1H-pyrazol-4-yl)pyrimidin-2-amine | 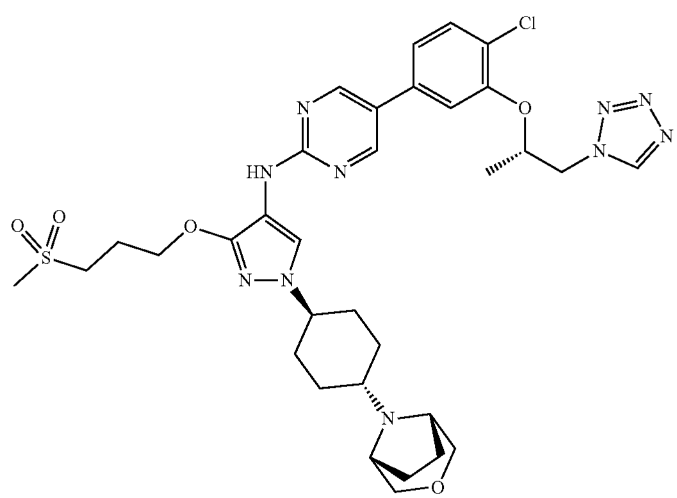 [SMILES: C[C@@H](Cn1cnnn1)Oc1cc(-c2cnc(Nc3cn([C@H]4CC[C@H](N5[C@@H]6CC[C@H]5COC6)CC4)nc3OCCCS(C)(=O)=O)nc2)ccc1Cl] | A |

TABLE 1-continued

| Ex. No. | IUPAC NAME | STRUCTURE | ACTIVITY |
|---|---|---|---|
| 143 | 2-(((S)-1-(1H-tetrazol-1-yl)propan-2-yl)oxy)-4-(2-((1-((1r,4r)-4-((2S,6R)-2,6-dimethylmorpholino)cyclohexyl)-3-(3-methoxypropoxy)-1H-pyrazol-4-yl)amino)pyrimidin-5-yl)benzonitrile | 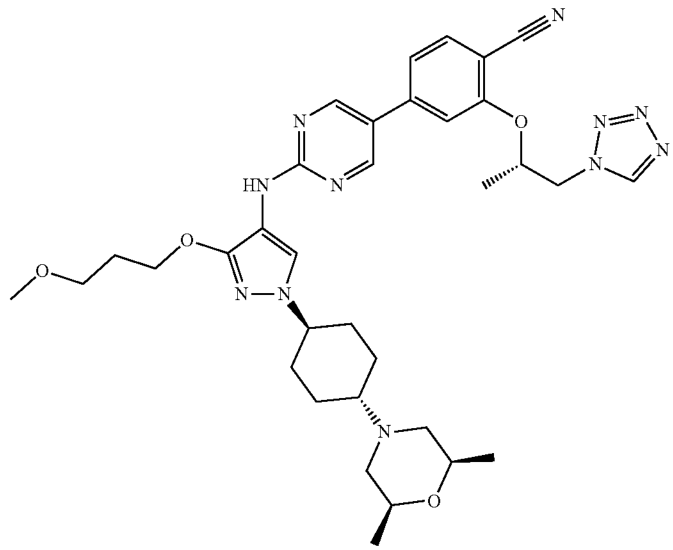 [SMILES: COCCCOc1nn([C@H]2CC[C@H](N3C[C@@H](C)O[C@@H](C)C3)CC2)cc1Nc1ncc(-c2ccc(C#N)c(O[C@@H](C)Cn3cnnn3)c2)cn1] | A |
| 150 | 2-(((S)-1-(1H-tetrazol-1-yl)propan-2-yl)oxy)-4-(2-((3-(4-methoxybutoxy)-1-((1r,4r)-4-morpholinocyclohexyl)-1H-pyrazol-4-yl)amino)pyrimidin-5-yl)benzonitrile | 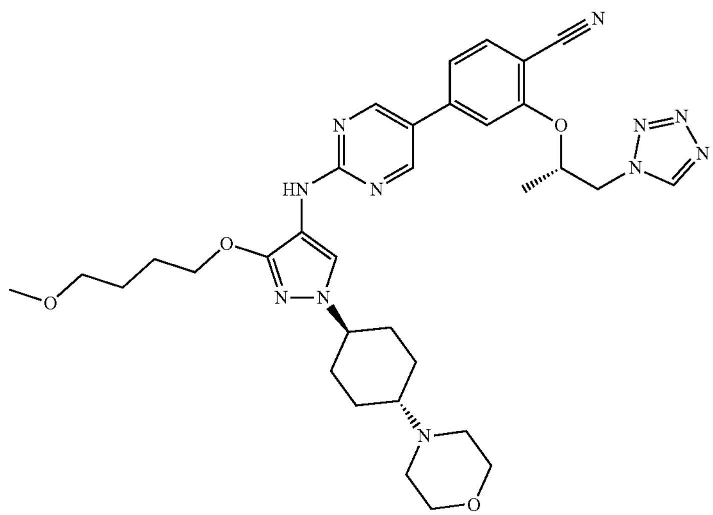 | A |
| 151 | 5-(3-(((S)-1-(1H-tetrazol-1-yl)propan-2-yl)oxy)-4-chlorophenyl)-N-(3-(4-methoxybutoxy)-1-((1r,4r)-4-morpholinocyclohexyl)-1H-pyrazol-4-yl)pyrimidin-2-amine | 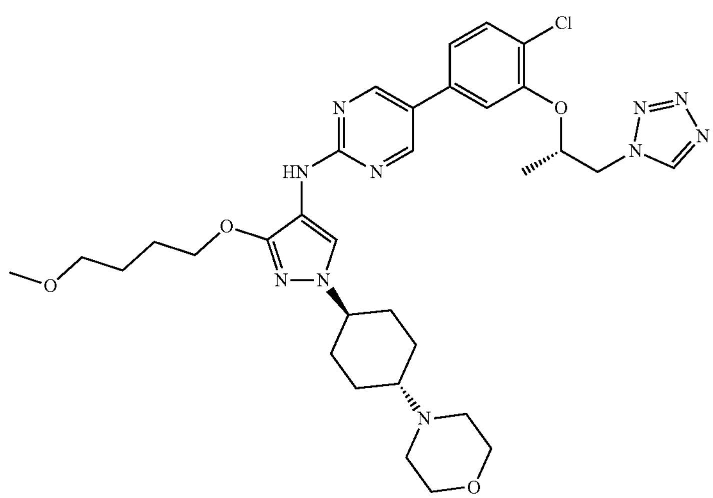 [SMILES: COCCCCOc1nn([C@H]2CC[C@H](N3CCOCC3)CC2)cc1Nc1ncc(-c2ccc(Cl)c(O[C@@H](C)Cn3cnnn3)c2)cn1] | A |

TABLE 1-continued

| Ex. No. | IUPAC NAME | STRUCTURE | ACTIVITY |
|---|---|---|---|
| 240 | 5-(3-(((S)-1-(1H-tetrazol-1-yl)propan-2-yl)oxy)-4-chlorophenyl)-N-(1-((1r,4r)-4-((2S,6R)-2,6-dimethylmorpholino)cyclohexyl)-3-(2-(2-methoxyethoxy)ethoxy)-1H-pyrazol-4-yl)pyrimidin-2-amine hydrochloride | 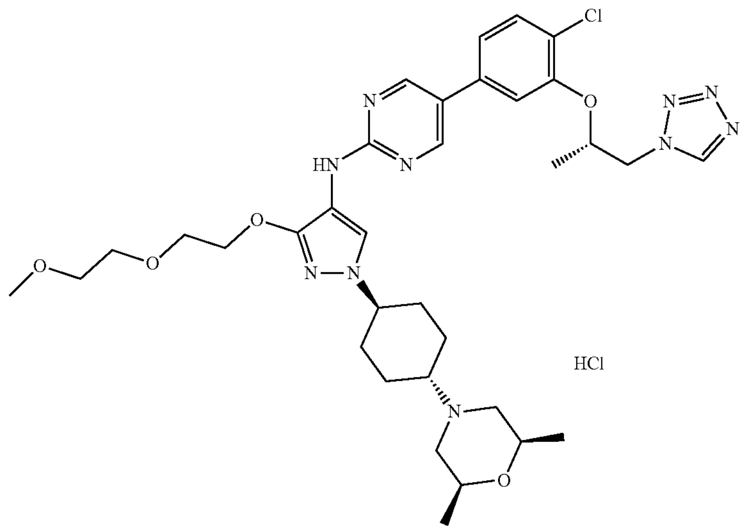 [SMILES: COCCOCCOc1nn([C@H]2CC[C@H](N3C[C@@H](C)O[C@@H](C)C3)CC2)cc1Nc1ncc(-c2ccc(Cl)c(O[C@@H](C)Cn3cnnn3)c2)cn1 ; Cl] | A |
| 241 | 2-(((S)-1-(1H-tetrazol-1-yl)propan-2-yl)oxy)-4-(2-((1-((1r,4r)-4-((2S,6R)-2,6-dimethylmorpholino)cyclohexyl)-3-(2-(2-methoxyethoxy)ethoxy)-1H-pyrazol-4-yl)amino)pyrimidin-5-yl)benzonitrile hydrochloride | 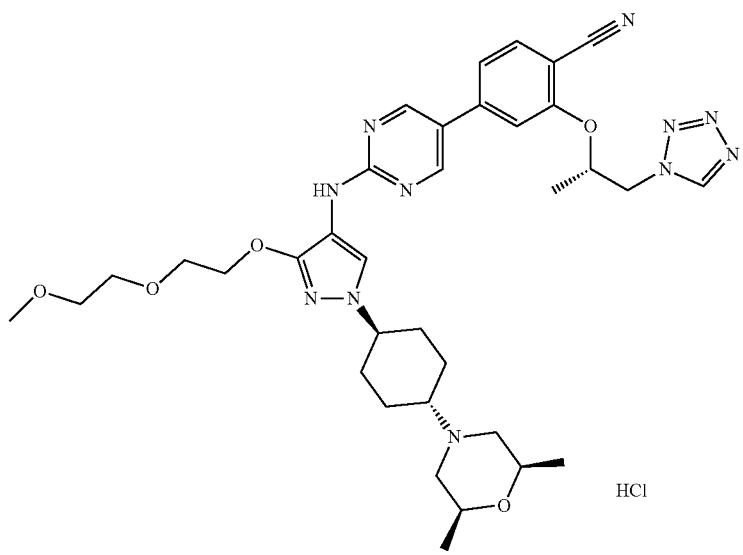 [SMILES: COCCOCCOc1nn([C@H]2CC[C@H](N3C[C@@H](C)O[C@@H](C)C3)CC2)cc1Nc1ncc(-c2ccc(C#N)c(O[C@@H](C)Cn3cnnn3)c2)cn1 ; Cl] | A |
| 242 | 5-(3-(((S)-1-(1H-tetrazol-1-yl)propan-2-yl)oxy)-4-chlorophenyl)-N-(1-((1r,4r)-4-((1R,5S)-3-oxa-8-azabicyclo[3.2.1]octan-8-yl)cyclohexyl)-3-(3-ethoxypropoxy)-1H-pyrazol-4-yl)pyrimidin-2-amine | 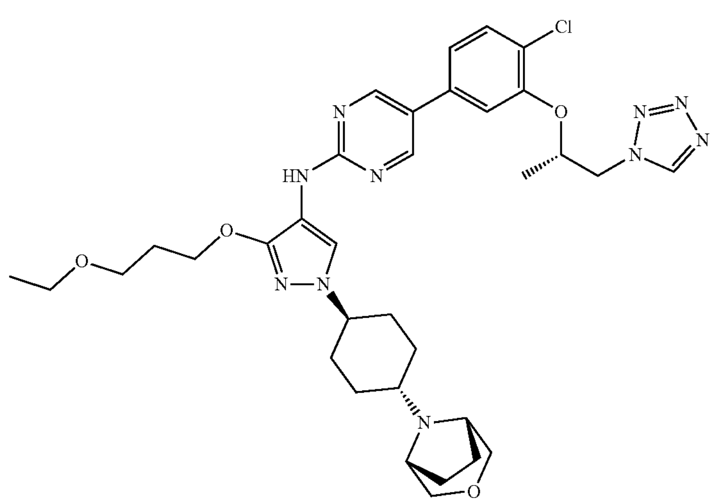 [SMILES: CCOCCCOc1nn([C@H]2CC[C@H](N3[C@@H]4CC[C@H]3COC4)CC2)cc1Nc1ncc(-c2ccc(Cl)c(O[C@@H](C)Cn3cnnn3)c2)cn1] | A |

TABLE 1-continued

| Ex. No. | IUPAC NAME | STRUCTURE | ACTIVITY |
|---|---|---|---|
| 243 | 2-((4-((5-(3-(((S)-1-(1H-tetrazol-1-yl)propan-2-yl)oxy)-4-chlorophenyl)pyrimidin-2-yl)amino)-1-((1r,4r)-4-((1R,5S)-3-oxa-8-azabicyclo[3.2.1]octan-8-yl)cyclohexyl)-1H-pyrazol-3-yl)oxy)ethan-1-ol | 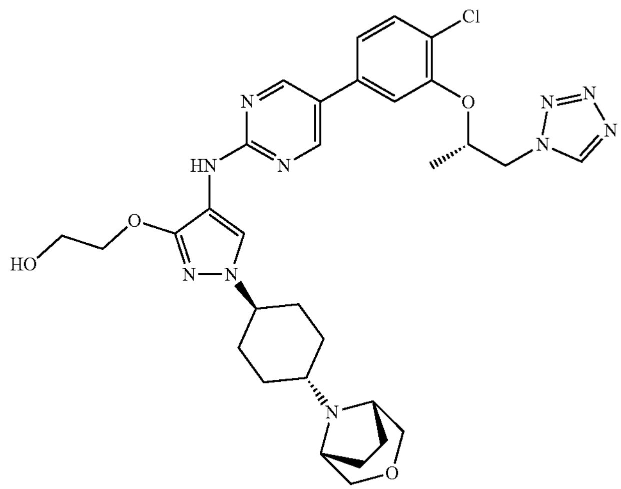 [SMILES: C[C@@H](Cn1cnnn1)Oc1cc(-c2cnc(Nc3cn([C@H]4CC[C@H](N5[C@@H]6CC[C@H]5COC6)CC4)nc3OCCO)nc2)ccc1Cl] | A |
| 244 | 2-(((S)-1-(1H-tetrazol-1-yl)propan-2-yl)oxy)-4-(2-((1-((1r,4r)-4-((1R,5S)-3-oxa-8-azabicyclo[3.2.1]octan-8-yl)cyclohexyl)-3-(2-hydroxyethoxy)-1H-pyrazol-4-yl)amino)pyrimidin-5-yl)benzonitrile | 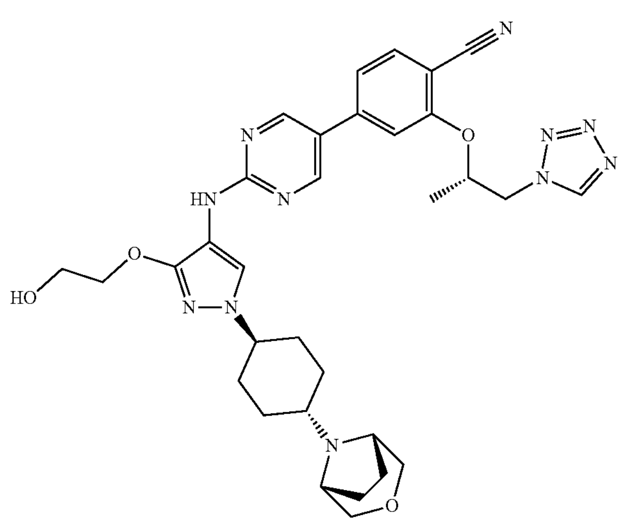 [SMILES: C[C@@H](Cn1cnnn1)Oc1cc(-c2cnc(Nc3cn([C@H]4CC[C@H](N5[C@@H]6CC[C@H]5COC6)CC4)nc3OCCO)nc2)ccc1C#N] | A |

TABLE 1-continued

| Ex. No. | IUPAC NAME | STRUCTURE | ACTIVITY |
|---|---|---|---|
| 461 | 2-(((S)-1-(1H-tetrazol-1-yl)propan-2-yl)oxy)-4-(2-((3-hydroxy-1-((1r,4r)-4-morpholinocyclohexyl)-1H-pyrazol-4-yl)amino)pyrimidin-5-yl)benzonitrile | 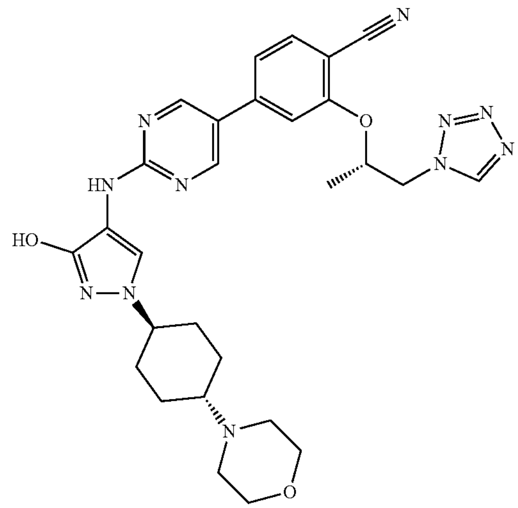 [SMILES: C[C@@H](Cn1cnnn1)Oc1cc(-c2cnc(Nc3cn([C@H]4CC[C@H](N5CCOCC5)CC4)nc3O)nc2)ccc1C#N] | A |
| 462 | 4-((5-(3-(((S)-1-(1H-tetrazol-1-yl)propan-2-yl)oxy)-4-chlorophenyl)pyrimidin-2-yl)amino)-1-((1r,4r)-4-morpholinocyclohexyl)-1H-pyrazol-3-ol | 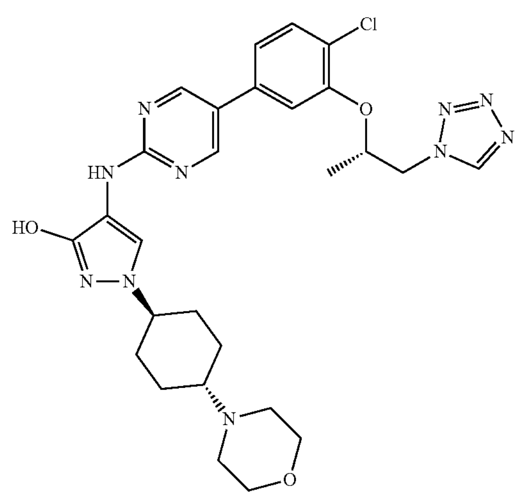 [SMILES: C[C@@H](Cn1cnnn1)Oc1cc(-c2cnc(Nc3cn([C@H]4CC[C@H](N5CCOCC5)CC4)nc3O)nc2)ccc1Cl] | A |

The compounds of Examples 3-7, 10, 11, 13, 15, 17-25, 29, 31, 32, 35, 37-45, 50-85, 87-128, 131-141, 144-149, 152-194, 196-239, 245-460 and 463-472 in the following tables can be produced according to the methods described in the above-mentioned Examples or methods analogous thereto. The compounds of Examples are shown in the following Table 2.

TABLE 2

| Ex. No. | IUPAC NAME | STRUCTURE |
|---|---|---|
| 3 | 5-(3-(((S)-1-(1H-1,2,4-triazol-1-yl)propan-2-yl)oxy)-4-chlorophenyl)-N-(3-(2-methoxyethoxy)-1-((1r,4r)-4-morpholinocyclohexyl)-1H-pyrazol-4-yl)pyrimidin-2-amine | 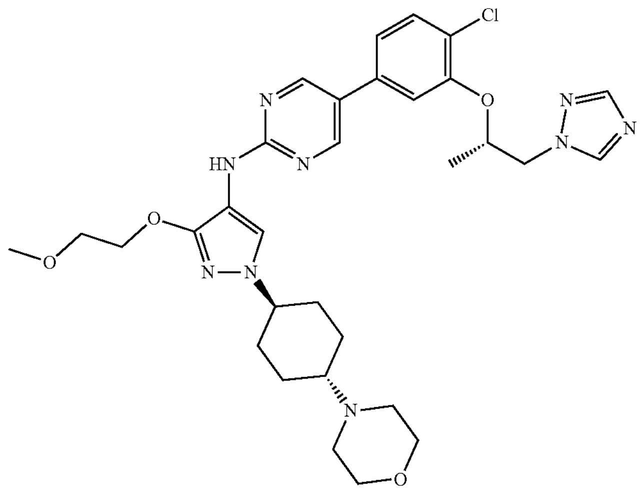 [SMILES: COCCOc1nn([C@H]2CC[C@H](N3CCOCC3)CC2)cc1Nc1ncc(-c2ccc(Cl)c(O[C@@H](C)Cn3cncn3)c2)cn1] |
| 4 | 2-(((S)-1-(1H-tetrazol-1-yl)propan-2-yl)oxy)-4-(2-((1-((1r,4r)-4-((1R,5S)-3-oxa-8-azabicyclo[3.2.1]octan-8-yl)cyclohexyl)-3-(2-methoxyethoxy)-1H-pyrazol-4-yl)amino)pyrimidin-5-yl)benzonitrile | 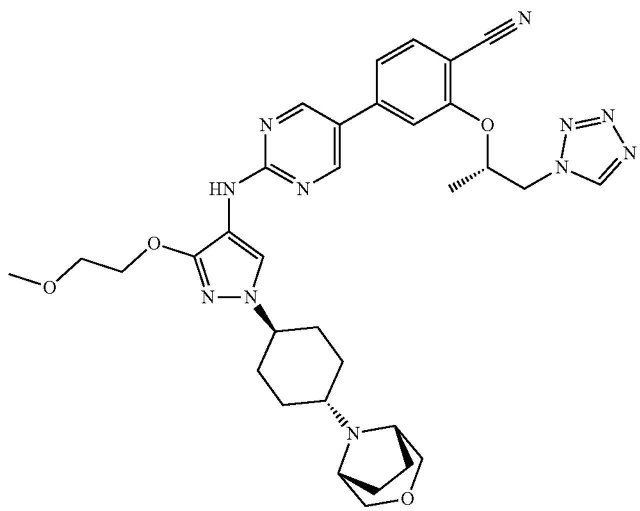 [SMILES: COCCOc1nn([C@H]2CC[C@H](N3[C@@H]4CC[C@H]3COC4)CC2)cc1Nc1ncc(-c2ccc(C#N)c(O[C@@H](C)Cn3cnnn3)c2)cn1] |
| 5 | 2-(((S)-1-(1H-1,2,4-triazol-1-yl)propan-2-yl)oxy)-4-(2-((1-((1r,4r)-4-((1R,5S)-3-oxa-8-azabicyclo[3.2.1]octan-8-yl)cyclohexyl)-3-(2-methoxyethoxy)-1H-pyrazol-4-yl)amino)pyrimidin-5-yl)benzonitrile | 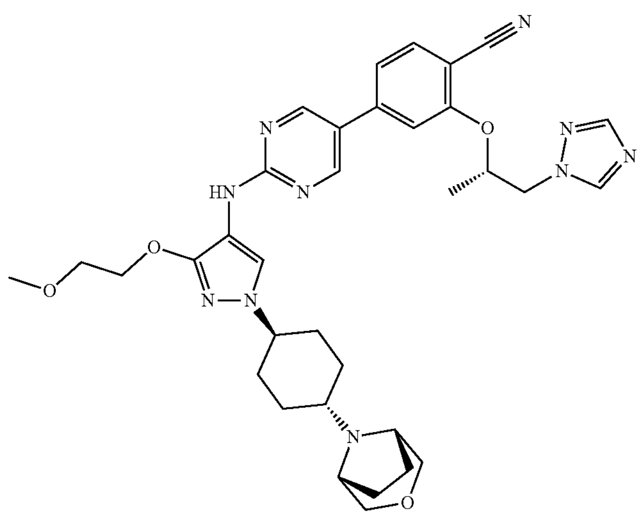 [SMILES: COCCOc1nn([C@H]2CC[C@H](N3[C@@H]4CC[C@H]3COC4)CC2)cc1Nc1ncc(-c2ccc(C#N)c(O[C@@H](C)Cn3cncn3)c2)cn1] |

TABLE 2-continued

| Ex. No. | IUPAC NAME |
|---|---|
| 6 | 5-(3-(((S)-1-(1H-1,2,4-triazol-1-yl)propan-2-yl)oxy)-4-chlorophenyl)-N-(1-((1r,4r)-4-((1R,5S)-3-oxa-8-azabicyclo[3.2.1]octan-8-yl)cyclohexyl)-3-(2-methoxyethoxy)-1H-pyrazol-4-yl)pyrimidin-2-amine |
| 7 | 2-(((S)-1-(1H-1,2,4-triazol-1-yl)propan-2-yl)oxy)-4-(2-((1-((1r,4r)-4-((2S,6R)-2,6-dimethylmorpholino)cyclohexyl)-3-(2-methoxyethoxy)-1H-pyrazol-4-yl)amino)pyrimidin-5-yl)benzonitrile |
| 10 | 2-(((S)-1-(1H-1,2,4-triazol-1-yl)propan-2-yl)oxy)-4-(2-((3-(2-ethoxyethoxy)-1-((1r,4r)-4-morpholinocyclohexyl)-1H-pyrazol-4-yl)amino)pyrimidin-5-yl)benzonitrile |

TABLE 2-continued

| Ex. No. | IUPAC NAME | STRUCTURE |
|---|---|---|
| 11 | 5-(3-(((S)-1-(1H-1,2,4-triazol-1-yl)propan-2-yl)oxy)-4-chlorophenyl)-N-(3-(2-ethoxyethoxy)-1-((1r,4r)-4-morpholinocyclohexyl)-1H-pyrazol-4-yl)pyrimidin-2-amine | 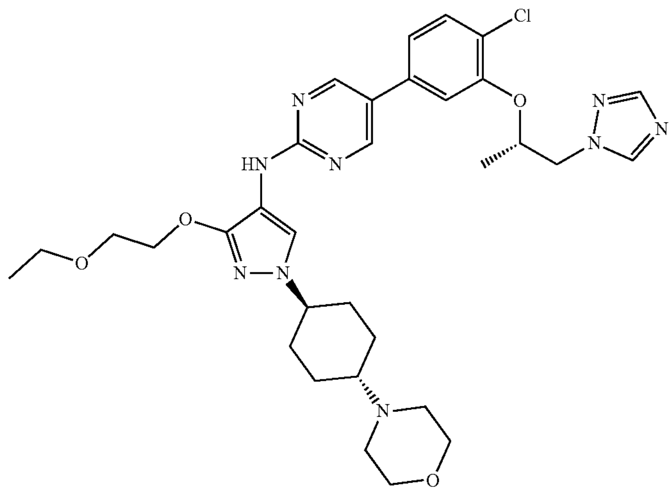 [SMILES: CCOCCOc1nn([C@H]2CC[C@H](N3CCOCC3)CC2)cc1Nc1ncc(-c2ccc(Cl)c(O[C@@H](C)Cn3cncn3)c2)cn1] |
| 13 | 2-(((S)-1-(1H-1,2,4-triazol-1-yl)propan-2-yl)oxy)-4-(2-((1-((1r,4r)-4-((1R,5S)-3-oxa-8-azabicyclo[3.2.1]octan-8-yl)cyclohexyl)-3-(2-ethoxyethoxy)-1H-pyrazol-4-yl)amino)pyrimidin-5-yl)benzonitrile | 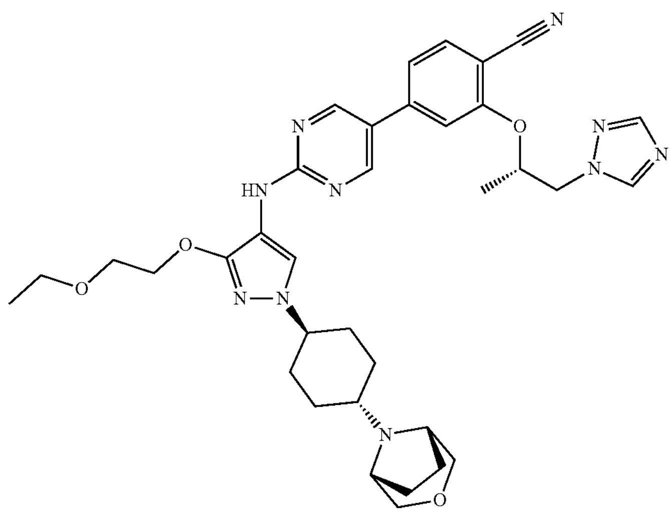 [SMILES: CCOCCOc1nn([C@H]2CC[C@H](N3[C@@H]4CC[C@H]3COC4)CC2)cc1Nc1ncc(-c2ccc(C#N)c(O[C@@H](C)Cn3cncn3)c2)cn1] |
| 15 | 5-(3-(((S)-1-(1H-tetrazol-1-yl)propan-2-yl)oxy)-4-chlorophenyl)-N-(3-(2-isopropoxyethoxy)-1-((1r,4r)-4-morpholinocyclohexyl)-1H-pyrazol-4-yl)pyrimidin-2-amine | 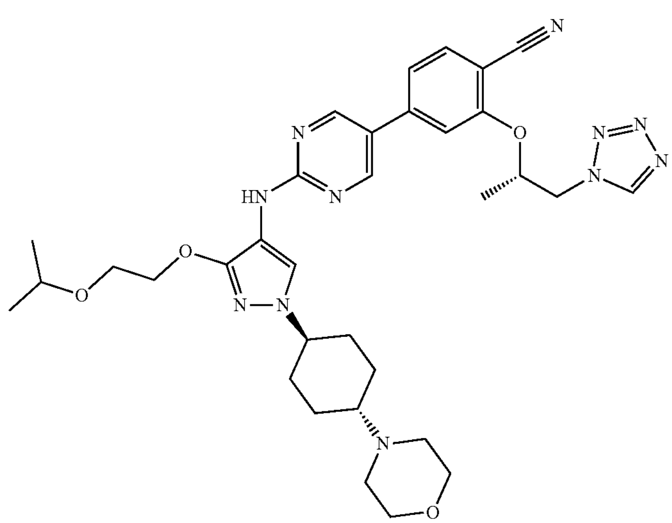 [SMILES: CC(C)OCCOc1nn([C@H]2CC[C@H](N3CCOCC3)CC2)cc1Nc1ncc(-c2ccc(C#N)c(O[C@@H](C)Cn3cnnn3)c2)cn1] |

TABLE 2-continued

| Ex. No. | IUPAC NAME | STRUCTURE |
| --- | --- | --- |
| 17 | 2-(((S)-1-(1H-1,2,4-triazol-1-yl)propan-2-yl)oxy)-4-(2-((1-((1r,4r)-4-((1R,5S)-3-oxa-8-azabicyclo[3.2.1]octan-8-yl)cyclohexyl)-3-(2-isopropoxyethoxy)-1H-pyrazol-4-yl)amino)pyrimidin-5-yl)benzonitrile | 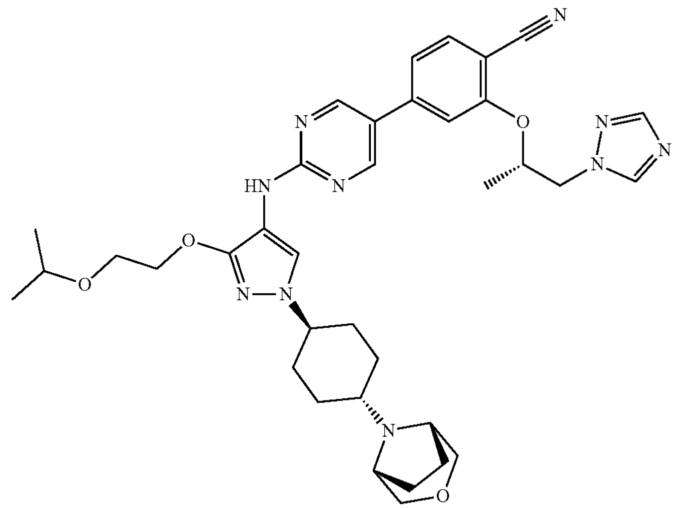 [SMILES: CC(C)OCCOc1nn([C@H]2CC[C@H](N3[C@@H]4CC[C@H]3COC4)CC2)cc1Nc1ncc(-c2ccc(C#N)c(O[C@@H](C)Cn3cncn3)c2)cn1] |
| 18 | 2-(((S)-1-(1H-tetrazol-1-yl)propan-2-yl)oxy)-4-(2-((1-((1r,4r)-4-morpholinocyclohexyl)-3-(2-(trifluoromethoxy)ethoxy)-1H-pyrazol-4-yl)amino)pyrimidin-5-yl)benzonitrile | 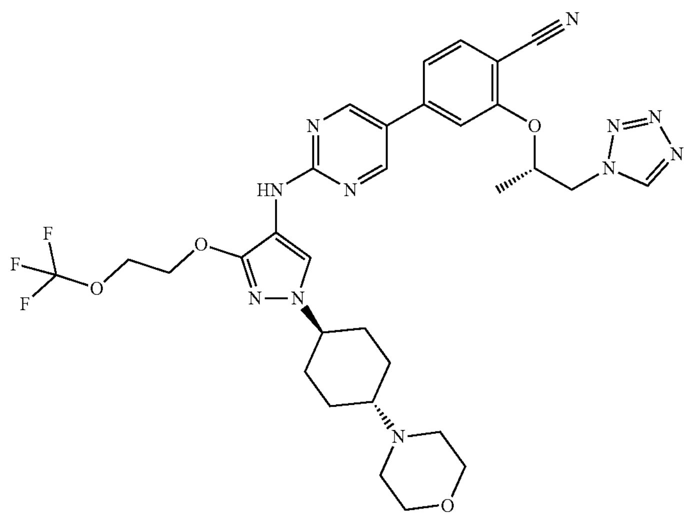 [SMILES: C[C@@H](Cn1cnnn1)Oc1cc(-c2cnc(Nc3cn([C@H]4CC[C@H](N5CCOCC5)CC4)nc3OCCOC(F)(F)F)nc2)ccc1C#N] |
| 19 | 5-(3-(((S)-1-(1H-tetrazol-1-yl)propan-2-yl)oxy)-4-chlorophenyl)-N-(1-((1r,4r)-4-morpholinocyclohexyl)-3-(2-(trifluoromethoxy)ethoxy)-1H-pyrazol-4-yl)pyrimidin-2-amine | 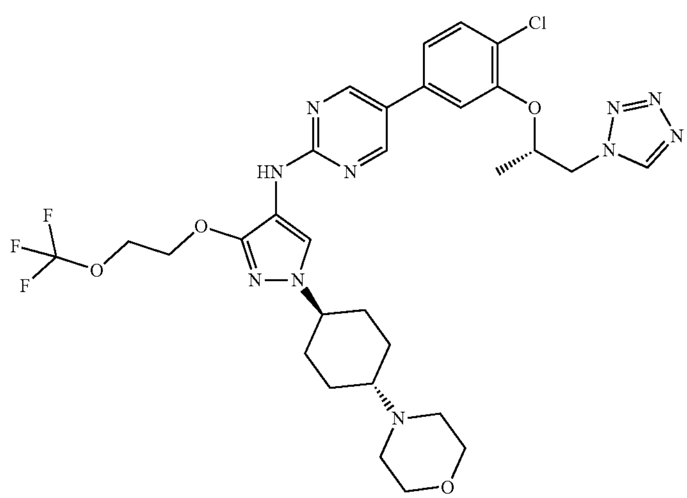 [SMILES: C[C@@H](Cn1cnnn1)Oc1cc(-c2cnc(Nc3cn([C@H]4CC[C@H](N5CCOCC5)CC4)nc3OCCOC(F)(F)F)nc2)ccc1Cl] |

TABLE 2-continued

| Ex. No. | IUPAC NAME | STRUCTURE |
|---|---|---|
| 20 | 2-(((S)-1-(1H-tetrazol-1-yl)propan-2-yl)oxy)-4-(2-((3-(2-(difluoromethoxy)ethoxy)-1-((1r,4r)-4-morpholinocyclohexyl)-1H-pyrazol-4-yl)amino)pyrimidin-5-yl)benzonitrile | 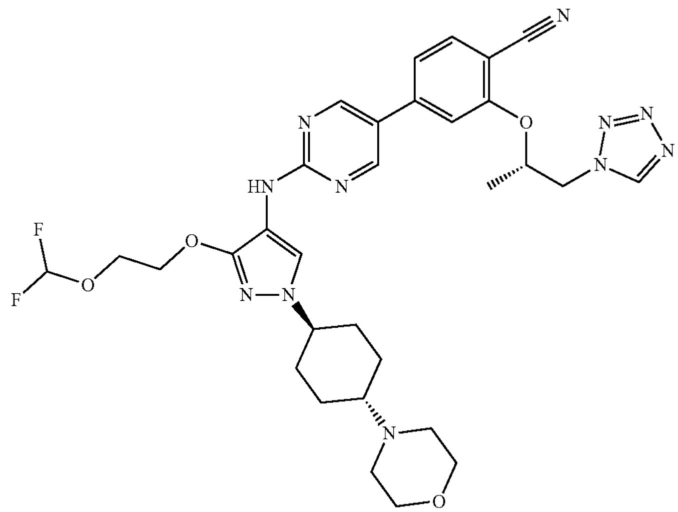 [SMILES: C[C@@H](Cn1cnnn1)Oc1cc(-c2cnc(Nc3cn([C@H]4CC[C@H](N5CCOCC5)CC4)nc3OCCOC(F)F)nc2)ccc1C#N] |
| 21 | 5-(3-(((S)-1-(1H-tetrazol-1-yl)propan-2-yl)oxy)-4-chlorophenyl)-N-(3-(2-(difluoromethoxy)ethoxy)-1-((1r,4r)-4-morpholinocyclohexyl)-1H-pyrazol-4-yl)pyrimidin-2-amine | 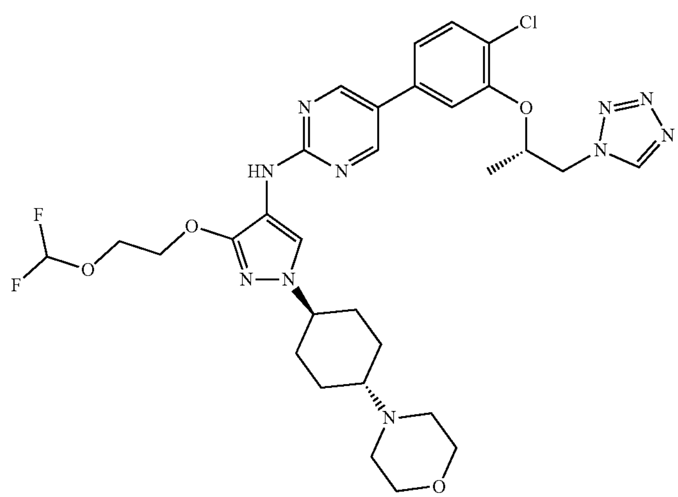 [SMILES: C[C@@H](Cn1cnnn1)Oc1cc(-c2cnc(Nc3cn([C@H]4CC[C@H](N5CCOCC5)CC4)nc3OCCOC(F)F)nc2)ccc1Cl] |
| 22 | 2-(((S)-1-(1H-tetrazol-1-yl)propan-2-yl)oxy)-4-(2-((1-((1r,4r)-4-morpholinocyclohexyl)-3-(2-(2,2,2-trifluoroethoxy)ethoxy)-1H-pyrazol-4-yl)amino)pyrimidin-5-yl)benzonitrile | 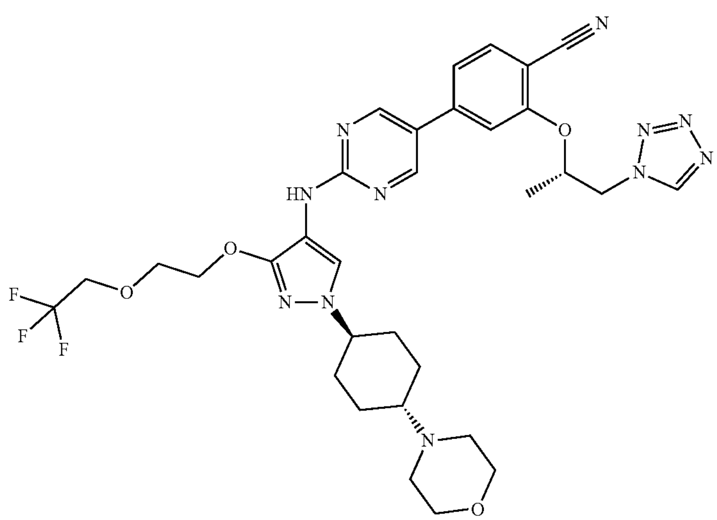 [SMILES: C[C@@H](Cn1cnnn1)Oc1cc(-c2cnc(Nc3cn([C@H]4CC[C@H](N5CCOCC5)CC4)nc3OCCOCC(F)(F)F)nc2)ccc1C#N] |

TABLE 2-continued

| Ex. No. | IUPAC NAME | STRUCTURE |
| --- | --- | --- |
| 23 | 5-(3-(((S)-1-(1H-tetrazol-1-yl)propan-2-yl)oxy)-4-chlorophenyl)-N-(1-((1r,4r)-4-morpholinocyclohexyl)-3-(2-(2,2,2-trifluoroethoxy)ethoxy)-1H-pyrazol-4-yl)pyrimidin-2-amine | 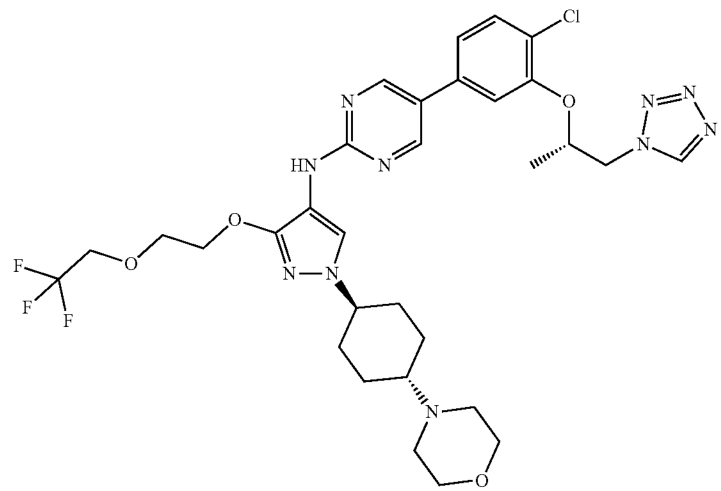 [SMILES: C[C@@H](Cn1cnnn1)Oc1cc(-c2cnc(Nc3cn([C@H]4CC[C@H](N5CCOCC5)CC4)nc3OCCOCC(F)(F)F)nc2)ccc1Cl] |
| 24 | 2-(((S)-1-(1H-tetrazol-1-yl)propan-2-yl)oxy)-4-(2-((3-(2-(2,2-difluoroethoxy)ethoxy)-1-((1r,4r)-4-morpholinocyclohexyl)-1H-pyrazol-4-yl)amino)pyrimidin-5-yl)benzonitrile | 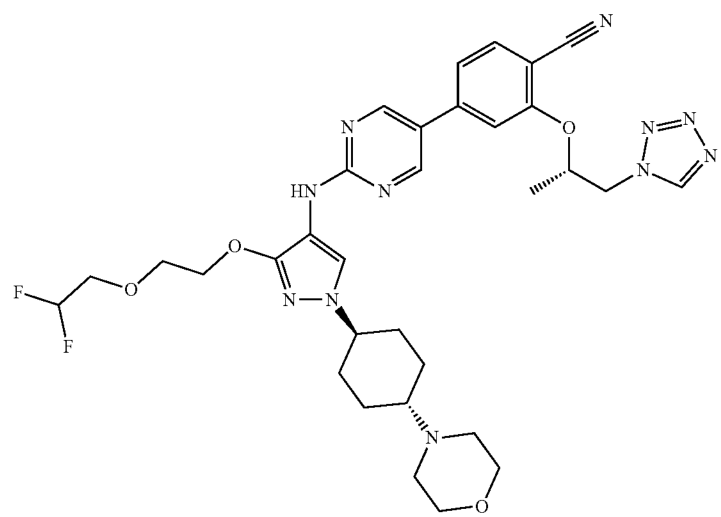 [SMILES: C[C@@H](Cn1cnnn1)Oc1cc(-c2cnc(Nc3cn([C@H]4CC[C@H](N5CCOCC5)CC4)nc3OCCOCC(F)F)nc2)ccc1C#N] |
| 25 | 5-(3-(((S)-1-(1H-tetrazol-1-yl)propan-2-yl)oxy)-4-chlorophenyl)-N-(3-(2-(2,2-difluoroethoxy)ethoxy)-1-((1r,4r)-4-morpholinocyclohexyl)-1H-pyrazol-4-yl)pyrimidin-2-amine | 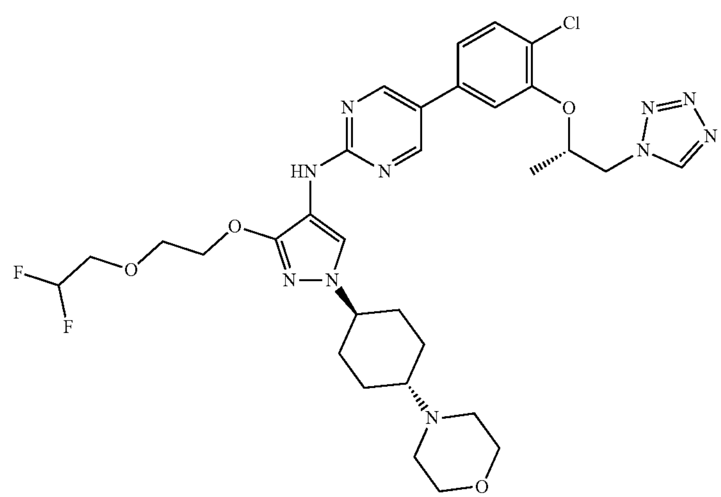 [SMILES: C[C@@H](Cn1cnnn1)Oc1cc(-c2cnc(Nc3cn([C@H]4CC[C@H](N5CCOCC5)CC4)nc3OCCOCC(F)F)nc2)ccc1Cl] |

TABLE 2-continued

| Ex. No. | IUPAC NAME | STRUCTURE |
|---|---|---|
| 29 | 5-(3-(((S)-1-(1H-1,2,4-triazol-1-yl)propan-2-yl)oxy)-4-chlorophenyl)-N-(3-(3-methoxypropoxy)-1-((1r,4r)-4-morpholinocyclohexyl)-1H-pyrazol-4-yl)pyrimidin-2-amine | 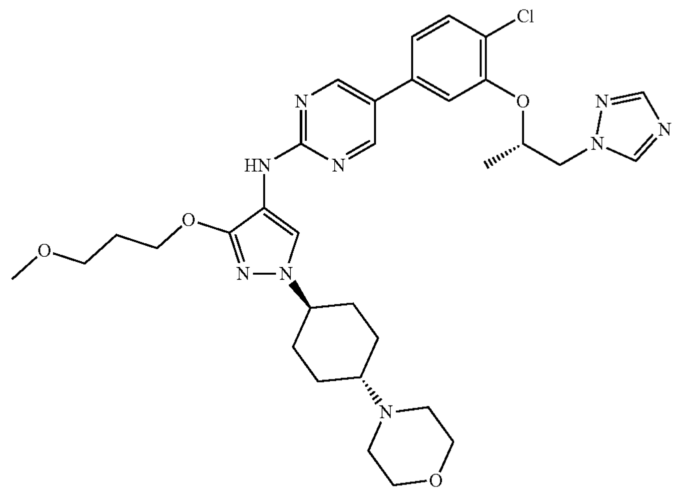 |
| 31 | 2-(((S)-1-(1H-1,2,4-triazol-1-yl)propan-2-yl)oxy)-4-(2-((1-((1r,4r)-4-((1R,5S)-3-oxa-8-azabicyclo[3.2.1]octan-8-yl)cyclohexyl)-3-(3-methoxypropoxy)-1H-pyrazol-4-yl)amino)pyrimidin-5-yl)benzonitrile | 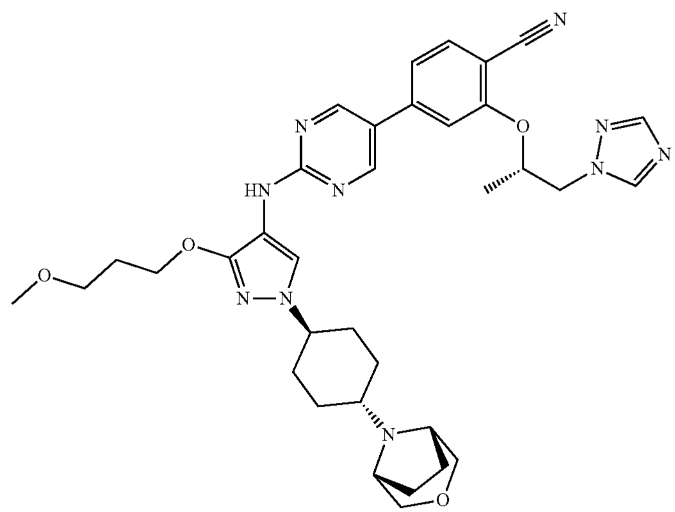 [SMILES: COCCCOc1nn([C@H]2CC[C@H](N3[C@@H]4CC[C@H]3COC4)CC2)cc1Nc1ncc(-c2ccc(C#N)c(O[C@@H](C)Cn3cncn3)c2)cn1] |
| 32 | 5-(3-(((S)-1-(1H-1,2,4-triazol-1-yl)propan-2-yl)oxy)-4-chlorophenyl)-N-(1-((1r,4r)-4-((1R,5S)-3-oxa-8-azabicyclo[3.2.1]octan-8-yl)cyclohexyl)-3-(3-methoxypropoxy)-1H-pyrazol-4-yl)pyrimidin-2-amine | 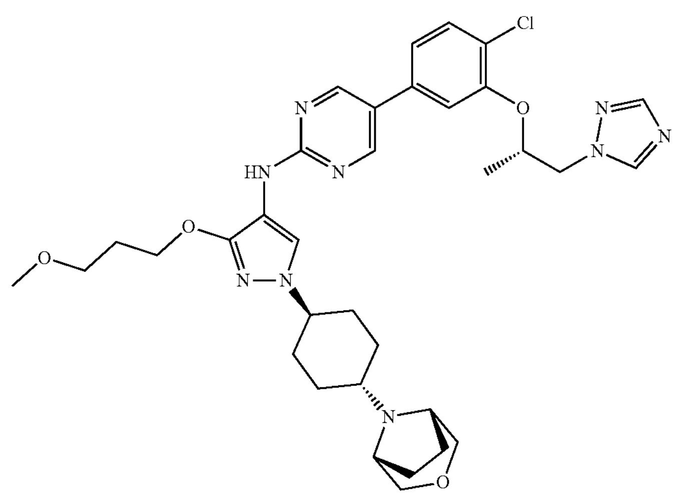 [SMILES: COCCCOc1nn([C@H]2CC[C@H](N3[C@@H]4CC[C@H]3COC4)CC2)cc1Nc1ncc(-c2ccc(Cl)c(O[C@@H](C)Cn3cncn3)c2)cn1] |

TABLE 2-continued

| Ex. No. | IUPAC NAME | STRUCTURE |
| --- | --- | --- |
| 35 | 2-(((S)-1-(1H-1,2,4-triazol-1-yl)propan-2-yl)oxy)-4-(2-((3-(3-ethoxypropoxy)-1-((1r,4r)-4-morpholinocyclohexyl)-1H-pyrazol-4-yl)amino)pyrimidin-5-yl)benzonitrile | 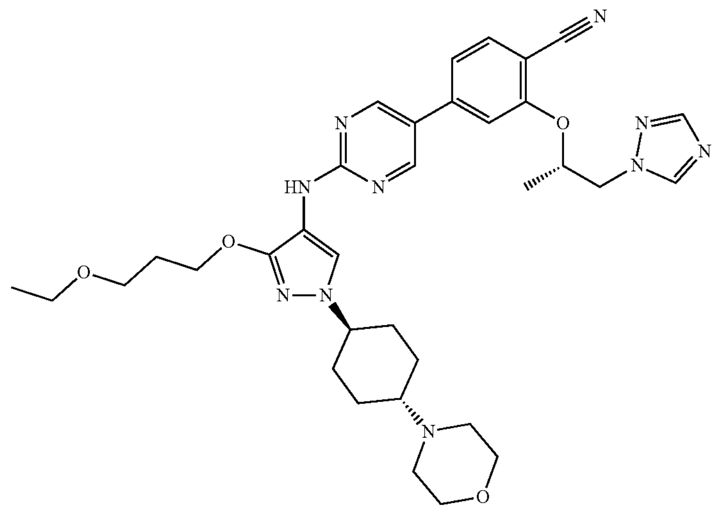 [SMILES: CCOCCCOc1nn([C@H]2CC[C@H](N3CCOCC3)CC2)cc1Nc1ncc(-c2ccc(C#N)c(O[C@@H](C)Cn3cncn3)c2)cn1] |
| 37 | 2-(((S)-1-(1H-1,2,4-triazol-1-yl)propan-2-yl)oxy)-4-(2-((1-((1r,4r)-4-((1R,5S)-3-oxa-8-azabicyclo[3.2.1]octan-8-yl)cyclohexyl)-3-(3-ethoxypropoxy)-1H-pyrazol-4-yl)amino)pyrimidin-5-yl)benzonitrile | 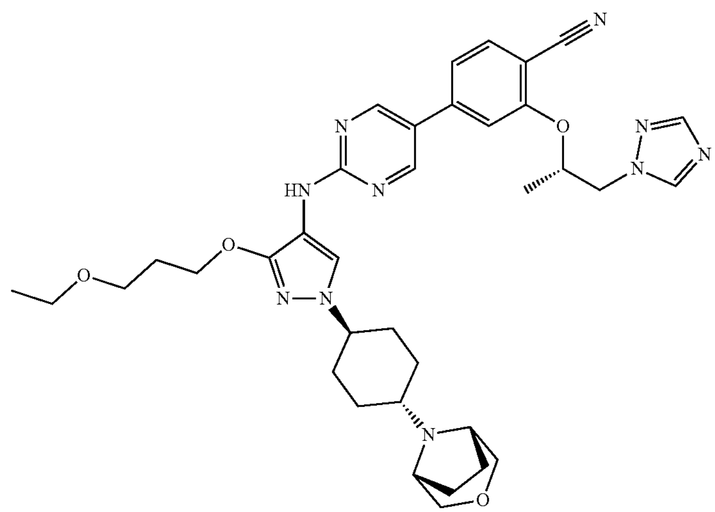 [SMILES: CCOCCCOc1nn([C@H]2CC[C@H](N3[C@@H]4CC[C@H]3COC4)CC2)cc1Nc1ncc(-c2ccc(C#N)c(O[C@@H](C)Cn3cncn3)c2)cn1] |
| 38 | 2-(((S)-1-(1H-tetrazol-1-yl)propan-2-yl)oxy)-4-(2-((3-(3-isopropoxypropoxy)-1-((1r,4r)-4-morpholinocyclohexyl)-1H-pyrazol-4-yl)amino)pyrimidin-5-yl)benzonitrile | 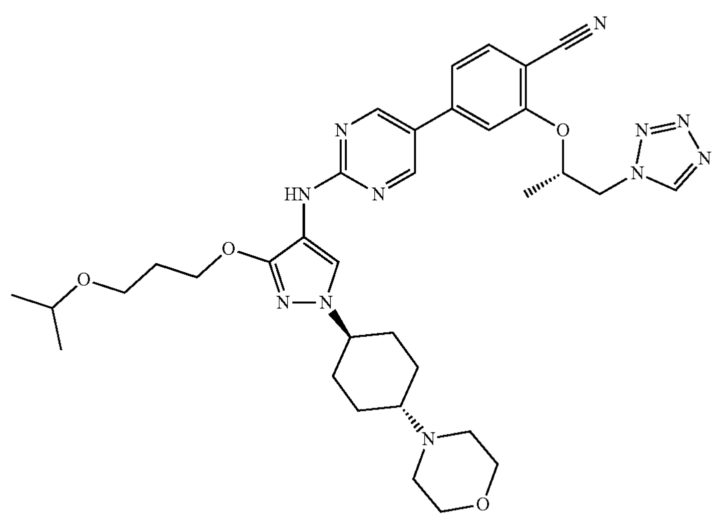 [SMILES: CC(C)OCCCOc1nn([C@H]2CC[C@H](N3CCOCC3)CC2)cc1Nc1ncc(-c2ccc(C#N)c(O[C@@H](C)Cn3cnnn3)c2)cn1] |

TABLE 2-continued

| Ex. No. | IUPAC NAME | STRUCTURE |
| --- | --- | --- |
| 39 | 5-(3-(((S)-1-(1H-tetrazol-1-yl)propan-2-yl)oxy)-4-chlorophenyl)-N-(3-(3-isopropoxypropoxy)-1-((1r,4r)-4-morpholinocyclohexyl)-1H-pyrazol-4-yl)pyrimidin-2-amine | 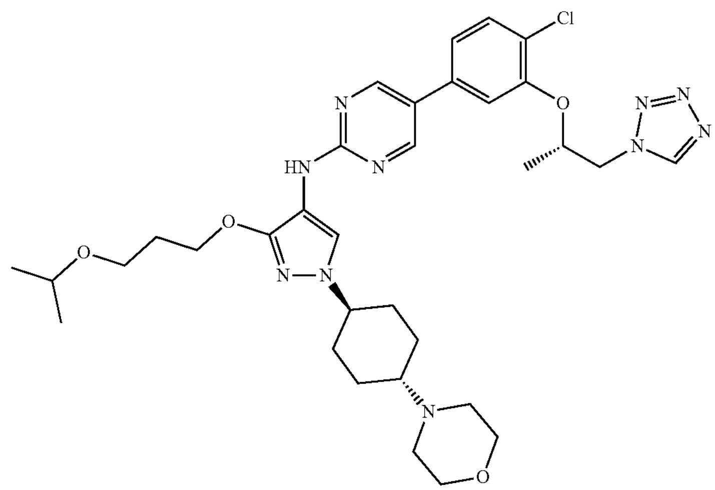 [SMILES: CC(C)OCCCOc1nn([C@H]2CC[C@H](N3CCOCC3)CC2)cc1Nc1ncc(-c2ccc(Cl)c(O[C@@H](C)Cn3cnnn3)c2)cn1] |
| 40 | 2-(((S)-1-(1H-tetrazol-1-yl)propan-2-yl)oxy)-4-(2-((1-((1r,4r)-4-morpholinocyclohexyl)-3-(3-(trifluoromethoxy)propoxy)-1H-pyrazol-4-yl)amino)pyrimidin-5-yl)benzonitrile | 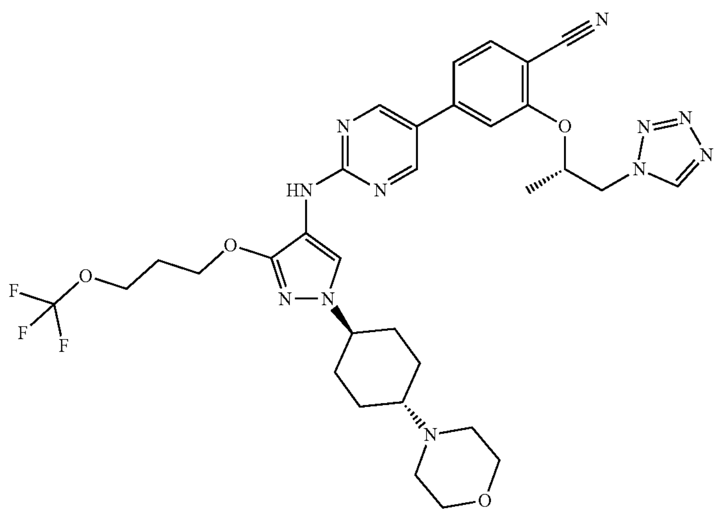 [SMILES: C[C@@H](Cn1cnnn1)Oc1cc(-c2cnc(Nc3cn([C@H]4CC[C@H](N5CCOCC5)CC4)nc3OCCCOC(F)(F)F)nc2)ccc1C#N] |
| 41 | 5-(3-(((S)-1-(1H-tetrazol-1-yl)propan-2-yl)oxy)-4-chlorophenyl)-N-(1-((1r,4r)-4-morpholinocyclohexyl)-3-(3-(trifluoromethoxy)propoxy)-1H-pyrazol-4-yl)pyrimidin-2-amine | 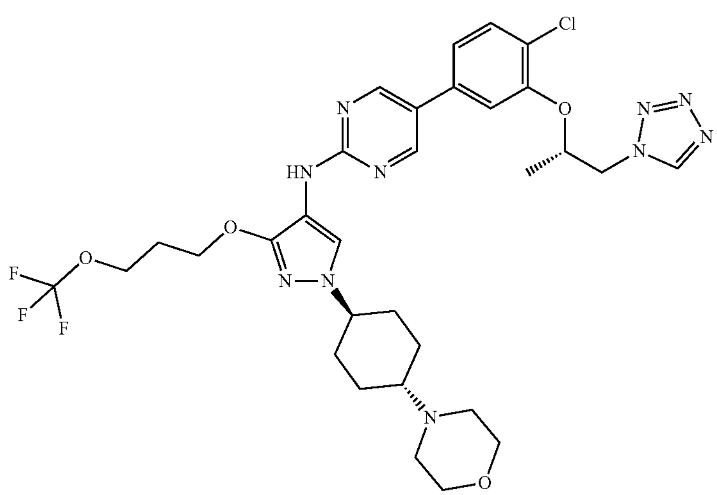 [SMILES: C[C@@H](Cn1cnnn1)Oc1cc(-c2cnc(Nc3cn([C@H]4CC[C@H](N5CCOCC5)CC4)nc3OCCCOC(F)(F)F)nc2)ccc1Cl] |

| Ex. No. | IUPAC NAME | STRUCTURE |
|---|---|---|
| 42 | 2-(((S)-1-(1H-tetrazol-1-yl)propan-2-yl)oxy)-4-(2-((3-(3-(difluoromethoxy)propoxy)-1-((1r,4r)-4-morpholinocyclohexyl)-1H-pyrazol-4-yl)amino)pyrimidin-5-yl)benzonitrile | 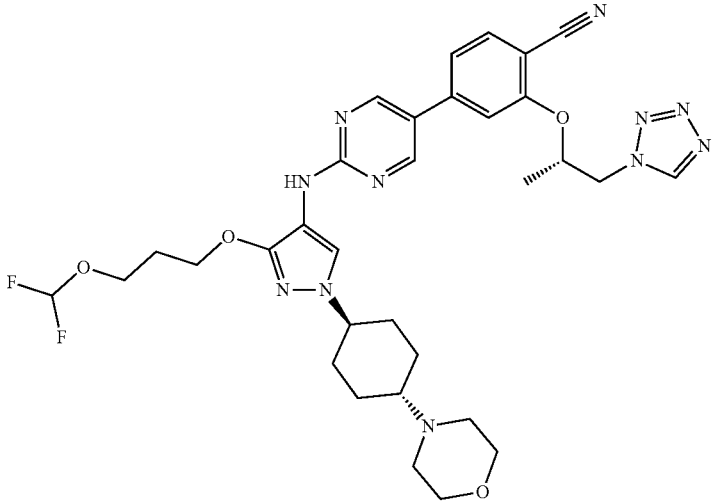 [SMILES: C[C@@H](Cn1cnnn1)Oc1cc(-c2cnc(Nc3cn([C@H]4CC[C@H](N5CCOCC5)CC4)nc3OCCCOC(F)F)nc2)ccc1C#N] |
| 43 | 5-(3-(((S)-1-(1H-tetrazol-1-yl)propan-2-yl)oxy)-4-chlorophenyl)-N-(3-(3-(difluoromethoxy)propoxy)-1-((1r,4r)-4-morpholinocyclohexyl)-1H-pyrazol-4-yl)pyrimidin-2-amine | 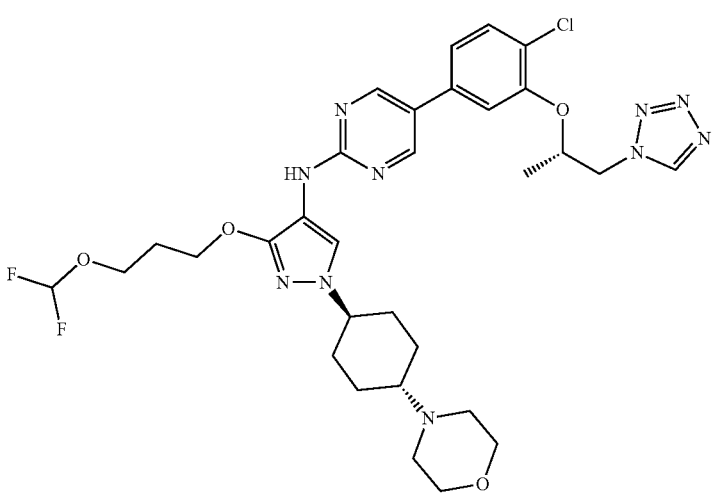 [SMILES: C[C@@H](Cn1cnnn1)Oc1cc(-c2cnc(Nc3cn([C@H]4CC[C@H](N5CCOCC5)CC4)nc3OCCCOC(F)F)nc2)ccc1Cl] |
| 44 | 2-(((S)-1-(1H-tetrazol-1-yl)propan-2-yl)oxy)-4-(2-((1-((1r,4r)-4-morpholinocyclohexyl)-3-(3-(2,2,2-trifluoroethoxy)propoxy)-1H-pyrazol-4-yl)amino)pyrimidin-5-yl)benzonitrile | 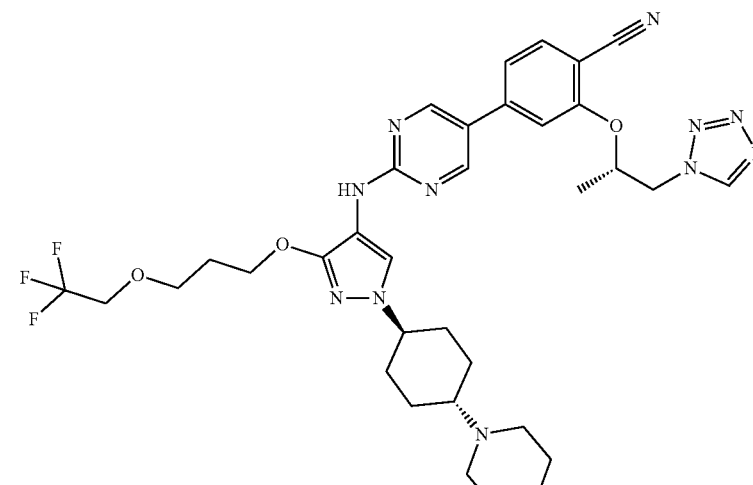 |

TABLE 2-continued

| Ex. No. | IUPAC NAME | STRUCTURE |
|---|---|---|
| 45 | 5-(3-(((S)-1-(1H-tetrazol-1-yl)propan-2-yl)oxy)-4-chlorophenyl)-N-(1-((1r,4r)-4-morpholinocyclohexyl)-3-(3-(2,2,2-trifluoroethoxy)propoxy)-1H-pyrazol-4-yl)pyrimidin-2-amine | 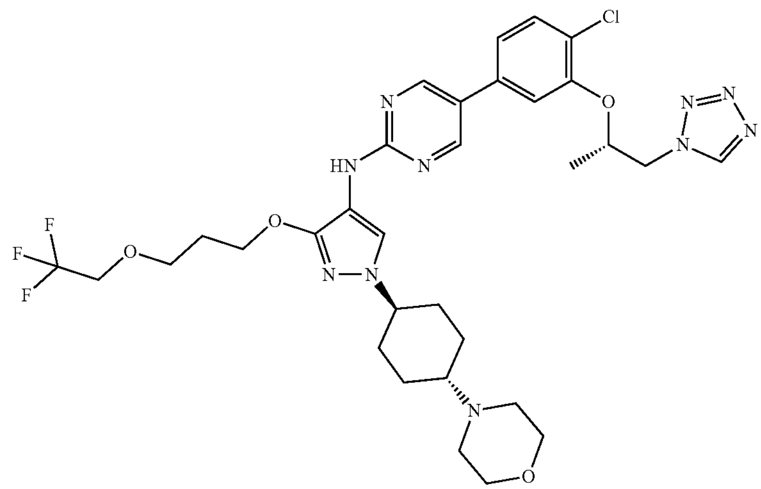 [SMILES: C[C@@H](Cn1cnnn1)Oc1cc(-c2cnc(Nc3cn([C@H]4CC[C@H](N5CCOCC5)CC4)nc3OCCCOCC(F)(F)F)nc2)ccc1Cl] |
| 50 | 5-(3-(((S)-1-(1H-1,2,4-triazol-1-yl)propan-2-yl)oxy)-4-chlorophenyl)-N-(3-(2-(2-methoxyethoxy)ethoxy)-1-((1r,4r)-4-morpholinocyclohexyl)-1H-pyrazol-4-yl)pyrimidin-2-amine | 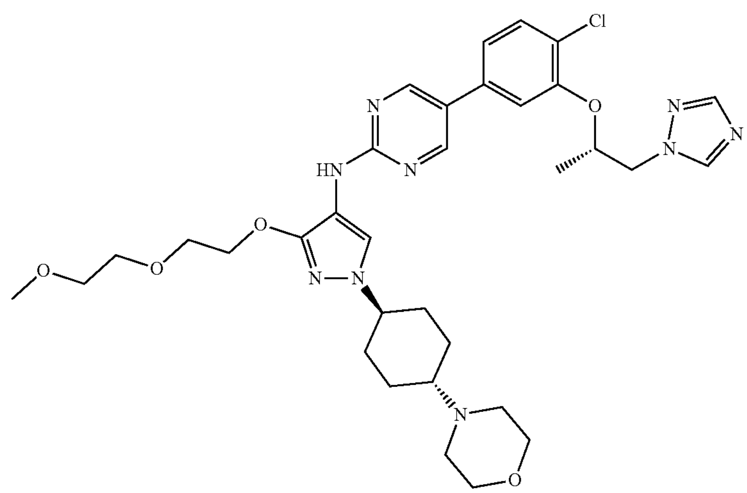 [SMILES: COCCOCCOc1nn([C@H]2CC[C@H](N3CCOCC3)CC2)cc1Nc1ncc(-c2ccc(Cl)c(O[C@@H](C)Cn3cncn3)c2)cn1] |
| 51 | 5-(3-(((S)-1-(1H-1,2,4-triazol-1-yl)propan-2-yl)oxy)-4-chlorophenyl)-N-(1-((1r,4r)-4-((1R,5S)-3-oxa-8-azabicyclo[3.2.1]octan-8-yl)cyclohexyl)-3-(2-(2-methoxyethoxy)ethoxy)-1H-pyrazol-4-yl)pyrimidin-2-amine | 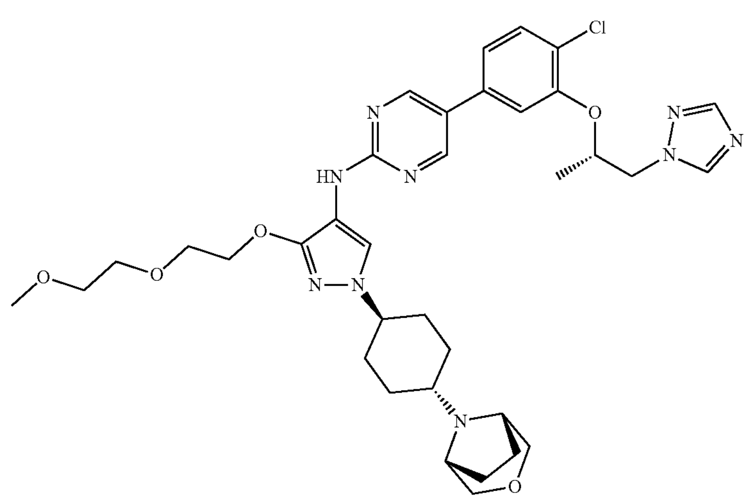 [SMILES: COCCOCCOc1nn([C@H]2CC[C@H](N3[C@@H]4CC[C@H]3COC4)CC2)cc1Nc1ncc(-c2ccc(Cl)c(O[C@@H](C)Cn3cncn3)c2)cn1] |

TABLE 2-continued

| Ex. No. | IUPAC NAME | STRUCTURE |
|---|---|---|
| 52 | 2-(((S)-1-(1H-1,2,4-triazol-1-yl)propan-2-yl)oxy)-4-(2-((1-((1r,4r)-4-((2S,6R)-2,6-dimethylmorpholino)cyclohexyl)-3-(2-(2-methoxyethoxy)ethoxy)-1H-pyrazol-4-yl)amino)pyrimidin-5-yl)benzonitrile | 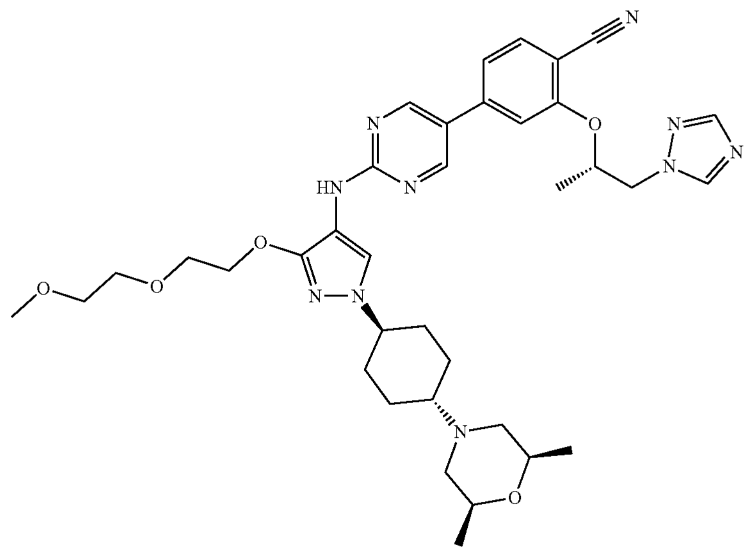 [SMILES: COCCOCCOc1nn([C@H]2CC[C@H](N3C[C@@H](C)O[C@@H](C)C3)CC2)cc1Nc1ncc(-c2ccc(C#N)c(O[C@@H](C)Cn3cncn3)c2)cn1] |
| 53 | 2-(((S)-1-(1H-tetrazol-1-yl)propan-2-yl)oxy)-4-(2-((3-(2-hydroxyethoxy)-1-((1r,4r)-4-morpholinocyclohexyl)-1H-pyrazol-4-yl)amino)pyrimidin-5-yl)benzonitrile | 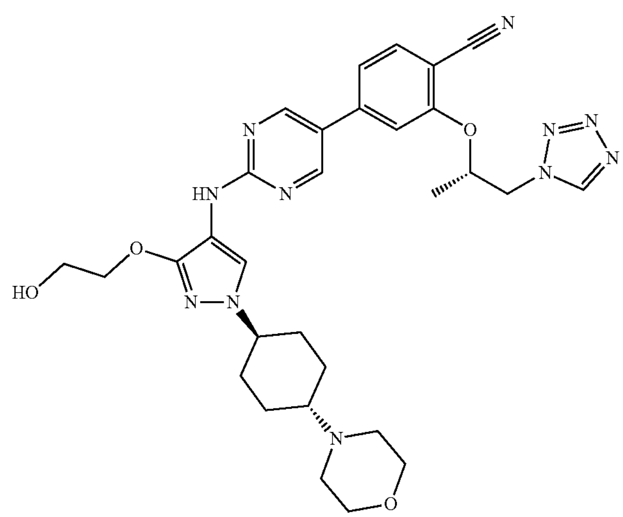 [SMILES: C[C@@H](Cn1cnnn1)Oc1cc(-c2cnc(Nc3cn([C@H]4CC[C@H](N5CCOCC5)CC4)nc3OCCO)nc2)ccc1C#N] |
| 54 | 2-((4-((5-(3-(((S)-1-(1H-tetrazol-1-yl)propan-2-yl)oxy)-4-chlorophenyl)pyrimidin-2-yl)amino)-1-((1r,4r)-4-morpholinocyclohexyl)-1H-pyrazol-3-yl)oxy)ethan-1-ol | 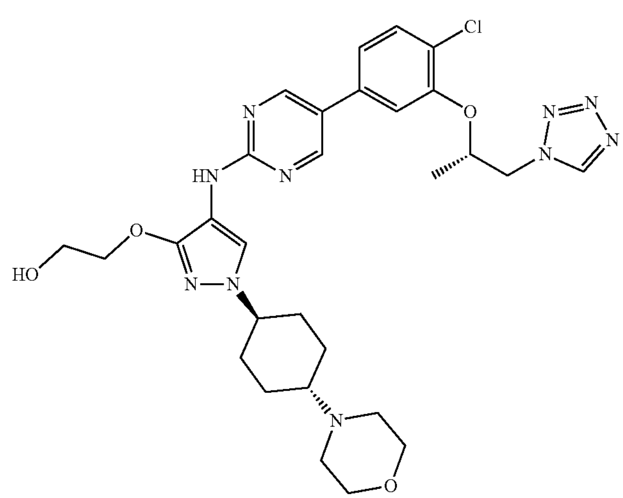 [SMILES: C[C@@H](Cn1cnnn1)Oc1cc(-c2cnc(Nc3cn([C@H]4CC[C@H](N5CCOCC5)CC4)nc3OCCO)nc2)ccc1Cl] |

TABLE 2-continued

| Ex. No. | IUPAC NAME | STRUCTURE |
| --- | --- | --- |
| 55 | 2-((4-((5-(3-(((S)-1-(1H-1,2,4-triazol-1-yl)propan-2-yl)oxy)-4-chlorophenyl)pyrimidin-2-yl)amino)-1-((1r,4r)-4-morpholinocyclohexyl)-1H-pyrazol-3-yl)oxy)ethan-1-ol | 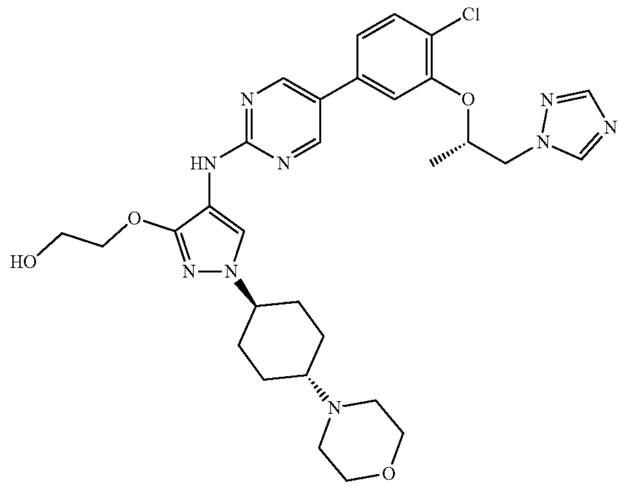 [SMILES: C[C@@H](Cn1cncn1)Oc1cc(-c2cnc(Nc3cn([C@H]4CC[C@H](N5CCOCC5)CC4)nc3OCCO)nc2)ccc1Cl] |
| 56 | 2-((4-((5-(3-(((S)-1-(1H-1,2,4-triazol-1-yl)propan-2-yl)oxy)-4-chlorophenyl)pyrimidin-2-yl)amino)-1-((1r,4r)-4-((1R,5S)-3-oxa-8-azabicyclo[3.2.1]octan-8-yl)cyclohexyl)-1H-pyrazol-3-yl)oxy)ethan-1-ol | 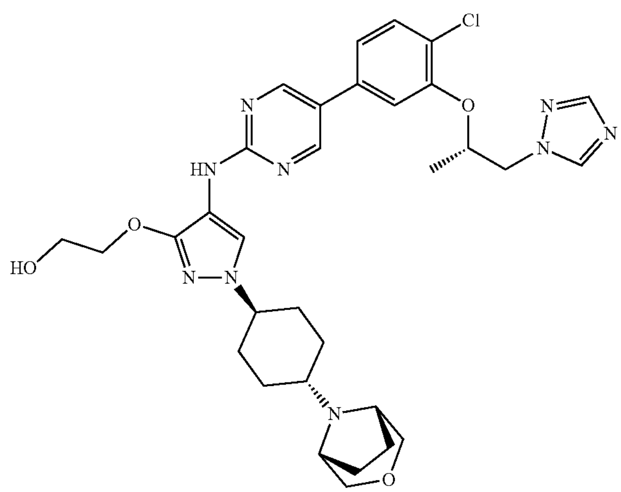 [SMILES: C[C@@H](Cn1cncn1)Oc1cc(-c2cnc(Nc3cn([C@H]4CC[C@H](N5[C@@H]6CC[C@H]5COC6)CC4)nc3OCCO)nc2)ccc1Cl] |
| 57 | 2-(((S)-1-(1H-tetrazol-1-yl)propan-2-yl)oxy)-4-(2-((3-(2-hydroxy-2-methylpropoxy)-1-((1r,4r)-4-morpholinocyclohexyl)-1H-pyrazol-4-yl)amino)pyrimidin-5-yl)benzonitrile | 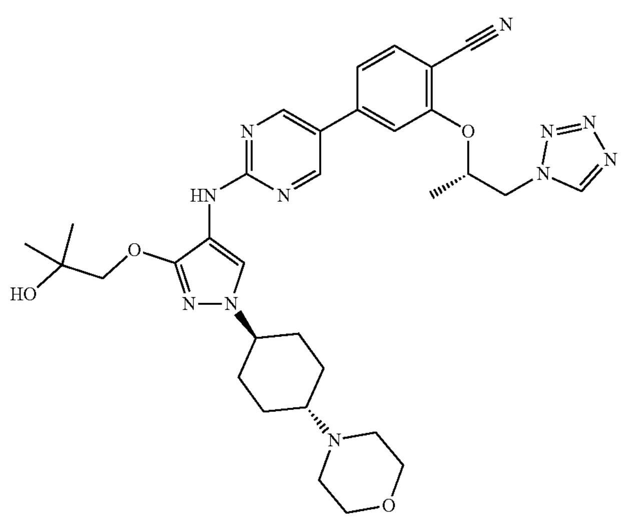 [SMILES: C[C@@H](Cn1cnnn1)Oc1cc(-c2cnc(Nc3cn([C@H]4CC[C@H](N5CCOCC5)CC4)nc3OCC(C)(C)O)nc2)ccc1C#N] |

TABLE 2-continued

| Ex. No. | IUPAC NAME | STRUCTURE |
|---|---|---|
| 58 | 1-((4-((5-(3-(((S)-1-(1H-tetrazol-1-yl)propan-2-yl)oxy)-4-chlorophenyl)pyrimidin-2-yl)amino)-1-((1r,4r)-4-morpholinocyclohexyl)-1H-pyrazol-3-yl)oxy)-2-methylpropan-2-ol | 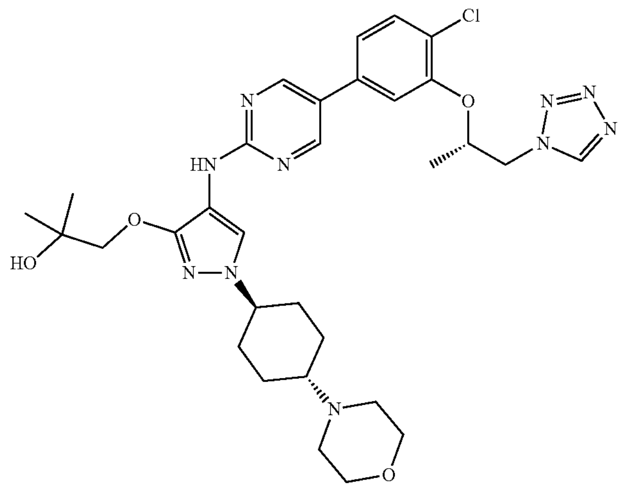 [SMILES: C[C@@H](Cn1cnnn1)Oc1cc(-c2cnc(Nc3cn([C@H]4CC[C@H](N5CCOCC5)CC4)nc3OCC(C)(C)O)nc2)ccc1Cl] |
| 59 | 1-((4-((5-(3-(((S)-1-(1H-1,2,4-triazol-1-yl)propan-2-yl)oxy)-4-chlorophenyl)pyrimidin-2-yl)amino)-1-((1r,4r)-4-morpholinocyclohexyl)-1H-pyrazol-3-yl)oxy)-2-methylpropan-2-ol | 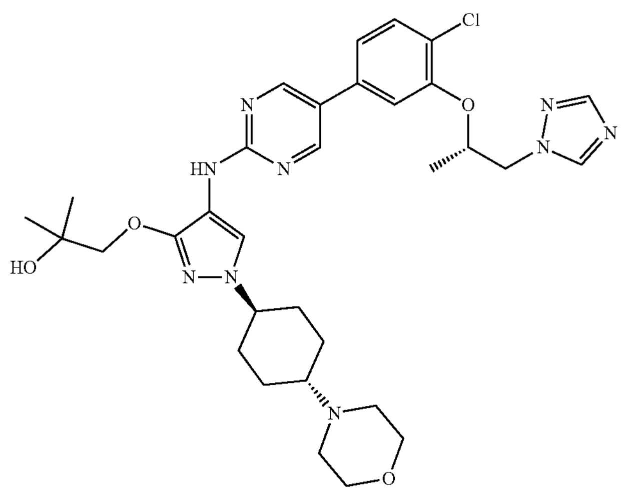 [SMILES: C[C@@H](Cn1cncn1)Oc1cc(-c2cnc(Nc3cn([C@H]4CC[C@H](N5CCOCC5)CC4)nc3OCC(C)(C)O)nc2)ccc1Cl] |
| 60 | 2-(((S)-1-(1H-1,2,4-triazol-1-yl)propan-2-yl)oxy)-4-(2-((1-((1r,4r)-4-((1R,5S)-3-oxa-8-azabicyclo[3.2.1]octan-8-yl)cyclohexyl)-3-(2-hydroxy-2-methylpropoxy)-1H-pyrazol-4-yl)amino)pyrimidin-5-yl)benzonitrile | 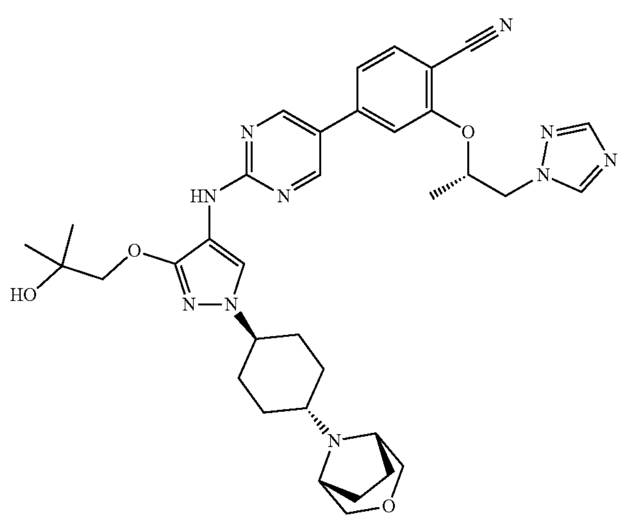 [SMILES: C[C@@H](Cn1cncn1)Oc1cc(-c2cnc(Nc3cn([C@H]4CC[C@H](N5[C@@H]6CC[C@H]5COC6)CC4)nc3OCC(C)(C)O)nc2)ccc1C#N] |

TABLE 2-continued

| Ex. No. | IUPAC NAME | STRUCTURE |
|---|---|---|
| 61 | 1-((4-((5-(3-(((S)-1-(1H-1,2,4-triazol-1-yl)propan-2-yl)oxy)-4-chlorophenyl)pyrimidin-2-yl)amino)-1-((1r,4r)-4-((1R,5S)-3-oxa-8-azabicyclo[3.2.1]octan-8-yl)cyclohexyl)-1H-pyrazol-3-yl)oxy)-2-methylpropan-2-ol | 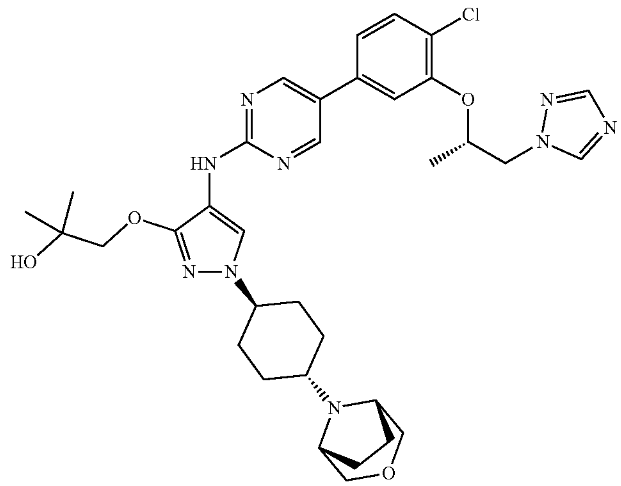 [SMILES: C[C@@H](Cn1cncn1)Oc1cc(-c2cnc(Nc3cn([C@H]4CC[C@H](N5[C@@H]6CC[C@H]5COC6)CC4)nc3OCC(C)(C)O)nc2)ccc1Cl] |
| 62 | 2-(((S)-1-(1H-1,2,4-triazol-1-yl)propan-2-yl)oxy)-4-(2-((1-((1r,4r)-4-((2S,6R)-2,6-dimethylmorpholino)cyclohexyl)-3-(2-hydroxy-2-methylpropoxy)-1H-pyrazol-4-yl)amino)pyrimidin-5-yl)benzonitrile | 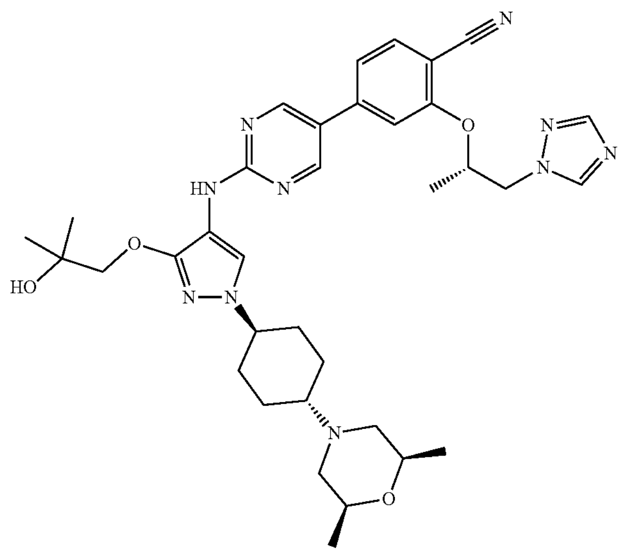 [SMILES: C[C@@H]1CN([C@H]2CC[C@H](n3cc(Nc4ncc(-c5ccc(C#N)c(O[C@@H](C)Cn6cncn6)c5)cn4)c(OCC(C)(C)O)n3)CC2)C[C@H](C)O1] |
| 63 | 2-(((S)-1-(1H-tetrazol-1-yl)propan-2-yl)oxy)-4-(2-((3-((1-hydroxycyclopropyl)methoxy)-1-((1r,4r)-4-morpholinocyclohexyl)-1H-pyrazol-4-yl)amino)pyrimidin-5-yl)benzonitrile | 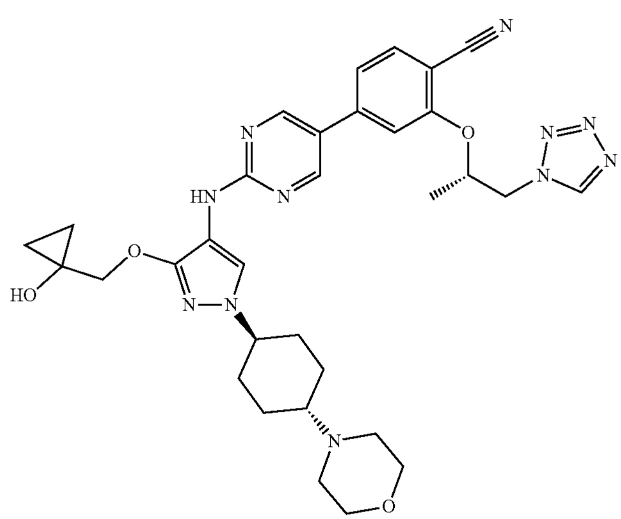 [SMILES: C[C@@H](Cn1cnnn1)Oc1cc(-c2cnc(Nc3cn([C@H]4CC[C@H](N5CCOCC5)CC4)nc3OCC3(O)CC3)nc2)ccc1C#N] |

TABLE 2-continued

| Ex. No. | IUPAC NAME | STRUCTURE |
| --- | --- | --- |
| 64 | 1-(((4-((5-(3-(((S)-1-(1H-tetrazol-1-yl)propan-2-yl)oxy)-4-chlorophenyl)pyrimidin-2-yl)amino)-1-((1r,4r)-4-morpholinocyclohexyl)-1H-pyrazol-3-yl)oxy)methyl)cyclopropan-1-ol | 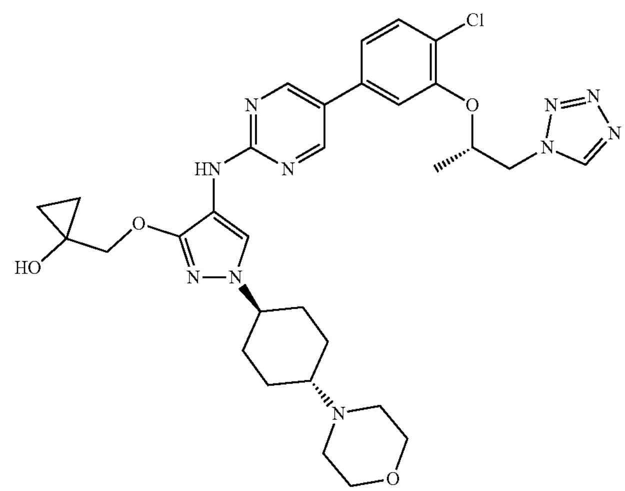 [SMILES: C[C@@H](Cn1cnnn1)Oc1cc(-c2cnc(Nc3cn([C@H]4CC[C@H](N5CCOCC5)CC4)nc3OCC3(O)CC3)nc2)ccc1Cl] |
| 65 | 2-(((S)-1-(1H-tetrazol-1-yl)propan-2-yl)oxy)-4-(2-((3-((1-hydroxycyclobutyl)methoxy)-1-((1r,4r)-4-morpholinocyclohexyl)-1H-pyrazol-4-yl)amino)pyrimidin-5-yl)benzonitrile | 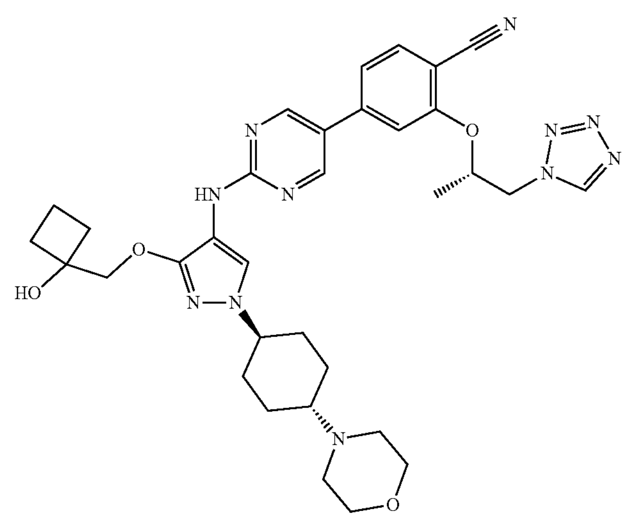 [SMILES: C[C@@H](Cn1cnnn1)Oc1cc(-c2cnc(Nc3cn([C@H]4CC[C@H](N5CCOCC5)CC4)nc3OCC3(O)CCC3)nc2)ccc1C#N] |
| 66 | 1-(((4-((5-(3-(((S)-1-(1H-tetrazol-1-yl)propan-2-yl)oxy)-4-chlorophenyl)pyrimidin-2-yl)amino)-1-((1r,4r)-4-morpholinocyclohexyl)-1H-pyrazol-3-yl)oxy)methyl)cyclobutan-1-ol | 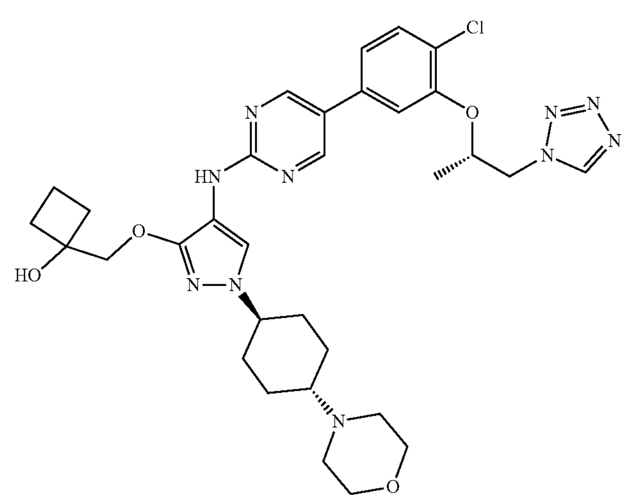 [SMILES: C[C@@H](Cn1cnnn1)Oc1cc(-c2cnc(Nc3cn([C@H]4CC[C@H](N5CCOCC5)CC4)nc3OCC3(O)CCC3)nc2)ccc1Cl] |

TABLE 2-continued

| Ex. No. | IUPAC NAME | STRUCTURE |
|---|---|---|
| 67 | 2-(((S)-1-(1H-tetrazol-1-yl)propan-2-yl)oxy)-4-(2-((3-(3-hydroxypropoxy)-1-((1r,4r)-4-morpholinocyclohexyl)-1H-pyrazol-4-yl)amino)pyrimidin-5-yl)benzonitrile | 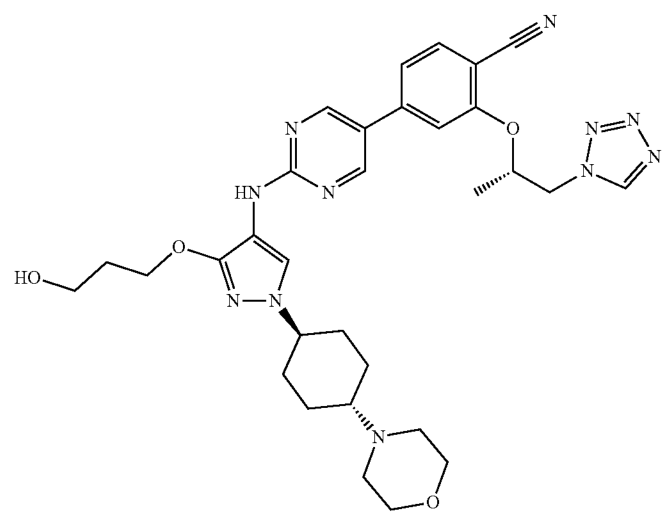 [SMILES: C[C@@H](Cn1cnnn1)Oc1cc(-c2cnc(Nc3cn([C@H]4CC[C@H](N5CCOCC5)CC4)nc3OCCCO)nc2)ccc1C#N] |
| 68 | 3-((4-((5-(3-(((S)-1-(1H-tetrazol-1-yl)propan-2-yl)oxy)-4-chlorophenyl)pyrimidin-2-yl)amino)-1-((1r,4r)-4-morpholinocyclohexyl)-1H-pyrazol-3-yl)oxy)propan-1-ol | 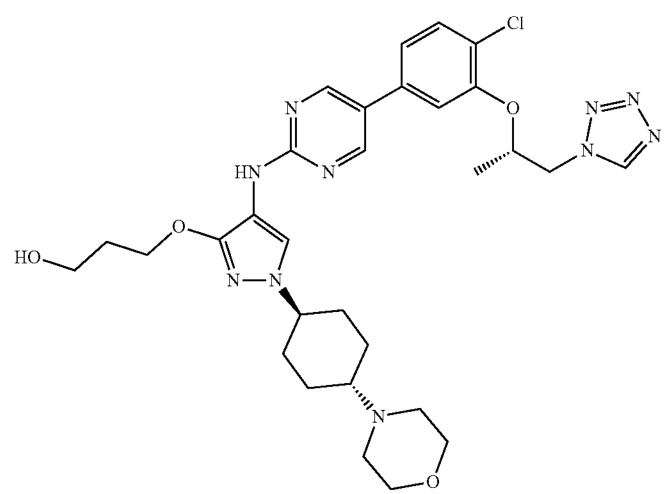 [SMILES: C[C@@H](Cn1cnnn1)Oc1cc(-c2cnc(Nc3cn([C@H]4CC[C@H](N5CCOCC5)CC4)nc3OCCCO)nc2)ccc1Cl] |
| 69 | 2-(((S)-1-(1H-tetrazol-1-yl)propan-2-yl)oxy)-4-(2-((3-(3-hydroxy-3-methylbutoxy)-1-((1r,4r)-4-morpholinocyclohexyl)-1H-pyrazol-4-yl)amino)pyrimidin-5-yl)benzonitrile | 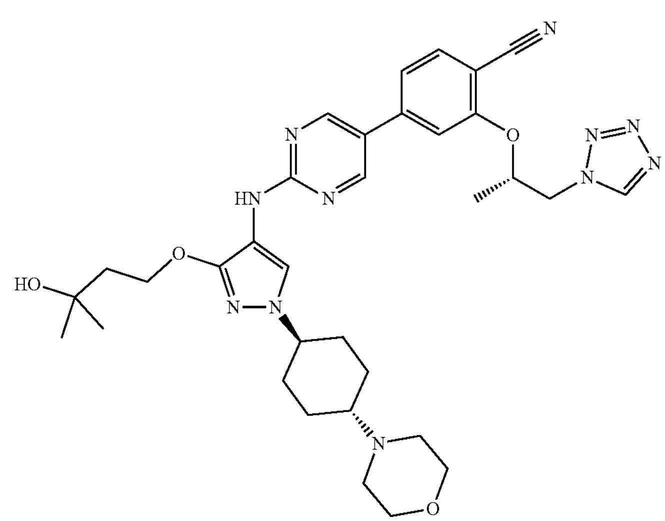 [SMILES: C[C@@H](Cn1cnnn1)Oc1cc(-c2cnc(Nc3cn([C@H]4CC[C@H](N5CCOCC5)CC4)nc3OCCC(C)(C)O)nc2)ccc1C#N] |

TABLE 2-continued

| Ex. No. | IUPAC NAME | STRUCTURE |
|---|---|---|
| 70 | 4-((4-((5-(3-(((S)-1-(1H-tetrazol-1-yl)propan-2-yl)oxy)-4-chlorophenyl)pyrimidin-2-yl)amino)-1-((1r,4r)-4-morpholinocyclohexyl)-1H-pyrazol-3-yl)oxy)-2-methylbutan-2-ol | 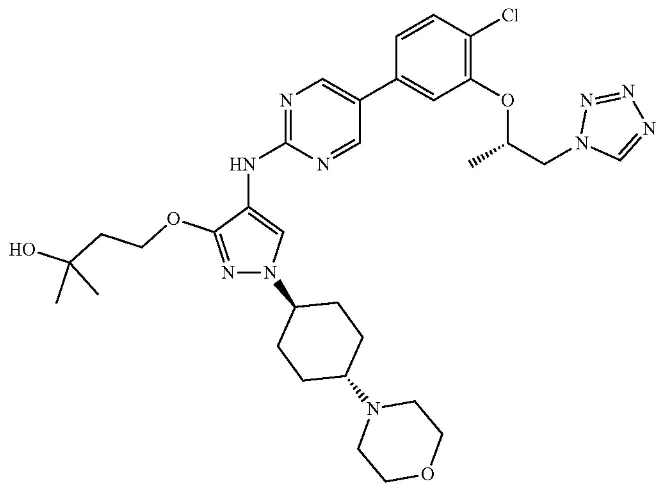 [SMILES: C[C@@H](Cn1cnnn1)Oc1cc(-c2cnc(Nc3cn([C@H]4CC[C@H](N5CCOCC5)CC4)nc3OCCC(C)(C)O)nc2)ccc1Cl] |
| 71 | 2-(((S)-1-(1H-tetrazol-1-yl)propan-2-yl)oxy)-4-(2-((3-(2-(1-hydroxycyclopropyl)ethoxy)-1-((1r,4r)-4-morpholinocyclohexyl)-1H-pyrazol-4-yl)amino)pyrimidin-5-yl)benzonitrile | 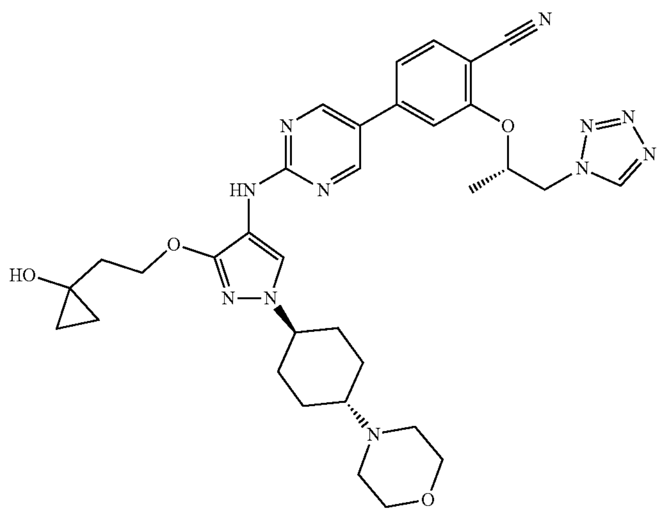 [SMILES: C[C@@H](Cn1cnnn1)Oc1cc(-c2cnc(Nc3cn([C@H]4CC[C@H](N5CCOCC5)CC4)nc3OCCC3(O)CC3)nc2)ccc1C#N] |
| 72 | 1-(2-((4-((5-(3-(((S)-1-(1H-tetrazol-1-yl)propan-2-yl)oxy)-4-chlorophenyl)pyrimidin-2-yl)amino)-1-((1r,4r)-4-morpholinocyclohexyl)-1H-pyrazol-3-yl)oxy)ethyl)cyclopropan-1-ol | 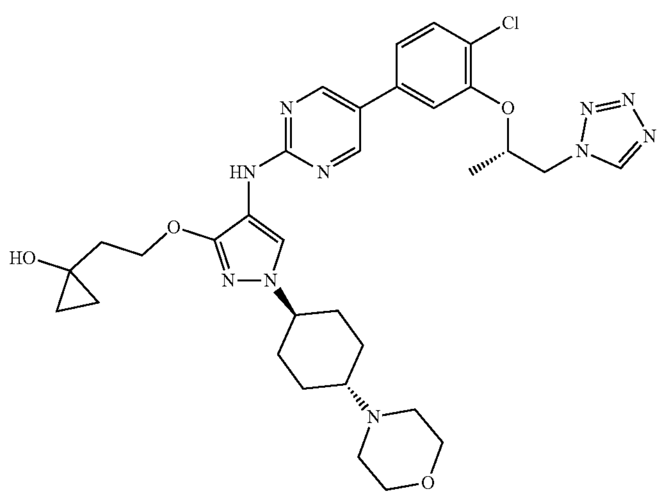 [SMILES: C[C@@H](Cn1cnnn1)Oc1cc(-c2cnc(Nc3cn([C@H]4CC[C@H](N5CCOCC5)CC4)nc3OCCC3(O)CC3)nc2)ccc1Cl] |

TABLE 2-continued

| Ex. No. | IUPAC NAME | STRUCTURE |
| --- | --- | --- |
| 73 | 2-(((S)-1-(1H-tetrazol-1-yl)propan-2-yl)oxy)-4-(2-((3-(2-(1-hydroxycyclobutyl)ethoxy)-1-((1r,4r)-4-morpholinocyclohexyl)-1H-pyrazol-4-yl)amino)pyrimidin-5-yl)benzonitrile | 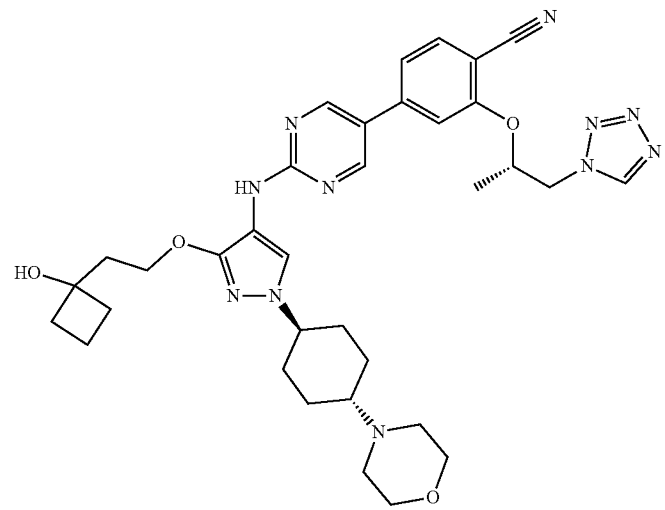 [SMILES: C[C@@H](Cn1cnnn1)Oc1cc(-c2cnc(Nc3cn([C@H]4CC[C@H](N5CCOCC5)CC4)nc3OCCC3(O)CCC3)nc2)ccc1C#N] |
| 74 | 1-(2-((4-((5-(3-(((S)-1-(1H-tetrazol-1-yl)propan-2-yl)oxy)-4-chlorophenyl)pyrimidin-2-yl)amino)-1-((1r,4r)-4-morpholinocyclohexyl)-1H-pyrazol-3-yl)oxy)ethyl)cyclobutan-1-ol | 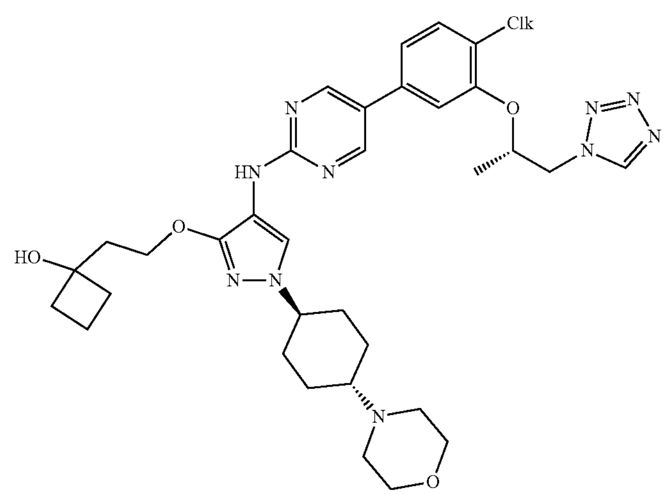 |
| 75 | 2-(((S)-1-(1H-tetrazol-1-yl)propan-2-yl)oxy)-4-(2-((3-(cyanomethoxy)-1-((1r,4r)-4-morpholinocyclohexyl)-1H-pyrazol-4-yl)amino)pyrimidin-5-yl)benzonitrile | 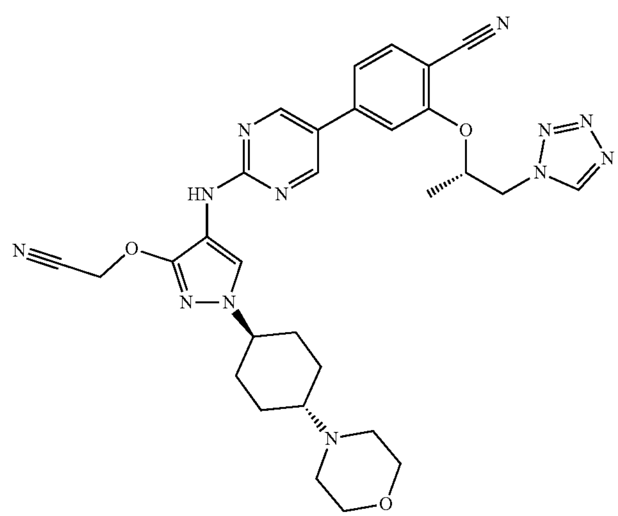 [SMILES: C[C@@H](Cn1cnnn1)Oc1cc(-c2cnc(Nc3cn([C@H]4CC[C@H](N5CCOCC5)CC4)nc3OCC#N)nc2)ccc1C#N] |

TABLE 2-continued

| Ex. No. | IUPAC NAME | STRUCTURE |
|---|---|---|
| 76 | 2-((4-((5-(3-(((S)-1-(1H-tetrazol-1-yl)propan-2-yl)oxy)-4-chlorophenyl)pyrimidin-2-yl)amino)-1-((1r,4r)-4-morpholinocyclohexyl)-1H-pyrazol-3-yl)oxy)acetonitrile | 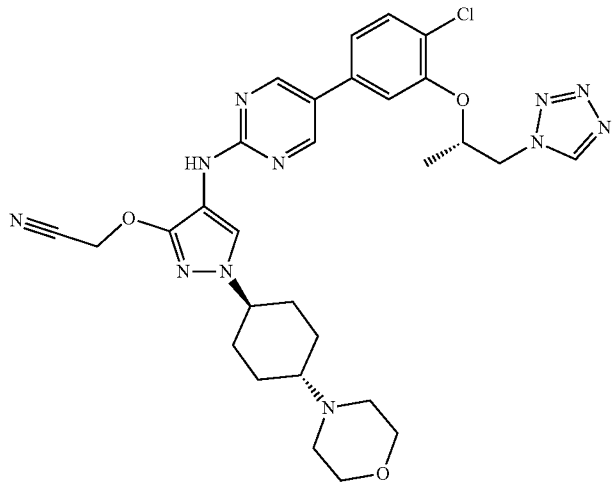 [SMILES: C[C@@H](Cn1cnnn1)Oc1cc(-c2cnc(Nc3cn([C@H]4CC[C@H](N5CCOCC5)CC4)nc3OCC#N)nc2)ccc1Cl] |
| 77 | 2-((4-((5-(3-(((S)-1-(1H-1,2,4-triazol-1-yl)propan-2-yl)oxy)-4-chlorophenyl)pyrimidin-2-yl)amino)-1-((1r,4r)-4-morpholinocyclohexyl)-1H-pyrazol-3-yl)oxy)acetonitrile | 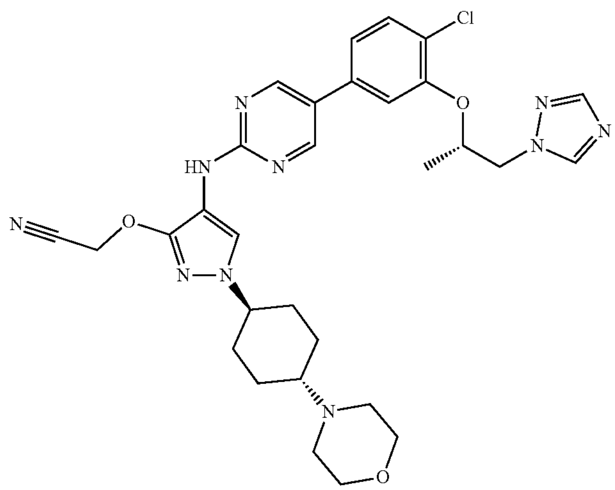 [SMILES: C[C@@H](Cn1cncn1)Oc1cc(-c2cnc(Nc3cn([C@H]4CC[C@H](N5CCOCC5)CC4)nc3OCC#N)nc2)ccc1Cl] |
| 78 | 2-((4-((5-(3-(((S)-1-(1H-1,2,4-triazol-1-yl)propan-2-yl)oxy)-4-chlorophenyl)pyrimidin-2-yl)amino)-1-((1r,4r)-4-((1R,5S)-3-oxa-8-azabicyclo[3.2.1]octan-8-yl)cyclohexyl)-1H-pyrazol-3-yl)oxy)acetonitrile | 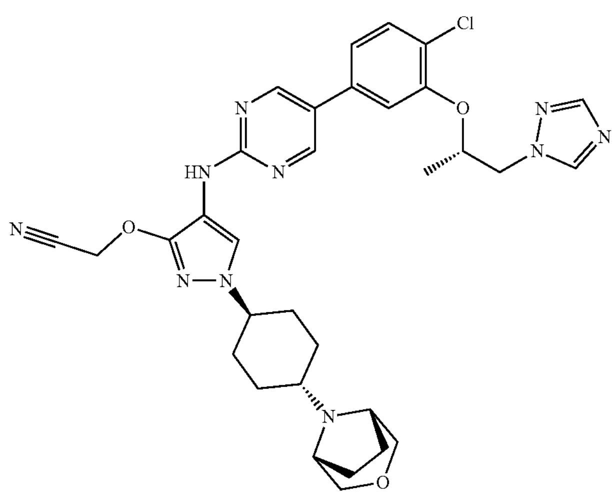 [SMILES: C[C@@H](Cn1cncn1)Oc1cc(-c2cnc(Nc3cn([C@H]4CC[C@H](N5[C@@H]6CC[C@H]5COC6)CC4)nc3OCC#N)nc2)ccc1Cl] |

TABLE 2-continued

| Ex. No. | IUPAC NAME | STRUCTURE |
|---|---|---|
| 79 | 2-(((S)-1-(1H-tetrazol-1-yl)propan-2-yl)oxy)-4-(2-((3-(2-cyanoethoxy)-1-((1r,4r)-4-morpholinocyclohexyl)-1H-pyrazol-4-yl)amino)pyrimidin-5-yl)benzonitrile | 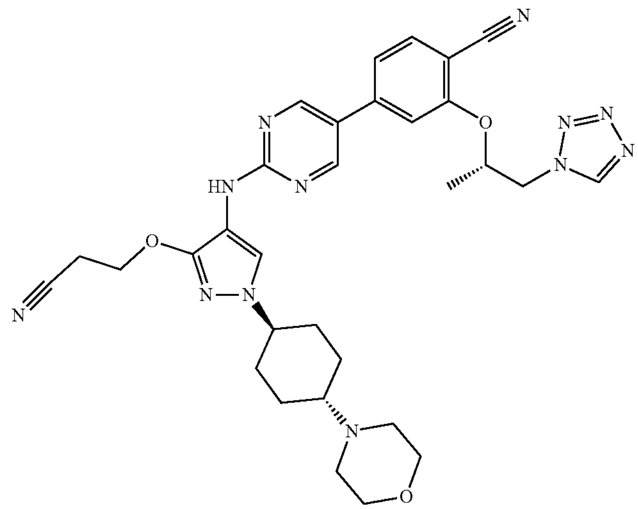 [SMILES: C[C@@H](Cn1cnnn1)Oc1cc(-c2cnc(Nc3cn([C@H]4CC[C@H](N5CCOCC5)CC4)nc3OCCC#N)nc2)ccc1C#N] |
| 80 | 3-((4-((5-(3-(((S)-1-(1H-tetrazol-1-yl)propan-2-yl)oxy)-4-chlorophenyl)pyrimidin-2-yl)amino)-1-((1r,4r)-4-morpholinocyclohexyl)-1H-pyrazol-3-yl)oxy)propanenitrile | 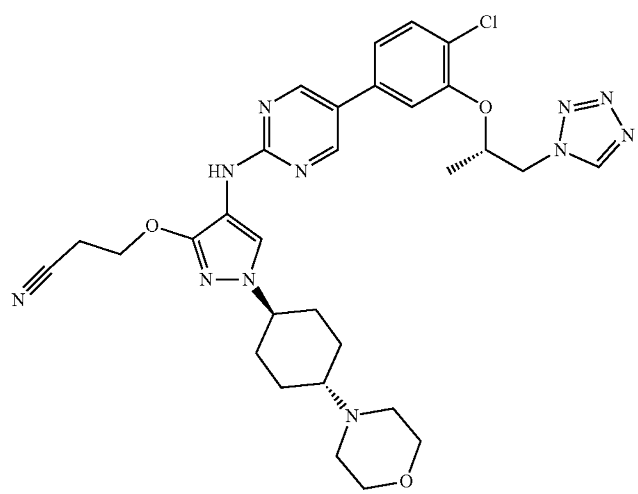 [SMILES: C[C@@H](Cn1cnnn1)Oc1cc(-c2cnc(Nc3cn([C@H]4CC[C@H](N5CCOCC5)CC4)nc3OCCC#N)nc2)ccc1Cl] |
| 81 | 3-((4-((5-(3-(((S)-1-(1H-1,2,4-triazol-1-yl)propan-2-yl)oxy)-4-chlorophenyl)pyrimidin-2-yl)amino)-1-((1r,4r)-4-morpholinocyclohexyl)-1H-pyrazol-3-yl)oxy)propanenitrile | 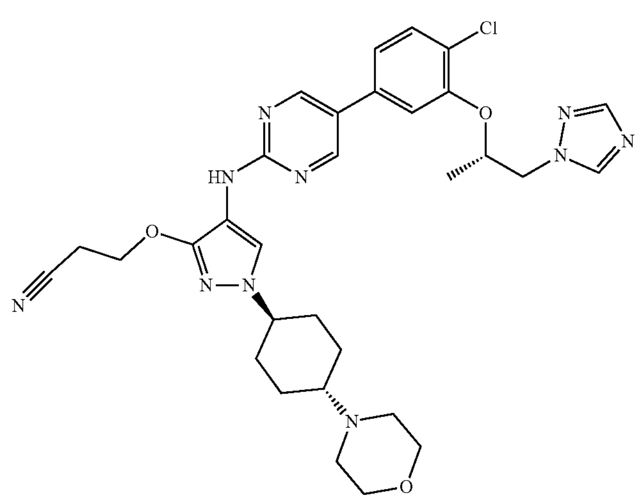 [SMILES: C[C@@H](Cn1cncn1)Oc1cc(-c2cnc(Nc3cn([C@H]4CC[C@H](N5CCOCC5)CC4)nc3OCCC#N)nc2)ccc1Cl] |

TABLE 2-continued

| Ex. No. | IUPAC NAME | STRUCTURE |
|---|---|---|
| 82 | 2-(((S)-1-(1H-tetrazol-1-yl)propan-2-yl)oxy)-4-(2-((3-(3-cyanopropoxy)-1-((1r,4r)-4-morpholinocyclohexyl)-1H-pyrazol-4-yl)amino)pyrimidin-5-yl)benzonitrile | 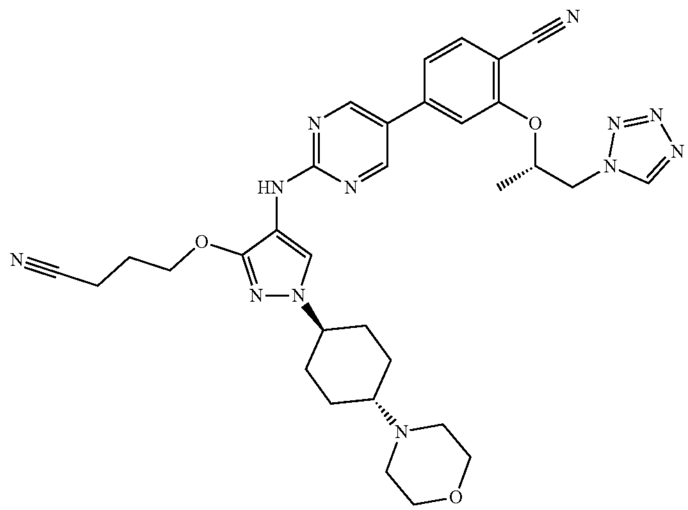 [SMILES: C[C@@H](Cn1cnnn1)Oc1cc(-c2cnc(Nc3cn([C@H]4CC[C@H](N5CCOCC5)CC4)nc3OCCCC#N)nc2)ccc1C#N] |
| 83 | 4-((4-((5-(3-(((S)-1-(1H-tetrazol-1-yl)propan-2-yl)oxy)-4-chlorophenyl)pyrimidin-2-yl)amino)-1-((1r,4r)-4-morpholinocyclohexyl)-1H-pyrazol-3-yl)oxy)butanenitrile | 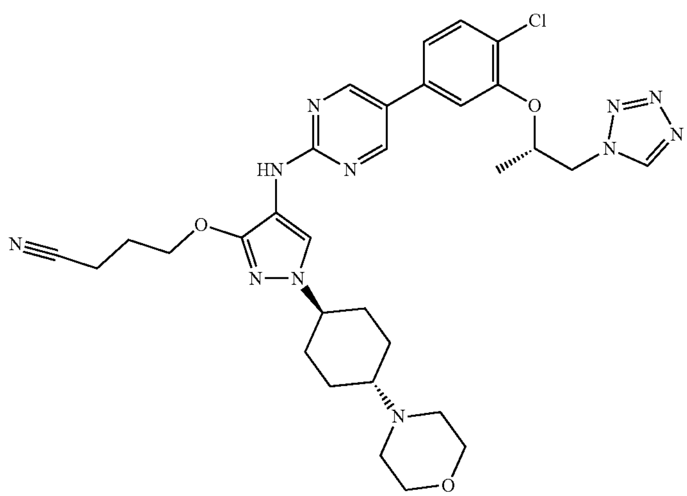 [SMILES: C[C@@H](Cn1cnnn1)Oc1cc(-c2cnc(Nc3cn([C@H]4CC[C@H](N5CCOCC5)CC4)nc3OCCCC#N)nc2)ccc1Cl] |
| 84 | 2-(((S)-1-(1H-tetrazol-1-yl)propan-2-yl)oxy)-4-(2-((3-(2-(methylsulfonyl)ethoxy)-1-((1r,4r)-4-morpholinocyclohexyl)-1H-pyrazol-4-yl)amino)pyrimidin-5-yl)benzonitrile | 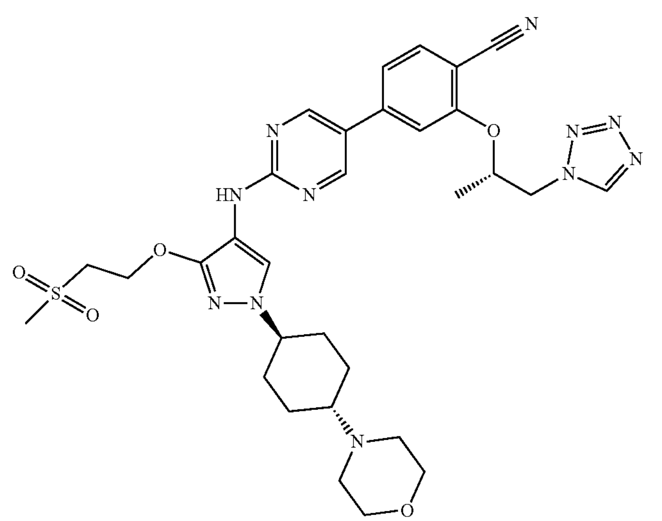 [SMILES: C[C@@H](Cn1cnnn1)Oc1cc(-c2cnc(Nc3cn([C@H]4CC[C@H](N5CCOCC5)CC4)nc3OCCS(C)(=O)=O)nc2)ccc1C#N] |

TABLE 2-continued

| Ex. No. | IUPAC NAME | STRUCTURE |
|---|---|---|
| 85 | 5-(3-(((S)-1-(1H-tetrazol-1-yl)propan-2-yl)oxy)-4-chlorophenyl)-N-(3-(2-(methylsulfonyl)ethoxy)-1-((1r,4r)-4-morpholinocyclohexyl)-1H-pyrazol-4-yl)pyrimidin-2-amine | 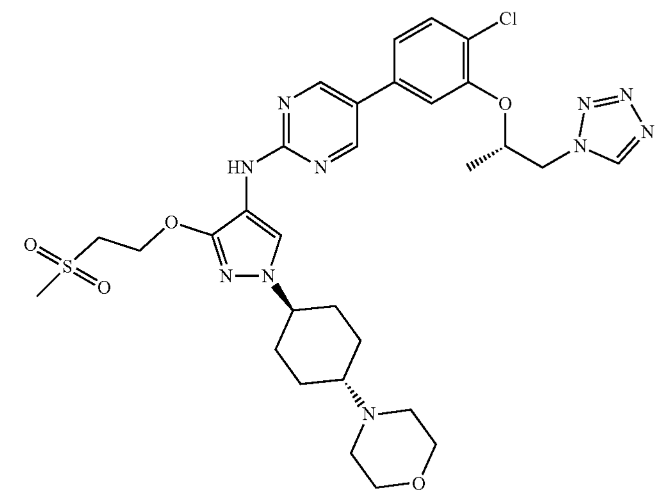 [SMILES: C[C@@H](Cn1cnnn1)Oc1cc(-c2cnc(Nc3cn([C@H]4CC[C@H](N5CCOCC5)CC4)nc3OCCS(C)(=O)=O)nc2)ccc1Cl] |
| 87 | 5-(3-(((S)-1-(1H-1,2,4-triazol-1-yl)propan-2-yl)oxy)-4-chlorophenyl)-N-(1-((1r,4r)-4-((1R,5S)-3-oxa-8-azabicyclo[3.2.1]octan-8-yl)cyclohexyl)-3-(2-(methylsulfonyl)ethoxy)-1H-pyrazol-4-yl)pyrimidin-2-amine | 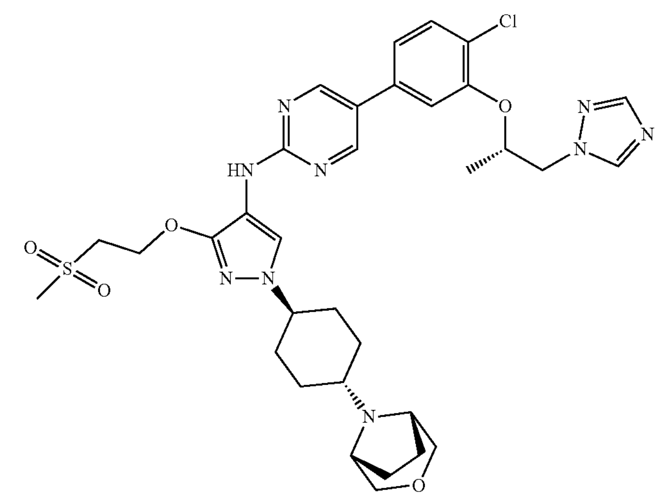 [SMILES: C[C@@H](Cn1cncn1)Oc1cc(-c2cnc(Nc3cn([C@H]4CC[C@H](N5[C@@H]6CC[C@H]5COC6)CC4)nc3OCCS(C)(=O)=O)nc2)ccc1Cl] |
| 88 | 2-(((S)-1-(1H-tetrazol-1-yl)propan-2-yl)oxy)-4-(2-((3-(2-(ethylsulfonyl)ethoxy)-1-((1r,4r)-4-morpholinocyclohexyl)-1H-pyrazol-4-yl)amino)pyrimidin-5-yl)benzonitrile | 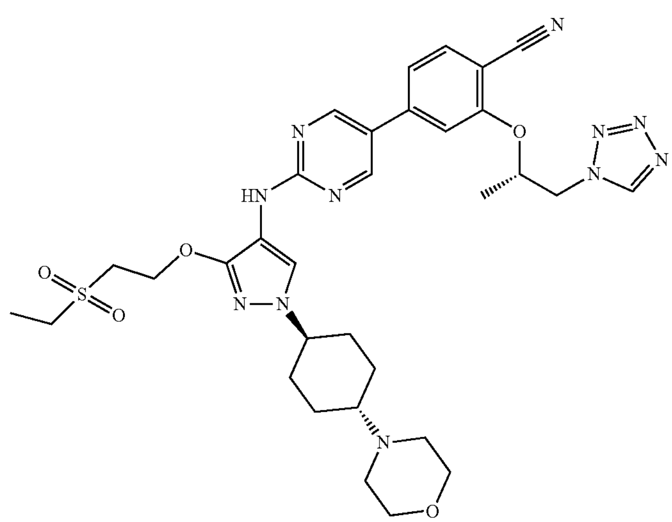 [SMILES: CCS(=O)(=O)CCOc1nn([C@H]2CC[C@H](N3CCOCC3)CC2)cc1Nc1ncc(-c2ccc(C#N)c(O[C@@H](C)Cn3cnnn3)c2)cn1] |

TABLE 2-continued

| Ex. No. | IUPAC NAME | STRUCTURE |
|---|---|---|
| 89 | 5-(3-(((S)-1-(1H-tetrazol-1-yl)propan-2-yl)oxy)-4-chlorophenyl)-N-(3-(2-(ethylsulfonyl)ethoxy)-1-((1r,4r)-4-morpholinocyclohexyl)-1H-pyrazol-4-yl)pyrimidin-2-amine | 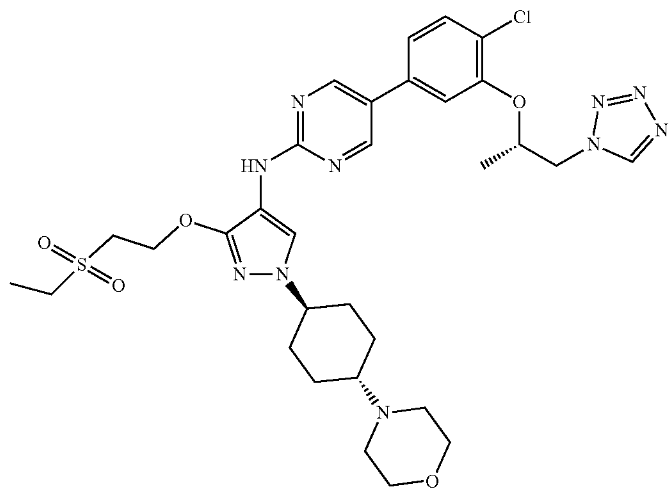 [SMILES: CCS(=O)(=O)CCOc1nn([C@H]2CC[C@H](N3CCOCC3)CC2)cc1Nc1ncc(-c2ccc(Cl)c(O[C@@H](C)Cn3cnnn3)c2)cn1] |
| 90 | 5-(3-(((S)-1-(1H-tetrazol-1-yl)propan-2-yl)oxy)-4-chlorophenyl)-N-(1-((1r,4r)-4-((1R,5S)-3-oxa-8-azabicyclo[3.2.1]octan-8-yl)cyclohexyl)-3-(2-(ethylsulfonyl)ethoxy)-1H-pyrazol-4-yl)pyrimidin-2-amine | 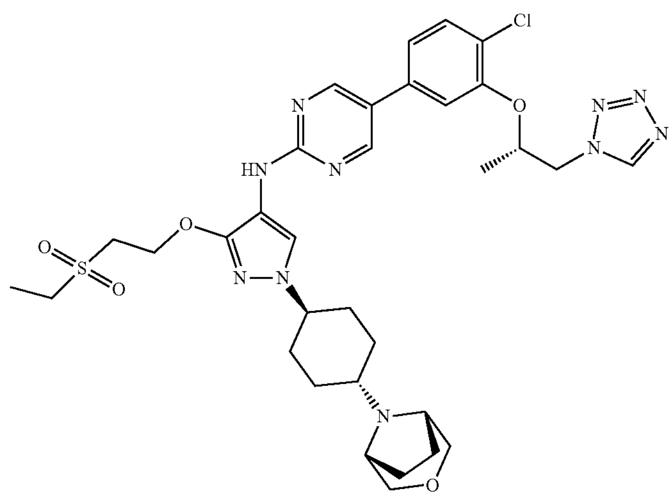 [SMILES: CCS(=O)(=O)CCOc1nn([C@H]2CC[C@H](N3[C@@H]4CC[C@H]3COC4)CC2)cc1Nc1ncc(-c2ccc(Cl)c(O[C@@H](C)Cn3cnnn3)c2)cn1] |
| 91 | 5-(3-(((S)-1-(1H-1,2,4-triazol-1-yl)propan-2-yl)oxy)-4-chlorophenyl)-N-(1-((1r,4r)-4-((2S,6R)-2,6-dimethylmorpholino)cyclohexyl)-3-(2-(ethylsulfonyl)ethoxy)-1H-pyrazol-4-yl)pyrimidin-2-amine | 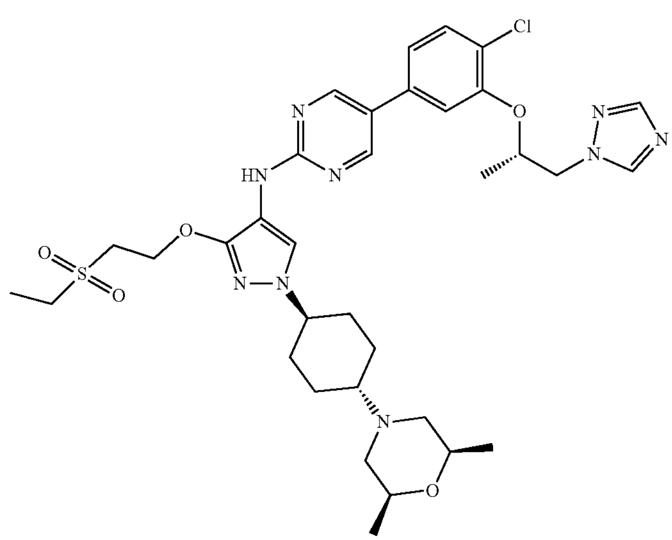 [SMILES: CCS(=O)(=O)CCOc1nn([C@H]2CC[C@H](N3C[C@@H](C)O[C@@H](C)C3)CC2)cc1Nc1ncc(-c2ccc(Cl)c(O[C@@H](C)Cn3cncn3)c2)cn1] |

TABLE 2-continued

| Ex. No. | IUPAC NAME | STRUCTURE |
|---|---|---|
| 92 | 2-(((S)-1-(1H-tetrazol-1-yl)propan-2-yl)oxy)-4-(2-((3-(3-(methylsulfonyl)propoxy)-1-((1r,4r)-4-morpholinocyclohexyl)-1H-pyrazol-4-yl)amino)pyrimidin-5-yl)benzonitrile | 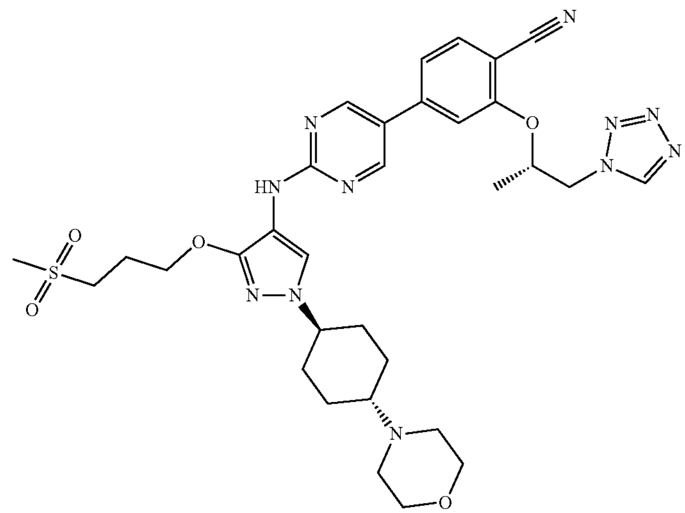 [SMILES: C[C@@H](Cn1cnnn1)Oc1cc(-c2cnc(Nc3cn([C@H]4CC[C@H](N5CCOCC5)CC4)nc3OCCCS(C)(=O)=O)nc2)ccc1C#N] |
| 93 | 5-(3-(((S)-1-(1H-tetrazol-1-yl)propan-2-yl)oxy)-4-chlorophenyl)-N-(3-(3-(methylsulfonyl)propoxy)-1-((1r,4r)-4-morpholinocyclohexyl)-1H-pyrazol-4-yl)pyrimidin-2-amine | 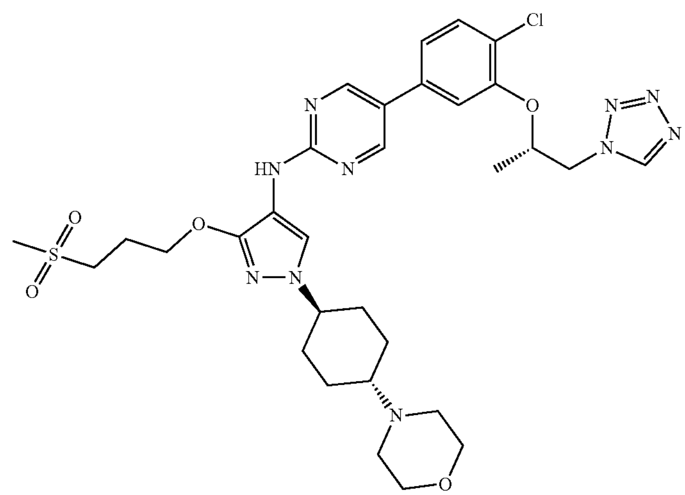 [SMILES: C[C@@H](Cn1cnnn1)Oc1cc(-c2cnc(Nc3cn([C@H]4CC[C@H](N5CCOCC5)CC4)nc3OCCCS(C)(=O)=O)nc2)ccc1Cl] |
| 94 | 2-(((S)-1-(1H-tetrazol-1-yl)propan-2-yl)oxy)-4-(2-((3-(3-(ethylsulfonyl)propoxy)-1-((1r,4r)-4-morpholinocyclohexyl)-1H-pyrazol-4-yl)amino)pyrimidin-5-yl)benzonitrile | 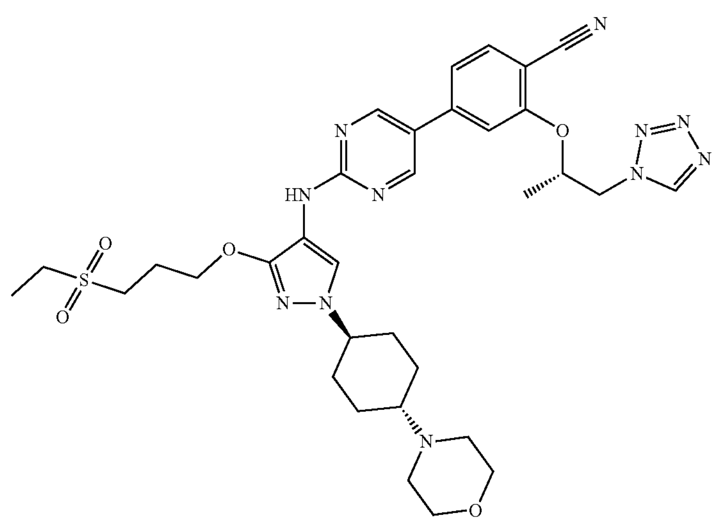 [SMILES: CCS(=O)(=O)CCCOc1nn([C@H]2CC[C@H](N3CCOCC3)CC2)cc1Nc1ncc(-c2ccc(C#N)c(O[C@@H](C)Cn3cnnn3)c2)cn1] |

TABLE 2-continued

| Ex. No. | IUPAC NAME | STRUCTURE |
| --- | --- | --- |
| 95 | 5-(3-(((S)-1-(1H-tetrazol-1-yl)propan-2-yl)oxy)-4-chlorophenyl)-N-(3-(ethylsulfonyl)propoxy)-1-((1r,4r)-4-morpholinocyclohexyl)-1H-pyrazol-4-yl)pyrimidin-2-amine | 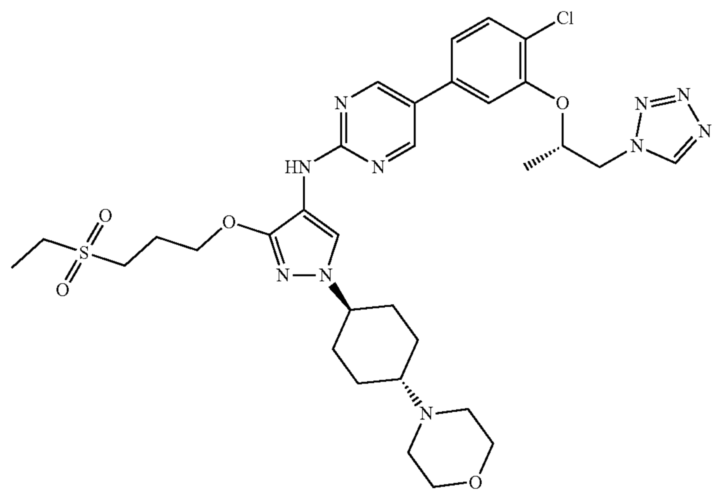 [SMILES: CCS(=O)(=O)CCCOc1nn([C@H]2CC[C@H](N3CCOCC3)CC2)cc1Nc1ncc(-c2ccc(Cl)c(O[C@@H](C)Cn3cnnn3)c2)cn1] |
| 96 | 2-(((S)-1-(1H-tetrazol-1-yl)propan-2-yl)oxy)-4-(2-((1-((1r,4r)-4-morpholinocyclohexyl)-3-(oxazol-2-yloxy)-1H-pyrazol-4-yl)amino)pyrimidin-5-yl)benzonitrile | 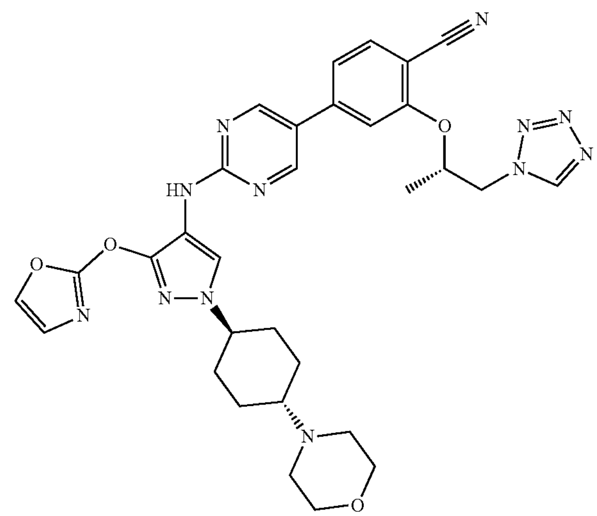 [SMILES: C[C@@H](Cn1cnnn1)Oc1cc(-c2cnc(Nc3cn([C@H]4CC[C@H](N5CCOCC5)CC4)nc3Oc3ncco3)nc2)ccc1C#N] |
| 97 | 5-(3-(((S)-1-(1H-tetrazol-1-yl)propan-2-yl)oxy)-4-chlorophenyl)-N-(1-((1r,4r)-4-morpholinocyclohexyl)-3-(oxazol-2-yloxy)-1H-pyrazol-4-yl)pyrimidin-2-amine | 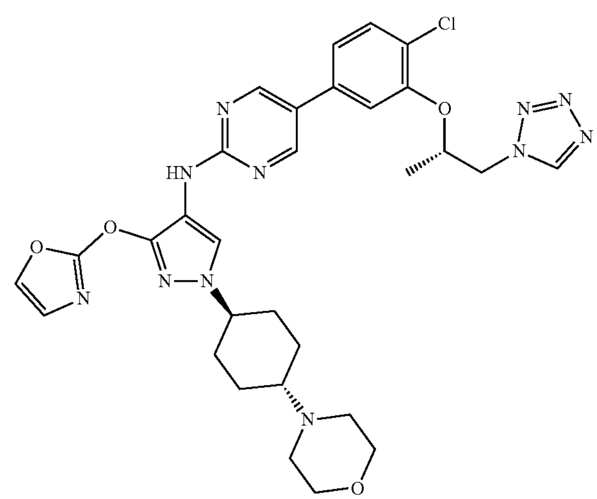 [SMILES: C[C@@H](Cn1cnnn1)Oc1cc(-c2cnc(Nc3cn([C@H]4CC[C@H](N5CCOCC5)CC4)nc3Oc3ncco3)nc2)ccc1Cl] |

TABLE 2-continued

| Ex. No. | IUPAC NAME | STRUCTURE |
|---|---|---|
| 98 | 2-(((S)-1-(1H-tetrazol-1-yl)propan-2-yl)oxy)-4-(2-((1-((1r,4r)-4-morpholinocyclohexyl)-3-(oxazol-2-ylmethoxy)-1H-pyrazol-4-yl)amino)pyrimidin-5-yl)benzonitrile | 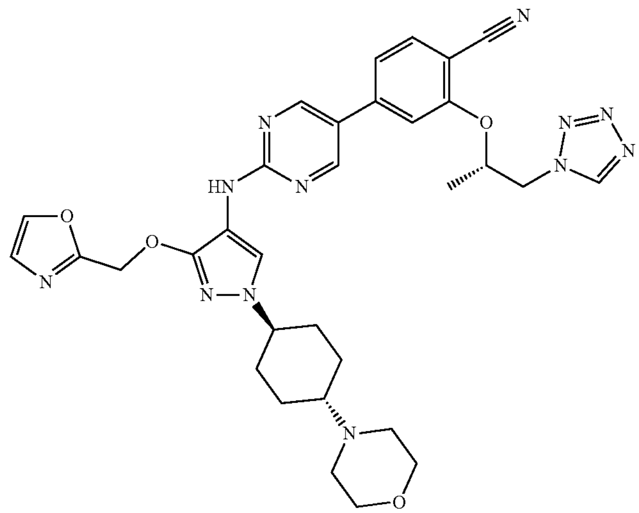 |
| 99 | 5-(3-(((S)-1-(1H-tetrazol-1-yl)propan-2-yl)oxy)-4-chlorophenyl)-N-(1-((1r,4r)-4-morpholinocyclohexyl)-3-(oxazol-2-ylmethoxy)-1H-pyrazol-4-yl)pyrimidin-2-amine | 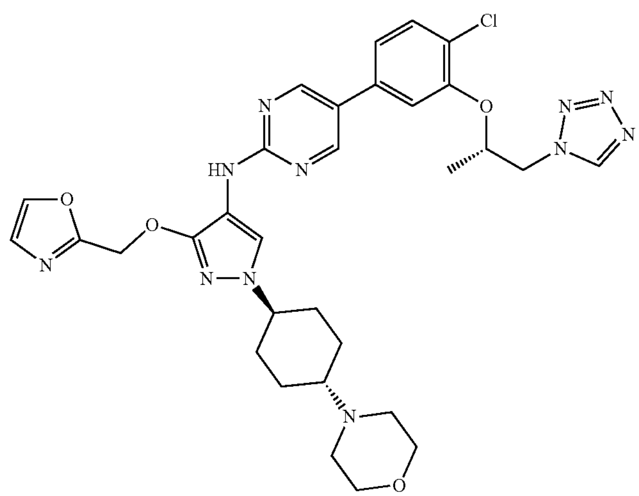 |
| 100 | 5-(3-(((S)-1-(1H-1,2,4-triazol-1-yl)propan-2-yl)oxy)-4-chlorophenyl)-N-(1-((1r,4r)-4-morpholinocyclohexyl)-3-(oxazol-2-ylmethoxy)-1H-pyrazol-4-yl)pyrimidin-2-amine | 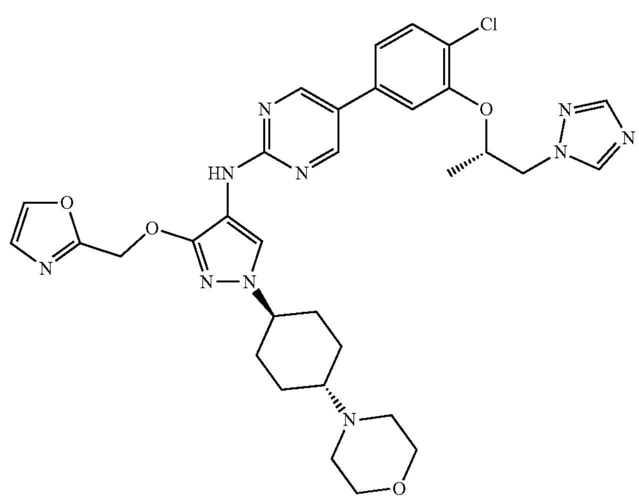 [SMILES: C[C@@H](Cn1cncn1)Oc1cc(-c2cnc(Nc3cn([C@H]4CC[C@H](N5CCOCC5)CC4)nc3OCc3ncco3)nc2)ccc1Cl] |

TABLE 2-continued

| Ex. No. | IUPAC NAME | STRUCTURE |
|---|---|---|
| 101 | 5-(3-(((S)-1-(1H-1,2,4-triazol-1-yl)propan-2-yl)oxy)-4-chlorophenyl)-N-(1-((1r,4r)-4-((1R,5S)-3-oxa-8-azabicyclo[3.2.1]octan-8-yl)cyclohexyl)-3-(oxazol-2-ylmethoxy)-1H-pyrazol-4-yl)pyrimidin-2-amine | 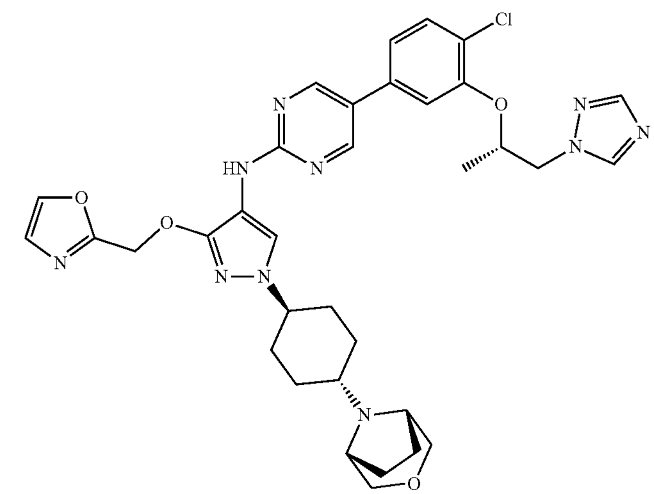 [SMILES: C[C@@H](Cn1cncn1)Oc1cc(-c2cnc(Nc3cn([C@H]4CC[C@H](N5[C@@H]6CC[C@H]5COC6)CC4)nc3OCc3ncco3)nc2)ccc1Cl] |
| 102 | 2-(((S)-1-(1H-tetrazol-1-yl)propan-2-yl)oxy)-4-(2-((1-((1r,4r)-4-morpholinocyclohexyl)-3-(2-(oxazol-2-yl)ethoxy)-1H-pyrazol-4-yl)amino)pyrimidin-5-yl)benzonitrile | 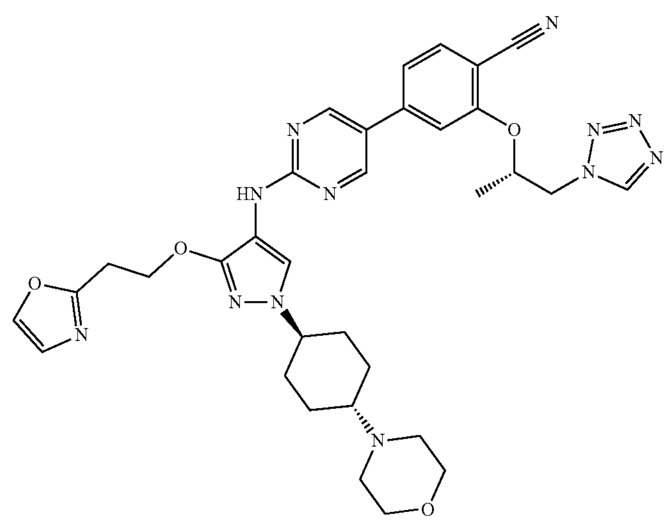 [SMILES: C[C@@H](Cn1cnnn1)Oc1cc(-c2cnc(Nc3cn([C@H]4CC[C@H](N5CCOCC5)CC4)nc3OCCc3ncco3)nc2)ccc1C#N] |
| 103 | 5-(3-(((S)-1-(1H-tetrazol-1-yl)propan-2-yl)oxy)-4-chlorophenyl)-N-(1-((1r,4r)-4-morpholinocyclohexyl)-3-(2-(oxazol-2-yl)ethoxy)-1H-pyrazol-4-yl)pyrimidin-2-amine | 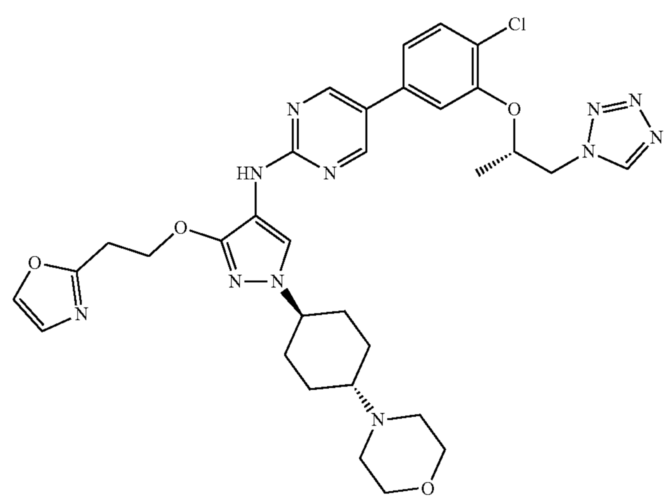 [SMILES: C[C@@H](Cn1cnnn1)Oc1cc(-c2cnc(Nc3cn([C@H]4CC[C@H](N5CCOCC5)CC4)nc3OCCc3ncco3)nc2)ccc1Cl] |

TABLE 2-continued

| Ex. No. | IUPAC NAME |
|---|---|
| 104 | 2-(((S)-1-(1H-tetrazol-1-yl)propan-2-yl)oxy)-4-(2-((1-((1r,4r)-4-morpholinocyclohexyl)-3-(3-(oxazol-2-yl)propoxy)-1H-pyrazol-4-yl)amino)pyrimidin-5-yl)benzonitrile |
| 105 | 5-(3-(((S)-1-(1H-tetrazol-1-yl)propan-2-yl)oxy)-4-chlorophenyl)-N-(1-((1r,4r)-4-morpholinocyclohexyl)-3-(3-(oxazol-2-yl)propoxy)-1H-pyrazol-4-yl)pyrimidin-2-amine |
| 106 | 2-(((S)-1-(1H-tetrazol-1-yl)propan-2-yl)oxy)-4-(2-((1-((1r,4r)-4-morpholinocyclohexyl)-3-(thiazol-2-ylmethoxy)-1H-pyrazol-4-yl)amino)pyrimidin-5-yl)benzonitrile |

TABLE 2-continued

| Ex. No. | IUPAC NAME | STRUCTURE |
|---|---|---|
| 107 | 5-(3-(((S)-1-(1H-tetrazol-1-yl)propan-2-yl)oxy)-4-chlorophenyl)-N-(1-((1r,4r)-4-morpholinocyclohexyl)-3-(thiazol-2-ylmethoxy)-1H-pyrazol-4-yl)pyrimidin-2-amine | 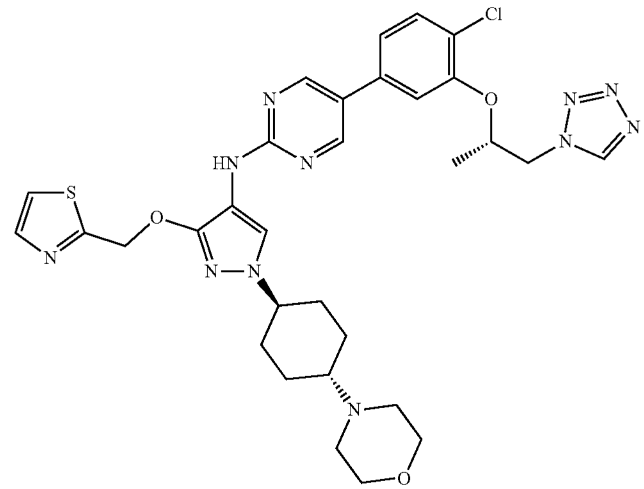 |
| 108 | 2-(((S)-1-(1H-1,2,4-triazol-1-yl)propan-2-yl)oxy)-4-(2-((1-((1r,4r)-4-morpholinocyclohexyl)-3-(thiazol-2-ylmethoxy)-1H-pyrazol-4-yl)amino)pyrimidin-5-yl)benzonitrile | 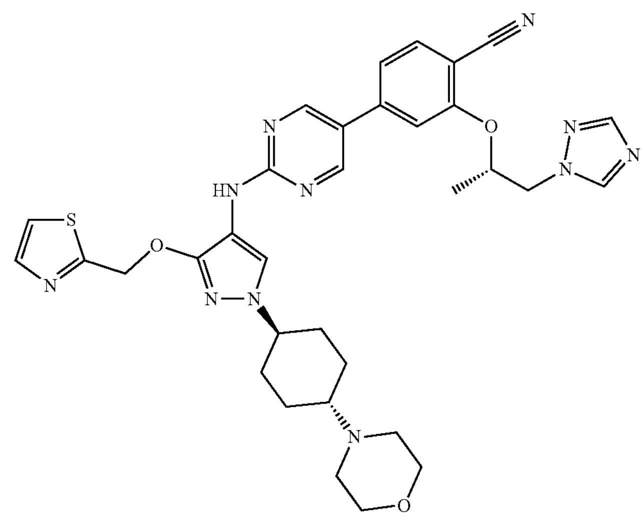 [SMILES: C[C@@H](Cn1cncn1)Oc1cc(-c2cnc(Nc3cn([C@H]4CC[C@H](N5CCOCC5)CC4)nc3OCc3nccs3)nc2)ccc1C#N] |
| 109 | 2-(((S)-1-(1H-tetrazol-1-yl)propan-2-yl)oxy)-4-(2-((1-((1r,4r)-4-morpholinocyclohexyl)-3-(2-(thiazol-2-yl)ethoxy)-1H-pyrazol-4-yl)amino)pyrimidin-5-yl)benzonitrile | 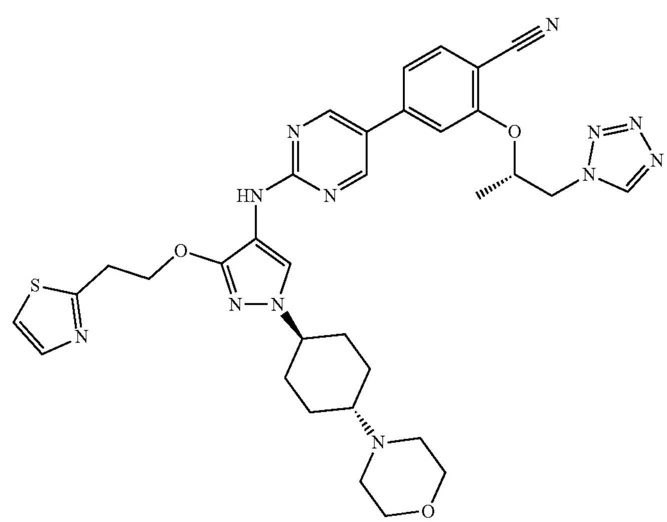 |

TABLE 2-continued

| Ex. No. | IUPAC NAME | STRUCTURE |
|---|---|---|
| 110 | 5-(3-(((S)-1-(1H-tetrazol-1-yl)propan-2-yl)oxy)-4-chlorophenyl)-N-(1-((1r,4r)-4-morpholinocyclohexyl)-3-(2-(thiazol-2-yl)ethoxy)-1H-pyrazol-4-yl)pyrimidin-2-amine | 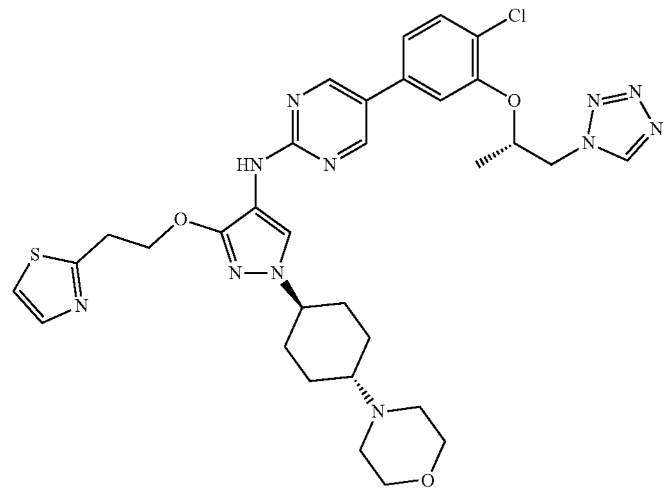 |
| 111 | 2-(((S)-1-(1H-tetrazol-1-yl)propan-2-yl)oxy)-4-(2-((1-((1r,4r)-4-morpholinocyclohexyl)-3-(3-(thiazol-2-yl)propoxy)-1H-pyrazol-4-yl)amino)pyrimidin-5-yl)benzonitrile | 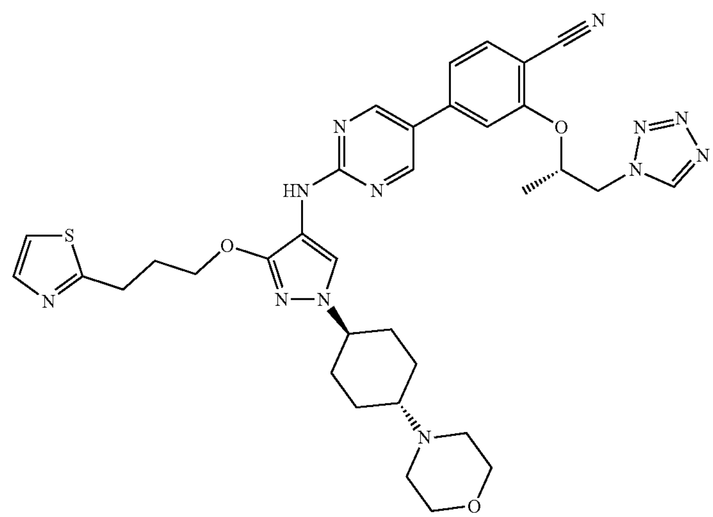 [SMILES: C[C@@H](Cn1cnnn1)Oc1cc(-c2cnc(Nc3cn([C@H]4CC[C@H](N5CCOCC5)CC4)nc3OCCCc3nccs3)nc2)ccc1C#N] |
| 112 | 5-(3-(((S)-1-(1H-tetrazol-1-yl)propan-2-yl)oxy)-4-chlorophenyl)-N-(1-((1r,4r)-4-morpholinocyclohexyl)-3-(3-(thiazol-2-yl)propoxy)-1H-pyrazol-4-yl)pyrimidin-2-amine | 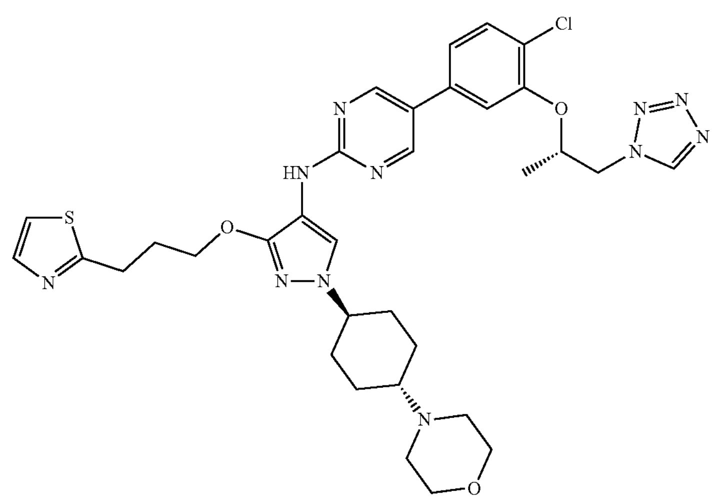 [SMILES: C[C@@H](Cn1cnnn1)Oc1cc(-c2cnc(Nc3cn([C@H]4CC[C@H](N5CCOCC5)CC4)nc3OCCCc3nccs3)nc2)ccc1Cl] |

TABLE 2-continued

| Ex. No. | IUPAC NAME | STRUCTURE |
|---|---|---|
| 113 | 4-(2-((3-((1H-pyrazol-1-yl)methoxy)-1-((1r,4r)-4-morpholinocyclohexyl)-1H-pyrazol-4-yl)amino)pyrimidin-5-yl)-2-(((S)-1-(1H-tetrazol-1-yl)propan-2-yl)oxy)benzonitrile | 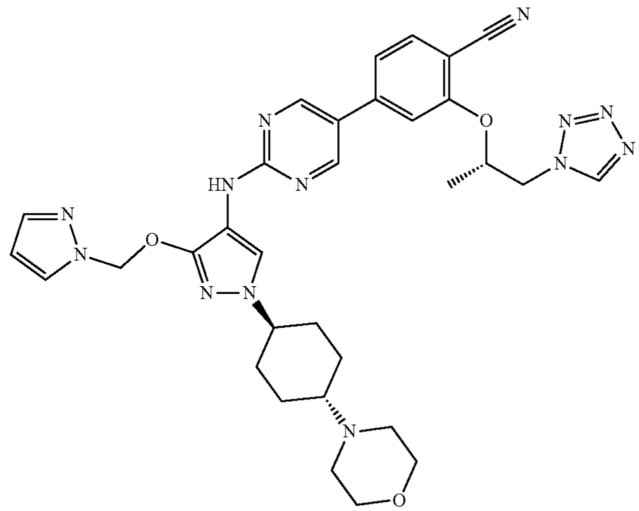 [SMILES: C[C@@H](Cn1cnnn1)Oc1cc(-c2cnc(Nc3cn([C@H]4CC[C@H](N5CCOCC5)CC4)nc3OCn3cccn3)nc2)ccc1C#N] |
| 114 | N-(3-((1H-pyrazol-1-yl)methoxy)-1-((1r,4r)-4-morpholinocyclohexyl)-1H-pyrazol-4-yl)-5-(3-(((S)-1-(1H-tetrazol-1-yl)propan-2-yl)oxy)-4-chlorophenyl)pyrimidin-2-amine | 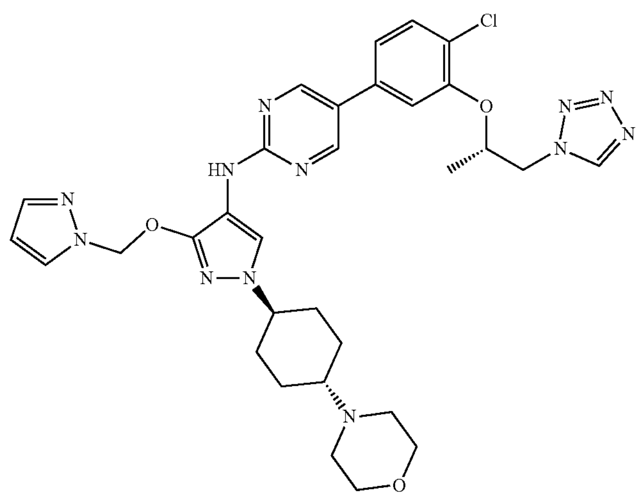 [SMILES: C[C@@H](Cn1cnnn1)Oc1cc(-c2cnc(Nc3cn([C@H]4CC[C@H](N5CCOCC5)CC4)nc3OCn3cccn3)nc2)ccc1Cl] |
| 115 | 2-(((S)-1-(1H-tetrazol-1-yl)propan-2-yl)oxy)-4-(2-((3-((1-methyl-1H-pyrazol-5-yl)methoxy)-1-((1r,4r)-4-morpholinocyclohexyl)-1H-pyrazol-4-yl)amino)pyrimidin-5-yl)benzonitrile | 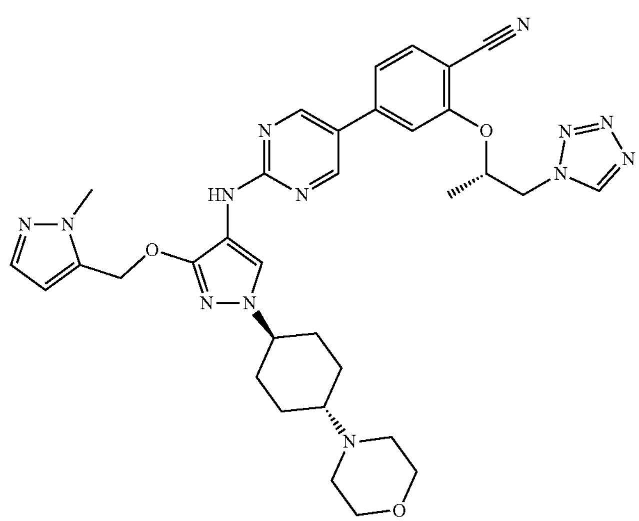 [SMILES: C[C@@H](Cn1cnnn1)Oc1cc(-c2cnc(Nc3cn([C@H]4CC[C@H](N5CCOCC5)CC4)nc3OCc3ccnn3C)nc2)ccc1C#N] |

TABLE 2-continued

| Ex. No. | IUPAC NAME | STRUCTURE |
|---|---|---|
| 116 | 5-(3-(((S)-1-(1H-tetrazol-1-yl)propan-2-yl)oxy)-4-chlorophenyl)-N-(3-((1-methyl-1H-pyrazol-5-yl)methoxy)-1-((1r,4r)-4-morpholinocyclohexyl)-1H-pyrazol-4-yl)pyrimidin-2-amine | 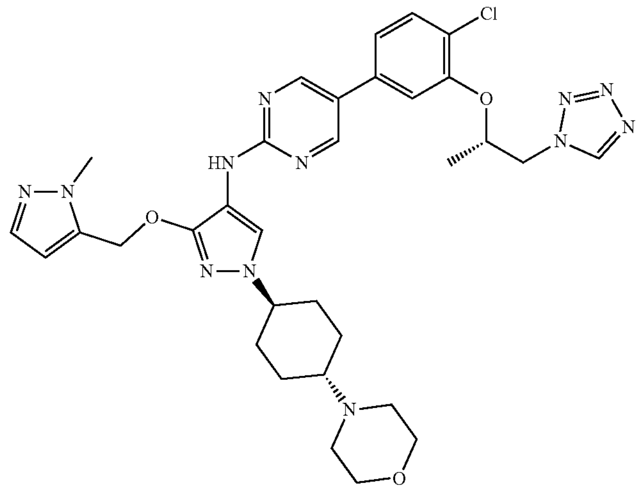 [SMILES: C[C@@H](Cn1cnnn1)Oc1cc(-c2cnc(Nc3cn([C@H]4CC[C@H](N5CCOCC5)CC4)nc3OCc3ccnn3C)nc2)ccc1Cl] |
| 117 | 5-(3-(((S)-1-(1H-1,2,4-triazol-1-yl)propan-2-yl)oxy)-4-chlorophenyl)-N-(3-((1-methyl-1H-pyrazol-5-yl)methoxy)-1-((1r,4r)-4-morpholinocyclohexyl)-1H-pyrazol-4-yl)pyrimidin-2-amine | 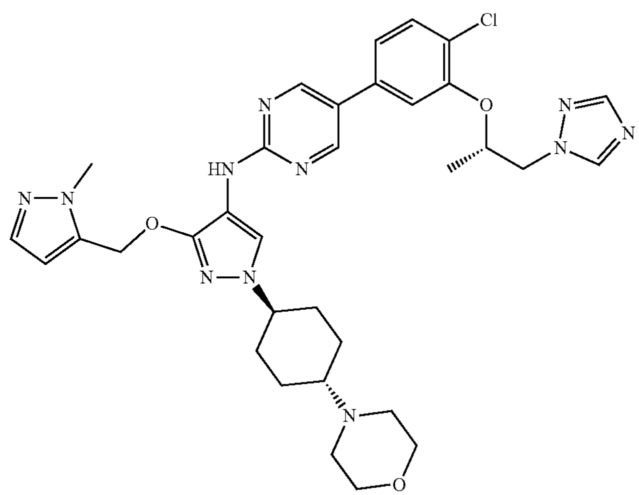 [SMILES: C[C@@H](Cn1cncn1)Oc1cc(-c2cnc(Nc3cn([C@H]4CC[C@H](N5CCOCC5)CC4)nc3OCc3ccnn3C)nc2)ccc1Cl] |
| 118 | 2-(((S)-1-(1H-1,2,4-triazol-1-yl)propan-2-yl)oxy)-4-(2-((1-((1r,4r)-4-((1R,5S)oxa-8-azabicyclo[3.2.1]octan-8-yl)cyclohexyl)-3-((1-methyl-1H-pyrazol-5-yl)methoxy)-1H-pyrazol-4-yl)amino)pyrimidin-5-yl)benzonitrile | 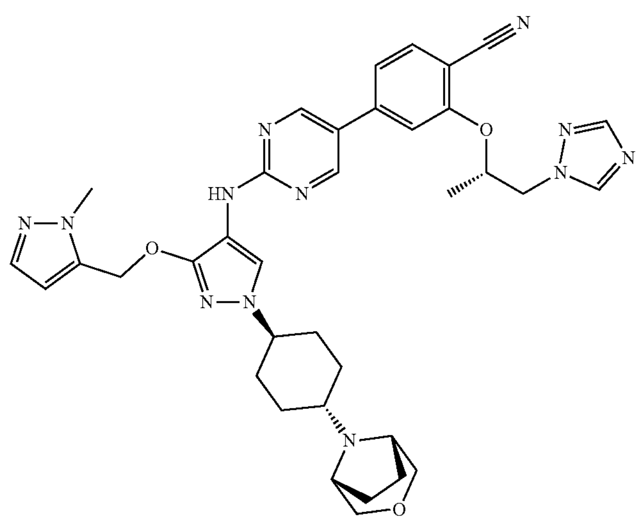 [SMILES: C[C@@H](Cn1cncn1)Oc1cc(-c2cnc(Nc3cn([C@H]4CC[C@H](N5[C@@H]6CC[C@H]5COC6)CC4)nc3OCc3ccnn3C)nc2)ccc1C#N] |

TABLE 2-continued

| Ex. No. | IUPAC NAME | STRUCTURE |
| --- | --- | --- |
| 119 | 2-(((S)-1-(1H-tetrazol-1-yl)propan-2-yl)oxy)-4-(2-((3-((1-methyl-1H-pyrazol-3-yl)methoxy)-1-((1r,4r)-4-morpholinocyclohexyl)-1H-pyrazol-4-yl)amino)pyrimidin-5-yl)benzonitrile | 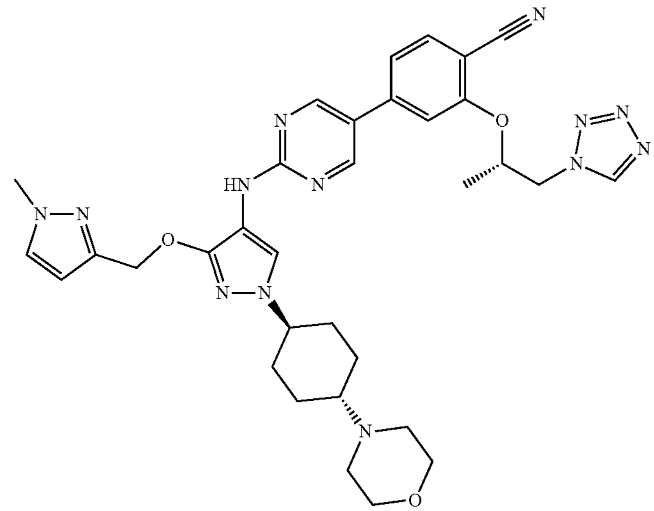 [SMILES: C[C@@H](Cn1cnnn1)Oc1cc(-c2cnc(Nc3cn([C@H]4CC[C@H](N5CCOCC5)CC4)nc3OCc3ccn(C)n3)nc2)ccc1C#N] |
| 120 | 5-(3-(((S)-1-(1H-tetrazol-1-yl)propan-2-yl)oxy)-4-chlorophenyl)-N-(3-((1-methyl-1H-pyrazol-3-yl)methoxy)-1-((1r,4r)-4-morpholinocyclohexyl)-1H-pyrazol-4-yl)pyrimidin-2-amine | 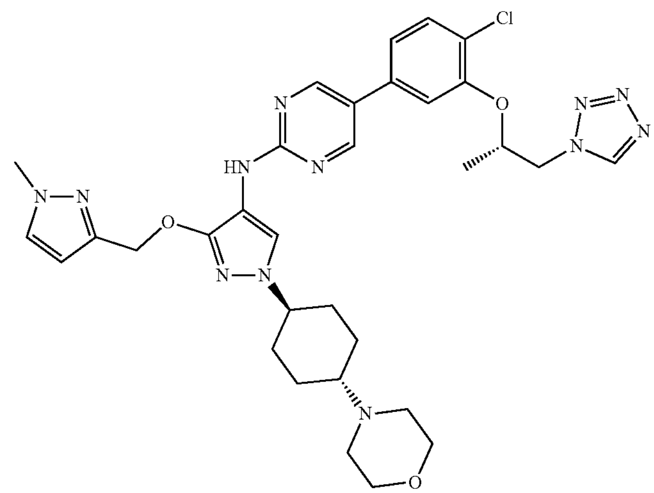 [SMILES: C[C@@H](Cn1cnnn1)Oc1cc(-c2cnc(Nc3cn([C@H]4CC[C@H](N5CCOCC5)CC4)nc3OCc3ccn(C)n3)nc2)ccc1Cl] |
| 121 | 4-(2-((3-(2-(1H-pyrazol-1-yl)ethoxy)-1-((1r,4r)-4-morpholinocyclohexyl)-1H-pyrazol-4-yl)amino)pyrimidin-5-yl)-2-(((S)-1-(1H-tetrazol-1-yl)propan-2-yl)oxy)benzonitrile | 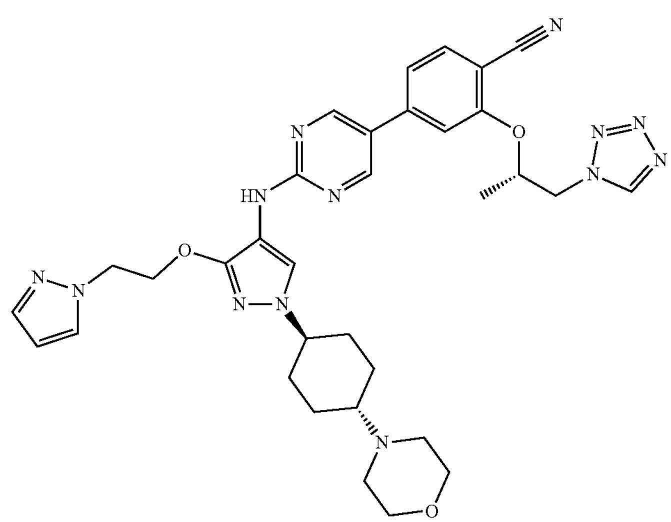 [SMILES: C[C@@H](Cn1cnnn1)Oc1cc(-c2cnc(Nc3cn([C@H]4CC[C@H](N5CCOCC5)CC4)nc3OCCn3cccn3)nc2)ccc1C#N] |

TABLE 2-continued

| Ex. No. | IUPAC NAME | STRUCTURE |
|---|---|---|
| 122 | N-(3-(2-(1H-pyrazol-1-yl)ethoxy)-1-((1r,4r)-4-morpholinocyclohexyl)-1H-pyrazol-4-yl)-5-(3-(((S)-1-(1H-tetrazol-1-yl)propan-2-yl)oxy)-4-chlorophenyl)pyrimidin-2-amine | 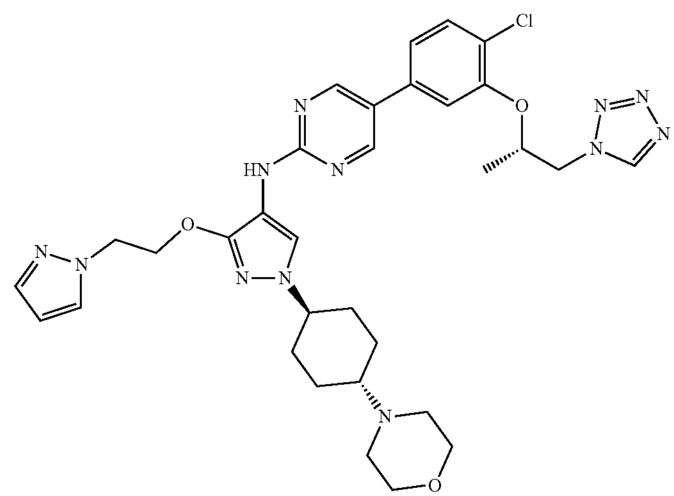 [SMILES: C[C@@H](Cn1cnnn1)Oc1cc(-c2cnc(Nc3cn([C@H]4CC[C@H](N5CCOCC5)CC4)nc3OCCn3cccn3)nc2)ccc1Cl] |
| 123 | 5-(3-(((S)-1-(1H-1,2,4-triazol-1-yl)propan-2-yl)oxy)-4-chlorophenyl)-N-(3-(2-(1H-pyrazol-1-yl)ethoxy)-1-((1r,4r)-4-morpholinocyclohexyl)-1H-pyrazol-4-yl)pyrimidin-2-amine | 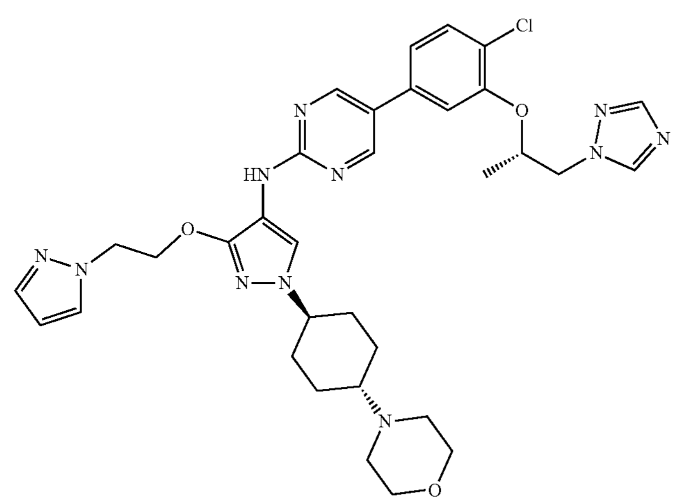 [SMILES: C[C@@H](Cn1cncn1)Oc1cc(-c2cnc(Nc3cn([C@H]4CC[C@H](N5CCOCC5)CC4)nc3OCCn3cccn3)nc2)ccc1Cl] |
| 124 | 2-(((S)-1-(1H-1,2,4-triazol-1-yl)propan-2-yl)oxy)-4-(2-((3-(2-(1H-pyrazol-1-yl)ethoxy)-1-((1r,4r)-4-((1R,5S)-3-oxa-8-azabicyclo[3.2.1]octan-8-yl)cyclohexyl)-1H-pyrazol-4-yl)amino)pyrimidin-5-yl)benzonitrile | 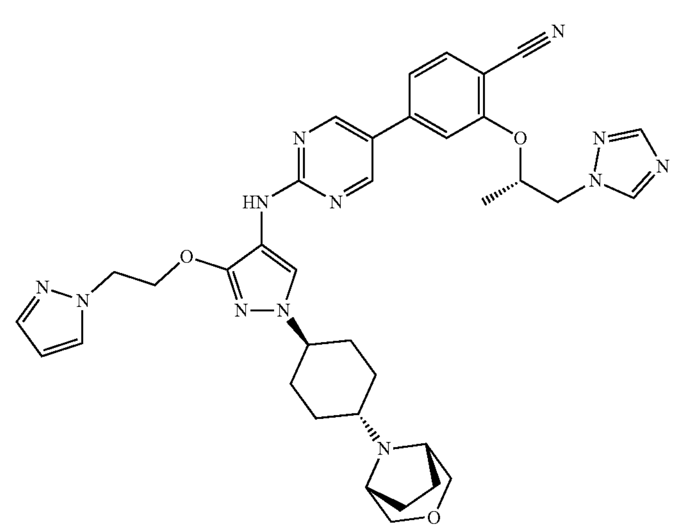 [SMILES: C[C@@H](Cn1cncn1)Oc1cc(-c2cnc(Nc3cn([C@H]4CC[C@H](N5[C@@H]6CC[C@H]5COC6)CC4)nc3OCCn3cccn3)nc2)ccc1C#N] |

| Ex. No. | IUPAC NAME | STRUCTURE |
|---|---|---|
| 125 | 2-(((S)-1-(1H-tetrazol-1-yl)propan-2-yl)oxy)-4-(2-((3-(2-(1-methyl-1H-pyrazol-5-yl)ethoxy)-1-((1r,4r)-4-morpholinocyclohexyl)-1H-pyrazol-4-yl)amino)pyrimidin-5-yl)benzonitrile | 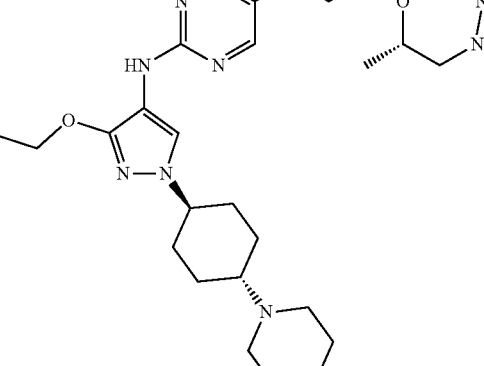 |
| 126 | 5-(3-(((S)-1-(1H-tetrazol-1-yl)propan-2-yl)oxy)-4-chlorophenyl)-N-(3-(2-(1-methyl-1H-pyrazol-5-yl)ethoxy)-1-((1r,4r)-4-morpholinocyclohexyl)-1H-pyrazol-4-yl)pyrimidin-2-amine | 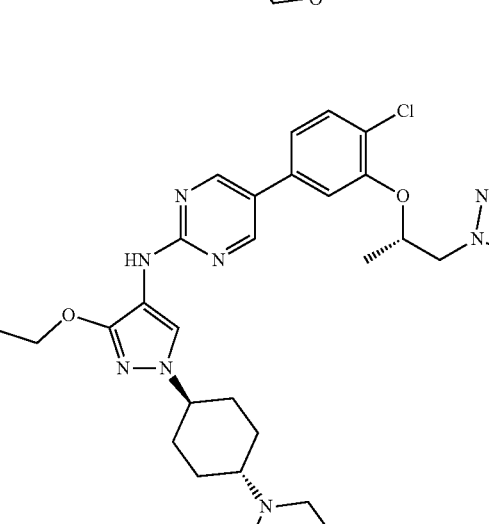 |
| 127 | 2-(((S)-1-(1H-tetrazol-1-yl)propan-2-yl)oxy)-4-(2-((3-(2-(1-methyl-1H-pyrazol-3-yl)ethoxy)-1-((1r,4r)-4-morpholinocyclohexyl)-1H-pyrazol-4-yl)amino)pyrimidin-5-yl)benzonitrile | 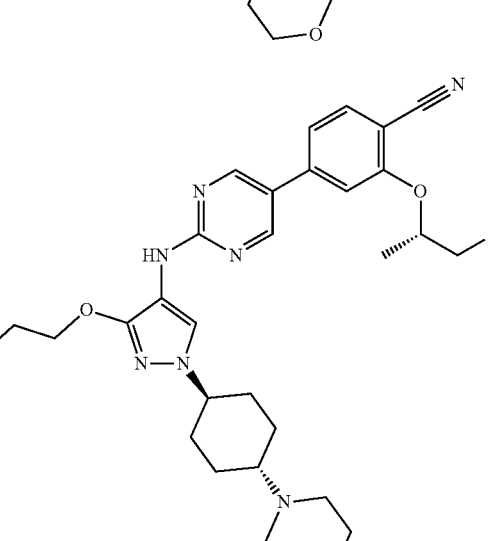 |

TABLE 2-continued

| Ex. No. | IUPAC NAME | STRUCTURE |
| --- | --- | --- |
| 128 | 5-(3-(((S)-1-(1H-tetrazol-1-yl)propan-2-yl)oxy)-4-chlorophenyl)-N-(3-(2-(1-methyl-1H-pyrazol-3-yl)ethoxy)-1-((1r,4r)-4-morpholinocyclohexyl)-1H-pyrazol-4-yl)pyrimidin-2-amine | 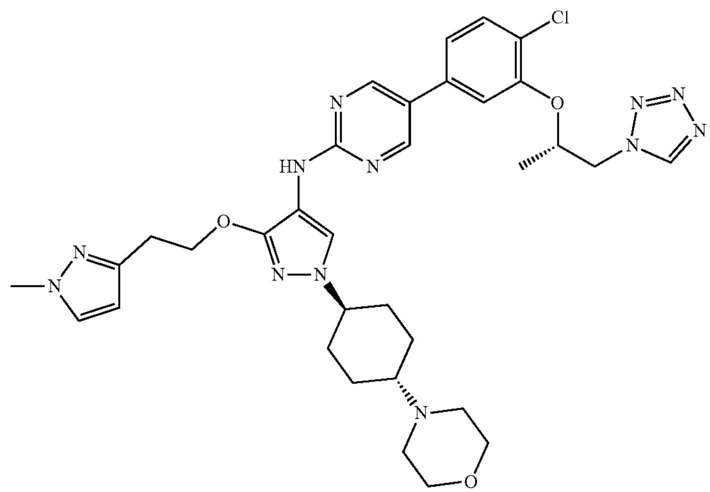 [SMILES: C[C@@H](Cn1cnnn1)Oc1cc(-c2cnc(Nc3cn([C@H]4CC[C@H](N5CCOCC5)CC4)nc3OCCc3ccn(C)n3)nc2)ccc1Cl] |
| 131 | 2-(((S)-1-(1H-1,2,4-triazol-1-yl)propan-2-yl)oxy)-4-(2-((1-((1r,4r)-4-morpholinocyclohexyl)-3-(pyridin-2-ylmethoxy)-1H-pyrazol-4-yl)amino)pyrimidin-5-yl)benzonitrile | 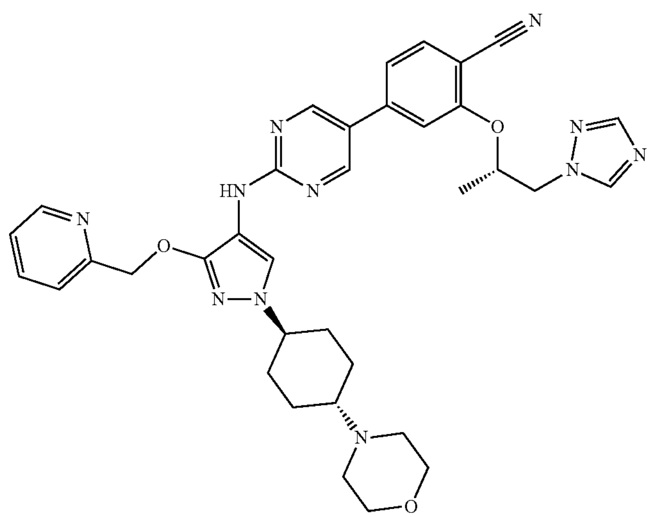 [SMILES: C[C@@H](Cn1cncn1)Oc1cc(-c2cnc(Nc3cn([C@H]4CC[C@H](N5CCOCC5)CC4)nc3OCc3ccccn3)nc2)ccc1C#N] |
| 132 | 5-(3-(((S)-1-(1H-1,2,4-triazol-1-yl)propan-2-yl)oxy)-4-chlorophenyl)-N-(1-((1r,4r)-4-morpholinocyclohexyl)-3-(pyridin-2-ylmethoxy)-1H-pyrazol-4-yl)pyrimidin-2-amine | 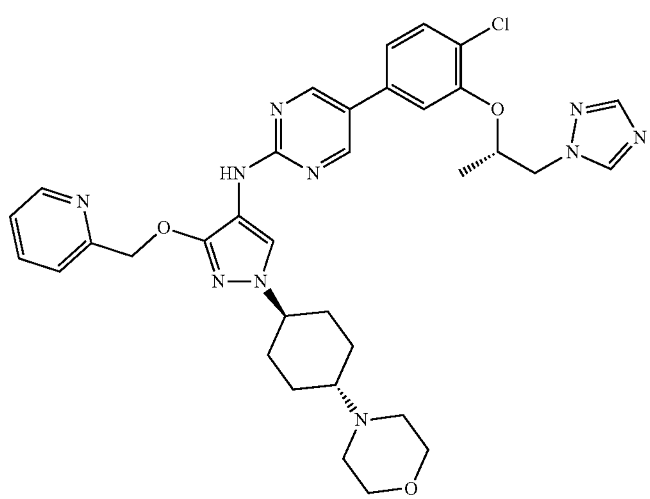 |

TABLE 2-continued

| Ex. No. | IUPAC NAME |
|---|---|
| 133 | 2-(((S)-1-(1H-1,2,4-triazol-1-yl)propan-2-yl)oxy)-4-(2-((1-((1r,4r)-4-((1R,5S)-3-oxa-8-azabicyclo[3.2.1]octan-8-yl)cyclohexyl)-3-(pyridin-2-ylmethoxy)-1H-pyrazol-4-yl)amino)pyrimidin-5-yl)benzonitrile |
| 134 | 2-(((S)-1-(1H-tetrazol-1-yl)propan-2-yl)oxy)-4-(2-((1-((1r,4r)-4-morpholinocyclohexyl)-3-(pyrimidin-2-ylmethoxy)-1H-pyrazol-4-yl)amino)pyrimidin-5-yl)benzonitrile |
| 135 | 5-(3-(((S)-1-(1H-tetrazol-1-yl)propan-2-yl)oxy)-4-chlorophenyl)-N-(1-((1r,4r)-4-morpholinocyclohexyl)-3-(pyrimidin-2-ylmethoxy)-1H-pyrazol-4-yl)pyrimidin-2-amine |

| Ex. No. | IUPAC NAME |
|---|---|
| 136 | 5-(3-(((S)-1-(1H-tetrazol-1-yl)propan-2-yl)oxy)-4-chlorophenyl)-N-(1-((1r,4r)-4-((1R,5S)-3-oxa-8-azabicyclo[3.2.1]octan-8-yl)cyclohexyl)-3-(pyrimidin-2-ylmethoxy)-1H-pyrazol-4-yl)pyrimidin-2-amine |
| 137 | 5-(3-(((S)-1-(1H-1,2,4-triazol-1-yl)propan-2-yl)oxy)-4-chlorophenyl)-N-(1-((1r,4r)-4-((1R,5S)-3-oxa-8-azabicyclo[3.2.1]octan-8-yl)cyclohexyl)-3-(pyrimidin-2-ylmethoxy)-1H-pyrazol-4-yl)pyrimidin-2-amine |
| 138 | 2-(((S)-1-(1H-tetrazol-1-yl)propan-2-yl)oxy)-4-(2-((1-((1r,4r)-4-morpholinocyclohexyl)-3-(2-(pyridin-2-yl)ethoxy)-1H-pyrazol-4-yl)amino)pyrimidin-5-yl)benzonitrile |

TABLE 2-continued

| Ex. No. | IUPAC NAME |
|---|---|
| 139 | 5-(3-(((S)-1-(1H-tetrazol-1-yl)propan-2-yl)oxy)-4-chlorophenyl)-N-(1-((1r,4r)-4-morpholinocyclohexyl)-3-(2-(pyridin-2-yl)ethoxy)-1H-pyrazol-4-yl)pyrimidin-2-amine |
| 140 | 2-(((S)-1-(1H-tetrazol-1-yl)propan-2-yl)oxy)-4-(2-((1-((1r,4r)-4-morpholinocyclohexyl)-3-(2-(pyrimidin-2-yl)ethoxy)-1H-pyrazol-4-yl)amino)pyrimidin-5-yl)benzonitrile |
| 141 | 5-(3-(((S)-1-(1H-tetrazol-1-yl)propan-2-yl)oxy)-4-chlorophenyl)-N-(1-((1r,4r)-4-morpholinocyclohexyl)-3-(2-(pyrimidin-2-yl)ethoxy)-1H-pyrazol-4-yl)pyrimidin-2-amine |

TABLE 2-continued

| Ex. No. | IUPAC NAME | STRUCTURE |
| --- | --- | --- |
| 144 | 2-(((S)-1-(1H-tetrazol-1-yl)propan-2-yl)oxy)-4-(2-((1-((1r,4r)-4-morpholinocyclohexyl)-3-(oxetan-3-ylmethoxy)-1H-pyrazol-4-yl)amino)pyrimidin-5-yl)benzonitrile | 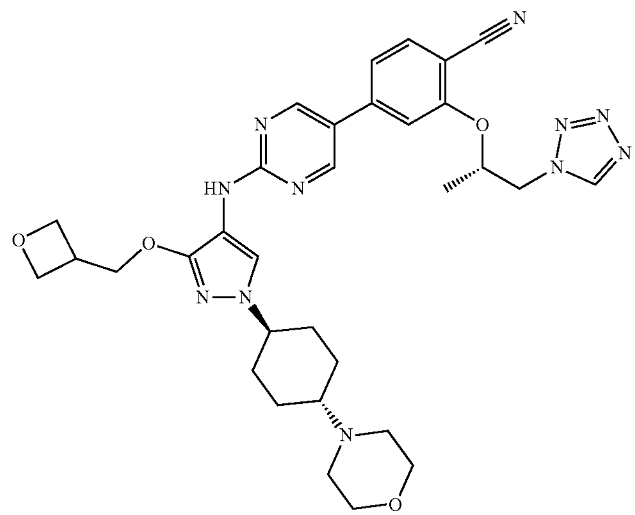 [SMILES: C[C@@H](Cn1cnnn1)Oc1cc(-c2cnc(Nc3cn([C@H]4CC[C@H](N5CCOCC5)CC4)nc3OCC3COC3)nc2)ccc1C#N] |
| 145 | 5-(3-(((S)-1-(1H-tetrazol-1-yl)propan-2-yl)oxy)-4-chlorophenyl)-N-(1-((1r,4r)-4-morpholinocyclohexyl)-3-(oxetan-3-ylmethoxy)-1H-pyrazol-4-yl)pyrimidin-2-amine | 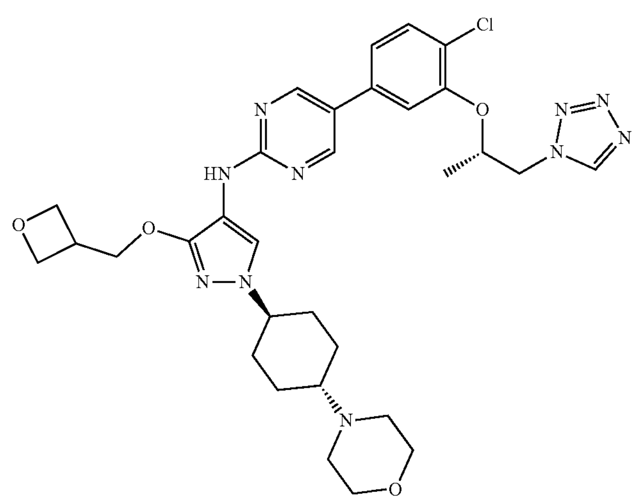 [SMILES: C[C@@H](Cn1cnnn1)Oc1cc(-c2cnc(Nc3cn([C@H]4CC[C@H](N5CCOCC5)CC4)nc3OCC3COC3)nc2)ccc1Cl] |
| 146 | 5-(3-(((S)-1-(1H-tetrazol-1-yl)propan-2-yl)oxy)-4-chlorophenyl)-N-(1-((1r,4r)-4-((1R,5S)-3-oxa-8-azabicyclo[3.2.1]octan-8-yl)cyclohexyl)-3-(oxetan-3-ylmethoxy)-1H-pyrazol-4-yl)pyrimidin-2-amine | 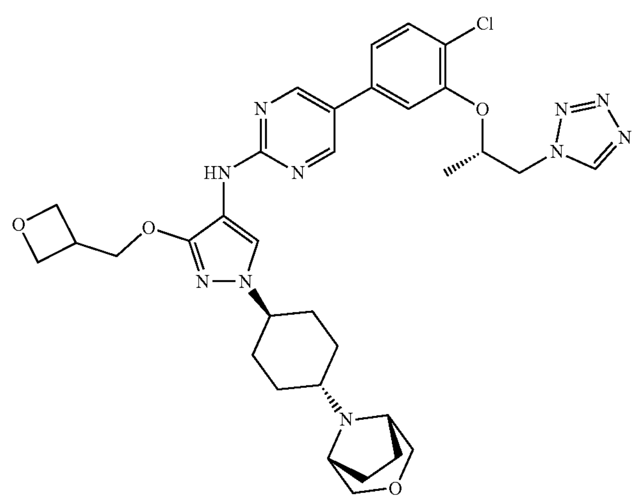 [SMILES: C[C@@H](Cn1cnnn1)Oc1cc(-c2cnc(Nc3cn([C@H]4CC[C@H](N5[C@@H]6CC[C@H]5COC6)CC4)nc3OCC3COC3)nc2)ccc1Cl] |

TABLE 2-continued

| Ex. No. | IUPAC NAME | STRUCTURE |
|---|---|---|
| 147 | 5-(3-(((S)-1-(1H-1,2,4-triazol-1-yl)propan-2-yl)oxy)-4-chlorophenyl)-N-(1-((1r,4r)-4-((1R,5S)-3-oxa-8-azabicyclo[3.2.1]octan-8-yl)cyclohexyl)-3-(oxetan-3-ylmethoxy)-1H-pyrazol-4-yl)pyrimidin-2-amine | 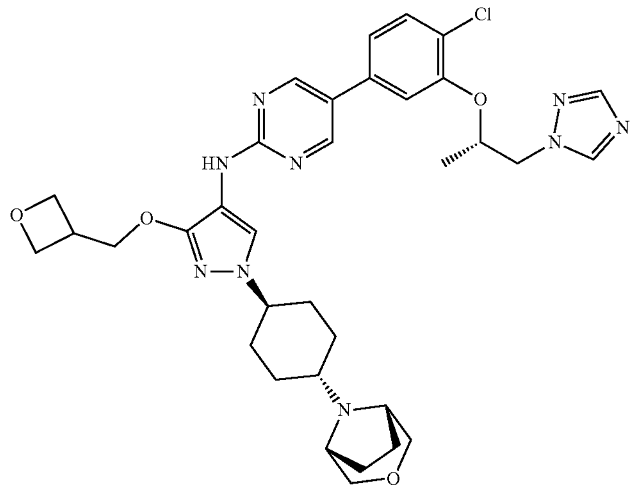 [SMILES: C[C@@H](Cn1cncn1)Oc1cc(-c2cnc(Nc3cn([C@H]4CC[C@H](N5[C@@H]6CC[C@H]5COC6)CC4)nc3OCC3COC3)nc2)ccc1Cl] |
| 148 | 2-(((S)-1-(1H-tetrazol-1-yl)propan-2-yl)oxy)-4-(2-((1-((1r,4r)-4-((2S,6R)-2,6-dimethylmorpholino)cyclohexyl)-3-(oxetan-3-ylmethoxy)-1H-pyrazol-4-yl)amino)pyrimidin-5-yl)benzonitrile | 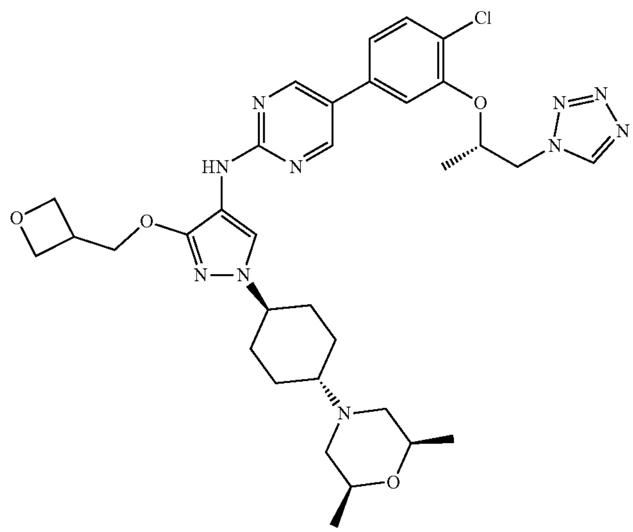 [SMILES: C[C@@H]1CN([C@H]2CC[C@H](n3cc(Nc4ncc(-c5ccc(Cl)c(O[C@@H](C)Cn6cnnn6)c5)cn4)c(OCC4COC4)n3)CC2)C[C@H](C)O1] |
| 149 | 5-(3-(((S)-1-(1H-1,2,4-triazol-1-yl)propan-2-yl)oxy)-4-chlorophenyl)-N-(1-((1r,4r)-4-((2S,6R)-2,6-dimethylmorpholino)cyclohexyl)-3-(oxetan-3-ylmethoxy)-1H-pyrazol-4-yl)pyrimidin-2-amine | 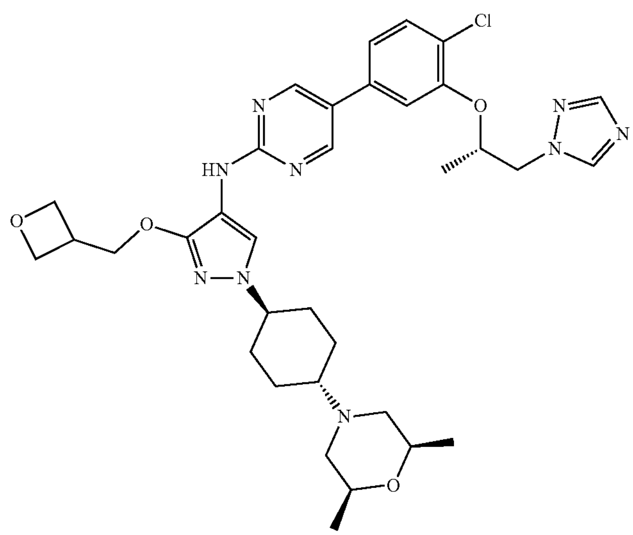 [SMILES: C[C@@H]1CN([C@H]2CC[C@H](n3cc(Nc4ncc(-c5ccc(Cl)c(O[C@@H](C)Cn6cncn6)c5)cn4)c(OCC4COC4)n3)CC2)C[C@H](C)O1] |

TABLE 2-continued

| Ex. No. | IUPAC NAME | STRUCTURE |
| --- | --- | --- |
| 152 | 2-(((S)-1-(1H-1,2,4-triazol-1-yl)propan-2-yl)oxy)-4-(2-((3-(4-methoxybutoxy)-1-((1r,4r)-4-morpholinocyclohexyl)-1H-pyrazol-4-yl)amino)pyrimidin-5-yl)benzonitrile | 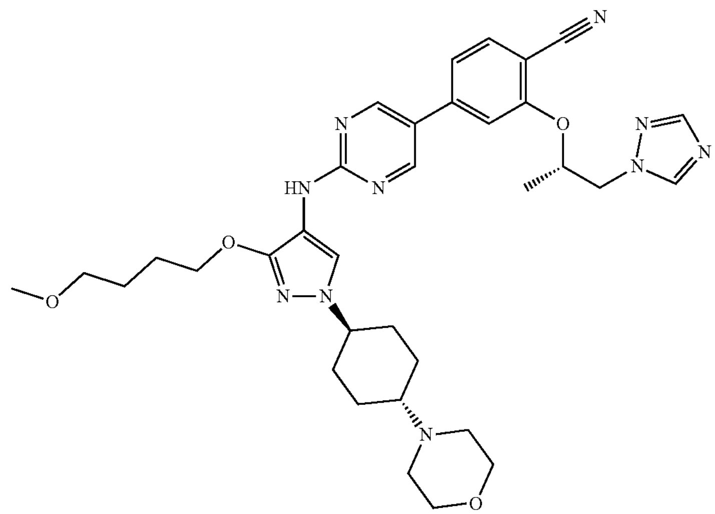 [SMILES: COCCCCOc1nn([C@H]2CC[C@H](N3CCOCC3)CC2)cc1Nc1ncc(-c2ccc(C#N)c(O[C@@H](C)Cn3cncn3)c2)cn1] |
| 153 | 5-(3-(((S)-1-(1H-1,2,4-triazol-1-yl)propan-2-yl)oxy)-4-chlorophenyl)-N-(3-(4-methoxybutoxy)-1-((1r,4r)-4-morpholinocyclohexyl)-1H-pyrazol-4-yl)pyrimidin-2-amine | 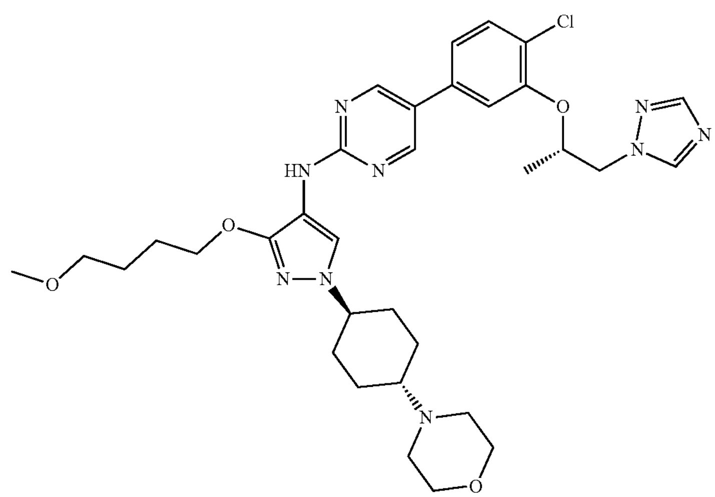 [SMILES: COCCCCOc1nn([C@H]2CC[C@H](N3CCOCC3)CC2)cc1Nc1ncc(-c2ccc(Cl)c(O[C@@H](C)Cn3cncn3)c2)cn1] |
| 154 | 2-(((S)-1-(1H-tetrazol-1-yl)propan-2-yl)oxy)-4-(2-((1-((1r,4r)-4-((1R,5S)-3-oxa-8-azabicyclo[3.2.1]octan-8-yl)cyclohexyl)-3-(4-methoxybutoxy)-1H-pyrazol-4-yl)amino)pyrimidin-5-yl)benzonitrile | 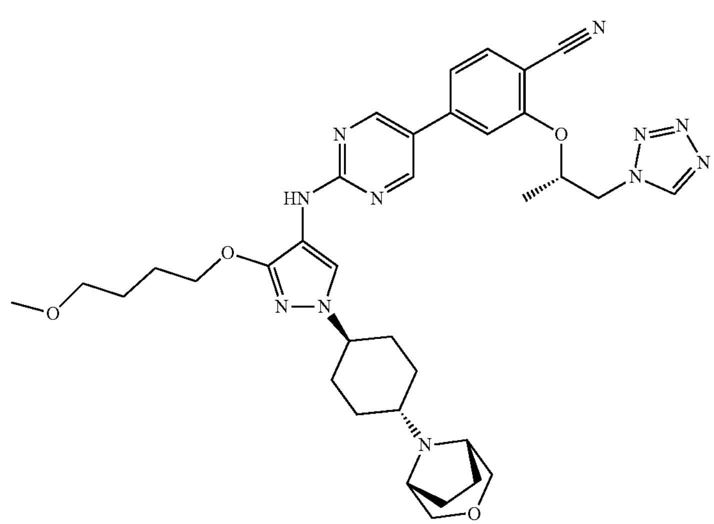 [SMILES: COCCCCOc1nn([C@H]2CC[C@H](N3[C@@H]4CC[C@H]3COC4)CC2)cc1Nc1ncc(-c2ccc(C#N)c(O[C@@H](C)Cn3cnnn3)c2)cn1] |

TABLE 2-continued

| Ex. No. | IUPAC NAME | STRUCTURE |
| --- | --- | --- |
| 155 | 2-(((S)-1-(1H-1,2,4-triazol-1-yl)propan-2-yl)oxy)-4-(2-((1-((1r,4r)-4-((1R,5S)-3-oxa-8-azabicyclo[3.2.1]octan-8-yl)cyclohexyl)-3-(4-methoxybutoxy)-1H-pyrazol-4-yl)amino)pyrimidin-4-yl)benzonitrile | 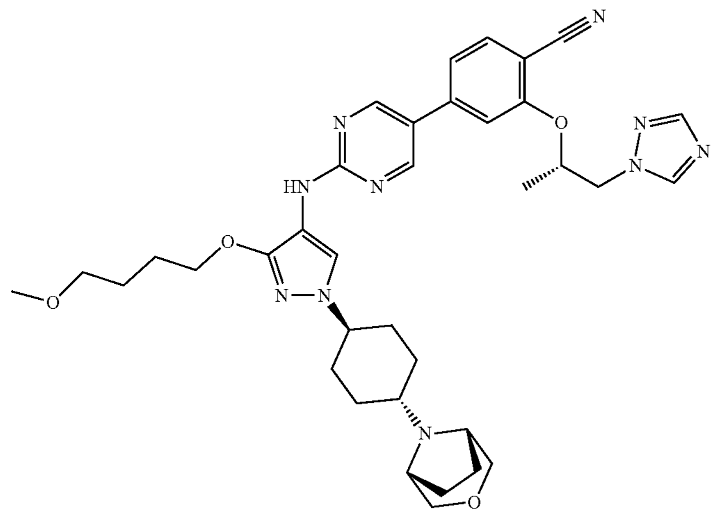 [SMILES: COCCCCOc1nn([C@H]2CC[C@H](N3[C@@H]4CC[C@H]3COC4)CC2)cc1Nc1ncc(-c2ccc(C#N)c(O[C@@H](C)Cn3cncn3)c2)cn1] |
| 156 | 2-(((S)-1-(1H-tetrazol-1-yl)propan-2-yl)oxy)-4-(2-((3-(3-methoxy-3-methylbutoxy)-1-((1r,4r)-4-morpholinocyclohexyl)-1H-pyrazol-4-yl)amino)pyrimidin-5-yl)benzonitrile | 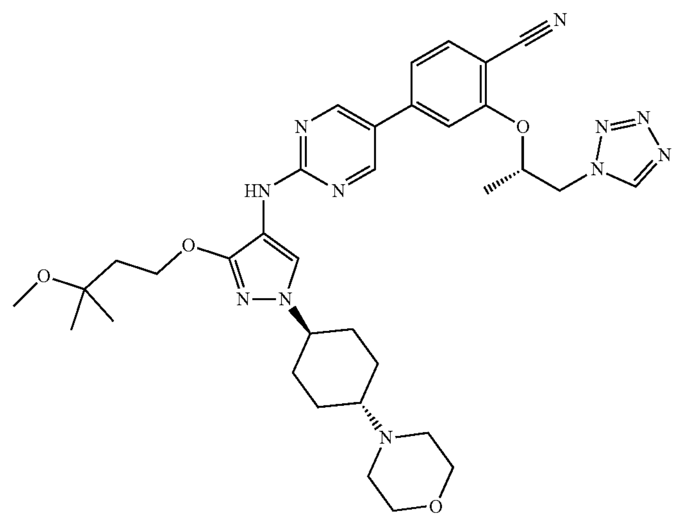 [SMILES: COC(C)(C)CCOc1nn([C@H]2CC[C@H](N3CCOCC3)CC2)cc1Nc1ncc(-c2ccc(C#N)c(O[C@@H](C)Cn3cnnn3)c2)cn1] |
| 157 | 5-(3-(((S)-1-(1H-tetrazol-1-yl)propan-2-yl)oxy)-4-chlorophenyl)-N-(3-(3-methoxy-3-methylbutoxy)-1-((1r,4r)-4-morpholinocyclohexyl)-1H-pyrazol-4-yl)pyrimidin-2-amine | 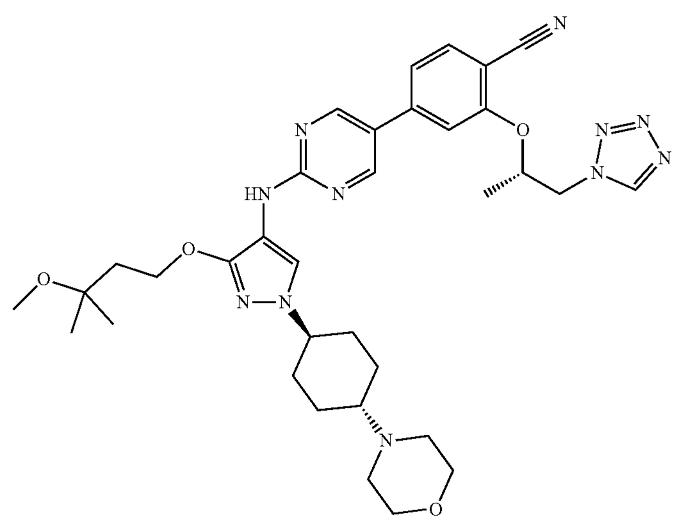 [SMILES: COC(C)(C)CCOc1nn([C@H]2CC[C@H](N3CCOCC3)CC2)cc1Nc1ncc(-c2ccc(C#N)c(O[C@@H](C)Cn3cnnn3)c2)cn1] |

TABLE 2-continued

| Ex. No. | IUPAC NAME | STRUCTURE |
|---|---|---|
| 158 | 2-(((S)-1-(1H-1,2,4-triazol-1-yl)propan-2-yl)oxy)-4-(2-((3-(3-methoxy-3-methylbutoxy)-1-((1r,4r)-4-morpholinocyclohexyl)-1H-pyrazol-4-yl)amino)pyrimidin-5-yl)benzonitrile | 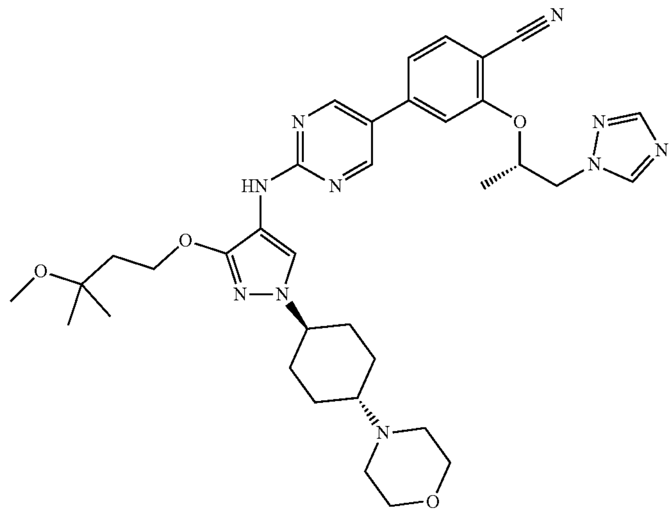 [SMILES: COC(C)(C)CCOc1nn([C@H]2CC[C@H](N3CCOCC3)CC2)cc1Nc1ncc(-c2ccc(C#N)c(O[C@@H](C)Cn3cncn3)c2)cn1] |
| 159 | 2-(((S)-1-(1H-tetrazol-1-yl)propan-2-yl)oxy)-4-(2-((1-((1r,4r)-4-morpholinocyclohexyl)-3-((tetrahydrofuran-3-yl)methoxy)-1H-pyrazol-4-yl)amino)pyrimidin-5-yl)benzonitrile | 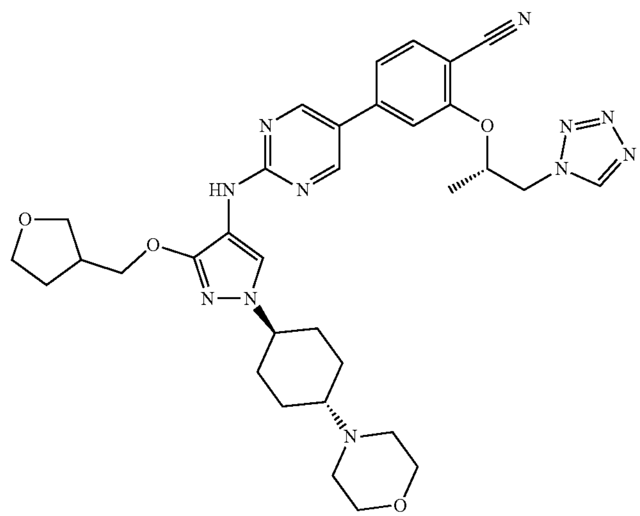 [SMILES: C[C@@H](Cn1cnnn1)Oc1cc(-c2cnc(Nc3cn([C@H]4CC[C@H](N5CCOCC5)CC4)nc3OCC3CCOC3)nc2)ccc1C#N] |
| 160 | 5-(3-(((S)-1-(1H-tetrazol-1-yl)propan-2-yl)oxy)-4-chlorophenyl)-N-(1-((1r,4r)-4-morpholinocyclohexyl)-3-((tetrahydrofuran-3-yl)methoxy)-1H-pyrazol-4-yl)pyrimidin-2-amine | 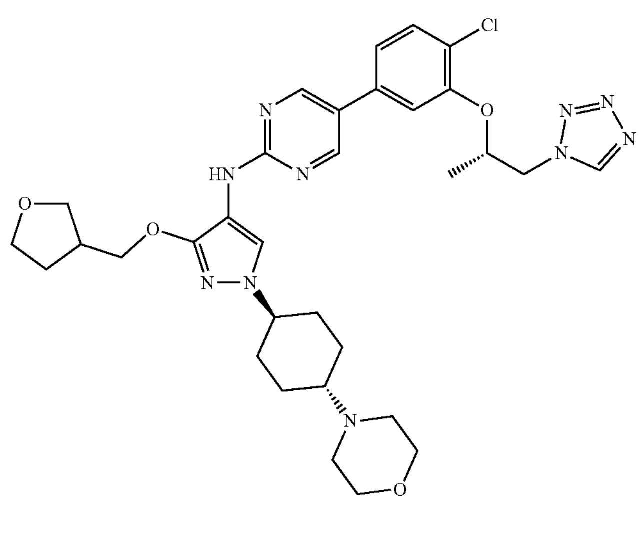 [SMILES: C[C@@H](Cn1cnnn1)Oc1cc(-c2cnc(Nc3cn([C@H]4CC[C@H](N5CCOCC5)CC4)nc3OCC3CCOC3)nc2)ccc1Cl] |

TABLE 2-continued

| Ex. No. | IUPAC NAME | STRUCTURE |
|---|---|---|
| 161 | 5-(3-(((S)-1-(1H-1,2,4-triazol-1-1-yl)propan-2-yl)oxy)-4-chlorophenyl)-N-(1-((1r,4r)-4-morpholinocyclohexyl)-3-((tetrahydrofuran-3-yl)methoxy)-1H-pyrazol-4-yl)pyrimidin-2-amine | 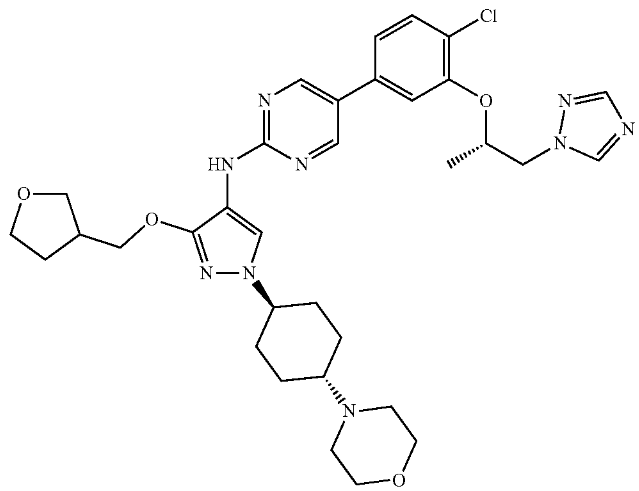 [SMILES: C[C@@H](Cn1cncn1)Oc1cc(-c2cnc(Nc3cn([C@H]4CC[C@H](N5CCOCC5)CC4)nc3OCC3CCOC3)nc2)ccc1Cl] |
| 162 | 2-(((S)-1-(1H-tetrazol-1-yl)propan-2-yl)oxy)-4-(2-((1-((1r,4r)-4-((1R,5S)-3-oxa-8-azabicyclo[3.2.1]octan-8-yl)cyclohexyl)-3-((tetrahydrofuran-3-yl)methoxy)-1H-pyrazol-4-yl)amino)pyrimidin-5-yl)benzonitrile | 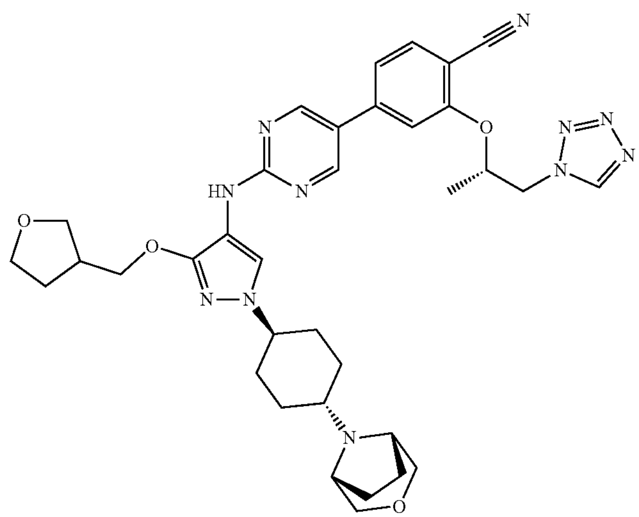 [SMILES: C[C@@H](Cn1cnnn1)Oc1cc(-c2cnc(Nc3cn([C@H]4CC[C@H](N5[C@@H]6CC[C@H]5COC6)CC4)nc3OCC3CCOC3)nc2)ccc1C#N] |
| 163 | 5-(3-(((S)-1-(1H-1,2,4-triazol-1-yl)propan-2-yl)oxy)-4-chlorophenyl)-N-(1-((1r,4r)-4-((1R,5S)-3-oxa-8-azabicyclo[3.2.1]octan-8-yl)cyclohexyl)-3-((tetrahydrofuran-3-yl)methoxy)-1H-pyrazol-4-yl)pyrimidin-2-amine | 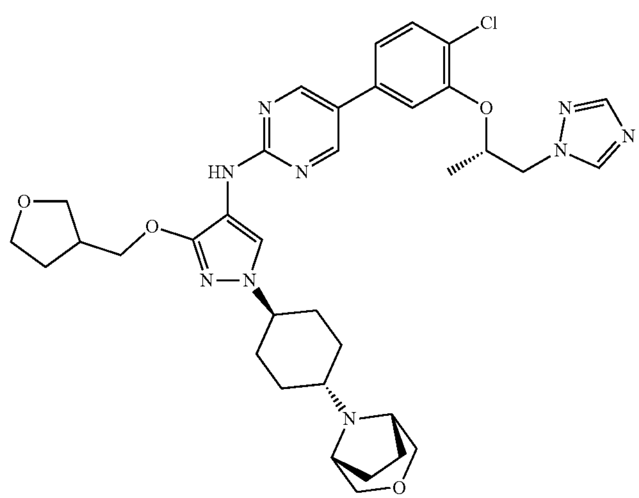 [SMILES: C[C@@H](Cn1cncn1)Oc1cc(-c2cnc(Nc3cn([C@H]4CC[C@H](N5[C@@H]6CC[C@H]5COC6)CC4)nc3OCC3CCOC3)nc2)ccc1Cl] |

TABLE 2-continued

| Ex. No. | IUPAC NAME | STRUCTURE |
|---|---|---|
| 164 | 2-(((S)-1-(1H-1,2,4-triazol-1-yl)propan-2-yl)oxy)-4-(2-((1-((1r,4r)-4-((2S,6R)-2,6-dimethylmorpholino)cyclohexyl)-3-((tetrahydrofuran-3-yl)methoxy)-1H-pyrazol-4-yl)amino)pyrimidin-5-yl)benzonitrile | 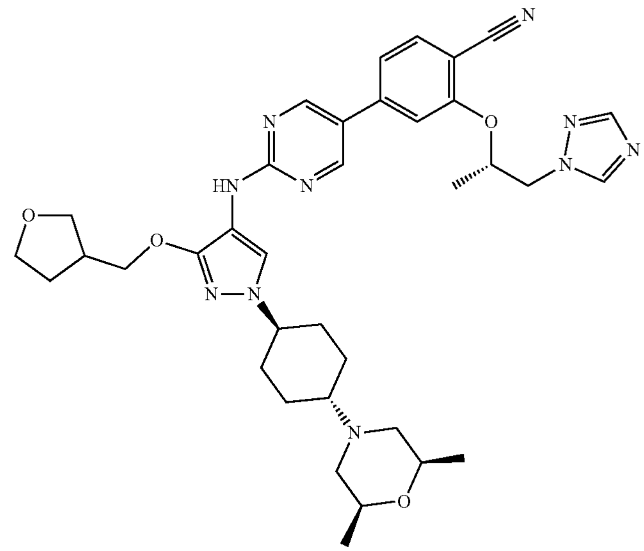 [SMILES: C[C@@H]1CN([C@H]2CC[C@H](n3cc(Nc4ncc(-c5ccc(C#N)c(O[C@@H](C)Cn6cncn6)c5)cn4)c(OCC4CCOC4)n3)CC2)C[C@H](C)O1] |
| 165 | 2-(((S)-1-(1H-tetrazol-1-yl)propan-2-yl)oxy)-4-(2-((1-((1r,4r)-4-morpholinocyclohexyl)-3-((tetrahydro-2H-pyran-4-yl)methoxy)-1H-pyrazol-4-yl)amino)pyrimidin-5-yl)benzonitrile | 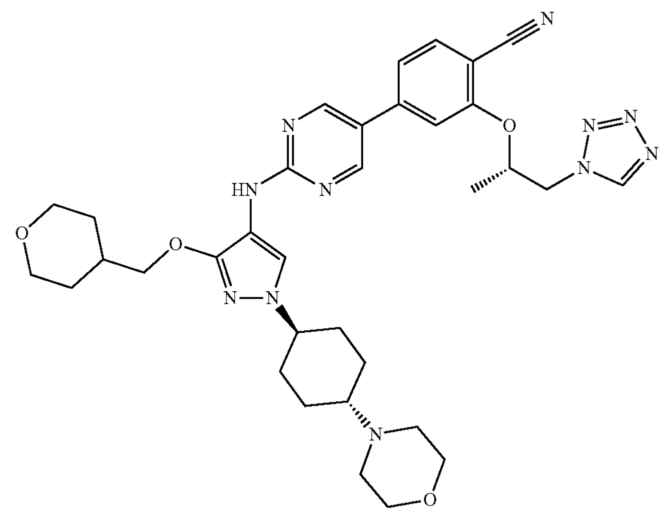 [SMILES: C[C@@H](Cn1cnnn1)Oc1cc(-c2cnc(Nc3cn([C@H]4CC[C@H](N5CCOCC5)CC4)nc3OCC3CCOCC3)nc2)ccc1C#N] |
| 166 | 5-(3-(((S)-1-(1H-tetrazol-1-yl)propan-2-yl)oxy)-4-chlorophenyl)-N-(1-((1r,4r)-4-morpholinocyclohexyl)-3-((tetrahydro-2H-pyran-4-yl)methoxy)-1H-pyrazol-4-yl)pyrimidin-2-amine | 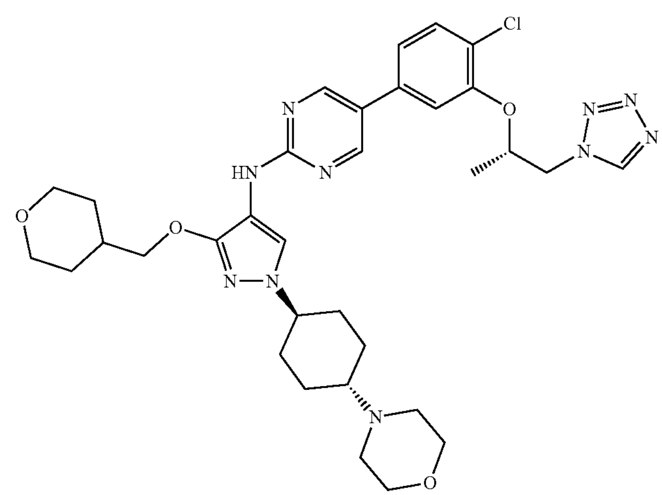 [SMILES: C[C@@H](Cn1cnnn1)Oc1cc(-c2cnc(Nc3cn([C@H]4CC[C@H](N5CCOCC5)CC4)nc3OCC3CCOCC3)nc2)ccc1Cl] |

TABLE 2-continued

| Ex. No. | IUPAC NAME | STRUCTURE |
| --- | --- | --- |
| 167 | 2-(((S)-1-(1H-1,2,4-triazol-1-yl)propan-2-yl)oxy)-4-(2-((1-((1r,4r)-4-morpholinocyclohexyl)-3-((tetrahydro-2H-pyran-3-yl)methoxy)-1H-pyrazolo-4-yl)amino)pyrimidin-5-yl)benzonitrile | 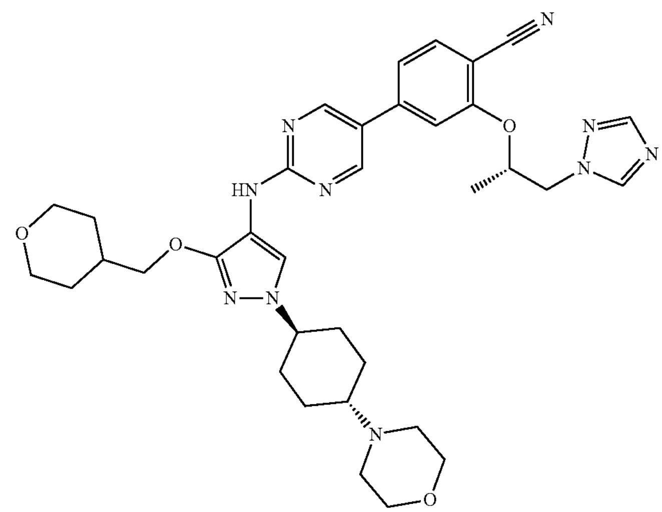 [SMILES: C[C@@H](Cn1cncn1)Oc1cc(-c2cnc(Nc3cn([C@H]4CC[C@H](N5CCOCC5)CC4)nc3OCC3CCOCC3)nc2)ccc1C#N] |
| 168 | 5-(3-(((S)-1-(1H-1,2,4-triazol-1-yl)propan-2-yl)oxy)-4-chlorophenyl)-N-(1-((1r,4r)-4-morpholinocyclohexyl)-3-((tetrahydro-2H-pyran-4-yl)methoxy)-1H-pyrazol-4-yl)pyrimidin-2-amine | 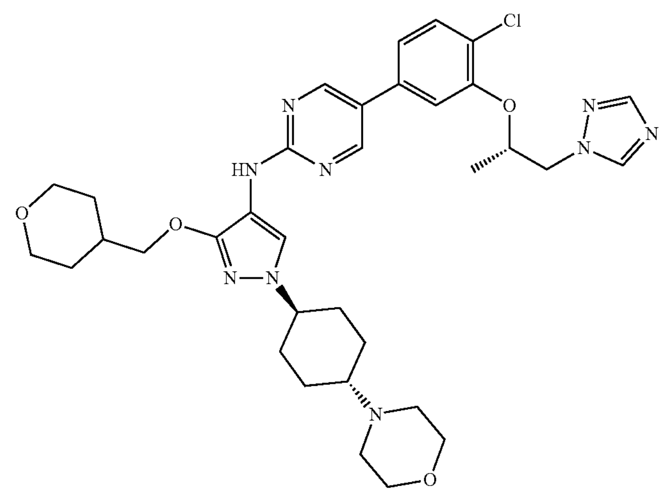 [SMILES: C[C@@H](Cn1cncn1)Oc1cc(-c2cnc(Nc3cn([C@H]4CC[C@H](N5CCOCC5)CC4)nc3OCC3CCOCC3)nc2)ccc1Cl] |
| 169 | 2-(((S)-1-(1H-tetrazol-1-yl)propan-2-yl)oxy)-4-(2-((1-((1r,4r)-4-((1R,5S)-3-oxa-8-azabicyclo[3.2.1]octan-8-yl)cyclohexyl)-3-((tetrahydro-2H-pyran-4-yl)methoxy)-1H-pyrazol-4-yl)amino)pyrimidin-5-yl)benzonitrile | 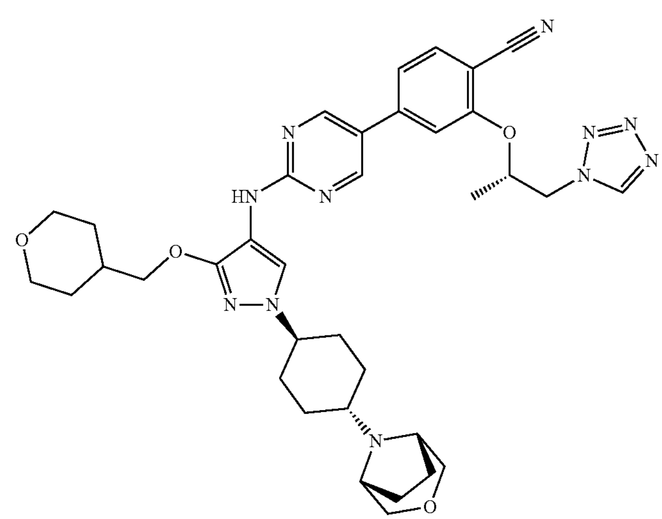 [SMILES: C[C@@H](Cn1cnnn1)Oc1cc(-c2cnc(Nc3cn([C@H]4CC[C@H](N5[C@@H]6CC[C@H]5COC6)CC4)nc3OCC3CCOCC3)nc2)ccc1C#N] |

TABLE 2-continued

| Ex. No. | IUPAC NAME | STRUCTURE |
|---|---|---|
| 170 | 2-(((S)-1-(1H-1,2,4-triazol-1-yl)propan-2-yl)oxy)-4-(2-((1-((1r,4r)-4-((1R,5S)-3-oxa-8-azabicyclo[3.2.1]octan-8-yl)cyclohexyl)-3-((tetrahydro-2H-pyran-4-yl)methoxy)-1H-pyrazol-4-yl)amino)pyrimidin-5-yl)benzonitrile | 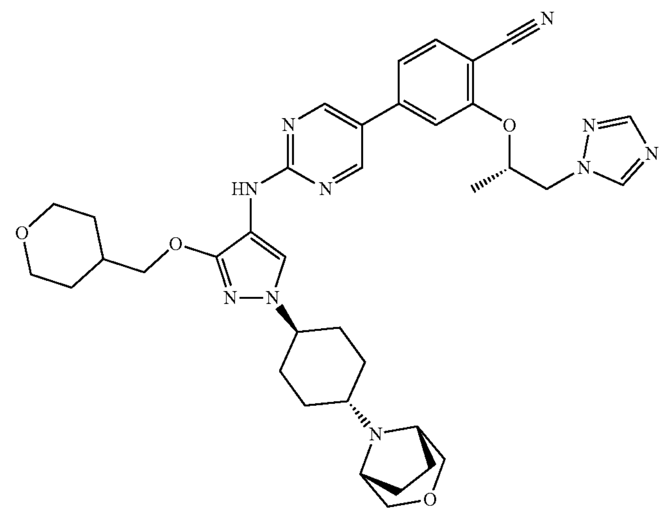 [SMILES: C[C@@H](Cn1cncn1)Oc1cc(-c2cnc(Nc3cn([C@H]4CC[C@H](N5[C@@H]6CC[C@H]5COC6)CC4)nc3OCC3CCOCC3)nc2)ccc1C#N] |
| 171 | 2-(((S)-1-(1H-1,2,4-triazol-1-yl)propan-2-yl)oxy)-4-(2-((1-((1r,4r)-4-((2S,6R)-2,6-dimethylmorpholino)cyclohexyl)-3-((tetrahydro-2H-pyran-4-yl)methoxy)-1H-pyrazol-4-yl)amino)pyrimidin-5-yl)benzonitrile | 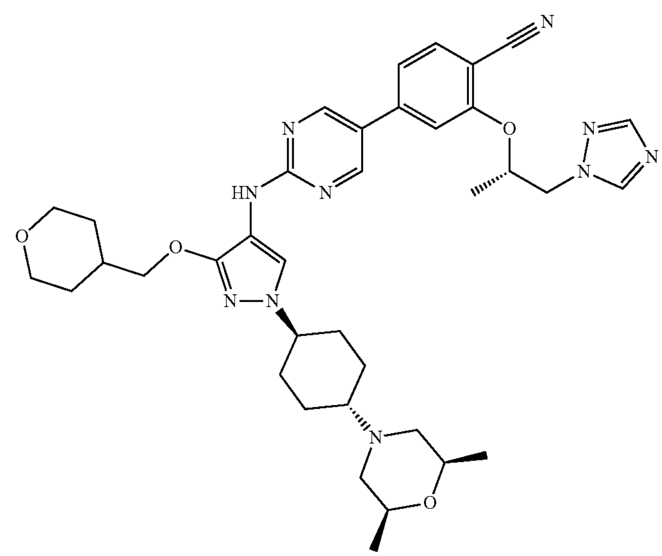 [SMILES: C[C@@H]1CN([C@H]2CC[C@H](n3cc(Nc4ncc(-c5ccc(C#N)c(O[C@@H](C)Cn6cncn6)c5)cn4)c(OCC4CCOCC4)n3)CC2)C[C@H](C)O1] |
| 172 | 2-(((S)-1-(1H-tetrazol-1-yl)propan-2-yl)oxy)-4-(2-((3-(3-(methoxy-d3)propoxy)-1-((1r,4r)-4-morpholinocyclohexyl)-1H-pyrazol-4-yl)amino)pyrimidin-5-yl)benzonitrile | 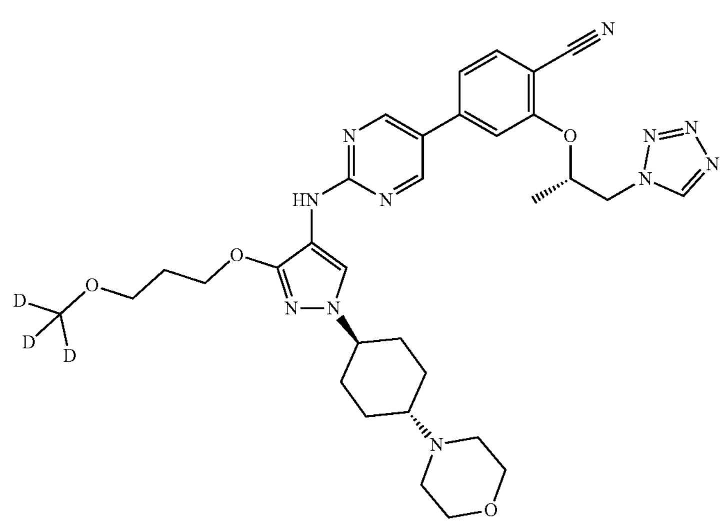 [SMILES: [2H]C([2H])([2H])OCCCOc1nn([C@H]2CC[C@H](N3CCOCC3)CC2)cc1Nc1ncc(-c2ccc(C#N)c(O[C@@H](C)Cn3cnnn3)c2)cn1] |

TABLE 2-continued

| Ex. No. | IUPAC NAME | STRUCTURE |
|---|---|---|
| 173 | 5-(3-(((S)-1-(1H-tetrazol-1-yl)propan-2-yl)oxy)-4-chlorophenyl)-N-(3-(3-(methoxy-d3)propoxy)-1-((1r,4r)-4-morpholinocyclohexyl)-1H-pyrazol-4-yl)pyrimidin-2-amine | 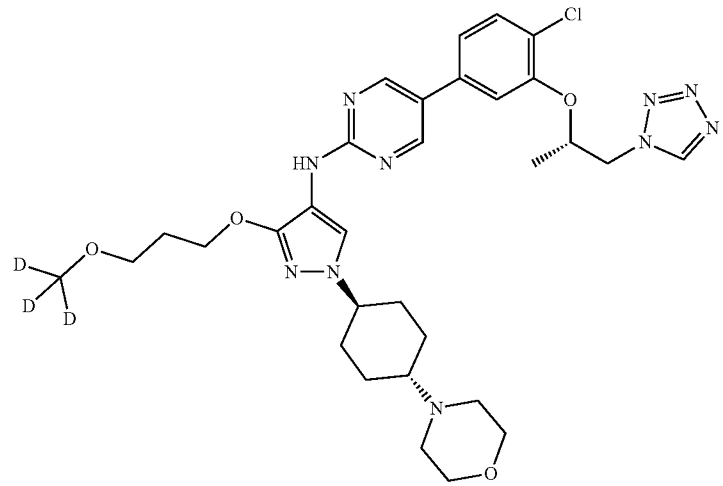 [SMILES: [2H]C([2H])([2H])OCCCOc1nn([C@H]2CC[C@H](N3CCOCC3)CC2)cc1Nc1ncc(-c2ccc(Cl)c(O[C@@H](C)Cn3cnnn3)c2)cn1] |
| 174 | 2-(((S)-1-(1H-tetrazol-1-yl)propan-2-yl)oxy)-4-(2-((1-((1r,4r)-4-((1R,5S)-3-oxa-8-azabicyclo[3.2.1]octan-8-yl)cyclohexyl)-3-(3-(methoxy-d3)propoxy)-1H-pyrazol-4-yl)amino)pyrimidin-5-yl)benzonitrile | 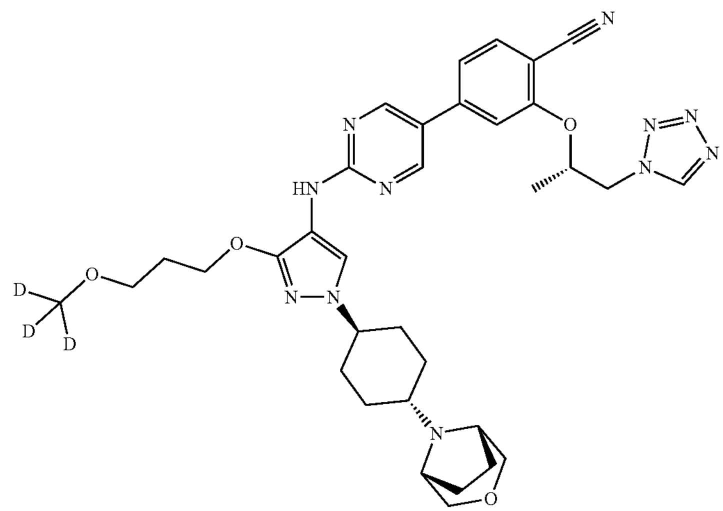 [SMILES: [2H]C([2H])([2H])OCCCOc1nn([C@H]2CC[C@H](N3[C@@H]4CC[C@H]3COC4)CC2)cc1Nc1ncc(-c2ccc(C#N)c(O[C@@H](C)Cn3cnnn3)c2)cn1] |
| 175 | 2-(((S)-1-(1H-tetrazol-1-yl)propan-2-yl)oxy)-4-(2-((1-((1r,4r)-4-((2S,6R)-2,6-dimethylmorpholino)cyclohexyl)-3-(3-(methoxy-d3)propoxy)-1H-pyrazol-4-yl)amino)pyrimidin-5-yl)benzonitrile | 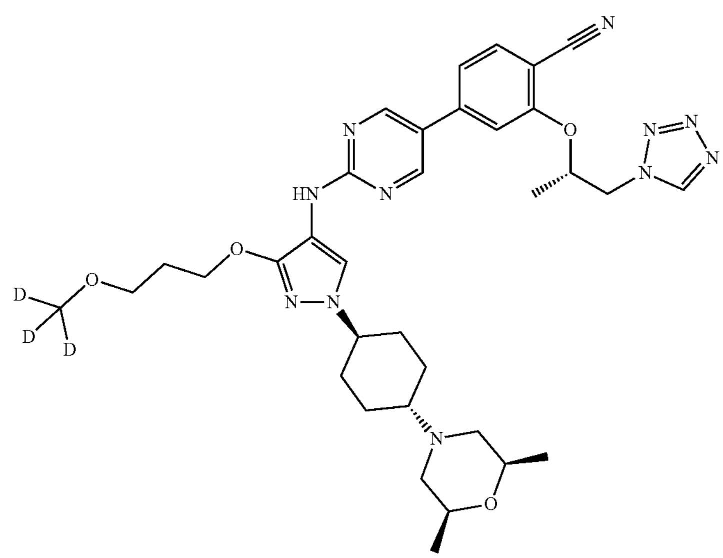 [SMILES: [2H]C([2H])([2H])OCCCOc1nn([C@H]2CC[C@H](N3C[C@@H](C)O[C@@H](C)C3)CC2)cc1Nc1ncc(-c2ccc(C#N)c(O[C@@H](C)Cn3cnnn3)c2)cn1] |

TABLE 2-continued

| Ex. No. | IUPAC NAME | STRUCTURE |
|---|---|---|
| 176 | 2-(((S)-1-(1H-tetrazol-1-yl)propan-2-yl)oxy)-4-(2-((1-((1r,4r)-4-((1R,5S)-3-oxa-8-azabicyclo[3.2.1]octan-8-yl)cyclohexyl)-3-(2-(trifluoromethoxy)ethoxy)-1H-pyrazol-4-yl)amino)pyrimidin-5-yl)benzonitrile | 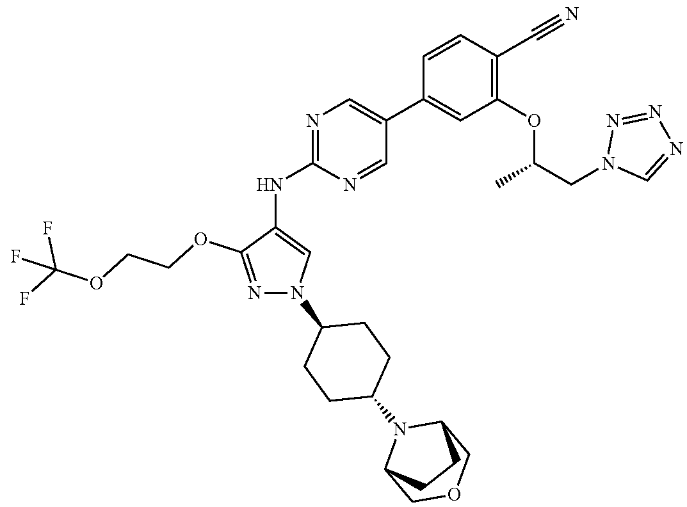 [SMILES: C[C@@H](Cn1cnnn1)Oc1cc(-c2cnc(Nc3cn([C@H]4CC[C@H](N5[C@@H]6CC[C@H]5COC6)CC4)nc3OCCOC(F)(F)F)nc2)ccc1C#N] |
| 177 | 2-(((S)-1-(1H-tetrazol-1-yl)propan-2-yl)oxy)-4-(2-((1-((1r,4r)-4-((2S,6R)-2,6-dimethylmorpholino)cyclohexyl)-3-(2-(trifluoromethoxy)ethoxy)-1H-pyrazol-4-yl)amino)pyrimidin-5-yl)benzonitrile | 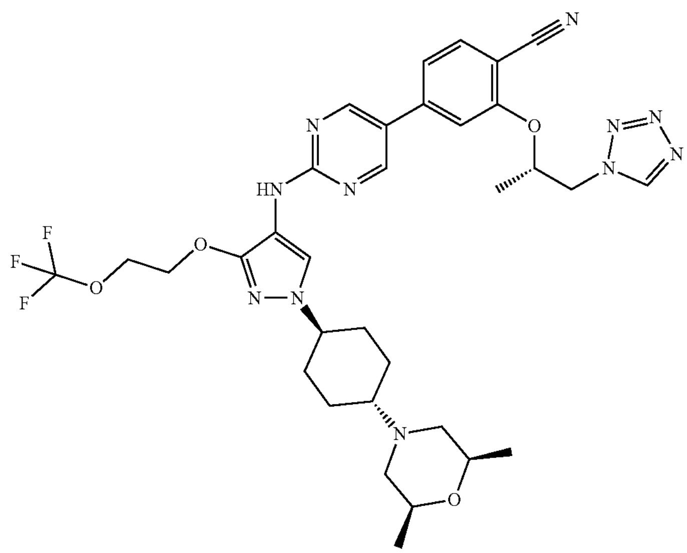 [SMILES: C[C@@H]1CN([C@H]2CC[C@H](n3cc(Nc4ncc(-c5ccc(C#N)c(O[C@@H](C)Cn6cnnn6)c5)cn4)c(OCCOC(F)(F)F)n3)CC2)C[C@H](C)O1] |
| 178 | 2-(((S)-1-(1H-tetrazol-1-yl)propan-2-yl)oxy)-4-(2-((1-((1r,4r)-4-((1R,5S)-3-oxa-8-azabicyclo[3.2.1]octan-8-yl)cyclohexyl)-3-(2-(difluoromethoxy)ethoxy)-1H-pyrazol-4-yl)amino)pyrimidin-5-yl)benzonitrile | 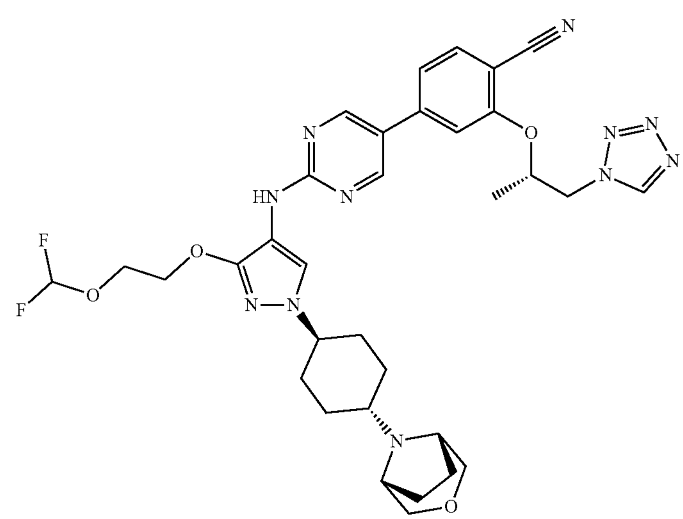 [SMILES: C[C@@H](Cn1cnnn1)Oc1cc(-c2cnc(Nc3cn([C@H]4CC[C@H](N5[C@@H]6CC[C@H]5COC6)CC4)nc3OCCOC(F)F)nc2)ccc1C#N] |

| Ex. No. | IUPAC NAME |
|---|---|
| 179 | 2-(((S)-1-(1H-tetrazol-1-yl)propan-2-yl)oxy)-4-(2-((3-(2-(difluoromethoxy)ethoxy)-1-((1r,4r)-4-((2S,6R)-2,6-dimethylmorpholino)cyclohexyl)-1H-pyrazol-4-yl)amino)pyrimidin-5-yl)benzonitrile |
| 180 | 2-(((S)-1-(1H-tetrazol-1-yl)propan-2-yl)oxy)-4-(2-((1-((1r,4r)-4-((1R,5S)-3-oxa-8-azabicyclo[3.2.1]octan-8-yl)cyclohexyl)-3-(2-(2,2,2-trifluoroethoxy)ethoxy)-1H-pyrazol-4-yl)amino)pyrimidin-5-yl)benzonitrile |
| 181 | 2-(((S)-1-(1H-tetrazol-1-yl)propan-2-yl)oxy)-4-(2-((1-((1r,4r)-4-((2S,6R)-2,6-dimethylmorpholino)cyclohexyl)-3-(2-(2,2,2-trifluoroethoxy)ethoxy)-1H-pyrazol-4-yl)amino)pyrimidin-5-yl)benzonitrile |

TABLE 2-continued

| Ex. No. | IUPAC NAME | STRUCTURE |
|---|---|---|
| 182 | 2-(((S)-1-(1H-tetrazol-1-yl)propan-2-yl)oxy)-4-(2-((1-((1r,4r)-4-((1R,5S)-3-oxa-8-azabicyclo[3.2.1]octan-8-yl)cyclohexyl)-3-(2-(2,2-difluoroethoxy)ethoxy)-1H-pyrazol-4-yl)amino)pyrimidin-5-yl)benzonitrile | 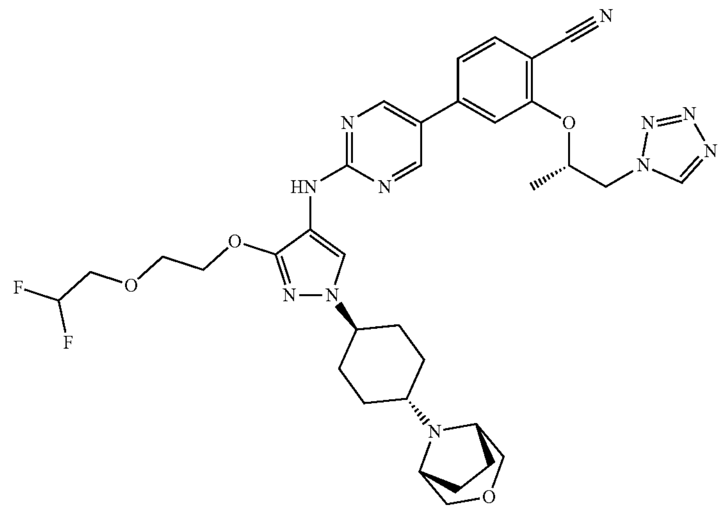 [SMILES: C[C@@H](Cn1cnnn1)Oc1cc(-c2cnc(Nc3cn([C@H]4CC[C@H](N5[C@@H]6CC[C@H]5COC6)CC4)nc3OCCOCC(F)F)nc2)ccc1C#N] |
| 183 | 2-(((S)-1-(1H-tetrazol-1-yl)propan-2-yl)oxy)-4-(2-((3-(2-(2,2-difluoroethoxy)ethoxy)-1-((1r,4r)-4-((2S,6R)-2,6-dimethylmorpholino)cyclohexyl)-1H-pyrazol-4-yl)amino)pyrimidin-5-yl)benzonitrile | 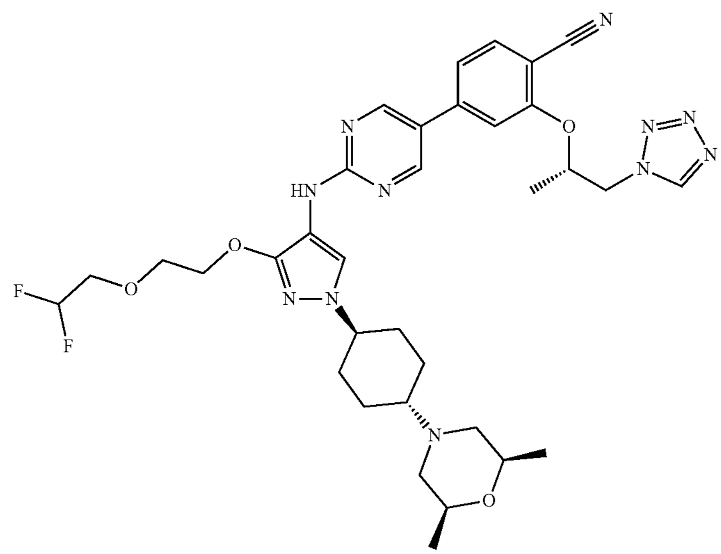 [SMILES: C[C@@H]1CN([C@H]2CC[C@H](n3cc(Nc4ncc(-c5ccc(C#N)c(O[C@@H](C)Cn6cnnn6)c5)cn4)c(OCCOCC(F)F)n3)CC2)C[C@H](C)O1] |
| 184 | 2-(((S)-1-(1H-tetrazol-1-yl)propan-2-yl)oxy)-4-(2-((1-((1r,4r)-4-((2S,6R)-2,6-dimethylmorpholino)cyclohexyl)-3-(3-ethoxypropoxy)-1H-pyrazol-4-yl)amino)pyrimidin-5-yl)benzonitrile | 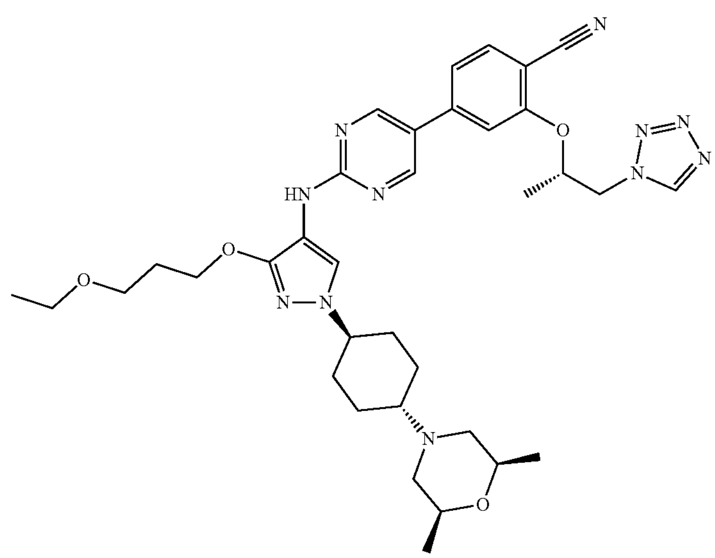 [SMILES: CCOCCCOc1nn([C@H]2CC[C@H](N3C[C@@H](C)O[C@@H](C)C3)CC2)cc1Nc1ncc(-c2ccc(C#N)c(O[C@@H](C)Cn3cnnn3)c2)cn1] |

TABLE 2-continued

| Ex. No. | IUPAC NAME | STRUCTURE |
|---|---|---|
| 185 | 2-(((S)-1-(1H-tetrazol-1-yl)propan-2-yl)oxy)-4-(2-((1-((1r,4r)-4-((1R,5S)-3-oxa-8-azabicyclo[3.2.1]octan-8-yl)cyclohexyl)-3-(3-isopropoxypropoxy)-1H-pyrazol-4-yl)amino)pyrimidin-5-yl)benzonitrile | 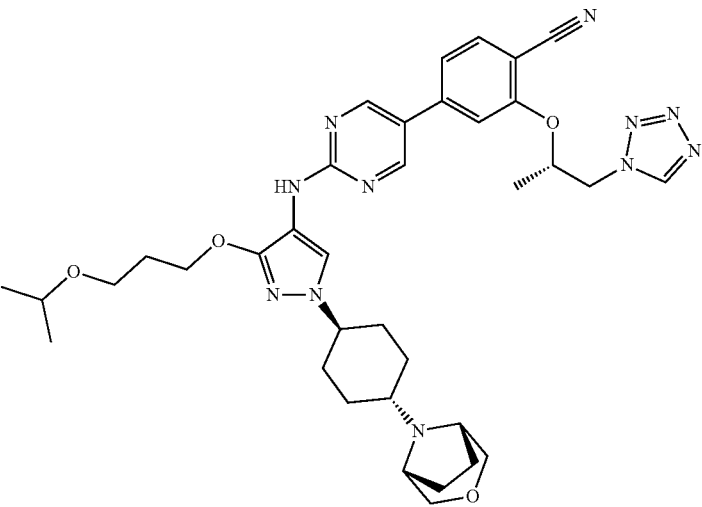 [SMILES: CC(C)OCCCOc1nn([C@H]2CC[C@H](N3[C@@H]4CC[C@H]3COC4)CC2)cc1Nc1ncc(-c2ccc(C#N)c(O[C@@H](C)Cn3cnnn3)c2)cn1] |
| 186 | 2-(((S)-1-(1H-tetrazol-1-yl)propan-2-yl)oxy)-4-(2-((1-((1r,4r)-4-((2S,6R)-2,6-dimethylmorpholino)cyclohexyl)-3-(3-isopropoxypropoxy)-1H-pyrazol-4-yl)amino)pyrimidin-5-yl)benzonitrile | 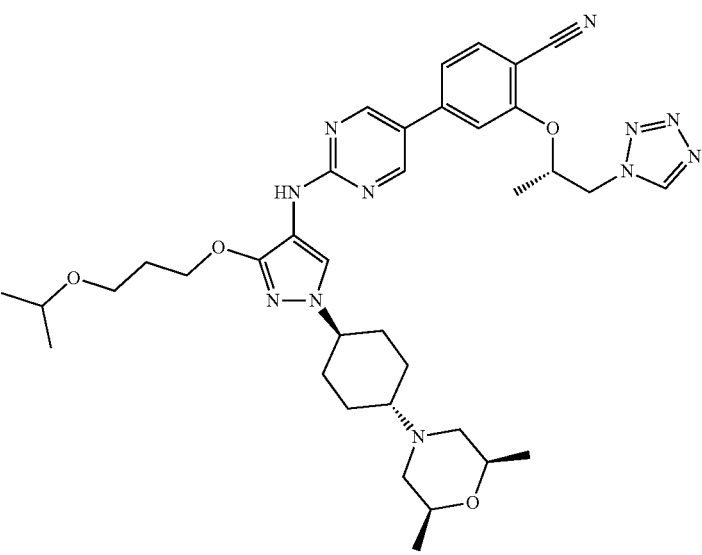 [SMILES: CC(C)OCCCOc1nn([C@H]2CC[C@H](N3C[C@@H](C)O[C@@H](C)C3)CC2)cc1Nc1ncc(-c2ccc(C#N)c(O[C@@H](C)Cn3cnnn3)c2)cn1] |
| 187 | 2-(((S)-1-(1H-tetrazol-1-yl)propan-2-yl)oxy)-4-(2-((1-((1r,4r)-4-((1R,5S)-3-oxa-8-azabicyclo[3.2.1]octan-8-yl)cyclohexyl)-3-(3-(trifluoromethoxy)propoxy)-1H-pyrazol-4-yl)amino)pyrimidin-5-yl)benzonitrile | 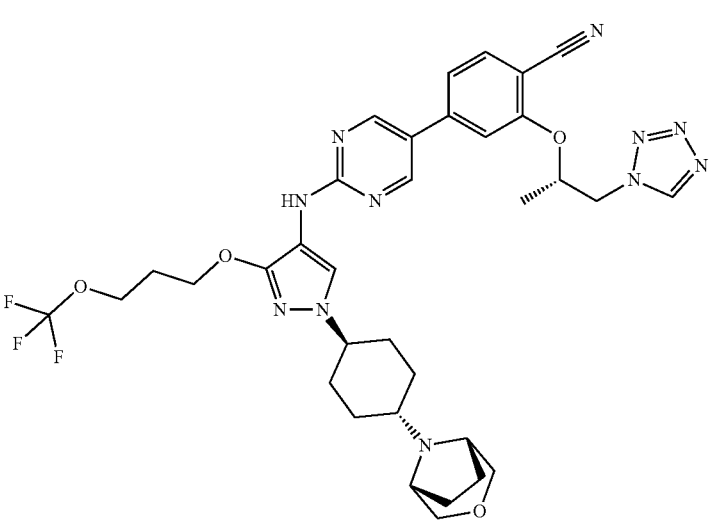 |

TABLE 2-continued

| Ex. No. | IUPAC NAME |
|---|---|
| 188 | 2-(((S)-1-(1H-tetrazol-1-yl)propan-2-yl)oxy)-4-(2-((1-((1r,4r)-4-((2S,6R)-2,6-dimethylmorpholino)cyclohexyl)-3-(3-(trifluoromethoxy)propoxy)-1H-pyrazol-4-yl)amino)pyrimidin-5-yl)benzonitrile |
| 189 | 2-(((S)-1-(1H-tetrazol-1-yl)propan-2-yl)oxy)-4-(2-((1-((1r,4r)-4-((1R,5S)-3-oxa-8-azabicyclo[3.2.1]octan-8-yl)cyclohexyl)-3-(3-(difluoromethoxy)propoxy)-1H-pyrazol-4-yl)amino)pyrimidin-5-yl)benzonitrile |
| 190 | 2-(((S)-1-(1H-tetrazol-1-yl)propan-2-yl)oxy)-4-(2-((3-(3-(difluoromethoxy)propoxy)-1-((1r,4r)-4-((2S,6R)-2,6-dimethylmorpholino)cyclohexyl)-1H-pyrazol-4-yl)amino)pyrimidin-5-yl)benzonitrile |

TABLE 2-continued

| Ex. No. | IUPAC NAME | STRUCTURE |
|---|---|---|
| 191 | 2-(((S)-1-(1H-tetrazol-1-yl)propan-2-yl)oxy)-4-(2-((1-((1r,4r)-4-((1R,5S)-3-oxa-8-azabicyclo[3.2.1]octan-8-yl)cyclohexyl)-3-(3-(2,2,2-trifluoroethoxy)propoxy)-1H-pyrazol-4-yl)amino)pyrimidin-5-yl)benzonitrile | 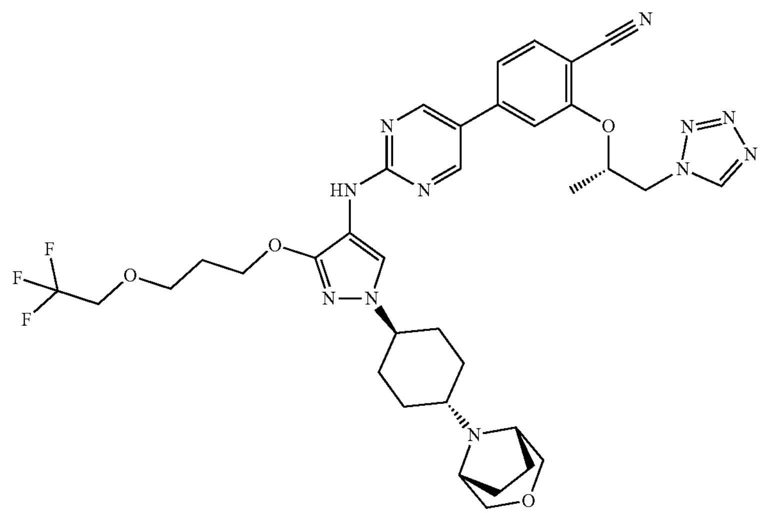 [SMILES: C[C@@H](Cn1cnnn1)Oc1cc(-c2cnc(Nc3cn([C@H]4CC[C@H](N5[C@@H]6CC[C@H]5COC6)CC4)nc3OCCCOCC(F)(F)F)nc2)ccc1C#N] |
| 192 | 2-(((S)-1-(1H-tetrazol-1-yl)propan-2-yl)oxy)-4-(2-((1-((1r,4r)-4-((2S,6R)-2,6-dimethylmorpholino)cyclohexyl)-3-(3-(2,2,2-trifluoroethoxy)propoxy)-1H-pyrazol-4-yl)amino)pyrimidin-5-yl)benzonitrile | 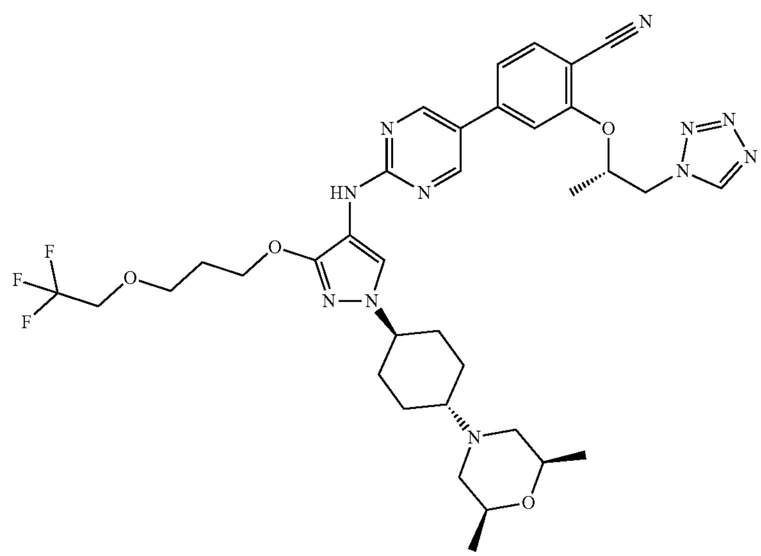 [SMILES: C[C@@H]1CN([C@H]2CC[C@H](n3cc(Nc4ncc(-c5ccc(C#N)c(O[C@@H](C)Cn6cnnn6)c5)cn4)c(OCCCOCC(F)(F)F)n3)CC2)C[C@H](C)O1] |
| 193 | 2-(((S)-1-(1H-tetrazol-1-yl)propan-2-yl)oxy)-4-(2-((1-((1r,4r)-4-((1R,5S)-3-oxa-8-azabicyclo[3.2.1]octan-8-yl)cyclohexyl)-3-(3-(2,2-difluoroethoxy)propoxy)-1H-pyrazol-4-yl)amino)pyrimidin-5-yl)benzonitrile | 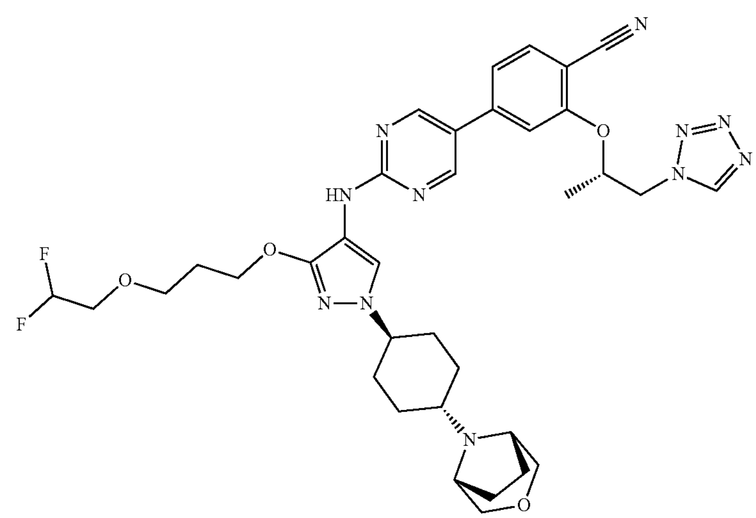 [SMILES: C[C@@H](Cn1cnnn1)Oc1cc(-c2cnc(Nc3cn([C@H]4CC[C@H](N5[C@@H]6CC[C@H]5COC6)CC4)nc3OCCCOCC(F)F)nc2)ccc1C#N] |

TABLE 2-continued

| Ex. No. | IUPAC NAME | STRUCTURE |
|---|---|---|
| 194 | 2-(((S)-1-(1H-tetrazol-1-yl)propan-2-yl)oxy)-4-(2-((3-(3-(2,2-difluoroethoxy)propoxy)-1-((1r,4r)-4-((2S,6R)-2,6-dimethylmorpholino)cyclohexyl)-1H-pyrazol-4-yl)amino)pyrimidin-5-yl)benzonitrile | 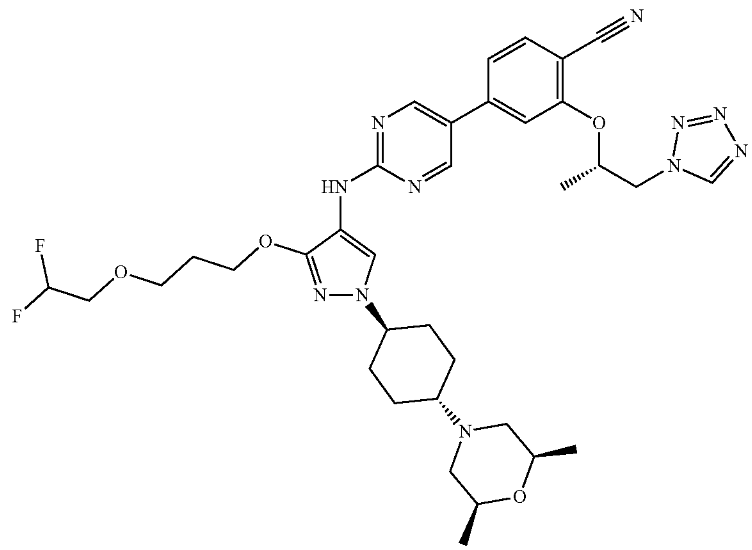 [SMILES: C[C@@H]1CN([C@H]2CC[C@H](n3cc(Nc4ncc(-c5ccc(C#N)c(O[C@@H](C)Cn6cnnn6)c5)cn4)c(OCCCOCC(F)F)n3)CC2)C[C@H](C)O1] |
| 196 | 2-(((S)-1-(1H-tetrazol-1-yl)propan-2-yl)oxy)-4-(2-((1-((1r,4r)-4-((2S,6R)-2,6-dimethylmorpholino)cyclohexyl)-3-(2-hydroxyethoxy)-1H-pyrazol-4-yl)amino)pyrimidin-5-yl)benzonitrile | 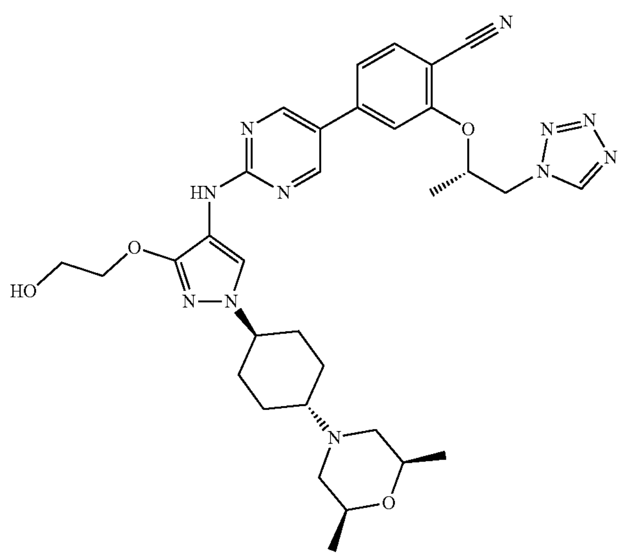 [SMILES: C[C@@H]1CN([C@H]2CC[C@H](n3cc(Nc4ncc(-c5ccc(C#N)c(O[C@@H](C)Cn6cnnn6)c5)cn4)c(OCCO)n3)CC2)C[C@H](C)O1] |
| 197 | 2-(((S)-1-(1H-tetrazol-1-yl)propan-2-yl)oxy)-4-(2-((1-((1r,4r)-4-((1R,5S)-3-oxa-8-azabicyclo[3.2.1]octan-8-yl)cyclohexyl)-3-(2-hydroxy-2-methylpropoxy)-1H-pyrazol-4-yl)amino)pyrimidin-4-yl)benzonitrile | 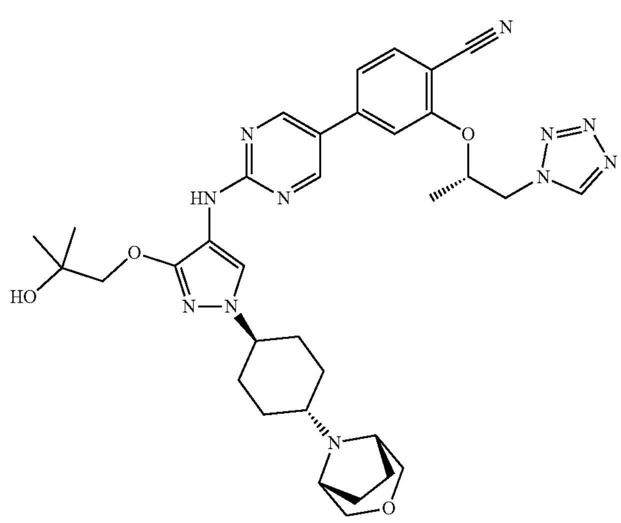 [SMILES: C[C@@H](Cn1cnnn1)Oc1cc(-c2cnc(Nc3cn([C@H]4CC[C@H](N5[C@@H]6CC[C@H]5COC6)CC4)nc3OCC(C)(C)O)nc2)ccc1C#N] |

TABLE 2-continued

| Ex. No. | IUPAC NAME | STRUCTURE |
|---|---|---|
| 198 | 2-(((S)-1-(1H-tetrazol-1-yl)propan-2-yl)oxy)-4-(2-((1-((1r,4r)-4-((2S,6R)-2,6-dimethylmorpholino)cyclohexyl)-3-(2-hydroxy-2-methylpropoxy)-1H-pyrazol-4-yl)amino)pyrimidin-5-yl)benzonitrile | 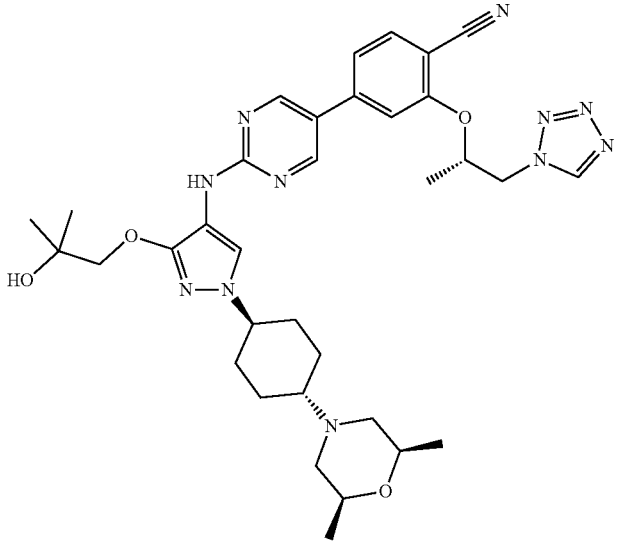 [SMILES: C[C@@H]1CN([C@H]2CC[C@H](n3cc(Nc4ncc(-c5ccc(C#N)c(O[C@@H](C)Cn6cnnn6)c5)cn4)c(OCC(C)(C)O)n3)CC2)C[C@H](C)O1] |
| 199 | 2-(((S)-1-(1H-tetrazol-1-yl)propan-2-yl)oxy)-4-(2-((1-((1r,4r)-4-((1R,5S)-3-oxa-8-azabicyclo[3.2.1]octan-8-yl)cyclohexyl)-3-((1-hydroxycyclopropyl)methoxy)-1H-pyrazol-4-yl)amino)pyrimidin-5-yl)benzonitrile | 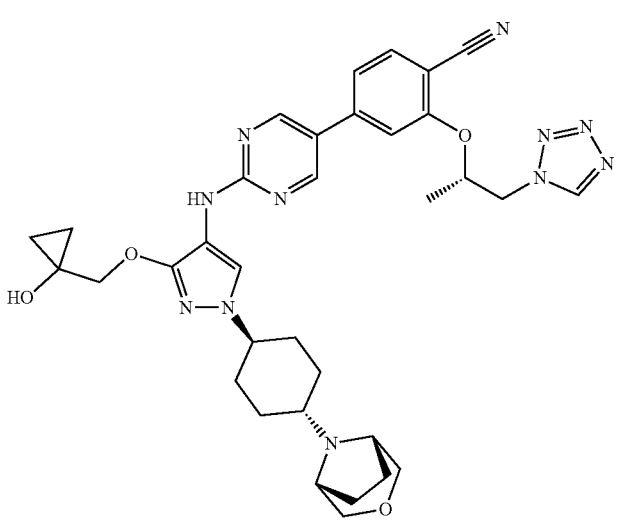 [SMILES: C[C@@H](Cn1cnnn1)Oc1cc(-c2cnc(Nc3cn([C@H]4CC[C@H](N5[C@@H]6CC[C@H]5COC6)CC4)nc3OCC3(O)CC3)nc2)ccc1C#N] |
| 200 | 2-(((S)-1-(1H-tetrazol-1-yl)propan-2-yl)oxy)-4-(2-((1-((1r,4r)-4-((2S,6R)-2,6-dimethylmorpholino)cyclohexyl)-3-((1-hydroxycyclopropyl)methoxy)-1H-pyrazol-4-yl)amino)pyrimidin-5-yl)benzonitrile | 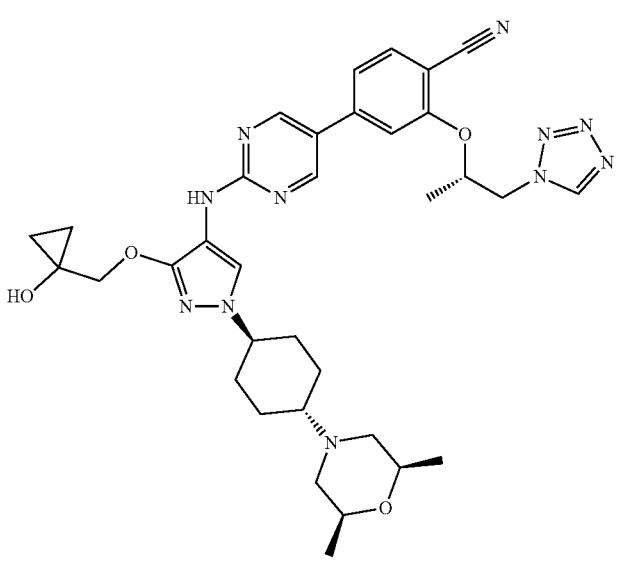 [SMILES: C[C@@H]1CN([C@H]2CC[C@H](n3cc(Nc4ncc(-c5ccc(C#N)c(O[C@@H](C)Cn6cnnn6)c5)cn4)c(OCC4(O)CC4)n3)CC2)C[C@H](C)O1] |

TABLE 2-continued

| Ex. No. | IUPAC NAME | STRUCTURE |
|---|---|---|
| 201 | 2-(((S)-1-(1H-tetrazol-1-yl)propan-2-yl)oxy)-4-(2-((1-((1r,4r)-4-((1R,5S)-3-oxa-8-azabicyclo[3.2.1]octan-8-yl)cyclohexyl)-3-((1-hydroxycyclobutyl)methoxy)-1H-pyrazol-4-yl)amino)pyrimidin-5-yl)benzonitrile | 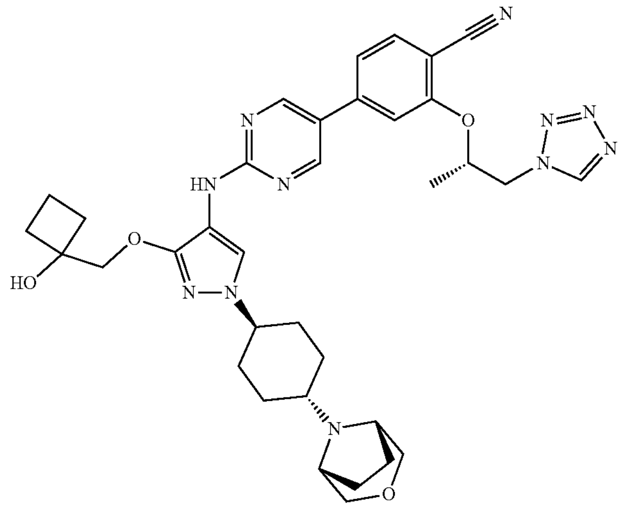 [SMILES: C[C@@H](Cn1cnnn1)Oc1cc(-c2cnc(Nc3cn([C@H]4CC[C@H](N5[C@@H]6CC[C@H]5COC6)CC4)nc3OCC3(O)CCC3)nc2)ccc1C#N] |
| 202 | 2-(((S)-1-(1H-tetrazol-1-yl)propan-2-yl)oxy)-4-(2-((1-((1r,4r)-4-((2S,6R)-2,6-dimethylmorpholino)cyclohexyl)-3-((1-hydroxycyclobutyl)methoxy)-1H-pyrazol-4-yl)amino)pyrimidin-5-yl)benzonitrile | 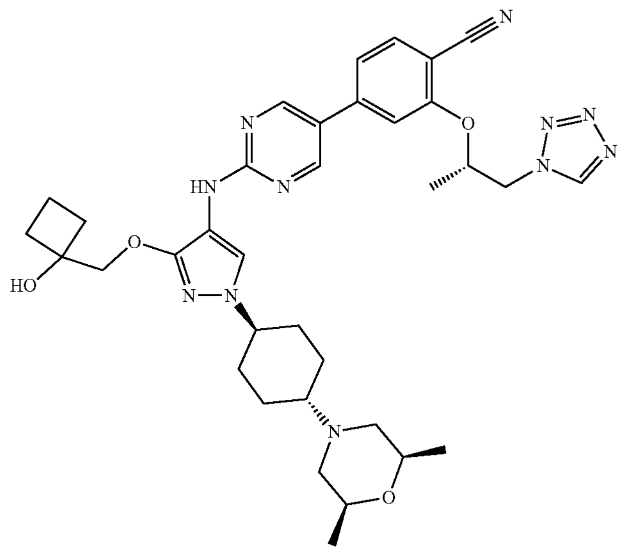 [SMILES: C[C@@H]1CN([C@H]2CC[C@H](n3cc(Nc4ncc(-c5ccc(C#N)c(O[C@@H](C)Cn6cnnn6)c5)cn4)c(OCC4(O)CCC4)n3)CC2)C[C@H](C)O1] |
| 203 | 2-(((S)-1-(1H-tetrazol-1-yl)propan-2-yl)oxy)-4-(2-((1-((1r,4r)-4-((1R,5S)-3-oxa-8-azabicyclo[3.2.1]octan-8-yl)cyclohexyl)-3-(3-hydroxypropoxy)-1H-pyrazol-4-yl)amino)pyrimidin-5-yl)benzonitrile | 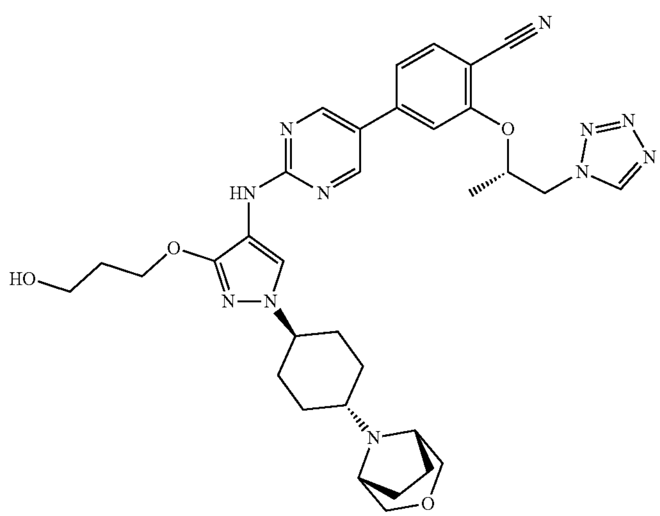 [SMILES: C[C@@H](Cn1cnnn1)Oc1cc(-c2cnc(Nc3cn([C@H]4CC[C@H](N5[C@@H]6CC[C@H]5COC6)CC4)nc3OCCCO)nc2)ccc1C#N] |

TABLE 2-continued

| Ex. No. | IUPAC NAME | STRUCTURE |
| --- | --- | --- |
| 204 | 2-(((S)-1-(1H-tetrazol-1-yl)propan-2-yl)oxy)-4-(2-((1-((1r,4r)-4-((2S,6R)-2,6-dimethylmorpholino)cyclohexyl)-3-(3-hydroxypropoxy)-1H-pyrazol-4-yl)amino)pyrimidin-5-yl)benzonitrile | 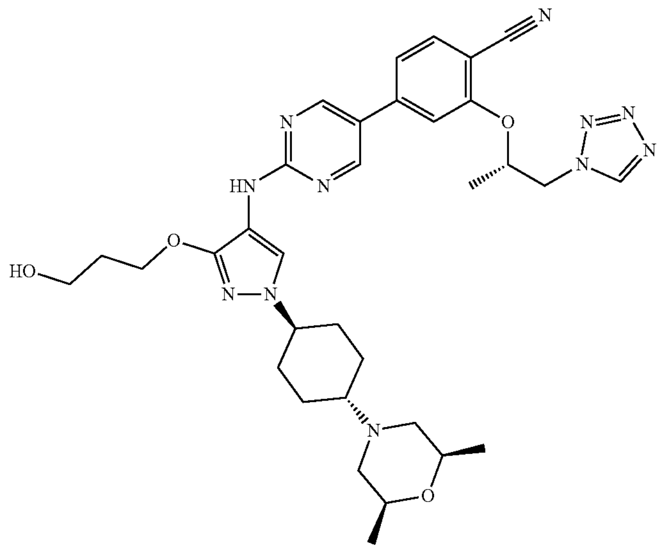 [SMILES: C[C@@H]1CN([C@H]2CC[C@H](n3cc(Nc4ncc(-c5ccc(C#N)c(O[C@@H](C)Cn6cnnn6)c5)cn4)c(OCCCO)n3)CC2)C[C@H](C)O1] |
| 205 | 2-(((S)-1-(1H-tetrazol-1-yl)propan-2-yl)oxy)-4-(2-((1-((1r,4r)-4-((1R,5S)-3-oxa-8-azabicyclo[3.2.1]octan-8-yl)cyclohexyl)-3-(3-hydroxy-3-methylbutoxy)-1H-pyrazol-4-yl)amino)pyrimidin-5-yl)benzonitrile | 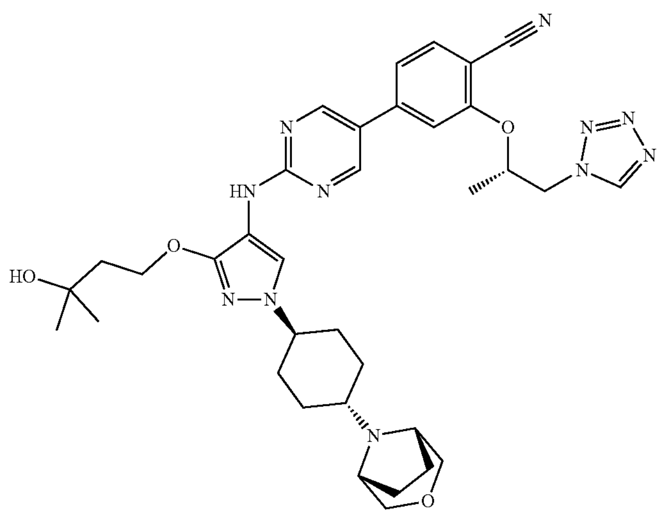 [SMILES: C[C@@H](Cn1cnnn1)Oc1cc(-c2cnc(Nc3cn([C@H]4CC[C@H](N5[C@@H]6CC[C@H]5COC6)CC4)nc3OCCC(C)(C)O)nc2)ccc1C#N] |
| 206 | 2-(((S)-1-(1H-tetrazol-1-yl)propan-2-yl)oxy)-4-(2-((1-((1r,4r)-4-((2S,6R)-2,6-dimethylmorpholino)cyclohexyl)-3-(3-hydroxy-3-methylbutoxy)-1H-pyrazol-4-yl)amino)pyrimidin-5-yl)benzonitrile | 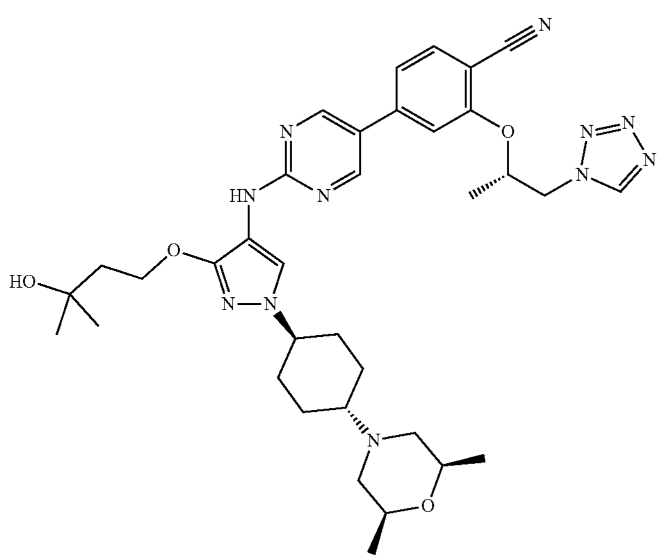 [SMILES: C[C@@H]1CN([C@H]2CC[C@H](n3cc(Nc4ncc(-c5ccc(C#N)c(O[C@@H](C)Cn6cnnn6)c5)cn4)c(OCCC(C)(C)O)n3)CC2)C[C@H](C)O1] |

TABLE 2-continued

| Ex. No. | IUPAC NAME | STRUCTURE |
|---|---|---|
| 207 | 2-(((S)-1-(1H-tetrazol-1-yl)propan-2-yl)oxy)-4-(2-((1-((1r,4r)-4-((1R,5S)-3-oxa-8-azabicyclo[3.2.1]octan-8-yl)cyclohexyl)-3-(2-(1-hydroxycyclopropyl)ethoxy)-1H-pyrazol-4-yl)amino)pyrimidin-5-yl)benzonitrile | 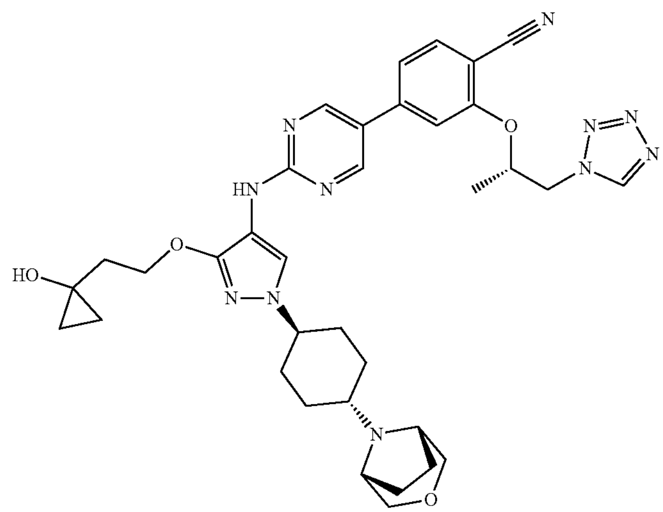 [SMILES: C[C@@H](Cn1cnnn1)Oc1cc(-c2cnc(Nc3cn([C@H]4CC[C@H](N5[C@@H]6CC[C@H]5COC6)CC4)nc3OCCC3(O)CC3)nc2)ccc1C#N] |
| 208 | 2-(((S)-1-(1H-tetrazol-1-yl)propan-2-yl)oxy)-4-(2-((1-((1r,4r)-4-((2S,6R)-2,6-dimethylmorpholino)cyclohexyl)-3-(2-(1-hydroxycyclopropyl)ethoxy)-1H-pyrazol-4-yl)amino)pyrimidin-5-yl)benzonitrile | 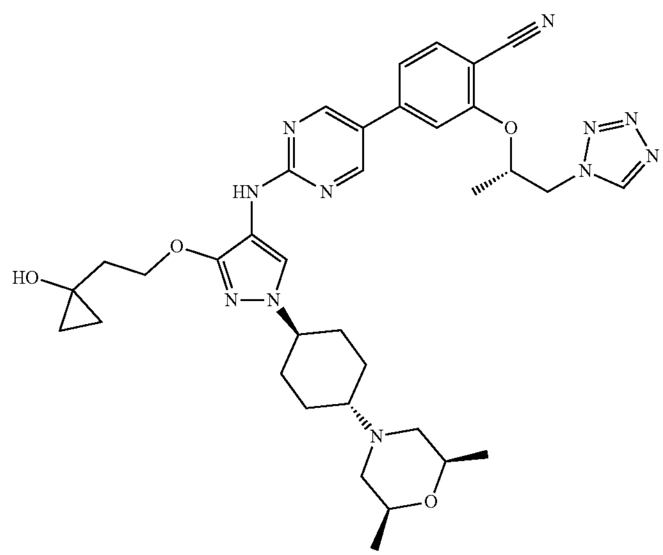 [SMILES: C[C@@H]1CN([C@H]2CC[C@H](n3cc(Nc4ncc(-c5ccc(C#N)c(O[C@@H](C)Cn6cnnn6)c5)cn4)c(OCCC4(O)CC4)n3)CC2)C[C@H](C)O1] |
| 209 | 2-(((S)-1-(1H-tetrazol-1-yl)propan-2-yl)oxy)-4-(2-((1-((1r,4r)-4-((1R,5S)-3-oxa-8-azabicyclo[3.2.1]octan-8-yl)cyclohexyl)-3-(2-(1-hydroxycyclobutyl)ethoxy)-1H-pyrazol-4-yl)amino)pyrimidin-5-yl)benzonitrile | 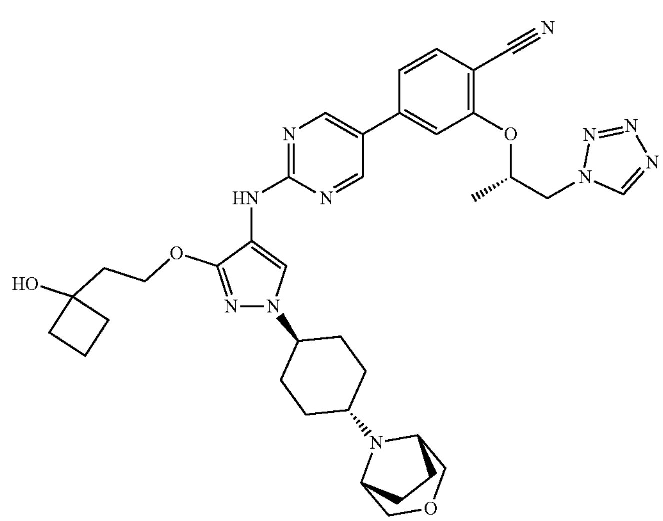 [SMILES: C[C@@H](Cn1cnnn1)Oc1cc(-c2cnc(Nc3cn([C@H]4CC[C@H](N5[C@@H]6CC[C@H]5COC6)CC4)nc3OCCC3(O)CCC3)nc2)ccc1C#N] |

| Ex. No. | IUPAC NAME |
|---|---|
| 210 | 2-(((S)-1-(1H-tetrazol-1-yl)propan-2-yl)oxy)-4-(2-((1-((1r,4r)-4-((2S,6R)-2,6-dimethylmorpholino)cyclohexyl)-3-(2-(1-hydroxycyclobutyl)ethoxy)-1H-pyrazol-4-yl)amino)pyrimidin-5-yl)benzonitrile |
| 211 | 2-(((S)-1-(1H-tetrazol-1-yl)propan-2-yl)oxy)-4-(2-((1-((1r,4r)-4-((1R,5S)-3-oxa-8-azabicyclo[3.2.1]octan-8-yl)cyclohexyl)-3-(cyanomethoxy)-1H-pyrazol-4-yl)amino)pyrimidin-5-yl)benzonitrile |
| 212 | 2-(((S)-1-(1H-tetrazol-1-yl)propan-2-yl)oxy)-4-(2-((3-(cyanomethyl)-1-((1r,4r)-4-((2S,6R)-2,6-dimethylmorpholino)cyclohexyl)-1H-pyrazol-4-yl)amino)pyrimidin-5-yl)benzonitrile |

TABLE 2-continued

| Ex. No. | IUPAC NAME | STRUCTURE |
|---|---|---|
| 213 | 2-(((S)-1-(1H-tetrazol-1-yl)propan-2-yl)oxy)-4-(2-((1-((1r,4r)-4-((1R,5S)-3-oxa-8-azabicyclo[3.2.1]octan-8-yl)cyclohexyl)-3-(2-cyanoethoxy)-1H-pyrazol-4-yl)amino)pyrimidin-5-yl)benzonitrile | 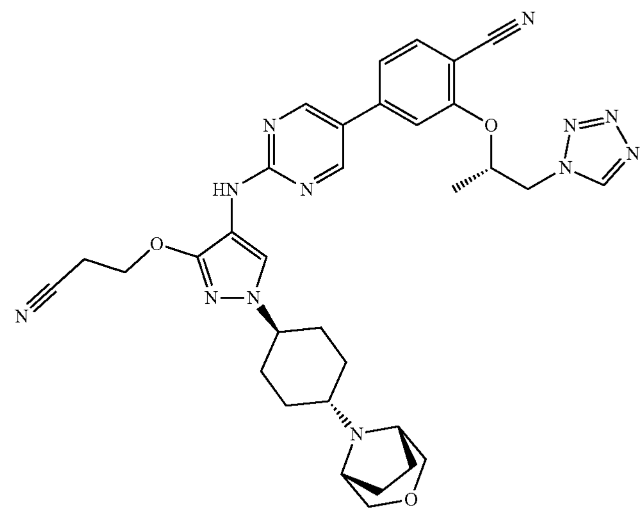 [SMILES: C[C@@H](Cn1cnnn1)Oc1cc(-c2cnc(Nc3cn([C@H]4CC[C@H](N5[C@@H]6CC[C@H]5COC6)CC4)nc3OCCC#N)nc2)ccc1C#N] |
| 214 | 2-(((S)-1-(1H-tetrazol-1-yl)propan-2-yl)oxy)-4-(2-((3-(2-cyanoethoxy)-1-((1r,4r)-4-((2S,6R)-2,6-dimethylmorpholino)cyclohexyl)-1H-pyrazol-4-yl)amino)pyrimidin-5-yl)benzonitrile | 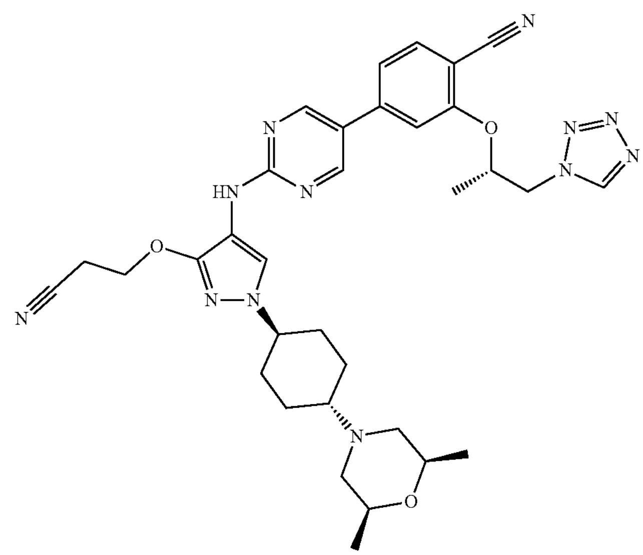 [SMILES: C[C@@H]1CN([C@H]2CC[C@H](n3cc(Nc4ncc(-c5ccc(C#N)c(O[C@@H](C)Cn6cnnn6)c5)cn4)c(OCCC#N)n3)CC2)C[C@H](C)O1] |
| 215 | 2-(((S)-1-(1H-tetrazol-1-yl)propan-2-yl)oxy)-4-(2-((1-((1r,4r)-4-((1R,5S)-3-oxa-8-azabicyclo[3.2.1]octan-8-yl)cyclohexyl)-3-(3-cyanopropoxy)-1H-pyrazol-4-yl)amino)pyrimidin-5-yl)benzonitrile | 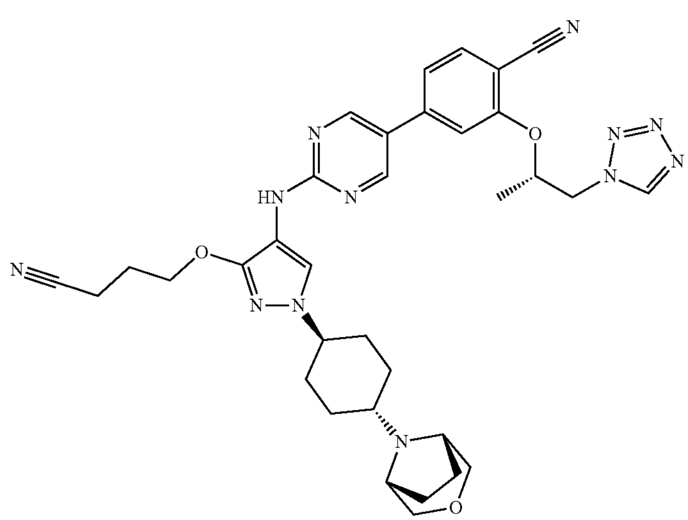 [SMILES: C[C@@H](Cn1cnnn1)Oc1cc(-c2cnc(Nc3cn([C@H]4CC[C@H](N5[C@@H]6CC[C@H]5COC6)CC4)nc3OCCCC#N)nc2)ccc1C#N] |

TABLE 2-continued

| Ex. No. | IUPAC NAME | STRUCTURE |
|---|---|---|
| 216 | 2-(((S)-1-(1H-tetrazol-1-yl)propan-2-yl)oxy)-4-(2-((3-(3-cyanopropoxy)-1-((1r,4r)-4-((2S,6R)-2,6-dimethylmorpholino)cyclohexyl)-1H-pyrazol-4-yl)amino)pyrimidin-5-yl)benzonitrile | 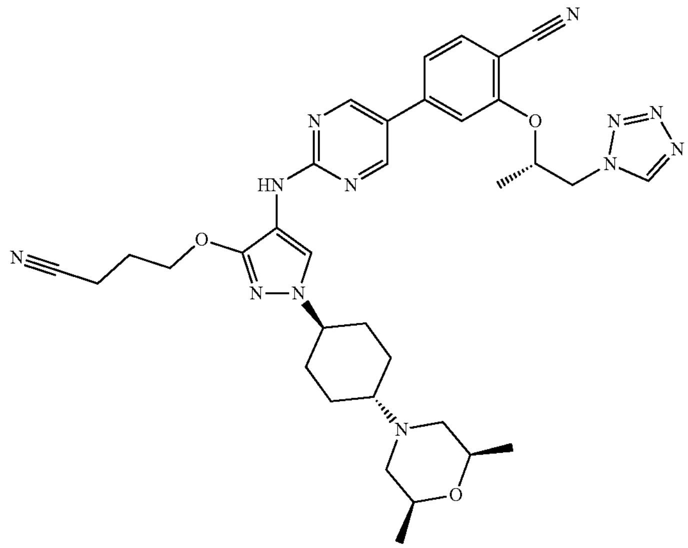 [SMILES: C[C@@H]1CN([C@H]2CC[C@H](n3cc(Nc4ncc(-c5ccc(C#N)c(O[C@@H](C)Cn6cnnn6)c5)cn4)c(OCCCC#N)n3)CC2)C[C@H](C)O1] |
| 217 | 2-(((S)-1-(1H-tetrazol-1-yl)propan-2-yl)oxy)-4-(2-((1-((1r,4r)-4-((1R,5S)-3-oxa-8-azabicyclo[3.2.1]octan-8-yl)cyclohexyl)-3-(oxazol-2-ylmethoxy)-1H-pyrazol-4-yl)amino)pyrimidin-4-yl)benzonitrile | 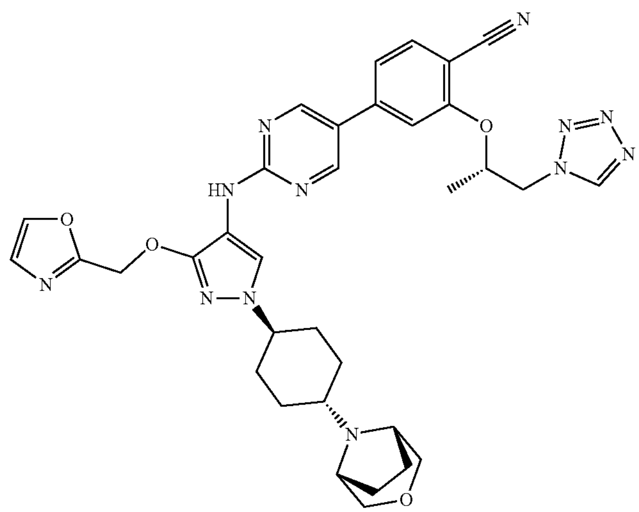 [SMILES: C[C@@H](Cn1cnnn1)Oc1cc(-c2cnc(Nc3cn([C@H]4CC[C@H](N5[C@@H]6CC[C@H]5COC6)CC4)nc3OCc3nccs3)nc2)ccc1C#N] |
| 218 | 5-(3-(((S)-1-(1H-tetrazol-1-yl)propan-2-yl)oxy)-4-chlorophenyl)-N-(1-((1r,4r)-4-((1R,5S)-3-oxa-8-azabicyclo[3.2.1]octan-8-yl)cyclohexyl)-3-(oxazol-2-ylmethoxy)-1H-pyrazol-4-yl)pyrimidin-2-amine | 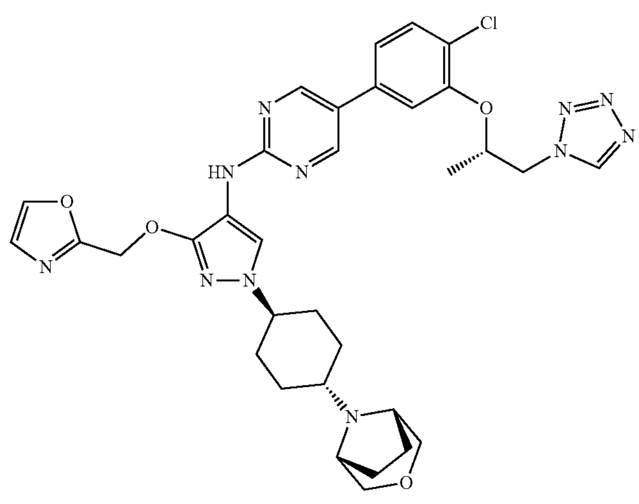 [SMILES: C[C@@H](Cn1cnnn1)Oc1cc(-c2cnc(Nc3cn([C@H]4CC[C@H](N5[C@@H]6CC[C@H]5COC6)CC4)nc3OCc3nccs3)nc2)ccc1Cl] |

TABLE 2-continued

| Ex. No. | IUPAC NAME | STRUCTURE |
|---|---|---|
| 219 | 2-(((S)-1-(1H-tetrazol-1-yl)propan-2-yl)oxy)-4-(2-((1-((1r,4r)-4-((2S,6R)-2,6-dimethylmorpholino)cyclohexyl)-3-(oxazol-2-ylmethoxy)-1H-pyrazol-4-yl)amino)pyrimidin-5-yl)benzonitrile | 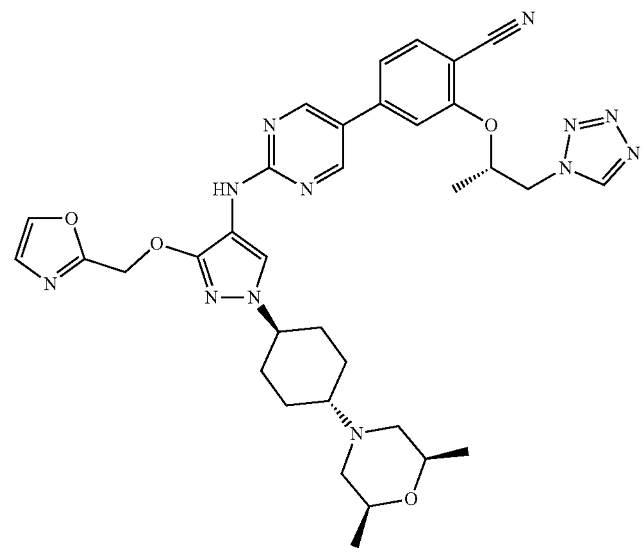 [SMILES: C[C@@H]1CN([C@H]2CC[C@H](n3cc(Nc4ncc(-c5ccc(C#N)c(O[C@@H](C)Cn6cnnn6)c5)cn4)c(OCc4nccs4)n3)CC2)C[C@H](C)O1] |
| 220 | 5-(3-(((S)-1-(1H-tetrazol-1-yl)propan-2-yl)oxy)-4-chlorophenyl)-N-(1-((1r,4r)-4-((2S,6R)-2,6-dimethylmorpholino)cyclohexyl)-3-(oxazol-2-ylmethoxy)-1H-pyrazol-4-yl)pyrimidin-2-amine | 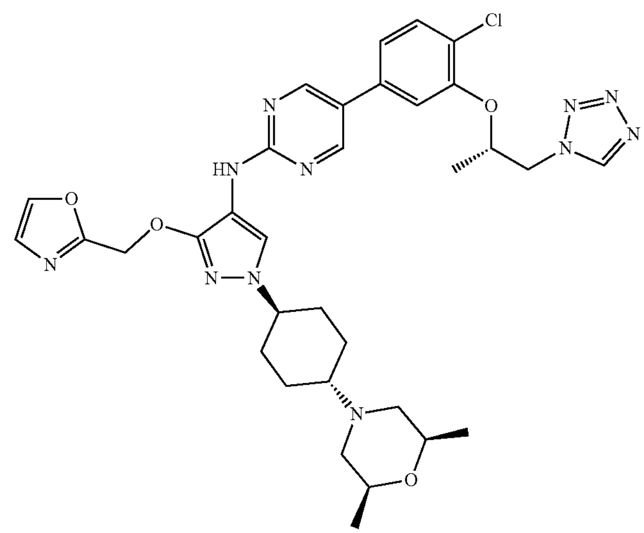 [SMILES: C[C@@H]1CN([C@H]2CC[C@H](n3cc(Nc4ncc(-c5ccc(Cl)c(O[C@@H](C)Cn6cnnn6)c5)cn4)c(OCc4nccs4)n3)CC2)C[C@H](C)O1] |
| 221 | 2-(((S)-1-(1H-tetrazol-1-yl)propan-2-yl)oxy)-4-(2-((1-((1r,4r)-4-((1R,5S)-3-oxa-8-azabicyclo[3.2.1]octan-8-yl)cyclohexyl)-3-(thiazol-2-ylmethoxy)-1H-pyrazol-4-yl)amino)pyrimidin-4-yl)benzonitrile | 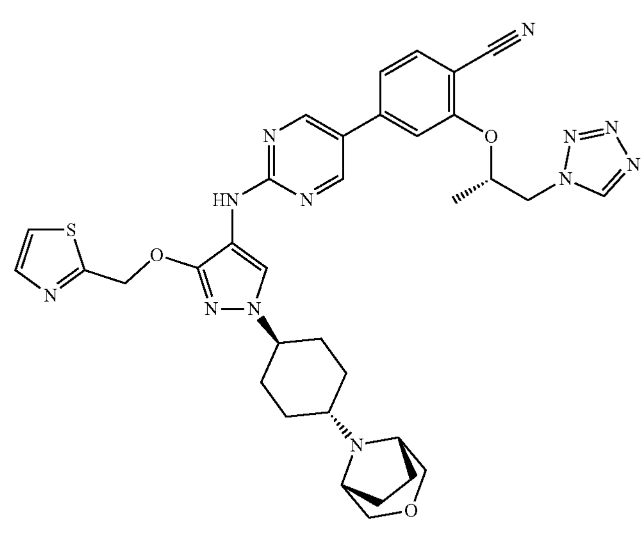 |

| Ex. No. | IUPAC NAME |
|---|---|
| 222 | 5-(3-(((S)-1-(1H-tetrazol-1-yl)propan-2-yl)oxy)-4-chlorophenyl)-N-(1-((1r,4r)-4-((1R,5S)-3-oxa-8-azabicyclo[3.2.1]octan-8-yl)cyclohexyl)-3-(thiazol-2-ylmethoxy)-1H-pyrazol-4-yl)pyrimidin-2-amine |
| 223 | 2-(((S)-1-(1H-tetrazol-1-yl)propan-2-yl)oxy)-4-(2-((1-((1r,4r)-4-((2S,6R)-2,6-dimethylmorpholino)cyclohexyl)-3-(thiazol-2-ylmethoxy)-1H-pyrazol-4-yl)amino)pyrimidin-5-yl)benzonitrile |
| 224 | 5-(3-(((S)-1-(1H-tetrazol-1-yl)propan-2-yl)oxy)-4-chlorophenyl)-N-(1-((1r,4r)-4-((2S,6R)-2,6-dimethylmorpholino)cyclohexyl)-3-(thiazol-2-ylmethoxy)-1H-pyrazol-4-yl)pyrimidin-2-amine |

TABLE 2-continued

| Ex. No. | IUPAC NAME | STRUCTURE |
| --- | --- | --- |
| 225 | 2-(((S)-1-(1H-tetrazol-1-yl)propan-2-yl)oxy)-4-(2-((1-((1r,4r)-4-((1R,5S)-3-oxa-8-azabicyclo[3.2.1]octan-8-yl)cyclohexyl)-3-((1-methyl-1H-pyrazol-5-yl)methoxy)-1H-pyrazol-4-yl)amino)pyrimidin-5-yl)benzonitrile | 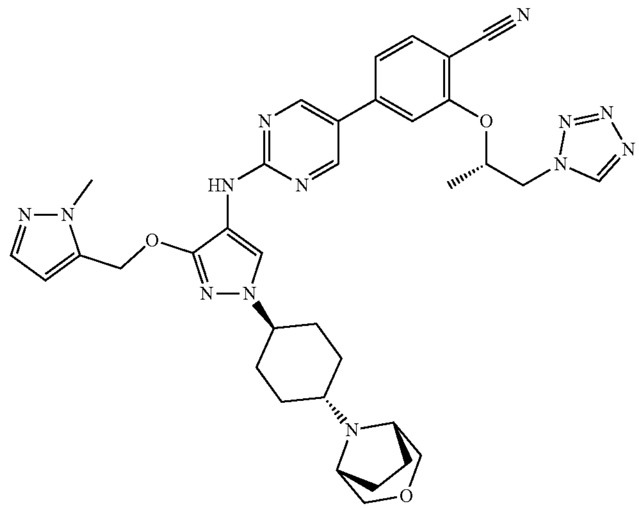 [SMILES: C[C@@H](Cn1cnnn1)Oc1cc(-c2cnc(Nc3cn([C@H]4CC[C@H](N5[C@@H]6CC[C@H]5COC6)CC4)nc3OCc3ccnn3C)nc2)ccc1C#N] |
| 226 | 5-(3-(((S)-1-(1H-tetrazol-1-yl)propan-2-yl)oxy)-4-chlorophenyl)-N-(1-((1r,4r)-4-((1R,5S)-3-oxa-8-azabicyclo[3.2.1]octan-8-yl)cyclohexyl)-3-((1-methyl-1H-pyrazol-5-yl)methoxy)-1H-pyrazol-4-yl)pyrimidin-2-amine | 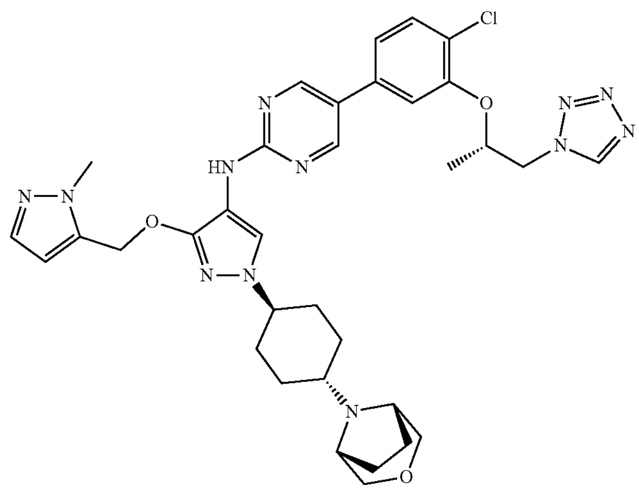 [SMILES: C[C@@H](Cn1cnnn1)Oc1cc(-c2cnc(Nc3cn([C@H]4CC[C@H](N5[C@@H]6CC[C@H]5COC6)CC4)nc3OCc3ccnn3C)nc2)ccc1Cl] |
| 227 | 2-(((S)-1-(1H-tetrazol-1-yl)propan-2-yl)oxy)-4-(2-((1-((1r,4r)-4-((2S,6R)-2,6-dimethylmorpholino)cyclohexyl)-3-((1-methyl-1H-pyrazol-5-yl)methoxy)-1H-pyrazol-4-yl)amino)pyrimidin-5-yl)benzonitrile | 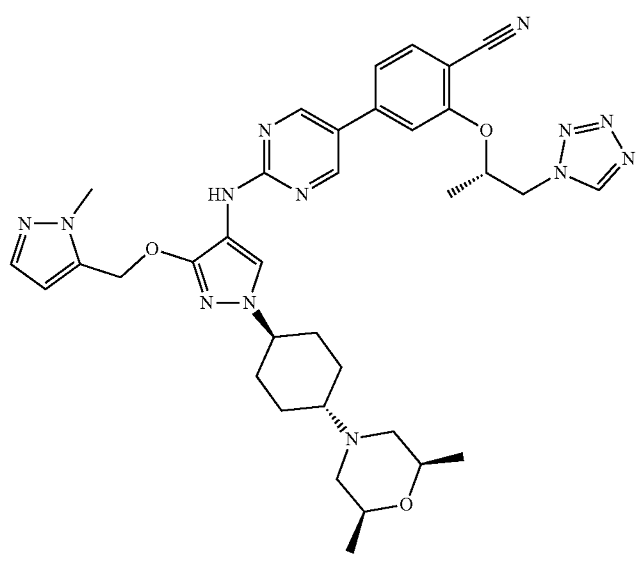 [SMILES: C[C@@H]1CN([C@H]2CC[C@H](n3cc(Nc4ncc(-c5ccc(C#N)c(O[C@@H](C)Cn6cnnn6)c5)cn4)c(OCc4ccnn4C)n3)CC2)C[C@H](C)O1] |

| Ex. No. | IUPAC NAME | STRUCTURE |
| --- | --- | --- |
| 228 | 5-(3-(((S)-1-(1H-tetrazol-1-yl)propan-2-yl)oxy)-4-chlorophenyl)-N-(1-((1r,4r)-4-((2S,6R)-2,6-dimethylmorpholino)cyclohexyl)-3-((1-methyl-1H-pyrazol-5-yl)methoxy)-1H-pyrazol-4-yl)pyrimidin-2-amine | 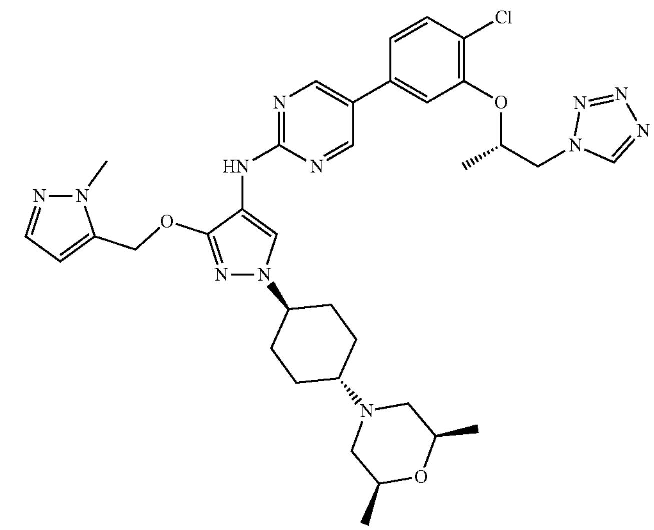 [SMILES: C[C@@H]1CN([C@H]2CC[C@H](n3cc(Nc4ncc(-c5ccc(Cl)c(O[C@@H](C)Cn6cnnn6)c5)cn4)c(OCc4ccnn4C)n3)CC2)C[C@H](C)O1] |
| 229 | 4-(2-((3-(2-(1H-pyrazol-1-yl)ethoxy)-1-((1r,4r)-4-((1R,5S)-3-oxa-8-azabicyclo[3.2.1]octan-8-yl)cyclohexyl)-1H-pyrazol-4-yl)amino)pyrimidin-5-yl)-2-(((S)-1-(1H-tetrazol-1-yl)propan-2-yl)oxy)benzonitrile | 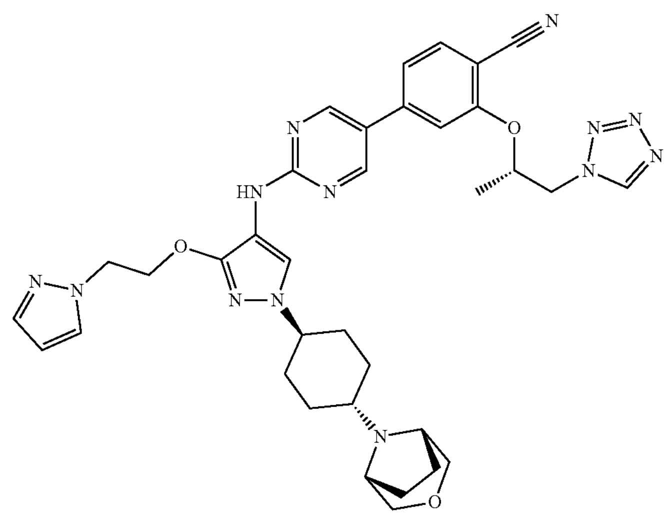 [SMILES: C[C@@H](Cn1cnnn1)Oc1cc(-c2cnc(Nc3cn([C@H]4CC[C@H](N5[C@@H]6CC[C@H]5COC6)CC4)nc3OCCn3cccn3)nc2)ccc1C#N] |
| 230 | N-(3-(2-(1H-pyrazol-1-yl)ethoxy)-1-((1r,4r)-4-((1R,5S)-3-oxa-8-azabicyclo[3.2.1]octan-8-yl)cyclohexyl)-1H-pyrazol-4-yl)-5-(3-(((S)-1-(1H-tetrazol-1-yl)propan-2-yl)oxy)-4-chlorophenyl)pyrimidin-2-amine | 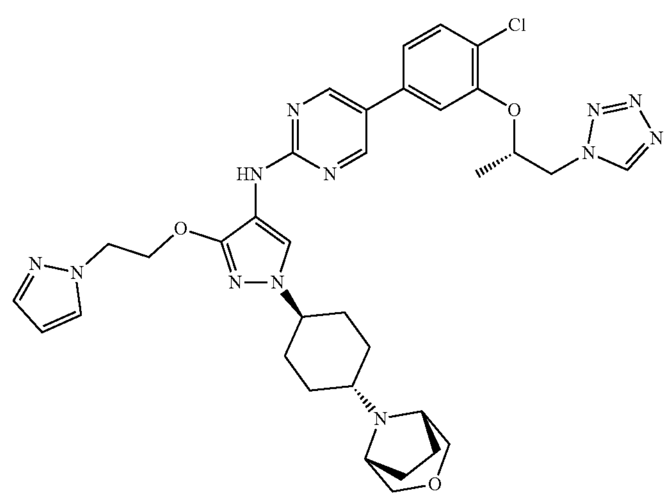 [SMILES: C[C@@H](Cn1cnnn1)Oc1cc(-c2cnc(Nc3cn([C@H]4CC[C@H](N5[C@@H]6CC[C@H]5COC6)CC4)nc3OCCn3cccn3)nc2)ccc1Cl] |

TABLE 2-continued

| Ex. No. | IUPAC NAME | STRUCTURE |
|---|---|---|
| 231 | 4-(2-((3-(2-(1H-pyrazol-1-yl)ethoxy)-1-((1r,4r)-4-((2S,6R)-2,6-dimethylmorpholino)cyclohexyl)-1H-pyrazol-4-yl)amino)pyrimidin-5-yl)-2-(((S)-1-(1H-tetrazol-1-yl)propan-2-yl)oxy)benzonitrile | 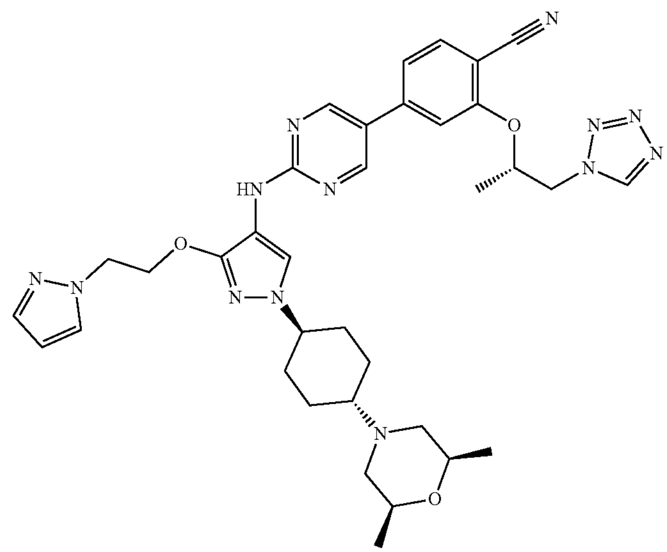 [SMILES: C[C@@H]1CN([C@H]2CC[C@H](n3cc(Nc4ncc(-c5ccc(C#N)c(O[C@@H](C)Cn6cnnn6)c5)cn4)c(OCCn4cccn4)n3)CC2)C[C@H](C)O1] |
| 232 | N-(3-(2-(1H-pyrazol-1-yl)ethoxy)-1-((1r,4r)-4-((2S,6R)-2,6-dimethylmorpholino)cyclohexyl)-1H-pyrazol-4-yl)-5-(3-(((S)-1-(1H-tetrazol-1-yl)propan-2-yl)oxy)-4-chlorophenyl)pyrimidin-2-amine | 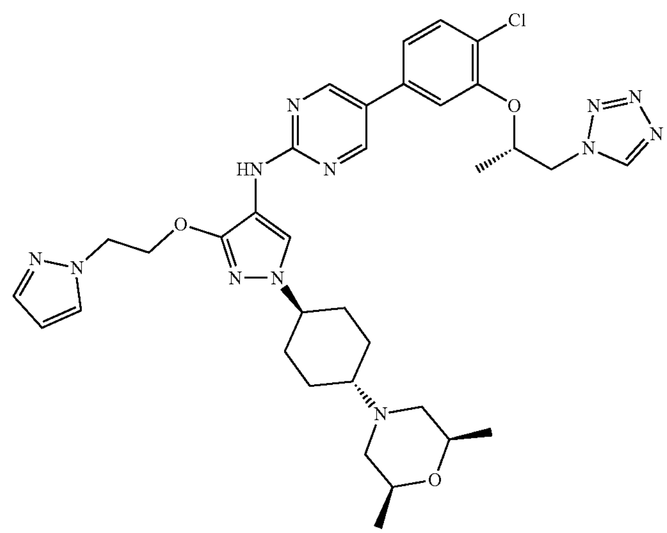 [SMILES: C[C@@H]1CN([C@H]2CC[C@H](n3cc(Nc4ncc(-c5ccc(Cl)c(O[C@@H](C)Cn6cnnn6)c5)cn4)c(OCCn4cccn4)n3)CC2)C[C@H](C)O1] |
| 233 | 2-(((S)-1-(1H-tetrazol-1-yl)propan-2-yl)oxy)-4-(2-((1-((1r,4r)-4-((1R,5S)-3-oxa-8-azabicyclo[3.2.1]octan-8-yl)cyclohexyl)-3-(pyridin-2-ylmethoxy)-1H-pyrazol-4-yl)amino)pyrimidin-5-yl)benzonitrile | 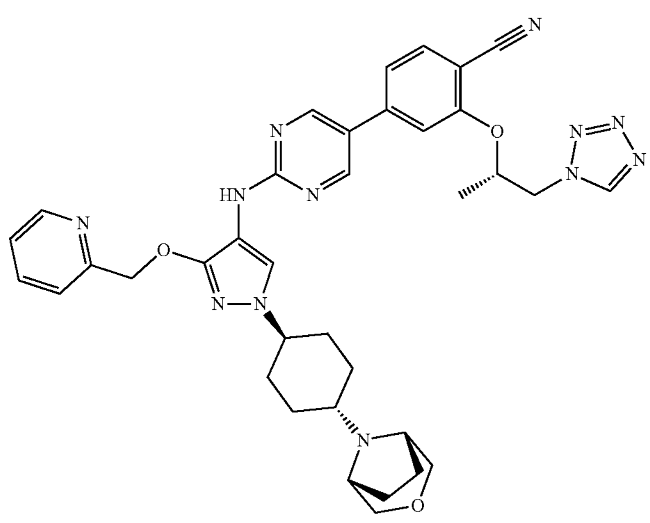 [SMILES: C[C@@H](Cn1cnnn1)Oc1cc(-c2cnc(Nc3cn([C@H]4CC[C@H](N5[C@@H]6CC[C@H]5COC6)CC4)nc3OCc3ccccn3)nc2)ccc1C#N] |

TABLE 2-continued

| Ex. No. | IUPAC NAME | STRUCTURE |
|---|---|---|
| 234 | 5-(3-(((S)-1-(1H-tetrazol-1-yl)propan-2-yl)oxy)-4-chlorophenyl)-N-(1-((1r,4r)-4-((1R,5S)-3-oxa-8-azabicyclo[3.2.1]octan-8-yl)cyclohexyl)-3-(pyridin-2-ylmethoxy)-1H-pyrazol-4-yl)pyrimidin-2-amine | 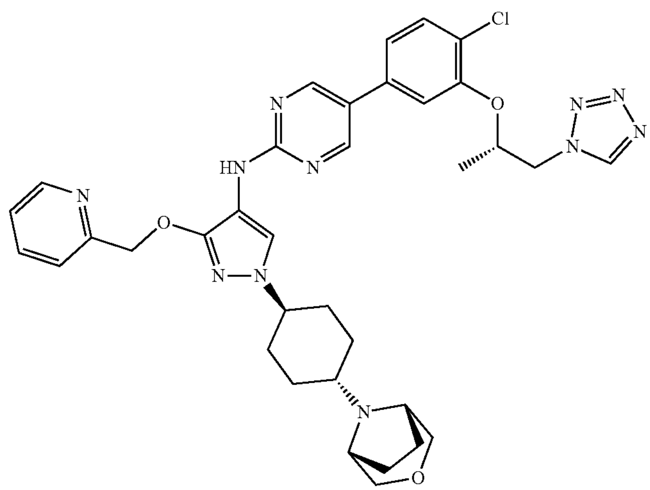 [SMILES: C[C@@H](Cn1cnnn1)Oc1cc(-c2cnc(Nc3cn([C@H]4CC[C@H](N5[C@@H]6CC[C@H]5COC6)CC4)nc3OCc3ccccn3)nc2)ccc1Cl] |
| 235 | 2-(((S)-1-(1H-tetrazol-1-yl)propan-2-yl)oxy)-4-(2-((1-((1r,4r)-4-((2S,6R)-2,6-dimethylmorpholino)cyclohexyl)-3-(pyridin-2-ylmethoxy)-1H-pyrazol-4-yl)amino)pyrimidin-5-yl)benzonitrile | 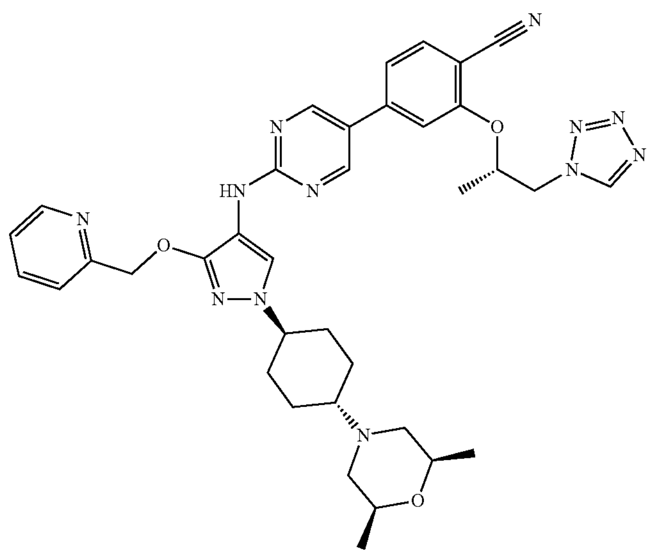 [SMILES: C[C@@H]1CN([C@H]2CC[C@H](n3cc(Nc4ncc(-c5ccc(C#N)c(O[C@@H](C)Cn6cnnn6)c5)cn4)c(OCc4ccccn4)n3)CC2)C[C@H](C)O1] |
| 236 | 5-(3-(((S)-1-(1H-tetrazol-1-yl)propan-2-yl)oxy)-4-chlorophenyl)-N-(1-((1r,4r)-4-((2S,6R)-2,6-dimethylmorpholino)cyclohexyl)-3-(pyridin-2-ylmethoxy)-1H-pyrazol-4-yl)pyrimidin-2-amine | 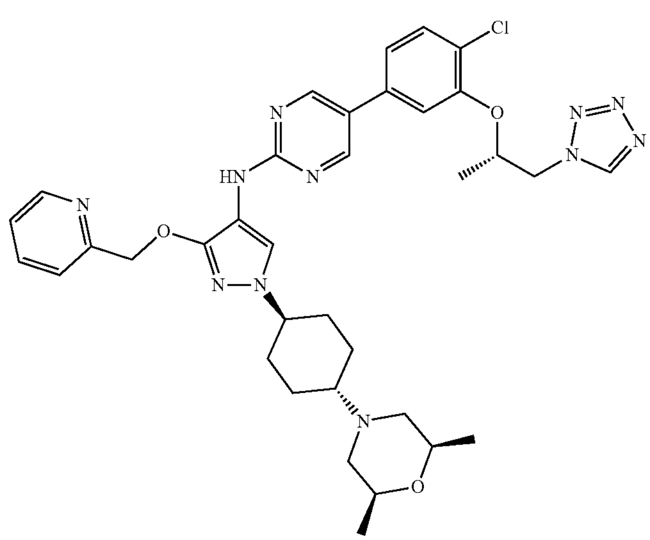 [SMILES: C[C@@H]1CN([C@H]2CC[C@H](n3cc(Nc4ncc(-c5ccc(Cl)c(O[C@@H](C)Cn6cnnn6)c5)cn4)c(OCc4ccccn4)n3)CC2)C[C@H](C)O1] |

TABLE 2-continued

| Ex. No. | IUPAC NAME | STRUCTURE |
| --- | --- | --- |
| 237 | 2-(((S)-1-(1H-tetrazol-1-yl)propan-2-yl)oxy)-4-(2-((1-((1r,4r)-4-((1R,5S)-3-oxa-8-azabicyclo[3.2.1]octan-8-yl)cyclohexyl)-3-(pyrimidin-2-ylmethoxy)-1H-pyrazol-4-yl)amino)pyrimidin-5-yl)benzonitrile | 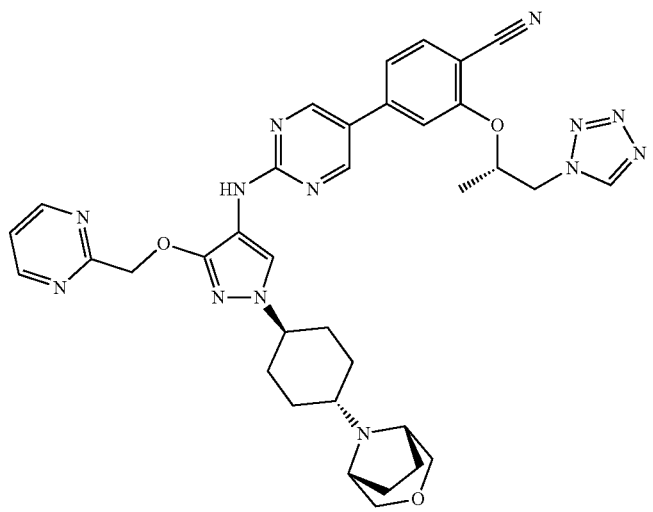 [SMILES: C[C@@H](Cn1cnnn1)Oc1cc(-c2cnc(Nc3cn([C@H]4CC[C@H](N5[C@@H]6CC[C@H]5COC6)CC4)nc3OCc3ncccn3)nc2)ccc1C#N] |
| 238 | 2-(((S)-1-(1H-tetrazol-1-yl)propan-2-yl)oxy)-4-(2-((1-((1r,4r)-4-((2S,6R)-2,6-dimethylmorpholino)cyclohexyl)-3-(pyrimidin-2-ylmethoxy)-1H-pyrazol-4-yl)amino)pyrimidin-5-yl)benzonitrile | 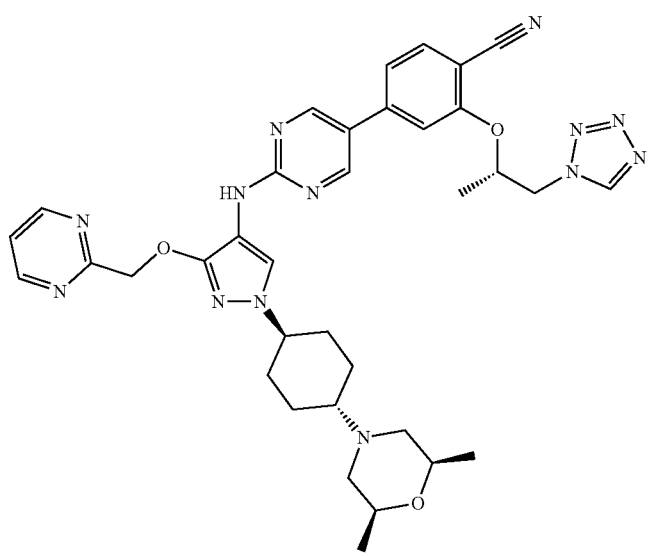 [SMILES: C[C@@H]1CN([C@H]2CC[C@H](n3cc(Nc4ncc(-c5ccc(C#N)c(O[C@@H](C)Cn6cnnn6)c5)cn4)c(OCc4ncccn4)n3)CC2)C[C@H](C)O1] |
| 239 | 5-(3-(((S)-1-(1H-tetrazol-1-yl)propan-2-yl)oxy)-4-chlorophenyl)-N-(1-((1r,4r)-4-((2S,6R)-2,6-dimethylmorpholino)cyclohexyl)-3-(pyrimidin-2-ylmethoxy)-1H-pyrazol-4-yl)pyrimidin-2-amine | 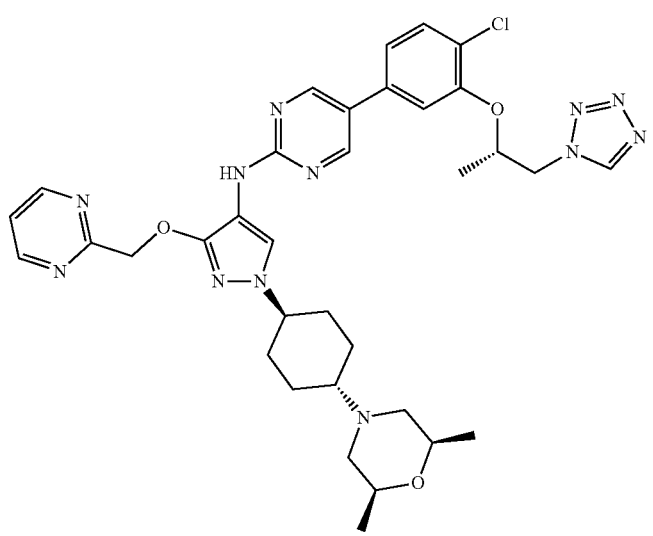 [SMILES: C[C@@H]1CN([C@H]2CC[C@H](n3cc(Nc4ncc(-c5ccc(Cl)c(O[C@@H](C)Cn6cnnn6)c5)cn4)c(OCc4ncccn4)n3)CC2)C[C@H](C)O1] |

TABLE 2-continued

| Ex. No. | IUPAC NAME | STRUCTURE |
|---|---|---|
| 245 | 2-(((S)-1-(1H-tetrazol-1-yl)propan-2-yl)oxy)-4-(2-((3-(2,2-difluoro-3-methoxypropoxy)-1-((1r,4r)-4-morpholinocyclohexyl)-1H-pyrazol-4-yl)amino)pyrimidin-5-yl)benzonitrile | 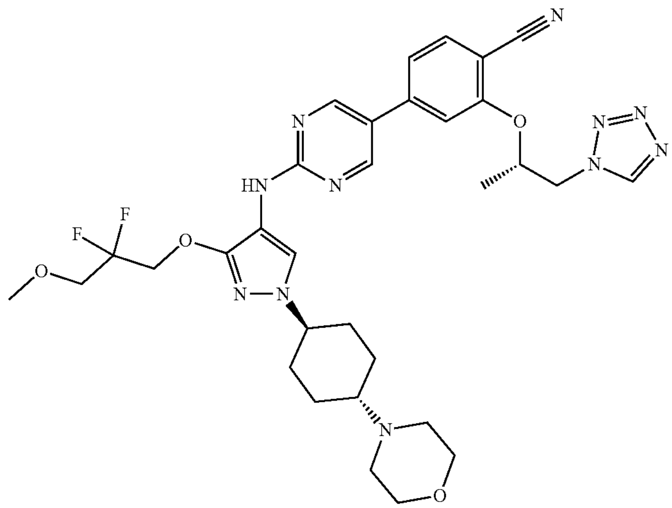 [SMILES: COCC(F)(F)COc1nn([C@H]2CC[C@H](N3CCOCC3)CC2)cc1Nc1ncc(-c2ccc(C#N)c(O[C@@H](C)Cn3cnnn3)c2)cn1] |
| 246 | 5-(3-(((S)-1-(1H-tetrazol-1-yl)propan-2-yl)oxy)-4-chlorophenyl)-N-(3-(2,2-difluoro-3-methoxypropoxy)-1-((1r,4r)-4-morpholinocyclohexyl)-1H-pyrazol-4-yl)pyrimidin-2-amine | 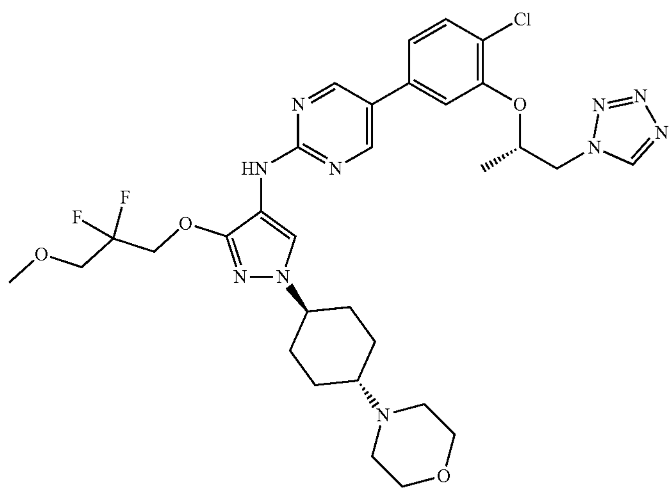 |
| 247 | 2-(((S)-1-(1H-1,2,4-triazol-1-yl)propan-2-yl)oxy)-4-(2-((3-(2,2-difluoro-3-methoxypropoxy)-1-((1r,4r)-4-morpholinocyclohexyl)-1H-pyrazol-4-yl)amino)pyrimidin-5-yl)benzonitrile | 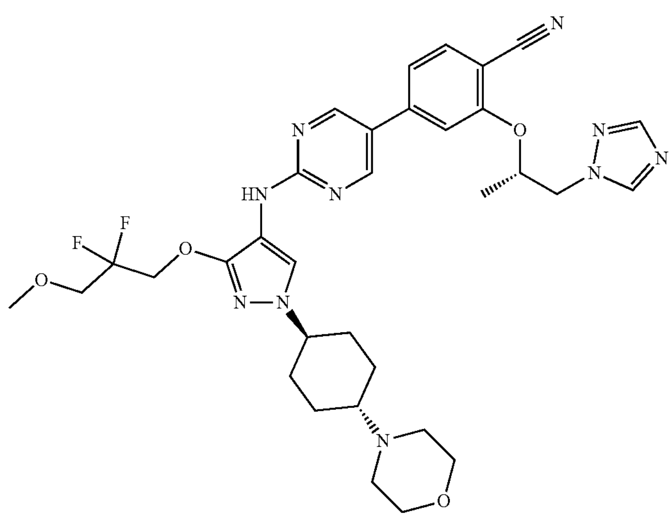 [SMILES: COCC(F)(F)COc1nn([C@H]2CC[C@H](N3CCOCC3)CC2)cc1Nc1ncc(-c2ccc(C#N)c(O[C@@H](C)Cn3cncn3)c2)cn1] |

| Ex. No. | IUPAC NAME |
|---|---|
| 248 | 5-(3-(((S)-1-(1H-1,2,4-triazol-1-yl)propan-2-yl)oxy)-4-chlorophenyl)-N-(3-(2,2-difluoro-3-methoxypropoxy)-1-((1r,4r)-4-morpholinocyclohexyl)-1H-pyrazol-4-yl)pyrimidin-2-amine |
| 249 | 2-(((S)-1-(1H-tetrazol-1-yl)propan-2-yl)oxy)-4-(2-((1-((1r,4r)-4-((1R,5S)-3-oxa-8-azabicyclo[3.2.1]octan-8-yl)cyclohexyl)-3-(2,2-difluoro-3-methoxypropoxy)-1H-pyrazol-4-yl)amino)pyrimidin-5-yl)benzonitrile |
| 250 | 5-(3-(((S)-1-(1H-tetrazol-1-yl)propan-2-yl)oxy)-4-chlorophenyl)-N-(1-((1r,4r)-4-((1R,5S)-3-oxa-8-azabicyclo[3.2.1]octan-8-yl)cyclohexyl)-3-(2,2-difluoro-3-methoxypropoxy)-1H-pyrazol-4-yl)pyrimidin-2-amine |

TABLE 2-continued

| Ex. No. | IUPAC NAME | STRUCTURE |
| --- | --- | --- |
| 251 | 2-(((S)-1-(1H-1,2,4-triazol-1-yl)propan-2-yl)oxy)-4-(2-((1-((1r,4r)-4-((1R,5S)-3-oxa-8-azabicyclo[3.2.1]octan-8-yl)cyclohexyl)-3-(2,2-difluoro-3-methoxypropoxy)-1H-pyrazol-4-yl)amino)pyrimidin-5-yl)benzonitrile | 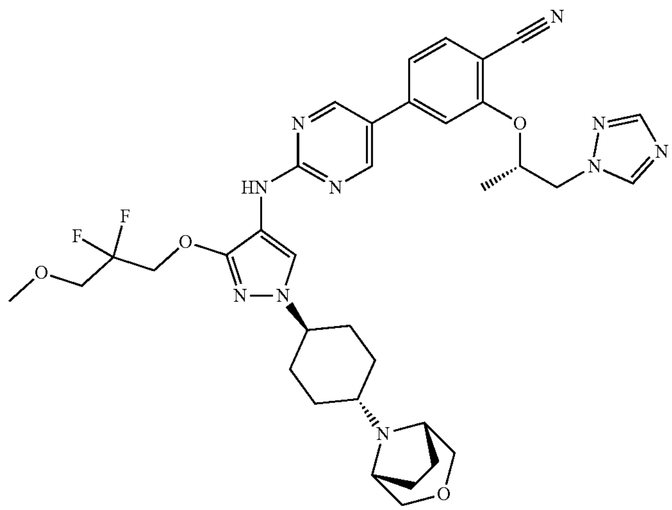 [SMILES: COCC(F)(F)COc1nn([C@H]2CC[C@H](N3[C@@H]4CC[C@H]3COC4)CC2)cc1Nc1ncc(-c2ccc(C#N)c(O[C@@H](C)Cn3cncn3)c2)cn1] |
| 252 | 5-(3-(((S)-1-(1H-1,2,4-triazol-1-yl)propan-2-yl)oxy)-4-chlorophenyl)-N-(1-((1r,4r)-4-((1R,5S)-3-oxa-8-azabicyclo[3.2.1]octan-8-yl)cyclohexyl)-3-(2,2-difluoro-3-methoxypropoxy)-1H-pyrazol-4-yl)pyrimidin-2-amine | 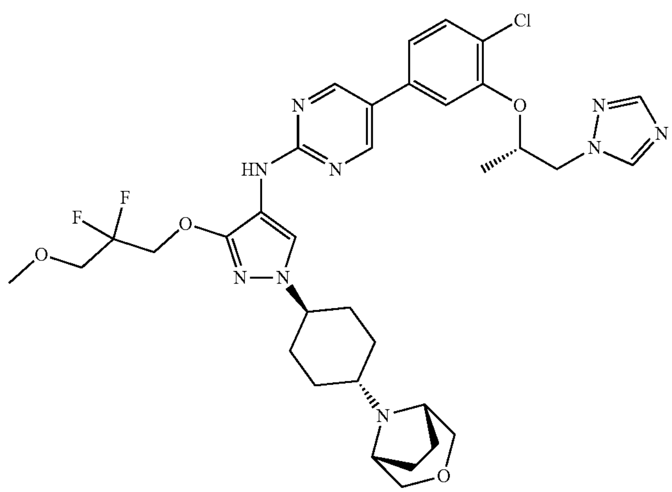 [SMILES: COCC(F)(F)COc1nn([C@H]2CC[C@H](N3[C@@H]4CC[C@H]3COC4)CC2)cc1Nc1ncc(-c2ccc(Cl)c(O[C@@H](C)Cn3cncn3)c2)cn1] |
| 253 | 2-(((S)-1-(1H-tetrazol-1-yl)propan-2-yl)oxy)-4-(2-((3-(2,2-difluoro-3-methoxypropoxy)-1-((1r,4r)-4-((2S,6R)-2,6-dimethylmorpholino)cyclohexyl)-1H-pyrazol-4-yl)amino)pyrimidin-5-yl)benzonitrile | 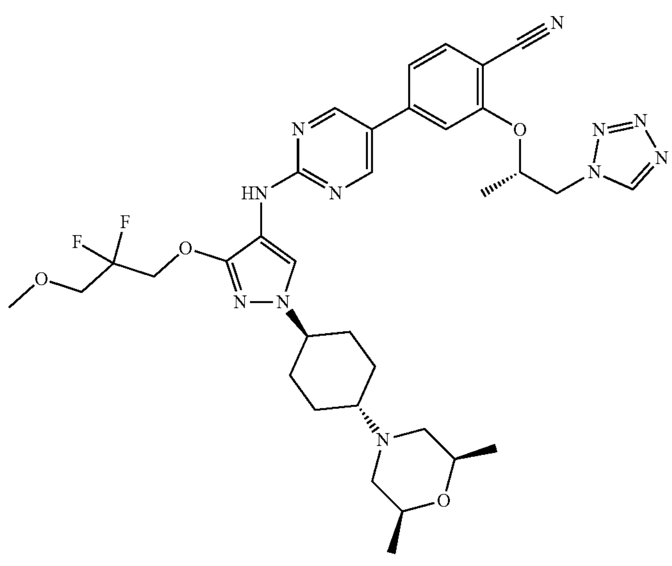 [SMILES: COCC(F)(F)COc1nn([C@H]2CC[C@H](N3C[C@@H](C)O[C@@H](C)C3)CC2)cc1Nc1ncc(-c2ccc(C#N)c(O[C@@H](C)Cn3cnnn3)c2)cn1] |

TABLE 2-continued

| Ex. No. | IUPAC NAME | STRUCTURE |
|---|---|---|
| 254 | 5-(3-(((S)-1-(1H-tetrazol-1-yl)propan-2-yl)oxy)-4-chlorophenyl)-N-(3-(2,2-difluoro-3-methoxypropoxy)-1-((1r,4r)-4-((2S,6R)-2,6-dimethylmorpholino)cyclohexyl)-1H-pyrazol-4-yl)pyrimidin-2-amine | 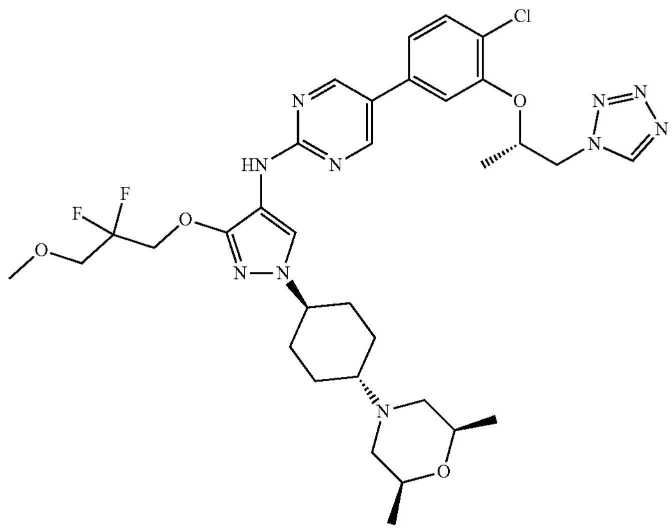 [SMILES: COCC(F)(F)COc1nn([C@H]2CC[C@H](N3C[C@@H](C)O[C@@H](C)C3)CC2)cc1Nc1ncc(-c2ccc(Cl)c(O[C@@H](C)Cn3cnnn3)c2)cn1] |
| 255 | 2-(((S)-1-(1H-1,2,4-triazol-1-yl)propan-2-yl)oxy)-4-(2-((3-(2,2-difluoro-3-methoxypropoxy)-1-((1r,4r)-4-((2S,6R)-2,6-dimethylmorpholino)cyclohexyl)-1H-pyrazol-4-yl)amino)pyrimidin-5-yl)benzonitrile | 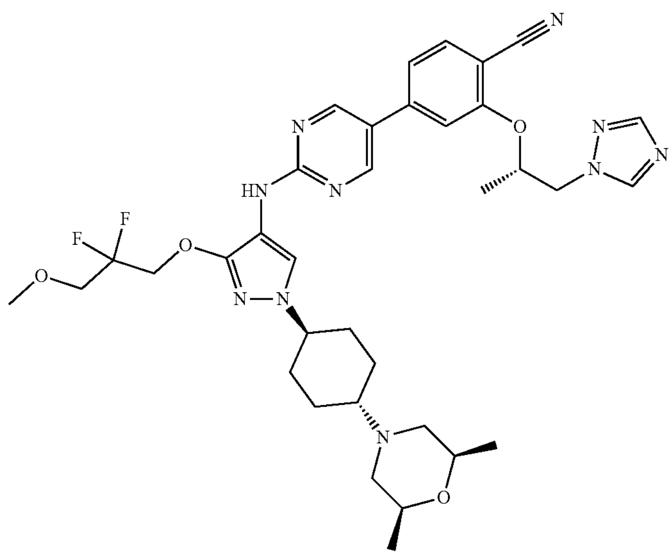 [SMILES: COCC(F)(F)COc1nn([C@H]2CC[C@H](N3C[C@@H](C)O[C@@H](C)C3)CC2)cc1Nc1ncc(-c2ccc(C#N)c(O[C@@H](C)Cn3cncn3)c2)cn1] |
| 256 | 5-(3-(((S)-1-(1H-1,2,4-triazol-1-yl)propan-2-yl)oxy)-4-chlorophenyl)-N-(3-(2,2-difluoro-3-methoxypropoxy)-1-((1r,4r)-4-((2S,6R)-2,6-dimethylmorpholino)cyclohexyl)-1H-pyrazol-4-yl)pyrimidin-2-amine | 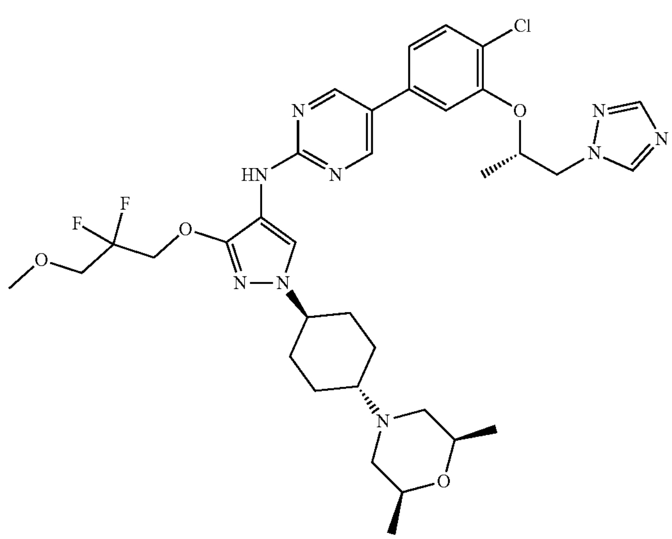 [SMILES: COCC(F)(F)COc1nn([C@H]2CC[C@H](N3C[C@@H](C)O[C@@H](C)C3)CC2)cc1Nc1ncc(-c2ccc(Cl)c(O[C@@H](C)Cn3cncn3)c2)cn1] |

TABLE 2-continued

| Ex. No. | IUPAC NAME | STRUCTURE |
| --- | --- | --- |
| 257 | 2-(((S)-1-(1H-tetrazol-1-yl)propan-2-yl)oxy)-4-(2-((3-(3-methoxy-2,2-dimethylpropoxy)-1-((1r,4r)-4-morpholinocyclohexyl)-1H-pyrazol-4-yl)amino)pyrimidin-5-yl)benzonitrile | 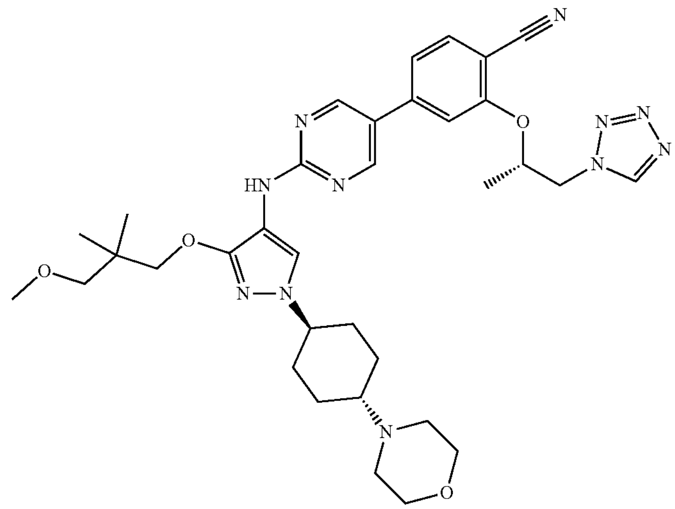 [SMILES: COCC(C)(C)COc1nn([C@H]2CC[C@H](N3CCOCC3)CC2)cc1Nc1ncc(-c2ccc(C#N)c(O[C@@H](C)Cn3cnnn3)c2)cn1] |
| 258 | 5-(3-(((S)-1-(1H-tetrazol-1-yl)propan-2-yl)oxy)-4-chlorophenyl)-N-(3-(3-methoxy-2,2-dimethylpropoxy)-1-((1r,4r)-4-morpholinocyclohexyl)-1H-pyrazol-4-yl)pyrimidin-2-amine | 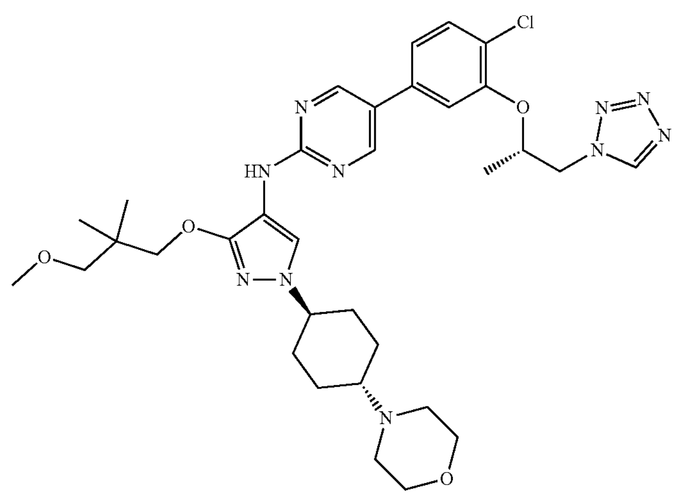 [SMILES: COCC(C)(C)COc1nn([C@H]2CC[C@H](N3CCOCC3)CC2)cc1Nc1ncc(-c2ccc(Cl)c(O[C@@H](C)Cn3cnnn3)c2)cn1] |
| 259 | 2-(((S)-1-(1H-1,2,4-triazol-1-yl)propan-2-yl)oxy)-4-(2-((3-(3-methoxy-2,2-dimethylpropoxy)-1-((1r,4r)-4-morpholinocyclohexyl)-1H-pyrazol-4-yl)amino)pyrimidin-5-yl)benzonitrile | 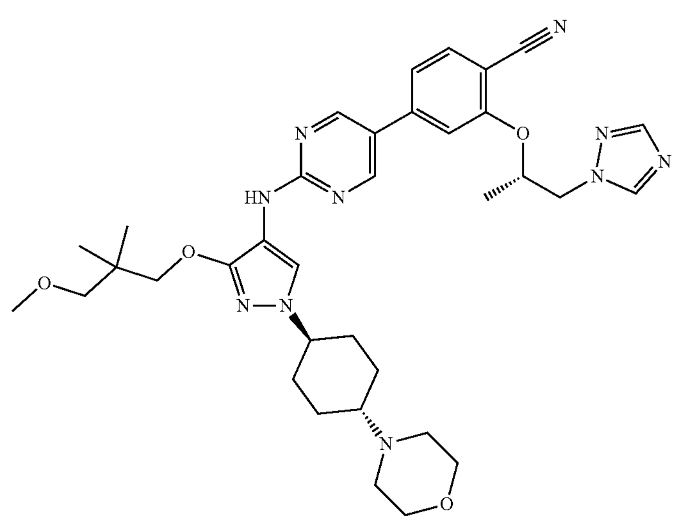 [SMILES: COCC(C)(C)COc1nn([C@H]2CC[C@H](N3CCOCC3)CC2)cc1Nc1ncc(-c2ccc(C#N)c(O[C@@H](C)Cn3cncn3)c2)cn1] |

TABLE 2-continued

| Ex. No. | IUPAC NAME | STRUCTURE |
|---|---|---|
| 260 | 5-(3-(((S)-1-(1H-1,2,4-triazol-1-yl)propan-2-yl)oxy)-4-chlorophenyl)-N-(3-(3-methoxy-2,2-dimethylpropoxy)-1-((1r,4r)-4-morpholinocyclohexyl)-1H-pyrazol-4-yl)pyrimidin-2-amine | 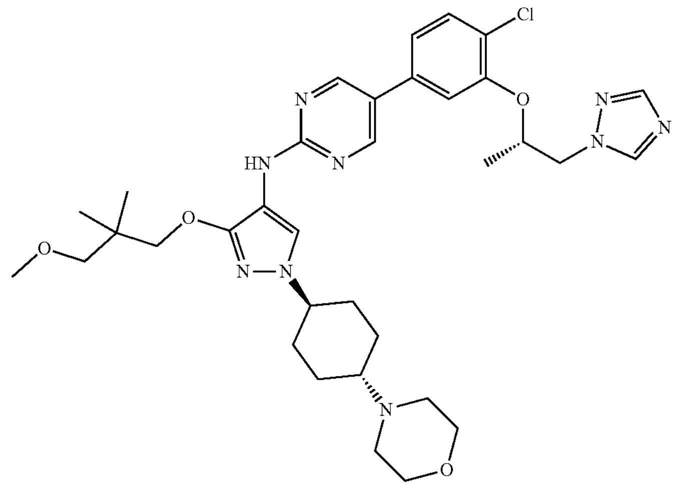 [SMILES: COCC(C)(C)COc1nn([C@H]2CC[C@H](N3CCOCC3)CC2)cc1Nc1ncc(-c2ccc(Cl)c(O[C@@H](C)Cn3cncn3)c2)cn1] |
| 261 | 2-(((S)-1-(1H-tetrazol-1-yl)propan-2-yl)oxy)-4-(2-((1-((1r,4r)-4-((1R,5S)-3-oxa-8-azabicyclo[3.2.1]octan-8-yl)cyclohexyl)-3-(3-methoxy-2,2-dimethylpropoxy)-1H-pyrazol-4-yl)amino)pyrimidin-5-yl)benzonitrile | 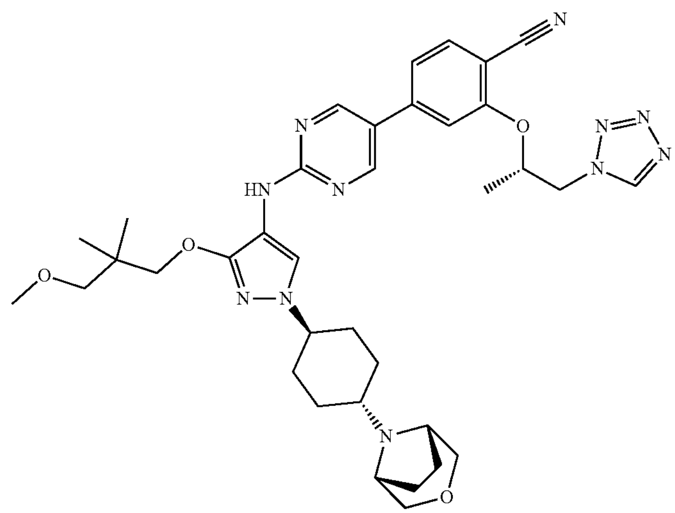 [SMILES: COCC(C)(C)COc1nn([C@H]2CC[C@H](N3[C@@H]4CC[C@H]3COC4)CC2)cc1Nc1ncc(-c2ccc(C#N)c(O[C@@H](C)Cn3cnnn3)c2)cn1] |
| 262 | 5-(3-(((S)-1-(1H-tetrazol-1-yl)propan-2-yl)oxy)-4-chlorophenyl)-N-(1-((1r,4r)-4-((1R,5S)-3-oxa-8-azabicyclo[3.2.1]octan-8-yl)cyclohexyl)-3-(3-methoxy-2,2-dimethylpropoxy)-1H-pyrazol-4-yl)pyrimidin-2-amine | 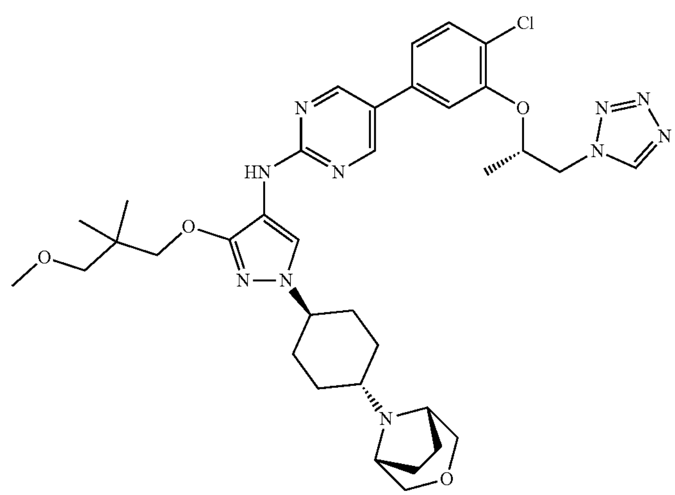 |

TABLE 2-continued

| Ex. No. | IUPAC NAME | STRUCTURE |
|---|---|---|
| 263 | 2-(((S)-1-(1H-1,2,4-triazol-1-yl)propan-2-yl)oxy)-4-(2-((1-((1r,4r)-4-((1R,5S)-3-oxa-8-azabicyclo[3.2.1]octan-8-yl)cyclohexyl)-3-(3-methoxy-2,2-dimethylpropoxy)-1H-pyrazol-4-yl)amino)pyrimidin-5-yl)benzonitrile | 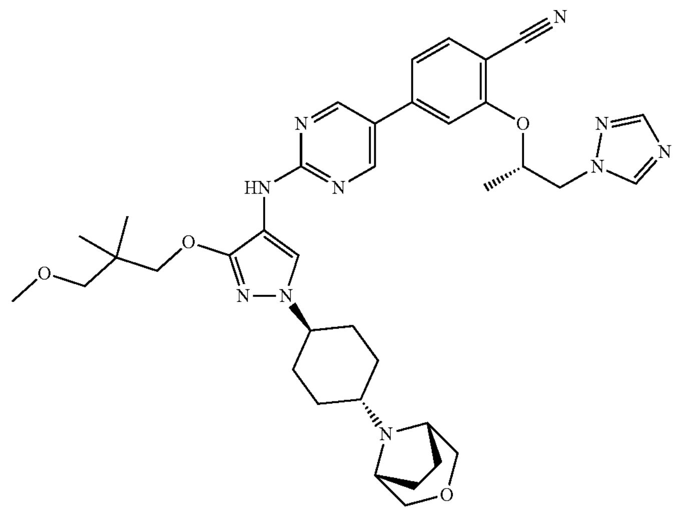 [SMILES: COCC(C)(C)COc1nn([C@H]2CC[C@H](N3[C@@H]4CC[C@H]3COC4)CC2)cc1Nc1ncc(-c2ccc(C#N)c(O[C@@H](C)Cn3cncn3)c2)cn1] |
| 264 | 5-(3-(((S)-1-(1H-1,2,4-triazol-1-yl)propan-2-yl)oxy)-4-chlorophenyl)-N-(1-((1r,4r)-4-((1R,5S)-3-oxa-8-azabicyclo[3.2.1]octan-8-yl)cyclohexyl)-3-(3-methoxy-2,2-dimethylpropoxy)-1H-pyrazol-4-yl)pyrimidin-2-amine | 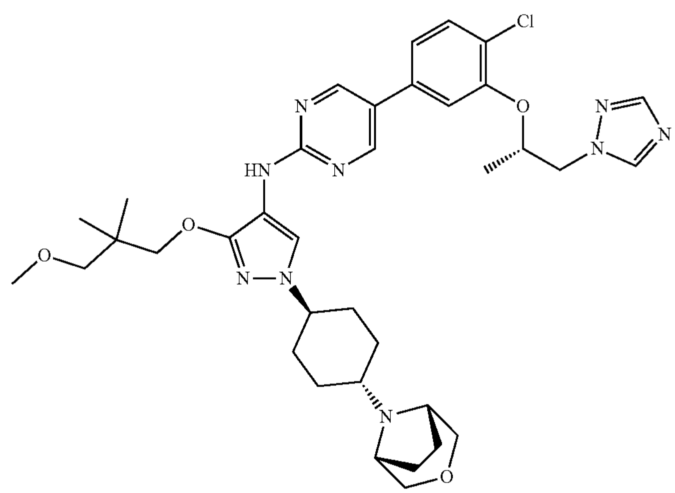 [SMILES: COCC(C)(C)COc1nn([C@H]2CC[C@H](N3[C@@H]4CC[C@H]3COC4)CC2)cc1Nc1ncc(-c2ccc(Cl)c(O[C@@H](C)Cn3cncn3)c2)cn1] |
| 265 | 2-(((S)-1-(1H-tetrazol-1-yl)propan-2-yl)oxy)-4-(2-((1-((1r,4r)-4-((2S,6R)-2,6-dimethylmorpholino)cyclohexyl)-3-(3-methoxy-2,2-dimethylpropoxy)-1H-pyrazol-4-yl)amino)pyrimidin-5-yl)benzonitrile | 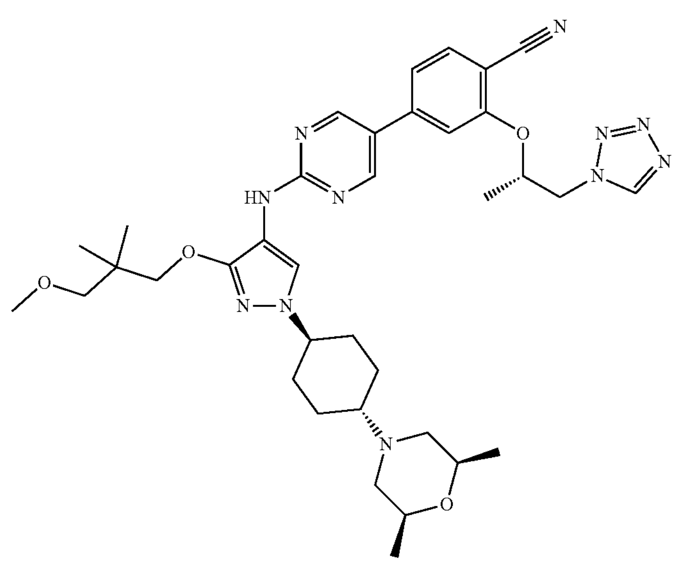 [SMILES: COCC(C)(C)COc1nn([C@H]2CC[C@H](N3C[C@@H](C)O[C@@H](C)C3)CC2)cc1Nc1ncc(-c2ccc(C#N)c(O[C@@H](C)Cn3cnnn3)c2)cn1] |

TABLE 2-continued

| Ex. No. | IUPAC NAME | STRUCTURE |
|---|---|---|
| 266 | 5-(3-(((S)-1-(1H-tetrazol-1-yl)propan-2-yl)oxy)-4-chlorophenyl)-N-(1-((1r,4r)-4-((2S,6R)-2,6-dimethylmorpholino)cyclohexyl)-3-(3-methoxy-2,2-dimethylpropoxy)-1H-pyrazol-4-yl)pyrimidin-2-amine | 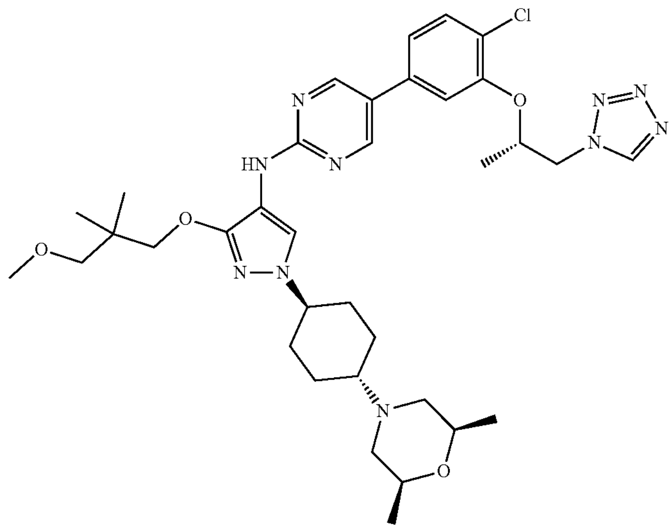 [SMILES: COCC(C)(C)COc1nn([C@H]2CC[C@H](N3C[C@@H](C)O[C@@H](C)C3)CC2)cc1Nc1ncc(-c2ccc(Cl)c(O[C@@H](C)Cn3cnnn3)c2)cn1] |
| 267 | 2-(((S)-1-(1H-1,2,4-triazol-1-yl)propan-2-yl)oxy)-4-(2-((1-((1r,4r)-4-((2S,6R)-2,6-dimethylmorpholino)cyclohexyl)-3-(3-methoxy-2,2-dimethylpropoxy)-1H-pyrazol-4-yl)amino)pyrimidin-5-yl)benzonitrile | 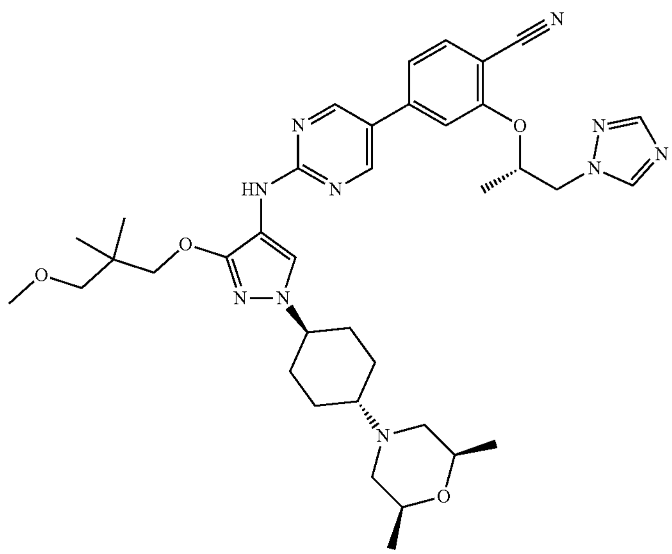 [SMILES: COCC(C)(C)COc1nn([C@H]2CC[C@H](N3C[C@@H](C)O[C@@H](C)C3)CC2)cc1Nc1ncc(-c2ccc(C#N)c(O[C@@H](C)Cn3cncn3)c2)cn1] |
| 268 | 5-(3-(((S)-1-(1H-1,2,4-triazol-1-yl)propan-2-yl)oxy)-4-chlorophenyl)-N-(1-((1r,4r)-4-((2S,6R)-2,6-dimethylmorpholino)cyclohexyl)-3-(3-methoxy-2,2-dimethylpropoxy)-1H-pyrazol-4-yl)pyrimidin-2-amine | 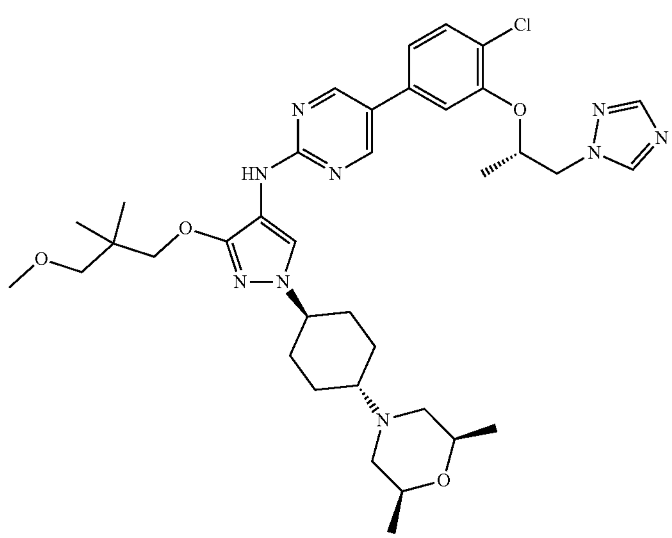 [SMILES: COCC(C)(C)COc1nn([C@H]2CC[C@H](N3C[C@@H](C)O[C@@H](C)C3)CC2)cc1Nc1ncc(-c2ccc(Cl)c(O[C@@H](C)Cn3cncn3)c2)cn1] |

TABLE 2-continued

| Ex. No. | IUPAC NAME | STRUCTURE |
|---|---|---|
| 269 | 2-(((S)-1-(1H-tetrazol-1-yl)propan-2-yl)oxy)-4-(2-((3-(3-methoxy-2-methylpropoxy)-1-((1r,4r)-4-morpholinocyclohexyl)-1H-pyrazol-4-yl)amino)pyrimidin-5-yl)benzonitrile | 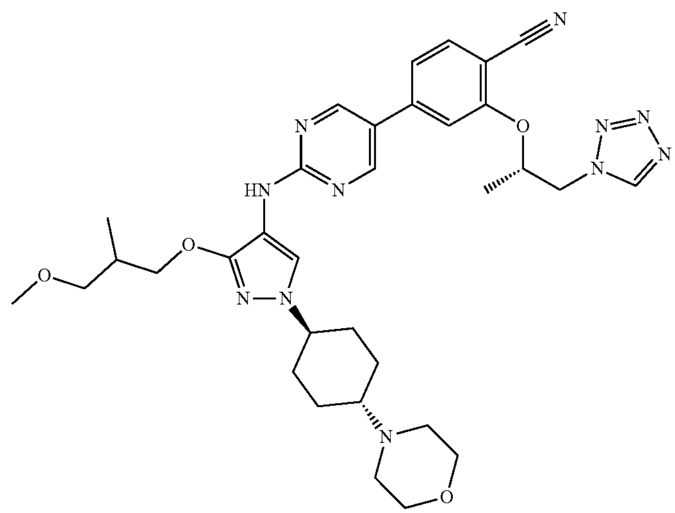 [SMILES: COCC(C)COc1nn([C@H]2CC[C@H](N3CCOCC3)CC2)cc1Nc1ncc(-c2ccc(C#N)c(O[C@@H](C)Cn3cnnn3)c2)cn1] |
| 270 | 5-(3-(((S)-1-(1H-tetrazol-1-yl)propan-2-yl)oxy)-4-chlorophenyl)-N-(3-(3-methoxy-2-methylpropoxy)-1-((1r,4r)-4-morpholinocyclohexyl)-1H-pyrazol-4-yl)pyrimidin-2-amine | 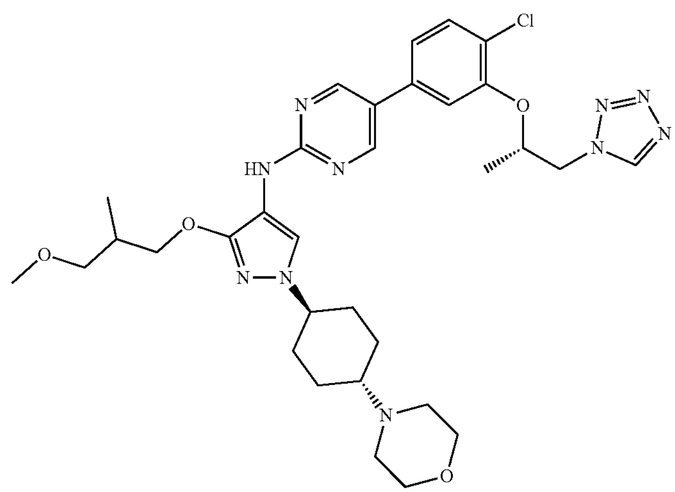 [SMILES: COCC(C)COc1nn([C@H]2CC[C@H](N3CCOCC3)CC2)cc1Nc1ncc(-c2ccc(Cl)c(O[C@@H](C)Cn3cnnn3)c2)cn1] |
| 271 | 2-(((S)-1-(1H-1,2,4-triazol-1-yl)propan-2-yl)oxy)-4-(2-((3-(3-methoxy-2-methylpropoxy)-1-((1r,4r)-4-morpholinocyclohexyl)-1H-pyrazol-4-yl)amino)pyrimidin-5-yl)benzonitrile | 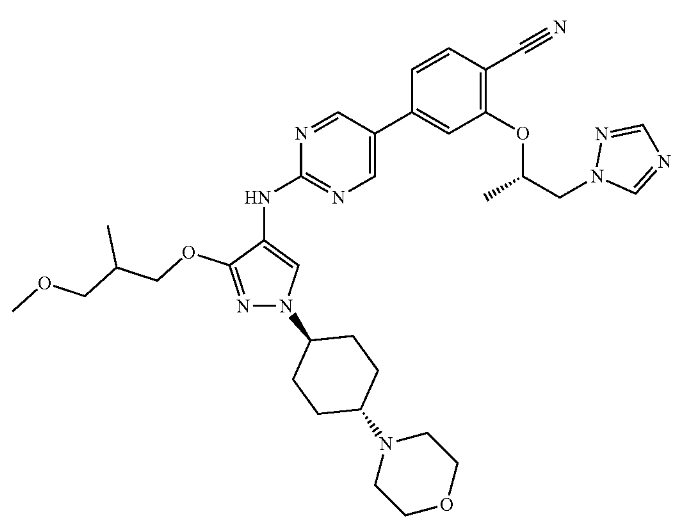 [SMILES: COCC(C)COc1nn([C@H]2CC[C@H](N3CCOCC3)CC2)cc1Nc1ncc(-c2ccc(C#N)c(O[C@@H](C)Cn3cncn3)c2)cn1] |

TABLE 2-continued

| Ex. No. | IUPAC NAME | STRUCTURE |
|---|---|---|
| 272 | 5-(3-(((S)-1-(1H-1,2,4-triazol-1-yl)propan-2-yl)oxy)-4-chlorophenyl)-N-(3-(3-methoxy-2-methylpropoxy)-1-((1r,4r)-4-morpholinocyclohexyl)-1H-pyrazol-4-yl)pyrimidin-2-amine | 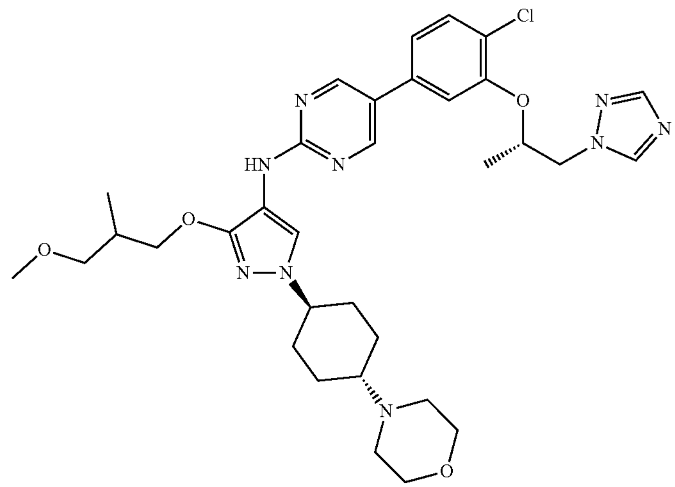 [SMILES: COCC(C)COc1nn([C@H]2CC[C@H](N3CCOCC3)CC2)cc1Nc1ncc(-c2ccc(Cl)c(O[C@@H](C)Cn3cncn3)c2)cn1] |
| 273 | 2-(((S)-1-(1H-tetrazol-1-yl)propan-2-yl)oxy)-4-(2-((1-((1r,4r)-4-((1R,5S)-3-oxa-8-azabicyclo[3.2.1]octan-8-yl)cyclohexyl)-3-(3-methoxy-2-methylpropoxy)-1H-pyrazol-4-yl)amino)pyrimidin-5-yl)benzonitrile | 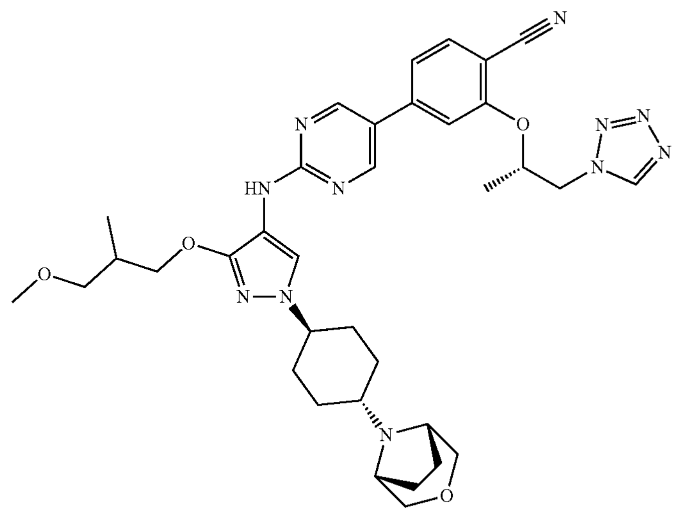 [SMILES: COCC(C)COc1nn([C@H]2CC[C@H](N3[C@@H]4CC[C@H]3COC4)CC2)cc1Nc1ncc(-c2ccc(C#N)c(O[C@@H](C)Cn3cnnn3)c2)cn1] |
| 274 | 5-(3-(((S)-1-(1H-tetrazol-1-yl)propan-2-yl)oxy)-4-chlorophenyl)-N-(1-((1r,4r)-4-((1R,5S)-3-oxa-8-azabicyclo[3.2.1]octan-8-yl)cyclohexyl)-3-(3-methoxy-2-methylpropoxy)-1H-pyrazol-4-yl)pyrimidin-2-amine | 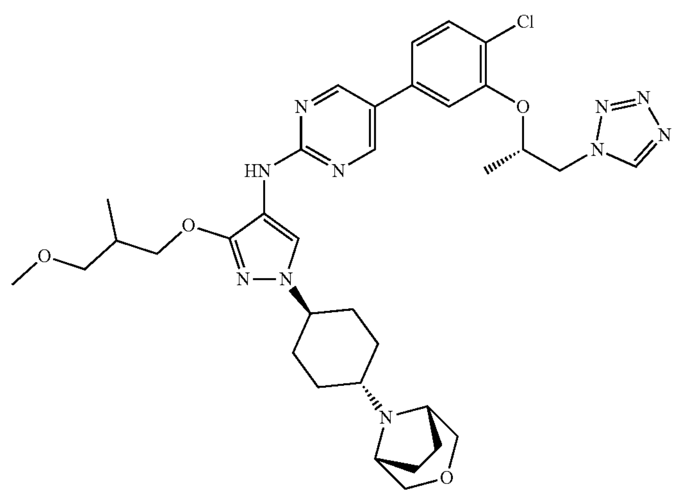 [SMILES: COCC(C)COc1nn([C@H]2CC[C@H](N3[C@@H]4CC[C@H]3COC4)CC2)cc1Nc1ncc(-c2ccc(Cl)c(O[C@@H](C)Cn3cnnn3)c2)cn1] |

TABLE 2-continued

| Ex. No. | IUPAC NAME | STRUCTURE |
|---|---|---|
| 275 | 2-(((S)-1-(1H-1,2,4-triazol-1-yl)propan-2-yl)oxy)-4-(2-((1-((1r,4r)-4-((1R,5S)-3-oxa-8-azabicyclo[3.2.1]octan-8-yl)cyclohexyl)-3-(3-methoxy-2-methylpropoxy)-1H-pyrazol-4-yl)amino)pyrimidin-5-yl)benzonitrile | 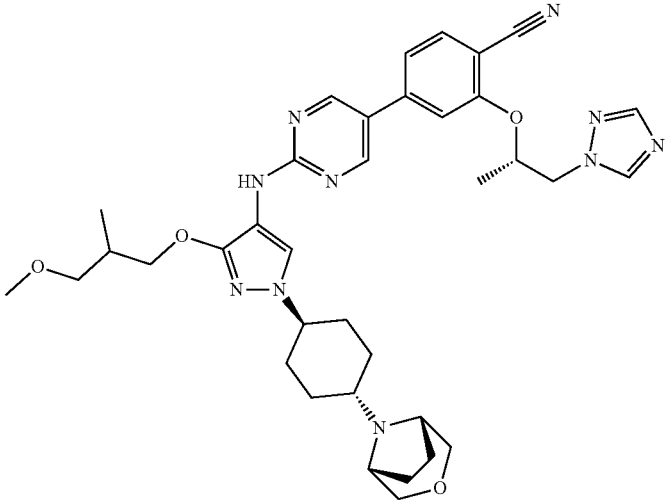 [SMILES: COCC(C)COc1nn([C@H]2CC[C@H](N3[C@@H]4CC[C@H]3COC4)CC2)cc1Nc1ncc(-c2ccc(C#N)c(O[C@@H](C)Cn3cncn3)c2)cn1] |
| 276 | 5-(3-(((S)-1-(1H-1,2,4-triazol-1-yl)propan-2-yl)oxy)-4-chlorophenyl)-N-(1-((1r,4r)-((1R,5S)-3-oxa-8-azabicyclo[3.2.1]octan-8-yl)cyclohexyl)-3-(3-methoxy-2-methylpropoxy)-1H-pyrazol-4-yl)pyrimidin-2-amine | 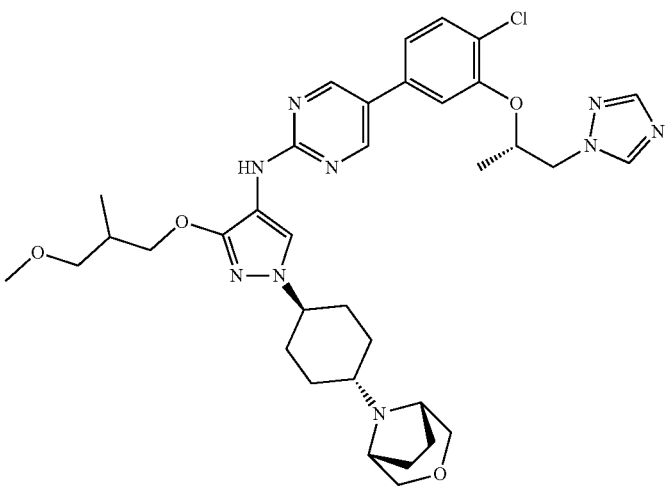 [SMILES: COCC(C)COc1nn([C@H]2CC[C@H](N3[C@@H]4CC[C@H]3COC4)CC2)cc1Nc1ncc(-c2ccc(Cl)c(O[C@@H](C)Cn3cncn3)c2)cn1] |
| 277 | 2-(((S)-1-(1H-tetrazol-1-yl)propan-2-yl)oxy)-4-(2-((1-((1r,4r)-4-((2S,6R)-2,6-dimethylmorpholino)cyclohexyl)-3-(3-methoxy-2-methylpropoxy)-1H-pyrazol-4-yl)amino)pyrimidin-4-yl)benzonitrile | 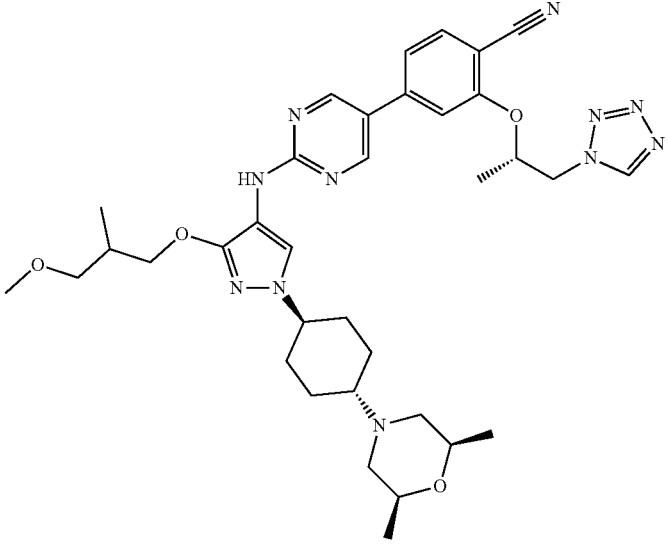 [SMILES: COCC(C)COc1nn([C@H]2CC[C@H](N3C[C@@H](C)O[C@@H](C)C3)CC2)cc1Nc1ncc(-c2ccc(C#N)c(O[C@@H](C)Cn3cnnn3)c2)cn1] |

TABLE 2-continued

| Ex. No. | IUPAC NAME | STRUCTURE |
|---|---|---|
| 278 | 5-(3-(((S)-1-(1H-tetrazol-1-yl)propan-2-yl)oxy)-4-chlorophenyl)-N-(1-((1r,4r)-4-((2S,6R)-2,6-dimethylmorpholino)cyclohexyl)-3-(3-methoxy-2-methylpropoxy)-1H-pyrazol-4-yl)pyrimidin-2-amine | 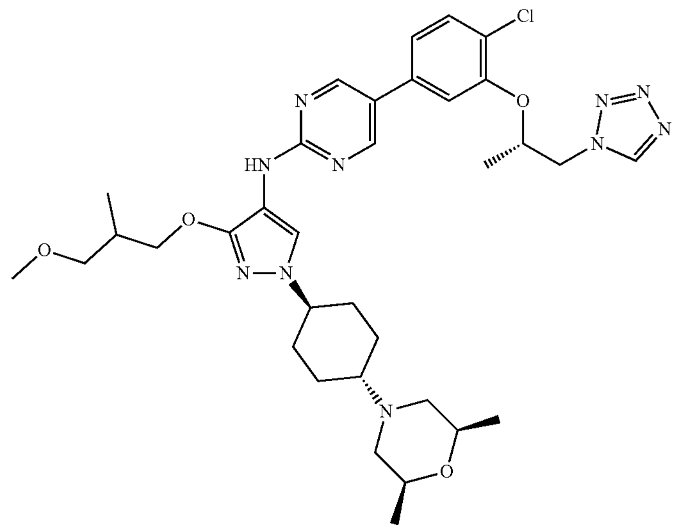 [SMILES: COCC(C)COc1nn([C@H]2CC[C@H](N3C[C@@H](C)O[C@@H](C)C3)CC2)cc1Nc1ncc(-c2ccc(Cl)c(O[C@@H](C)Cn3cnnn3)c2)cn1] |
| 279 | 2-(((S)-1-(1H-1,2,4-triazol-1-yl)propan-2-yl)oxy)-4-(2-((1-((1r,4r)-4-((2S,6R)-2,6-dimethylmorpholino)cyclohexyl)-3-(3-methoxy-2-methylpropoxy)-1H-pyrazol-4-yl)amino)pyrimidin-5-yl)benzonitrile | 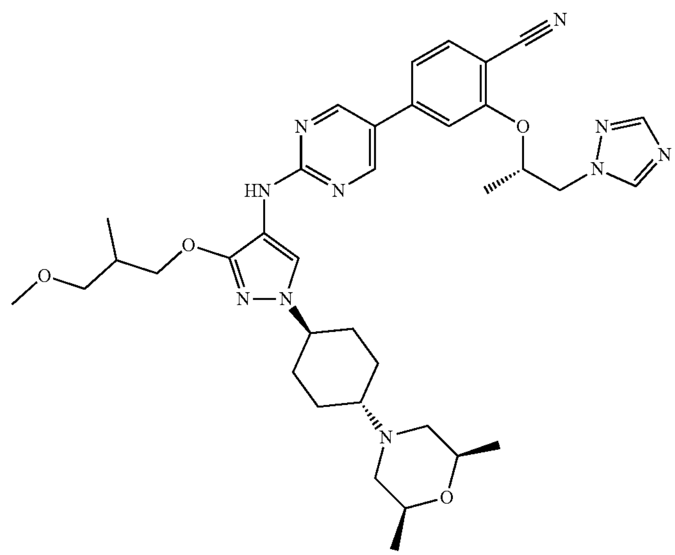 [SMILES: COCC(C)COc1nn([C@H]2CC[C@H](N3C[C@@H](C)O[C@@H](C)C3)CC2)cc1Nc1ncc(-c2ccc(C#N)c(O[C@@H](C)Cn3cncn3)c2)cn1] |
| 280 | 5-(3-(((S)-1-(1H-1,2,4-triazol-1-yl)propan-2-yl)oxy)-4-chlorophenyl)-N-(1-((1r,4r)-4-((2S,6R)-2,6-dimethylmorpholino)cyclohexyl)-3-(3-methoxy-2-methylpropoxy)-1H-pyrazol-4-yl)pyrimidin-2-amine | 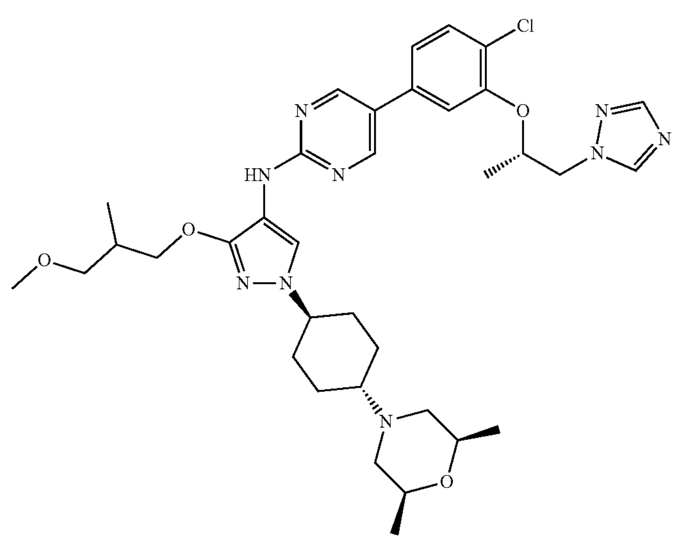 [SMILES: COCC(C)COc1nn([C@H]2CC[C@H](N3C[C@@H](C)O[C@@H](C)C3)CC2)cc1Nc1ncc(-c2ccc(Cl)c(O[C@@H](C)Cn3cncn3)c2)cn1] |

TABLE 2-continued

| Ex. No. | IUPAC NAME | STRUCTURE |
|---|---|---|
| 281 | 2-(((S)-1-(1H-tetrazol-1-yl)propan-2-yl)oxy)-4-(2-((3-((4-methoxybutan-2-yl)oxy)-1-((1r,4r)-4-morpholinocyclohexyl)-1H-pyrazol-4-yl)amino)pyrimidin-5-yl)benzonitrile | 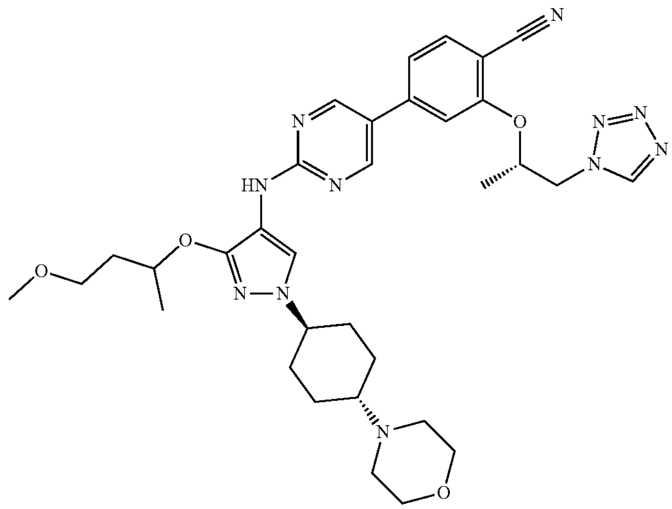 [SMILES: COCCC(C)Oc1nn([C@H]2CC[C@H](N3CCOCC3)CC2)cc1Nc1ncc(-c2ccc(C#N)c(O[C@@H](C)Cn3cnnn3)c2)cn1] |
| 282 | 5-(3-(((S)-1-(1H-tetrazol-1-yl)propan-2-yl)oxy)-4-chlorophenyl)-N-(3-((4-methoxybutan-2-yl)oxy)-1-((1r,4r)-4-morpholinocyclohexyl)-1H-pyrazol-4-yl)pyrimidin-2-amine | 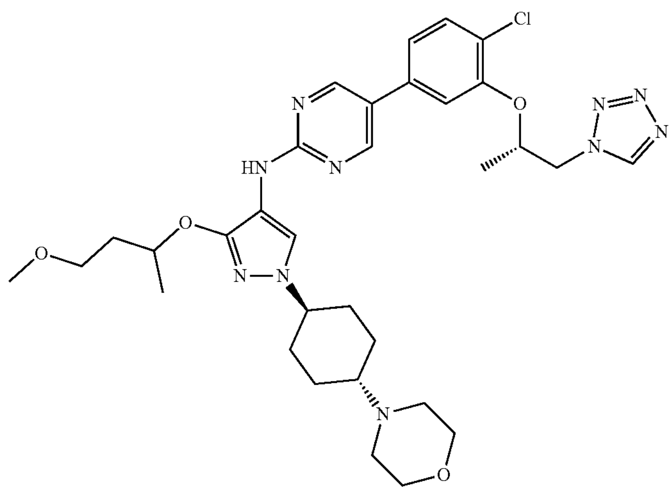 [SMILES: COCCC(C)Oc1nn([C@H]2CC[C@H](N3CCOCC3)CC2)cc1Nc1ncc(-c2ccc(Cl)c(O[C@@H](C)Cn3cnnn3)c2)cn1] |
| 283 | 2-(((S)-1-(1H-1,2,4-triazol-1-yl)propan-2-yl)oxy)-4-(2-((3-((4-methoxybutan-2-yl)oxy)-1-((1r,4r)-4-morpholinocyclohexyl)-1H-pyrazol-4-yl)amino)pyrimidin-5-yl)benzonitrile | 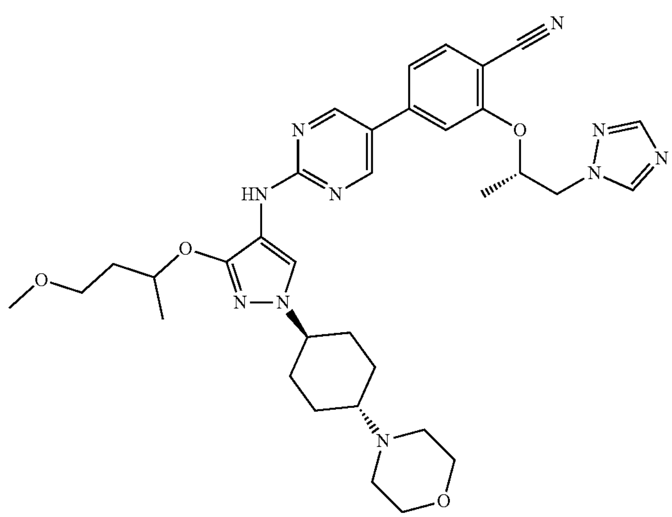 [SMILES: COCCC(C)Oc1nn([C@H]2CC[C@H](N3CCOCC3)CC2)cc1Nc1ncc(-c2ccc(C#N)c(O[C@@H](C)Cn3cncn3)c2)cn1] |

TABLE 2-continued

| Ex. No. | IUPAC NAME | STRUCTURE |
| --- | --- | --- |
| 284 | 5-(3-(((S)-1-(1H-1,2,4-triazol-1-yl)propan-2-yl)oxy)-4-chlorophenyl)-N-(3-((4-methoxybutan-2-yl)oxy)-1-((1r,4r)-4-morpholinocyclohexyl)-1H-pyrazol-4-yl)pyrimidin-2-amine | 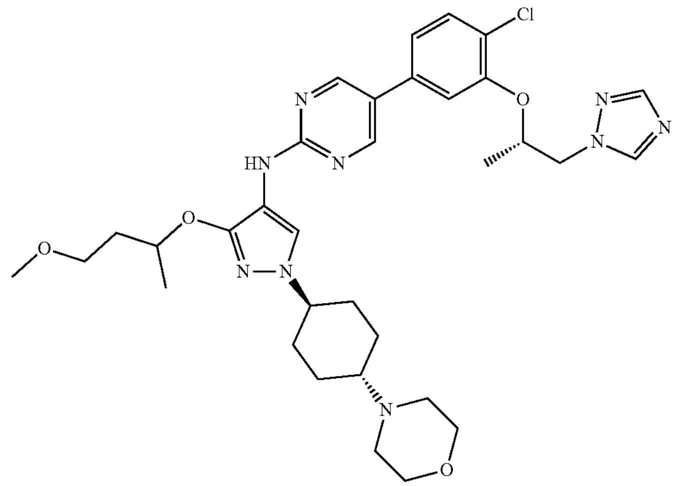 [SMILES: COCCC(C)Oc1nn([C@H]2CC[C@H](N3CCOCC3)CC2)cc1Nc1ncc(-c2ccc(Cl)c(O[C@@H](C)Cn3cncn3)c2)cn1] |
| 285 | 2-(((S)-1-(1H-tetrazol-1-yl)propan-2-yl)oxy)-4-(2-((1-((1r,4r)-4-((1R,5S)-3-oxa-8-azabicyclo[3.2.1]octan-8-yl)cyclohexyl)-3-((4-methoxybutan-2-yl)oxy)-1H-pyrazol-4-yl)amino)pyrimidin-5-yl)benzonitrile | 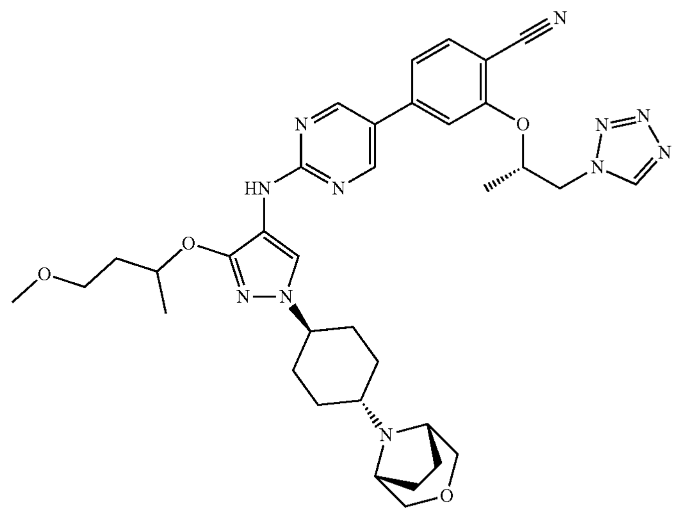 [SMILES: COCCC(C)Oc1nn([C@H]2CC[C@H](N3[C@@H]4CC[C@H]3COC4)CC2)cc1Nc1ncc(-c2ccc(C#N)c(O[C@@H](C)Cn3cnnn3)c2)cn1] |
| 286 | 5-(3-(((S)-1-(1H-tetrazol-1-yl)propan-2-yl)oxy)-4-chlorophenyl)-N-(1-((1r,4r)-4-((1R,5S)-3-oxa-8-azabicyclo[3.2.1]octan-8-yl)cyclohexyl)-3-((4-methoxybutan-2-yl)oxy)-1H-pyrazol-4-yl)pyrimidin-2-amine | 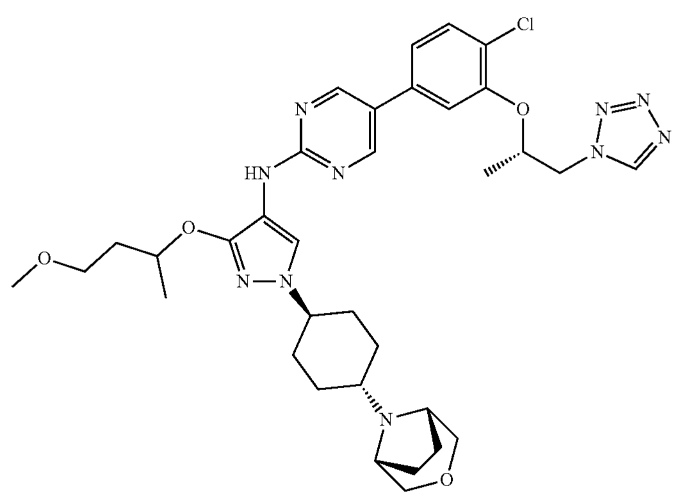 [SMILES: COCCC(C)Oc1nn([C@H]2CC[C@H](N3[C@@H]4CC[C@H]3COC4)CC2)cc1Nc1ncc(-c2ccc(Cl)c(O[C@@H](C)Cn3cnnn3)c2)cn1] |

TABLE 2-continued

| Ex. No. | IUPAC NAME | STRUCTURE |
|---|---|---|
| 287 | 2-(((S)-1-(1H-1,2,4-triazol-1-yl)propan-2-yl)oxy)-4-(2-((1-((1r,4r)-4-((1R,5S)-3-oxa-8-azabicyclo[3.2.1]octan-8-yl)cyclohexyl)-3-((4-methoxybutan-2-yl)oxy)-1H-pyrazol-4-yl)amino)pyrimidin-5-yl)benzonitrile | 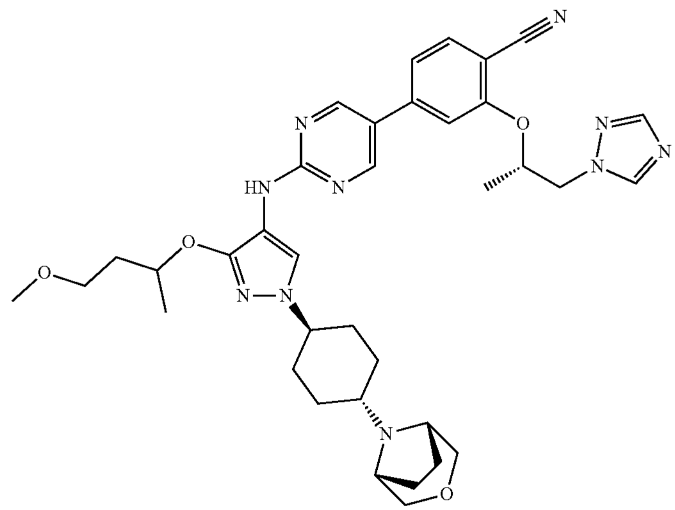 [SMILES: COCCC(C)Oc1nn([C@H]2CC[C@H](N3[C@@H]4CC[C@H]3COC4)CC2)cc1Nc1ncc(-c2ccc(C#N)c(O[C@@H](C)Cn3cncn3)c2)cn1] |
| 288 | 5-(3-(((S)-1-(1,2,4-triazol-1-yl)propan-2-yl)oxy)-4-chlorophenyl)-N-(1-((1r,4r)-4-((1R,5S)-3-oxa-8-azabicyclo[3.2.1]octan-8-yl)cyclohexyl)-3-((4-methoxybutan-2-yl)oxy)-1H-pyrazol-4-yl)pyrimidin-2-amine | 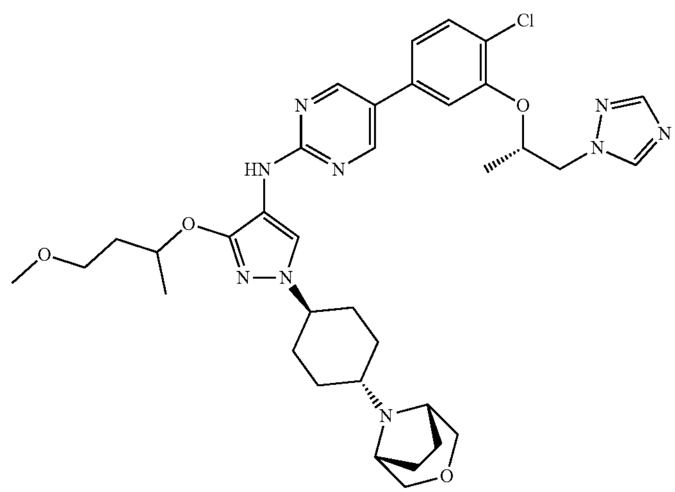 [SMILES: COCCC(C)Oc1nn([C@H]2CC[C@H](N3[C@@H]4CC[C@H]3COC4)CC2)cc1Nc1ncc(-c2ccc(Cl)c(O[C@@H](C)Cn3cncn3)c2)cn1] |
| 289 | 2-(((S)-1-(1H-tetrazol-1-yl)propan-2-yl)oxy)-4-(2-((1-((1r,4r)-4-((2S,6R)-2,6-dimethylmorpholino)cyclohexyl)-3-((4-methoxybutan-2-yl)oxy)-1H-pyrazol-4-yl)amino)pyrimidin-5-yl)benzonitrile | 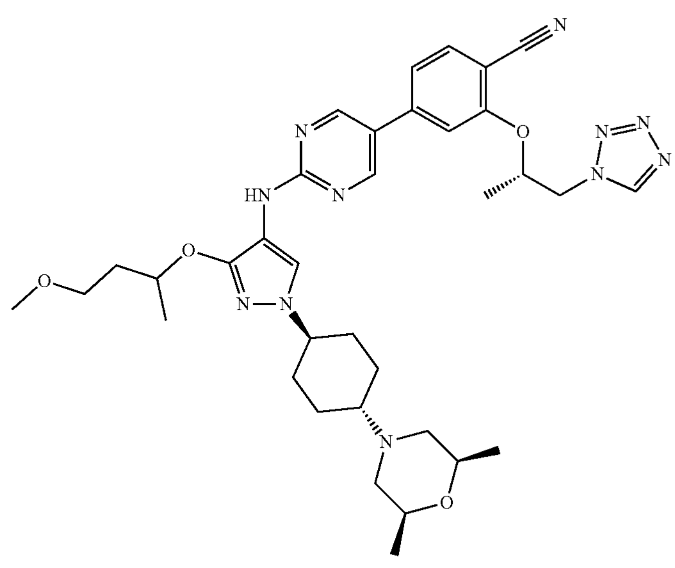 [SMILES: COCCC(C)Oc1nn([C@H]2CC[C@H](N3C[C@@H](C)O[C@@H](C)C3)CC2)cc1Nc1ncc(-c2ccc(C#N)c(O[C@@H](C)Cn3cnnn3)c2)cn1] |

TABLE 2-continued

| Ex. No. | IUPAC NAME | STRUCTURE |
|---|---|---|
| 290 | 5-(3-(((S)-1-(1H-tetrazol-1-yl)propan-2-yl)oxy)-4-chlorophenyl)-N-(1-((1r,4r)-4-((2S,6R)-2,6-dimethylmorpholino)cyclohexyl)-3-((4-methoxybutan-2-yl)oxy)-1H-pyrazol-4-yl)pyrimidin-2-amine | 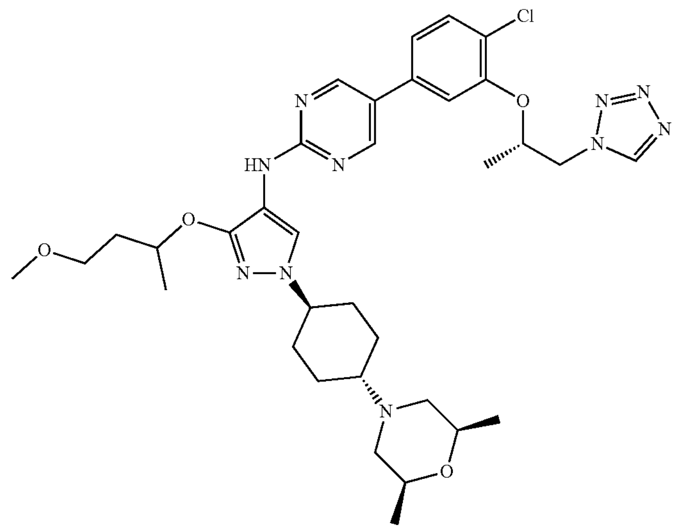 [SMILES: COCCC(C)Oc1nn([C@H]2CC[C@H](N3C[C@@H](C)O[C@@H](C)C3)CC2)cc1Nc1ncc(-c2ccc(Cl)c(O[C@@H](C)Cn3cnnn3)c2)cn1] |
| 291 | 2-(((S)-1-(1H-1,2,4-triazol-1-yl)propan-2-yl)oxy)-4-(2-((1-((1r,4r)-4-((2S,6R)-2,6-dimethylmorpholino)cyclohexyl)-3-((4-methoxybutan-2-yl)oxy)-1H-pyrazol-4-yl)amino)pyrimidin-5-yl)benzonitrile | 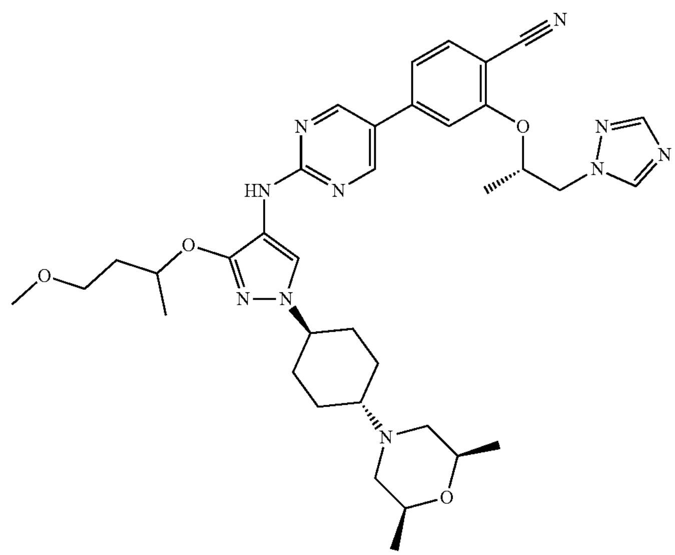 [SMILES: COCCC(C)Oc1nn([C@H]2CC[C@H](N3C[C@@H](C)O[C@@H](C)C3)CC2)cc1Nc1ncc(-c2ccc(C#N)c(O[C@@H](C)Cn3cncn3)c2)cn1] |
| 292 | 5-(3-(((S)-1-(1H-1,2,4-triazol-1-yl)propan-2-yl)oxy)-4-chlorophenyl)-N-(1-((1r,4r)-4-((2S,6R)-2,6-dimethylmorpholino)cyclohexyl)-3-((4-methoxybutan-2-yl)oxy)-1H-pyrazol-4-yl)pyrimidin-2-amine | 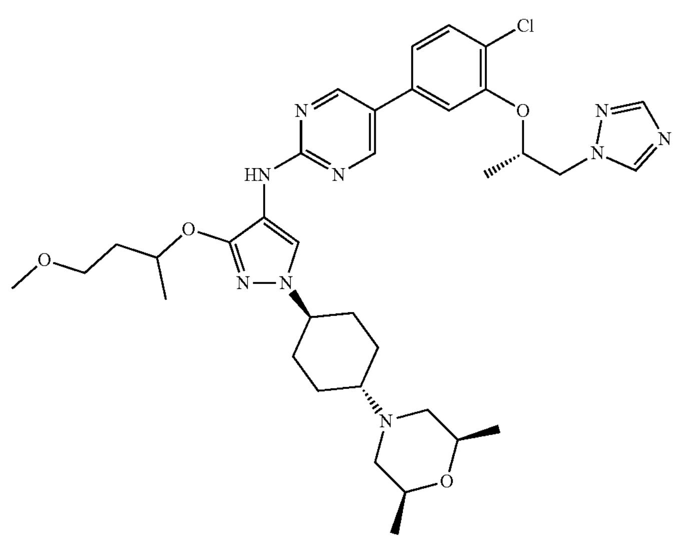 [SMILES: COCCC(C)Oc1nn([C@H]2CC[C@H](N3C[C@@H](C)O[C@@H](C)C3)CC2)cc1Nc1ncc(-c2ccc(Cl)c(O[C@@H](C)Cn3cncn3)c2)cn1] |

TABLE 2-continued

| Ex. No. | IUPAC NAME | STRUCTURE |
|---|---|---|
| 293 | 2-(((S)-1-(1H-tetrazol-1-yl)propan-2-yl)oxy)-4-(2-((3-(3-methoxybutoxy)-1-((1r,4r)-4-morpholinocyclohexyl)-1H-pyrazol-4-yl)amino)pyrimidin-5-yl)benzonitrile | 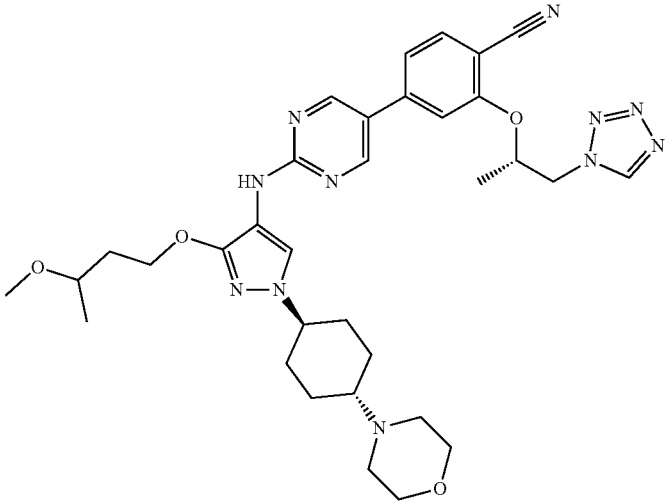 [SMILES: COC(C)CCOc1nn([C@H]2CC[C@H](N3CCOCC3)CC2)cc1Nc1ncc(-c2ccc(C#N)c(O[C@@H](C)Cn3cnnn3)c2)cn1] |
| 294 | 5-(3-(((S)-1-(1H-tetrazol-1-yl)propan-2-yl)oxy)-4-chlorophenyl)-N-(3-(3-methoxybutoxy)-1-((1r,4r)-4-morpholinocyclohexyl)-1H-pyrazol-4-yl)pyrimidin-2-amine | 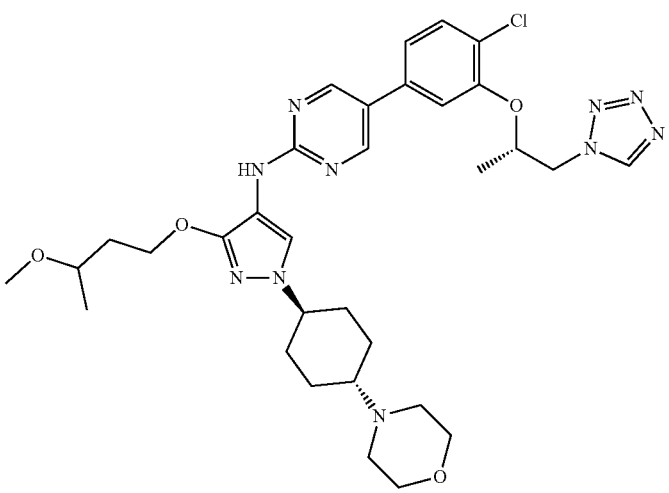 [SMILES: COC(C)CCOc1nn([C@H]2CC[C@H](N3CCOCC3)CC2)cc1Nc1ncc(-c2ccc(Cl)c(O[C@@H](C)Cn3cnnn3)c2)cn1] |
| 295 | 2-(((S)-1-(1H-1,2,4-triazol-1-yl)propan-2-yl)oxy)-4-(2-((3-(3-methoxybutoxy)-1-((1r,4r)-4-morpholinocyclohexyl)-1H-pyrazol-4-yl)amino)pyrimidin-5-yl)benzonitrile | 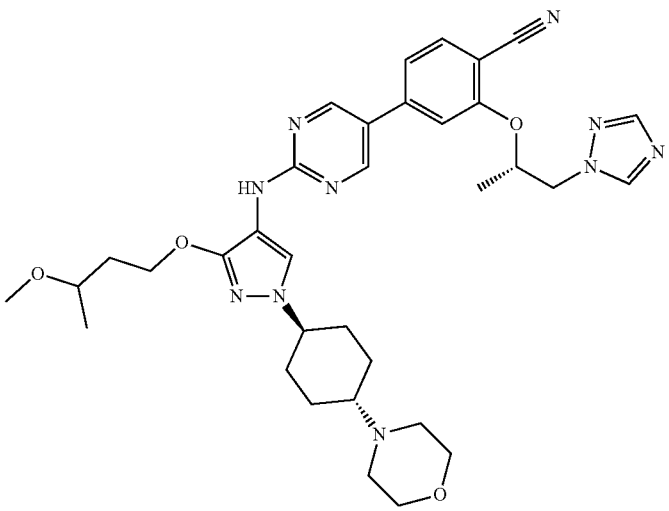 [SMILES: COC(C)CCOc1nn([C@H]2CC[C@H](N3CCOCC3)CC2)cc1Nc1ncc(-c2ccc(C#N)c(O[C@@H](C)Cn3cncn3)c2)cn1] |

TABLE 2-continued

| Ex. No. | IUPAC NAME | STRUCTURE |
| --- | --- | --- |
| 296 | 5-(3-(((S)-1-(1H-1,2,4-triazol-1-yl)propan-2-yl)oxy)-4-chlorophenyl)-N-(3-(3-methoxybutoxy)-1-((1r,4r)-4-morpholinocyclohexyl)-1H-pyrazol-4-yl)pyrimidin-2-amine | 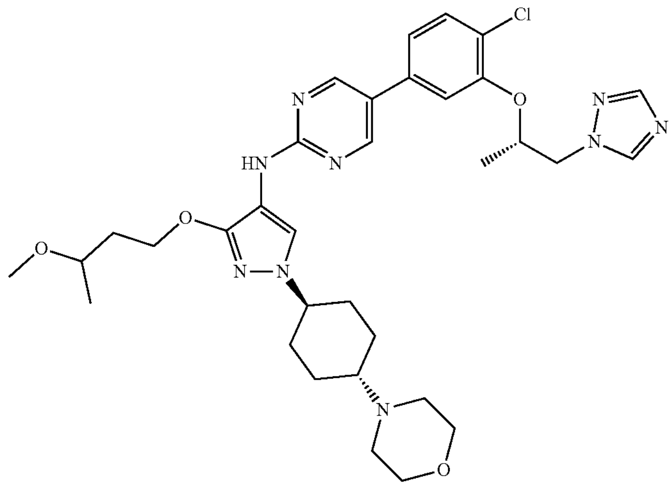 [SMILES: COC(C)CCOc1nn([C@H]2CC[C@H](N3CCOCC3)CC2)cc1Nc1ncc(-c2ccc(Cl)c(O[C@@H](C)Cn3cncn3)c2)cn1] |
| 297 | 2-(((S)-1-(1H-tetrazol-1-yl)propan-2-yl)oxy)-4-(2-((1-((1r,4r)-4-((1R,5S)-3-oxa-8-azabicyclo[3.2.1]octan-8-yl)cyclohexyl)-3-(3-methoxybutoxy)-1H-pyrazol-4-yl)amino)pyrimidin-5-yl)benzonitrile | 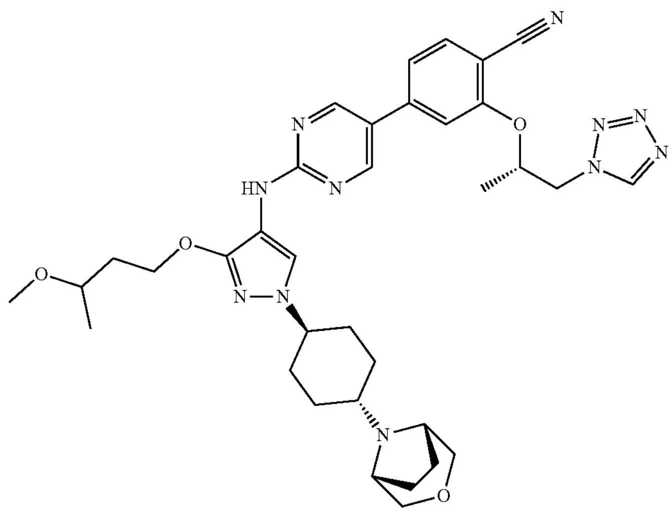 [SMILES: COC(C)CCOc1nn([C@H]2CC[C@H](N3[C@@H]4CC[C@H]3COC4)CC2)cc1Nc1ncc(-c2ccc(C#N)c(O[C@@H](C)Cn3cnnn3)c2)cn1] |
| 298 | 5-(3-(((S)-1-(1H-tetrazol-1-yl)propan-2-yl)oxy)-4-chlorophenyl)-N-(1-((1r,4r)-4-((1R,5S)-3-oxa-8-azabicyclo[3.2.1]octan-8-yl)cyclohexyl)-3-(3-methoxybutoxy)-1H-pyrazol-4-yl)pyrimidin-2-amine | 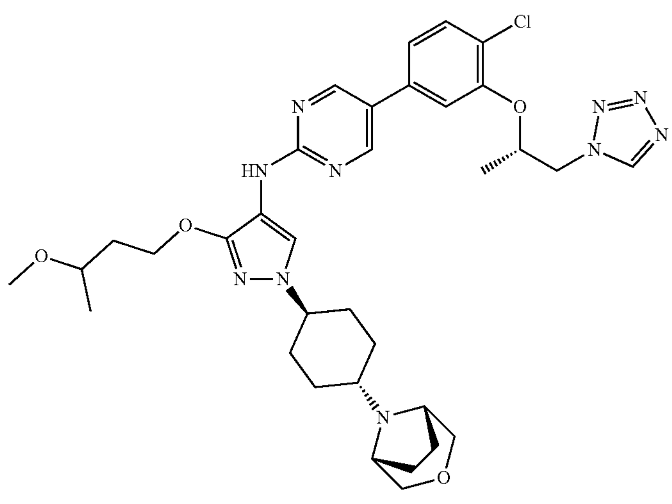 [SMILES: COC(C)CCOc1nn([C@H]2CC[C@H](N3[C@@H]4CC[C@H]3COC4)CC2)cc1Nc1ncc(-c2ccc(Cl)c(O[C@@H](C)Cn3cnnn3)c2)cn1] |

TABLE 2-continued

| Ex. No. | IUPAC NAME | STRUCTURE |
|---|---|---|
| 299 | 2-(((S)-1-(1H-1,2,4-triazol-1-yl)propan-2-yl)oxy)-4-(2-((1-((1r,4r)-4-((1R,5S)-3-oxa-8-azabicyclo[3.2.1]octan-8-yl)cyclohexyl)-3-(3-methoxybutoxy)-1H-pyrazol-4-yl)amino)pyrimidin-5-yl)benzonitrile | 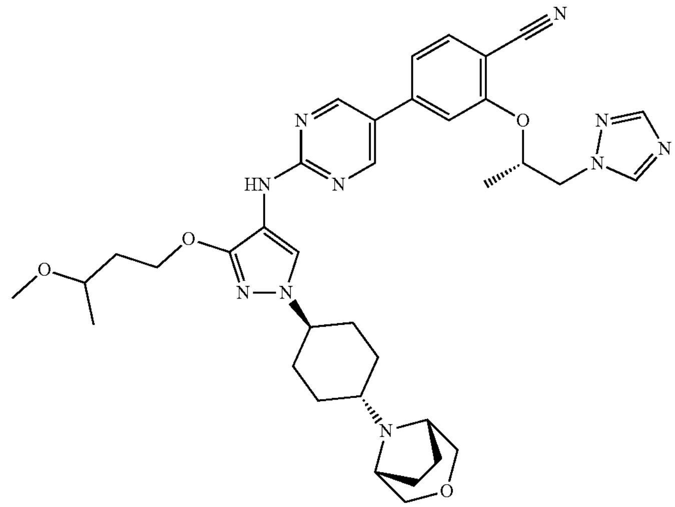 [SMILES: COC(C)CCOc1nn([C@H]2CC[C@H](N3[C@@H]4CC[C@H]3COC4)CC2)cc1Nc1ncc(-c2ccc(C#N)c(O[C@@H](C)Cn3cncn3)c2)cn1] |
| 300 | 5-(3-(((S)-1-(1H-1,2,4-triazol-1-yl)propan-2-yl)oxy)-4-chlorophenyl)-N-(1-((1r,4r)-4-((1R,5S)-3-oxa-8-azabicyclo[3.2.1]octan-8-yl)cyclohexyl)-3-(3-methoxybutoxy)-1H-pyrazol-4-yl)pyrimidin-2-amine | 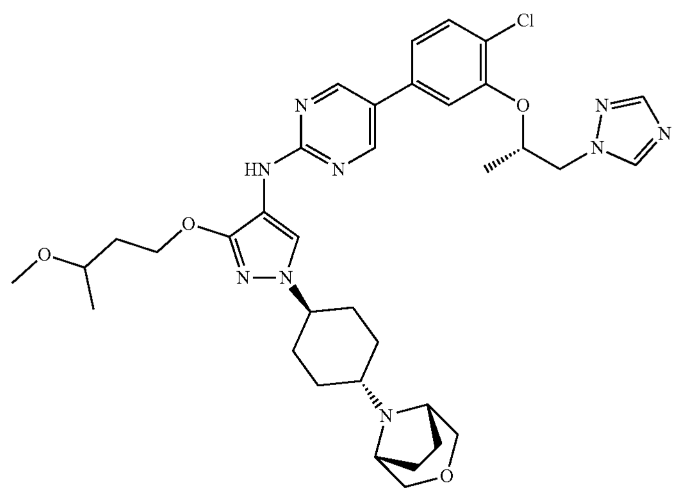 [SMILES: COC(C)CCOc1nn([C@H]2CC[C@H](N3[C@@H]4CC[C@H]3COC4)CC2)cc1Nc1ncc(-c2ccc(Cl)c(O[C@@H](C)Cn3cncn3)c2)cn1] |
| 301 | 2-(((S)-1-(1H-tetrazol-1-yl)propan-2-yl)oxy)-4-(2-((1-((1r,4r)-4-((2S,6R)-2,6-dimethylmorpholino)cyclohexyl)-3-(3-methoxybutoxy)-1H-pyrazol-4-yl)amino)pyrimidin-5-yl)benzonitrile | 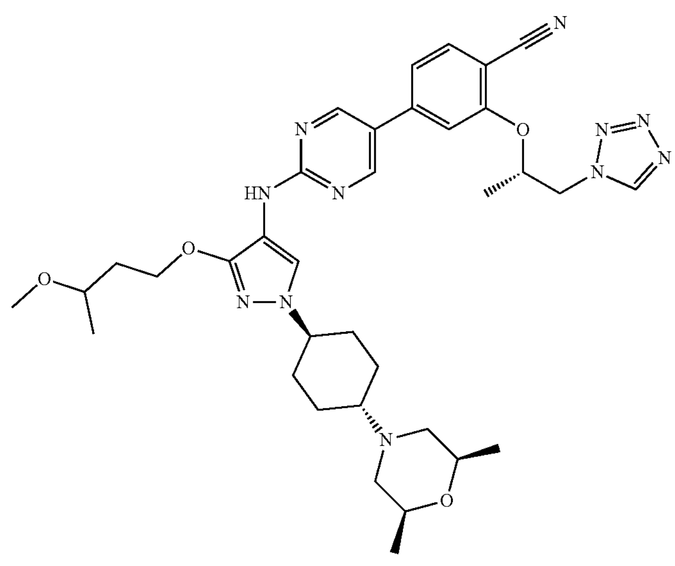 [SMILES: COC(C)CCOc1nn([C@H]2CC[C@H](N3C[C@@H](C)O[C@@H](C)C3)CC2)cc1Nc1ncc(-c2ccc(C#N)c(O[C@@H](C)Cn3cnnn3)c2)cn1] |

TABLE 2-continued

| Ex. No. | IUPAC NAME | STRUCTURE |
|---|---|---|
| 302 | 5-(3-(((S)-1-(1H-tetrazol-1-yl)propan-2-yl)oxy)-4-chlorophenyl)-N-(1-((1r,4r)-4-((2S,6R)-2,6-dimethylmorpholino)cyclohexyl)-3-(3-methoxybutoxy)-1H-pyrazol-4-yl)pyrimidin-2-amine | 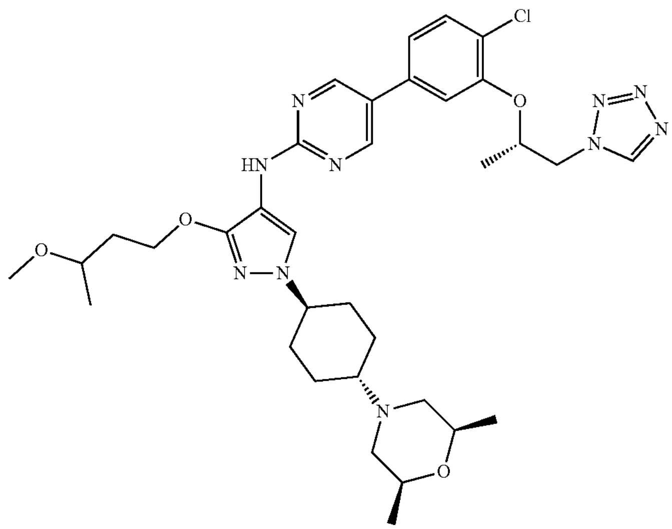 [SMILES: COC(C)CCOc1nn([C@H]2CC[C@H](N3C[C@@H](C)O[C@@H](C)C3)CC2)cc1Nc1ncc(-c2ccc(Cl)c(O[C@@H](C)Cn3cnnn3)c2)cn1] |
| 303 | 2-(((S)-1-(1H-1,2,4-triazol-1-yl)propan-2-yl)oxy)-4-(2-((1-((1r,4r)-4-((2S,6R)-2,6-dimethylmorpholino)cyclohexyl)-3-(3-methoxybutoxy)-1H-pyrazol-4-yl)amino)pyrimidin-5-yl)benzonitrile | 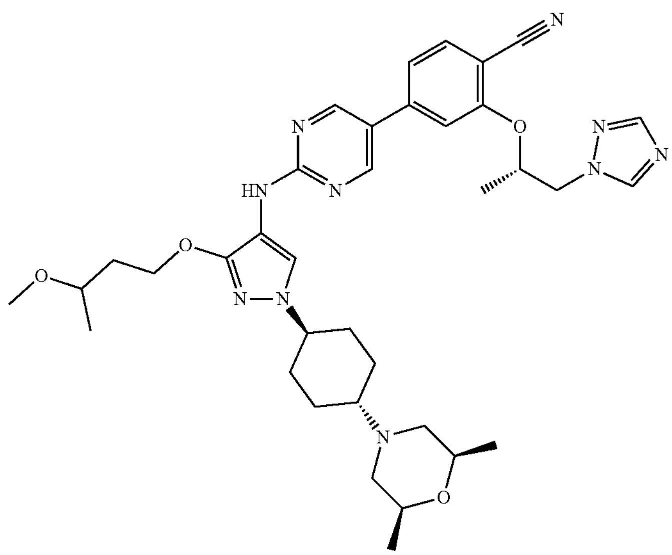 [SMILES: COC(C)CCOc1nn([C@H]2CC[C@H](N3C[C@@H](C)O[C@@H](C)C3)CC2)cc1Nc1ncc(-c2ccc(C#N)c(O[C@@H](C)Cn3cncn3)c2)cn1] |
| 304 | 5-(3-(((S)-1-(1H-1,2,4-triazol-1-yl)propan-2-yl)oxy)-4-chlorophenyl)-N-(1-((1r,4r)-4-((2S,6R)-2,6-dimethylmorpholino)cyclohexyl)-3-(3-methoxybutoxy)-1H-pyrazol-4-yl)pyrimidin-2-amine | 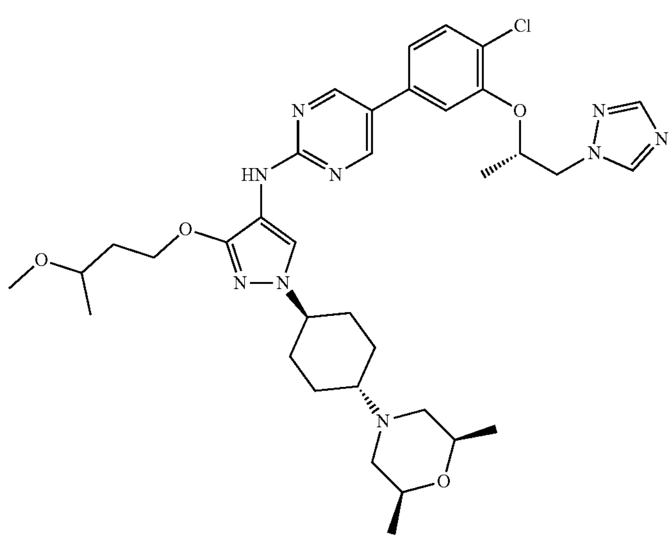 [SMILES: COC(C)CCOc1nn([C@H]2CC[C@H](N3C[C@@H](C)O[C@@H](C)C3)CC2)cc1Nc1ncc(-c2ccc(Cl)c(O[C@@H](C)Cn3cncn3)c2)cn1] |

TABLE 2-continued

| Ex. No. | IUPAC NAME | STRUCTURE |
| --- | --- | --- |
| 305 | 2-(((S)-1-(1H-tetrazol-1-yl)propan-2-yl)oxy)-4-(2-((3-(2-(2-(2-methoxyethoxy)ethoxy)ethoxy)-1-((1r,4r)-4-morpholinocyclohexyl)-1H-pyrazol-4-yl)amino)pyrimidin-5-yl)benzonitrile | 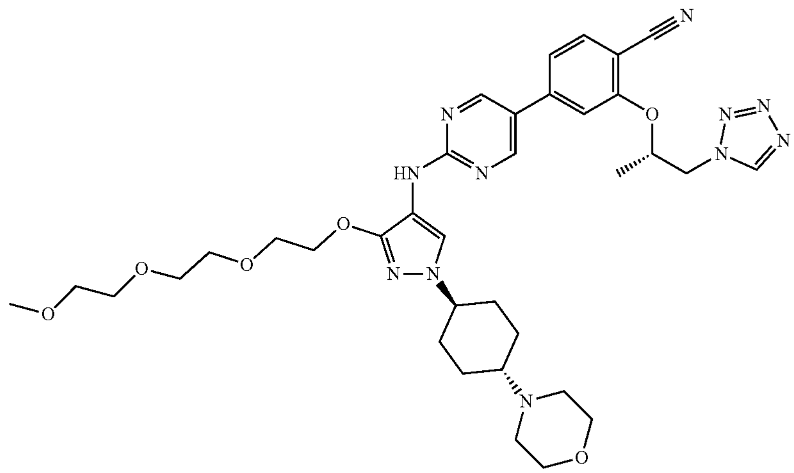 [SMILES: COCCOCCOCCOc1nn([C@H]2CC[C@H](N3CCOCC3)CC2)cc1Nc1ncc(-c2ccc(C#N)c(O[C@@H](C)Cn3cnnn3)c2)cn1] |
| 306 | 5-(3-(((S)-1-(1H-tetrazol-1-yl)propan-2-yl)oxy)-4-chlorophenyl)-N-(3-(2-(2-(2-methoxyethoxy)ethoxy)ethoxy)-1-((1r,4r)-4-morpholinocyclohexyl)-1H-pyrazol-4-yl)pyrimidin-2-amine | 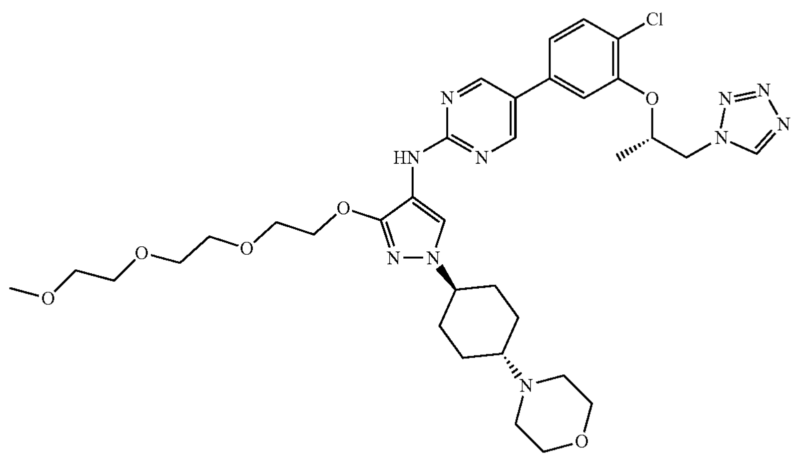 [SMILES: COCCOCCOCCOc1nn([C@H]2CC[C@H](N3CCOCC3)CC2)cc1Nc1ncc(-c2ccc(Cl)c(O[C@@H](C)Cn3cnnn3)c2)cn1] |
| 307 | 2-(((S)-1-(1H-1,2,4-triazol-1-yl)propan-2-yl)oxy)-4-(2-((3-(2-(2-(2-methoxyethoxy)ethoxy)ethoxy)-1-((1r,4r)-4-morpholinocyclohexyl)-1H-pyrazol-4-yl)amino)pyrimidin-5-yl)benzonitrile | 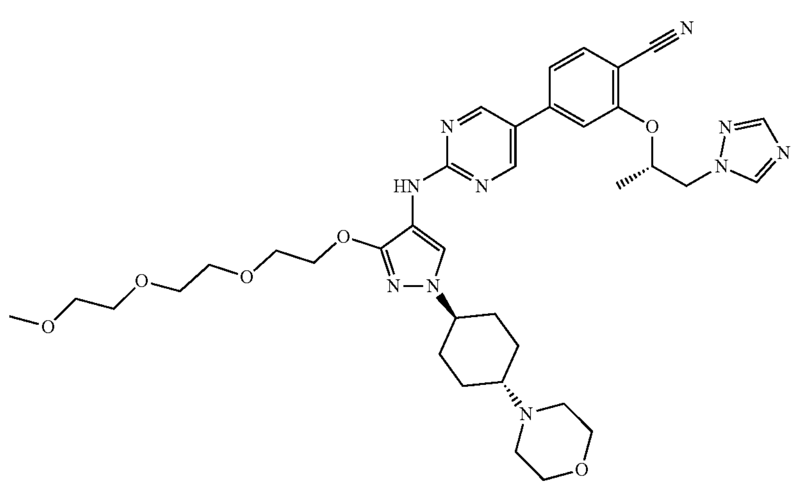 [SMILES: COCCOCCOCCOc1nn([C@H]2CC[C@H](N3CCOCC3)CC2)cc1Nc1ncc(-c2ccc(C#N)c(O[C@@H](C)Cn3cncn3)c2)cn1] |

TABLE 2-continued

| Ex. No. | IUPAC NAME | STRUCTURE |
| --- | --- | --- |
| 308 | 5-(3-(((S)-1-(1H-1,2,4-triazol-1-yl)propan-2-yl)oxy)-4-chlorophenyl)-N-(3-(2-(2-(2-methoxyethoxy)ethoxy)ethoxy)-1-((1r,4r)-4-morpholinocyclohexyl)-1H-pyrazol-4-yl)pyrimidin-2-amine | 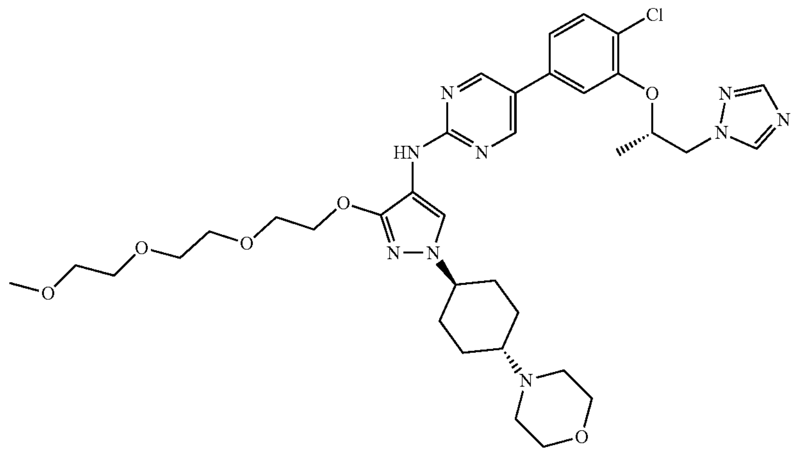 [SMILES: COCCOCCOCCOc1nn([C@H]2CC[C@H](N3CCOCC3)CC2)cc1Nc1ncc(-c2ccc(Cl)c(O[C@@H](C)Cn3cncn3)c2)cn1] |
| 309 | 2-(((S)-1-(1H-tetrazol-1-yl)propan-2-yl)oxy)-4-(2-((1-((1r,4r)-4-((1R,5S)-3-oxa-8-azabicyclo[3.2.1]octan-8-yl)cyclohexyl)-3-(2-(2-(2-methoxyethoxy)ethoxy)ethoxy)-1H-pyrazol-4-yl)amino)pyrimidin-5-yl)benzonitrile | 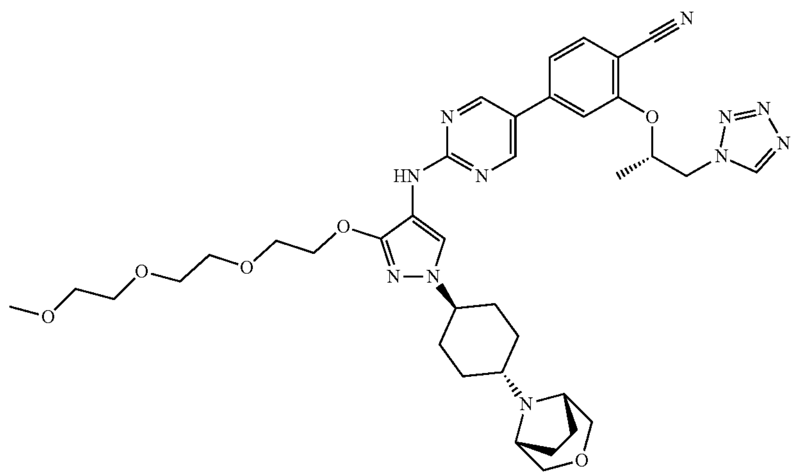 [SMILES: COCCOCCOCCOc1nn([C@H]2CC[C@H](N3[C@@H]4CC[C@H]3COC4)CC2)cc1Nc1ncc(-c2ccc(C#N)c(O[C@@H](C)Cn3cnnn3)c2)cn1] |
| 310 | 5-(3-(((S)-1-(1H-tetrazol-1-yl)propan-2-yl)oxy)-4-chlorophenyl)-N-(1-((1r,4r)-4-((1R,5S)-3-oxa-8-azabicyclo[3.2.1]octan-8-yl)cyclohexyl)-3-(2-(2-(2-methoxyethoxy)ethoxy)ethoxy)-1H-pyrazol-4-yl)pyrimidin-2-amine | 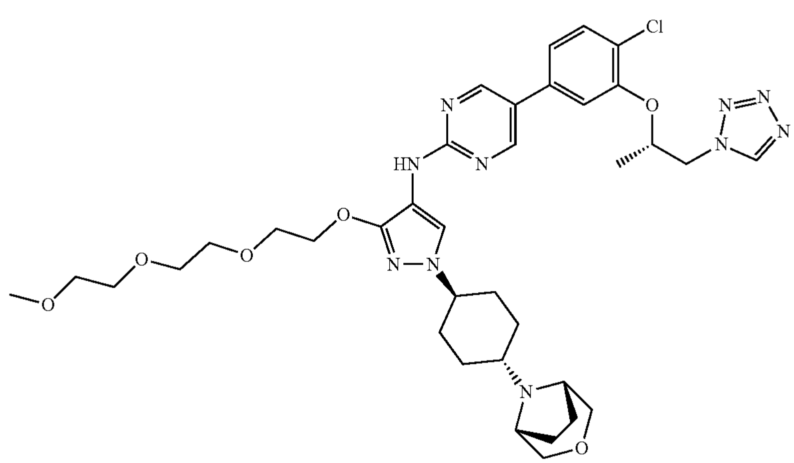 [SMILES: COCCOCCOCCOc1nn([C@H]2CC[C@H](N3[C@@H]4CC[C@H]3COC4)CC2)cc1Nc1ncc(-c2ccc(Cl)c(O[C@@H](C)Cn3cnnn3)c2)cn1] |

TABLE 2-continued

| Ex. No. | IUPAC NAME | STRUCTURE |
|---|---|---|
| 311 | 2-(((S)-1-(1H-1,2,4-triazol-1-yl)propan-2-yl)oxy)-4-(2-((1-((1r,4r)-4-((1R,5S)-3-oxa-8-azabicyclo[3.2.1]octan-8-yl)cyclohexyl)-3-(2-(2-(2-methoxyethoxy)ethoxy)ethoxy)-1H-pyrazol-4-yl)amino)pyrimidin-5-yl)benzonitrile | 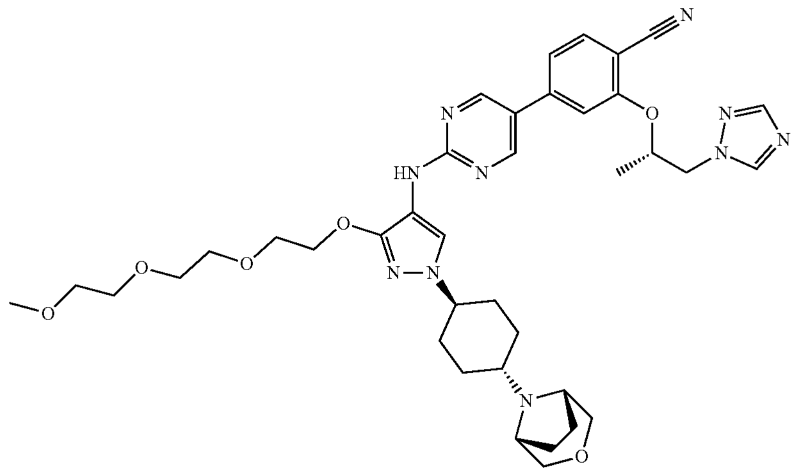 [SMILES: COCCOCCOCCOc1nn([C@H]2CC[C@H](N3[C@@H]4CC[C@H]3COC4)CC2)cc1Nc1ncc(-c2ccc(C#N)c(O[C@@H](C)Cn3cncn3)c2)cn1] |
| 312 | 5-(3-(((S)-1-(1H-1,2,4-triazol-1-yl)propan-2-yl)oxy)-4-chlorophenyl)-N-(1-((1r,4r)-4-((1R,5S)-3-oxa-8-azabicyclo[3.2.1]octan-8-yl)cyclohexyl)-3-(2-(2-(2-methoxyethoxy)ethoxy)ethoxy)-1H-pyrazol-4-yl)pyrimidin-2-amine | 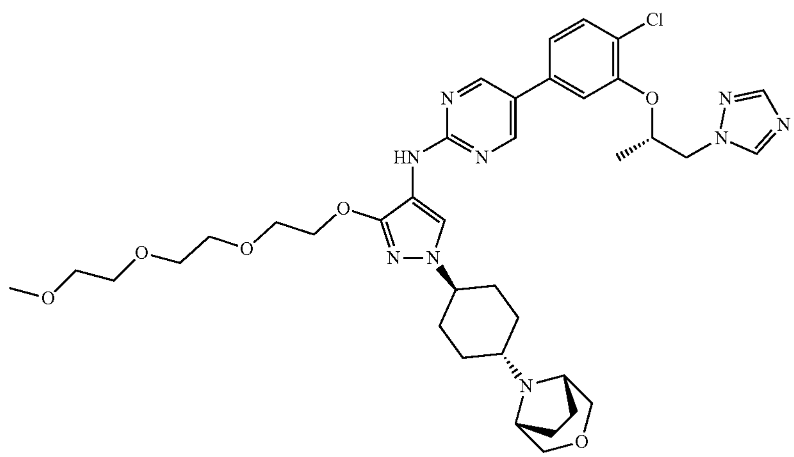 [SMILES: COCCOCCOCCOc1nn([C@H]2CC[C@H](N3[C@@H]4CC[C@H]3COC4)CC2)cc1Nc1ncc(-c2ccc(Cl)c(O[C@@H](C)Cn3cncn3)c2)cn1] |
| 313 | 2-(((S)-1-(1H-tetrazol-1-yl)propan-2-yl)oxy)-4-(2-((1-((1r,4r)-4-((2S,6R)-2,6-dimethylmorpholino)cyclohexyl)-3-(2-(2-(2-methoxyethoxy)ethoxy)ethoxy)-1H-pyrazol-4-yl)amino)pyrimidin-5-yl)benzonitrile | 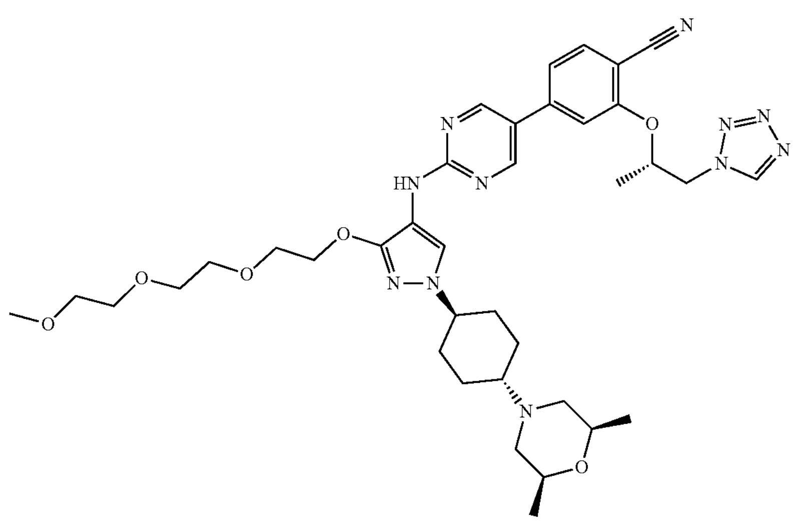 [SMILES: COCCOCCOCCOc1nn([C@H]2CC[C@H](N3C[C@@H](C)O[C@@H](C)C3)CC2)cc1Nc1ncc(-c2ccc(C#N)c(O[C@@H](C)Cn3cnnn3)c2)cn1] |

TABLE 2-continued

| Ex. No. | IUPAC NAME | STRUCTURE |
|---|---|---|
| 314 | 5-(3-(((S)-1-(1H-tetrazol-1-yl)propan-2-yl)oxy)-4-chlorophenyl)-N-(1-((1r,4r)-4-((2S,6R)-2,6-dimethylmorpholino)cyclohexyl)-3-(2-(2-(2-methoxyethoxy)ethoxy)ethoxy)-1H-pyrazol-4-yl)pyrimidin-2-amine | 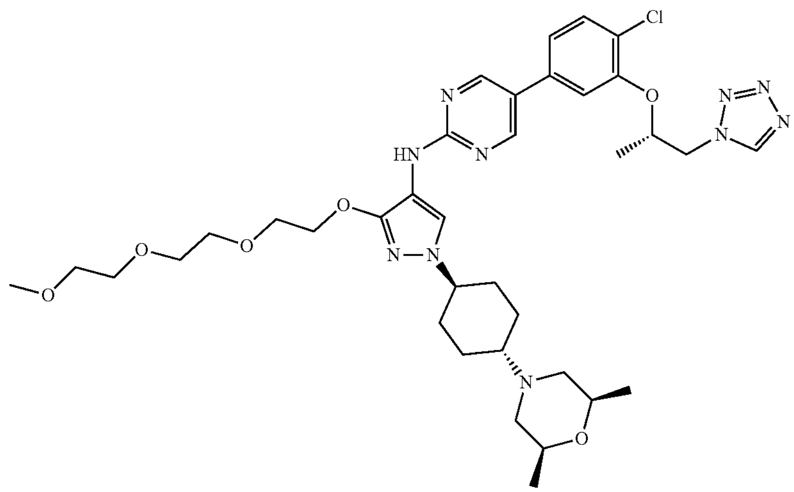 [SMILES: COCCOCCOCCOc1nn([C@H]2CC[C@H](N3C[C@@H](C)O[C@@H](C)C3)CC2)cc1Nc1ncc(-c2ccc(Cl)c(O[C@@H](C)Cn3cnnn3)c2)cn1] |
| 315 | 2-(((S)-1-(1H-1,2,4-triazol-1-yl)propan-2-yl)oxy)-4-(2-((1-((1r,4r)-4-((2S,6R)-2,6-dimethylmorpholino)cyclohexyl)-3-(2-(2-(2-methoxyethoxy)ethoxy)ethoxy)-1H-pyrazol-4-yl)amino)pyrimidin-5-yl)benzonitrile | 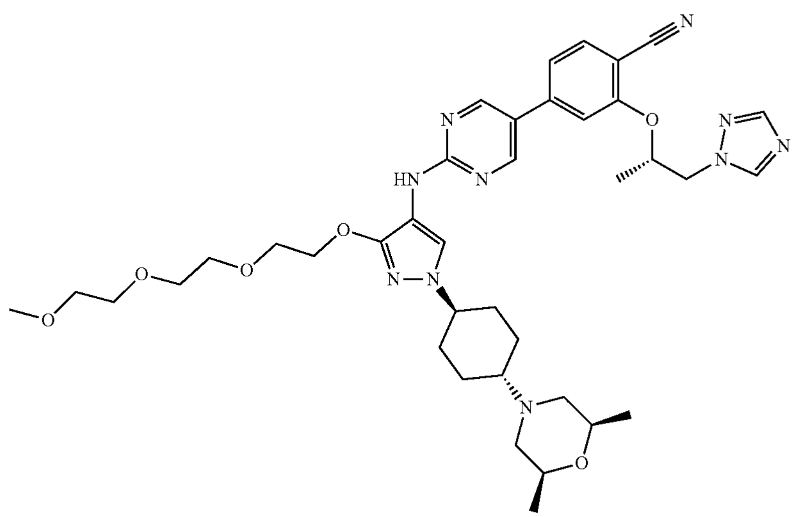 [SMILES: COCCOCCOCCOc1nn([C@H]2CC[C@H](N3C[C@@H](C)O[C@@H](C)C3)CC2)cc1Nc1ncc(-c2ccc(C#N)c(O[C@@H](C)Cn3cncn3)c2)cn1] |
| 316 | 5-(3-(((S)-1-(1H-1,2,4-triazol-1-yl)propan-2-yl)oxy)-4-chlorophenyl)-N-(1-((1r,4r)-4-((2S,6R)-2,6-dimethylmorpholino)cyclohexyl)-3-(2-(2-(2-methoxyethoxy)ethoxy)ethoxy)-1H-pyrazol-4-yl)pyrimidin-2-amine | 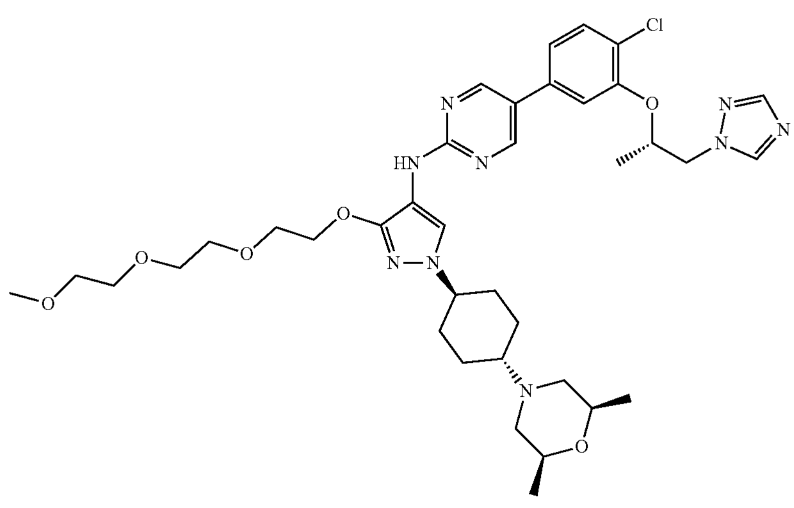 [SMILES: COCCOCCOCCOc1nn([C@H]2CC[C@H](N3C[C@@H](C)O[C@@H](C)C3)CC2)cc1Nc1ncc(-c2ccc(Cl)c(O[C@@H](C)Cn3cncn3)c2)cn1] |

TABLE 2-continued

| Ex. No. | IUPAC NAME | STRUCTURE |
| --- | --- | --- |
| 317 | 2-(((S)-1-(1H-tetrazol-1-yl)propan-2-yl)oxy)-4-(2-((3-(3-(2-methoxyethoxy)propoxy)-1-((1r,4r)-4-morpholinocyclohexyl)-1H-pyrazol-4-yl)amino)pyrimidin-5-yl)benzonitrile | 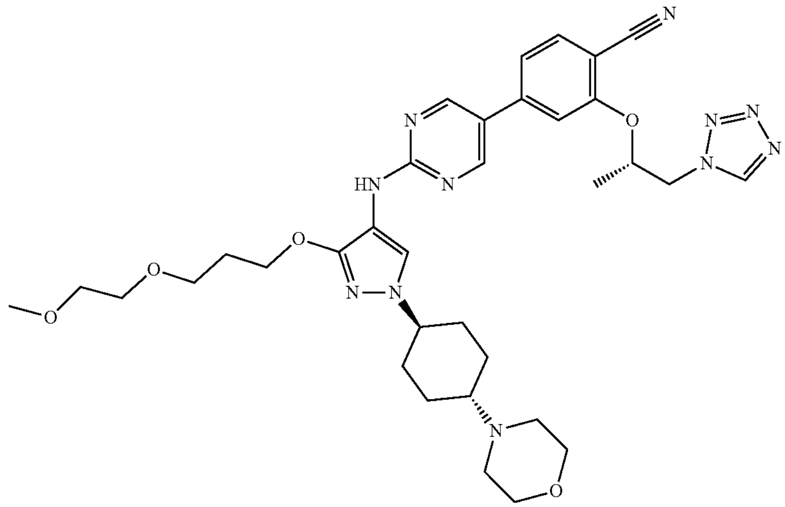 [SMILES: COCCOCCCOc1nn([C@H]2CC[C@H](N3CCOCC3)CC2)cc1Nc1ncc(-c2ccc(C#N)c(O[C@@H](C)Cn3cnnn3)c2)cn1] |
| 318 | 5-(3-(((S)-1-(1H-tetrazol-1-yl)propan-2-yl)oxy)-4-chlorophenyl)-N-(3-(3-(2-methoxyethoxy)propoxy)-1-((1r,4r)-4-morpholinocyclohexyl)-1H-pyrazol-4-yl)pyrimidin-2-amine | 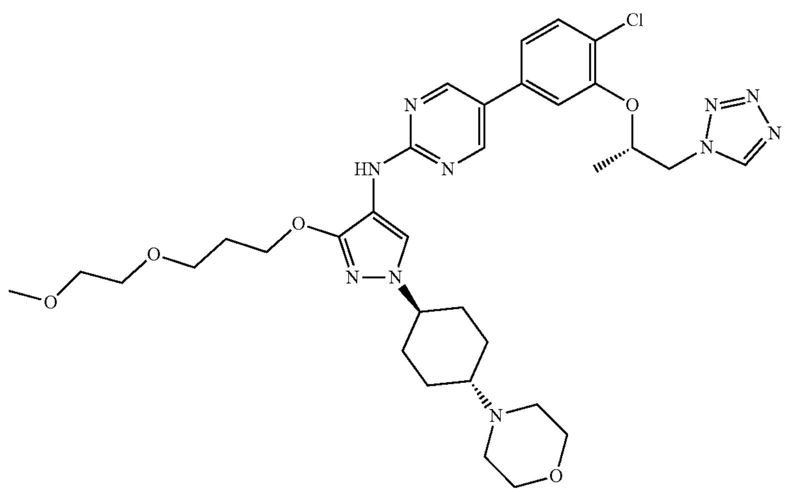 [SMILES: COCCOCCCOc1nn([C@H]2CC[C@H](N3CCOCC3)CC2)cc1Nc1ncc(-c2ccc(Cl)c(O[C@@H](C)Cn3cnnn3)c2)cn1] |
| 319 | 2-(((S)-1-(1H-1,2,4-triazol-1-yl)propan-2-yl)oxy)-4-(2-((3-(3-(2-methoxyethoxy)propoxy)-1-((1r,4r)-4-morpholinocyclohexyl)-1H-pyrazol-4-yl)amino)pyrimidin-5-yl)benzonitrile | 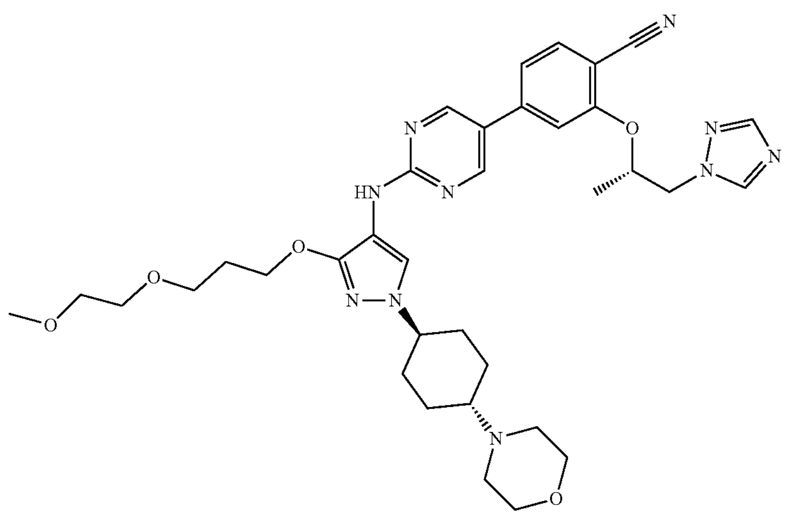 [SMILES: COCCOCCCOc1nn([C@H]2CC[C@H](N3CCOCC3)CC2)cc1Nc1ncc(-c2ccc(C#N)c(O[C@@H](C)Cn3cncn3)c2)cn1] |

TABLE 2-continued

| Ex. No. | IUPAC NAME | STRUCTURE |
|---|---|---|
| 320 | 5-(3-(((S)-1-(1H-1,2,4-triazol-1-yl)propan-2-yl)oxy)-4-chlorophenyl)-N-(3-(3-(2-methoxyethoxy)propoxy)-1-((1r,4r)-4-morpholinocyclohexyl)-1H-pyrazol-4-yl)pyrimidin-2-amine | 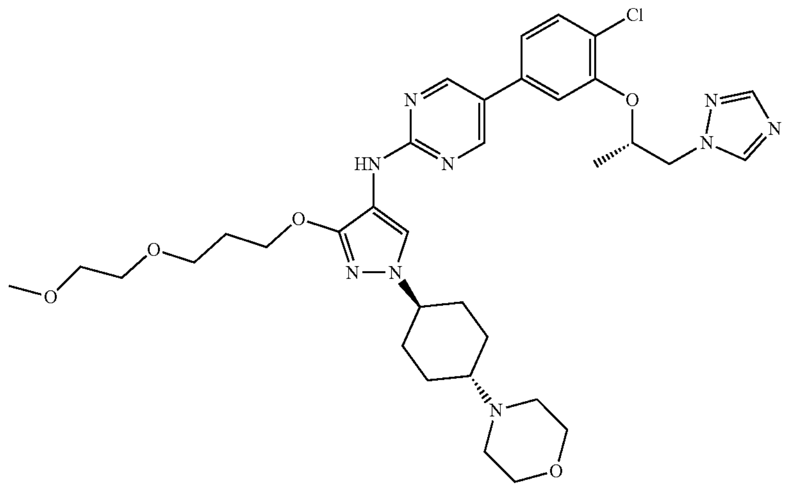 [SMILES: COCCOCCCOc1nn([C@H]2CC[C@H](N3CCOCC3)CC2)cc1Nc1ncc(-c2ccc(Cl)c(O[C@@H](C)Cn3cncn3)c2)cn1] |
| 321 | 2-(((S)-1-(1H-tetrazol-1-yl)propan-2-yl)oxy)-4-(2-((1-((1r,4r)-4-((1R,5S)-3-oxa-8-azabicyclo[3.2.1]octan-8-yl)cyclohexyl)-3-(3-(2-methoxyethoxy)propoxy)-1H-pyrazol-4-yl)amino)pyrimidin-5-yl)benzonitrile | 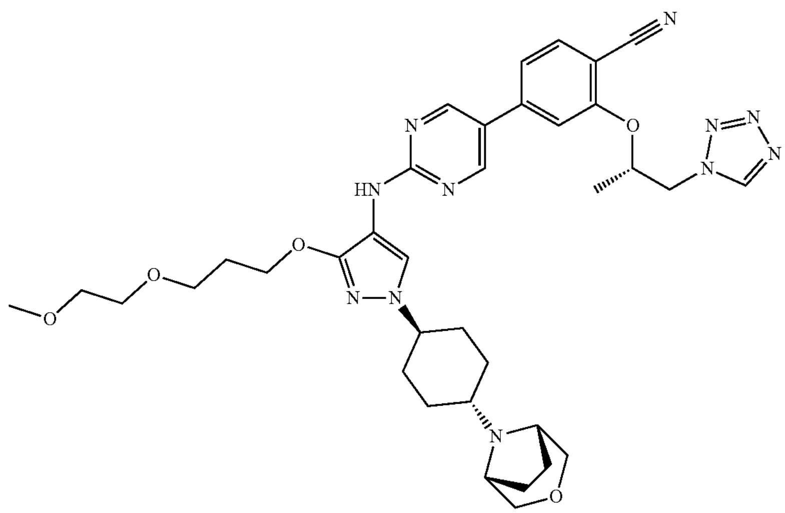 [SMILES: COCCOCCCOc1nn([C@H]2CC[C@H](N3[C@@H]4CC[C@H]3COC4)CC2)cc1Nc1ncc(-c2ccc(C#N)c(O[C@@H](C)Cn3cnnn3)c2)cn1] |
| 322 | 5-(3-(((S)-1-(1H-tetrazol-1-yl)propan-2-yl)oxy)-4-chlorophenyl)-N-(1-((1r,4r)-4-((1R,5S)-3-oxa-8-azabicyclo[3.2.1]octan-8-yl)cyclohexyl)-3-(3-(2-methoxyethoxy)propoxy)-1H-pyrazol-4-yl)pyrimidin-2-amine | 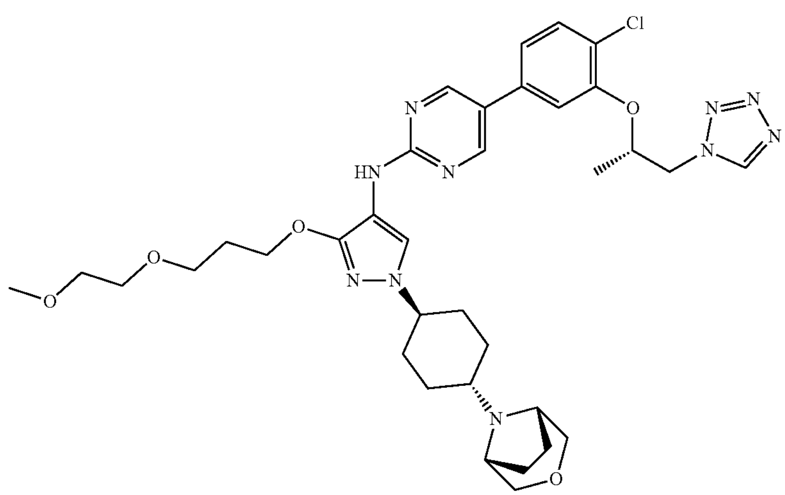 [SMILES: COCCOCCCOc1nn([C@H]2CC[C@H](N3[C@@H]4CC[C@H]3COC4)CC2)cc1Nc1ncc(-c2ccc(Cl)c(O[C@@H](C)Cn3cnnn3)c2)cn1] |

TABLE 2-continued

| Ex. No. | IUPAC NAME | STRUCTURE |
|---|---|---|
| 323 | 2-(((S)-1-(1H-1,2,4-triazol-1-yl)propan-2-yl)oxy)-4-(2-((1-((1r,4r)-4-((1R,5S)-3-oxa-8-azabicyclo[3.2.1]octan-8-yl)cyclohexyl)-3-(3-(2-methoxyethoxy)propoxy)-1H-pyrazol-4-yl)amino)pyrimidin-5-yl)benzonitrile | 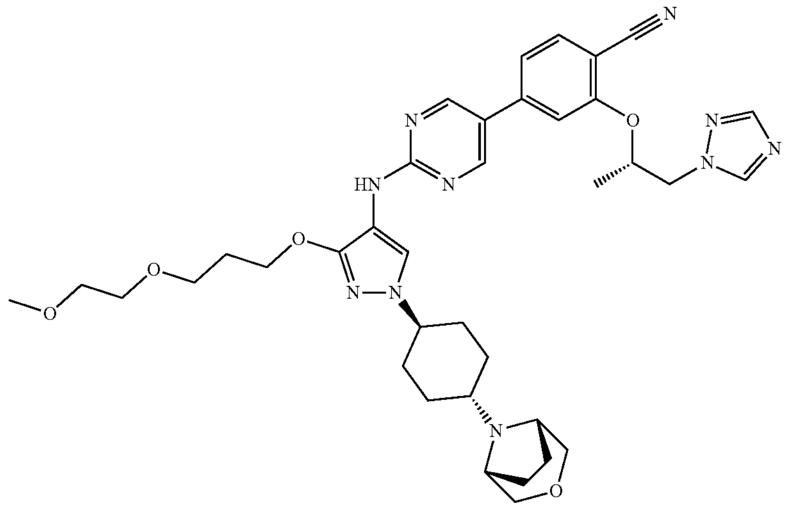 [SMILES: COCCOCCCOc1nn([C@H]2CC[C@H](N3[C@@H]4CC[C@H]3COC4)CC2)cc1Nc1ncc(-c2ccc(C#N)c(O[C@@H](C)Cn3cncn3)c2)cn1] |
| 324 | 5-(3-(((S)-1-(1H-1,2,4-triazol-1-yl)propan-2-yl)oxy)-4-chlorophenyl)-N-(1-((1r,4r)-4-((1R,5S)-3-oxa-8-azabicyclo[3.2.1]octan-8-yl)cyclohexyl)-3-(3-(2-methoxyethoxy)propoxy)-1H-pyrazol-4-yl)pyrimidin-2-amine | 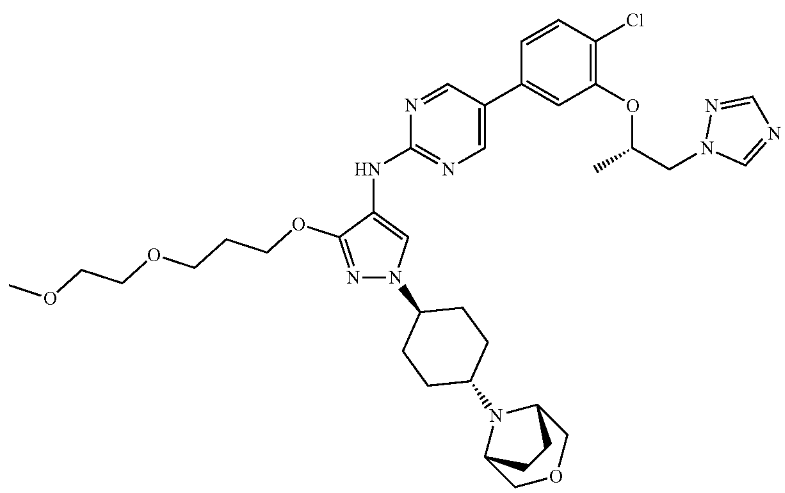 [SMILES: COCCOCCCOc1nn([C@H]2CC[C@H](N3[C@@H]4CC[C@H]3COC4)CC2)cc1Nc1ncc(-c2ccc(Cl)c(O[C@@H](C)Cn3cncn3)c2)cn1] |
| 325 | 2-(((S)-1-(1H-tetrazol-1-yl)propan-2-yl)oxy)-4-(2-((1-((1r,4r)-4-((2S,6R)-2,6-dimethylmorpholino)cyclohexyl)-3-(3-(2-methoxyethoxy)propoxy)-1H-pyrazol-4-yl)amino)pyrimidin-5-yl)benzonitrile | 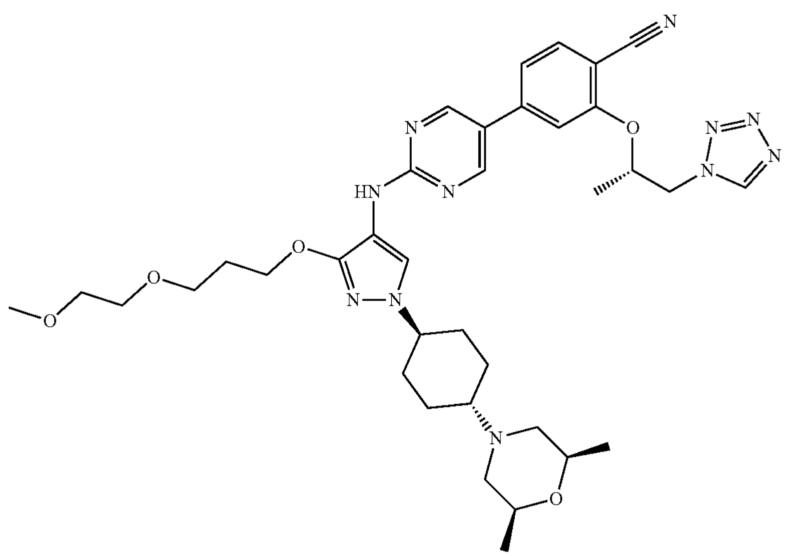 [SMILES: COCCOCCCOc1nn([C@H]2CC[C@H](N3C[C@@H](C)O[C@@H](C)C3)CC2)cc1Nc1ncc(-c2ccc(C#N)c(O[C@@H](C)Cn3cnnn3)c2)cn1] |

TABLE 2-continued

| Ex. No. | IUPAC NAME | STRUCTURE |
|---|---|---|
| 326 | 5-(3-(((S)-1-(1H-tetrazol-1-yl)propan-2-yl)oxy)-4-chlorophenyl)-N-(1-((1r,4r)-4-((2S,6R)-2,6-dimethylmorpholino)cyclohexyl)-3-(3-(2-methoxyethoxy)propoxy)-1H-pyrazol-4-yl)pyrimidin-2-amine | 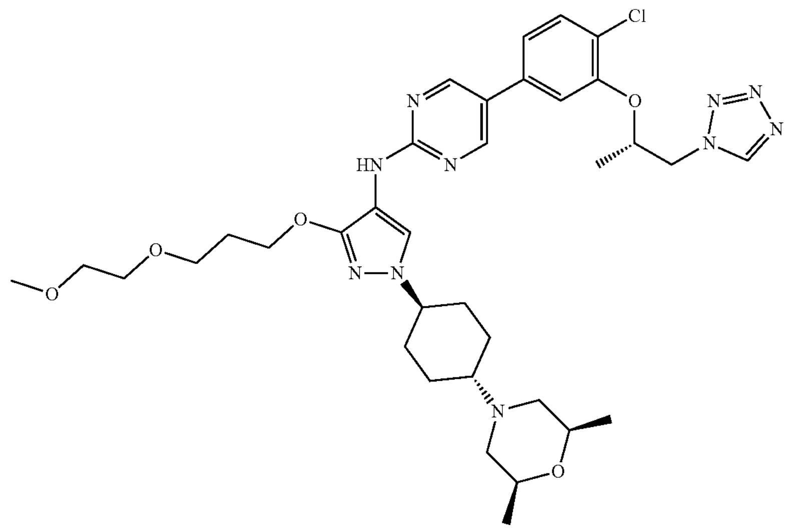 [SMILES: COCCOCCCOc1nn([C@H]2CC[C@H](N3C[C@@H](C)O[C@@H](C)C3)CC2)cc1Nc1ncc(-c2ccc(Cl)c(O[C@@H](C)Cn3cnnn3)c2)cn1] |
| 327 | 2-(((S)-1-(1H-1,2,4-triazol-1-yl)propan-2-yl)oxy)-4-(2-((1-((1r,4r)-4-((2S,6R)-2,6-dimethylmorpholino)cyclohexyl)-3-(3-(2-methoxyethoxy)propoxy)-1H-pyrazol-4-yl)amino)pyrimidin-5-yl)benzonitrile | 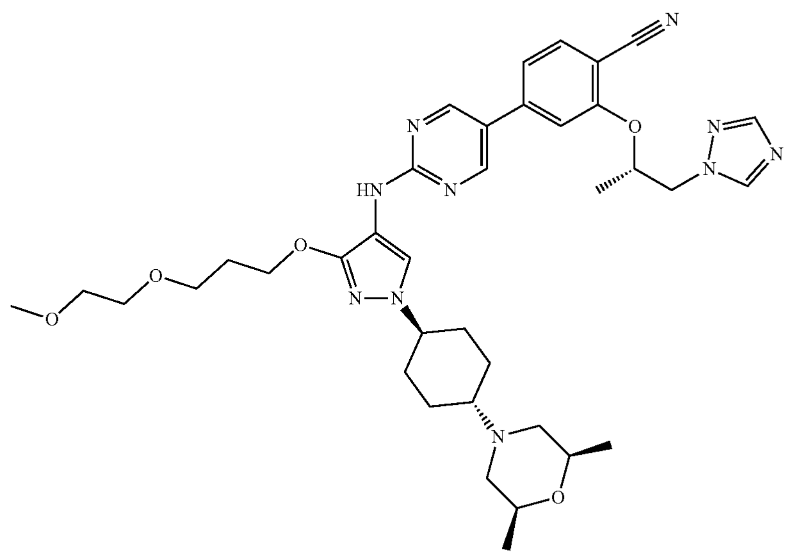 [SMILES: COCCOCCCOc1nn([C@H]2CC[C@H](N3C[C@@H](C)O[C@@H](C)C3)CC2)cc1Nc1ncc(-c2ccc(C#N)c(O[C@@H](C)Cn3cncn3)c2)cn1] |
| 328 | 5-(3-(((S)-1-(1H-1,2,4-triazol-1-yl)propan-2-yl)oxy)-4-chlorophenyl)-N-(1-((1r,4r)-4-((2S,6R)-2,6-dimethylmorpholino)cyclohexyl)-3-(3-(2-methoxyethoxy)propoxy)-1H-pyrazol-4-yl)pyrimidin-2-amine | 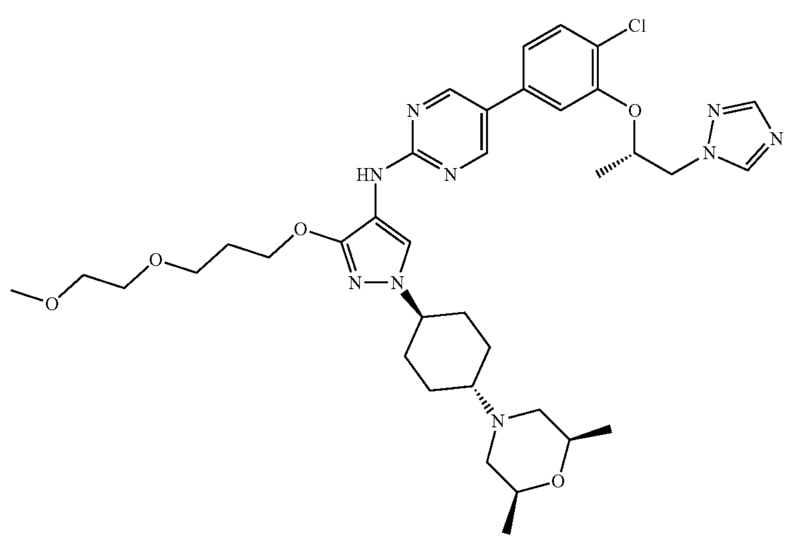 [SMILES: COCCOCCCOc1nn([C@H]2CC[C@H](N3C[C@@H](C)O[C@@H](C)C3)CC2)cc1Nc1ncc(-c2ccc(Cl)c(O[C@@H](C)Cn3cncn3)c2)cn1] |

TABLE 2-continued

| Ex. No. | IUPAC NAME | STRUCTURE |
| --- | --- | --- |
| 329 | 2-(((S)-1-(1H-tetrazol-1-yl)propan-2-yl)oxy)-4-(2-((3-(3-(2-(2-methoxyethoxy)ethoxy)propoxy)-1-((1r,4r)-4-morpholinocyclohexyl)-1H-pyrazol-4-yl)amino)pyrimidin-5-yl)benzonitrile | 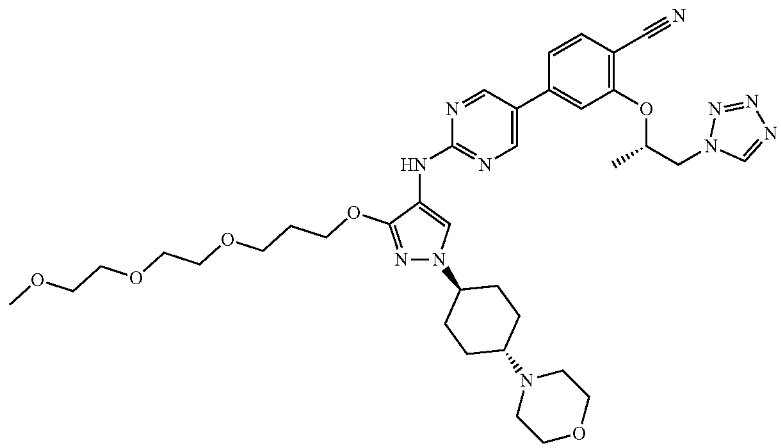 [SMILES: COCCOCCOCCCOc1nn([C@H]2CC[C@H](N3CCOCC3)CC2)cc1Nc1ncc(-c2ccc(C#N)c(O[C@@H](C)Cn3cnnn3)c2)cn1] |
| 330 | 5-(3-(((S)-1-(1H-tetrazol-1-yl)propan-2-yl)oxy)-4-chlorophenyl)-N-(3-(2-(2-methoxyethoxy)ethoxy)propoxy)-1-((1r,4r)-4-morpholinocyclohexyl)-1H-pyrazol-4-yl)pyrimidin-2-amine | 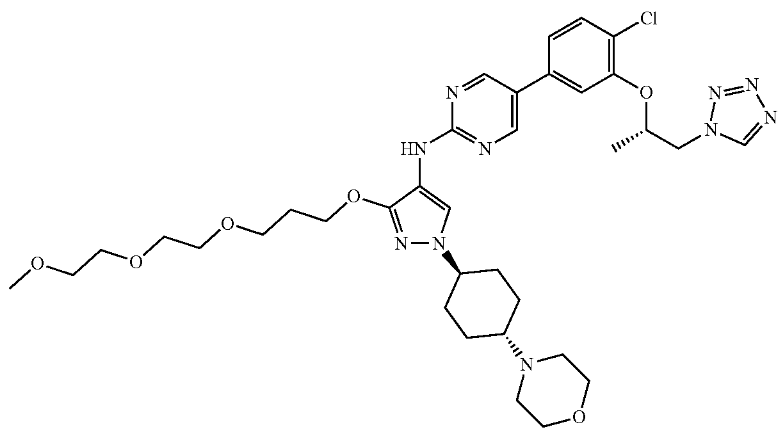 [SMILES: COCCOCCOCCCOc1nn([C@H]2CC[C@H](N3CCOCC3)CC2)cc1Nc1ncc(-c2ccc(Cl)c(O[C@@H](C)Cn3cnnn3)c2)cn1] |
| 331 | 2-(((S)-1-(1H-1,2,4-triazol-1-yl)propan-2-yl)oxy)-4-(2-((3-(3-(2-(2-methoxyethoxy)ethoxy)propoxy)-1-((1r,4r)-4-morpholinocyclohexyl)-1H-pyrazol-4-yl)amino)pyrimidin-5-yl)benzonitrile | 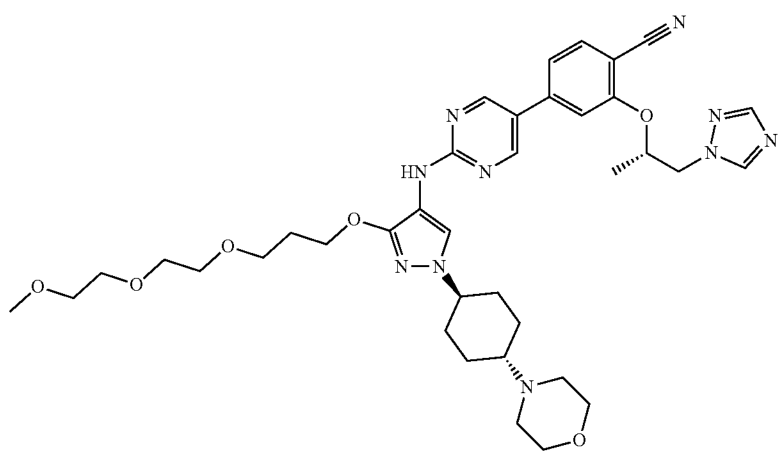 [SMILES: COCCOCCOCCCOc1nn([C@H]2CC[C@H](N3CCOCC3)CC2)cc1Nc1ncc(-c2ccc(C#N)c(O[C@@H](C)Cn3cncn3)c2)cn1] |

TABLE 2-continued

| Ex. No. | IUPAC NAME | STRUCTURE |
|---|---|---|
| 332 | 5-(3-(((S)-1-(1H-1,2,4-triazol-1-yl)propan-2-yl)oxy)-4-chlorophenyl)-N-(3-(3-(2-(2-methoxyethoxy)ethoxy)propoxy)-1-((1r,4r)-4-morpholinocyclohexyl)-1H-pyrazol-4-yl)pyrimidin-2-amine | 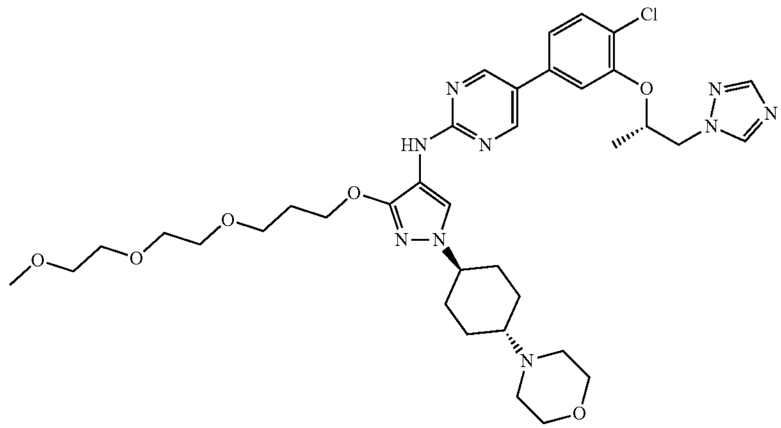 [SMILES: COCCOCCOCCCOc1nn([C@H]2CC[C@H](N3CCOCC3)CC2)cc1Nc1ncc(-c2ccc(Cl)c(O[C@@H](C)Cn3cncn3)c2)cn1] |
| 333 | 2-(((S)-1-(1H-tetrazol-1-yl)propan-2-yl)oxy)-4-(2-((1-((1r,4r)-4-((1R,5S)-3-oxa-8-azabicyclo[3.2.1]octan-8-yl)cyclohexyl)-3-(3-(2-(2-methoxyethoxy)ethoxy)propoxy)-1H-pyrazol-4-yl)amino)pyrimidin-5-yl)benzonitrile | 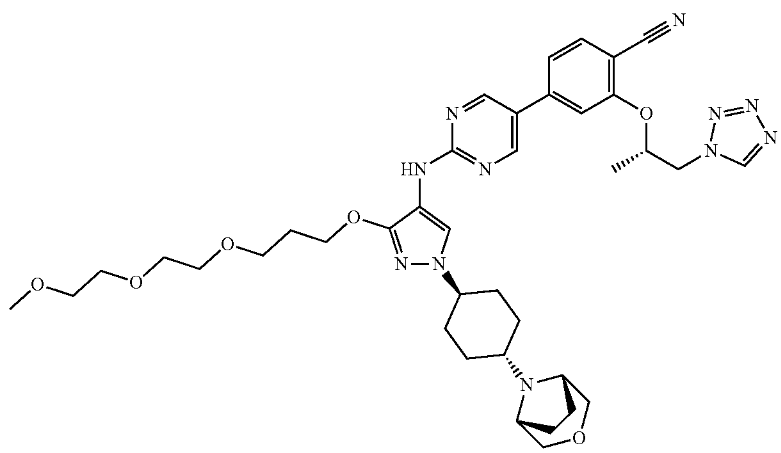 [SMILES: COCCOCCOCCCOc1nn([C@H]2CC[C@H](N3[C@@H]4CC[C@H]3COC4)CC2)cc1Nc1ncc(-c2ccc(C#N)c(O[C@@H](C)Cn3cnnn3)c2)cn1] |
| 334 | 5-(3-(((S)-1-(1H-tetrazol-1-yl)propan-2-yl)oxy)-4-chlorophenyl)-N-(1-((1r,4r)-4-((1R,5S)-3-oxa-8-azabicyclo[3.2.1]octan-8-yl)cyclohexyl)-3-(3-(2-(2-methoxyethoxy)ethoxy)propoxy)-1H-pyrazol-4-yl)pyrimidin-2-amine | 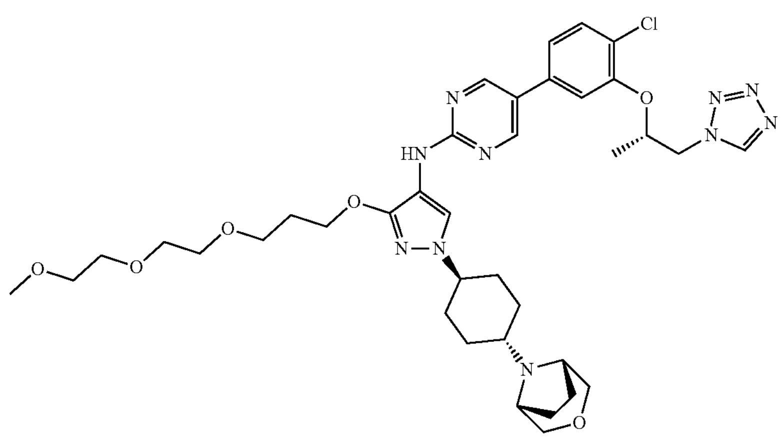 [SMILES: COCCOCCOCCCOc1nn([C@H]2CC[C@H](N3[C@@H]4CC[C@H]3COC4)CC2)cc1Nc1ncc(-c2ccc(Cl)c(O[C@@H](C)Cn3cnnn3)c2)cn1] |

TABLE 2-continued

| Ex. No. | IUPAC NAME | STRUCTURE |
|---|---|---|
| 335 | 2-(((S)-1-(1H-1,2,4-triazol-1-yl)propan-2-yl)oxy)-4-(2-((1-((1r,4r)-4-((1R,5S)-3-oxa-8-azabicyclo[3.2.1]octan-8-yl)cyclohexyl)-3-(3-(2-(2-methoxyethoxy)ethoxy)propoxy)-1H-pyrazol-4-yl)amino)pyrimidin-5-yl)benzonitrile | 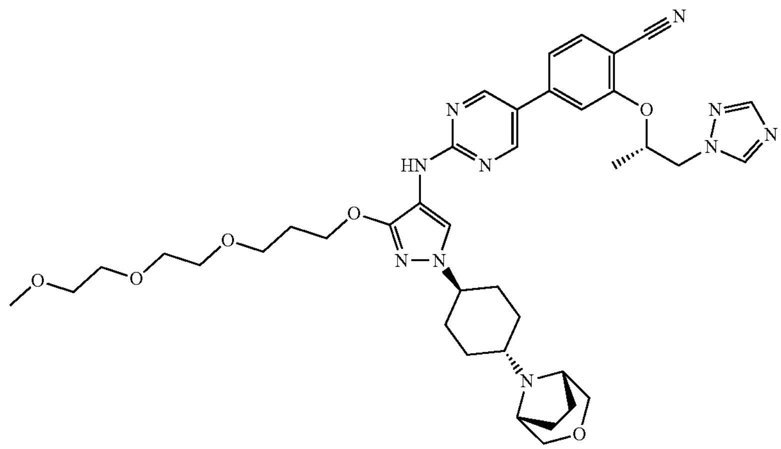 [SMILES: COCCOCCOCCCOc1nn([C@H]2CC[C@H](N3[C@@H]4CC[C@H]3COC4)CC2)cc1Nc1ncc(-c2ccc(C#N)c(O[C@@H](C)Cn3cncn3)c2)cn1] |
| 336 | 5-(3-(((S)-1-(1H-1,2,4-triazol-1-yl)propan-2-yl)oxy)-4-chlorophenyl)-N-(1-((1r,4r)-4-((1R,5S)-3-oxa-8-azabicyclo[3.2.1]octan-8-yl)cyclohexyl)-3-(3-(2-(2-methoxyethoxy)ethoxy)propoxy)-1H-pyrazol-4-yl)pyrimidin-2-amine | 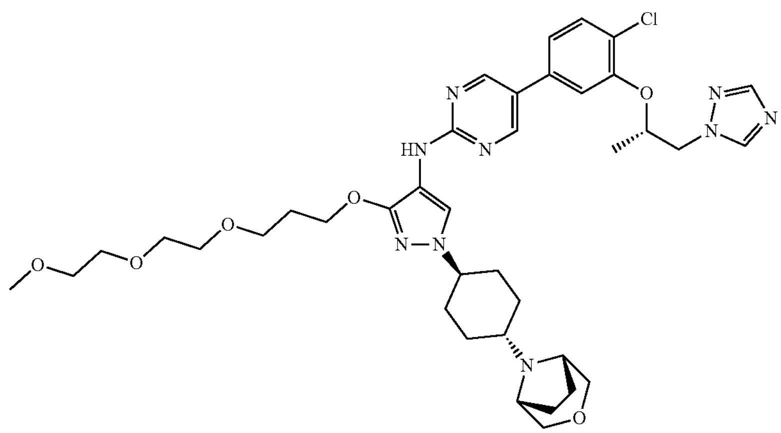 [SMILES: COCCOCCOCCCOc1nn([C@H]2CC[C@H](N3[C@@H]4CC[C@H]3COC4)CC2)cc1Nc1ncc(-c2ccc(Cl)c(O[C@@H](C)Cn3cncn3)c2)cn1] |
| 337 | 2-(((S)-1-(1H-tetrazol-1-yl)propan-2-yl)oxy)-4-(2-((1-((1r,4r)-4-((2S,6R)-2,6-dimethylmorpholino)cyclohexyl)-3-(3-(2-(2-methoxyethoxy)ethoxy)propoxy)-1H-pyrazol-4-yl)amino)pyrimidin-5-yl)benzonitrile | 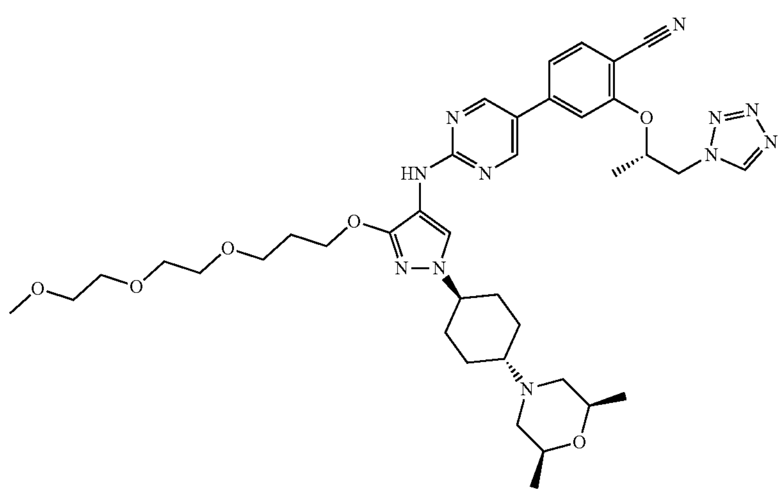 [SMILES: COCCOCCOCCCOc1nn([C@H]2CC[C@H](N3C[C@@H](C)O[C@@H](C)C3)CC2)cc1Nc1ncc(-c2ccc(C#N)c(O[C@@H](C)Cn3cnnn3)c2)cn1] |

TABLE 2-continued

| Ex. No. | IUPAC NAME | STRUCTURE |
|---|---|---|
| 338 | 5-(3-(((S)-1-(1H-tetrazol-1-yl)propan-2-yl)oxy)-4-chlorophenyl)-N-(1-((1r,4r)-4-((2S,6R)-2,6-dimethylmorpholino)cyclohexyl)-3-(3-(2-(2-methoxyethoxy)ethoxy)propoxy)-1H-pyrazol-4-yl)pyrimidin-2-amine | 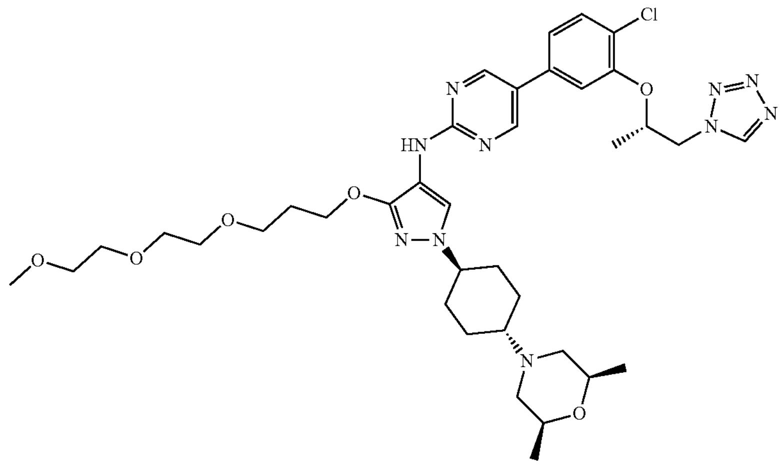 [SMILES: COCCOCCOCCCOc1nn([C@H]2CC[C@H](N3C[C@@H](C)O[C@@H](C)C3)CC2)cc1Nc1ncc(-c2ccc(Cl)c(O[C@@H](C)Cn3cnnn3)c2)cn1] |
| 339 | 2-(((S)-1-(1H-1,2,4-triazol-1-yl)propan-2-yl)oxy)-4-(2-((1-((1r,4r)-4-((2S,6R)-2,6-dimethylmorpholino)cyclohexyl)-3-(3-(2-(2-methoxyethoxy)ethoxy)propoxy)-1H-pyrazol-4-yl)amino)pyrimidin-5-yl)benzonitrile | 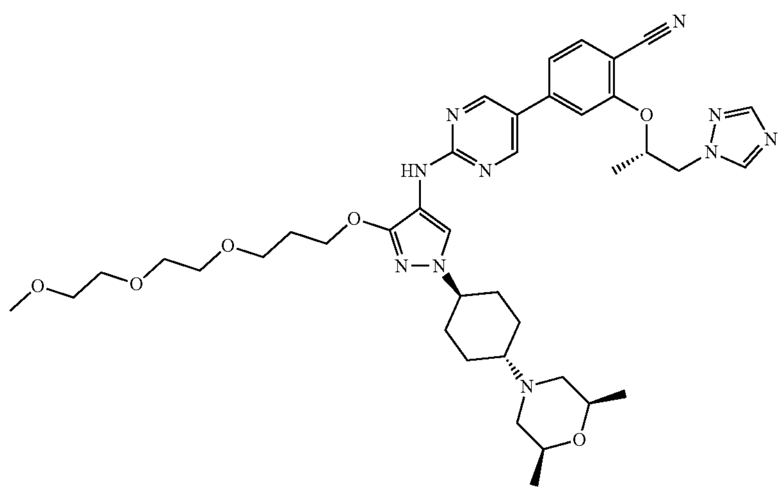 [SMILES: COCCOCCOCCCOc1nn([C@H]2CC[C@H](N3C[C@@H](C)O[C@@H](C)C3)CC2)cc1Nc1ncc(-c2ccc(C#N)c(O[C@@H](C)Cn3cncn3)c2)cn1] |
| 340 | 5-(3-(((S)-1-(1H-1,2,4-triazol-1-yl)propan-2-yl)oxy)-4-chlorophenyl)-N-(1-((1r,4r)-4-((2S,6R)-2,6-dimethylmorpholino)cyclohexyl)-3-(3-(2-(2-methoxyethoxy)ethoxy)propoxy)-1H-pyrazol-4-yl)pyrimidin-2-amine | 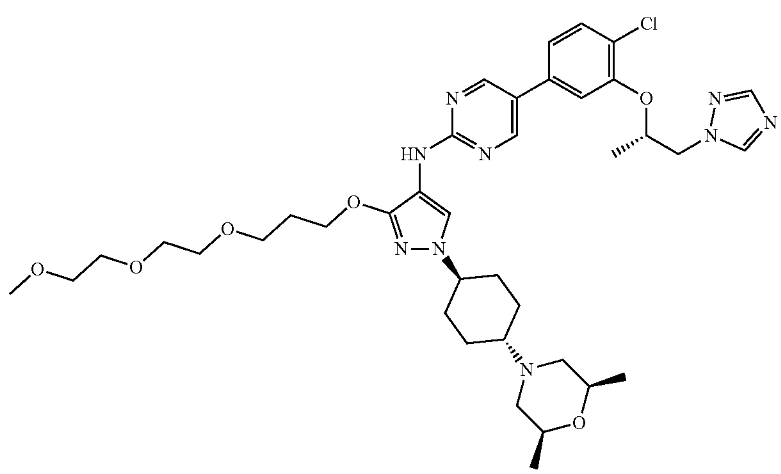 [SMILES: COCCOCCOCCCOc1nn([C@H]2CC[C@H](N3C[C@@H](C)O[C@@H](C)C3)CC2)cc1Nc1ncc(-c2ccc(Cl)c(O[C@@H](C)Cn3cncn3)c2)cn1] |

| Ex. No. | IUPAC NAME |
|---|---|
| 341 | 2-(((S)-1-(1H-tetrazol-1-yl)propan-2-yl)oxy)-4-(2-((3-((2,5,8,11-tetraoxatridecan-13-yl)oxy)-1-((1r,4r)-4-morpholinocyclohexyl)-1H-pyrazol-4-yl)amino)pyrimidin-5-yl)benzonitrile |
| 342 | 5-(3-(((S)-1-(1H-tetrazol-1-yl)propan-2-yl)oxy)-4-chlorophenyl)-N-(3-((2,5,8,11-tetraoxatridecan-13-yl)oxy)-1-((1r,4r)-4-morpholinocyclohexyl)-1H-pyrazol-4-yl)pyrimidin-2-amine |
| 343 | 2-(((S)-1-(1H-1,2,4-triazol-1-yl)propan-2-yl)oxy)-4-(2-((3-((2,5,8,11-tetraoxatridecan-13-yl)oxy)-1-((1r,4r)-4-morpholinocyclohexyl)-1H-pyrazol-4-yl)amino)pyrimidin-5-yl)benzonitrile |

TABLE 2-continued

| Ex. No. | IUPAC NAME | STRUCTURE |
|---|---|---|
| 344 | 5-(3-(((S)-1-(1H-1,2,4-triazol-1-yl)propan-2-yl)oxy)-4-chlorophenyl)-N-(3-((2,5,8,11-tetraoxatridecan-13-yl)oxy)-1-((1r,4r)-4-morpholinocyclohexyl)-1H-pyrazol-4-yl)pyrimidin-2-amine | 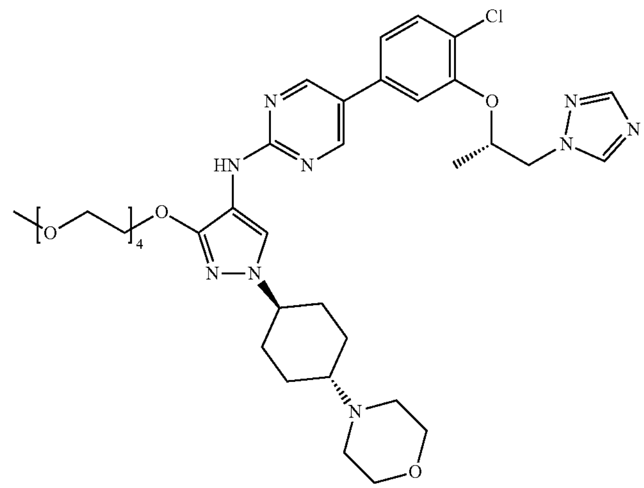 |
| 345 | 2-(((S)-1-(1H-tetrazol-1-yl)propan-2-yl)oxy)-4-(2-((3-((2,5,8,11-tetraoxatridecan-13-yl)oxy)-1-((1r,4r)-4-((1R,5S)-3-oxa-8-azabicyclo[3.2.1]octan-8-yl)cyclohexyl)-1H-pyrazol-4-yl)amino)pyrimidin-5-yl)benzonitrile | 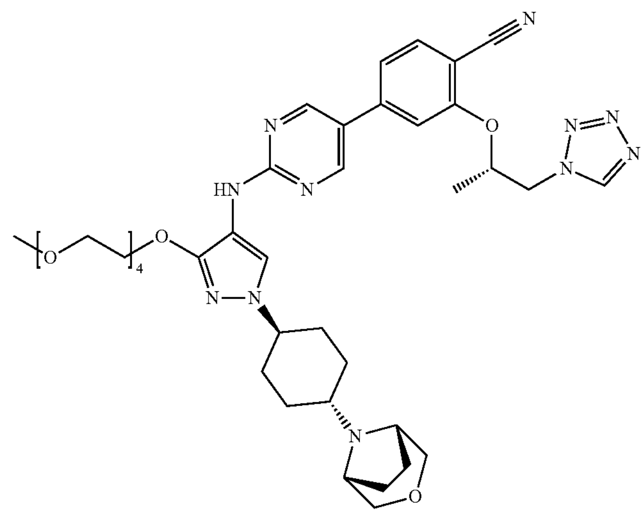 |
| 346 | 5-(3-(((S)-1-(1H-tetrazol-1-yl)propan-2-yl)oxy)-4-chlorophenyl)-N-(3-((2,5,8,11-tetraoxatridecan-13-yl)oxy)-1-((1r,4r)-4-((1R,5S)-3-oxa-8-azabicyclo[3.2.1]octan-8-yl)cyclohexyl)-1H-pyrazol-4-yl)pyrimidin-2-amine | 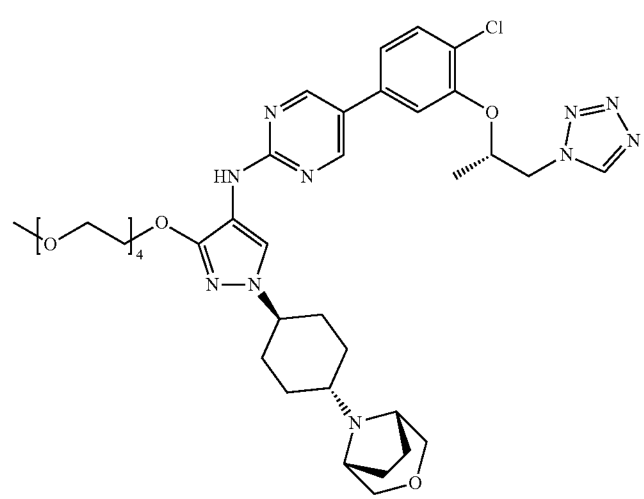 |

TABLE 2-continued

| Ex. No. | IUPAC NAME | STRUCTURE |
|---|---|---|
| 347 | 2-(((S)-1-(1H-1,2,4-triazol-1-yl)propan-2-yl)oxy)-4-(2-((3-((2,5,8,11-tetraoxatridecan-13-yl)oxy)-1-((1r,4r)-4-((1R,5S)-3-oxa-8-azabicyclo[3.2.1]octan-8-yl)cyclohexyl)-1H-pyrazol-4-yl)amino)pyrimidin-5-yl)benzonitrile | 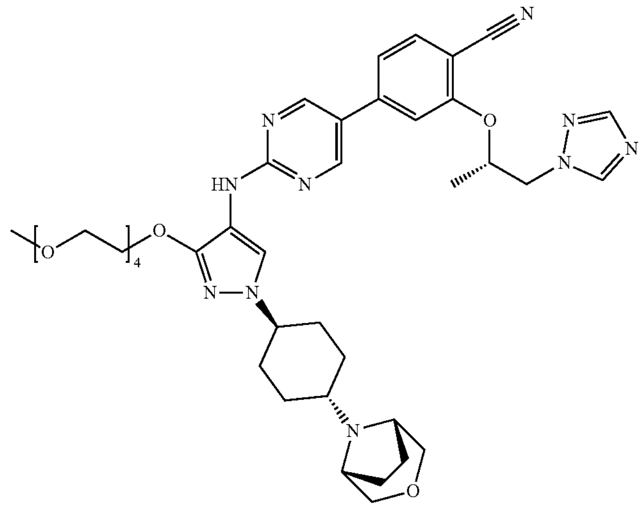 |
| 348 | 5-(3-(((S)-1-(1H-1,2,4-triazol-1-yl)propan-2-yl)oxy)-4-chlorophenyl)-N-(3-((2,5,8-tetraoxatridecan-13-yl)oxy)-1-((1r,4r)-4-((1R,5S)-3-oxa-8-azabicyclo[3.2.1]octan-8-yl)cyclohexyl)-1H-pyrazol-4-yl)pyrimidin-2-amine | 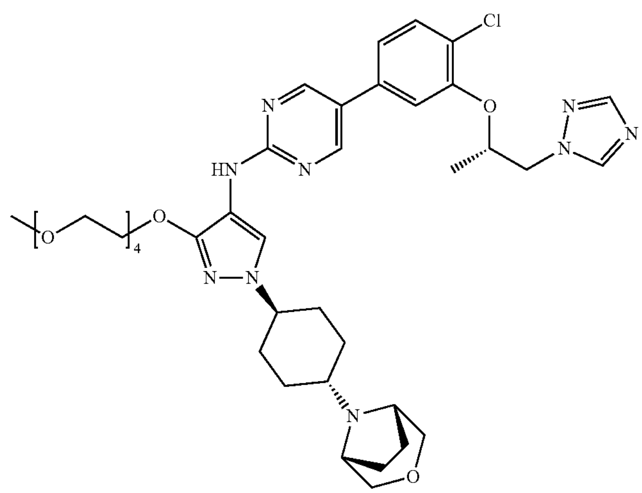 |
| 349 | 2-(((S)-1-(1H-tetrazol-1-yl)propan-2-yl)oxy)-4-(2-((3-((2,5,8,11-tetraoxatridecan-13-yl)oxy)-1-((1r,4r)-4-((2S,6R)-2,6-dimethylmorpholino)cyclohexyl)-1H-pyrazol-4-yl)amino)pyrimidin-5-yl)benzonitrile | 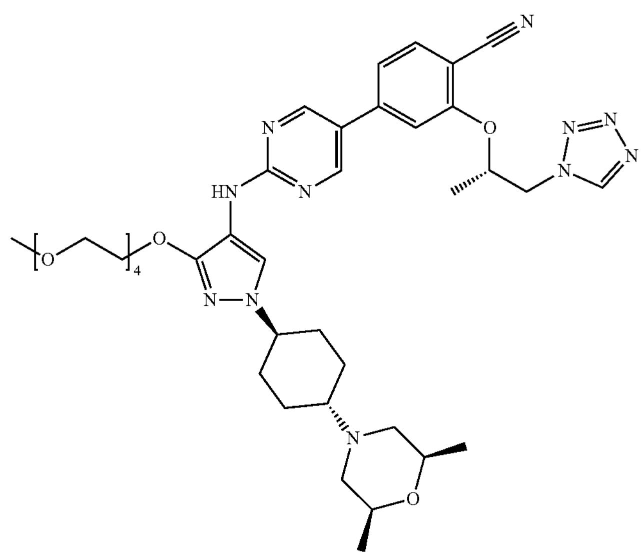 |

TABLE 2-continued

| Ex. No. | IUPAC NAME | STRUCTURE |
|---|---|---|
| 350 | 5-(3-(((S)-1-(1H-tetrazol-1-yl)propan-2-yl)oxy)-4-chlorophenyl)-N-(3-((2,5,8,11-tetraoxatridecan-13-yl)oxy)-1-((1r,4r)-4-((2S,6R)-2,6-dimethylmorpholino)cyclohexyl)-1H-pyrazol-4-yl)pyrimidin-2-amine | 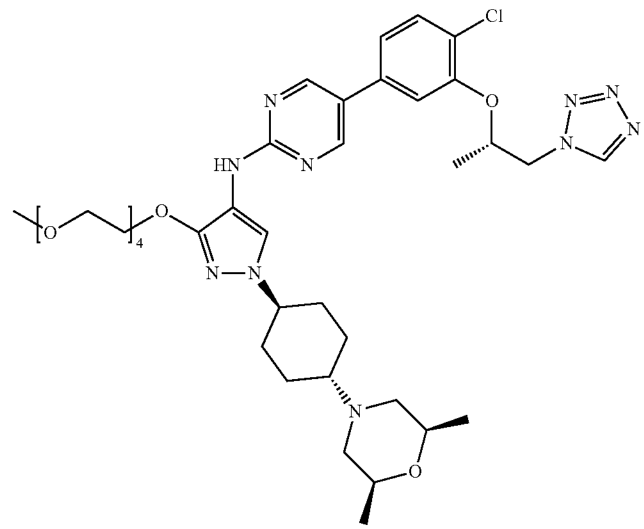 |
| 351 | 2-(((S)-1-(1H-1,2,4-triazol-1-yl)propan-2-yl)oxy)-4-(2-((3-((2,5,8,11-tetraoxatridecan-13-yl)oxy)-1-((1r,4r)-4-((2S,6R)-2,6-dimethylmorpholino)cyclohexyl)-1H-pyrazol-4-yl)amino)pyrimidin-5-yl)benzonitrile | 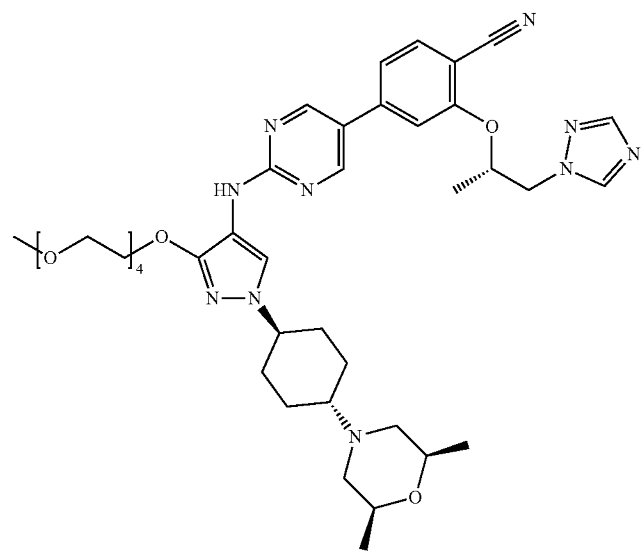 |
| 352 | 5-(3-(((S)-1-(1H-1,2,4-triazol-1-yl)propan-2-yl)oxy)-4-chlorophenyl)-N-(3-((2,5,8,11-tetraoxatridecan-13-yl)oxy)-1-((1r,4r)-4-((2S,6R)-2,6-dimethylmorpholino)cyclohexyl)-1H-pyrazol-4-yl)pyrimidin-2-amine | 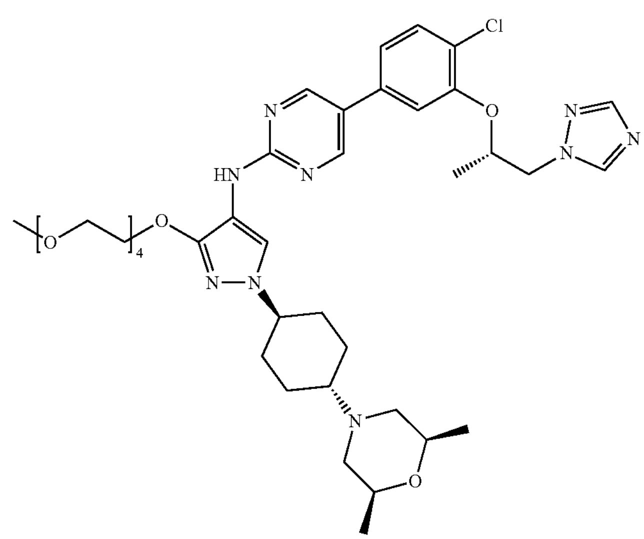 |

TABLE 2-continued

| Ex. No. | IUPAC NAME | STRUCTURE |
|---|---|---|
| 353 | 2-(((S)-1-(1H-tetrazol-1-yl)propan-2-yl)oxy)-4-(2-((3-((2,5,8,11,14-pentaoxahexadecan-16-yl)oxy)-1-((1r,4r)-4-morpholinohexadecan-16-yl)oxy)-1-((1r,4r)-4-morpholinocyclohexyl)-1H-pyrazol-4-yl)amino)pyrimidin-5-yl)benzonitrile | 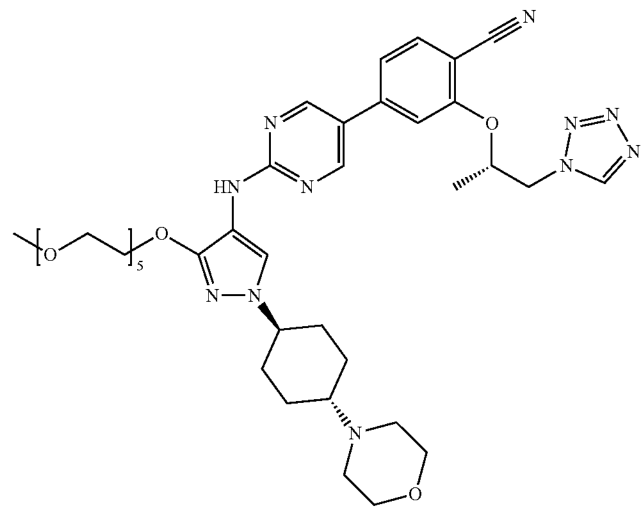 |
| 354 | 5-(3-(((S)-1-(1H-tetrazol-1-yl)propan-2-yl)oxy)-4-chlorophenyl)-N-(3-((2,5,8,11,14-pentaoxahexadecan-16-yl)oxy)-1-((1r,4r)-4-morpholinocyclohexyl)-1H-pyrazol-4-yl)pyrimidin-2-amine | 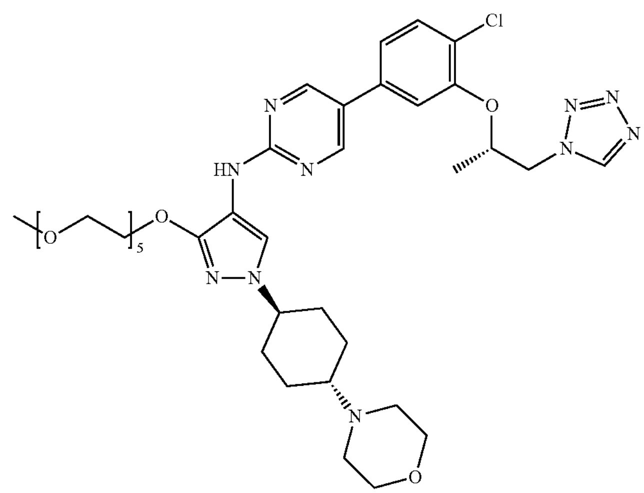 |
| 355 | 2-(((S)-1-(1H-1,2,4-triazol-1-yl)propan-2-yl)oxy)-4-(2-((3-((2,5,8,11,14-pentaoxahexadecan-16-yl)oxy)-1-((1r,4r)-4-morpholinocyclohexyl)-1H-pyrazol-4-yl)amino)pyrimidin-5-yl)benzonitrile | 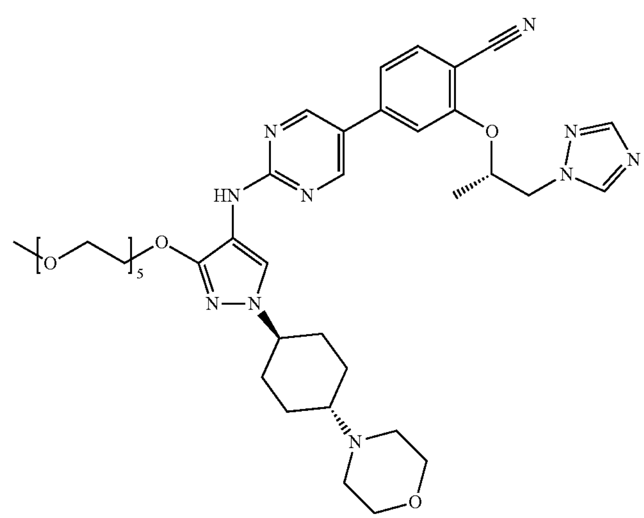 |

TABLE 2-continued

| Ex. No. | IUPAC NAME | STRUCTURE |
|---|---|---|
| 356 | 5-(3-(((S)-1-(1H-1,2,4-triazol-1-yl)propan-2-yl)oxy)-4-chlorophenyl)-N-(3-((2,5,8,11,14-pentaoxahexadecan-16-yl)oxy)-1-((1r,4r)-4-morpholinocyclohexyl)-1H-pyrazol-4-yl)pyrimidin-2-amine | 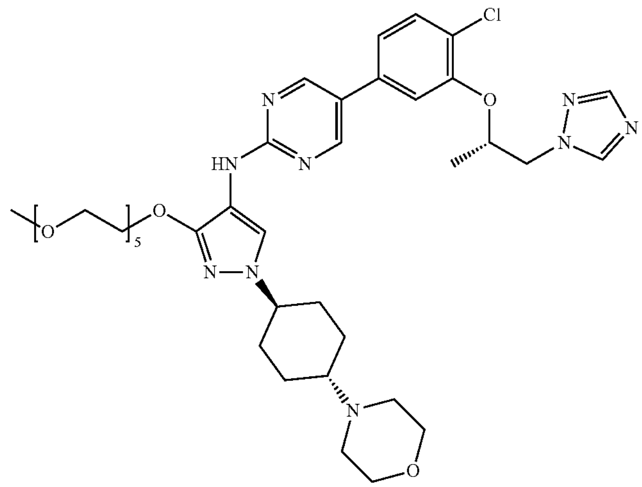 |
| 357 | 2-(((S)-1-(1H-tetrazol-1-yl)propan-2-yl)oxy)-4-(2-((3-((2,5,8,11,14-pentaoxahexadecan-16-yl)oxy)-1-((1r,4r)-4-((1R,5S)-3-oxa-8-azabicyclo[3.2.1]octan-8-yl)cyclohexyl)-1H-pyrazol-4-yl)amino)pyrimidin-4-yl)benzonitrile | 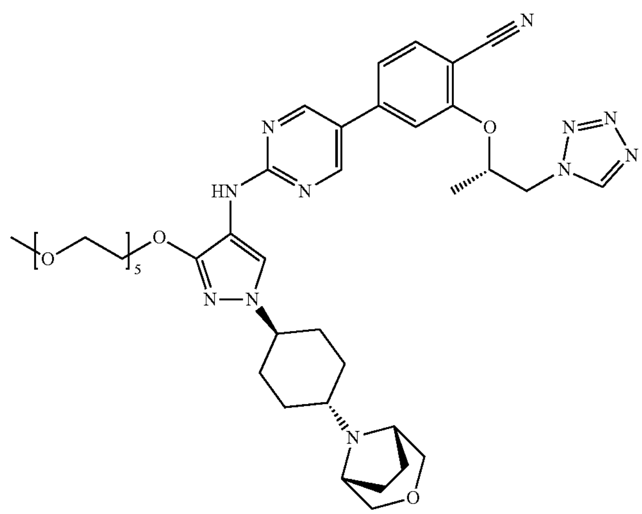 |
| 358 | 5-(3-(((S)-1-(1H-tetrazol-1-yl)propan-2-yl)oxy)-4-chlorophenyl)-N-(3-((2,5,8,11,14-pentaoxahexadecan-16-yl)oxy)-1-((1r,4r)-4-((1R,5S)-3-oxa-8-azabicyclo[3.2.1]octan-8-yl)cyclohexyl)-1H-pyrazol-4-yl)pyrimidin-2-amine | 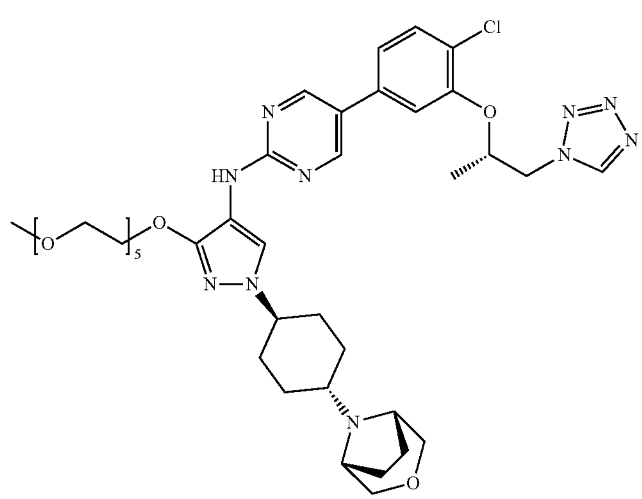 |

TABLE 2-continued

| Ex. No. | IUPAC NAME | STRUCTURE |
|---|---|---|
| 359 | 2-(((S)-1-(1H-1,2,4-triazol-1-yl)propan-2-yl)oxy)-4-(2-((3-((2,5,8,11,14-pentaoxahexadecan-16-yl)oxy)-1-((1r,4r)-4-((1R,5S)-3-oxa-8-azabicyclo[3.2.1]octan-8-yl)cyclohexyl)-1H-pyrazol-4-yl)amino)pyrimidin-5-yl)benzonitrile | 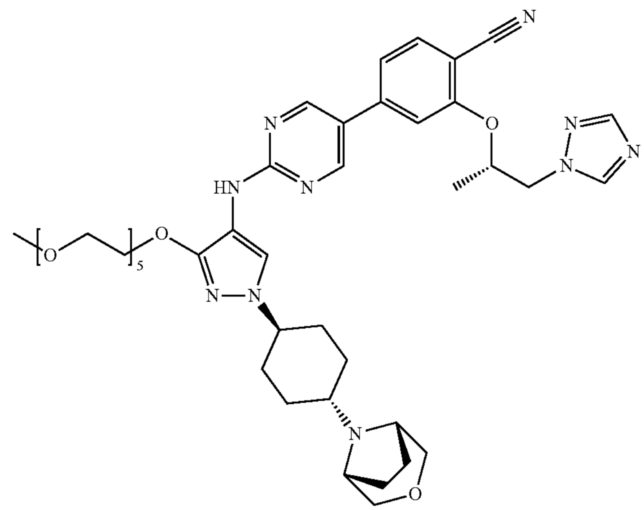 |
| 360 | 5-(3-(((S)-1-(1H-1,2,4-triazol-1-yl)propan-2-yl)oxy)-4-chlorophenyl)-N-(3-((2,5,8,11,14-pentaoxahexadecan-16-yl)oxy)-1-((1r,4r)-4-((1R,5S)-3-oxa-8-azabicyclo[3.2.1]octan-8-yl)cyclohexyl)-1H-pyrazol-4-yl)pyrimidin-2-amine | 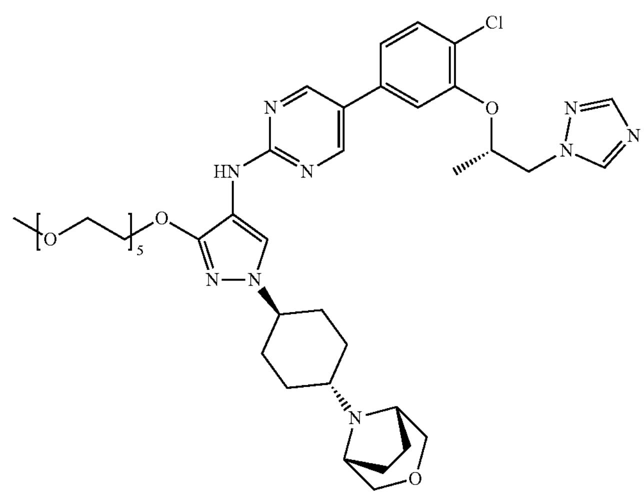 |
| 361 | 2-(((S)-1-(1H-tetrazol-1-yl)propan-2-yl)oxy)-4-chlorophenyl)-N-(3-((2,5,8,11,14-pentaoxadecan-16-yl)oxy)-1-((1r,4r)-4-((2S,6R)-2,6-dimethylmorpholino)cyclohexyl)-1H-pyrazol-4-yl)amino)pyrimidin-5-yl)benzonitrile | 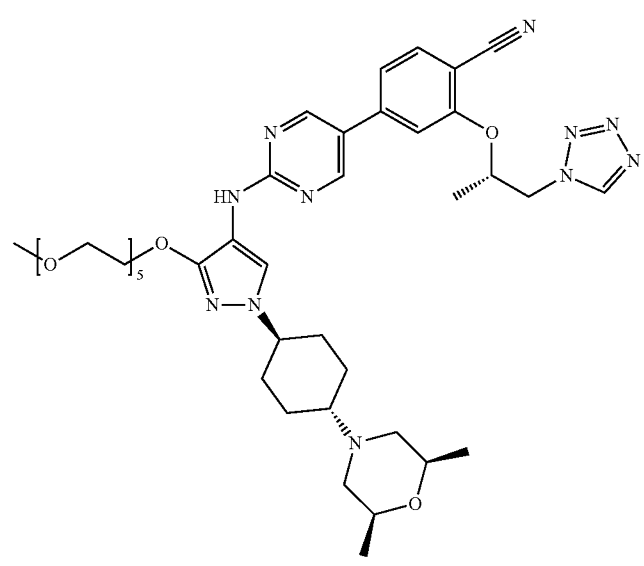 |

TABLE 2-continued

| Ex. No. | IUPAC NAME | STRUCTURE |
|---|---|---|
| 362 | 5-(3-(((S)-1-(1H-tetrazol-1-yl)propan-2-yl)oxy)-4-chlorophenyl)-N-(3-((2,5,8,11,14-pentaoxahexadecan-16-yl)oxy)-1-((1r,4r)-4-((2S,6R)-2,6-dimethylmorpholino)cyclohexyl)-1H-pyrazol-4-yl)pyrimidin-2-amine | 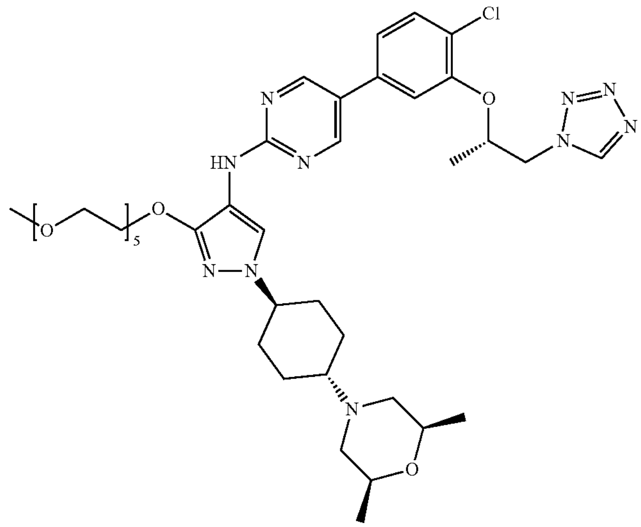 |
| 363 | 2-(((S)-1-(1H-1,2,4-triazol-1-yl)propan-2-yl)oxy)-4-(2-((3-((2,5,8,11,14-pentaoxahexadecan-16-yl)oxy)-1-((1r,4r)-4-((2S,6R)-2,6-dimethylmorpholino)cyclohexyl)-1H-pyrazol-4-yl)amino)pyrimidin-5-yl)benzonitrile | 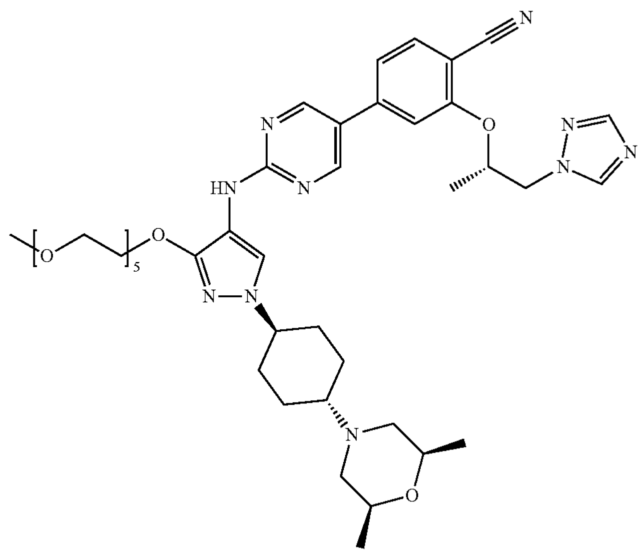 |
| 364 | 5-(3-(((S)-1-(1H-1,2,4-triazol-1-yl)propan-2-yl)oxy)-4-chlorophenyl)-N-(3-((2,5,8,11,14-pentaoxahexadecan-16-yl)oxy)-1-((1r,4r)-4-((2S,6R)-2,6-dimethylmorpholino)cyclohexyl)-1H-pyrazol-4-yl)pyrimidin-2-amine | 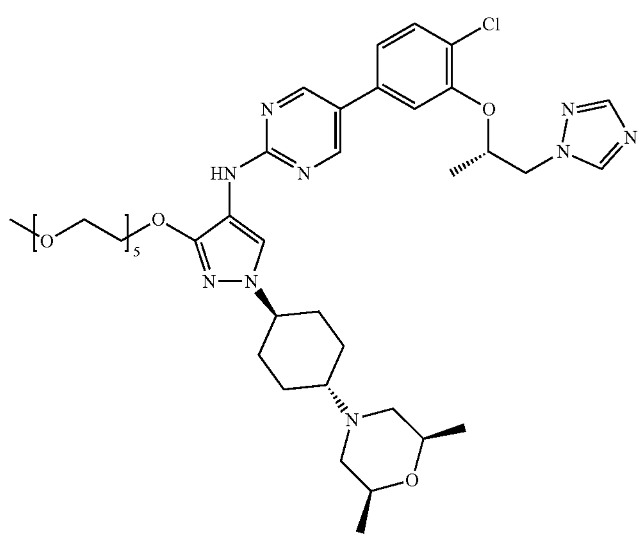 |

TABLE 2-continued

| Ex. No. | IUPAC NAME | STRUCTURE |
|---|---|---|
| 365 | 2-(((S)-1-(1H-tetrazol-1-yl)propan-2-yl)oxy)-4-(2-((3-((2,5,8,11,14,17-hexaoxanonadecan-19-yl)oxy)-1-((1r,4r)-4-morpholinocyclohexyl)-1H-pyrazol-4-yl)amino)pyrimidin-5-yl)benzonitrile | 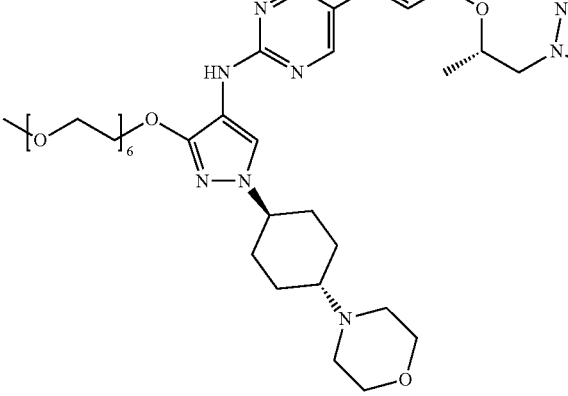 |
| 366 | 5-(3-(((S)-1-(1H-tetrazol-1-yl)propan-2-yl)oxy)-4-chlorophenyl)-N-(3-((2,5,8,11,14,17-hexaoxanonadecan-19-yl)oxy)-1-((1r,4r)-4-morpholinocyclohexyl)-1H-pyrazol-4-yl)pyrimidin-2-amine | 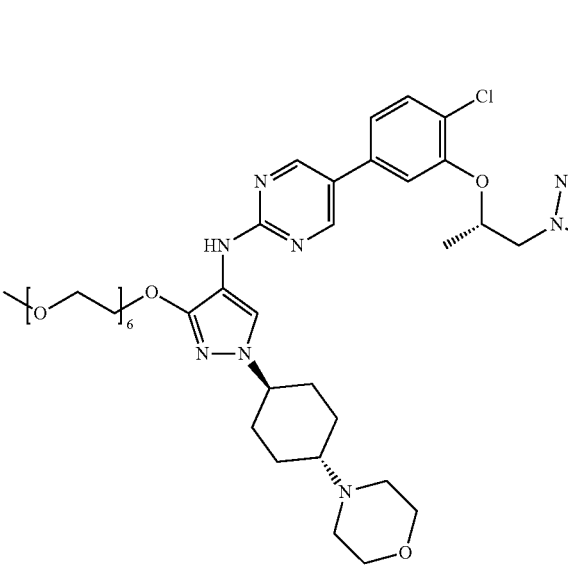 |
| 367 | 2-(((S)-1-(1H-1,2,4-triazol-1-yl)propan-2-yl)oxy)-4-(2-((3-((2,5,8,11,14,17-hexaoxanonadecan-19-yl)oxy)-1-((1r,4r)-4-morpholinocyclohexyl)-1H-pyrazol-4-yl)amino)pyrimidin-5-yl)benzonitrile | 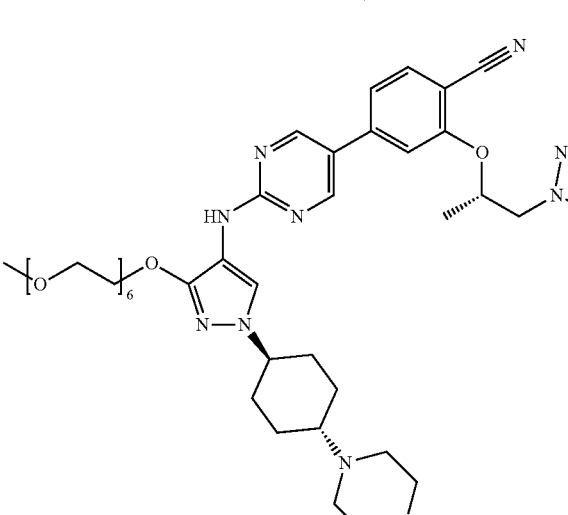 |

TABLE 2-continued

| Ex. No. | IUPAC NAME | STRUCTURE |
|---|---|---|
| 368 | 5-(3-(((S)-1-(1H-1,2,4-triazol-1-yl)propan-2-yl)oxy)-4-chlorophenyl)-N-(3-((2,5,8,11,14,17-hexaoxanonadecan-19-yl)oxy)-1-((1r,4r)-4-morpholinocyclohexyl)-1H-pyrazol-4-yl)pyrimidin-2-amine | 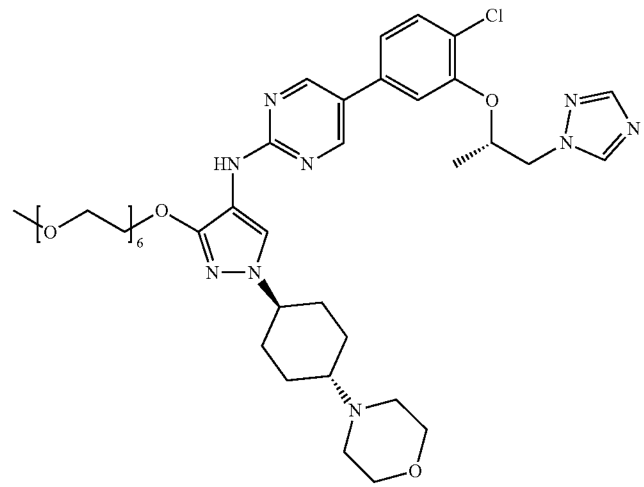 |
| 369 | 2-(((S)-1-(1H-tetrazol-1-yl)propan-2-yl)oxy)-4-(2-((3-((2,5,8,11,14,17-hexaoxanonadecan-19-yl)oxy)-1-((1r,4r)-4-((1R,5S)-3-oxa-8-azabicyclo[3.2.1]octan-8-yl)cyclohexyl)-1H-pyrazol-4-yl)amino)pyrimidin-5-yl)benzonitrile | 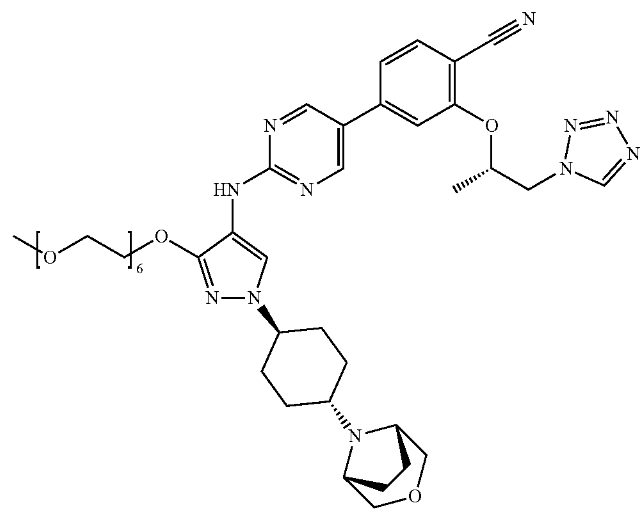 |
| 370 | 5-(3-(((S)-1-(1H-tetrazol-1-yl)propan-2-yl)oxy)-4-chlorophenyl)-N-(3-((2,5,8,11,14,17-hexaoxanonadecan-19-yl)oxy)-1-((1r,4r)-4-((1R,5S)-3-oxa-8-azabicyclo[3.2.1]octan-8-yl)cyclohexyl)-1H-pyrazol-4-yl)pyrimidin-2-amine | 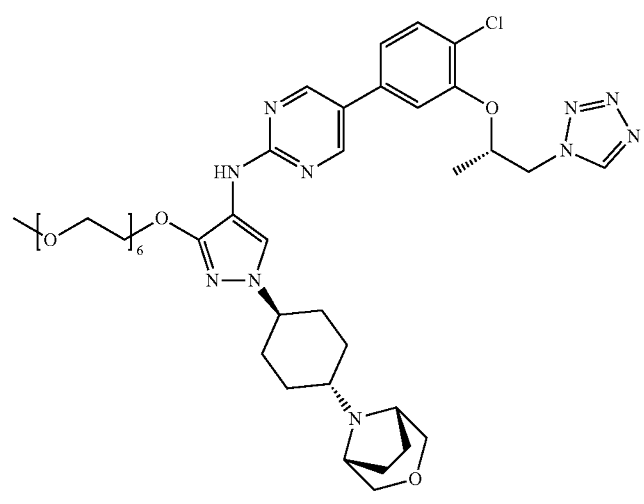 |

TABLE 2-continued

| Ex. No. | IUPAC NAME | STRUCTURE |
| --- | --- | --- |
| 371 | 2-(((S)-1-(1H-1,2,4-triazol-1-yl)propan-2-yl)oxy)-4-(2-((3-((2,5,8,11,14,17-hexaoxanonadecan-19-yl)oxy)-1-((1r,4r)-4-((1R,5S)-3-oxa-8-azabicyclo[3.2.1]octan-8-yl)cyclohexyl)-1H-pyrazol-4-yl)amino)pyrimidin-5-yl)benzonitrile | 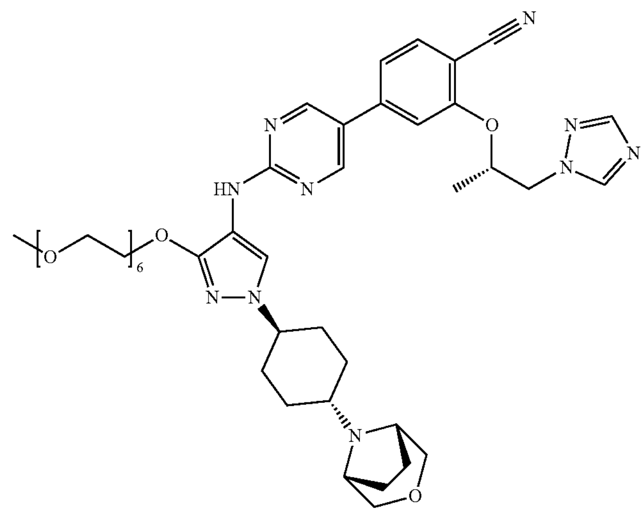 |
| 372 | 5-(3-(((S)-1-(1H-1,2,4-triazol-1-yl)propan-2-yl)oxy)-4-chlorophenyl)-N-(3-((2,5,8,11,14,17-hexaoxanonadecan-19-yl)oxy)-1-((1r,4r)-4-((1R,5S)-3-oxa-8-azabicyclo[3.2.1]octan-8-yl)cyclohexyl)-1H-pyrazol-4-yl)pyrimidin-2-amine | 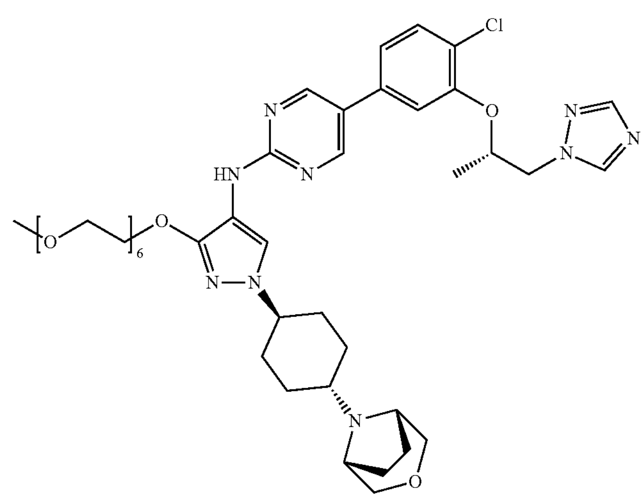 |
| 373 | 2-(((S)-1-(1H-tetrazol-1-yl)propan-2-yl)oxy)-4-(2-((3-((2,5,8,11,14,17-hexaoxanonadecan-19-yl)oxy)-1-((1r,4r)-4-((2S,6R)-2,6-dimethylmorpholino)cyclohexyl)-1H-pyrazol-4-yl)amino)pyrimidin-5-yl)benzonitrile | 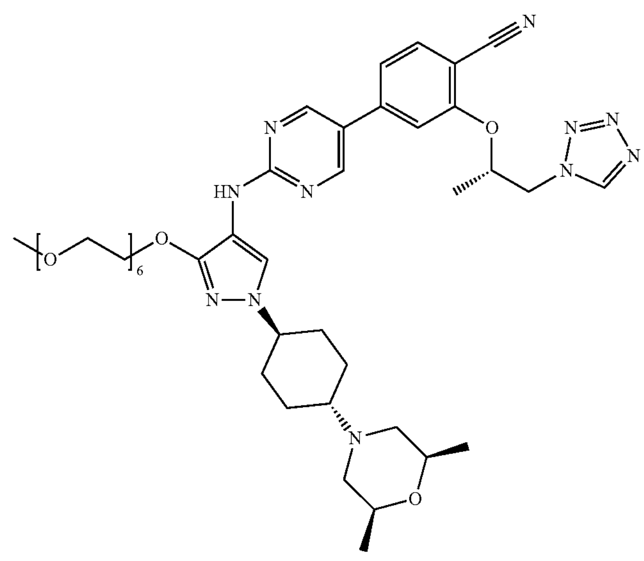 |

TABLE 2-continued

| Ex. No. | IUPAC NAME | STRUCTURE |
|---|---|---|
| 374 | 5-(3-(((S)-1-(1H-tetrazol-1-yl)propan-2-yl)oxy)-4-chlorophenyl)-N-(3-((2,5,8,11,14,17-hexaoxanonadecan-19-yl)oxy)-1-((1r,4r)-4-((2S,6R)-2,6-dimethylmorpholino)cyclohexyl)-1H-pyrazol-4-yl)pyrimidin-2-amine | 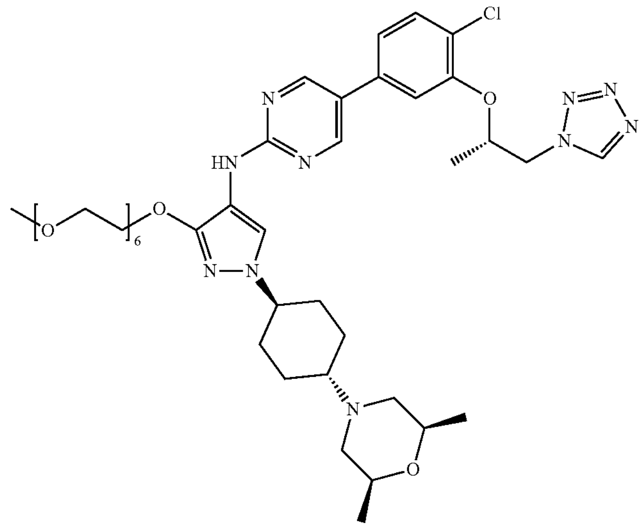 |
| 375 | 2-(((S)-1-(1H-1,2,4-triazol-1-yl)propan-2-yl)oxy)-4-(2-((3-((2,5,8,11,14,17-hexaoxanonadecan-19-yl)oxy)-1-((1r,4r)-4-((2S,6R)-2,6-dimethylmorpholino)cyclohexyl)-1H-pyrazol-4-yl)amino)pyrimidin-5-yl)benzonitrile | 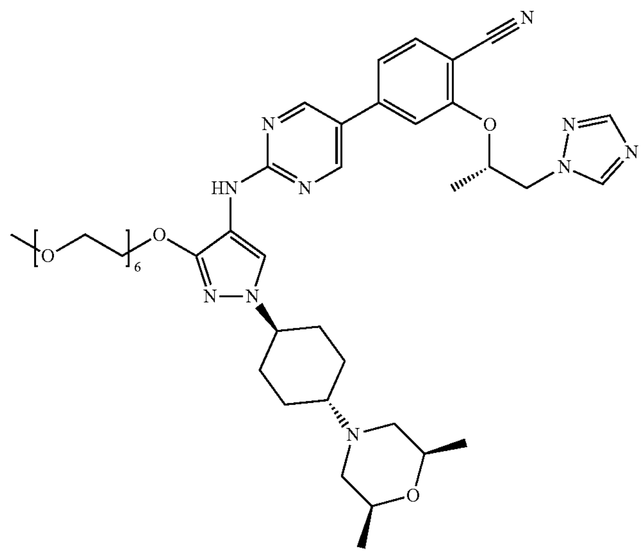 |
| 376 | 5-(3-(((S)-1-(1H-1,2,4-triazol-1-yl)propan-2-yl)oxy)-4-chlorophenyl)-N-(3-((2,5,8,11,14,17-hexaoxanonadecan-19-yl)oxy)-1-((1r,4r)-4-((2S,6R)-2,6-dimethylmorpholino)cyclohexyl)-1H-pyrazol-4-yl)pyrimidin-2-amine | 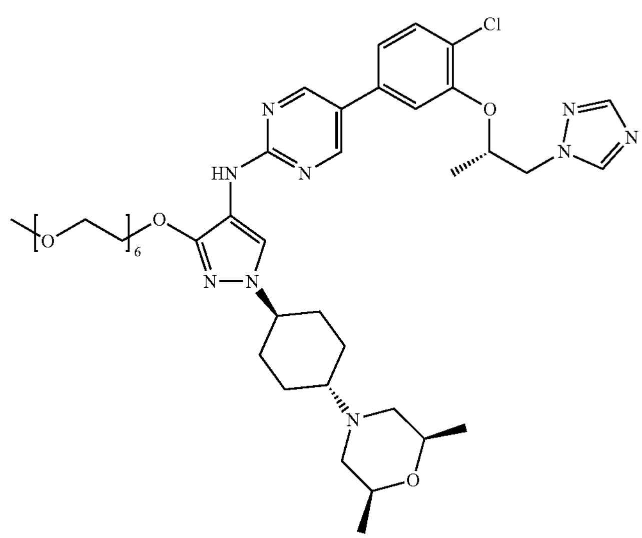 |

TABLE 2-continued

| Ex. No. | IUPAC NAME | STRUCTURE |
| --- | --- | --- |
| 377 | 2-(((S)-1-(1H-tetrazol-1-yl)propan-2-yl)oxy)-4-(2-((3-((2,5,8,11,14,17,20-heptaoxadocosan-22-yl)oxy)-1-((1r,4r)-4-morpholinocyclohexyl)-1H-pyrazol-4-yl)amino)pyrimidin-5-yl)benzonitrile | 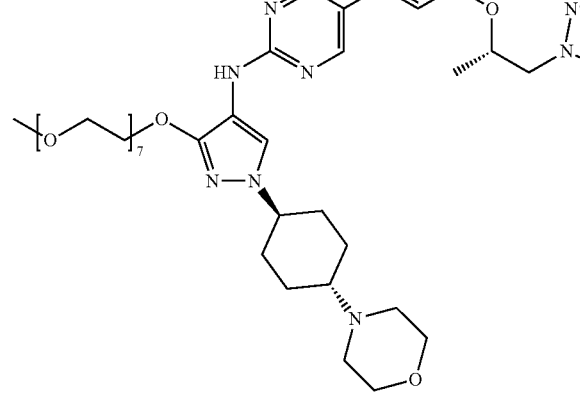 |
| 378 | 5-(3-(((S)-1-(1H-tetrazol-1-yl)propan-2-yl)oxy)-4-chlorophenyl)-N-(3-((2,5,8,11,14,17,20-heptaoxadocosan-22-yl)oxy)-1-((1r,4r)-4-morpholinocyclohexyl)-1H-pyrazol-4-yl)pyrimidin-2-amine | 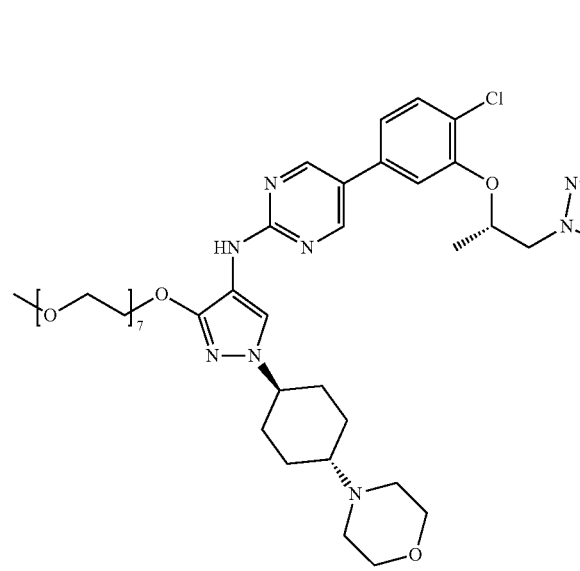 |
| 379 | 2-(((S)-1-(1H-1,2,4-triazol-1-yl)propan-2-yl)oxy)-4-(2-((3-((2,5,8,11,14,17,20-heptaoxadocosan-22-yl)oxy)-1-((1r,4r)-4-morpholinocyclohexyl)-1H-pyrazol-4-yl)amino)pyrimidin-5-yl)benzonitrile | 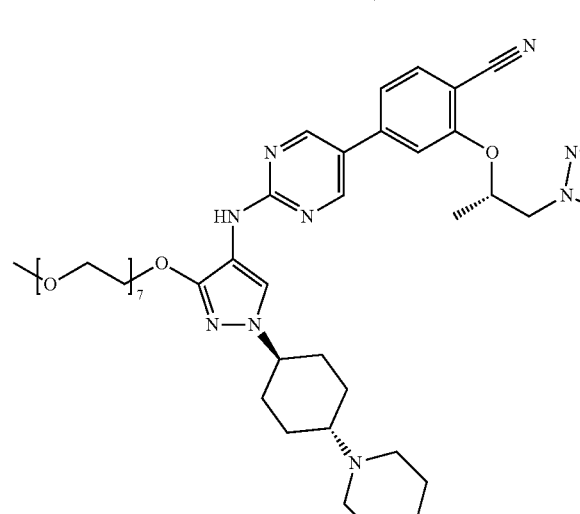 |

TABLE 2-continued

| Ex. No. | IUPAC NAME | STRUCTURE |
|---|---|---|
| 380 | 5-(3-(((S)-1-(1H-1,2,4-triazol-1-yl)propan-2-yl)oxy)-4-chlorophenyl)-N-(3-((2,5,8,11,14,17,20-heptaoxadocosan-22-yl)oxy)-1-((1r,4r)-4-mrorpholinocyclohexyl)-1H-pyrazol-4-yl)pyrimidin-2-amine | 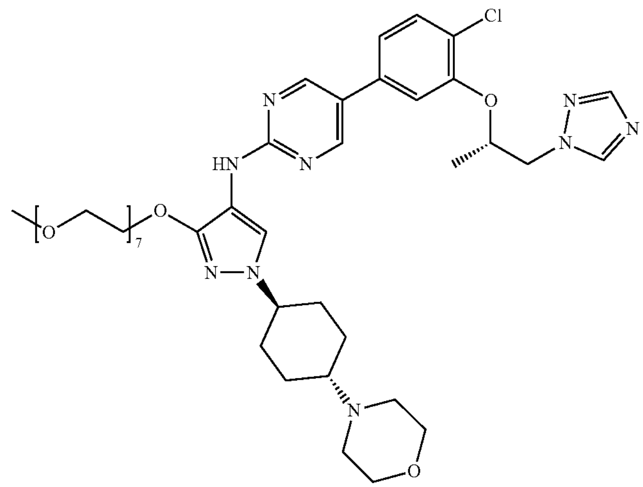 |
| 381 | 2-(((S)-1-(1H-tetrazol-1-yl)propan-2-yl)oxy)-4-(2-((3-((2,5,8,11,14,17,20-heptaoxadocosan-22-yl)oxy)-1-((1r,4r)-4-((1R,5S)-3-oxa-8-azabicyclo[3.2.1]octan-8-yl)cyclohexyl)-1H-pyrazol-4-yl)amino)pyrimidin-5-yl)benzonitrile | 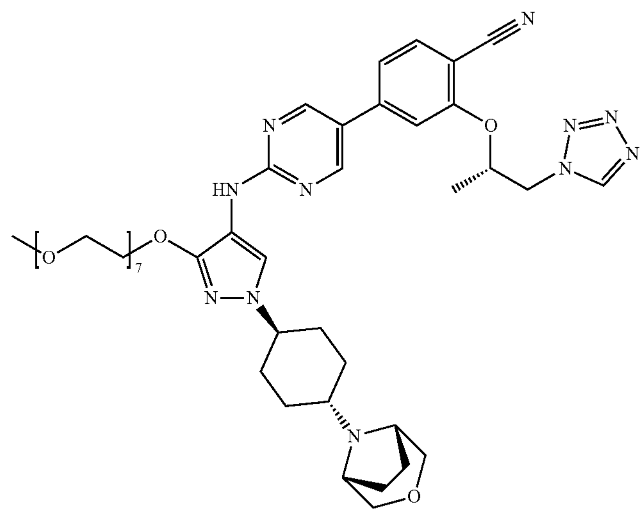 |
| 382 | 5-(3-(((S)-1-(1H-tetrazol-1-yl)propan-2-yl)oxy)-4-chlorophenyl)-N-(3-((2,5,8,11,14,17,20-heptaoxadocosan-22-yl)oxy)-1-((1r,4r)-4-((1R,5S)-3-oxa-8-azabicyclo[3.2.1]octan-8-yl)cyclohexyl)-1H-pyrazol-4-yl)pyrimidin-2-amine | 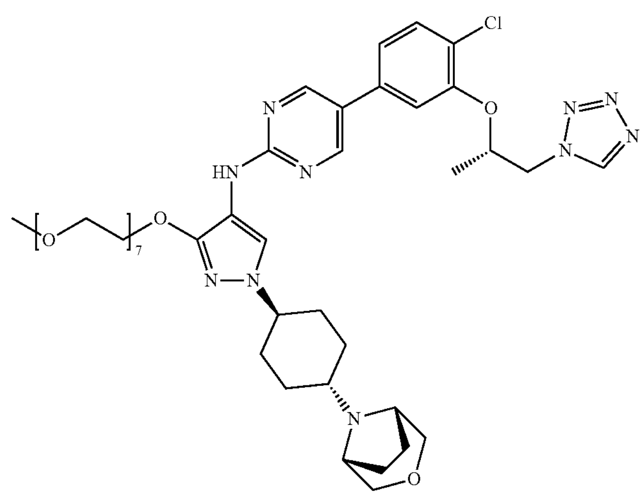 |

TABLE 2-continued

| Ex. No. | IUPAC NAME | STRUCTURE |
| --- | --- | --- |
| 383 | 2-(((S)-1-(1H-1,2,4-triazol-1-yl)propan-2-yl)oxy)-4-(2-((3-((2,5,8,11,14,17,20-heptaoxadocosan-22-yl)oxy)-1-((1r,4r)-4-((1R,5S)-3-oxa-8-azabicyclo[3.2.1]octan-8-yl)cyclohexyl)-1H-pyrazol-4-yl)amino)pyrimidin-5-yl)benzonitrile | 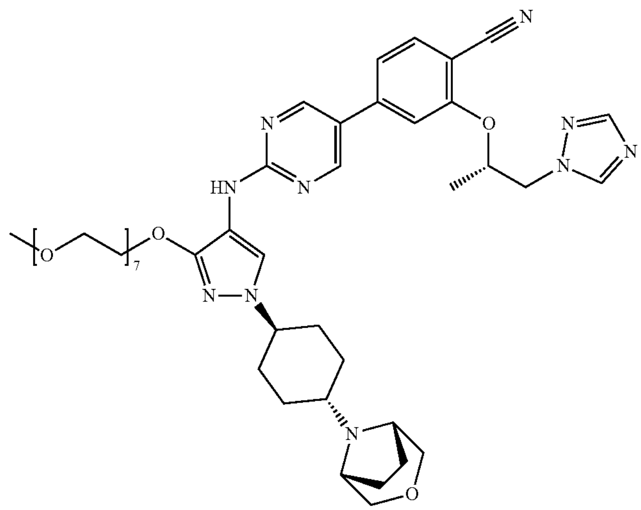 |
| 384 | 5-(3-(((S)-1-(1H-1,2,4-triazol-1-yl)propan-2-yl)oxy)-4-chlorophenyl)-N-(3-((2,5,8,11,14,17,20-heptaoxadocosan-22-yl)oxy)-1-((1r,4r)-4-((1R,5S)-3-oxa-8-azabicyclo[3.2.1]octan-8-yl)cyclohexyl)-1H-pyrazol-4-yl)pyrimidin-2-amine | 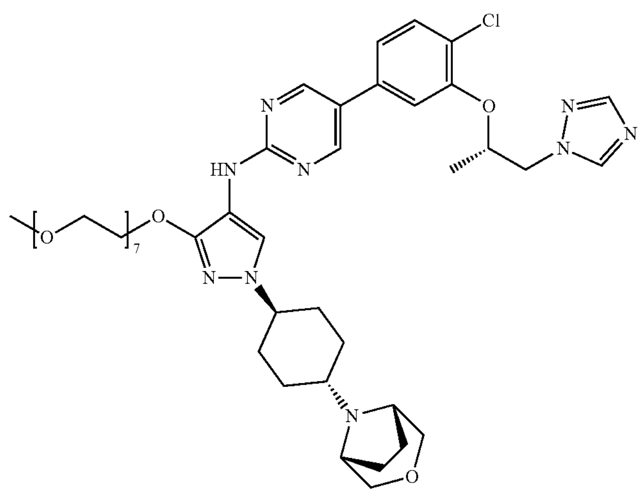 |
| 385 | 2-(((S)-1-(1H-tetrazol-1-yl)propan-2-yl)oxy)-4-(2-((3-((2,5,8,11,14,17,20-heptaoxadocosan-22-yl)oxy)-1-((1r,4r)-4-((2S,6R)-2,6-dimethylmorpholino)cyclohexyl)-1H-pyrazol-4-yl)amino)pyrimidin-5-yl)benzonitrile | 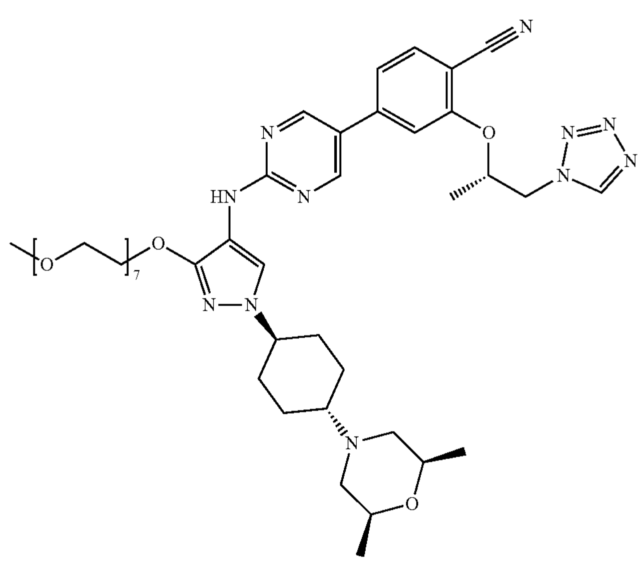 |

TABLE 2-continued

| Ex. No. | IUPAC NAME | STRUCTURE |
|---|---|---|
| 386 | 5-(3-(((S)-1-(1H-tetrazol-1-yl)propan-2-yl)oxy)-4-chlorophenyl)-N-(3-((2,5,8,11,14,17,20-heptaoxadocosan-22-yl)oxy)-1-((1r,4r)-4-((2S,6R)-2,6-dimethylmorpholino)cyclohexyl)-1H-pyrazol-4-yl)pyrimidin-2-amine | 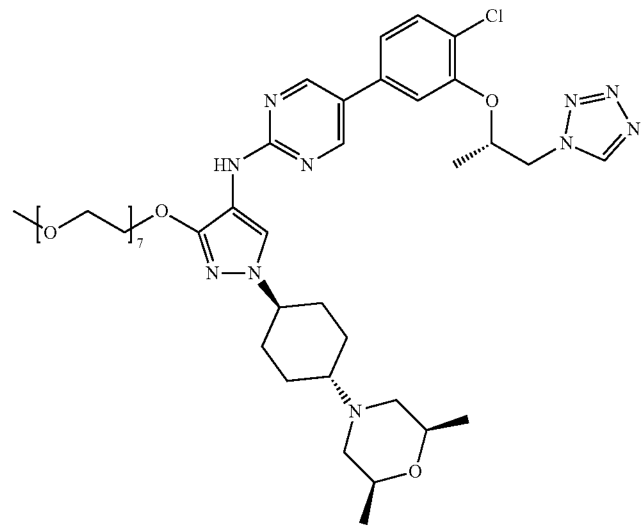 |
| 387 | 2-(((S)-1-(1H-1,2,4-triazol-1-yl)propan-2-yl)oxy)-4-(2-((3-((2,5,8,11,14,17,20-heptaoxadocosan-22-yl)oxy)-1-((1r,4r)-4-((2S,6R)-2,6-dimethylmorpholino)cyclohexyl)-1H-pyrazol-4-yl)amino)pyrimidin-5-yl)benzonitrile | 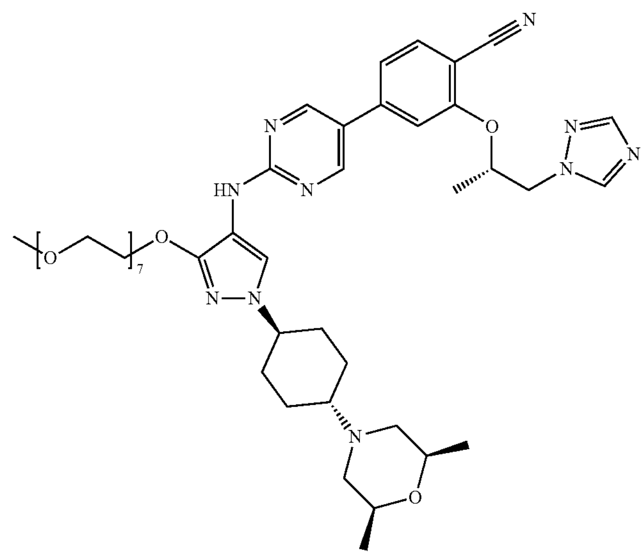 |
| 388 | 5-(3-(((S)-1-(1H-1,2,4-triazol-1-yl)propan-2-yl)oxy)-4-chlorophenyl)-N-(3-((2,5,8,11,14,17,20-heptaoxadocosan-22-yl)oxy)-1-((1r,4r)-4-((2S,6R)-2,6-dimethylmorpholino)cyclohexyl)-1H-pyrazol-4-yl)pyrimidin-2-amine | 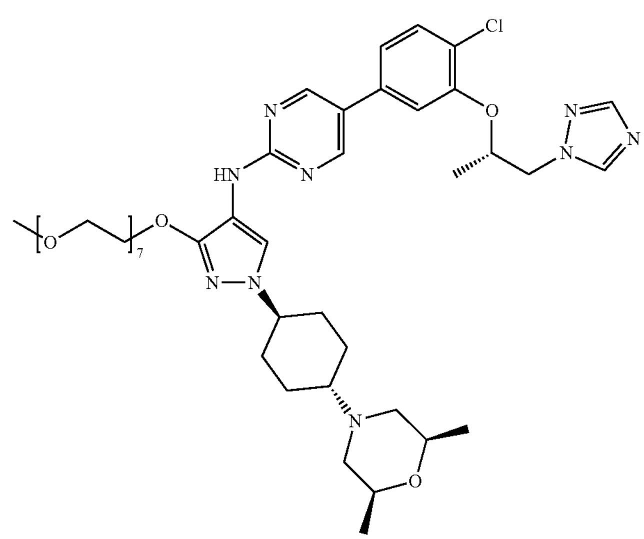 |

TABLE 2-continued

| Ex. No. | IUPAC NAME | STRUCTURE |
|---|---|---|
| 389 | 2-(((S)-1-(1H-tetrazol-1-yl)propan-2-yl)oxy)-4-(2-((3-((2,5,8,11,14,17,20,23-octaoxapentacosan-25-yl)oxy)-1-((1r,4r)-4-morpholinocyclohexyl)-1H-pyrazol-4-yl)amino)pyrimidin-5-yl)benzonitrile | 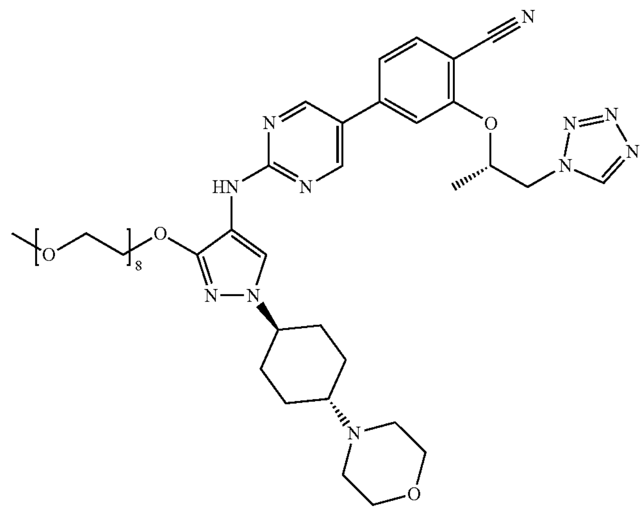 |
| 390 | 5-(3-(((S)-1-(1H-tetrazol-1-yl)propan-2-yl)oxy)-4-chlorophenyl)-N-(3-((2,5,8,11,14,17,20,23-octaoxapentacosan-25-yl)oxy)-1-((1r,4r)-4-morpholinocyclohexyl)-1H-pyrazol-4-yl)pyrimidin-2-amine | 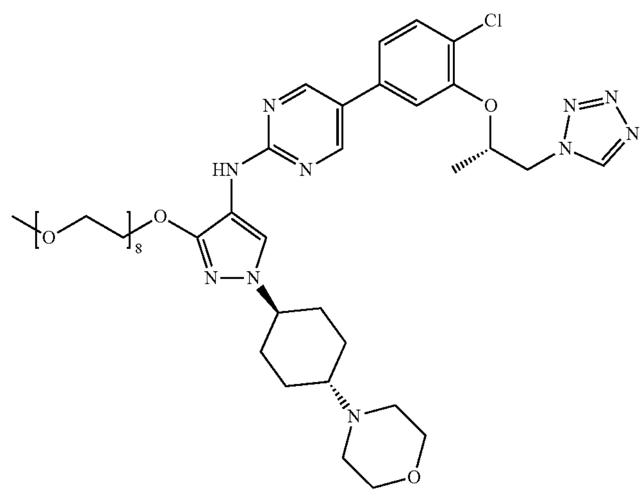 |
| 391 | 2-(((S)-1-(1H-1,2,4-triazol-1-yl)propan-2-yl)oxy)-4-(2-((3-((2,5,8,11,14,17,20,23-octaoxapentacosan-25-yl)oxy)-1-((1r,4r)-4-morpholinocyclohexyl)-1H-pyrazol-4-yl)amino)pyrimidin-5-yl)benzonitrile | 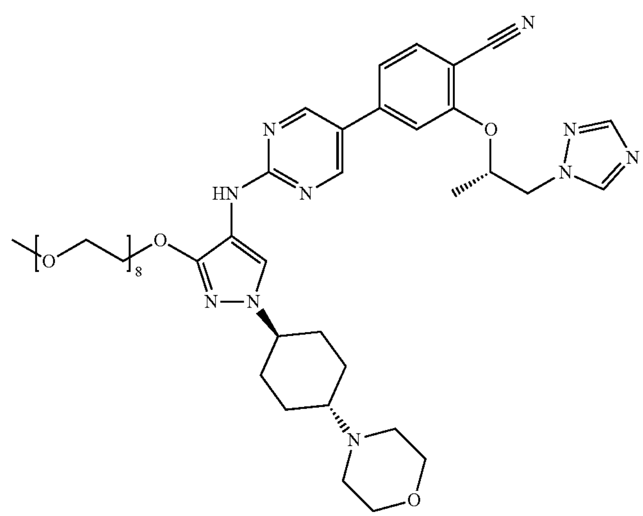 |

TABLE 2-continued

| Ex. No. | IUPAC NAME | STRUCTURE |
|---|---|---|
| 392 | 5-(3-(((S)-1-(1H-1,2,4-triazol-1-yl)propan-2-yl)oxy)-4-chlorophenyl)-N-(3-((2,5,8,11,14,17,20,23-octaoxapentacosan-25-yl)oxy)-1-((1r,4r)-4-morpholinocyclohexyl)-1H-pyrazol-4-yl)pyrimidin-2-amine | 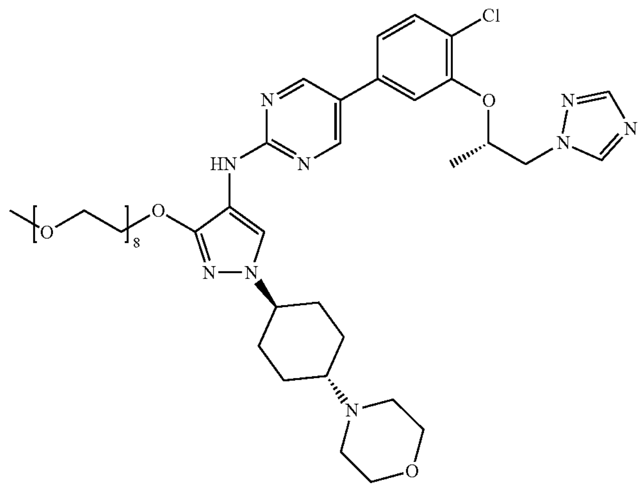 |
| 393 | 2-(((S)-1-(1H-tetrazol-1-yl)propan-2-yl)oxy)-4-(2-((3-((2,5,8,11,14,17,20,23-octaoxapentacosan-25-yl)oxy)-1-((1r,4r)-4-((1R,5S)-3-oxa-8-azabicyclo[3.2.1]octan-8-yl)cyclohexyl)-1H-pyrazol-4-yl)amino)pyrimidin-5-yl)benzonitrile | 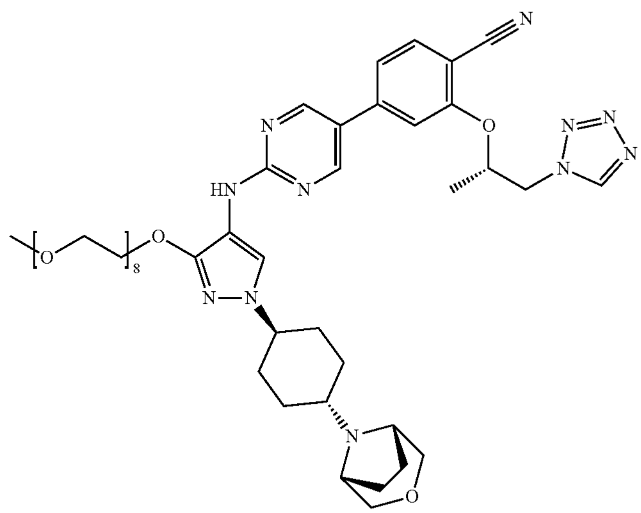 |
| 394 | 5-(3-(((S)-1-(1H-tetrazol-1-yl)propan-2-yl)oxy)-4-chlorophenyl)-N-(3-((2,5,8,11,14,17,20,23-octaoxapentacosan-25-yl)oxy)-1-((1r,4r)-4-((1R,5S)-3-oxa-8-azabicyclo[3.2.1]octan-8-yl)cyclohexyl)-1H-pyrazol-4-yl)pyrimidin-2-amine | 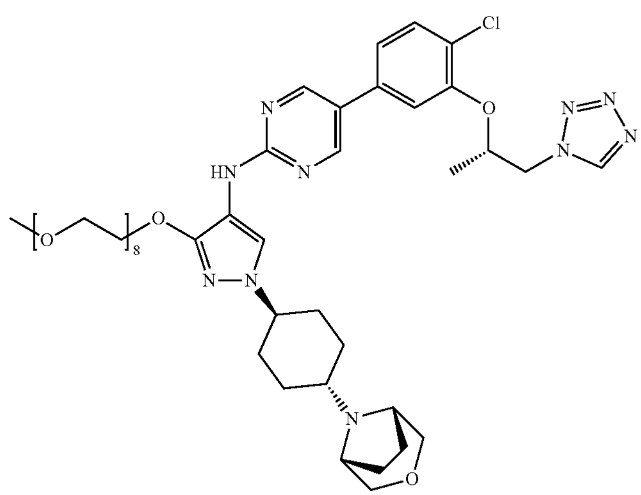 |

TABLE 2-continued

| Ex. No. | IUPAC NAME | STRUCTURE |
|---|---|---|
| 395 | 2-(((S)-1-(1H-1,2,4-triazol-1-yl)propan-2-yl)oxy)-4-(2-((3-((2,5,8,11,14,17,20,23-octaoxapentacosan-25-yl)oxy)-1-((1r,4r)-4-((1R,5S)-3-oxa-8-azabicyclo[3.2.1]octan-8-yl)cyclohexyl)-1H-pyrazol-4-yl)amino)pyrimidin-5-yl)benzonitrile | 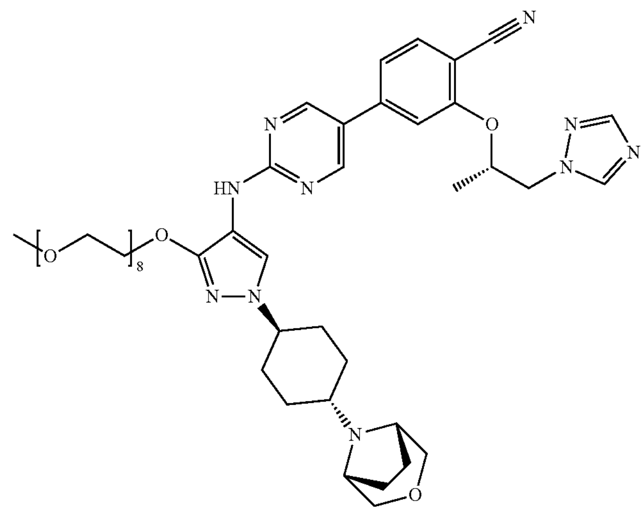 |
| 396 | 5-(3-(((S)-1-(1H-1,2,4-triazol-1-yl)propan-2-yl)oxy)-4-chlorophenyl)-N-(3-((2,5,8,11,14,17,20,23-octaoxapentacosan-25-yl)oxy)-1-((1r,4r)-4-((1R,5S)-3-oxa-8-azabicyclo[3.2.1]octan-8-yl)cyclohexyl)-1H-pyrazol-4-yl)pyrimidin-2-amine | 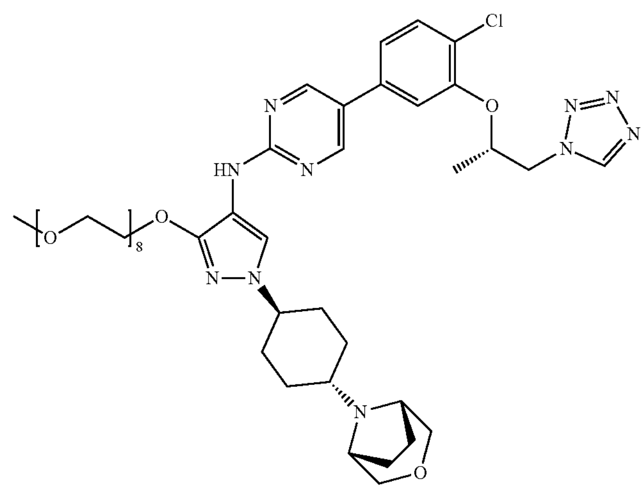 |
| 397 | 2-(((S)-1-(1H-tetrazol-1-yl)propan-2-yl)oxy)-4-(2-((3-((2,5,8,11,14,17,20,23-octaoxapentacosan-25-yl)oxy)-1-((1r,4r)-4-((2S,6R)-2,6-dimethylmorpholino)cyclohexyl)-1H-pyrazol-4-yl)amino)pyrimidin-5-yl)benzonitrile | 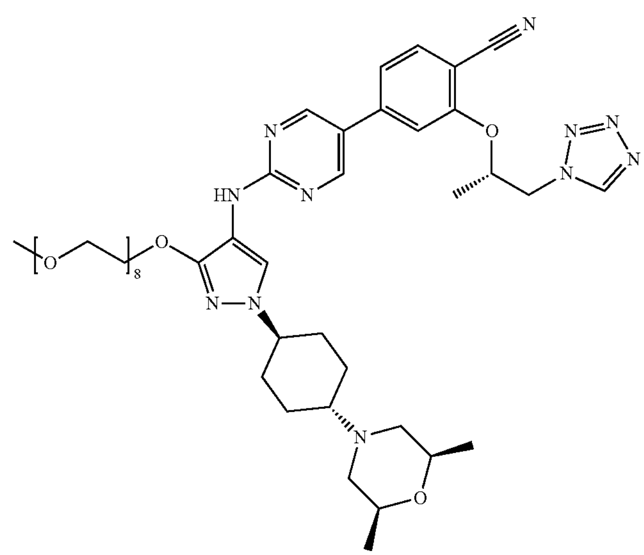 |

TABLE 2-continued

| Ex. No. | IUPAC NAME | STRUCTURE |
|---|---|---|
| 398 | 5-(3-(((S)-1-(1H-tetrazol-1-yl)propan-2-yl)oxy)-4-chlorophenyl)-N-(3-((2,5,8,11,14,17,20,23-octaoxapentacosan-25-yl)oxy)-1-((1r,4r)-4-((2S,6R)-2,6-dimethylmorpholino)cyclohexyl)-1H-pyrazol-4-yl)pyrimidin-2-amine | 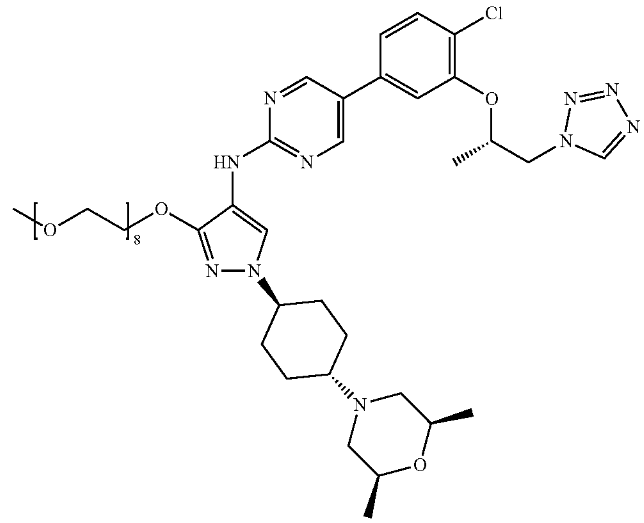 |
| 399 | 2-(((S)-1-(1H-1,2,4-triazol-1-yl)propan-2-yl)oxy)-4-(2-((3-((2,5,8,11,14,17,20,23-octaoxapentacosan-25-yl)oxy)-1-((1r,4r)-4-((2S,6R)-2,6-dimethylmorpholino)cyclohexyl)-1H-pyrazol-4-yl)amino)pyrimidin-5-yl)benzonitrile | 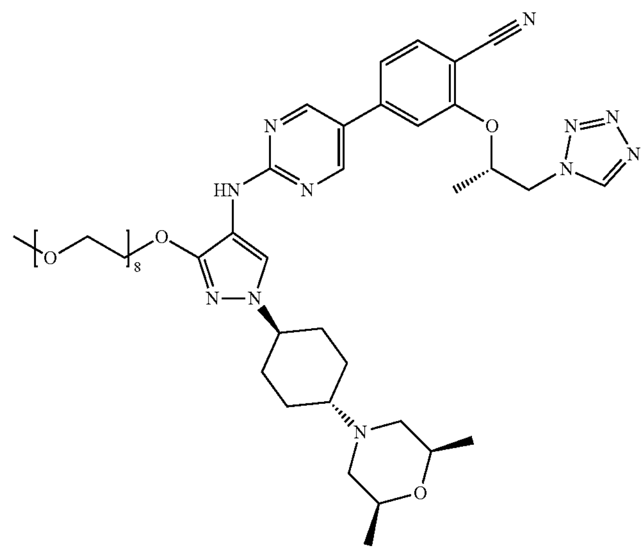 |
| 400 | 5-(3-(((S)-1-(1H-1,2,4-triazol-1-yl)propan-2-yl)oxy)-4-chlorophenyl)-N-(3-((2,5,8,11,14,17,20,23-octaoxapentacosan-25-yl)oxy)-1-((1r,4r)-4-((2S,6R)-2,6-dimethylmorpholino)cyclohexyl)-1H-pyrazol-4-yl)pyrimidin-2-amine | 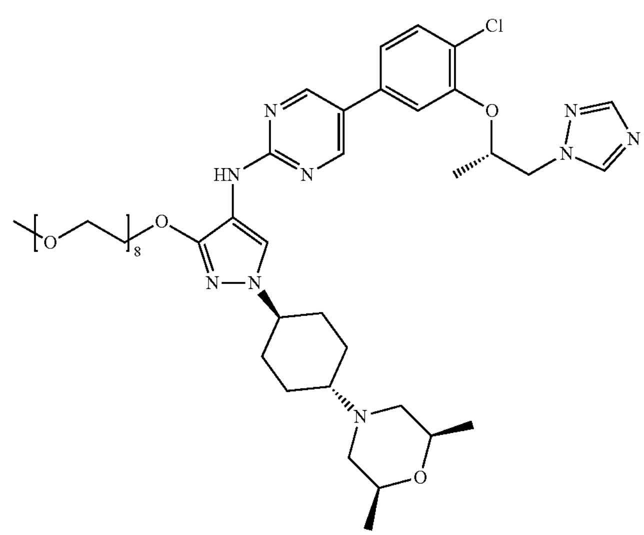 |

TABLE 2-continued

| Ex. No. | IUPAC NAME | STRUCTURE |
|---|---|---|
| 401 | 2-(((S)-1-(1H-tetrazol-1-yl)propan-2-yl)oxy)-4-(2-((3-((2,5,8,11-tetraoxatetradecan-14-yl)oxy)-1-((1r,4r)-4-morpholinocyclohexyl)-1H-pyrazol-4-yl)amino)pyrimidin-5-yl)benzonitrile | 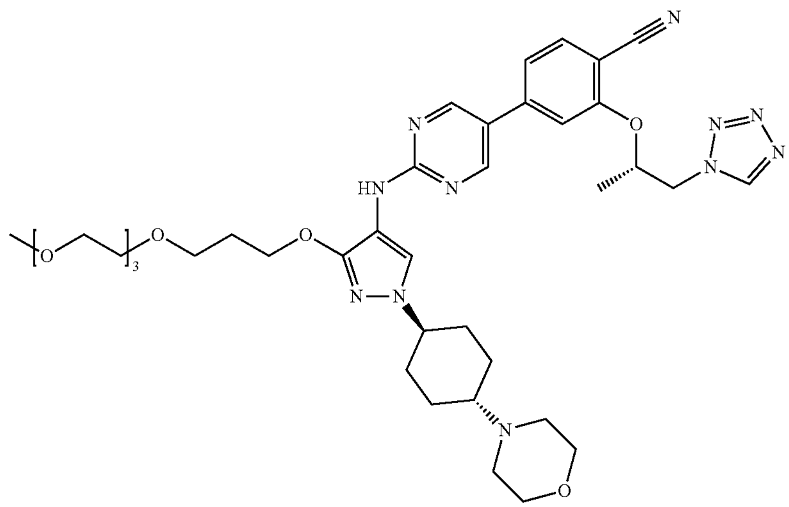 |
| 402 | 5-(3-(((S)-1-(1H-tetrazol-1-yl)propan-2-yl)oxy)-4-chlorophenyl)-N-(3-((2,5,8,11-tetraoxatetradecan-14-yl)oxy)-1-((1r,4r)-4-morpholinocyclohexyl)-1H-pyrazol-4-yl)pyrimidin-2-amine | 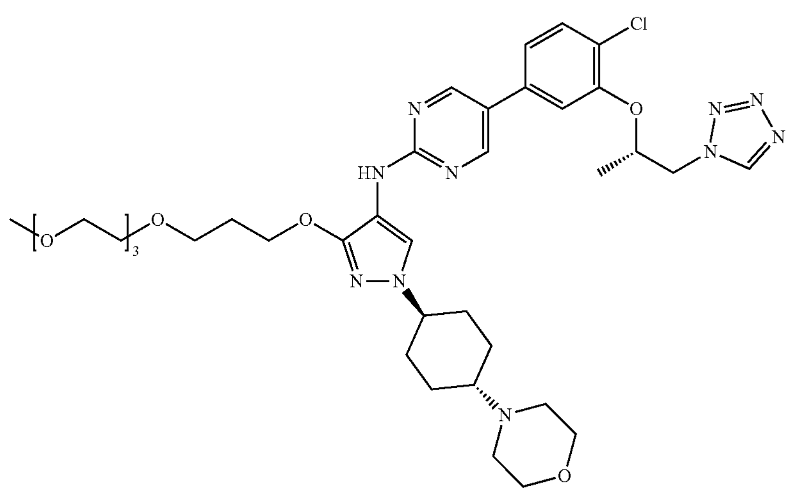 |
| 403 | 2-(((S)-1-(1H-1,2,4-triazol-1-yl)propan-2-yl)oxy)-4-(2-((3-((2,5,8,11-tetraoxatetradecan-14-yl)oxy)-1-((1r,4r)-4-morpholinocyclohexyl)-1H-pyrazol-4-yl)amino)pyrimidin-5-yl)benzonitrile | 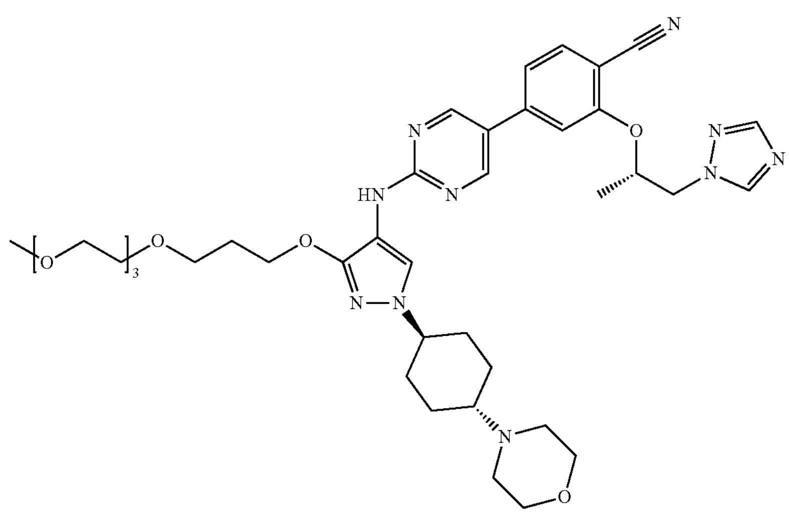 |

TABLE 2-continued

| Ex. No. | IUPAC NAME | STRUCTURE |
|---|---|---|
| 404 | 5-(3-(((S)-1-(1H-1,2,4-triazol-1-yl)propan-2-yl)oxy)-4-chlorphenyl)-N-(3-((2,5,8,11-tetraoxatetradecan-14-yl)oxy)-1-((1r,4r)-4-morpholinocyclohexyl)-1H-pyrazol-4-yl)pyrimidin-2-amine | 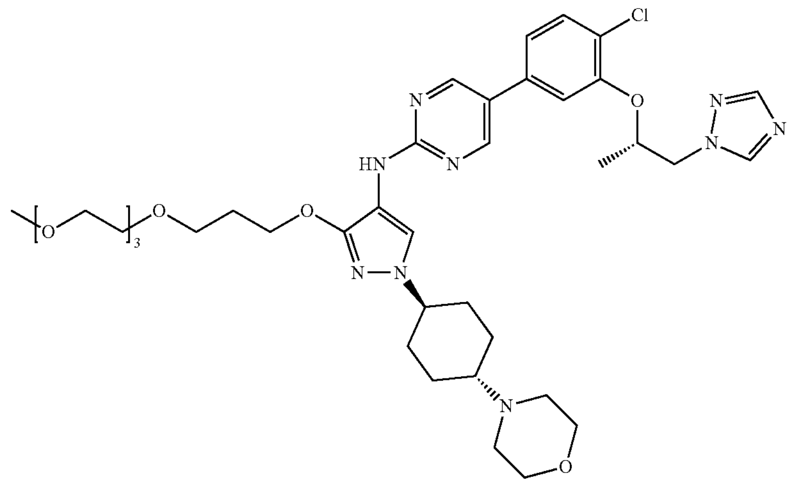 |
| 405 | 2-(((S)-1-(1H-tetrazol-1-yl)propan-2-yl)oxy)-4-(2-((3-((2,5,8,11-tetraoxatetradecan-14-yl)oxy)-1-((1r,4r)-4-((1R,5S)-3-oxa-8-azabicyclo[3.2.1]octan-8-yl)cyclohexyl)-1H-pyrazol-4-yl)amino)pyrimidin-5-yl)benzonitrile | 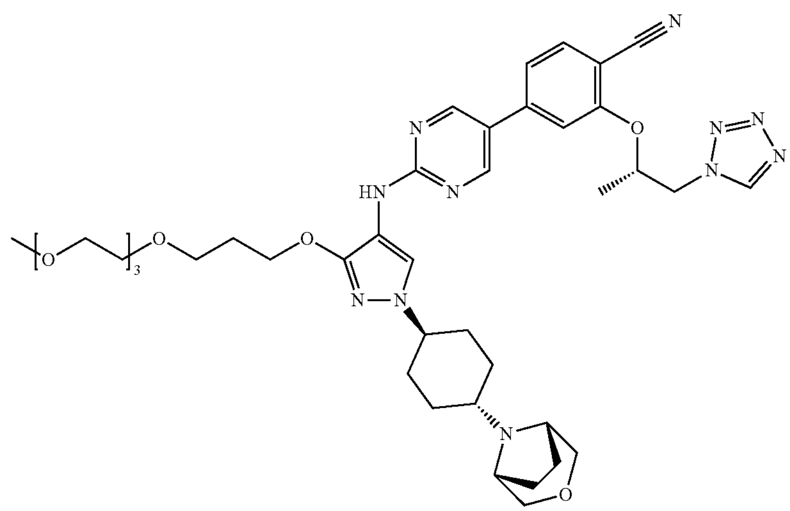 |
| 406 | 5-(3-(((S)-1-(1H-tetrazol-1-yl)propan-2-yl)oxy)-4-chlorophenyl)-N-(3-((2,5,8,11-tetraoxatetradecan-14-yl)oxy)-1-((1r,4r)-4-((1R,5S)-3-oxa-8-azabicyclo[3.2.1]octan-8-yl)cyclohexyl)-1H-pyrazol-4-yl)pyrimidin-2-amine | 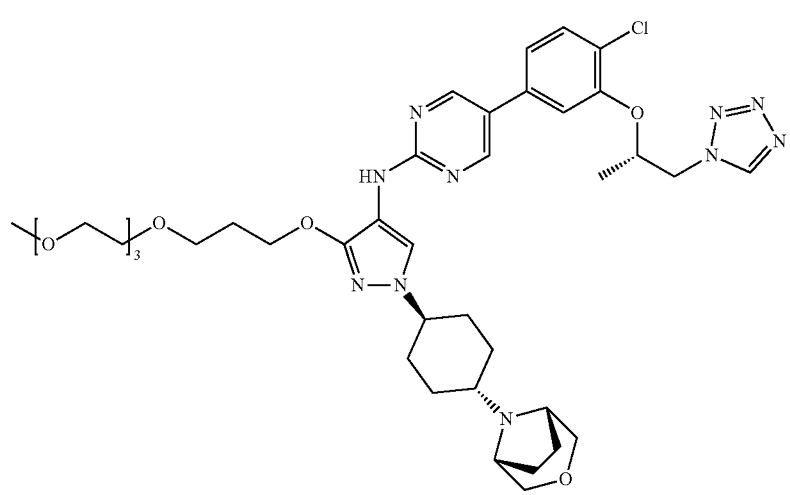 |

TABLE 2-continued

| Ex. No. | IUPAC NAME | STRUCTURE |
|---|---|---|
| 407 | 2-(((S)-1-(1H-1,2,4-triazol-1-yl)propan-2-yl)oxy)-4-(2-((3-((2,5,8,11-tetraoxatetradecan-14-yl)oxy)-1-((1r,4r)-4-((1R,5S)-3-oxa-8-azabicyclo[3.2.1]octan-8-yl)cyclohexyl)-1H-pyrazol-4-yl)amino)pyrimidin-5-yl)benzonitrile | 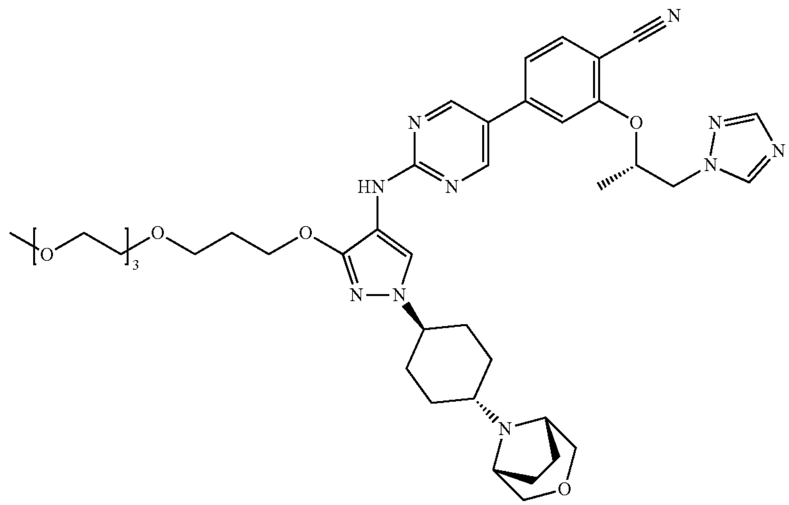 |
| 408 | 5-(3-(((S)-1-(1H-1,2,4-triazol-1-yl)propan-2-yl)oxy)-4-chlorophenyl)-N-(3-((2,5,8,11-tetraoxatetradecan-14-yl)oxy)-1-((1r,4r)-4-((1R,5S)-3-oxa-8-azabicyclo[3.2.1]octan-8-yl)cyclohexyl)-1H-pyrazol-4-yl)pyrimidin-2-amine | 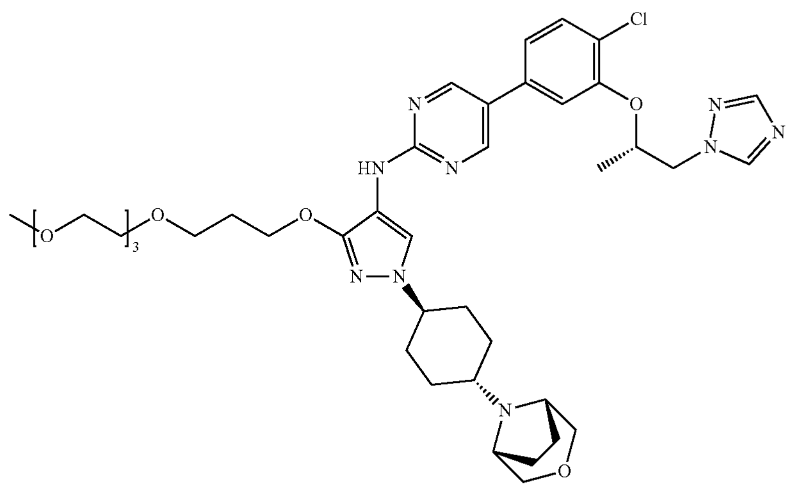 |
| 409 | 2-(((S)-1-(1H-tetrazol-1-yl)propan-2-yl)oxy)-4-(2-((3-((2,5,8,11-tetraoxatetradecan-14-yl)oxy)-1-((1r,4r)-4-((2S,6R)-2,6-dimethylmorpholino)cyclohexyl)-1H-pyrazol-4-yl)amino)pyrimidin-5-yl)benzonitrile | 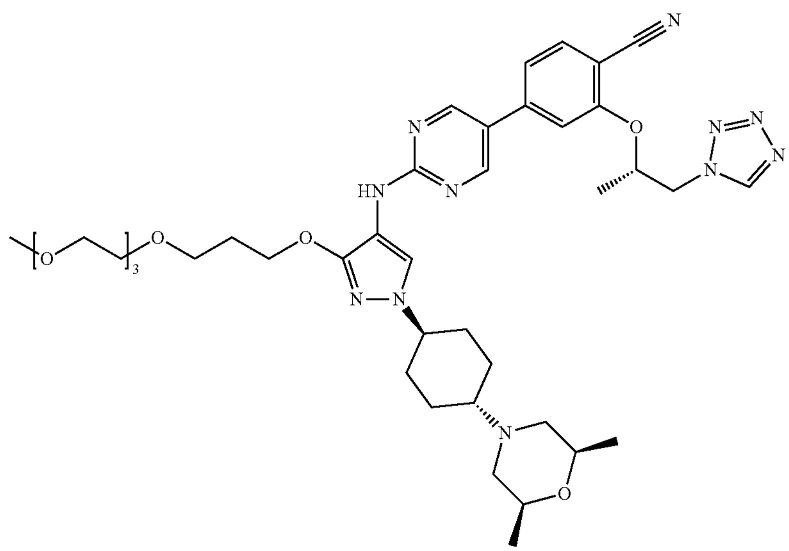 |

TABLE 2-continued

| Ex. No. | IUPAC NAME | STRUCTURE |
|---|---|---|
| 410 | 5-(3-(((S)-1-(1H-tetrazol-1-yl)propan-2-yl)oxy)-4-chlorophenyl)-N-(3-((2,5,8,11-tetraoxatetradecan-14-yl)oxy)-1-((1r,4r)-4-((2S,6R)-2,6-dimethylmorpholino)cyclohexyl)-1H-pyrazol-4-yl)pyrimidin-2-amine | 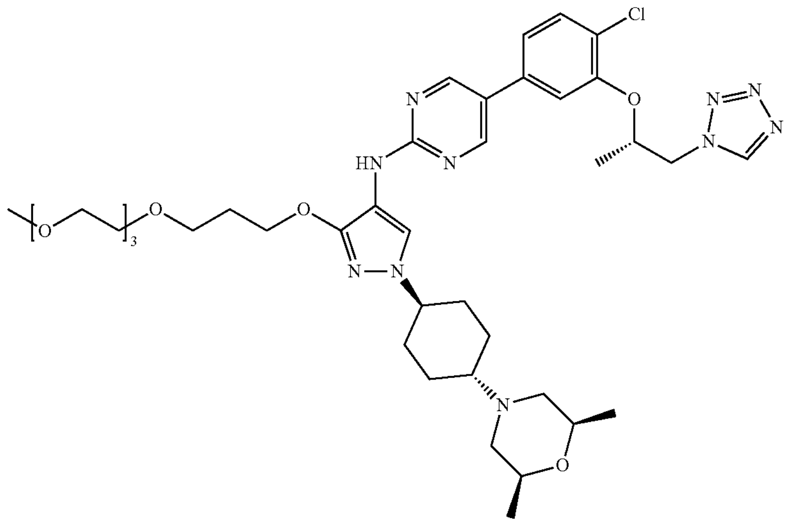 |
| 411 | 2-(((S)-1-(1H-1,2,4-triazol-1-yl)propan-2-yl)oxy)-4-(2-((3-((2,5,8,11-tetraoxatetradecan-14-yl)oxy)-1-((1r,4r)-4-((2S,6R)-2,6-dimethylmorpholino)cyclohexyl)-1H-pyrazol-4-yl)amino)pyrimidin-5-yl)benzonitrile | 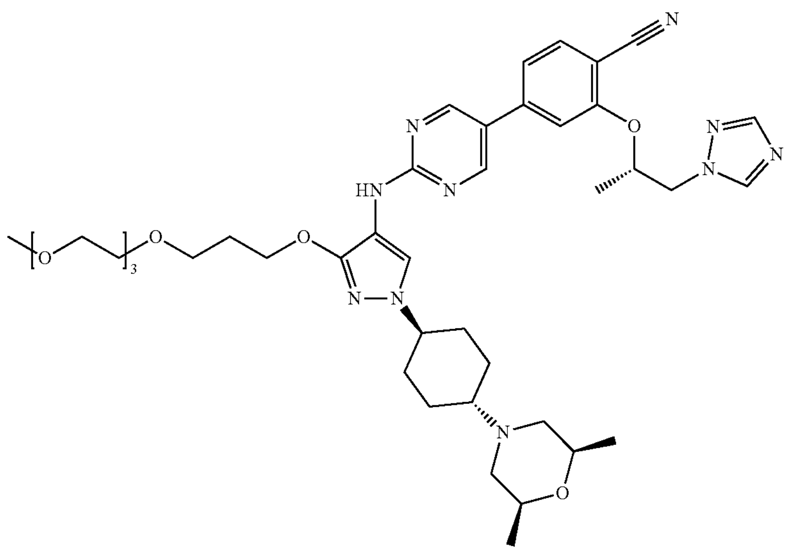 |
| 412 | 5-(3-(((S)-1-(1H-1,2,4-triazol-1-yl)propan-2-yl)oxy)-4-chlorophenyl)-N-(3-((2,5,8,11-tetraoxatetradecan-14-yl)oxy)-1-((1r,4r)-4-((2S,6R)-2,6-dimethylmorpholino)cyclohexyl)-1H-pyrazol-4-yl)pyrimidin-2-amine | 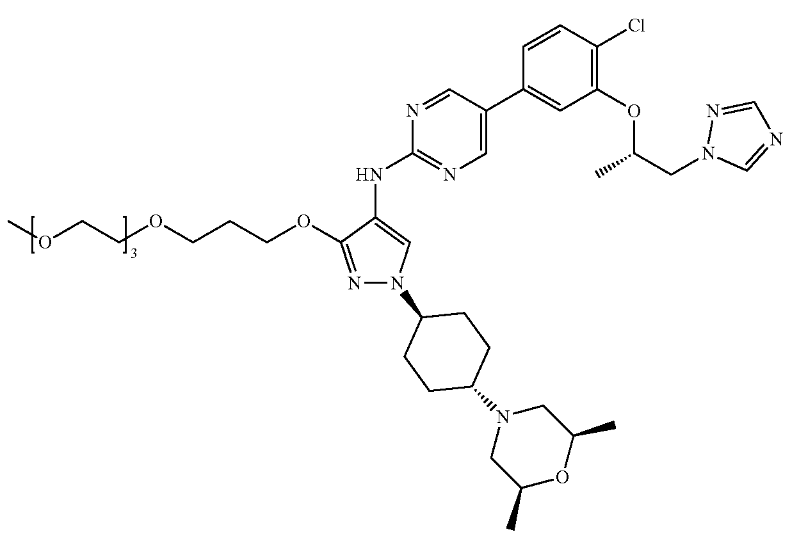 |

TABLE 2-continued

| Ex. No. | IUPAC NAME | STRUCTURE |
| --- | --- | --- |
| 413 | 2-(((S)-1-(1H-tetrazol-1-yl)propan-2-yl)oxy)-4-(2-((3-((2,5,8,11,14-pentaoxaheptadecan-17-yl)oxy)-1-((1r,4r)-4-morpholinocyclohexyl)-1H-pyrazol-4-yl)amino)pyrimidin-5-yl)benzonitrile | 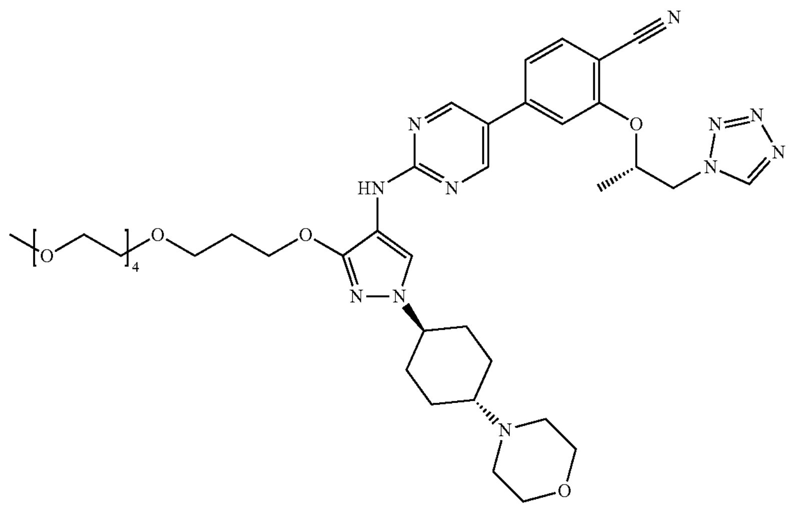 |
| 414 | 5-(3-(((S)-1-(1H-tetrazol-1-yl)propan-2-yl)oxy)-4-chlorophenyl)-N-(3-((2,5,8,11,14-pentaoxaheptadecan-17-yl)oxy)-1-((1r,4r)-4-morpholinocyclohexyl)-1H-pyrazol-4-yl)pyrimidin-2-amine | 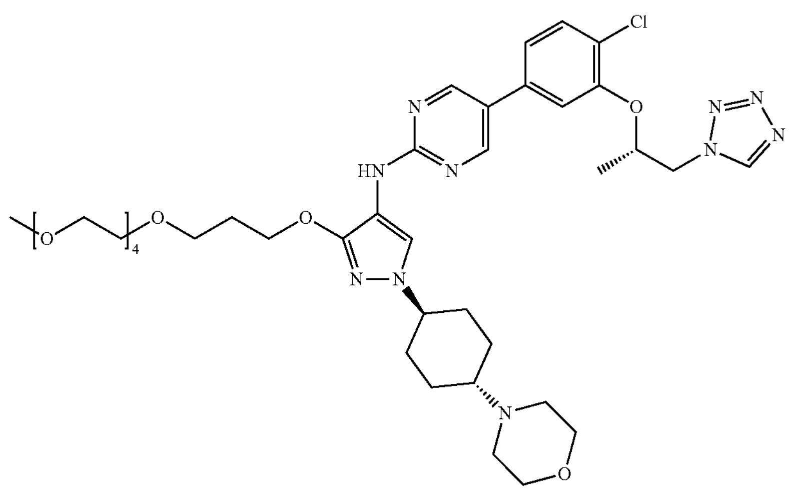 |
| 415 | 2-(((S)-1-(1H-1,2,4-triazol-1-yl)propan-2-yl)oxy)-4-(2-((3-((2,5,8,11,14-pentaoxaheptadecan-17-yl)oxy)-1-((1r,4r)-4-morpholinocyclohexyl)-1H-pyrazol-4-yl)amino)pyrimidin-5-yl)benzonitrile | 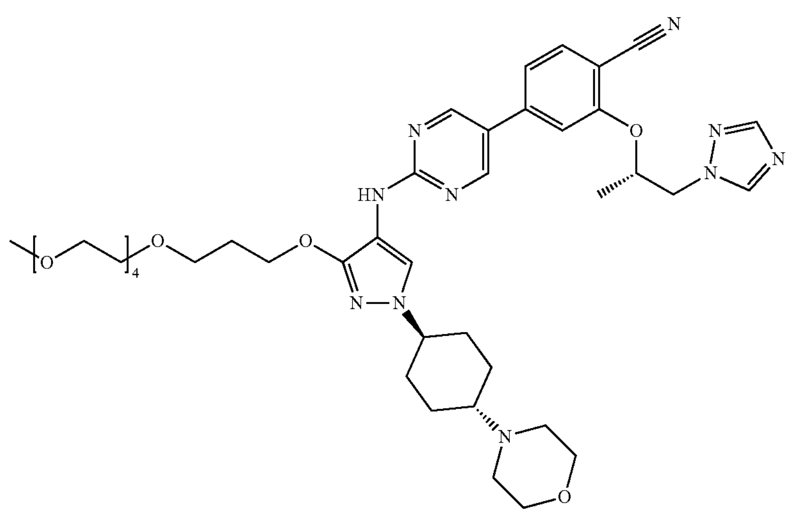 |

TABLE 2-continued

| Ex. No. | IUPAC NAME | STRUCTURE |
| --- | --- | --- |
| 416 | 5-(3-(((S)-1-(1H-1,2,4-triazol-1-yl)propan-2-yl)oxy)-4-chlorophenyl)-N-(3-((2,5,8,11,14-pentaoxaheptadecan-17-yl)oxy)-1-((1r,4r)-4-morpholinocyclohexyl)-1H-pyrazol-4-yl)pyrimidin-2-amine | 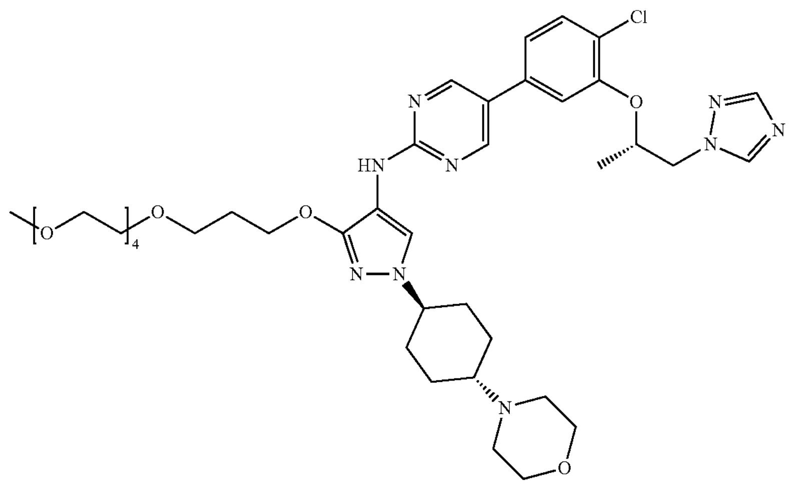 |
| 417 | 2-(((S)-1-(1H-tetrazol-1-yl)propan-2-yl)oxy)-4-(2-((3-((2,5,8,11,14-pentaoxaheptadecan-17-yl)oxy)-1-((1r,4r)-4-((1R,5S)-3-oxa-8-azabicyclo[3.2.1]octan-8-yl)cyclohexyl)-1H-pyrazol-4-yl)amino)pyrimidin-5-yl)benzonitrile | 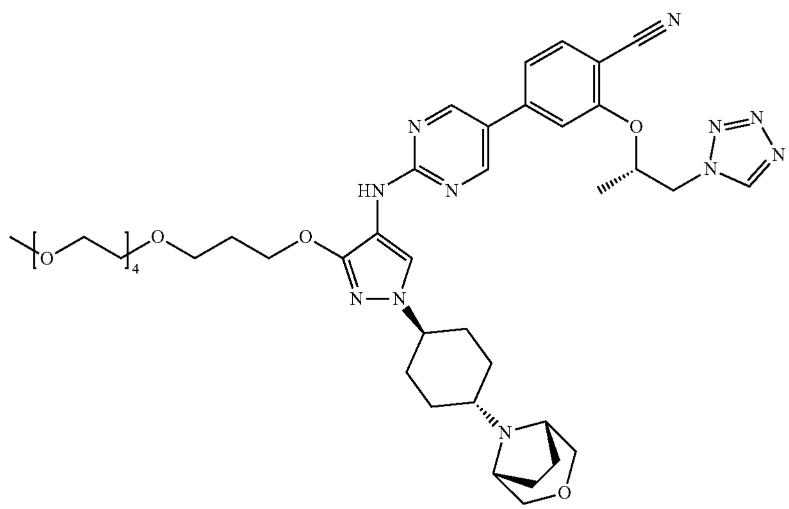 |
| 418 | 5-(3-(((S)-1-(1H-tetrazol-1-yl)propan-2-yl)oxy)-4-chlorophenyl)-N-(3-((2,5,8,11,14-pentaoxaheptadecan-17-yl)oxy)-1-((1r,4r)-4-((1R,5S)-3-oxa-8-azabicyclo[3.2.1]octan-8-yl)cyclohexyl)-1H-pyrazol-4-yl)pyrimidin-2-amine | 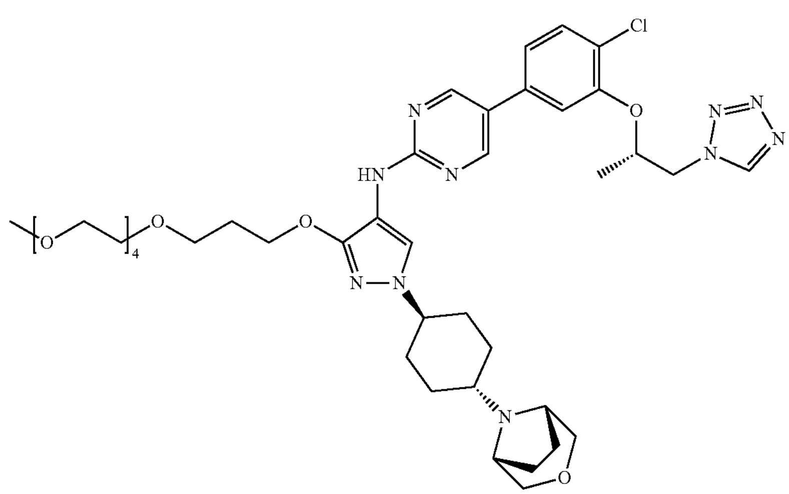 |

TABLE 2-continued

| Ex. No. | IUPAC NAME | STRUCTURE |
|---|---|---|
| 419 | 2-(((S)-1-(1H-1,2,4-triazol-1-yl)propan-2-yl)oxy)-4-(2 ((3-((2,5,8,11,14-pentaoxaheptadecan-17-yl)oxy)-1-((1r,4r)-4-((1R,5S)-3-oxa-8-azabicyclo[3.2.1]octan-8-yl)amino)pyrimidin-5-yl)benzonitrile | 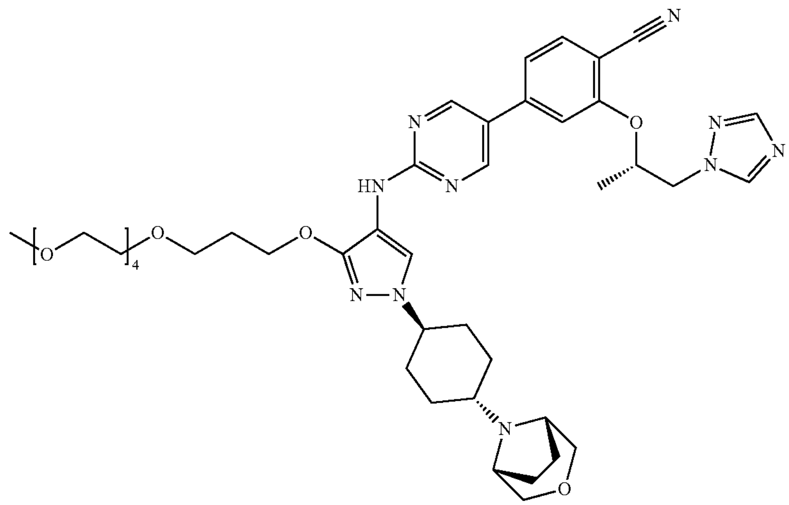 |
| 420 | 5-(3-(((S)-1-(1H-1,2,4-triazol-1-yl)propan-2-yl)oxy)-4-chlorophenyl)-N-(3-((2,5,8,11,14-pentaoxaheptadecan-17-yl)oxy)-1-((1r,4r)-4-((1R,5S)-3-oxa-8-azabicyclo[3.2.1]octan-8-yl)cyclohexyl)-1H-pyrazol-4-yl)pyrimidin-2-amine | 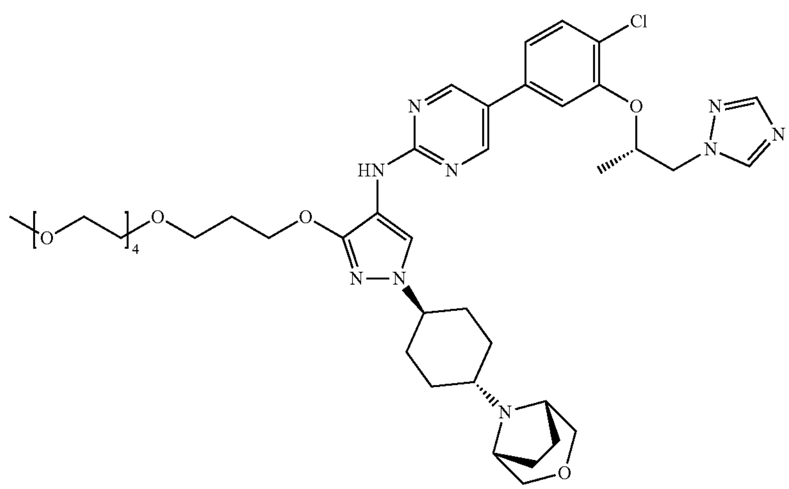 |
| 421 | 2-(((S)-1-(1H-tetrazol-1-yl)propan-2-yl)oxy)-4-(2-((3-((2,5,8,11,14-pentaoxaheptadecan-17-yl)oxy)-1-((1r,4r)-4-((2S,6R)-2,6-dimethylmorpholino)cyclohexyl)-1H-pyrazol-4-yl)amino)pyrimidin-5-yl)benzonitrile | 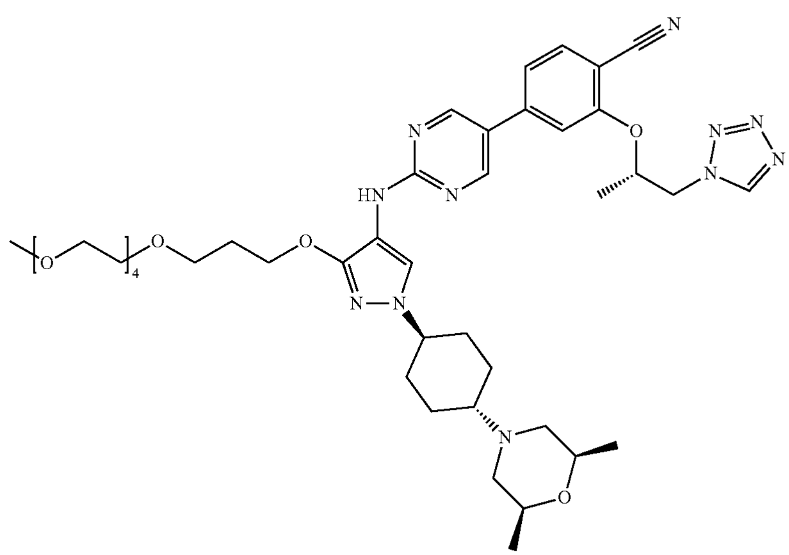 |

TABLE 2-continued

| Ex. No. | IUPAC NAME | STRUCTURE |
|---|---|---|
| 422 | 5-(3-(((S)-1-(1H-tetrazol-1-yl)propan-2-yl)oxy)-4-chlorophenyl)-N-(3-((2,5,8,11,14-pentaoxaheptadecan-17-yl)oxy)-1-((1r,4r)-4-((2S,6R)-2,6-dimethylmorpholino)cyclohexyl)-1H-pyrazol-4-yl)pyrimidin-2-amine | 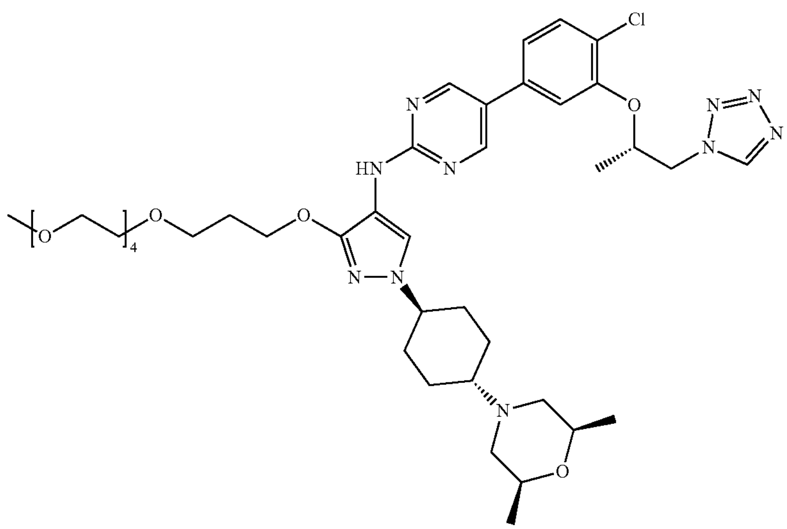 |
| 423 | 2-(((S)-1-(1H-1,2,4-triazol-1-yl)propan-2-yl)oxy)-4-(2-((3-((2,5,8,11,14-pentaoxaheptadecan-17-yl)oxy)-1-((1r,4r)-4-((2S,6R)-2,6-dimethylmorpholino)cyclohexyl)-1H-pyrazol-4-yl)amino)pyrimidin-5-yl)benzonitrile | 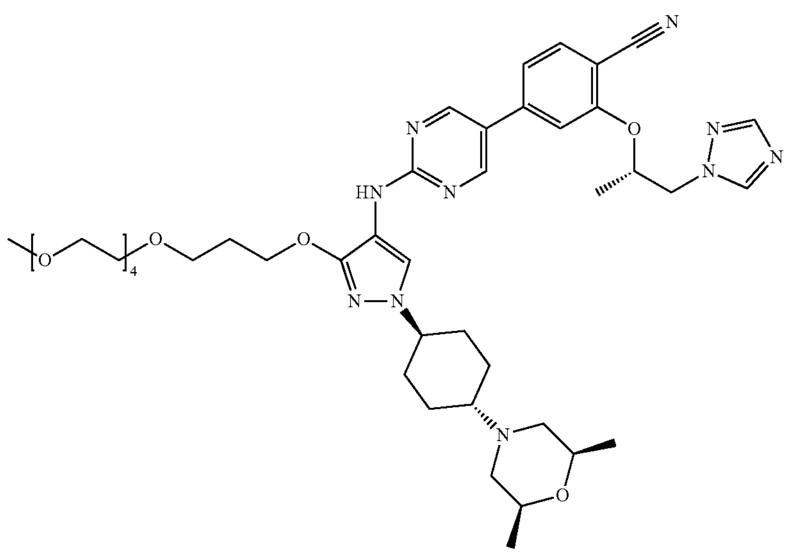 |
| 424 | 5-(3-(((S)-1-(1H-1,2,4-triazol-1-yl)propan-2-yl)oxy)-4-chlorophenyl)-N-(3-((2,5,8,11,14-pentaoxaheptadecan-17-yl)oxy)-1-((1r,4r)-4-((2S,6R)-2,6-dimethylmorpholino)cyclohexyl)-1H-pyrazol-4-yl)pyrimidin-2-amine | 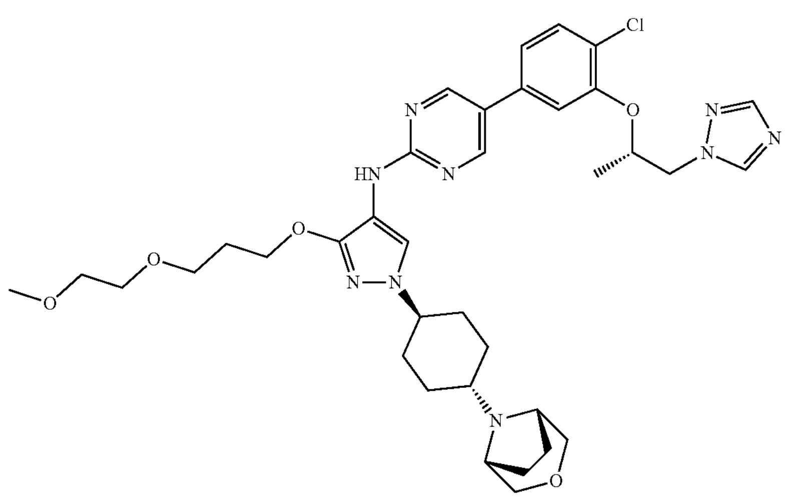 [SMILES: COCCOCCCOc1nn([C@H]2CC[C@H](N3[C@@H]4CC[C@H]3COC4)CC2)cc1Nc1ncc(-c2ccc(Cl)c(O[C@@H](C)Cn3cncn3)c2)cn1] |

TABLE 2-continued

| Ex. No. | IUPAC NAME | STRUCTURE |
|---|---|---|
| 425 | 2-(((S)-1-(1H-tetrazol-1-yl)propan-2-yl)oxy)-4-(2-((3-((2,5,8,11,14-hexaoxaicosan-20-yl)oxy)-1-((1r,4r)-4-morpholinocyclohexyl)-1H-pyrazol-4-yl)amino)pyrimidin-5-yl)benzonitrile | 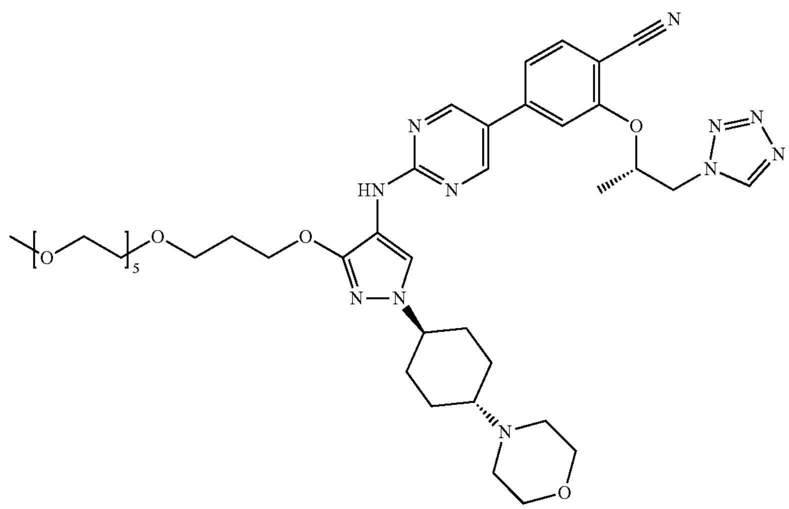 |
| 426 | 5-(3-(((S)-1-(1H-tetrazol-1-yl)propan-2-yl)oxy)-4-chlorophenyl)-N-(3-((2,5,8,11,14,17-hexaoxaicosan-20-yl)oxy)-1-((1r,4r)-4-morpholinocyclohexyl)-1H-pyrazol-4-yl)pyrimidin-2-amine | 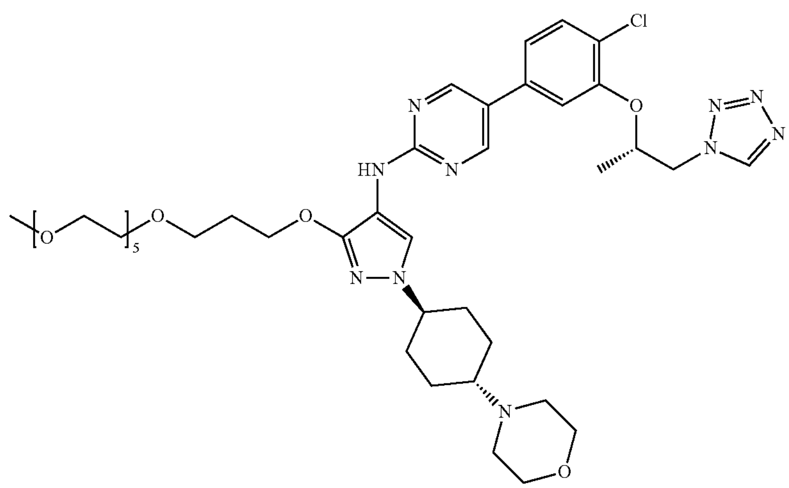 |
| 427 | 2-(((S)-1-(1H-1,2,4-triazol-1-yl)propan-2-yl)oxy)-4-(2-((3-((2,5,8,11,14,17-hexaoxaicosan-20-yl)oxy)-1-((1r,4r)-4-morpholinocyclohexyl)-1H-pyrazol-4-yl)amino)pyrimidin-5-yl)benzonitrile | 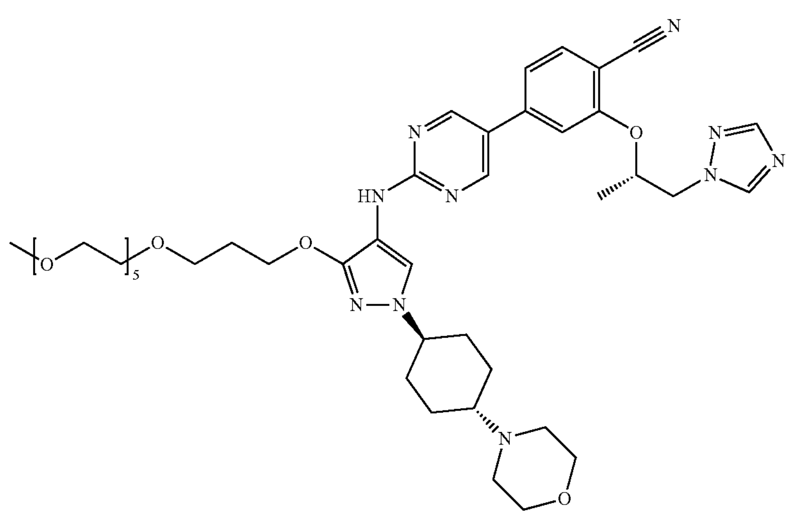 |

| Ex. No. | IUPAC NAME | STRUCTURE |
| --- | --- | --- |
| 428 | 5-(3-(((S)-1-(1H-1,2,4-triazol-1-yl)propan-2-yl)oxy)-4-chlorophenyl)-N-(3-((2,5,8,11,14,17-hexaoxaicosan-20-yl)oxy)-1-((1r,4r)-4-morpholinocyclohexyl)-1H-pyrazol-4-yl)pyrimidin-2-amine | 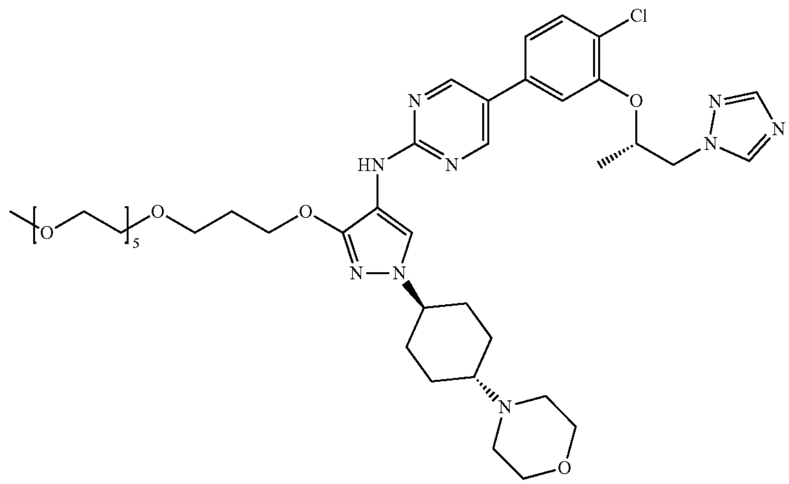 |
| 429 | 2-(((S)-1-(1H-tetrazol-1-yl)propan-2-yl)oxy)-4-(2-((3-((2,5,8,11,14,17-hexaoxaicosan-20-yl)oxy)-1-((1r,4r)-4-((1R,5S)-3-oxa-8-azabicyclo[3.2.1]octan-8-yl)cyclohexyl)-1H-pyrazol-4-yl)amino)pyrimidin-5-yl)benzonitrile | 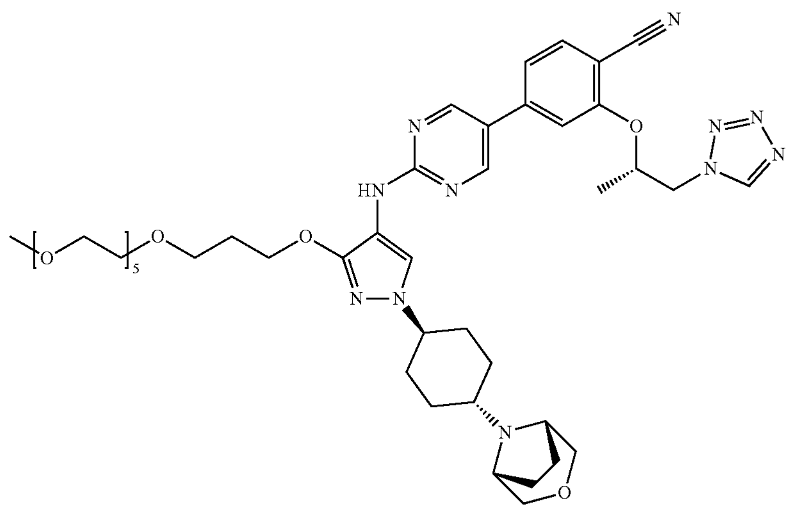 |
| 430 | 5-(3-(((S)-1-(1H-tetrazol-1-yl)propan-2-yl)oxy)-4-chlorophenyl)-N-(3-((2,5,8,11,14,17-hexaoxaicosan-20-yl)oxy)-1-((1r,4r)-4-((1R,5S)-3-oxa-8-azabicyclo[3.2.1]octan-8-yl)cyclohexyl)-1H-pyrazol-4-yl)pyrimidin-2-amine | 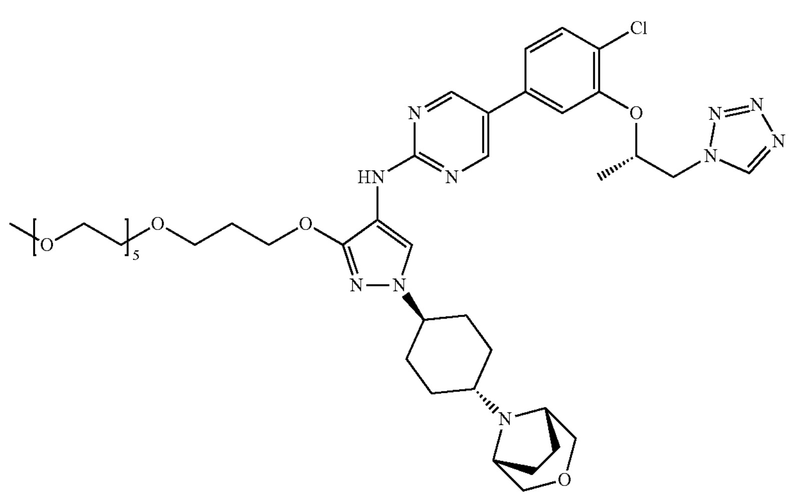 |

TABLE 2-continued

| Ex. No. | IUPAC NAME |
|---|---|
| 431 | 2-(((S)-1-(1H-1,2,4-triazol-1-yl)propan-2-yl)oxy)-4-(2-((3-((2,5,8,11,14,17-hexaoxaicosan-20-yl)oxy)-1-((1r,4r)-4-((1R,5S)-3-oxa-8-azabicyclo[3.2.1]octan-8-yl)cyclohexyl)-1H-pyrazol-4-yl)amino)pyrimidin-5-yl)benzonitrile |
| 432 | 5-(3-(((S)-1-(1H-1,2,4-triazol-1-yl)propan-2-yl)oxy)-4-chlorophenyl)-N-(3-((2,5,8,11,14,17-hexaoxaicosan-20-yl)oxy)-1-((1r,4r)-4-((1R,5S)-3-oxa-8-azabicyclo[3.2.1]octan-8-yl)cyclohexyl)-1H-pyrazol-4-yl)pyrimidin-2-amine |
| 433 | 2-(((S)-1-(1H-tetrazol-1-yl)propan-2-yl)oxy)-4-(2-((3-((2,5,8,11,14,17-hexaoxaicosan-20-yl)oxy)-1-((1r,4r)-4-((2S,6R)-2,6-dimethylmorpholino)cyclohexyl)-1H-pyrazol-4-yl)amino)pyrimidin-5-yl)benzonitrile |

| Ex. No. | IUPAC NAME | STRUCTURE |
| --- | --- | --- |
| 434 | 5-(3-(((S)-1-(1H-tetrazol-1-yl)propan-2-yl)oxy)-4-chlorophenyl)-N-(3-((2,5,8,11,14,17-hexaoxaicosan-20-yl)oxy)-1-((1r,4r)-4-((2S,6R)-2,6-dimethylmorpholino)cyclohexyl)-1H-pyrazol-4-yl)pyrimidin-2-amine | 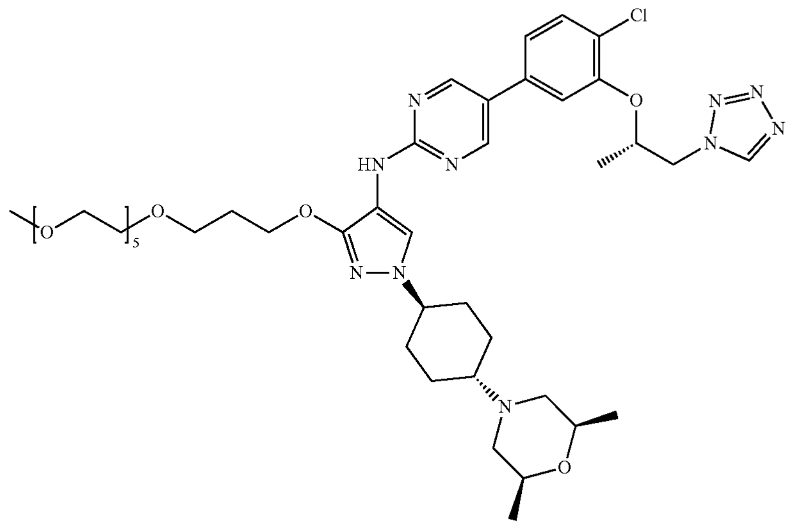 |
| 435 | 2-(((S)-1-(1H-1,2,4-triazol-1-yl)propan-2-yl)oxy)-4-(2-((3-((2,5,8,11,14,17-hexaoxaicosan-20-yl)oxy)-1-((1r,4r)-4-((2S,6R)-2,6-dimethylmorpholino)cyclohexyl)-1H-pyrazol-4-yl)amino)pyrimidin-5-yl)benzonitrile | 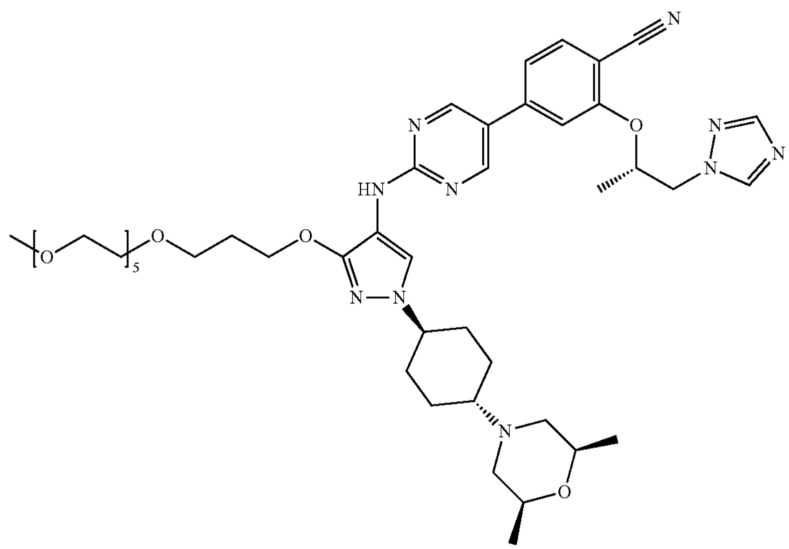 |
| 436 | 5-(3-(((S)-1-(1H-1,2,4-triazol-1-yl)propan-2-yl)oxy)-4-chlorophenyl)-N-(3-((2,5,8,11,14,17-hexaoxaicosan-20-yl)oxy)-1-((1r,4r)-4-((2S,6R)-2,6-dimethylmorpholino)cyclohexyl)-1H-pyrazol-4-yl)pyrimidin-2-amine | 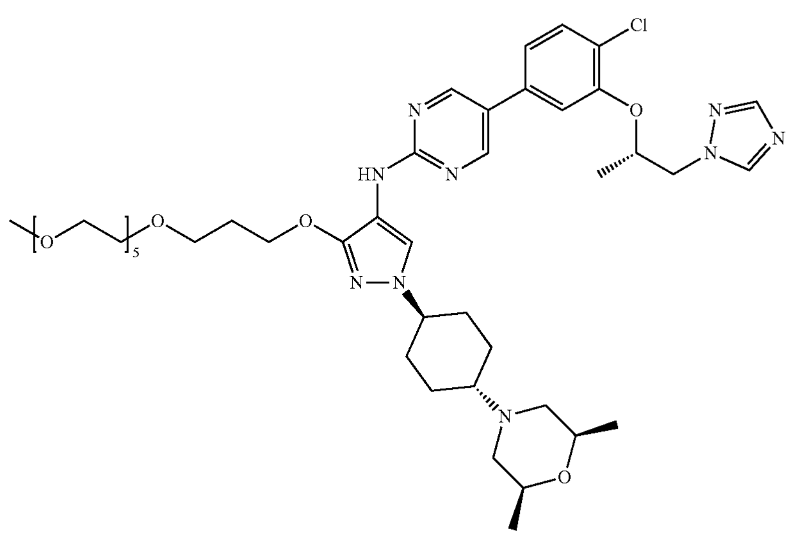 |

TABLE 2-continued

| Ex. No. | IUPAC NAME | STRUCTURE |
| --- | --- | --- |
| 437 | 2-(((S)-1-(1H-tetrazol-1-yl)propan-2-yl)oxy)-4-(2-((3-((2,5,8,11,14,17-heptaoxatricosan-23-yl)oxy)-1-((1r,4r)-4-morpholinocyclohexyl)-1H-pyrazol-4-yl)amino)pyrimidin-5-yl)benzonitrile | 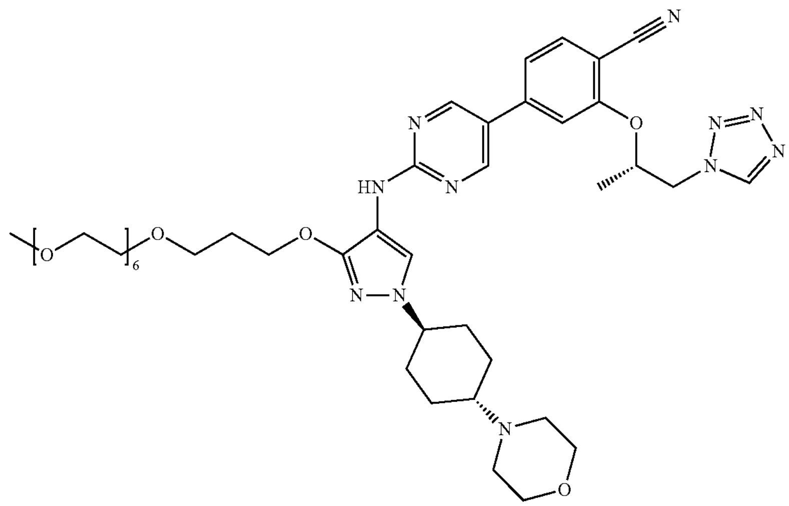 |
| 438 | 5-(3-(((S)-1-(1H-tetrazol-1-yl)propan-2-yl)oxy)-4-chlorophenyl)-N-(3-((2,5,8,11,14,17,20-heptaoxatricosan-23-yl)oxy)-1-((1r,4r)-4-morpholinocyclohexyl)-1H-pyrazol-4-yl)pyrimidin-2-amine | 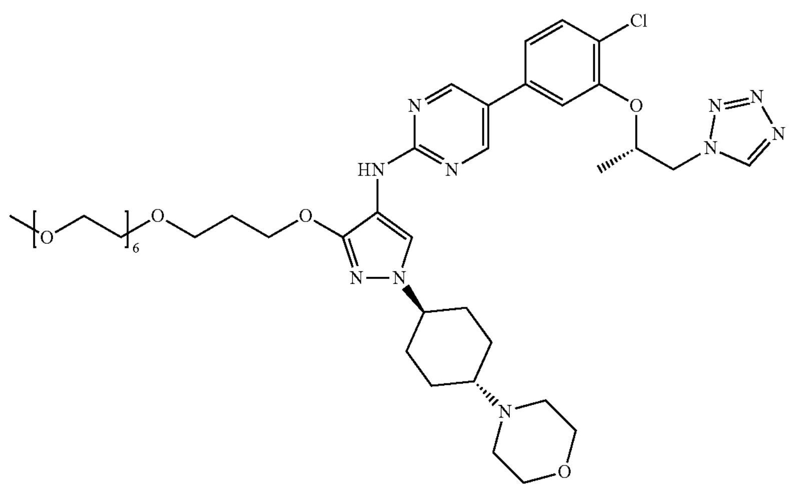 |
| 439 | 2-(((S)-1-(1H-1,2,4-triazol-1-yl)propan-2-yl)oxy)-4-(2-((3-((2,5,8,11,14,17,20-heptaoxatricosan-23-yl)oxy)-1-((1r,4r)-4-morpholinocyclohexyl)-1H-pyrazol-4-yl)amino)pyrimidin-5-yl)benzonitrile | 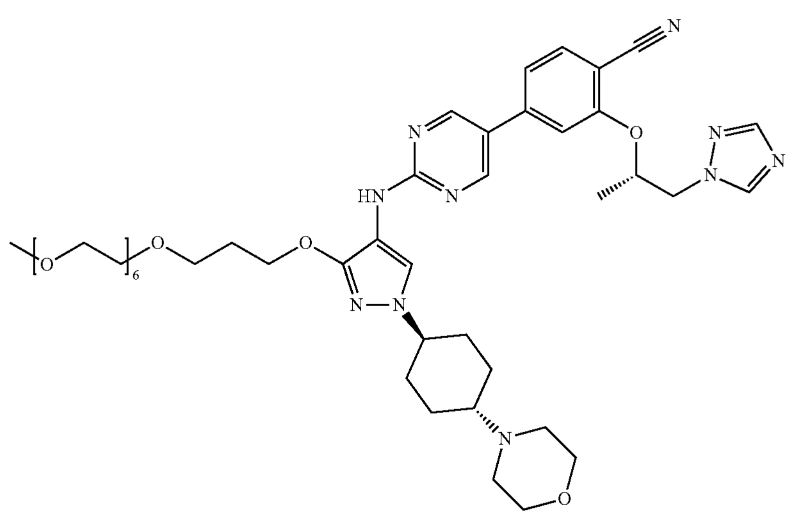 |

TABLE 2-continued

| Ex. No. | IUPAC NAME | STRUCTURE |
|---|---|---|
| 440 | 5-(3-(((S)-1-(1H-1,2,4-triazol-1-yl)propan-2-yl)oxy)-4-chlorophenyl)-N-(3-((2,5,8,11,14,17,20-heptaoxatricosan-23-yl)oxy)-1-((1r,4r)-4-morpholinocyclohexyl)-1H-pyrazol-4-yl)pyrimidin-2-amine | 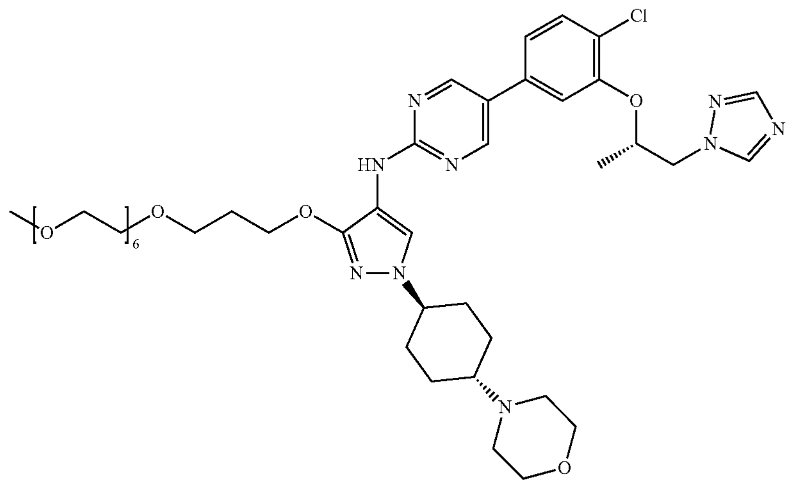 |
| 441 | 2-(((S)-1-(1H-tetrazol-1-yl)propan-2-yl)oxy)-4-(2-((3-((2,5,8,11,14,17,20-heptaoxatricosan-23-yl)oxy)-1-((1r,4r)-4-((1R,5S)-3-oxa-8-azabicyclo[3.2.1]octan-8-yl)cyclohexyl)-1H-pyrazol-4-yl)amino)pyrimidin-5-yl)benzonitrile | 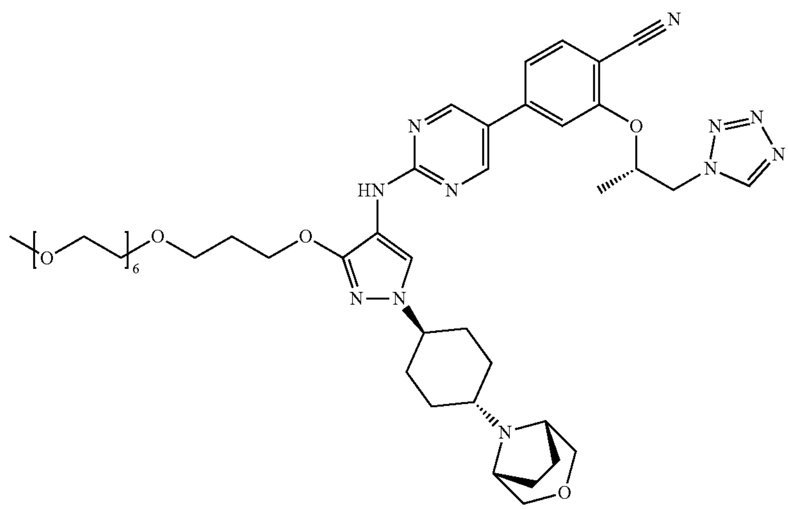 |
| 442 | 5-(3-(((S)-1-(1H-tetrazol-1-yl)propan-2-yl)oxy)-4-chlorophenyl)-N-(3-((2,5,8,11,14,17,20-heptaoxatricosan-23-yl)oxy)-1-((1r,4r)-4-((1R,5S)-3-oxa-8-azabicyclo[3.2.1]octan-8-yl)cyclohexyl)-1H-pyrazol-4-yl)pyrimidin-2-amine | 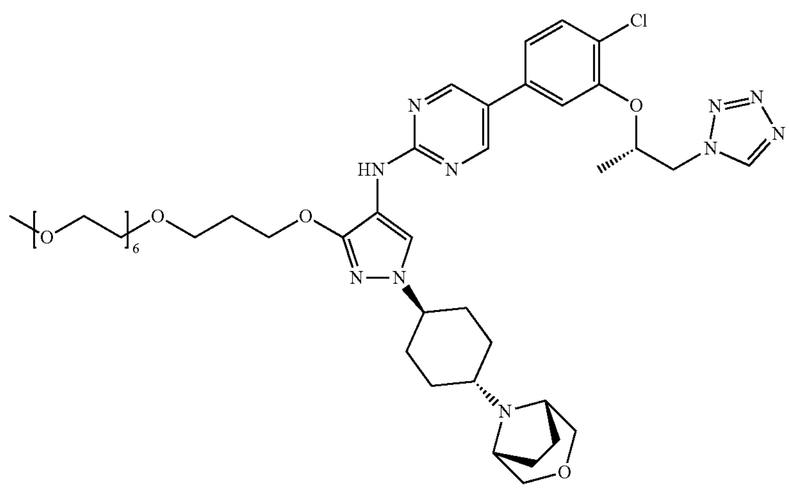 |

TABLE 2-continued

| Ex. No. | IUPAC NAME | STRUCTURE |
|---|---|---|
| 443 | 2-(((S)-1-(1H-1,2,4-triazol-1-yl)propan-2-yl)oxy)-4-(2-((3-((2,5,8,11,14,17,20-heptaoxatricosan-23-yl)oxy)-1-((1r,4r)-4-((1R,5S)-3-oxa-8-azabicyclo[3.2.1]octan-8-yl)cyclohexyl)-1H-pyrazol-4-yl)amino)pyrimidin-5-yl)benzonitrile | 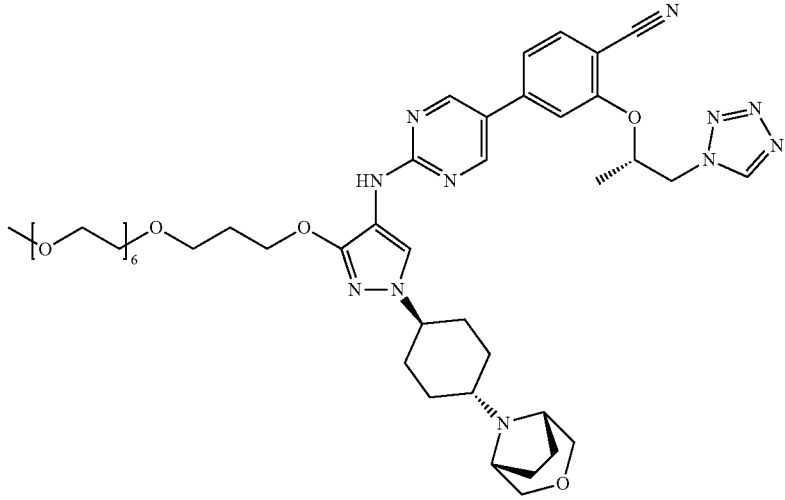 |
| 444 | 5-(3-(((S)-1-(1H-1,2,4-triazol-1-yl)propan-2-yl)oxy)-4-chlorophenyl)-N-(3-((2,5,8,11,14,17,20-heptaoxatricosan-23-yl)oxy)-1-((1r,4r)-4-((1R,5S)-3-oxa-8-azabicyclo[3.2.1]octan-8-yl)cyclohexyl)-1H-pyrazol-4-yl)pyrimidin-2-amine | 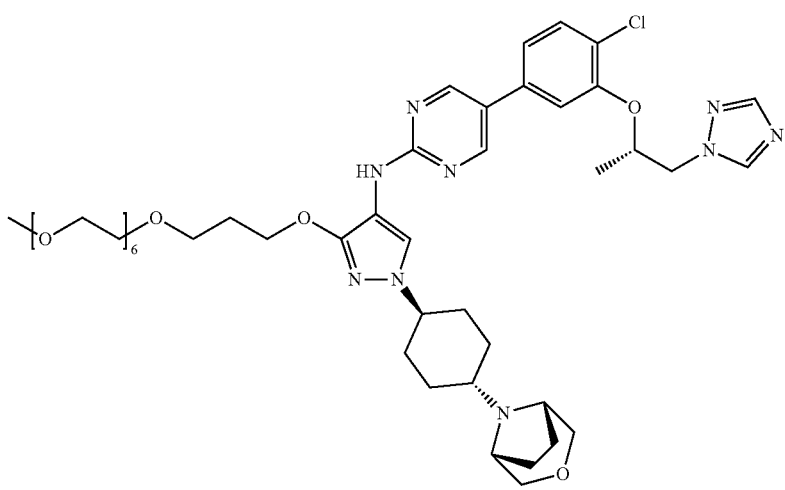 |
| 445 | 2-(((S)-1-(1H-tetrazol-1-yl)propan-2-yl)oxy)-4-(2-((3-((2,5,8,11,14,17,20-heptaoxatricosan-23-yl)oxy)-1-((1r,4r)-4-((2S,6R)-2,6-dimethylmorpholino)cyclohexyl)-1H-pyrazol-4-yl)amino)pyrimidin-5-yl)benzonitrile | 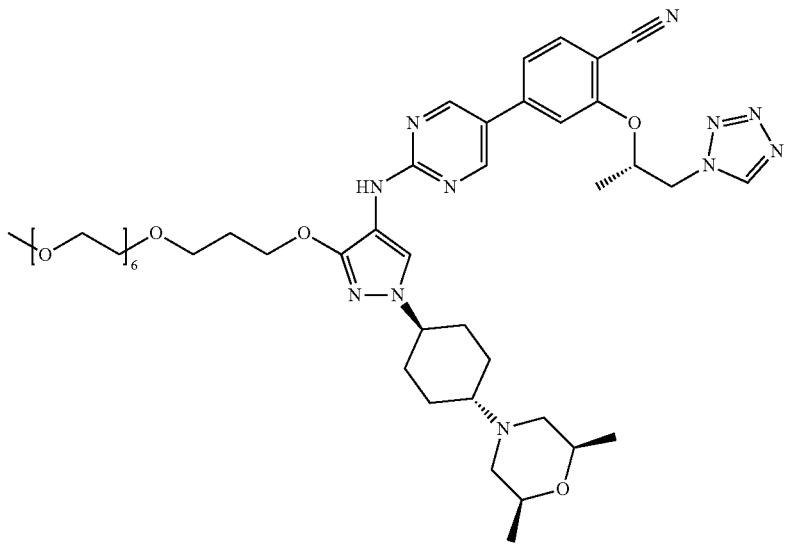 |

TABLE 2-continued

| Ex. No. | IUPAC NAME | STRUCTURE |
|---|---|---|
| 446 | 5-(3-(((S)-1-(1H-tetrazol-1-yl)propan-2-yl)oxy)-4-chlorophenyl)-N-(3-((2,5,8,11,14,17,20-heptaoxatricosan-23-yl)oxy)-1-((1r,4r)-4-((2S,6R)-2,6-dimethylmorpholino)cyclohexyl)-1H-pyrazol-4-yl)pyrimidin-2-amine | 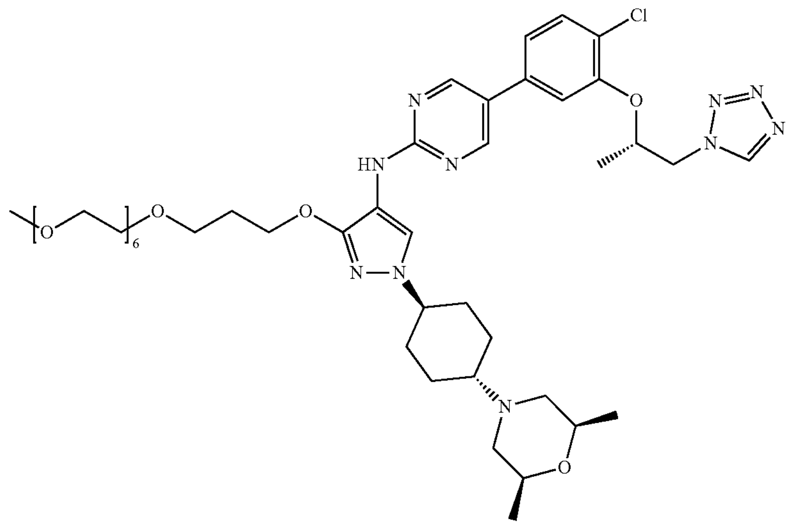 |
| 447 | 2-(((S)-1-(1H-1,2,4-triazol-1-yl)propan-2-yl)oxy)-4-(2-((3-((2,5,8,11,14,17,20-heptaoxatricosan-23-yl)oxy)-1-((1r,4r)-4-((2S,6R)-2,6-dimethylmorpholino)cyclohexyl)-1H-pyrazol-4-yl)amino)pyrimidin-5-yl)benzonitrile | 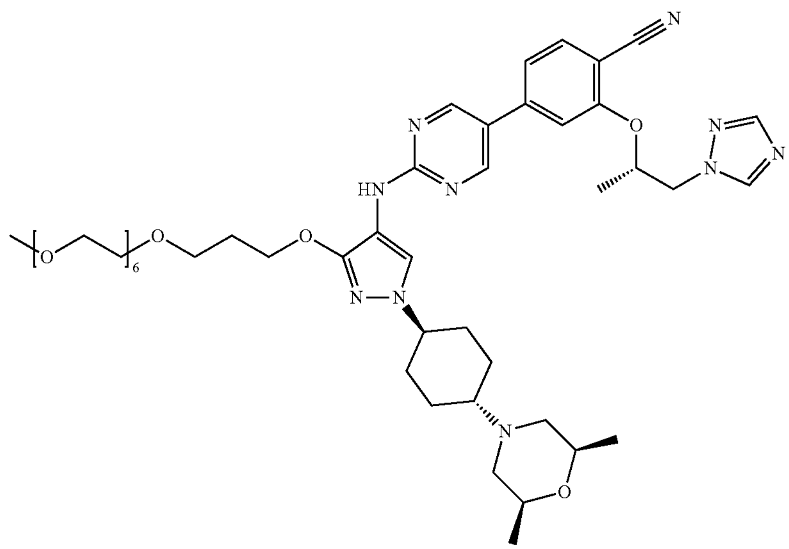 |
| 448 | 5-(3-(((S)-1-(1H-1,2,4-triazol-1-yl)propan-2-yl)oxy)-4-chlorophenyl)-N-(3-((2,5,8,11,14,17,20-heptaoxatricosan-23-yl)oxy)-1-((1r,4r)-4-((2S,6R)-2,6-dimethylmorpholino)cyclohexyl)-1H-pyrazol-4-yl)pyrimidin-2-amine | 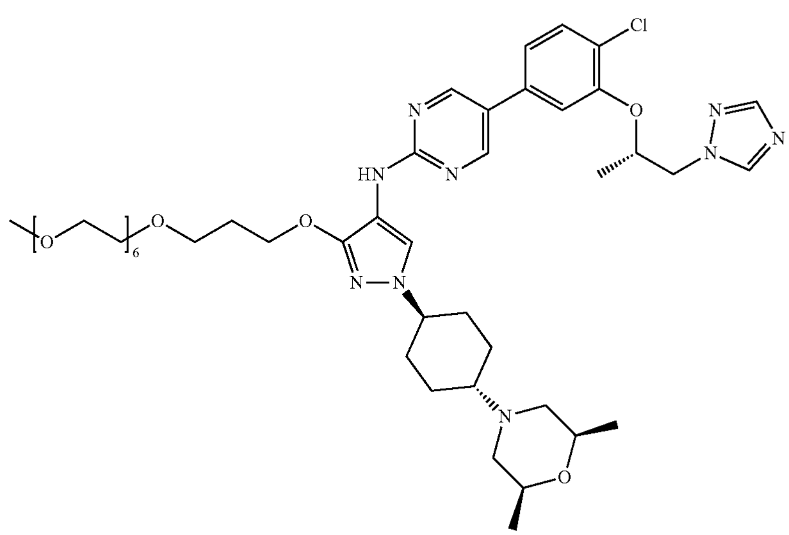 |

TABLE 2-continued

| Ex. No. | IUPAC NAME | STRUCTURE |
| --- | --- | --- |
| 449 | 2-(((S)-1-(1H-tetrazol-1-yl)propan-2-yl)oxy)-4-(2-((3-((2,5,8,11,14,17,23-octaoxahexacosan-26-yl)oxy)-1-((1r,4r)-4-morpholinocyclohexyl)-1H-pyrazol-4-yl)amino)pyrimidin-5-yl)benzonitrile | 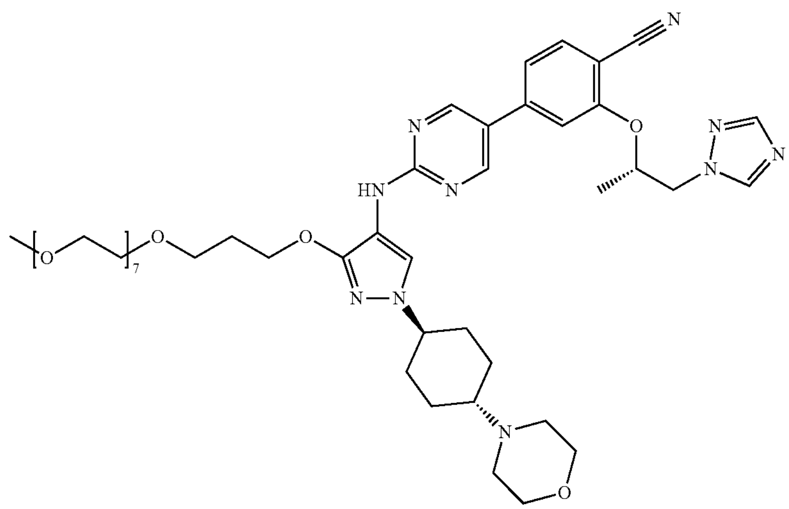 |
| 450 | 5-(3-(((S)-1-(1H-tetrazol-1-yl)propan-2-yl)oxy)-4-chlorophenyl)-N-(3-((2,5,8,11,14,17,20,23-octaoxahexacosan-26-yl)oxy)-1-((1r,4r)-4-morpholinocyclohexyl)-1H-pyrazol-4-yl)pyrimidin-2-amine | 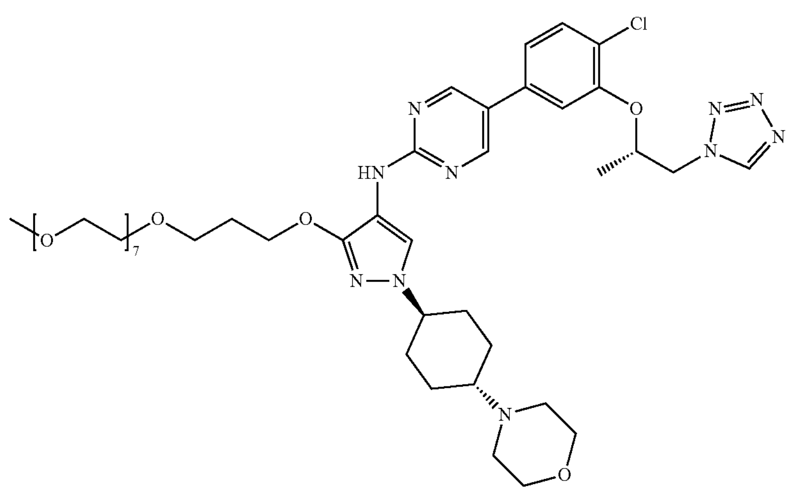 |
| 451 | 2-(((S)-1-(1H-1,2,4-triazol-1-yl)propan-2-yl)oxy)-4-(2-((3-((2,5,8,11,14,17,20,23-octaoxahexacosan-26-yl)oxy)-1-((1r,4r)-4-morpholinocyclohexyl)-1H-pyrazol-4-yl)amino)pyrimidin-5-yl)benzonitrile | 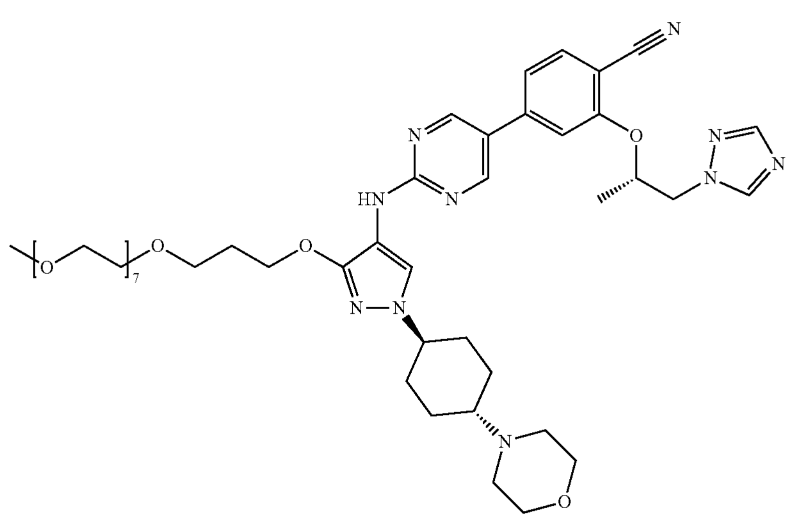 |

TABLE 2-continued

| Ex. No. | IUPAC NAME | STRUCTURE |
| --- | --- | --- |
| 452 | 5-(3-(((S)-1-(1H-1,2,4-triazol-1-yl)propan-2-yl)oxy)-4-chlorophenyl)-N-(3-((2,5,8,11,14,17,20,23-octaoxahexacosan-26-yl)oxy)-1-((1r,4r)-4-morpholinocyclohexyl)-1H-pyrazol-4-yl)pyrimidin-2-amine | 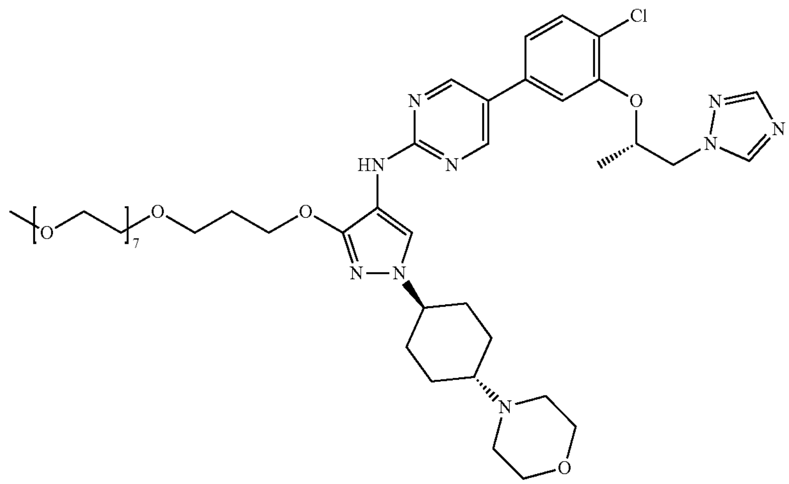 |
| 453 | 2-(((S)-1-(1H-tetrazol-1-yl)propan-2-yl)oxy)-4-(2-((3-((2,5,8,11,14,17,20,23-octaoxahexacosan-26-yl)oxy)-1-((1r,4r)-4-((1R,5S)-3-oxa-8-azabicyclo[3.2.1]octan-8-yl)cyclohexyl)-1H-pyrazol-4-yl)amino)pyrimidin-5-yl)benzonitrile | 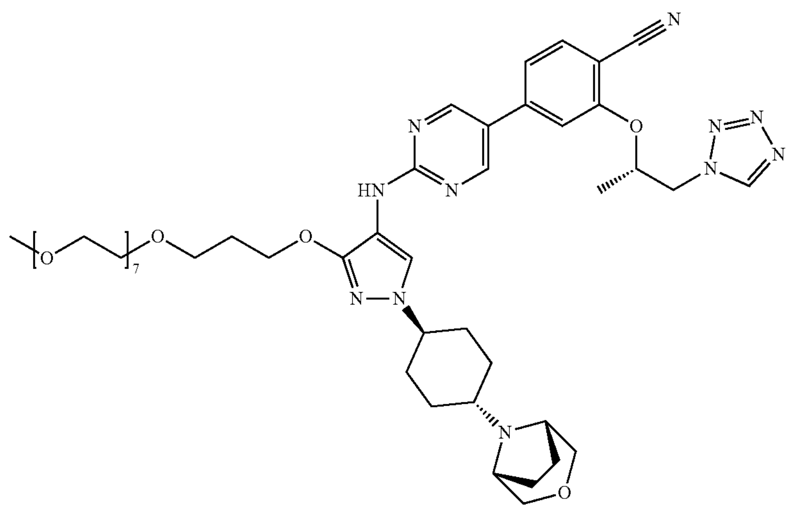 |
| 454 | 5-(3-(((S)-1-(1H-tetrazol-1-yl)propan-2-yl)oxy)-4-chlorophenyl)-N-(3-((2,5,8,11,14,17,20,23-octaoxahexacosan-26-yl)oxy)-1-((1r,4r)-4-((1R,5S)-3-oxa-8-azabicyclo[3.2.1]octan-8-yl)cyclohexyl)-1H-pyrazol-4-yl)pyrimidin-2-amine | 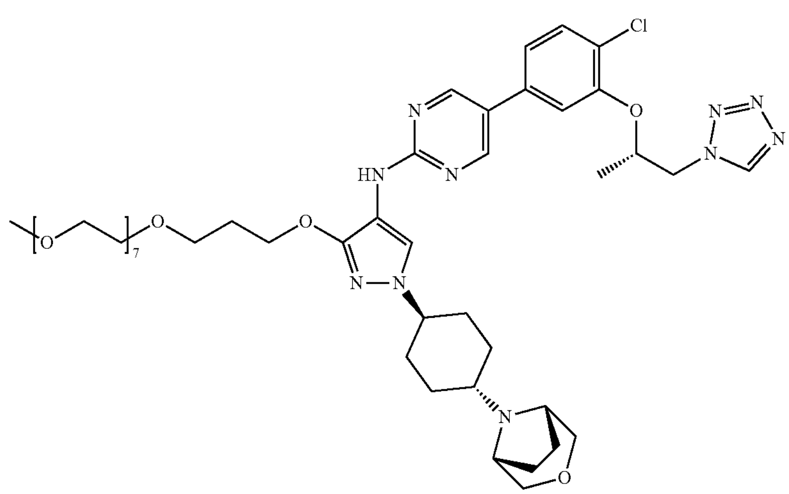 |

TABLE 2-continued

| Ex. No. | IUPAC NAME | STRUCTURE |
|---|---|---|
| 455 | 2-(((S)-1-(1H-1,2,4-triazol-1-yl)propan-2-yl)oxy)-4-(2-((3-((2,5,8,11,14,17,20,23-octaoxahexacosan-26-yl)oxy)-1-((1r,4r)-4-((1R,5S)-3-oxa-8-azabicyclo[3.2.1]octan-8-yl)cyclohexyl)-1H-pyrazol-4-yl)amino)pyrimidin-5-yl)benzonitrile | 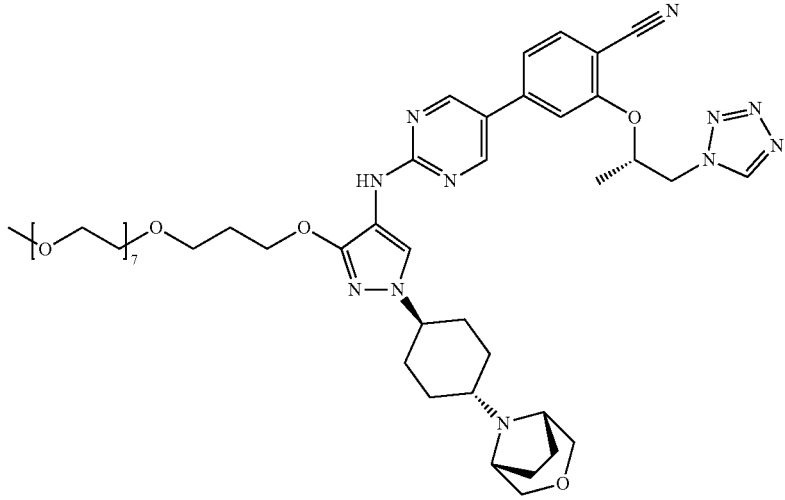 |
| 456 | 5-(3-(((S)-1-(1H-1,2,4-triazol-1-yl)propan-2-yl)oxy)-4-chlorophenyl)-N-(3-((2,5,8,11,14,17,20,23-octaoxahexacosan-26-yl)oxy)-1-((1r,4r)-4-((1R,5S)-3-oxa-8-azabicyclo[3.2.1]octan-8-yl)cyclohexyl)-1H-pyrazol-4-yl)pyrimidin-2-amine | 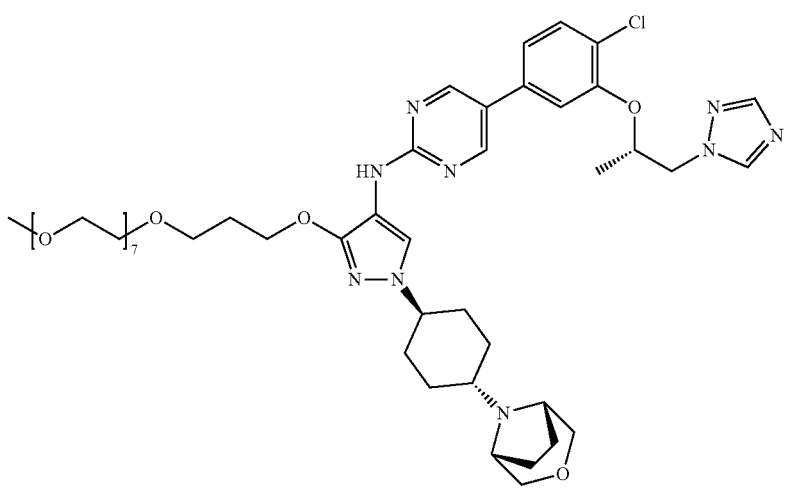 |
| 457 | 2-(((S)-1-(1H-tetrazol-1-yl)propan-2-yl)oxy)-4-(2-((3-((2,5,8,11,14,17,20,23-octaoxahexacosan-26-yl)oxy)-1-((1r,4r)-4-((2S,6R)-2,6-dimethylmorpholino)cyclohexyl)-1H-pyrazol-4-yl)amino)pyrimidin-5-yl)benzonitrile | 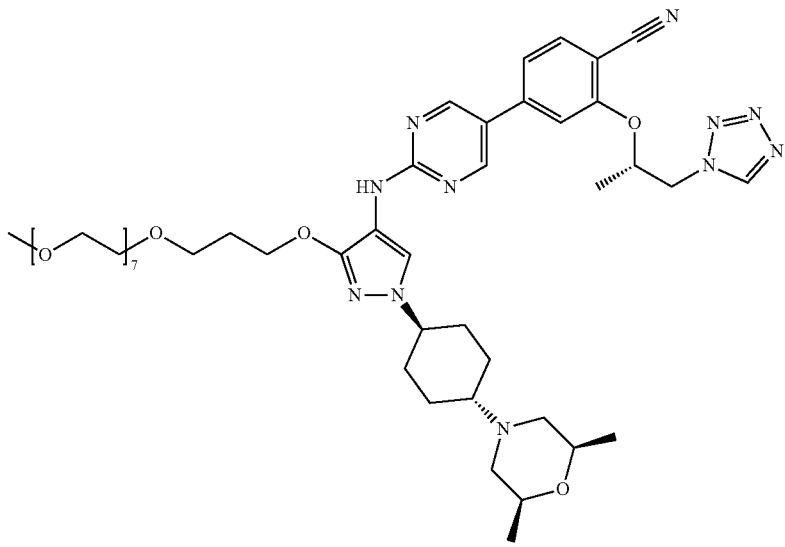 |

TABLE 2-continued

| Ex. No. | IUPAC NAME | STRUCTURE |
|---|---|---|
| 458 | 5-(3-(((S)-1-(1H-tetrazol-1-yl)propan-2-yl)oxy)-4-chlorophenyl)-N-(3-((2,5,8,11,14,17,20,23-octaoxahexacosan-26-yl)oxy)-1-((1r,4r)-4-((2S,6R)-2,6-dimethylmorpholino)cyclohexyl)-1H-pyrazol-4-yl)pyrimidin-2-amine | 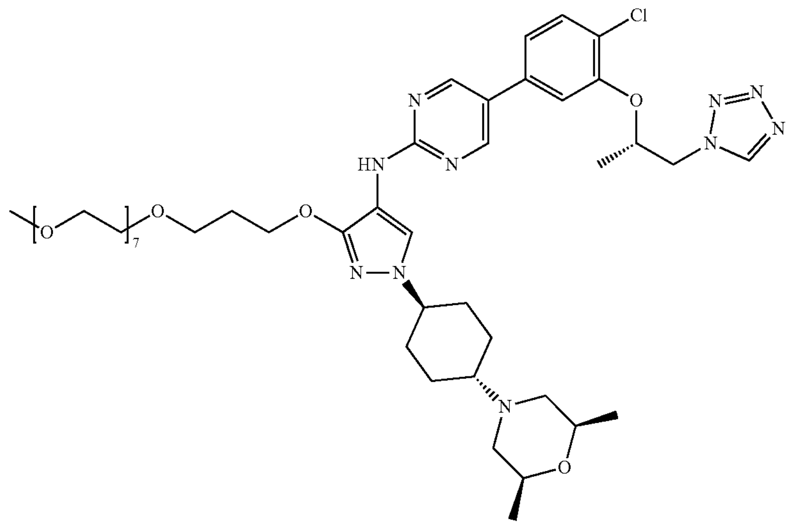 |
| 459 | 2-(((S)-1-(1H-1,2,4-triazol-1-yl)propan-2-yl)oxy)-4-(2-((3-((2,5,8,11,14,17,20,23-octaoxahexacosan-26-yl)oxy)-1-((1r,4r)-4-((2S,6R)-2,6-dimethylmorpholino)cyclohexyl)-1H-pyrazol-4-yl)amino)pyrimidin-5-yl)benzonitrile | 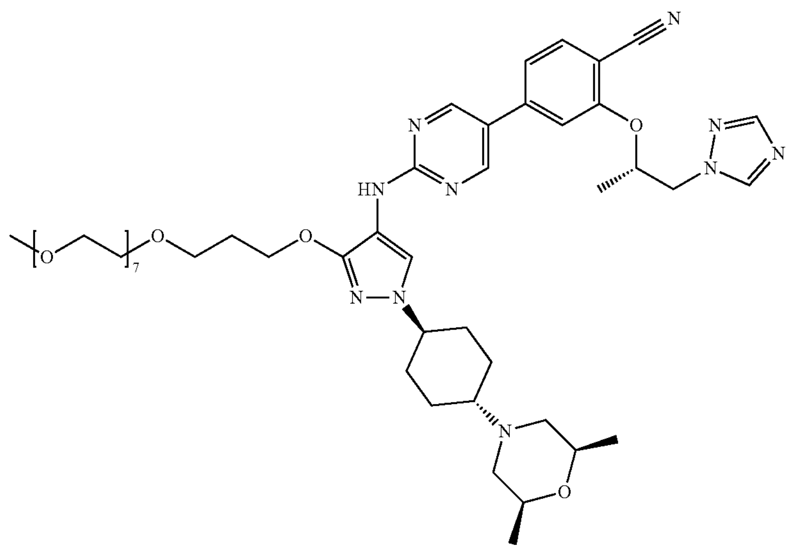 |
| 460 | 5-(3-(((S)-1-(1H-1,2,4-triazol-1-yl)propan-2-yl)oxy)-4-chlorophenyl)-N-(3-((2,5,8,11,14,17,20,23-octaoxahexacosan-26-yl)oxy)-1-((1r,4r)-4-((2S,6R)-2,6-dimethylmorpholino)cyclohexyl)-1H-pyrazol-4-yl)pyrimidin-2-amine | 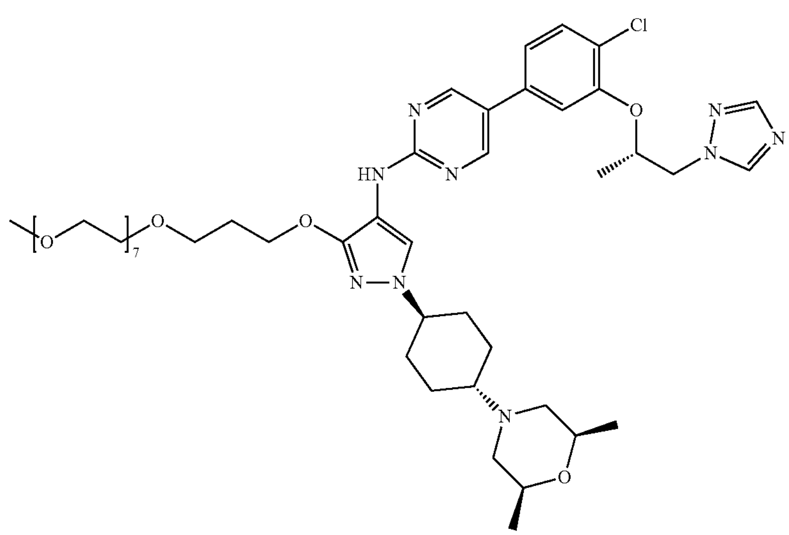 |

TABLE 2-continued

| Ex. No. | IUPAC NAME | STRUCTURE |
| --- | --- | --- |
| 463 | 2-(((S)-1-(1H-1,2,4-triazol-1-yl)propan-2-yl)oxy)-4-(2-((3-hydroxy-1-((1r,4r)-4-morpholinocyclohexyl)-1H-pyrazol-4-yl)amino)pyrimidin-5-yl)benzonitrile | 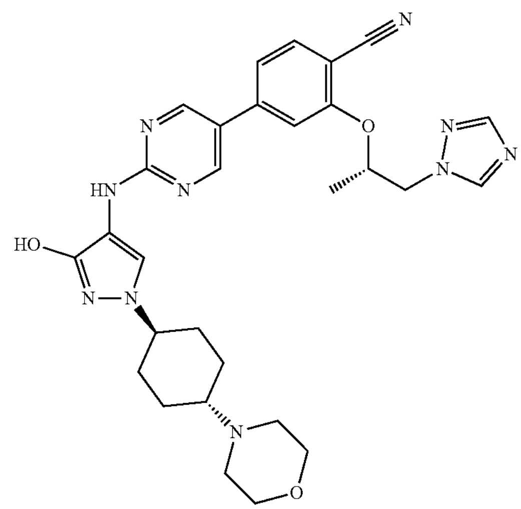 [SMILES: C[C@@H](Cn1cncn1)Oc1cc(-c2cnc(Nc3cn([C@H]4CC[C@H](N5CCOCC5)CC4)nc3O)nc2)ccc1C#N] |
| 464 | 4-((5-(3-(((S)-1-(1H-1,2,4-triazol-1-yl)propan-2-yl)oxy)-4-chlorophenyl)pyrimidin-2-yl)amino)-1-((1r,4r)-4-morpholinocyclohexyl)-1H-pyrazol-3-ol | 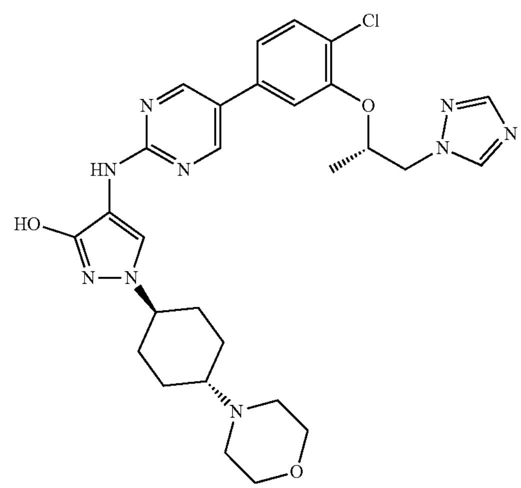 [SMILES: C[C@@H](Cn1cncn1)Oc1cc(-c2cnc(Nc3cn([C@H]4CC[C@H](N5CCOCC5)CC4)nc3O)nc2)ccc1Cl] |
| 465 | 2-(((S)-1-(1H-tetrazol-1-yl)propan-2-yl)oxy)-4-(2-((1-((1r,4r)-4-((1R,5S)-3-oxa-8-azabicyclo[3.2.1]octan-8-yl)cyclohexyl)-3-hydroxy-1H-pyrazol-4-yl)amino)pyrimidin-5-yl)benzonitrile | 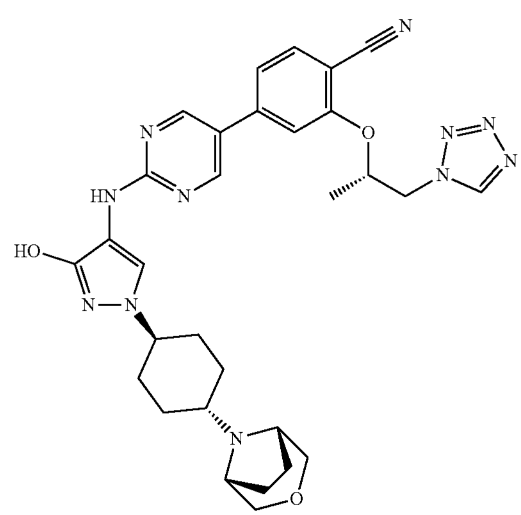 [SMILES: C[C@@H](Cn1cnnn1)Oc1cc(-c2cnc(Nc3cn([C@H]4CC[C@H](N5[C@@H]6CC[C@H]5COC6)CC4)nc3O)nc2)ccc1C#N] |

TABLE 2-continued

| Ex. No. | IUPAC NAME | STRUCTURE |
| --- | --- | --- |
| 466 | 4-((5-(3-(((S)-1-(1H-tetrazol-1-yl)propan-2-yl)oxy)-4-chlorophenyl)pyrimidin-2-yl)amino)-1-((1r,4r)-4-((1R,5S)-3-oxa-8-azabicyclo[3.2.1]octan-8-yl)cyclohexyl)-1H-pyrazol-3-ol | 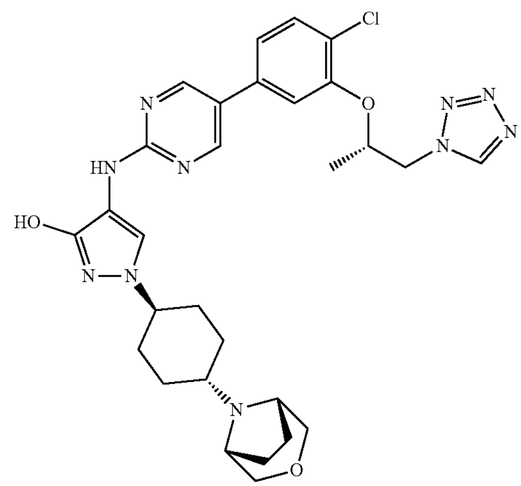 [SMILES: C[C@@H](Cn1cnnn1)Oc1cc(-c2cnc(Nc3cn([C@H]4CC[C@H](N5[C@@H]6CC[C@H]5COC6)CC4)nc3O)nc2)ccc1Cl] |
| 467 | 2-(((S)-1-(1H-1,2,4-triazol-1-yl)propan-2-yl)oxy)-4-(2-((1-((1r,4r)-4-((1R,5S)-3-oxa-8-azabicyclo[3.2.1]octan-8-yl)cyclohexyl)-3-hydroxy-1H-pyrazol-4-yl)amino)pyrimidin-5-yl)benzonitrile | 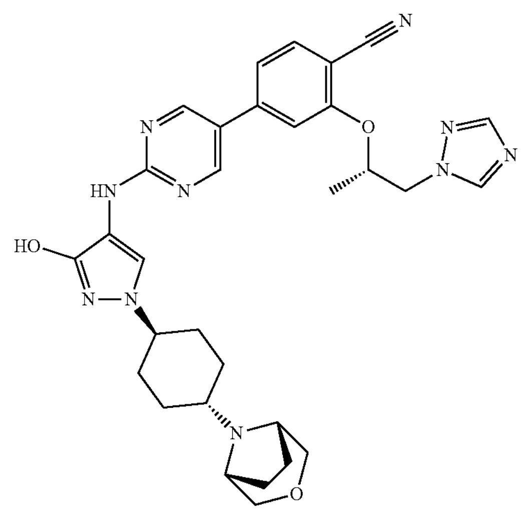 [SMILES: C[C@@H](Cn1cncn1)Oc1cc(-c2cnc(Nc3cn([C@H]4CC[C@H](N5[C@@H]6CC[C@H]5COC6)CC4)nc3O)nc2)ccc1C#N] |
| 468 | 4-((5-(3-(((S)-1-(1H-1,2,4-triazol-1-yl)propan-2-yl)oxy)-4-chlorophenyl)pyrimidin-2-yl)amino)-1-((1r,4r)-4-((1R,5S)-3-oxa-8-azabicyclo[3.2.1]octan-8-yl)cyclohexyl)-1H-pyrazol-3-ol | 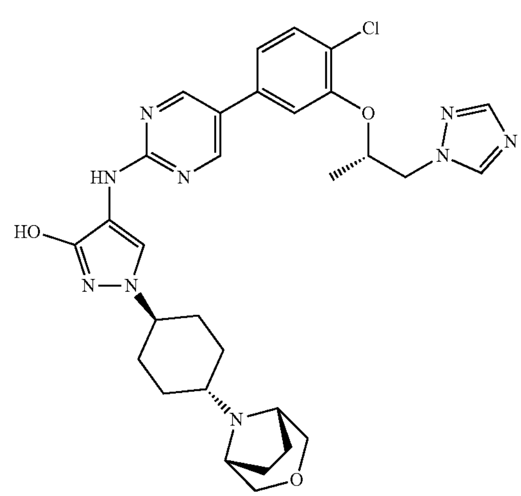 [SMILES: C[C@@H](Cn1cncn1)Oc1cc(-c2cnc(Nc3cn([C@H]4CC[C@H](N5[C@@H]6CC[C@H]5COC6)CC4)nc3O)nc2)ccc1Cl] |

TABLE 2-continued

| Ex. No. | IUPAC NAME | STRUCTURE |
|---|---|---|
| 469 | 2-(((S)-1-(1H-tetrazol-1-yl)propan-2-yl)oxy)-4-(2-((1-((1r,4r)-4-((2S,6R)-2,6-dimethylmorpholino)cyclohexyl)-3-hydroxy-1H-pyrazol-4-yl)amino)pyrimidin-5-yl)benzonitrile | 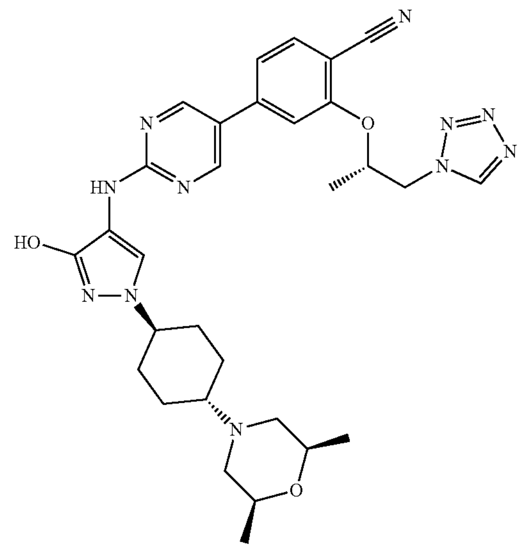 [SMILES: C[C@@H]1CN([C@H]2CC[C@H](n3cc(Nc4ncc(-c5ccc(C#N)c(O[C@@H](C)Cn6cnnn6)c5)cn4)c(O)n3)CC2)C[C@H](C)O1] |
| 470 | 4-((5-(3-(((S)-1-(1H-tetrazol-1-yl)propan-2-yl)oxy)-4-chlorophenyl)pyrimidin-2-yl)amino)-1-((1r,4r)-4-((2S,6R)-2,6-dimethylmorpholino)cyclohexyl)-1H-pyrazol-3-ol | 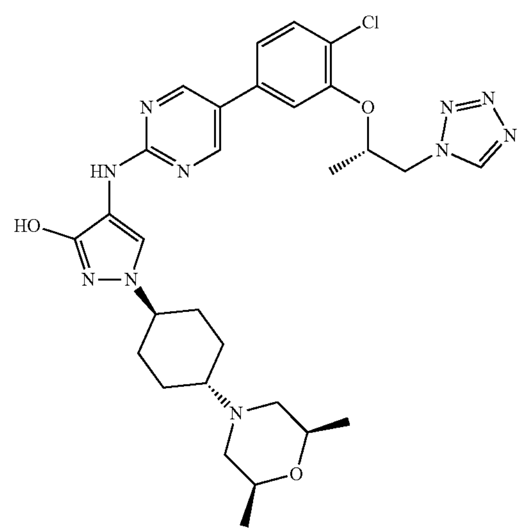 [SMILES: C[C@@H]1CN([C@H]2CC[C@H](n3cc(Nc4ncc(-c5ccc(Cl)c(O[C@@H](C)Cn6cnnn6)c5)cn4)c(O)n3)CC2)C[C@H](C)O1] |
| 471 | 2-(((S)-1-(1H-1,2,4-triazol-1-yl)propan-2-yl)oxy)-4-(2-((1-((1r,4r)-4-((2S,6R)-2,6-dimethylmorpholino)cyclohexyl)-3-hydroxy-1H-pyrazol-4-yl)amino)pyrimidin-5-yl)benzonitrile | 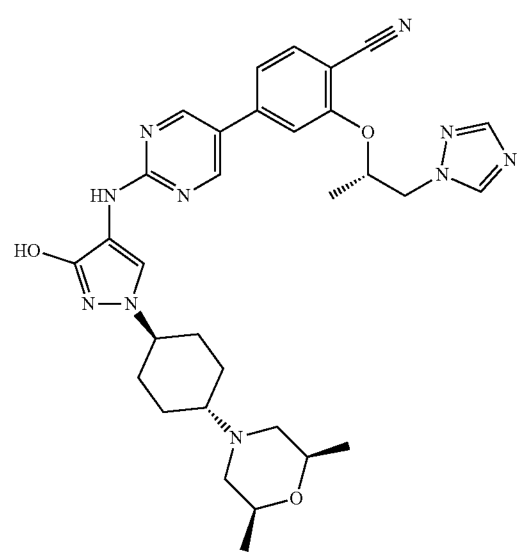 [SMILES: C[C@@H]1CN([C@H]2CC[C@H](n3cc(Nc4ncc(-c5ccc(C#N)c(O[C@@H](C)Cn6cncn6)c5)cn4)c(O)n3)CC2)C[C@H](C)O1] |

| Ex. No. | IUPAC NAME | STRUCTURE |
|---|---|---|
| 472 | 4-((5-(3-(((S)-1-(1H-1,2,4-triazol-1-yl)propan-2-yl)oxy)-4-chlorophenyl)pyrimidin-2-yl)amino)-1-((1r,4r)-4-((2S,6R)-2,6-dimethylmorpholino)cyclohexyl)-1H-pyrazol-3-ol | 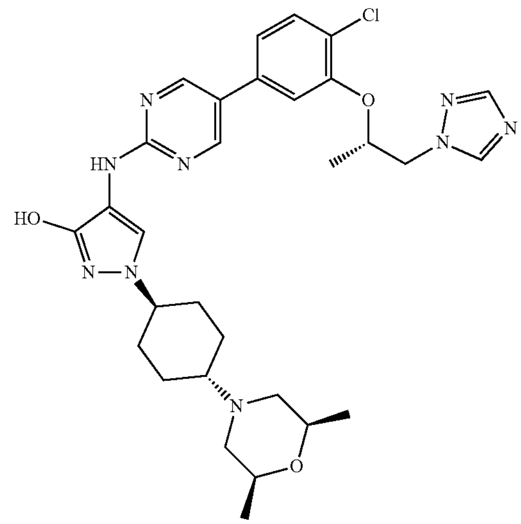 [SMILES: C[C@@H]1CN([C@H]2CC[C@H](n3cc(Nc4ncc(-c5ccc(Cl)c(O[C@@H](C)Cn6cncn6)c5)cn4)c(O)n3)CC2)C[C@H](C)O1] |

Example 473

5-(3-(((S)-1-(1H-tetrazol-1-yl) propan-2-yl)oxy)-4-chlorophenyl)-N-(1-((1r,4r)-4-((2S,6R)-2,6-dimethylmorpholino)cyclohexyl)-3-((4-methyl-4H-1,2,4-triazol-3-yl)methoxy)-1H-pyrazol-4-yl)pyrimidin-2-amine

A) ethyl 3-(benzyloxy)-1-{1,4-dioxaspiro[4.5]decan-8-yl}-1H-pyrazole-4-carboxylate To a solution of ethyl 3-(benzyloxy)-1H-pyrazole-4-carboxylate (15.0 g) and 1,4-dioxaspiro[4.5]decan-8-yl methanesulfonate (21.5 g) in DMF (200 mL) was added cesium carbonate (39.4 g) at room temperature. The mixture was stirred at 90° C. under nitrogen atmosphere overnight. The mixture was quenched with water at room temperature and extracted with ethyl acetate. The organic layer was separated, washed with water and saturated brine, dried over anhydrous magnesium sulfate and concentrated under reduced pressure. The residue was purified by silica gel column chromatography (NH, ethyl acetate/hexane) to give the title compound (21.5 g).
MS m/z 387.2 [M+H]+.

B) 3-(benzyloxy)-1-{1,4-dioxaspiro[4.5]decan-8-yl}-1H-pyrazole-4-carboxylic acid To a solution of ethyl 3-(benzyloxy)-1-{1,4-dioxaspiro[4.5]decan-8-yl}-1H-pyrazole-4-carboxylate (34.0 g) in EtOH (180 mL) was added 8 M aqueous sodium hydroxide solution (17.2 mL) at room temperature. The mixture was stirred at 50° C. for 15 hr. The reaction mixture was concentrated under reduced pressure, and the residue was acidified with 6 M hydrochloric acid at 0° C. and extracted with ethyl acetate. The organic layer was separated, washed with saturated brine, dried over anhydrous magnesium sulfate and concentrated under reduced pressure to give the title compound (31.3 g).
1H NMR (300 MHz, DMSO-d6) δ 11.95 (brs, 1H), 8.03 (s, 1H), 7.43-7.51 (m, 2H), 7.29-7.42 (m, 3H), 5.21 (s, 2H), 4.06-4.21 (m, 1H), 3.85-3.92 (m, 4H), 1.90-1.98 (m, 4H), 1.72-1.82 (m, 2H), 1.58-1.71 (m, 2H).

C) benzyl N-[3-(benzyloxy)-1-{1,4-dioxaspiro[4.5]decan-8-yl}-1H-pyrazol-4-yl]carbamate To a mixture of 3-(benzyloxy)-1-{1,4-dioxaspiro[4.5]decan-8-yl}-1H-pyrazole-4-carboxylic acid (32.0 g) and triethylamine (14.2 g) in toluene (200 mL) was added DPPA (36.3 g) at room temperature. After being stirred at room temperature for 1 hr, benzyl alcohol (14.4 g) was added to the reaction mixture. The mixture was stirred at 90° C. under nitrogen atmosphere for 2 hr. The mixture was quenched with water at room temperature and extracted with ethyl acetate. The organic layer was separated, washed with water and saturated brine, dried over anhydrous magnesium sulfate and concentrated under reduced pressure. The residue was purified by silica gel column chromatography (ethyl acetate/hexane) to give the title compound (38.0 g).
MS m/z 464.3 [M+H]+.

D) benzyl N-[3-(benzyloxy)-1-(4-oxocyclohexyl)-1H-pyrazol-4-yl]carbamate

2 M Hydrochloric acid (8.60 g) was added to a solution of benzyl N-[3-(benzyloxy)-1-{1,4-dioxaspiro[4.5]decan-8-yl}-1H-pyrazol-4-yl]carbamate (55.0 g) in THF (100 mL) at 50° C., and the mixture was stirred for 14 hr. The mixture was neutralized with 8 M aqueous sodium hydroxide solution at 0° C. and extracted with ethyl acetate. The organic layer was separated, washed with saturated brine, dried over anhydrous magnesium sulfate and concentrated under reduced pressure. The residue was purified by silica gel column chromatography (MeOH/ethyl acetate) to give the title compound (39.0 g).
MS m/z 420.2 [M+H]+.

E) benzyl N-[3-(benzyloxy)-1-[(1r,4r)-4-[(2R,6S)-2,6-dimethylmorpholin-4-yl]cyclohexyl]-1H-pyrazol-4-yl]carbamate 2-Methylpyridine-borane (8.02 g) was added to a mixture of benzyl N-[3-(benzyloxy)-1-(4-oxocyclohexyl)-1H-pyrazol-4-yl]carbamate (21.0 g) and cis-2,6-dimethylmorpholine (8.63 g) in AcOH (10 mL) and MeOH (200 mL) at room temperature and the mixture was stirred at 60° C. for 10 hr. The mixture was quenched with 8 M aqueous sodium hydroxide solution and extracted with ethyl acetate. The organic layer was separated, washed with saturated brine, dried over anhydrous magnesium sulfate and concentrated under reduced pressure. The residue was purified by silica gel column chromatography (ethyl acetate/hexane and MeOH/ethyl acetate) to give the title compound (10.3 g).

MS m/z 519.4 [M+H]+.

F) 3-(benzyloxy)-1-[(r,4r)-4-[(2R,6S)-2,6-dimethyl-morpholin-4-yl]cyclohexyl]-1H-pyrazol-4-amine To a mixture of benzyl N-[3-(benzyloxy)-1-[(1r,4r)-4-[(2R,6S)-2,6-dimethylmorpholin-4-yl]cyclohexyl]-1H-pyrazol-4-yl]carbamate (15.0 g) in EtOH (100 mL) was added 8 M aqueous sodium hydroxide solution (36.1 mL) at room temperature. The mixture was stirred at 90° C. for 14 hr. The mixture was concentrated under reduced pressure. 6 M Hydrochloric acid was added to the residue to bring the pH of the solution to 7-8, and the mixture was extracted with ethyl acetate. The organic layer was separated, washed with saturated brine, dried over anhydrous magnesium sulfate and concentrated under reduced pressure to give the title compound (12.8 g).

MS m/z 385.3 [M+H]+.

G) 4-((5-(3-(((S)-1-(1H-tetrazol-1-yl)propan-2-yl)oxy)-4-chlorophenyl)pyrimidin-2-yl)amino)-1-((1r,4r)-4-((2S,6R)-2,6-dimethylmorpholino)cyclohexyl)-1H-pyrazol-3-ol To a mixture of 3-(benzyloxy)-1-[(1r,4r)-4-[(2R,6S)-2,6-dimethylmorpholin-4-yl]cyclohexyl]-1H-pyrazol-4-amine (12.0 g) in EtOH (5.0 ml) was added 4 M hydrogen chloride-ethyl acetate (39.0 mL) at room temperature. After being stirred at room temperature for 10 min, the mixture was concentrated under reduced pressure. To a mixture of the residue in NMP (35 mL) was added 2-chloro-5-(4-chloro-3-{[(2S)-1-(1H-tetrazol-1-yl)propan-2-yl]oxy}phenyl)pyrimidine (13.1 g) at room temperature. The mixture was stirred at 110° C. under nitrogen atmosphere for 14 hr. The mixture was quenched with 2 M hydrochloric acid at room temperature and extracted with ethyl acetate. The aqueous layer was separated. Sodium hydroxide was added to the mixrure to bring the pH of the solution to 8-9. The mixture was azeotroped with toluene. The insoluble material in EtOH/water (120 mL, 3:1) was collected by filtration, washed with EtOH/EtOAc/water (3:3:1), and dried under reduced pressure to give the title compound (19.0 g).

MS m/z 609.5 [M+H]+.

H) 5-(3-(((S)-1-(1H-tetrazol-1-yl)propan-2-yl)oxy)-4-chlorophenyl)-N-(1-((1r,4r)-4-((2S,6R)-2,6-dimethylmorpholino)cyclohexyl)-3-((4-methyl-4H-1,2,4-triazol-3-yl)methoxy)-1H-pyrazol-4-yl)pyrimidin-2-amine A mixture of 4-((5-(3-(((S)-1-(1H-tetrazol-1-yl)propan-2-yl)oxy)-4-chlorophenyl)pyrimidin-2-yl)amino)-1-((1r,4r)-4-((2S,6R)-2,6-dimethylmorpholino)cyclohexyl)-1H-pyrazol-3-ol (206 mg), (4-methyl-4H-1,2,4-triazol-3-yl)methanol (38.2 mg), triphenylphosphine (106 mg) and 2.2 M diethyl azodicarboxylate in toluene (184 uL) in THF (10 mL) was stirred at room temperature under argon atmosphere for 40 min. The reaction mixture was purified by silica gel column chromatography (NH, ethyl acetate/hexane and MeOH/ethyl acetate), and the residue was purified by preparative HPLC (water/CH3CN containing 0.1% TFA). The desired fraction was neutralized with saturated aqueous sodium hydrogencarbonate solution and extracted with ethyl acetate. The organic layer was separated, dried over anhydrous magnesium sulfate and concentrated under reduced pressure to give the title compound (15.6 mg).

1H NMR (300 MHz, DMSO-d6) δ 9.37 (s, 1H), 8.76 (s, 1H), 8.69 (s, 2H), 8.47 (s, 1H), 7.79 (s, 1H), 7.45 (d, J=8.25 Hz, 1H), 7.35 (d, J=1.74 Hz, 1H), 7.23 (dd, J=1.97, 8.21 Hz, 1H), 5.30 (s, 2H), 5.14-5.20 (m, 1H), 4.87-4.94 (m, 1H), 4.76-4.84 (m, 1H), 3.88-3.97 (m, 1H), 3.67 (s, 3H), 3.48-3.56 (m, 2H), 2.73 (d, J=9.45 Hz, 2H), 2.25-2.30 (m, 1H), 2.02-2.12 (m, 2H), 1.81-1.94 (m, 4H), 1.63-1.77 (m, 2H), 1.35-1.46 (m, 2H), 1.33 (d, J=6.14 Hz, 3H), 1.05 (d, J=6.24 Hz, 6H); MS m/z 704.5 [M+H]+.

Example 474

2-(3-((4-((5-(3-(((S)-1-(1H-tetrazol-1-yl)propan-2-yl)oxy)-4-chlorophenyl)pyrimidin-2-yl)amino)-1-((1r,4r)-4-((2S,6R)-2,6-dimethylmorpholino)cyclohexyl)-1H-pyrazol-3-yl)oxy)propoxy)ethan-1-ol A) 2-{3-[(4-{[5-(4-chloro-3-{[(2S)-1-(1H-tetrazol-1-yl)propan-2-yl]oxy}phenyl)pyrimidin-2-yl]amino}-1-[(1r,4r)-4-[(2R,6S)-2,6-dimethylmorpholin-4-yl]cyclohexyl]-1H-pyrazol-3-yl)oxy]propoxy}ethyl acetate To a mixture of 4-((5-(3-(((S)-1-(1H-tetrazol-1-yl)propan-2-yl)oxy)-4-chlorophenyl)pyrimidin-2-yl)amino)-1-((1r,4r)-4-((2S,6R)-2,6-dimethylmorpholino)cyclohexyl)-1H-pyrazol-3-ol (500 mg) and cyanomethylenetributylphosphorane (395 mg) in toluene (3.0 mL) was added 2-(3-hydroxypropoxy)ethyl acetate (199 mg) at room temperature. The mixture was stirred at 100° C. under nitrogen atmosphere for 10 min. The mixture was concentrated under reduced pressure. The residue was purified by silica gel column chromatography (MeOH/ethyl acetate) to give the crude title compound (370 mg). The obtained product (80.0 mg) was purified by preparative HPLC (water/CH3CN containing 0.1% TFA). The desired fraction was neutralized with saturated aqueous sodium hydrogencarbonate solution and extracted with ethyl acetate. The organic layer was separated, dried over anhydrous magnesium sulfate and concentrated under reduced pressure to give the title compound (50.0 mg).

MS m/z 753.0 [M+H]+.

B) 2-(3-((4-((5-(3-(((S)-1-(1H-tetrazol-1-yl)propan-2-yl)oxy)-4-chlorophenyl)pyrimidin-2-yl)amino)-1-((1r,4r)-4-((2S,6R)-2,6-dimethylmorpholino)cyclohexyl)-1H-pyrazol-3-yl)oxy)propoxy)ethan-1-ol To a mixture of 2-{3-[(4-{[5-(4-chloro-3-{[(2S)-1-(1H-tetrazol-1-yl)propan-2-yl]oxy}phenyl)pyrimidin-2-yl]amino}-1-[(1r,4r)-4-[(2R,6S)-2,6-dimethylmorpholin-4-yl]cyclohexyl]-1H-pyrazol-3-yl)oxy]propoxy}ethyl acetate (250 mg) in methanol (5.0 mL) was added 2 M aqueous sodium hydroxide solution (331 μL) at room temperature. The mixture was stirred at 50° C. for 4 hr. The mixture was concentrated under reduced pressure. The residue was purified by silica gel column chromatography (MeOH/ethyl acetate) to give the title compound (37.0 mg).

¹H NMR (300 MHz, DMSO-d₆) δ 9.37 (s, 1H), 8.70 (s, 2H), 8.59 (s, 1H), 7.73 (s, 1H), 7.45 (d, J=8.25 Hz, 1H), 7.37 (d, J=1.93 Hz, 1H), 7.24 (dd, J=1.97, 8.30 Hz, 1H), 5.12-5.22 (m, 1H), 4.86-4.96 (m, 1H), 4.75-4.84 (m, 1H), 4.57 (t, J=5.46 Hz, 1H), 4.14 (t, J=6.37 Hz, 2H), 3.81-3.93 (m, 1H), 3.43-3.56 (m, 6H), 3.35-3.39 (m, 2H), 2.68-2.75 (m, 2H), 2.24-2.31 (m, 1H), 2.04 (d, J=11.10 Hz, 2H), 1.80-1.95 (m, 6H), 1.59-1.75 (m, 2H), 1.29-1.45 (m, 5H), 1.04 (d, J=6.24 Hz, 6H); MS m/z 711.6 [M+H]⁺.

Example 475

3-((4-((5-(3-(((S)-1-(1H-tetrazol-1-yl)propan-2-yl)oxy)-4-chlorophenyl)pyrimidin-2-yl)amino)-1-((1r,4r)-4-((2S,6R)-2,6-dimethylmorpholino)cyclohexyl)-1H-pyrazol-3-yl)oxy)propan-1-ol A) 3-[(4-{[5-(4-chloro-3-{[(2S)-1-(1H-tetrazol-1-yl)propan-2-yl]oxy}phenyl)pyrimidin-2-yl]amino}-1-[(1r,4r)-4-[(2R,6S)-2,6-dimethylmorpholin-4-yl]cyclohexyl]-1H-pyrazol-3-yl)oxy]propyl acetate To a mixture of 4-((5-(3-(((S)-1-(1H-tetrazol-1-yl)propan-2-yl)oxy)-4-chlorophenyl)pyrimidin-2-yl)amino)-1-((1r,4r)-4-((2S,6R)-2,6-dimethylmorpholino)cyclohexyl)-1H-pyrazol-3-ol (400 mg) and 3-hydroxypropyl acetate (116 mg) in toluene (3.0 mL) was added cyanomethylenetributylphosphorane (316 mg) at room temperature. The mixture was stirred at 100° C. under nitrogen atmosphere for 2 hr. The mixture was quenched with water at room temperature and extracted with ethyl acetate. The organic layer was separated, washed with water and saturated brine, dried over anhydrous magnesium sulfate and concentrated under reduced pressure. The residue was purified by silica gel column chromatography (MeOH/ethyl acetate) and silica gel column chromatography (NH, ethyl acetate/hexane) to give the crude title compound (228 mg). The obtained product (80.0 mg) was purified by preparative HPLC (water/CH₃CN containing 0.1% TFA). The desired fraction was neutralized with saturated aqueous sodium hydrogencarbonate solution and extracted with ethyl acetate. The organic layer was separated, dried over anhydrous magnesium sulfate and concentrated under reduced pressure. The residue was washed with ethyl acetate/hexane (1:5), and under reduced pressure to give the title compound (30.0 mg).
MS m/z 709.5 [M+H]⁺.

B) 3-((4-((5-(3-(((S)-1-(1H-tetrazol-1-yl)propan-2-yl)oxy)-4-chlorophenyl)pyrimidin-2-yl)amino)-1-((1r,4r)-4-((2S,6R)-2,6-dimethylmorpholino)cyclohexyl)-1H-pyrazol-3-yl)oxy)propan-1-ol To a mixture of 3-[(4-{[5-(4-chloro-3-{[(2S)-1-(1H-tetrazol-1-yl)propan-2-yl]oxy}phenyl)pyrimidin-2-yl]amino}-1-[(1r,4r)-4-[(2R,6S)-2,6-dimethylmorpholin-4-yl]cyclohexyl]-1H-pyrazol-3-yl)oxy]propyl acetate (145 mg) in MeOH (5.0 mL) was added 2 M aqueous sodium hydroxide solution (204 μL) at room temperature. The mixture was stirred at 50° C. for 4 hr. The mixture was concentrated under reduced pressure. The residue was purified by silica gel column chromatography (MeOH/ethyl acetate). The residue was crystallized from ethyl acetate/hexane to give the title compound (55.0 mg).
¹H NMR (300 MHz, DMSO-d₆) δ 9.37 (s, 1H), 8.70 (s, 2H), 8.58 (s, 1H), 7.73 (s, 1H), 7.45 (d, J=8.25 Hz, 1H), 7.37 (d, J=1.83 Hz, 1H), 7.24 (dd, J=1.79, 8.12 Hz, 1H), 5.12-5.22 (m, 1H), 4.87-4.95 (m, 1H), 4.76-4.84 (m, 1H), 4.47 (t, J=5.09 Hz, 1H), 4.15 (t, J=6.42 Hz, 2H), 3.81-3.93 (m, 1H), 3.47-3.63 (m, 4H), 2.68-2.74 (m, 2H), 2.23-2.32 (m, 1H), 2.00-2.08 (m, 2H), 1.74-1.94 (m, 6H), 1.58-1.72 (m, 2H), 1.28-1.45 (m, 5H), 1.04 (d, J=6.24 Hz, 6H); MS m/z 667.5 [M+H]+.

Example 476

2-(((S)-1-(1H-tetrazol-1-yl)propan-2-yl)oxy)-4-(2-((1-((1r,4r)-4-((2S,6R)-2,6-dimethylmorpholino)cyclohexyl)-3-((2-methylthiazol-5-yl)methoxy)-1H-pyrazol-4-yl)amino)pyrimidin-5-yl)benzonitrile A) 5-(4-chloro-3-{[(2S)-1-(1H-tetrazol-1-yl)propan-2-yl]oxy}phenyl)-N-{3-[(2-methyl-1,3-thiazol-5-yl)methoxy]-1-[(1r,4r)-4-[(2R,6S)-2,6-dimethylmorpholin-4-yl]cyclohexyl]-1H-pyrazol-4-yl}pyrimidin-2-amine 2.2 M Diethyl azodicarboxylate in toluene (159 uL) was added to a mixture of 4-((5-(3-(((S)-1-(1H-tetrazol-1-yl)propan-2-yl)oxy)-4-chlorophenyl)pyrimidin-2-yl)amino)-1-((1r,4r)-4-((2S,6R)-2,6-dimethylmorpholino)cyclohexyl)-1H-pyrazol-3-ol (178 mg), (2-methyl-1,3-thiazol-5-yl)methanol (37.7 mg) and triphenylphosphine (91.9 mg) in toluene (3.0 mL) at 0° C. The mixture was stirred at room temperature for 25 min. The reaction mixture was purified by by silica gel column chromatography (MeOH/ethyl acetate) and silica gel column chromatography (NH, ethyl acetate/hexane) to give the title compound (38.3 mg).
MS m/z 720.5 [M+H]+.

B) 2-(((S)-1-(1H-tetrazol-1-yl)propan-2-yl)oxy)-4-(2-((1-((1r,4r)-4-((2S,6R)-2,6-dimethylmorpholino)cyclohexyl)-3-((2-methylthiazol-5-yl)methoxy)-1H-pyrazol-4-yl)amino)pyrimidin-5-yl)benzonitrile To a mixture of 5-(4-chloro-3-{[(2S)-1-(1H-tetrazol-1-yl)propan-2-yl]oxy}phenyl)-N-{3-[(2-methyl-1,3-thiazol-5-yl)methoxy]-1-[(1r,4r)-4-[(2R,6S)-2,6-dimethylmorpholin-4-yl]cyclohexyl]-1H-pyrazol-4-yl}pyrimidin-2-amine (133 mg), potassium hexacyanoferrate(II) trihydrate (156 mg) and potassium acetate (57.0 mg) in CPME (5.0 mL) and water (5.0 mL) were added XPhos Pd G2 (16.0 mg) and XPhos (18.0 mg). After being stirred under nitrogen atmosphere at 110° C. for 24 hr, the mixture was poured into water and extracted with ethyl acetate. The organic layer was separated, washed with saturated brine, dried over anhydrous sodium sulfate and concentrated under reduced pressure. The residue was purified by silica gel column chromatography (MeOH/ethyl acetate) and by preparative HPLC (water/CH₃CN containing 0.1% TFA). The desired fraction was neutralized with saturated aqueous sodium hydrogencarbonate solution and extracted with ethyl acetate. The organic layer was separated, dried over anhydrous magnesium sulfate and concentrated under reduced pressure. The residue was purified by silica gel column chromatography (NH, ethyl acetate/hexane) and crystallized from EtOH/diethyl ether to give the title compound (30.0 mg).
¹H NMR (300 MHz, DMSO-d₆) δ 9.35 (s, 1H), 8.74-8.83 (m, 3H), 7.71-7.80 (m, 2H), 7.68 (s, 1H), 7.46 (s, 1H), 7.39 (dd, J=1.10, 8.16 Hz, 1H), 5.28-5.38 (m, 3H), 4.90-4.98 (m, 1H), 4.79-4.88 (m, 1H), 3.84-4.00 (m, 1H), 3.45-3.58 (m, 2H), 2.68-2.79 (m, 2H), 2.59 (s, 3H), 2.22-2.33 (m, 1H), 2.03-2.15 (m, 2H), 1.81-1.99 (m, 4H), 1.62-1.80 (m, 2H), 1.28-1.47 (m, 5H), 1.05 (d, J=6.24 Hz, 6H); MS m/z 711.4 [M+H]⁺.

Example 477

2-(((S)-1-(1H-tetrazol-1-yl)propan-2-yl)oxy)-4-(2-
((1-((1r,4r)-4-((2S,6R)-2,6-dimethylmorpholino)
cyclohexyl)-3-(2-(oxetan-3-yl)ethoxy)-1H-pyrazol-
4-yl)amino)pyrimidin-5-yl)benzonitrile A) 5-(4-chloro-3-{[(2S)-1-(1H-tetrazol-1-yl)propan-
2-yl]oxy}phenyl)-N-{3-[2-(oxetan-3-yl)ethoxy]-1-
[(1r,4r)-4-[(2R,6S)-2,6-dimethylmorpholin-4-yl]
cyclohexyl]-1H-pyrazol-4-yl}pyrimidin-2-amine A mixture of 4-((5-(3-(((S)-1-(1H-tetrazol-1-yl)propan-2-yl)oxy)-4-chlorophenyl)pyrimidin-2-yl)amino)-1-((r,4r)-4-((2S,6R)-2,6-dimethylmorpholino)cyclohexyl)-1H-pyrazol-3-ol (200 mg), 2-(oxetan-3-yl)ethanol (67.0 mg) and cyanomethylenetributylphosphorane (332 mg) in toluene (10 mL) was stirred at 100° C. under argon atmosphere for 1.5 hr. The reaction mixture was purified by silica gel column chromatography (NH, ethyl acetate/hexane) and silica gel column chromatography (MeOH/ethyl acetate) to give the title compound (113 mg).
MS m/z 693.4 [M+H]+.

B) 2-(((S)-1-(1H-tetrazol-1-yl)propan-2-yl)oxy)-4-
(2-((1-(1r,4r)-4-((2S,6R)-2,6-dimethylmorpholino)
cyclohexyl)-3-(2-(oxetan-3-yl)ethoxy)-1H-pyrazol-
4-yl)amino)pyrimidin-5-yl)benzonitrile A mixture of 5-(4-chloro-3-{[(2S)-1-(1H-tetrazol-1-yl)propan-2-yl]oxy}phenyl)-N-{3-[2-(oxetan-3-yl)ethoxy]-1-[(1r,4r)-4-[(2R,6S)-2,6-dimethylmorpholin-4-yl]cyclohexyl]-1H-pyrazol-4-yl}pyrimidin-2-amine (105 mg), potassium hexacyanoferrate(II) trihydrate (191 mg), XPhos Pd G2 (11.9 mg), XPhos (14.4 mg) and potassium acetate (66.8 mg) in CPME (5.0 mL) and water (5.0 mL) was stirred at 110° C. under argon atmosphere for 13 hr. The residue was partitioned between ethyl acetate and water. The organic layer was washed with saturated brine, dried over anhydrous sodium sulfate and concentrated under reduced pressure. The residue was purified by silica gel column chromatography (MeOH/ethyl acetate) and crystallized from EtOH/heptane to give the title compound (74.7 mg).
¹H NMR (300 MHz, DMSO-d₆) δ 9.35 (s, 1H), 8.80 (s, 2H), 8.74 (s, 1H), 7.75 (d, J=8.07 Hz, 1H), 7.72 (s, 1H), 7.47 (s, 1H), 7.40 (d, J=8.25 Hz, 1H), 5.34 (dt, J=4.31, 6.33 Hz, 1H), 4.89-5.00 (m, 1H), 4.80-4.89 (m, 1H), 4.57 (dd, J=5.87, 7.79 Hz, 2H), 4.26 (t, J=6.14 Hz, 2H), 4.05 (t, J=6.19 Hz, 2H), 3.82-3.91 (m, 1H), 3.48-3.58 (m, 2H), 3.03-3.13 (m, 1H), 2.68-2.75 (m, 2H), 2.22-2.31 (m, 1H), 1.98-2.08 (m, 4H), 1.81-1.93 (m, 4H), 1.60-1.74 (m, 2H), 1.37-1.45 (m, 2H), 1.35 (d, J=6.05 Hz, 3H), 1.05 (d, J=6.05 Hz, 6H); MS m/z 684.5 [M+H]+.

Example 478

2-(((S)-1-(1H-tetrazol-1-yl)propan-2-yl)oxy)-4-(2-
((1-((1r,4r)-4-((2S,6R)-2,6-dimethylmorpholino)
cyclohexyl)-3-(3-methoxy-3-methylbutoxy)-1H-
pyrazol-4-yl)amino)pyrimidin-5-yl)benzonitrile A) 5-(4-chloro-3-{[(2S)-1-(1H-tetrazol-1-yl)propan-
2-yl]oxy}phenyl)-N-[3-(3-methoxy-3-methylbu-
toxy)-1-[(1r,4r)-4-[(2R,6S)-2,6-dimethylmorpholin-
4-yl]cyclohexyl]-1H-pyrazol-4-yl]pyrimidin-2-
amine To a mixture of 4-((5-(3-(((S)-1-(1H-tetrazol-1-yl)pro-
pan-2-yl)oxy)-4-chlorophenyl)pyrimidin-2-yl)amino)-1-((1r,4r)-4-((2S,6R)-2,6-dimethylmorpholino)cyclohexyl)-1H-pyrazol-3-ol (111 mg) and 3-methoxy-3-methylbutan-1-ol (43.0 mg) in toluene (4.0 mL) was added cyanomethylenetributylphosphorane (175 mg) at room temperature. The mixture was stirred at 100° C. under nitrogen atmosphere for 2 hr. The mixture was quenched with water at room temperature and extracted with ethyl acetate. The organic layer was separated, washed with water and saturated brine, dried over anhydrous magnesium sulfate and concentrated under reduced pressure. The residue was purified by silica gel column chromatography (MeOH/ethyl acetate) and crystallized from MeOH/IPE to give the title compound (68.0 mg).
MS m/z 709.4 [M+H]+.

B) 2-(((S)-1-(1H-tetrazol-1-yl)propan-2-yl)oxy)-4-
(2-((1-(1r,4r)-4-((2S,6R)-2,6-dimethylmorpholino)
cyclohexyl)-3-(3-methoxy-3-methylbutoxy)-1H-
pyrazol-4-yl)amino)pyrimidin-5-yl)benzonitrile To a mixture of 5-(4-chloro-3-{[(2S)-1-(1H-tetrazol-1-yl)propan-2-yl]oxy}phenyl)-N-[3-(3-methoxy-3-methylbutoxy)-1-[(1r,4r)-4-[(2R,6S)-2,6-dimethylmorpholin-4-yl]cyclohexyl]-1H-pyrazol-4-yl]pyrimidin-2-amine (87.0 mg) and potassium hexacyanoferrate(II) trihydrate (103 mg) in CPME (5.5 mL) and water (5.5 mL) were added XPhos Pd G2 (19.2 mg), XPhos (23.3 mg) and potassium acetate (36.0 mg) at room temperature. The mixture was stirred at 100° C. under argon atmosphere for 14 hr. The mixture was poured into water at room temperature and extracted with ethyl acetate. The organic layer was separated, washed with saturated brine, dried over anhydrous magnesium sulfate and concentrated under reduced pressure. The residue was purified twice by silica gel column chromatography (MeOH/ethyl acetate) and crystallized from MeOH/IPE to give the title compound (38.0 mg).
¹H NMR (300 MHz, CDCl₃) δ 8.97 (s, 1H), 8.52-8.59 (m, 2H), 7.86-7.89 (m, 1H), 7.58-7.65 (m, 1H), 7.14-7.21 (m, 1H), 7.01-7.05 (m, 1H), 6.84-6.89 (m, 1H), 4.92-5.01 (m, 1H), 4.82-4.91 (m, 1H), 4.67-4.77 (m, 1H), 4.29-4.38 (m, 2H), 3.84-3.96 (m, 1H), 3.62-3.76 (m, 2H), 3.24 (s, 3H), 2.73-2.83 (m, 2H), 2.18-2.42 (m, 3H), 2.05 (s, 7H), 1.67-1.86 (m, 4H), 1.33-1.50 (m, 2H), 1.24 (s, 6H), 1.18 (d, J=6.24 Hz, 6H); MS m/z 700.5 [M+H]+.

Example 479

2-(((S)-1-(1H-tetrazol-1-yl)propan-2-yl)oxy)-4-(2-
((1-((1r,4r)-4-((2S,6R)-2,6-dimethylmorpholino)
cyclohexyl)-3-(oxetan-3-ylmethoxy)-1H-pyrazol-4-
yl)amino)pyrimidin-5-yl)benzonitrile A) N-[3-(benzyloxy)-1-[(1r,4r)-4-[(2R,6S)-2,6-dim-
ethylmorpholin-4-yl]cyclohexyl]-1H-pyrazol-4-yl]-
5-(4-chloro-3-{[(2S)-1-(1H-tetrazol-1-yl)propan-2-
yl]oxy}phenyl)pyrimidin-2-amine To a mixture of 4-((5-(3-(((S)-1-(1H-tetrazol-1-yl)pro-
pan-2-yl)oxy)-4-chlorophenyl)pyrimidin-2-yl)amino)-1-(1r,4r)-4-((2S,6R)-2,6-dimethylmorpholino)cyclohexyl)-1H-pyrazol-3-ol (20.0 g) and potassium carbonate (566 mg) in DMF (50 mL) was added benzyl bromide (974 μL) at room temperature. The mixture was stirred at 70° C. under nitrogen atmosphere for 2 hr. The mixture was quenched with water at room temperature and extracted with ethyl acetate. The organic layer was separated, washed with saturated brine, dried over anhydrous magnesium sulfate and concentrated under reduced pressure. The residue was purified twice by silica gel column chromatography (MeOH/ethyl acetate) to give the title compound (2.00 g).

MS m/z 699.6 [M+H]+.

B) 4-(2-{[3-(benzyloxy)-1-[(1r,4r)-4-[(2R,6S)-2,6-dimethylmorpholin-4-yl]cyclohexyl]-1H-pyrazol-4-yl]amino}pyrimidin-5-yl)-2-{[(2S)-1-(1H-tetrazol-1-yl)propan-2-yl]oxy}benzonitrile To a mixture of N-[3-(benzyloxy)-1-[(1r,4r)-4-[(2R,6S)-2,6-dimethylmorpholin-4-yl]cyclohexyl]-1H-pyrazol-4-yl]-5-(4-chloro-3-{[(2S)-1-(1H-tetrazol-1-yl)propan-2-yl]oxy}phenyl)pyrimidin-2-amine (2.00 g) and potassium hexacyanoferrate(II) trihydrate (3.62 g) in CPME (60 mL) and water (60 mL) was added potassium acetate (1.25 g) at room temperature. After being stirred at room temperature for 15 min, XPhos Pd G2 (225 mg) and XPhos (272 mg) were added to the reaction mixture. The mixture was stirred at 90° C. under nitrogen atmosphere for 14 hr. The mixture was quenched with water at room temperature and extracted with ethyl acetate. The organic layer was separated, washed with water and saturated brine, dried over anhydrous magnesium sulfate and concentrated under reduced pressure. The residue was purified by silica gel column chromatography (MeOH/ethyl acetate) and the residue was purified by silica gel column chromatography (NH, ethyl acetate/hexane) to give the title compound (1.66 g).

MS m/z 690.6 [M+H]+.

C) 2-(((S)-1-(1H-tetrazol-1-yl)propan-2-yl)oxy)-4-(2-((1-(1r,4r)-4-((2S,6R)-2,6-dimethylmorpholino)cyclohexyl)-3-hydroxy-1H-pyrazol-4-yl)amino)pyrimidin-5-yl)benzonitrile To a mixture of 4-(2-{[3-(benzyloxy)-1-[(1r,4r)-4-[(2R,6S)-2,6-dimethylmorpholin-4-yl]cyclohexyl]-1H-pyrazol-4-yl]amino}pyrimidin-5-yl)-2-{[(2S)-1-(1H-tetrazol-1-yl)propan-2-yl]oxy}benzonitrile (170 mg) in toluene (5.0 mL) was added TFA (93.9 μL) at room temperature. The mixture was stirred at 50° C. under nitrogen atmosphere for 14 hr. Additional TFA (400 μL) was added to the mixture. And then, the mixture was stirred at 90° C. under nitrogen atmosphere for 4 hr. The mixture was neutralized with 2 M aqueous sodium hydroxide solution and concentrated under reduced pressure. The residue was washed with water/2-propanol (5:1) and dried under reduced pressure to give the title compound (40.0 mg).

MS m/z 600.5 [M+H]+.

D) 2-(((S)-1-(1H-tetrazol-1-yl)propan-2-yl)oxy)-4-(2-((1-(1r,4r)-4-((2S,6R)-2,6-dimethylmorpholino)cyclohexyl)-3-(oxetan-3-ylmethoxy)-1H-pyrazol-4-yl)amino)pyrimidin-5-yl)benzonitrile To a mixture of 2-(((S)-1-(1H-tetrazol-1-yl)propan-2-yl)oxy)-4-(2-((1-((1r,4r)-4-((2S,6R)-2,6-dimethylmorpholino)cyclohexyl)-3-hydroxy-1H-pyrazol-4-yl)amino)pyrimidin-5-yl)benzonitrile (200 mg) and (oxetan-3-yl)methanol (44.0 mg) in toluene (3.0 mL) was added cyanomethylenetributylphosphorane (160 mg) at room temperature. The mixture was stirred at 100° C. under nitrogen atmosphere for 1 hr. Additional cyanomethylenetributylphosphorane (160 mg) and (oxetan-3-yl)methanol (15 mg) were added to the mixture. The mixture was stirred at 100° C. under nitrogen atmosphere for 30 min. The mixture was concentrated under reduced pressure. The residue was purified by silica gel column chromatography (MeOH/ethyl acetate), and the residue was purified by silica gel column chromatography (NH, ethyl acetate/hexane). The residue was crystallized from ethyl acetate/hexane to give the title compound (60.0 mg).

$^1$H NMR (300 MHz, DMSO-d$_6$) δ 9.35 (s, 1H), 8.80 (s, 1H), 8.79 (s, 2H), 7.75 (t, J=4.08 Hz, 2H), 7.46 (s, 1H), 7.39 (dd, J=1.24, 7.75 Hz, 1H), 5.29-5.39 (m, 1H), 4.90-4.98 (m, 1H), 4.79-4.88 (m, 1H), 4.63 (dd, J=6.01, 7.93 Hz, 2H), 4.39 (t, J=6.01 Hz, 2H), 4.31 (d, J=6.69 Hz, 2H), 3.82-3.96 (m, 1H), 3.45-3.57 (m, 2H), 2.67-2.74 (m, 2H), 2.44-2.47 (m, 1H), 2.22-2.30 (m, 1H), 2.00-2.10 (m, 2H), 1.80-1.94 (m, 4H), 1.59-1.75 (m, 2H), 1.29-1.46 (m, 5H), 1.05 (d, J=6.33 Hz, 6H); MS m/z 670.6 [M+H]+.

Example 480

5-(3-(((S)-1-(1H-tetrazol-1-yl) propan-2-yl)oxy)-4-chlorophenyl)-N-(1-((1r,4r)-4-((2S,6R)-2,6-dimethylmorpholino)cyclohexyl)-3-(oxetan-3-ylmethoxy)-1H-pyrazol-4-yl)pyrimidin-2-amine To a mixture of 4-((5-(3-(((S)-1-(1H-tetrazol-1-yl)propan-2-yl)oxy)-4-chlorophenyl)pyrimidin-2-yl)amino)-1-(1r,4r)-4-((2S,6R)-2,6-dimethylmorpholino)cyclohexyl)-1H-pyrazol-3-ol (200 mg) and (oxetan-3-yl)methanol (43.3 mg) in toluene (8.0 mL) was added cyanomethylenetributylphosphorane (316 mg) at room temperature. The mixture was stirred at 100° C. under nitrogen atmosphere for 1 hr. Additional (oxetan-3-yl)methanol (43.3 mg) and cyanomethylenetributylphosphorane (316 mg) were added to the mixture. The mixture was stirred at 100° C. under nitrogen atmosphere for 2 hr. The mixture was quenched with water at room temperature and extracted with ethyl acetate. The organic layer was separated, washed with water and saturated brine, dried over anhydrous magnesium sulfate and concentrated under reduced pressure. The residue was purified by silica gel column chromatography (MeOH/ethyl acetate) to give the title compound (116 mg).

$^1$H NMR (300 MHz, DMSO-d$_6$) δ 9.37 (s, 1H), 8.70 (s, 2H), 8.62 (s, 1H), 7.74 (s, 1H), 7.45 (d, J=8.34 Hz, 1H), 7.36 (d, J=1.83 Hz, 1H), 7.24 (dd, J=1.88, 8.30 Hz, 1H), 5.17 (dt, J=3.76, 6.42 Hz, 1H), 4.87-4.96 (m, 1H), 4.74-4.84 (m, 1H), 4.63 (dd, J=6.01, 7.93 Hz, 2H), 4.39 (t, J=6.05 Hz, 2H), 4.31 (d, J=6.69 Hz, 2H), 3.80-3.94 (m, 1H), 3.45-3.57 (m, 2H), 3.25-3.37 (m, 1H), 2.72 (d, J=9.81 Hz, 2H), 2.22-2.33 (m, 1H), 2.01-2.12 (m, 2H), 1.80-1.95 (m, 4H), 1.60-1.77 (m, 2H), 1.25-1.47 (m, 5H), 1.05 (d, J=6.24 Hz, 6H); MS m/z 679.4 [M+H]+.

Example 481

2-((4-((5-(3-(((S)-1-(1H-tetrazol-1-yl)propan-2-yl)oxy)-4-chlorophenyl)pyrimidin-2-yl)amino)-1-((1r,4r)-4-((2S,6R)-2,6-dimethylmorpholino)cyclohexyl)-1H-pyrazol-3-yl)oxy)ethan-1-ol A) N-{3-[2-(tert-butoxy)ethoxy]-1-[(1r,4r)-4-[(2R,6S)-2,6-dimethylmorpholin-4-yl]cyclohexyl]-1H-pyrazol-4-yl}-5-(4-chloro-3-{[(2S)-1-(1H-tetrazol-1-yl)propan-2-yl]oxy}phenyl)pyrimidin-2-amine To a mixture of 4-((5-(3-(((S)-1-(1H-tetrazol-1-yl)propan-2-yl)oxy)-4-chlorophenyl)pyrimidin-2-yl)amino)-1-((1r,4r)-4-((2S,6R)-2,6-dimethylmorpholino)cyclohexyl)-1H-pyrazol-3-ol (100 mg) and 2-(tert-butoxy)ethan-1-ol (38.7 mg) in toluene (4.0 mL) was added cyanomethylenetributylphosphorane (158 mg) at room temperature. The mixture was stirred at 100° C. under nitrogen atmosphere for 4 hr. The mixture was purified by silica gel column chromatography (NH, ethyl acetate/hexane) to give the crude title compound (105 mg).

MS m/z 709.4 [M+H]+.

B) 2-((4-((5-(3-(((S)-1-(1H-tetrazol-1-yl)propan-2-yl)oxy)-4-chlorophenyl)pyrimidin-2-yl)amino)-1-((1r,4r)-4-((2S,6R)-2,6-dimethylmorpholino)cyclohexyl)-1H-pyrazol-3-yl)oxy)ethan-1-ol To a mixture of N-{3-[2-(tert-butoxy)ethoxy]-1-[(1r,4r)-4-[(2R,6S)-2,6-dimethylmorpholin-4-yl]cyclohexyl]-1H-pyrazol-4-yl}-5-(4-chloro-3-{[(2S)-1-(1H-tetrazol-1-yl)propan-2-yl]oxy}phenyl)pyrimidin-2-amine (105 mg) in toluene (2.0 mL) was added TFA (16.8 mg) at room temperature. The mixture was stirred at room temperature for 14 hr. After concentration, the residue was purified by silica gel column chromatography (NH, MeOH/ethyl acetate) and purified by preparative HPLC (water/CH$_3$CN containing 0.1% TFA). The desired fraction was neutralized with saturated aqueous sodium hydrogencarbonate solution and extracted with ethyl acetate. The organic layer was separated, dried over anhydrous magnesium sulfate and concentrated under reduced pressure to give the title compound (7.10 mg).

$^1$H NMR (300 MHz, methanol-d$_6$) δ 9.26 (s, 1H), 8.62 (s, 1H), 8.66 (s, 1H), 7.90 (s, 1H), 7.40-7.49 (m, 1H), 7.13-7.24 (m, 2H), 5.03-5.18 (m, 1H), 4.23-4.33 (m, 2H), 3.82-4.02 (m, 3H), 3.61-3.77 (m, 2H), 3.36 (s, 2H), 2.89 (d, J=10.64 Hz, 2H), 2.35-2.52 (m, 1H), 1.91-2.26 (m, 6H), 1.70-1.90 (m, 2H), 1.32-1.60 (m, 5H), 1.17 (d, J=6.33 Hz, 6H); MS m/z 653.4 [M+H]$^+$.

Example 482

(R)-1-((4-((5-(3-(((S)-1-(1H-tetrazol-1-yl)propan-2-yl)oxy)-4-chlorophenyl)pyrimidin-2-yl)amino)-1-((1r,4r)-4-((2S,6R)-2,6-dimethylmorpholino)cyclohexyl)-1H-pyrazol-3-yl)oxy)propan-2-ol

A) 5-(4-chloro-3-{[(2S)-1-(1H-tetrazol-1-yl)propan-2-yl]oxy}phenyl)-N-{3-[(2R)-2-(oxan-2-yloxy)propoxy]-1-[(1r,4r)-4-[(2R,6S)-2,6-dimethylmorpholin-4-yl]cyclohexyl]-1H-pyrazol-4-yl}pyrimidin-2-amine To a mixture of 4-((5-(3-(((S)-1-(1H-tetrazol-1-yl)propan-2-yl)oxy)-4-chlorophenyl)pyrimidin-2-yl)amino)-1-(1r,4r)-4-((2S,6R)-2,6-dimethylmorpholino)cyclohexyl)-1H-pyrazol-3-ol (100 mg) and (2R)-2-(oxan-2-yloxy)propan-1-ol (39.4 mg) in toluene (4.0 mL) was added cyanomethylenetributylphosphorane (158 mg) at room temperature. The mixture was stirred at 100° C. under nitrogen atmosphere for 2 hr. Additional (2R)-2-(oxan-2-yloxy)propan-1-ol (39.4 mg) and cyanomethylenetributylphosphorane (158 mg) were added to the mixture. The mixture was stirred at 100° C. under nitrogen atmosphere for 2 hr. The mixture was quenched with water at room temperature and extracted with ethyl acetate. The organic layer was separated, washed with water and saturated brine, dried over anhydrous magnesium sulfate and concentrated under reduced pressure. The residue was purified by silica gel column chromatography (NH, ethyl acetate/hexane) and silica gel column chromatography (MeOH/ethyl acetate) to give the crude title compound (161 mg).

MS m/z 751.3 [M+H]$^+$.

B) (R)-1-((4-((5-(3-(((S)-1-(1H-tetrazol-1-yl)propan-2-yl)oxy)-4-chlorophenyl)pyrimidin-2-yl)amino)-1-((1r,4r)-4-((2S,6R)-2,6-dimethylmorpholino)cyclohexyl)-1H-pyrazol-3-yl)oxy)propan-2-ol To a mixture of 5-(4-chloro-3-{[(2S)-1-(1H-tetrazol-1-yl)propan-2-yl]oxy}phenyl)-N-{3-[(2R)-2-(oxan-2-yloxy)propoxy]-1-[(1r,4r)-4-[(2R,6S)-2,6-dimethylmorpholin-4-yl]cyclohexyl]-1H-pyrazol-4-yl}pyrimidin-2-amine (123 mg) in MeOH (3.0 mL) was added p-toluenesulfonic acid monohydrate (31.0 mg) at room temperature. The mixture was stirred at room temperature for 14 hr. The mixture was neutralized with saturated aqueous sodium hydrogencarbonate solution and extracted with ethyl acetate. The organic layer was separated, washed with water and saturated brine, dried over anhydrous magnesium sulfate and concentrated under reduced pressure. The residue was purified by silica gel column chromatography (NH, ethyl acetate/hexane) to give the title compound (55.0 mg).

$^1$H NMR (300 MHz, DMSO-d$_6$) δ 9.37 (s, 1H), 8.79 (s, 1H), 8.74 (s, 2H), 7.82 (s, 1H), 7.45 (d, J=8.34 Hz, 1H), 7.39 (d, J=1.74 Hz, 1H), 7.26 (dd, J=1.88, 8.30 Hz, 1H), 5.10-5.26 (m, 1H), 4.74-4.95 (m, 3H), 3.79-4.08 (m, 4H), 3.43-3.59 (m, 2H), 2.66-2.77 (m, 2H), 2.20-2.34 (m, 1H), 1.97-2.11 (m, 2H), 1.79-1.95 (m, 4H), 1.56-1.77 (m, 2H), 1.28-1.47 (m, 5H), 0.98-1.13 (m, 9H); MS m/z 667.4 [M+H].

Example 483

2-(((S)-1-(1H-tetrazol-1-yl)propan-2-yl)oxy)-4-(2-((1-((1r,4r)-4-((2S,6R)-2,6-dimethylmorpholino)cyclohexyl)-3-((tetrahydro-2H-pyran-4-yl)methoxy)-1H-pyrazol-4-yl)amino)pyrimidin-5-yl)benzonitrile

A) 5-(4-chloro-3-{[(2S)-1-(1H-tetrazol-1-yl)propan-2-yl]oxy}phenyl)-N-{3-[(oxan-4-yl)methoxy]-1-[(r,4r)-4-[(2R,6S)-2,6-dimethylmorpholin-4-yl]cyclohexyl]-1H-pyrazol-4-yl}pyrimidin-2-amine To a mixture of 4-((5-(3-(((S)-1-(1H-tetrazol-1-yl)propan-2-yl)oxy)-4-chlorophenyl)pyrimidin-2-yl)amino)-1-((1r,4r)-4-((2S,6R)-2,6-dimethylmorpholino)cyclohexyl)-1H-pyrazol-3-ol (201 mg), (tetrahydro-2H-pyran-4-yl)methanol (88.0 mg) and toluene (10 mL) was added cyanomethylenetributylphosphorane (0.26 mL). After being stirred under nitrogen atmosphere at 100° C. for 3 hr, the mixture was concentrated under reduced pressure. The residue was purified by silica gel column chromatography (NH, ethyl acetate/hexane) and silica gel column chromatography (MeOH/ethyl acetate) to give the title compound (185 mg).

MS m/z 707.4 [M+H]+.

B) 2-(((S)-1-(1H-tetrazol-1-yl)propan-2-yl)oxy)-4-(2-((1-((1r,4r)-4-((2S,6R)-2,6-dimethylmorpholino)cyclohexyl)-3-((tetrahydro-2H-pyran-4-yl)methoxy)-1H-pyrazol-4-yl)amino)pyrimidin-5-yl)benzonitrile To a mixture of 5-(4-chloro-3-{[(2S)-1-(1H-tetrazol-1-yl)propan-2-yl]oxy}phenyl)-N-{3-[(oxan-4-yl)methoxy]-1-[(1r,4r)-4-[(2R,6S)-2,6-dimethylmorpholin-4-yl]cyclohexyl]-1H-pyrazol-4-yl}pyrimidin-2-amine (174 mg), potassium hexacyanoferrate(II) trihydrate (209 mg) and potassium acetate (77.0 mg) in CPME (8.0 mL) and water (8.0 mL) were added XPhos Pd G2 (20.0 mg) and XPhos (25.0 mg). After being stirred under nitrogen atmosphere at 110° C. for 14 hr, the mixture was poured into water and extracted with ethyl acetate. The organic layer was separated, washed with water and saturated brine, dried over anhydrous sodium sulfate and concentrated under reduced pressure. The residue was purified by silica gel column chromatography (NH, ethyl acetate/hexane) and by preparative HPLC (water/CH$_3$CN containing 0.1% TFA). The desired fraction was neutralized with saturated aqueous sodium hydrogencarbonate solution and extracted with ethyl acetate. The organic layer was separated, dried over anhydrous sodium sulfate and concentrated under reduced pressure to give the title compound (54.0 mg).

$^1$H NMR (300 MHz, DMSO-d$_6$) δ 9.35 (s, 1H), 8.77-8.89 (m, 3H), 7.72-7.80 (m, 2H), 7.46 (s, 1H), 7.39 (dd, J=1.24, 8.12 Hz, 1H), 5.29-5.41 (m, 1H), 4.90-4.99 (m, 1H), 4.79-4.89 (m, 1H), 3.94 (d, J=6.51 Hz, 2H), 3.78-3.91 (m, 3H), 3.37-3.60 (m, 2H), 3.21-3.31 (m, 2H), 2.59-2.81 (m, 2H), 1.99-2.35 (m, 4H), 1.78-1.97 (m, 4H), 1.57-1.75 (m, 4H), 1.19-1.46 (m, 7H), 0.99-1.19 (m, 6H); MS m/z 698.5 [M+H]$^+$.

Example 485

2-(((S)-1-(1H-tetrazol-1-yl)propan-2-yl)oxy)-4-(2-((1-((1r,4r)-4-((2S,6R)-2,6-dimethylmorpholino)cyclohexyl)-3-(3-hydroxy-3-methylbutoxy)-1H-pyrazol-4-yl)amino)pyrimidin-5-yl)benzonitrile A) 4-[(4-{[5-(4-chloro-3-{[(2S)-1-(1H-tetrazol-1-yl)propan-2-yl]oxy}phenyl)pyrimidin-2-yl]amino}-1-[(1r,4r)-4-[(2R,6S)-2,6-dimethylmorpholin-4-yl]cyclohexyl]-1H-pyrazol-3-yl)oxy]-2-methylbutan-2-yl acetate To a mixture of 4-((5-(3-(((S)-1-(1H-tetrazol-1-yl)propan-2-yl)oxy)-4-chlorophenyl)pyrimidin-2-yl)amino)-1-(1r,4r)-4-((2S,6R)-2,6-dimethylmorpholino)cyclohexyl)-1H-pyrazol-3-ol (395 mg), 4-hydroxy-2-methylbutan-2-yl acetate (195 mg) and toluene (20 mL) was added cyanomethylenetributylphosphorane (460 mg). After being stirred under nitrogen atmosphere at 100° C. for 2 hr, the mixture was concentrated under reduced pressure. The residue was purified by silica gel column chromatography (MeOH/ethyl acetate) and silica gel column chromatography (NH, ethyl acetate/hexane) to give the title compound (275 mg).

MS m/z 737.4 [M+H]$^+$.

B) 4-[(4-{[5-(4-cyano-3-{[(2S)-1-(1H-tetrazol-1-yl)propan-2-yl]oxy}phenyl)pyrimidin-2-yl]amino}-1-[(1r,4r)-4-[(2R,6S)-2,6-dimethylmorpholin-4-yl]cyclohexyl]-1H-pyrazol-3-yl)oxy]-2-methylbutan-2-yl acetate To a mixture of 4-[(4-{[5-(4-chloro-3-{[(2S)-1-(1H-tetrazol-1-yl)propan-2-yl]oxy}phenyl)pyrimidin-2-yl]amino}-1-[(1r,4r)-4-[(2R,6S)-2,6-dimethylmorpholin-4-yl]cyclohexyl]-1H-pyrazol-3-yl)oxy]-2-methylbutan-2-yl acetate (160 mg), potassium hexacyanoferrate(II) trihydrate (186 mg), potassium acetate (67.0 mg), CPME (8.0 mL) and water (8.0 mL) were added XPhos Pd G2 (18.0 mg) and XPhos (21.0 mg). After being stirred under nitrogen atmosphere at 110° C. for 3 hr, the mixture was poured into water and extracted with ethyl acetate. The organic layer was washed with water and saturated brine, dried over anhydrous sodium sulfate and concentrated under reduced pressure. The residue was purified by silica gel column chromatography (MeOH/ethyl acetate) and silica gel column chromatography (NH, ethyl acetate/hexane) to give the title compound (116 mg).

MS m/z 728.4 [M+H]$^+$.

C) 2-(((S)-1-(1H-tetrazol-1-yl)propan-2-yl)oxy)-4-(2-((1-((1r,4r)-4-((2S,6R)-2,6-dimethylmorpholino)cyclohexyl)-3-(3-hydroxy-3-methylbutoxy)-1H-pyrazol-4-yl)amino)pyrimidin-5-yl)benzonitrile To a solution of 4-[(4-{[5-(4-cyano-3-{[(2S)-1-(1H-tetrazol-1-yl)propan-2-yl]oxy}phenyl)pyrimidin-2-yl]amino}-1-[(1r,4r)-4-[(2R,6S)-2,6-dimethylmorpholin-4-yl]cyclohexyl]-1H-pyrazol-3-yl)oxy]-2-methylbutan-2-yl acetate (104 mg) in MeOH (5.0 mL) was added 2 M aqueous sodium hydroxide solution (0.36 mL). After being stirred at 50° C. for 14 hr, the mixture was poured into water and extracted with ethyl acetate. The organic layer was washed with water and saturated brine, dried over anhydrous sodium sulfate and concentrated under reduced pressure. The residue was purified by silica gel column chromatography (NH, ethyl acetate/hexane) and crystallized from EtOH/diethyl ether/hexane to give the title compound (77.0 mg).

$^1$H NMR (300 MHz, DMSO-d$_6$) δ 9.35 (s, 1H), 8.79 (s, 2H), 8.72 (s, 1H), 7.71-7.78 (m, 2H), 7.46 (s, 1H), 7.39 (dd, J=1.19, 8.16 Hz, 1H), 5.29-5.41 (m, 1H), 4.90-4.99 (m, 1H), 4.80-4.89 (m, 1H), 4.30 (s, 1H), 4.19 (t, J=7.24 Hz, 2H), 3.82-3.95 (m, 1H), 3.44-3.60 (m, 2H), 2.65-2.81 (m, 2H), 2.20-2.35 (m, 1H), 2.01-2.12 (m, 2H), 1.75-1.97 (m, 6H), 1.58-1.74 (m, 2H), 1.29-1.48 (m, 5H), 1.11 (s, 6H), 1.05 (d, J=6.14 Hz, 6H); MS m/z 686.4 [M+H]+.

Example 486

4-((4-((5-(3-(((S)-1-(1H-tetrazol-1-yl)propan-2-yl)oxy)-4-chlorophenyl)pyrimidin-2-yl)amino)-1-((1r,4r)-4-((2S,6R)-2,6-dimethylmorpholino)cyclohexyl)-1H-pyrazol-3-yl)oxy)-2-methylbutan-2-ol To a mixture of 4-[(4-{[5-(4-chloro-3-{[(2S)-1-(1H-tetrazol-1-yl)propan-2-yl]oxy}phenyl)pyrimidin-2-yl]amino}-1-[(1r,4r)-4-[(2R,6S)-2,6-dimethylmorpholin-4-yl]cyclohexyl]-1H-pyrazol-3-yl)oxy]-2-methylbutan-2-yl acetate (7.68 g) and EtOH (50 mL) was added 2 M aqueous sodium hydroxide solution (10 mL). After being stirred at 50° C. for 3 hr, the mixture was poured into water and extracted with ethyl acetate. The organic layer was washed with water and saturated brine, dried over anhydrous sodium sulfate and concentrated under reduced pressure. The residue was purified by silica gel column chromatography (MeOH/ethyl acetate) and silica gel column chromatography (NH, ethyl acetate/hexane) to give the title compound (1.67 g).

$^1$H NMR (300 MHz, DMSO-d$_6$) δ 9.37 (s, 1H), 8.69 (s, 2H), 8.53 (s, 1H), 7.72 (s, 1H), 7.45 (d, J=8.25 Hz, 1H), 7.36 (d, J=1.83 Hz, 1H), 7.23 (dd, J=1.93, 8.34 Hz, 1H), 5.10-5.24 (m, 1H), 4.86-4.95 (m, 1H), 4.74-4.85 (m, 1H), 4.30 (s, 1H), 4.18 (t, J=7.24 Hz, 2H), 3.79-3.97 (m, 1H), 3.44-3.57 (m, 2H), 2.67-2.79 (m, 2H), 2.23-2.34 (m, 1H), 1.99-2.12 (m, 2H), 1.74-1.95 (m, 6H), 1.58-1.73 (m, 2H), 1.29-1.45 (m, 5H), 1.11 (s, 6H), 1.05 (d, J=6.20 Hz, 6H); MS m/z 695.6 [M+H]$^+$.

Example 487

5-(3-(((S)-1-(1H-tetrazol-1-yl) propan-2-yl)oxy)-4-chlorophenyl)-N-(1-((1r,4r)-4-((2S,6R)-2,6-dimethylmorpholino)cyclohexyl)-3-(3-(2-methoxyethoxy)propoxy)-1H-pyrazol-4-yl)pyrimidin-2-amine hydrochloride

A) ethyl 1-acetyl-3-[3-(2-methoxyethoxy)propoxy]-1H-pyrazole-4-carboxylate

To the mixture of ethyl 1-acetyl-3-hydroxy-1H-pyrazole-4-carboxylate (3.40 g), triphenylphosphine (5.42 g) and 3-(2-methoxyethoxy)propan-1-ol (2.55 g) in toluene (100 mL) was added DIAD (4.18 g) at room temperature. The mixture was stirred at room temperature for 14 hr. The mixture was quenched with water at room temperature and extracted with ethyl acetate. The organic layer was washed with water and saturated brine, dried over anhydrous magnesium sulfate and concentrated under reduced pressure. The residue was purified by silica gel column chromatography (ethyl acetate/hexane) to give the title compound (8.25 g).

MS m/z 315.2 [M+H]$^+$.

B) ethyl 1-{1,4-dioxaspiro[4.5]decan-8-yl}-3-[3-(2-methoxyethoxy)propoxy]-1H-pyrazole-4-carboxylate To a solution of ethyl 1-acetyl-3-[3-(2-methoxyethoxy)propoxy]-1H-pyrazole-4-carboxylate (5.40 g) in DMF (60 mL) was added potassium carbonate (7.08 g) at room temperature. The mixture was stirred at 100° C. for 2 hr. 1,4-Dioxaspiro[4.5]decan-8-yl methanesulfonate (6.85 g) was added to the mixture at 100° C. The mixture was stirred at 100° C. under nitrogen atmosphere for 4 hr. Additional 1,4-dioxaspiro[4.5]decan-8-yl methanesulfonate (2.00 g) and potassium carbonate (2.00 g) were added to the mixture at 100° C. The mixture was stirred at 100° C. under nitrogen atmosphere for 14 hr. The mixture was poured into water and extracted with ethyl acetate. The organic layer was washed with water and saturated brine, dried over anhydrous magnesium sulfate and concentrated under reduced pressure. The residue was purified by silica gel column chromatography (NH, ethyl acetate/hexane) to give the crude title compound (10.3 g).

MS m/z 413.3 [M+H]$^+$.

C) 1-{1,4-dioxaspiro[4.5]decan-8-yl}-3-[3-(2-methoxyethoxy)propoxy]-1H-pyrazole-4-carboxylic acid To a mixture of ethyl 1-{1,4-dioxaspiro[4.5]decan-8-yl}-3-[3-(2-methoxyethoxy)propoxy]-1H-pyrazole-4-carboxylate (10.3 g) in EtOH (100 mL) was added 2 M aqueous sodium hydroxide solution (50 mL) at room temperature. The mixture was stirred at 70° C. for 2 hr. The mixture was neutralized with 2 M hydrochloric acid at 0° C. and extracted with ethyl acetate. The organic layer was washed with water and saturated brine, dried over anhydrous magnesium sulfate and concentrated under reduced pressure to give the crude title compound (8.00 g).

MS m/z 385.3 [M+H]$^+$.

D) benzyl N-(1-{1,4-dioxaspiro[4.5]decan-8-yl}-3-[3-(2-methoxyethoxy)propoxy]-1H-pyrazol-4-yl)carbamate To a mixture of 1-{1,4-dioxaspiro[4.5]decan-8-yl}-3-[3-(2-methoxyethoxy)propoxy]-1H-pyrazole-4-carboxylic acid (8.00 g) and triethylamine (3.15 g) in toluene (80 mL) was added DPPA (4.72 mL) at 0° C. The mixture was stirred at 0° C. under nitrogen atmosphere for 5 min. Benzylalcohol (4.49 g) was added to the mixture at 0° C. The mixture was stirred at 100° C. for 4 hr. The mixture was stirred at room temperature for 14 hr. The mixture was quenched with water at room temperature and extracted with ethyl acetate. The organic layer was washed with water and saturated brine, dried over anhydrous magnesium sulfate and concentrated under reduced pressure. The residue was purified by silica gel column chromatography (ethyl acetate/hexane) to give the title compound (4.56 g).

MS m/z 490.3 [M+H]$^+$.

E) benzyl N-{3-[3-(2-methoxyethoxy)propoxy]-1-(4-oxocyclohexyl)-1H-pyrazol-4-yl}carbamate To a mixture of benzyl N-(1-{1,4-dioxaspiro[4.5]decan-8-yl}-3-[3-(2-methoxyethoxy)propoxy]-1H-pyrazol-4-yl)carbamate (4.56 g) in THF (45 mL) was added 1 M hydrochloric acid (45 mL) at room temperature. The mixture was stirred at 50° C. for 4 hr. The mixture was neutralized with saturated aqueous sodium hydrogencarbonate solution at room temperature and extracted with ethyl acetate. The organic layer was separated, washed with water and saturated brine, dried over anhydrous magnesium sulfate and concentrated under reduced pressure to give the crude title compound (3.98 g).

MS m/z 446.3 [M+H]$^+$.

F) benzyl N-{3-[3-(2-methoxyethoxy)propoxy]-1-[(1r,4r)-4-[(2R,6S)-2,6-dimethylmorpholin-4-yl]cyclohexyl]-1H-pyrazol-4-yl}carbamate To a mixture of benzyl N-{3-[3-(2-methoxyethoxy)propoxy]-1-(4-oxocyclohexyl)-1H-pyrazol-4-yl}carbamate (1.48 g) and cis-2,6-dimethylmorpholine (572 mg) in MeOH (20 mL) and AcOH (1.0 mL) was added 2-methylpyridine-borane (710 mg) at room temperature. The mixture was stirred at room temperature for 14 hr. The mixture was neutralized with saturated aqueous sodium hydrogencarbonate solution at room temperature and extracted with ethyl acetate. The organic layer was separated, washed with water and saturated brine, dried over anhydrous magnesium sulfate and concentrated under reduced pressure. The residue was purified by silica gel column chromatography (NH, ethyl acetate/hexane) to give the title compound (750 mg).

MS m/z 545.3 [M+H]$^+$.

G) 3-[3-(2-methoxyethoxy)propoxy]-1-[(1r,4r)-4-[(2R,6S)-2,6-dimethylmorpholin-4-yl]cyclohexyl]-1H-pyrazol-4-amine A mixture of benzyl N-{3-[3-(2-methoxyethoxy)propoxy]-1-[(1r,4r)-4-[(2R,6S)-2,6-dimethylmorpholin-4-yl]cyclohexyl]-1H-pyrazol-4-yl}carbamate (750 mg) and 10% palladium-carbon (145 mg) in EtOH (10 mL) and THF (10 mL) was stirred under normal pressure of hydrogen atmosphere at room temperature for 2 hr. The catalyst was removed by filtration, and then the filtrate was concentrated under reduced pressure to give the title compound (524 mg).

MS m/z 411.3 [M+H]$^+$.

H) 5-(3-(((S)-1-(1H-tetrazol-1-yl)propan-2-yl)oxy)-4-chlorophenyl)-N-(1-((1r,4r)-4-((2S,6R)-2,6-dimethylmorpholino)cyclohexyl)-3-(3-(2-methoxyethoxy)propoxy)-1H-pyrazol-4-yl)pyrimidin-2-amine hydrochloride To a mixture of 3-[3-(2-methoxyethoxy)propoxy]-1-[(1r,4r)-4-[(2R,6S)-2,6-dimethylmorpholin-4-yl]cyclohexyl]-1H-pyrazol-4-amine (524 mg) and 2-chloro-5-(4-chloro-3-{[(2S)-1-(1H-tetrazol-1-yl)propan-2-yl]oxy}phenyl)pyrimidine (667 mg) in NMP (6.0 ml) was added methanesulfonic acid (366 mg) at room temperature, and the mixture was stirred at 110° C. for 4 hr. The mixture was poured into saturated aqueous sodium hydrogencarbonate solution at room temperature and extracted with ethyl acetate. The organic layer was separated, washed with water and saturated brine, dried over anhydrous magnesium sulfate and concentrated under reduced pressure. The residue was purified by silica gel column chromatography (NH, ethyl acetate/hexane) and silica gel column chromatography (MeOH/ethyl acetate) to give the crude title compound (350 mg). To a solution of the obtained solid (281 mg) in EtOH (5.0 mL) was added 4 M hydrogen chloride-ethyl acetate (482 µL) at room temperature. Diethylether (10 mL) was added to the mixture dropwise at room temperature. The mixture was stirred at room temperature for 14 hr. The precipitating solid was collected by filtration. The solid was washed with diethyl ether and dried under reduced pressure to give the title compound (269 mg).

$^1$H NMR (300 MHz, DMSO-$d_6$) δ 10.98-11.16 (m, 1H), 9.38 (s, 1H), 8.62-8.75 (m, 3H), 7.77 (s, 1H), 7.45 (d, J=8.25 Hz, 1H), 7.36 (d, J=1.83 Hz, 1H), 7.24 (dd, J=1.88, 8.30 Hz, 1H), 5.11-5.23 (m, 1H), 4.75-4.95 (m, 2H), 4.14 (t, J=6.42 Hz, 2H), 3.70-4.10 (m, 3H), 3.36-3.54 (m, 8H), 3.15-3.30 (m, 4H), 2.57-2.74 (m, 2H), 2.22-2.35 (m, 2H), 2.05-2.20 (m, 2H), 1.89 (quin, J=6.35 Hz, 2H), 1.61-1.80 (m, 4H), 1.33 (d, J=6.14 Hz, 3H), 1.15 (d, J=6.24 Hz, 6H); MS m/z 725.4 [M+H]$^+$.

Example 488

2-(((S)-1-(1H-tetrazol-1-yl)propan-2-yl)oxy)-4-(2-((1-((1r,4r)-4-((2S,6R)-2,6-dimethylmorpholino)cyclohexyl)-3-(3-(2-methoxyethoxy)propoxy)-1H-pyrazol-4-yl)amino)pyrimidin-5-yl)benzonitrile To a mixture of 5-(3-(((S)-1-(1H-tetrazol-1-yl)propan-2-yl)oxy)-4-chlorophenyl)-N-(1-((1r,4r)-4-((2S,6R)-2,6-dimethylmorpholino)cyclohexyl)-3-(3-(2-methoxyethoxy)propoxy)-1H-pyrazol-4-yl)pyrimidin-2-amine (70.0 mg), potassium hexacyanoferrate(II) trihydrate (81.5 mg), XPhos (9.20 mg) and potassium acetate (28.3 mg) in CPME (15 mL) and water (15 mL) was added XPhos Pd G2 (7.59 mg) at room temperature. The mixture was stirred at 100° C. under nitrogen atmosphere for 14 hr. The mixture was quenched with saturated aqueous sodium hydrogencarbonate solution at room temperature and extracted with ethyl acetate. The organic layer was separated, washed with water and saturated brine, dried over anhydrous magnesium sulfate and concentrated under reduced pressure. The residue was purified by silica gel column chromatography (NH, ethyl acetate/hexane). To a mixture of the obtained solid, XPhos (9.20 mg), potassium hexacyanoferrate(II) trihydrate (81.5 mg) and potassium acetate (28.3 mg) in CPME (5.0 mL) and water (5.0 mL) was added XPhos Pd G2 (7.59 mg) at room temperature. The mixture was stirred at 100° C. under nitrogen atmosphere for 14 hr. The mixture was quenched with water at room temperature and extracted with ethyl acetate. The organic layer was separated, washed with water and saturated brine, dried over anhydrous magnesium sulfate and concentrated under reduced pressure. The residue was purified by silica gel column chromatography (NH, ethyl acetate/hexane), and the residue was purified by preparative HPLC (water/CH$_3$CN containing 0.1% TFA). The desired fraction was neutralized with saturated aqueous sodium hydrogencarbonate solution and extracted with ethyl acetate. The organic layer was separated, dried over anhydrous magnesium sulfate and concentrated under reduced pressure to give the title compound (18.0 mg).

$^1$H NMR (300 MHz, DMSO-$d_6$) δ 9.35 (s, 1H), 8.73-8.84 (m, 3H), 7.70-7.79 (m, 2H), 7.47 (s, 1H), 7.40 (dd, J=1.24, 8.12 Hz, 1H), 5.27-5.40 (m, 1H), 4.78-4.99 (m, 2H), 4.13 (t, J=6.42 Hz, 2H), 3.81-3.96 (m, 1H), 3.36-3.61 (m, 8H), 3.21 (s, 3H), 2.62-2.85 (m, 2H), 2.18-2.41 (m, 1H), 1.99-2.13 (m, 2H), 1.78-1.98 (m, 6H), 1.58-1.76 (m, 2H), 1.28-1.48 (m, 5H), 1.05 (d, J=6.24 Hz, 6H); MS m/z 716.4 [M+H]$^+$.

Example 489

5-(3-(((S)-1-(1H-tetrazol-1-yl) propan-2-yl)oxy)-4-chlorophenyl)-N-(1-((1r,4r)-4-((2S,6R)-2,6-dimethylmorpholino)cyclohexyl)-3-(3-methoxypropoxy)-1H-pyrazol-4-yl)pyrimidin-2-amine To a mixture of 3-(3-methoxypropoxy)-1-[(1r,4r)-4-[(2R,6S)-2,6-dimethylmorpholin-4-yl]cyclohexyl]-1H-pyrazol-4-amine dihydrochloride (2.62 g) in NMP (10 ml) was added 2-chloro-5-(4-chloro-3-{[(2S)-1-(1H-tetrazol-1-yl)propan-2-yl]oxy}phenyl)pyrimidine (3.42 g) at room temperature, and the mixture was stirred at 110° C. for 2 hr. The mixture was poured into 1 M hydrochloric acid and washed with ethyl acetate. The aqueous layer was neutralized with saturated aqueous sodium hydrogencarbonate solution and extracted with ethyl acetate. The organic layer was separated, washed with saturated brine, dried over anhydrous magnesium sulfate and concentrated under reduced pressure. The residue was purified by silica gel column chromatography (NH, ethyl acetate/hexane) to give the title compound (2.70 g).

$^1$H NMR (300 MHz, DMSO-$d_6$) δ 9.34-9.41 (m, 1H), 8.67-8.75 (m, 2H), 8.53-8.62 (m, 1H), 7.67-7.76 (m, 1H), 7.41-7.48 (m, 1H), 7.32-7.38 (m, 1H), 7.19-7.27 (m, 1H), 5.10-5.25 (m, 1H), 4.72-4.96 (m, 2H), 4.08-4.17 (m, 2H), 3.81-3.94 (m, 1H), 3.46-3.57 (m, 2H), 3.38-3.45 (m, 2H), 3.18-3.24 (m, 3H), 2.66-2.78 (m, 2H), 2.20-2.34 (m, 1H), 2.00-2.12 (m, 2H), 1.77-1.95 (m, 6H), 1.59-1.77 (m, 2H), 1.28-1.47 (m, 5H), 1.00-1.08 (m, 6H); MS m/z 681.4 [M+H]$^+$.

Example 490

2-(((S)-1-(1H-tetrazol-1-yl)propan-2-yl)oxy)-4-(2-((3-(3-(2-methoxyethoxy)propoxy)-1-((1r,4r)-4-morpholinocyclohexyl)-1H-pyrazol-4-yl)amino)pyrimidin-5-yl)benzonitrile A) 5-(4-chloro-3-{[(2S)-1-(1H-tetrazol-1-yl)propan-2-yl]oxy}phenyl)-N-{3-[3-(2-methoxyethoxy)propoxy]-1-[(1r,4r)-4-(morpholin-4-yl)cyclohexyl]-1H-pyrazol-4-yl}pyrimidin-2-amine To a mixture of 4-((5-(3-(((S)-1-(1H-tetrazol-1-yl)propan-2-yl)oxy)-4-chlorophenyl)pyrimidin-2-yl)amino)-1-

((1r,4r)-4-morpholinocyclohexyl)-1H-pyrazol-3-ol (200 mg) and 3-(2-methoxyethoxy)propan-1-ol (69.2 mg) in toluene (8.0 mL) was added cyanomethylenetributylphosphorane (248 mg) at room temperature. The mixture was stirred at 100° C. under nitrogen atmosphere for 14 hr. The mixture was quenched with water at room temperature and extracted with ethyl acetate. The organic layer was separated, washed with saturated brine, dried over anhydrous magnesium sulfate and concentrated under reduced pressure. The residue was purified by silica gel column chromatography (MeOH/ethyl acetate) to give the title compound (184 mg).

MS m/z 697.4 [M+H]$^+$.

B) 2-(((S)-1-(1H-tetrazol-1-yl)propan-2-yl)oxy)-4-(2-((3-(3-(2-methoxyethoxy)propoxy)-1-((1r,4r)-4-morpholinocyclohexyl)-1H-pyrazol-4-yl)amino)pyrimidin-5-yl)benzonitrile To a mixture of 5-(4-chloro-3-{[(2S)-1-(1H-tetrazol-1-yl)propan-2-yl]oxy}phenyl)-N-{3-[3-(2-methoxyethoxy)propoxy]-1-[(1r,4r)-4-(morpholin-4-yl)cyclohexyl]-1H-pyrazol-4-yl}pyrimidin-2-amine (130 mg) and potassium hexacyanoferrate(II) trihydrate (468 mg) in CPME (5 mL) and water (5.0 mL) was added potassium acetate (163 mg) at room temperature. After being stirred at room temperature for 15 min, XPhos (53.2 mg) and XPhos Pd G2 (43.9 mg) were added to the reaction mixture. The mixture was stirred at 90° C. under nitrogen atmosphere for 14 hr. The mixture was quenched with water at room temperature and extracted with ethyl acetate. The organic layer was separated, washed with water and saturated brine, dried over anhydrous magnesium sulfate and concentrated under reduced pressure. The residue was purified by silica gel column chromatography (MeOH/ethyl acetate). The residue was washed with EtOH/hexane (1:2) and dried under reduced pressure to give the title compound (56.0 mg).

$^1$H NMR (300 MHz, DMSO-d$_6$) δ 9.35 (s, 1H), 8.80 (s, 2H), 8.76 (s, 1H), 7.72-7.77 (m, 2H), 7.46 (s, 1H), 7.39 (dd, J=1.28, 8.07 Hz, 1H), 5.28-5.38 (m, 1H), 4.89-4.98 (m, 1H), 4.80-4.88 (m, 1H), 4.13 (t, J=6.28 Hz, 2H), 3.83-3.94 (m, 1H), 3.53-3.59 (m, 4H), 3.37-3.52 (m, 6H), 3.21 (s, 3H), 2.45-2.48 (m, 4H), 2.22-2.32 (m, 1H), 2.00-2.10 (m, 2H), 1.82-1.98 (m, 4H), 1.60-1.75 (m, 2H), 1.29-1.44 (m, 5H); MS m/z 688.4 [M+H]$^+$.

Example 491

5-(3-(((S)-1-(1H-tetrazol-1-yl) propan-2-yl)oxy)-4-chlorophenyl)-N-(1-((1r,4r)-4-morpholinocyclohexyl)-3-(oxetan-3-ylmethoxy)-1H-pyrazol-4-yl)pyrimidin-2-amine To a mixture of 4-((5-(3-(((S)-1-(1H-tetrazol-1-yl)propan-2-yl)oxy)-4-chlorophenyl)pyrimidin-2-yl)amino)-1-((1r,4r)-4-morpholinocyclohexyl)-1H-pyrazol-3-ol (100 mg) and (oxetan-3-yl)methanol (18.1 mg) in toluene (8.0 mL) was added cyanomethylenetributylphosphorane (90.6 µL) at room temperature. The mixture was stirred at 100° C. under nitrogen atmosphere for 1 hr. Additional (oxetan-3-yl)methanol (18.1 mg) and cyanomethylenetributylphosphorane (90.6 µL) were added to the mixture. The mixture was stirred at 100° C. under nitrogen atmosphere for 2 hr. The mixture was quenched with water at room temperature and extracted with ethyl acetate. The organic layer was separated, washed with water and saturated brine, dried over anhydrous magnesium sulfate and concentrated under reduced pressure. The residue was purified by silica gel column chromatography (MeOH/ethyl acetate) to give the title compound (100 mg).

$^1$H NMR (300 MHz, DMSO-d$_6$) δ 9.37 (s, 1H), 8.70 (s, 2H), 8.62 (s, 1H), 7.74 (s, 1H), 7.45 (d, J=8.25 Hz, 1H), 7.36 (d, J=1.83 Hz, 1H), 7.24 (dd, J=1.88, 8.30 Hz, 1H), 5.09-5.23 (m, 1H), 4.86-4.96 (m, 1H), 4.74-4.83 (m, 1H), 4.63 (dd, J=6.05, 7.89 Hz, 2H), 4.39 (t, J=6.05 Hz, 2H), 4.31 (d, J=6.69 Hz, 2H), 3.83-3.96 (m, 1H), 3.51-3.62 (m, 4H), 2.44-2.48 (m, 4H), 2.24-2.30 (m, 1H), 2.01-2.10 (m, 2H), 1.88-1.97 (m, 2H), 1.60-1.77 (m, 2H), 1.24-1.45 (m, 6H); MS m/z 651.3 [M+H]$^+$.

Example 492

2-(((S)-1-(1H-tetrazol-1-yl)propan-2-yl)oxy)-4-(2-((1-((1r,4r)-4-morpholinocyclohexyl)-3-(oxetan-3-ylmethoxy)-1H-pyrazol-4-yl)amino)pyrimidin-5-yl)benzonitrile To a mixture of 5-(3-(((S)-1-(1H-tetrazol-1-yl)propan-2-yl)oxy)-4-chlorophenyl)-N-(1-((1r,4r)-4-morpholinocyclohexyl)-3-(oxetan-3-ylmethoxy)-1H-pyrazol-4-yl)pyrimidin-2-amine (100 mg) and potassium hexacyanoferrate(II) trihydrate (389 mg) in CPME (5.0 mL) and water (5.0 mL) was added potassium acetate (135 mg) at room temperature. After being stirred at room temperature for 10 min, XPhos (43.9 mg) and XPhos Pd G2 (36.2 mg) were added to the reaction mixture. The mixture was stirred at 90° C. under nitrogen atmosphere for 14 hr. The mixture was quenched with water at room temperature and extracted with ethyl acetate. The organic layer was separated, washed with water and saturated brine, dried over anhydrous magnesium sulfate and concentrated under reduced pressure. The residue was purified by silica gel column chromatography (MeOH/ethyl acetate). The residue was washed with EtOAc/hexane (1:2) and dried under reduced pressure to give the title compound (55.0 mg).

$^1$H NMR (300 MHz, DMSO-d$_6$) δ 9.35 (s, 1H), 8.77-8.82 (m, 3H), 7.75 (t, J=4.08 Hz, 2H), 7.46 (s, 1H), 7.39 (dd, J=1.28, 8.07 Hz, 1H), 5.29-5.39 (m, 1H), 4.90-4.99 (m, 1H), 4.79-4.89 (m, 1H), 4.63 (dd, J=6.05, 7.89 Hz, 2H), 4.39 (t, J=6.05 Hz, 2H), 4.31 (d, J=6.79 Hz, 2H), 3.82-3.96 (m, 1H), 3.52-3.61 (m, 4H), 2.44-2.49 (m, 5H), 2.22-2.32 (m, 1H), 2.01-2.10 (m, 2H), 1.93 (d, J=13.30 Hz, 2H), 1.60-1.76 (m, 2H), 1.30-1.46 (m, 5H); MS m/z 642.4 [M+H]$^+$.

Example 493

4-((4-((5-(3-(((S)-1-(1H-tetrazol-1-yl)propan-2-yl)oxy)-4-chlorophenyl)pyrimidin-2-yl)amino)-1-((1r,4r)-4-morpholinocyclohexyl)-1H-pyrazol-3-yl)oxy)butanenitrile To a mixture of 4-((5-(3-(((S)-1-(1H-tetrazol-1-yl)propan-2-yl)oxy)-4-chlorophenyl)pyrimidin-2-yl)amino)-1-((1r,4r)-4-morpholinocyclohexyl)-1H-pyrazol-3-ol (200 mg) and 4-hydroxybutanenitrile (58.5 mg) in toluene (8.0 mL) was added cyanomethylenetributylphosphorane (181 µL) at room temperature. The mixture was stirred at 100° C. under nitrogen atmosphere for 14 hr. The mixture was quenched with water at room temperature and extracted with ethyl acetate. The organic layer was separated, washed with water and saturated brine, dried over anhydrous magnesium sulfate and concentrated under reduced pressure. The residue was purified by silica gel column chromatography (MeOH/ethyl acetate) to give the title compound (114 mg).

¹H NMR (300 MHz, DMSO-d₆) δ 9.35-9.39 (m, 1H), 8.71-8.76 (m, 3H), 7.80 (s, 1H), 7.45 (d, J=8.25 Hz, 1H), 7.37 (d, J=1.93 Hz, 1H), 7.25 (dd, J=1.93, 8.25 Hz, 1H), 5.11-5.24 (m, 1H), 4.87-4.96 (m, 1H), 4.75-4.85 (m, 1H), 4.15 (t, J=5.96 Hz, 2H), 3.84-3.95 (m, 1H), 3.52-3.61 (m, 4H), 2.69 (t, J=7.15 Hz, 2H), 2.44-2.48 (m, 4H), 2.23-2.29 (m, 1H), 2.01-2.09 (m, 2H), 1.87-2.00 (m, 4H), 1.59-1.75 (m, 2H), 1.29-1.45 (m, 5H); MS m/z 648.4 [M+H]⁺.

Example 494

2-(((S)-1-(1H-tetrazol-1-yl)propan-2-yl)oxy)-4-(2-((3-(3-cyanopropoxy)-1-((1r,4r)-4-morpholinocyclohexyl)-1H-pyrazol-4-yl)amino)pyrimidin-5-yl)benzonitrile To a mixture of 4-((4-((5-(3-(((S)-1-(1H-tetrazol-1-yl)propan-2-yl)oxy)-4-chlorophenyl)pyrimidin-2-yl)amino)-1-(1r,4r)-4-morpholinocyclohexyl)-1H-pyrazol-3-yl)oxy)butanenitrile (110 mg) and potassium hexacyanoferrate(II) trihydrate (143 mg) in CPME (5.0 mL) and water (5.0 mL) was added potassium acetate (49.9 mg) at room temperature. After being stirred at room temperature for 5 min, XPhos (16.1 mg) and XPhos Pd G2 (13.3 mg) were added to the reaction mixture. The mixture was stirred at 100° C. under nitrogen atmosphere for 14 hr. The mixture was quenched with water at room temperature and extracted with ethyl acetate. The organic layer was separated, washed with water and saturated brine, dried over anhydrous magnesium sulfate and concentrated under reduced pressure. The residue was purified by silica gel column chromatography (MeOH/ethyl acetate). The residue was washed with EtOAc/hexane (1:1) and dried under reduced pressure to give the title compound (38.0 mg).
¹H NMR (300 MHz, DMSO-d₆) δ 9.35 (s, 1H), 8.92 (s, 1H), 8.81 (s, 2H), 7.81 (s, 1H), 7.75 (d, J=8.07 Hz, 1H), 7.47 (s, 1H), 7.37-7.43 (m, 1H), 5.29-5.38 (m, 1H), 4.91-4.99 (m, 1H), 4.79-4.88 (m, 1H), 4.15 (t, J=5.91 Hz, 2H), 3.83-3.96 (m, 1H), 3.52-3.60 (m, 4H), 2.69 (t, J=7.20 Hz, 2H), 2.45-2.49 (m, 4H), 2.22-2.31 (m, 1H), 2.01-2.10 (m, 2H), 1.87-1.99 (m, 4H), 1.60-1.76 (m, 2H), 1.31-1.45 (m, 5H); MS m/z 639.4 [M+H]⁺.

Example 495

2-(((S)-1-(1H-tetrazol-1-yl)propan-2-yl)oxy)-4-(2-((3-(3-hydroxy-3-methylbutoxy)-1-((1r,4r)-4-morpholinocyclohexyl)-1H-pyrazol-4-yl)amino)pyrimidin-5-yl)benzonitrile A) 4-[(4-{[5-(4-chloro-3-{[(2S)-1-(1H-tetrazol-1-yl)propan-2-yl]oxy}phenyl)pyrimidin-2-yl]amino}-1-[(r,4r)-4-(morpholin-4-yl)cyclohexyl]-1H-pyrazol-3-yl)oxy]-2-methylbutan-2-yl acetate To a mixture of 4-((5-(3-(((S)-1-(1H-tetrazol-1-yl)propan-2-yl)oxy)-4-chlorophenyl)pyrimidin-2-yl)amino)-1-((1r,4r)-4-morpholinocyclohexyl)-1H-pyrazol-3-ol (218 mg), 4-hydroxy-2-methylbutan-2-yl acetate (105 mg) and toluene (5.0 mL) was added cyanomethylenetributylphosphorane (0.20 mL). After being stirred under nitrogen atmosphere at 100° C. for 2 hr, additional cyanomethylenetributylphosphorane (0.20 mL) was added to the mixture. After being stirred under nitrogen atmosphere at 100° C. for 1 hr, the mixture was concentrated under reduced pressure. The residue was purified by silica gel column chromatography (NH, ethyl acetate/hexane) and silica gel column chromatography (MeOH/ethyl acetate) to give the title compound (211 mg).
MS m/z 709.4 [M+H]⁺.

B) 4-[(4-{[5-(4-cyano-3-{[(2S)-1-(1H-tetrazol-1-yl)propan-2-yl]oxy}phenyl)pyrimidin-2-yl]amino}-1-[(r,4r)-4-(morpholin-4-yl)cyclohexyl]-1H-pyrazol-3-yl)oxy]-2-methylbutan-2-yl acetate To a mixture of 4-[(4-{[5-(4-chloro-3-{[(2S)-1-(1H-tetrazol-1-yl)propan-2-yl]oxy}phenyl)pyrimidin-2-yl]amino}-1-[(1r,4r)-4-(morpholin-4-yl)cyclohexyl]-1H-pyrazol-3-yl)oxy]-2-methylbutan-2-yl acetate (197 mg), potassium hexacyanoferrate(II) trihydrate (236 mg), potassium acetate (86.0 mg), CPME (10 mL) and water (10 mL) were added XPhos Pd G2 (22.0 mg) and XPhos (27.0 mg). After being stirred under nitrogen atmosphere at 100° C. for 14 hr, the mixture was poured into water and extracted with ethyl acetate. The organic layer was separated, washed with water and saturated brine, dried over anhydrous sodium sulfate and concentrated under reduced pressure. The residue was purified by silica gel column chromatography (NH, ethyl acetate/hexane) and crystallized from EtOH/hexane to give the title compound (150 mg).
MS m/z 700.5 [M+H]⁺.

C) 2-(((S)-1-(1H-tetrazol-1-yl)propan-2-yl)oxy)-4-(2-((3-(3-hydroxy-3-methylbutoxy)-1-((1r,4r)-4-morpholinocyclohexyl)-1H-pyrazol-4-yl)amino)pyrimidin-5-yl)benzonitrile To a solution of 4-[(4-{[5-(4-cyano-3-{[(2S)-1-(1H-tetrazol-1-yl)propan-2-yl]oxy}phenyl)pyrimidin-2-yl]amino}-1-[(1r,4r)-4-(morpholin-4-yl)cyclohexyl]-1H-pyrazol-3-yl)oxy]-2-methylbutan-2-yl acetate (106 mg) in MeOH (2.0 mL) and THF (2.0 mL) was added 2 M aqueous sodium hydroxide solution (0.23 mL). After being stirred at room temperature for 14 hr and then at 80° C. for 1 hr, the mixture was poured into water and extracted with ethyl acetate. The organic layer was separated, washed with saturated brine, dried over anhydrous sodium sulfate and concentrated under reduced pressure. The residue was purified by silica gel column chromatography (NH, ethyl acetate/hexane) and crystallized from EtOH/hexane to give the title compound (80.0 mg).
¹H NMR (300 MHz, DMSO-d₆) δ 9.35 (s, 1H), 8.79 (s, 2H), 8.71 (s, 1H), 7.71-7.77 (m, 2H), 7.46 (s, 1H), 7.39 (dd, J=1.10, 8.16 Hz, 1H), 5.27-5.41 (m, 1H), 4.90-4.98 (m, 1H), 4.79-4.89 (m, 1H), 4.29 (s, 1H), 4.19 (t, J=7.24 Hz, 2H), 3.82-3.96 (m, 1H), 3.52-3.61 (m, 4H), 2.44-2.49 (m, 4H), 2.21-2.34 (m, 1H), 2.01-2.12 (m, 2H), 1.87-1.97 (m, 2H), 1.78 (t, J=7.29 Hz, 2H), 1.59-1.73 (m, 2H), 1.31-1.45 (m, 5H), 1.11 (s, 6H); MS m/z 658.4 [M+H]⁺.

Example 496

2-(((S)-1-(1H-tetrazol-1-yl)propan-2-yl)oxy)-4-(2-((3-(3-methoxy-3-methylbutoxy)-1-((1r,4r)-4-morpholinocyclohexyl)-1H-pyrazol-4-yl)amino)pyrimidin-5-yl)benzonitrile A) 5-(4-chloro-3-{[(2S)-1-(1H-tetrazol-1-yl)propan-2-yl]oxy}phenyl)-N-[3-(3-methoxy-3-methylbutoxy)-1-[(1r,4r)-4-(morpholin-4-yl)cyclohexyl]-1H-pyrazol-4-yl]pyrimidin-2-amine To a mixture of 4-((5-(3-(((S)-1-(1H-tetrazol-1-yl)propan-2-yl)oxy)-4-chlorophenyl)pyrimidin-2-yl)amino)-1-((1r,4r)-4-morpholinocyclohexyl)-1H-pyrazol-3-ol (200 mg) and 3-methoxy-3-methylbutan-1-ol (48.7 mg) in toluene (8.0 mL) was added cyanomethylenetributylphosphorane (99.6 mg) at room temperature. The mixture was stirred at 100° C. under nitrogen atmosphere for 1 hr. Additional 3-methoxy-3-methylbutan-1-ol (48.7 mg) and cyanomethylenetributylphosphorane (99.6 mg) were added to the mixture. The mixture was stirred at 100° C. under nitrogen atmosphere for 10 hr. The mixture was quenched with water at room temperature and extracted with ethyl acetate. The organic layer was separated, washed with saturated brine, dried over anhydrous magnesium sulfate and concentrated under reduced pressure. The residue was purified by silica gel column chromatography (MeOH/ethyl acetate) and silica gel column chromatography (NH, ethyl acetate/hexane). The residue was purified by preparative HPLC (water/CH$_3$CN containing 0.1% TFA) The desired fraction was neutralized with saturated aqueous sodium hydrogencarbonate solution and extracted with ethyl acetate. The organic layer was separated, dried over anhydrous magnesium sulfate and concentrated under reduced pressure to give the title compound (148 mg).
681.4 [M+H]$^+$.

B) 2-(((S)-1-(1H-tetrazol-1-yl)propan-2-yl)oxy)-4-(2-((3-(3-methoxy-3-methylbutoxy)-1-((1r,4r)-4-morpholinocyclohexyl)-1H-pyrazol-4-yl)amino)pyrimidin-5-yl)benzonitrile To a mixture of 5-(4-chloro-3-{[(2S)-1-(1H-tetrazol-1-yl)propan-2-yl]oxy}phenyl)-N-[3-(3-methoxy-3-methylbutoxy)-1-[(1r,4r)-4-(morpholin-4-yl)cyclohexyl]-1H-pyrazol-4-yl]pyrimidin-2-amine (140 mg) and potassium hexacyanoferrate(II) trihydrate (173 mg) in CPME (5.0 mL) and water (5.0 mL) was added potassium acetate (60.4 mg) at room temperature. After being stirred at room temperature for 10 min, XPhos Pd G2 (16.1 mg) and XPhos (19.5 mg) were added to the reaction mixture. The mixture was stirred at 100° C. under nitrogen atmosphere for 14 hr. The mixture was quenched with water at room temperature and extracted with ethyl acetate. The organic layer was separated, washed with saturated brine, dried over anhydrous magnesium sulfate and concentrated under reduced pressure. The residue was purified by silica gel column chromatography (MeOH/ethyl acetate) to give the title compound (51.0 mg).
$^1$H NMR (300 MHz, DMSO-d$_6$) δ 9.35 (s, 1H), 8.79 (s, 2H), 8.68 (s, 1H), 7.70-7.78 (m, 2H), 7.46 (s, 1H), 7.39 (d, J=8.44 Hz, 1H), 5.28-5.38 (m, 1H), 4.90-4.98 (m, 1H), 4.78-4.88 (m, 1H), 4.10-4.18 (m, 2H), 3.82-3.95 (m, 1H), 3.53-3.59 (m, 4H), 3.08 (s, 3H), 2.45-2.48 (m, 4H), 2.24-2.31 (m, 1H), 2.01-2.09 (m, 2H), 1.89-1.97 (m, 2H), 1.86 (t, J=7.24 Hz, 2H), 1.63-1.73 (m, 2H), 1.30-1.44 (m, 5H), 1.11 (s, 6H); MS m/z 672.4 [M+H]+.

The compounds of the Examples 497 to 513 in the following Table 4 were produced according to the methods described in the above-mentioned Examples, or methods analogous thereto. The MS of the compounds of Examples 497 to 513 are shown in the following Table 3. MS in the tables means actual measured value.

TABLE 3

| Ex. No. | MS |
|---|---|
| 497 | 679.4 |
| 498 | 665.4 |
| 499 | 679.3 |
| 500 | 667.3 |
| 501 | 378.2 |
| 502 | 675.3 |
| 503 | 662.3 |
| 504 | 678.2 |
| 505 | 675.3 |
| 506 | 690.3 |
| 507 | 675.3 |
| 508 | 690.3 |
| 509 | 673.3 |
| 510 | 686.3 |
| 511 | 727.3 |
| 512 | 656.4 |
| 513 | 675.3 |

The compounds of Examples 473 to 483 and 485 to 513 are shown in the following Table 4. The activity (IC$_{50}$) in the table is calculated in Experimental Example 1 and classified according to the following three activity ranks;

A: less than 10 nM,

B: 10 nM or more and less than 100 nM,

C: 100 nM or more.

TABLE 4

| Ex. No. | IUPAC NAME | STRUCTURE | ACTIVITY |
|---|---|---|---|
| 473 | 5-(3-(((S)-1-(1H-tetrazol-1-yl)propan-2-yl)oxy)-4-chlorophenyl)-N-(1-((1r,4r)-4-((2S,6R)-2,6-dimethylmorpholino)cyclohexyl)-3-((4-methyl-4H-1,2,4-triazol-3-yl)methoxy)-1H-pyrazol-4-yl)pyrimidin-2-amine | 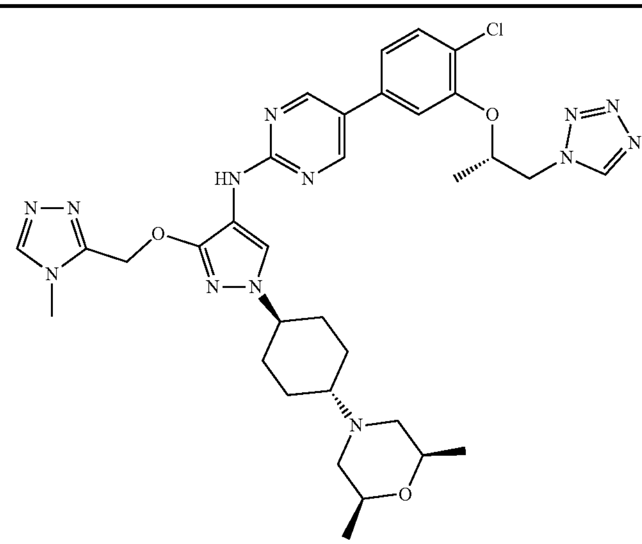 | A |

TABLE 4-continued

| Ex. No. | IUPAC NAME | STRUCTURE | ACTIVITY |
|---|---|---|---|
| 474 | 2-(3-((4-((5-(3-(((S)-1-(1H-tetrazol-1-yl)propan-2-yl)oxy)-4-chlorophenyl)pyrimidin-2-yl)amino)-1-((1r,4r)-4-((2S,6R)-2,6-dimethylmorpholino)cyclohexyl)-1H-pyrazol-3-yl)oxy)propoxy)ethan-1-ol | 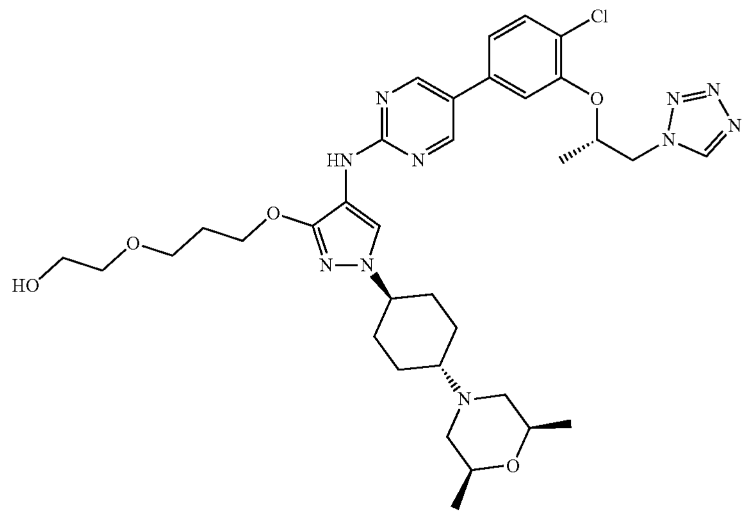 [SMILES: C[C@@H]1CN([C@H]2CC[C@H](n3cc(Nc4ncc(-c5ccc(Cl)c(O[C@@H](C)Cn6cnnn6)c5)cn4)c(OCCCOCCO)n3)CC2)C[C@H](C)O1] | A |
| 475 | 3-((4-((5-(3-(((S)-1-(1H-tetrazol-1-yl)propan-2-yl)oxy)-4-chlorophenyl)pyrimidin-2-yl)amino)-1-((1r,4r)-4-((2S,6R)-2,6-dimethylmorpholino)cyclohexyl)-1H-pyrazol-3-yl)oxy)propan-1-ol | 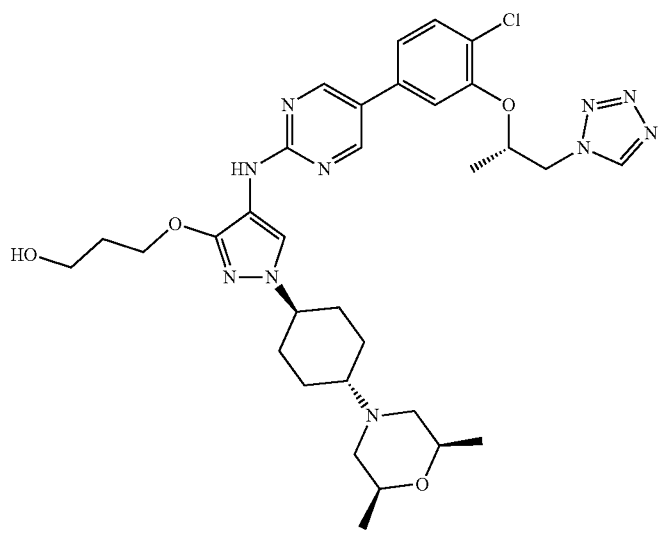 [SMILES: C[C@@H]1CN([C@H]2CC[C@H](n3cc(Nc4ncc(-c5ccc(Cl)c(O[C@@H](C)Cn6cnnn6)c5)cn4)c(OCCCO)n3)CC2)C[C@H](C)O1] | A |
| 476 | 2-(((S)-1-(1H-tetrazol-1-yl)propan-2-yl)oxy)-4-(2-((1-((1r,4r)-4-((2S,6R)-2,6-dimethylmorpholino)cyclohexyl)-3-((2-methylthiazol-5-yl)methoxy)-1H-pyrazol-4-yl)amino)pyrimidin-5-yl)benzonitrile | 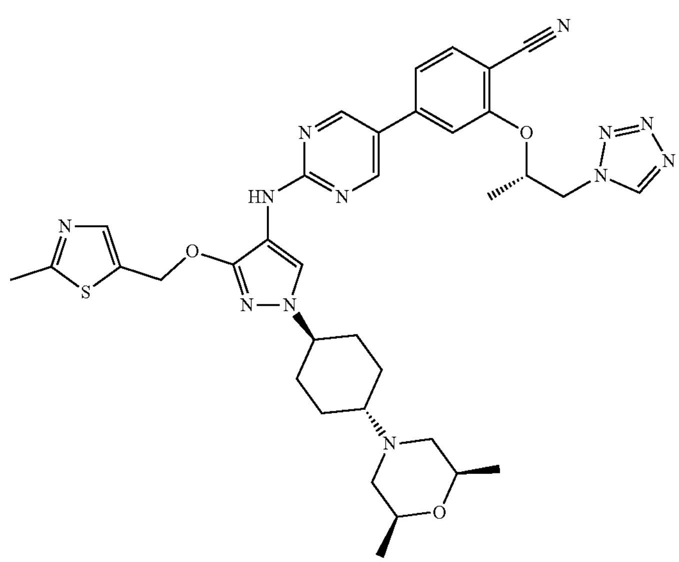 [SMILES: Cc1ncc(COc2nn([C@H]3CC[C@H](N4C[C@@H](C)O[C@@H](C)C4)CC3)cc2Nc2ncc(-c3ccc(C#N)c(O[C@@H](C)Cn4cnnn4)c3)cn2)s1] | A |

TABLE 4-continued

| Ex. No. | IUPAC NAME | STRUCTURE | ACTIVITY |
|---|---|---|---|
| 477 | 2-(((S)-1-(1H-tetrazol-1-yl)propan-2-yl)oxy)-4-(2-((1-(((1r,4r)-4-((2S,6R)-2,6-dimethylmorpholino)cyclohexyl)-3-(2-(oxetan-3-yl)ethoxy)-1H-pyrazol-4-yl)amino)pyrimidin-5-yl)benzonitrile | 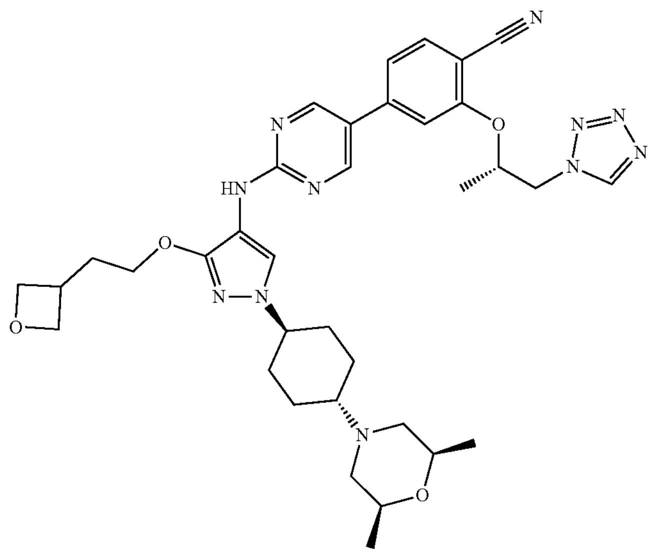 [SMILES: C[C@@H]1CN([C@H]2CC[C@H](n3cc(Nc4ncc(-c5ccc(C#N)c(O[C@@H](C)Cn6cnnn6)c5)cn4)c(OCCC4COC4)n3)CC2)C[C@H](C)O1] | A |
| 478 | 2-(((S)-1-(1H-tetrazol-1-yl)propan-2-yl)oxy)-4-(2-((1-(((1r,4r)-4-((2S,6R)-2,6-dimethylmorpholino)cyclohexyl)-3-(3-methoxy-3-methylbutoxy)-1H-pyrazol-4-yl)amino)pyrimidin-5-yl)benzonitrile | 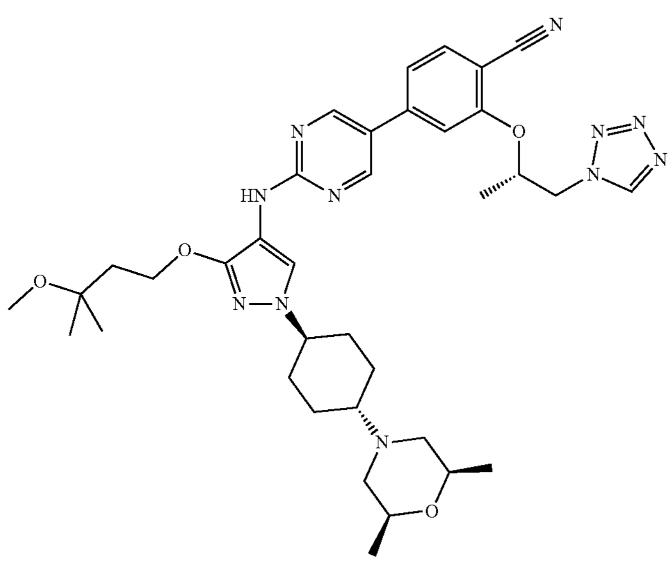 [SMILES: COC(C)(C)CCOc1nn([C@H]2CC[C@H](N3C[C@@H](C)O[C@@H](C)C3)CC2)cc1Nc1ncc(-c2ccc(C#N)c(O[C@@H](C)Cn3cnnn3)c2)cn1] | A |

| Ex. No. | IUPAC NAME | STRUCTURE | ACTIVITY |
|---|---|---|---|
| 479 | 2-(((S)-1-(1H-tetrazol-1-yl)propan-2-yl)oxy)-4-(2-((1-((1r,4r)-4-((2S,6R)-2,6-dimethylmorpholino)cyclohexyl)-3-(oxetan-3-ylmethoxy)-1H-pyrazol-4-yl)amino)pyrimidin-5-yl)benzonitrile | 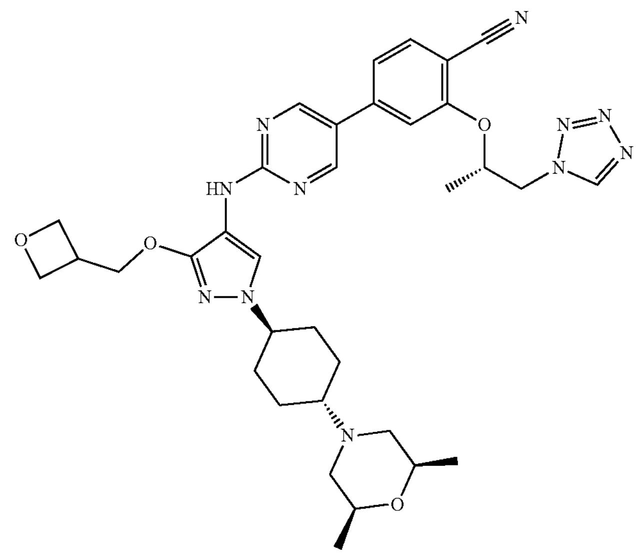 [SMILES: C[C@@H]1CN([C@H]2CC[C@H](n3cc(Nc4ncc(-c5ccc(C#N)c(O[C@@H](C)Cn6cnnn6)c5)cn4)c(OCC4COC4)n3)CC2)C[C@H](C)O1] | A |
| 480 | 5-(3-(((S)-1-(1H-tetrazol-1-yl)propan-2-yl)oxy)-4-chlorophenyl)-N-(1-((1r,4r)-4-((2S,6R)-2,6-dimethylmorpholino)cyclohexyl)-3-(oxetan-3-ylmethoxy)-1H-pyrazol-4-yl)pyrimidin-2-amine | 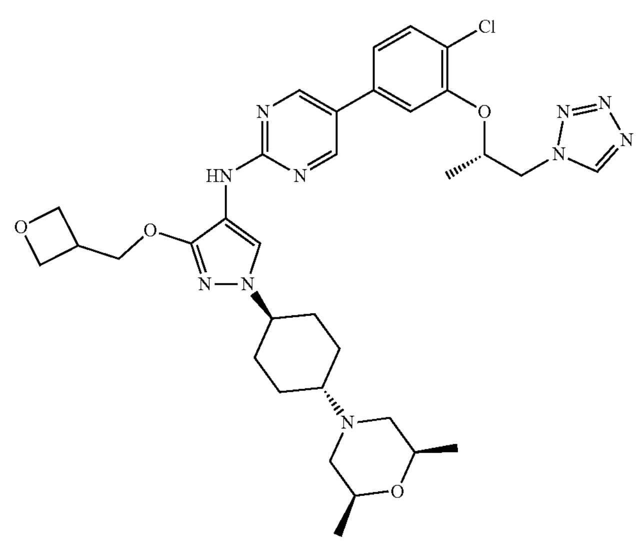 | A |

TABLE 4-continued

| Ex. No. | IUPAC NAME | STRUCTURE | ACTIVITY |
|---|---|---|---|
| 481 | 2-((4-((5-(3-(((S)-1-(1H-tetrazol-1-yl)propan-2-yl)oxy)-4-chlorophenyl)pyrimidin-2-yl)amino)-1-((1r,4r)-4-((2S,6R)-2,6-dimethylmorpholino)cyclohexyl)-1H-pyrazol-3-yl)oxy)ethan-1-ol | 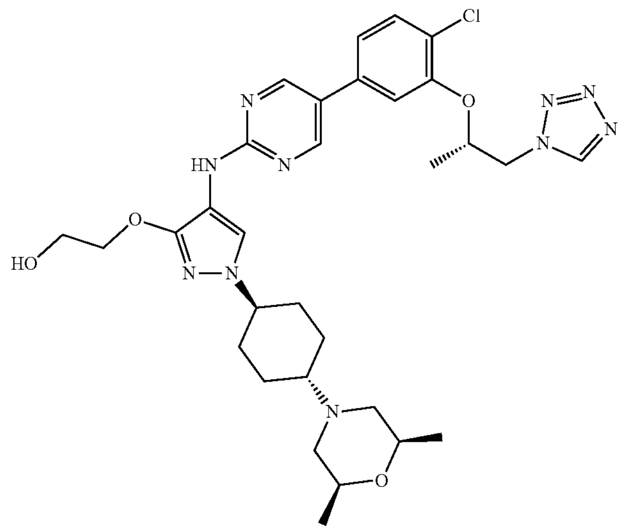 [SMILES: C[C@@H]1CN([C@H]2CC[C@H](n3cc(Nc4ncc(-c5ccc(Cl)c(O[C@@H](C)Cn6cnnn6)c5)cn4)c(OCCO)n3)CC2)C[C@H](C)O1] | A |
| 482 | (R)-1-((4-((5-(3-(((S)-1-(1H-tetrazol-1-yl)propan-2-yl)oxy)-4-chlorophenyl)pyrimidin-2-yl)amino)-1-((1r,4r)-4-((2S,6R)-2,6-dimethylmorpholino)cyclohexyl)-1H-pyrazol-3-yl)oxy)propan-2-ol | 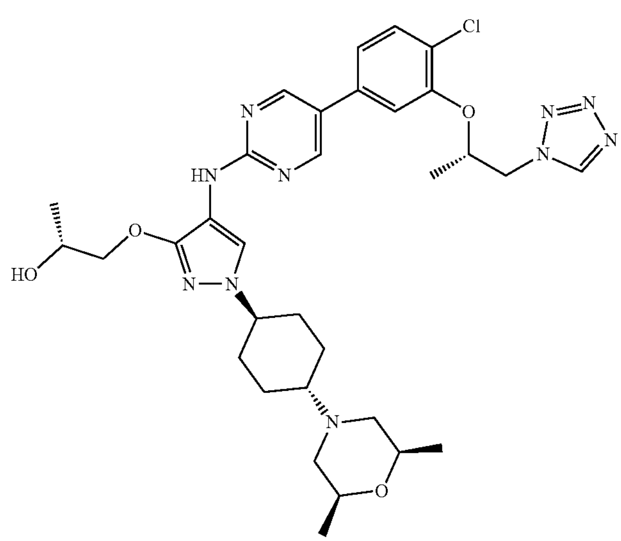 [SMILES: C[C@@H]1CN([C@H]2CC[C@H](n3cc(Nc4ncc(-c5ccc(Cl)c(O[C@@H](C)Cn6cnnn6)c5)cn4)c(OC[C@@H](C)O)n3)CC2)C[C@H](C)O1] | A |

TABLE 4-continued

| Ex. No. | IUPAC NAME | STRUCTURE | ACTIVITY |
|---|---|---|---|
| 483 | 2-(((S)-1-(1H-tetrazol-1-yl)propan-2-yl)oxy)-4-(2-((1-((1r,4r)-4-((2S,6R)-2,6-dimethylmorpholino)cyclohexyl)-3-((tetrahydro-2H-pyran-4-yl)methoxy)-1H-pyrazol-4-yl)amino)pyrimidin-5-yl)benzonitrile | 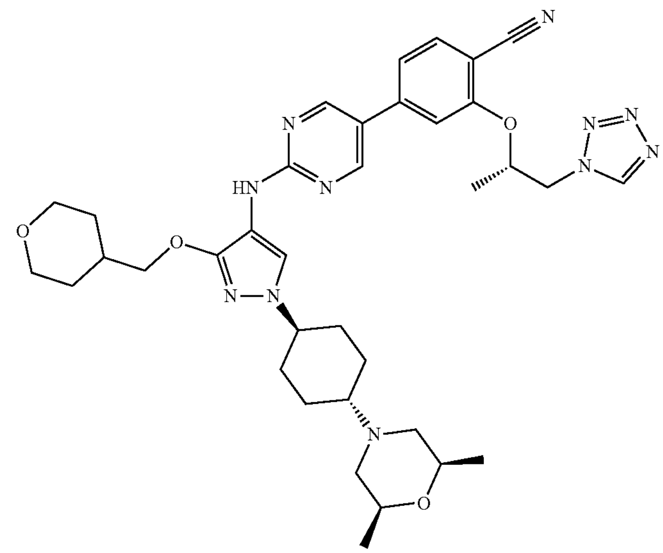 [SMILES: C[C@@H]1CN([C@H]2CC[C@H](n3cc(Nc4ncc(-c5ccc(C#N)c(O[C@@H](C)Cn6cnnn6)c5)cn4)c(OCC4CCOCC4)n3)CC2)C[C@H](C)O1] | A |
| 485 | 2-(((S)-1-(1H-tetrazol-1-yl)propan-2-yl)oxy)-4-(2-((1-((1r,4r)-4-((2S,6R)-2,6-dimethylmorpholino)cyclohexyl)-3-(3-hydroxy-3-methylbutoxy)-1H-pyrazol-4-yl)amino)pyrimidin-5-yl)benzonitrile | 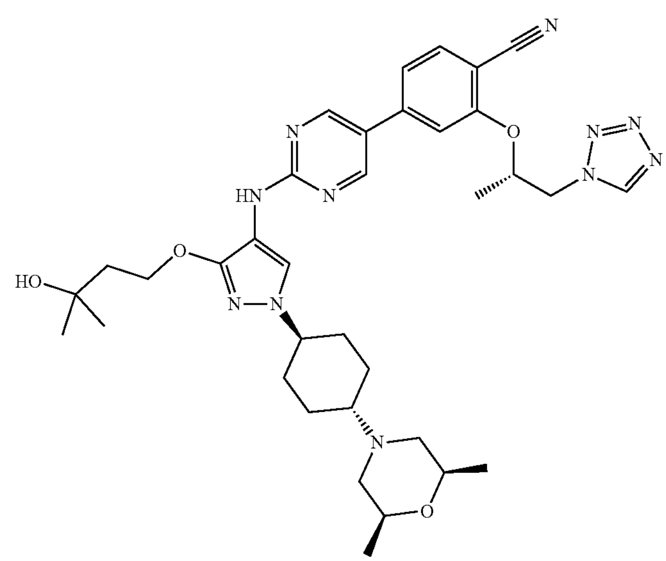 [SMILES: C[C@@H]1CN([C@H]2CC[C@H](n3cc(Nc4ncc(-c5ccc(C#N)c(O[C@@H](C)Cn6cnnn6)c5)cn4)c(OCCC(C)(C)O)n3)CC2)C[C@H](C)O1] | A |

TABLE 4-continued

| Ex. No. | IUPAC NAME | STRUCTURE | ACTIVITY |
|---|---|---|---|
| 486 | 4-((4-((5-(3-(((S)-1-(1H-tetrazol-1-yl)propan-2-yl)oxy)-4-chlorophenyl)pyrimidin-2-yl)amino)-1-((1r,4r)-4-((2S,6R)-2,6-dimethylmorpholino)cyclohexyl)-1H-pyrazol-3-yl)oxy)-2-methylbutan-2-ol | 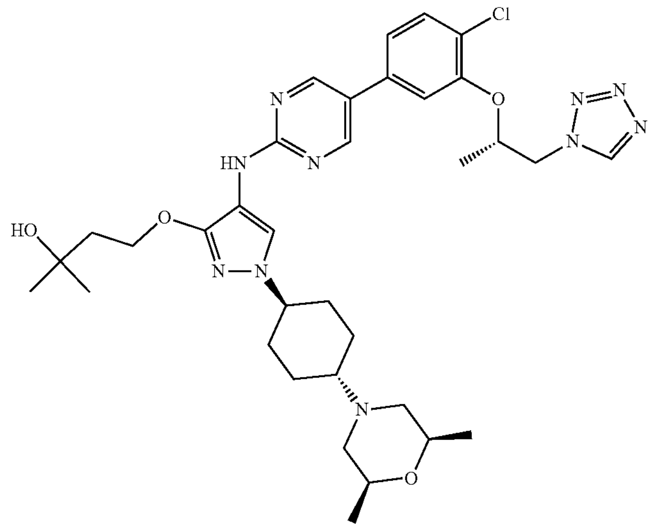 [SMILES: C[C@@H]1CN([C@H]2CC[C@H](n3cc(Nc4ncc(-c5ccc(Cl)c(O[C@@H](C)Cn6cnnn6)c5)cn4)c(OCCC(C)(C)O)n3)CC2)C[C@H](C)O1] | A |
| 487 | 5-(3-(((S)-1-(1H-tetrazol-1-yl)propan-2-yl)oxy)-4-chlorophenyl)-N-(1-((1r,4r)-4-((2S,6R)-2,6-dimethylmorpholino)cyclohexyl)-3-(3-(2-methoxyethoxy)propoxy)-1H-pyrazol-4-yl)pyrimidin-2-amine | 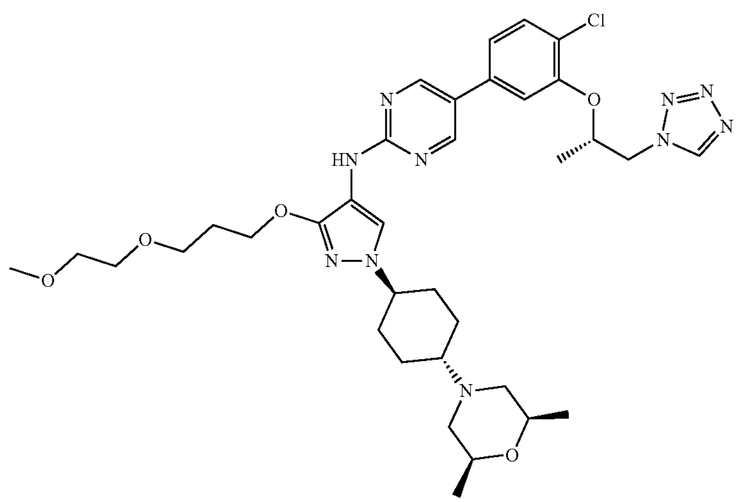 [SMILES: COCCOCCCOc1nn([C@H]2CC[C@H](N3C[C@@H](C)O[C@@H](C)C3)CC2)cc1Nc1ncc(-c2ccc(Cl)c(O[C@@H](C)Cn3cnnn3)c2)cn1] | A |
| 488 | 2-(((S)-1-(1H-tetrazol-1-yl)propan-2-yl)oxy)-4-(2-((1-((1r,4r)-4-((2S,6R)-2,6-dimethylmorpholino)cyclohexyl)-3-(3-(2-methoxyethoxy)propoxy)-1H-pyrazol-4-yl)amino)pyrimidin-5-yl)benzonitrile | 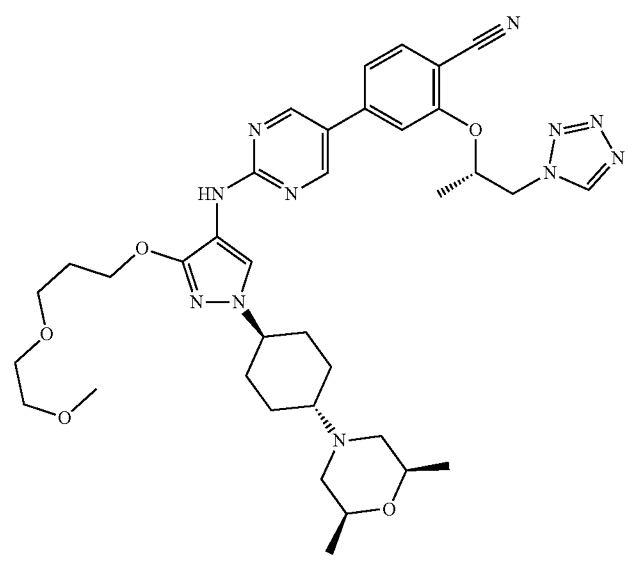 [SMILES: COCCOCCCOc1nn([C@H]2CC[C@H](N3C[C@@H](C)O[C@@H](C)C3)CC2)cc1Nc1ncc(-c2ccc(C#N)c(O[C@@H](C)Cn3cnnn3)c2)cn1] | A |

TABLE 4-continued

| Ex. No. | IUPAC NAME | STRUCTURE | ACTIVITY |
|---|---|---|---|
| 489 | 5-(3-(((S)-1-(1H-tetrazol-1-yl)propan-2-yl)oxy)-4-chlorophenyl)-N-(1-((1r,4r)-4-((2S,6R)-2,6-dimethylmorpholino)cyclohexyl)-3-(3-methoxypropoxy)-1H-pyrazol-4-yl)pyrimidin-2-amine | 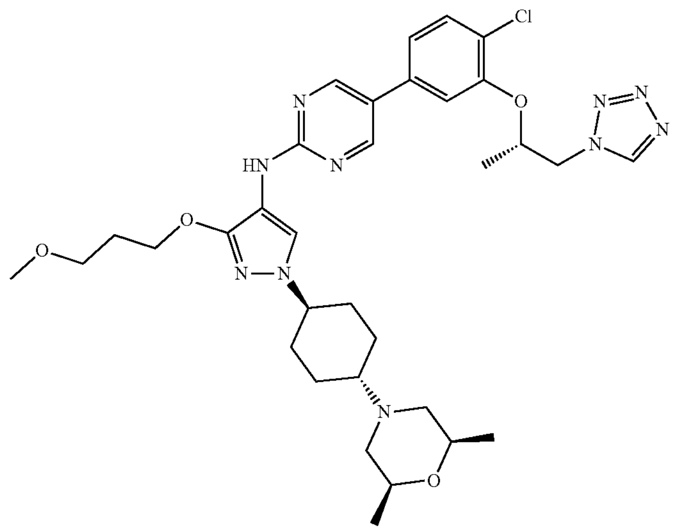 [SMILES: COCCCOc1nn([C@H]2CC[C@H](N3C[C@@H](C)O[C@@H](C)C3)CC2)cc1Nc1ncc(-c2ccc(Cl)c(O[C@@H](C)Cn3cnnn3)c2)cn1] | A |
| 490 | 2-(((S)-1-(1H-tetrazol-1-yl)propan-2-yl)oxy)-4-(2-((3-(3-(2-methoxyethoxy)propoxy)-1-((1r,4r)-4-morpholinocyclohexyl)-1H-pyrazol-4-yl)amino)pyrimidin-5-yl)benzonitrile | 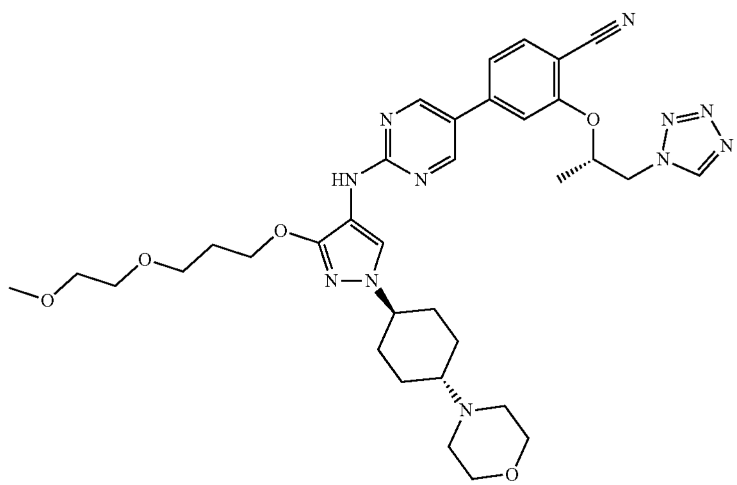 [SMILES: COCCOCCCOc1nn([C@H]2CC[C@H](N3CCOCC3)CC2)cc1Nc1ncc(-c2ccc(C#N)c(O[C@@H](C)Cn3cnnn3)c2)cn1] | A |
| 491 | 5-(3-(((S)-1-(1H-tetrazol-1-yl)propan-2-yl)oxy)-4-chlorophenyl)-N-(1-((1r,4r)-4-morpholinocyclohexyl)-3-(oxetan-3-ylmethoxy)-1H-pyrazol-4-yl)pyrimidin-2-amine | 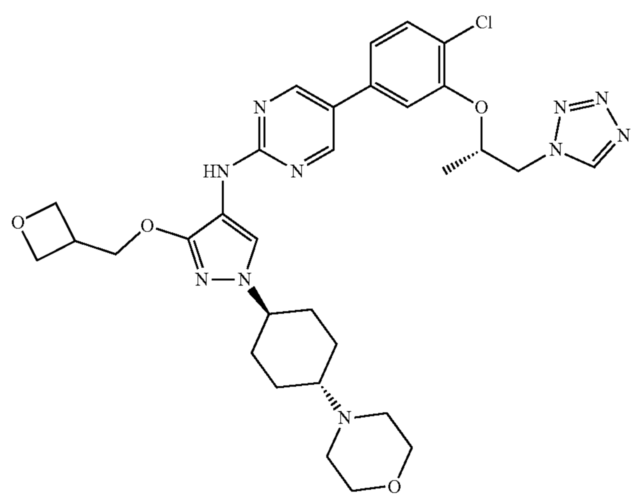 [SMILES: C[C@@H](Cn1cnnn1)Oc1cc(-c2cnc(Nc3cn([C@H]4CC[C@H](N5CCOCC5)CC4)nc3OCC3COC3)nc2)ccc1Cl] | A |

TABLE 4-continued

| Ex. No. | IUPAC NAME | STRUCTURE | ACTIVITY |
|---|---|---|---|
| 492 | 2-(((S)-1-(1H-tetrazol-1-yl)propan-2-yl)oxy)-4-(2-((1-((1r,4r)-4-morpholinocyclohexyl)-3-(oxetan-3-ylmethoxy)-1H-pyrazol-4-yl)amino)pyrimidin-5-yl)benzonitrile | 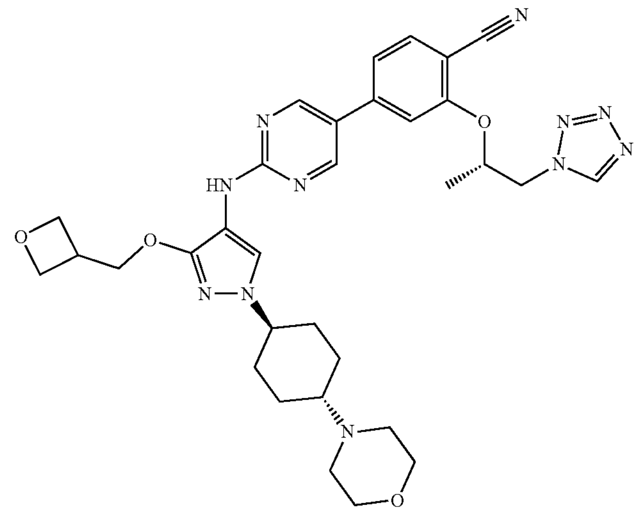 [SMILES: C[C@@H](Cn1cnnn1)Oc1cc(-c2cnc(Nc3cn([C@H]4CC[C@H](N5CCOCC5)CC4)nc3OCC3COC3)nc2)ccc1C#N] | A |
| 493 | 4-((4-((5-(3-(((S)-1-(1H-tetrazol-1-yl)propan-2-yl)oxy)-4-chlorophenyl)pyrimidin-2-yl)amino)-1-((1r,4r)-4-morpholinocyclohexyl)-1H-pyrazol-3-yl)oxy)butanenitrile | 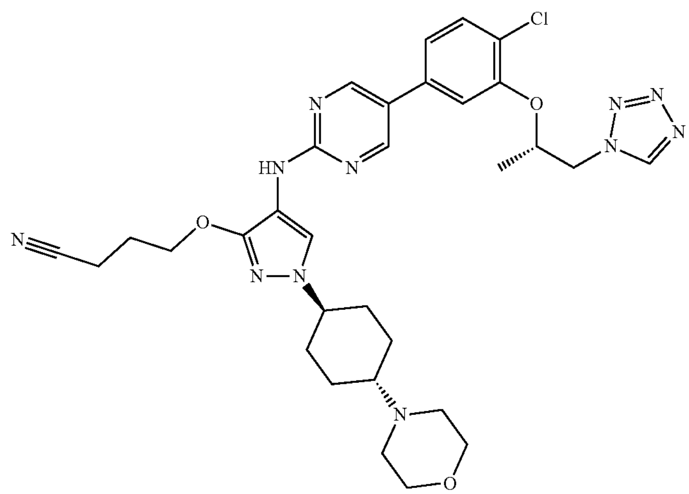 [SMILES: C[C@@H](Cn1cnnn1)Oc1cc(-c2cnc(Nc3cn([C@H]4CC[C@H](N5CCOCC5)CC4)nc3OCCCC#N)nc2)ccc1Cl] | A |
| 494 | 2-(((S)-1-(1H-tetrazol-1-yl)propan-2-yl)oxy)-4-(2-((3-(3-cyanopropoxy)-1-((1r,4r)-4-morpholinocyclohexyl)-1H-pyrazol-4-yl)amino)pyrimidin-5-yl)benzonitrile | 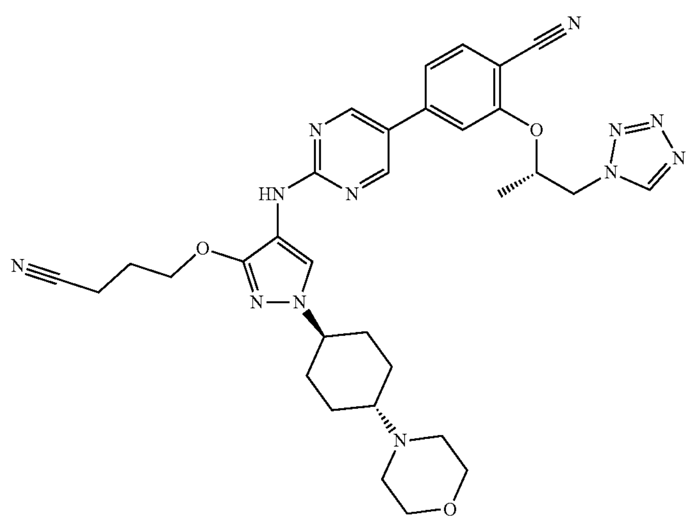 [SMILES: C[C@@H](Cn1cnnn1)Oc1cc(-c2cnc(Nc3cn([C@H]4CC[C@H](N5CCOCC5)CC4)nc3OCCCC#N)nc2)ccc1C#N] | A |

TABLE 4-continued

| Ex. No. | IUPAC NAME | STRUCTURE | ACTIVITY |
|---|---|---|---|
| 495 | 2-(((S)-1-(1H-tetrazol-1-yl)propan-2-yl)oxy)-4-(2-((3-(3-hydroxy-3-methylbutoxy)-1-((1r,4r)-4-morpholinocyclohexyl)-1H-pyrazol-4-yl)amino)pyrimidin-5-yl)benzonitrile | 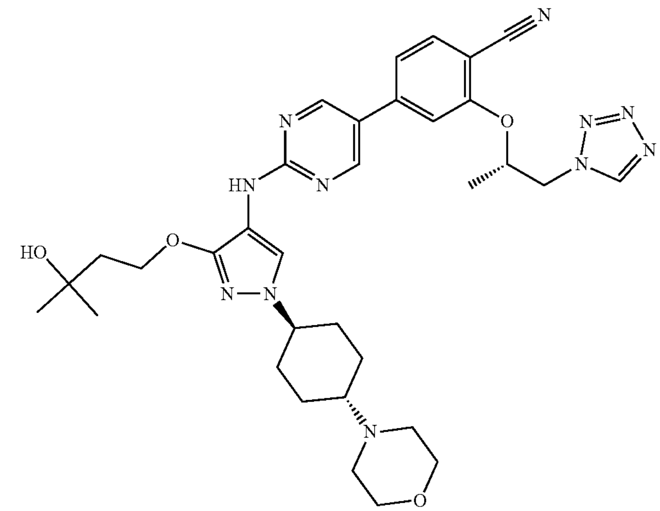 [SMILES: C[C@@H](Cn1cnnn1)Oc1cc(-c2cnc(Nc3cn([C@H]4CC[C@H](N5CCOCC5)CC4)nc3OCCC(C)(C)O)nc2)ccc1C#N] | A |
| 496 | 2-(((S)-1-(1H-tetrazol-1-yl)propan-2-yl)oxy)-4-(2-((3-(3-methoxy-3-methylbutoxy)-1-((1r,4r)-4-morpholinocyclohexyl)-1H-pyrazol-4-yl)amino)pyrimidin-5-yl)benzonitrile | 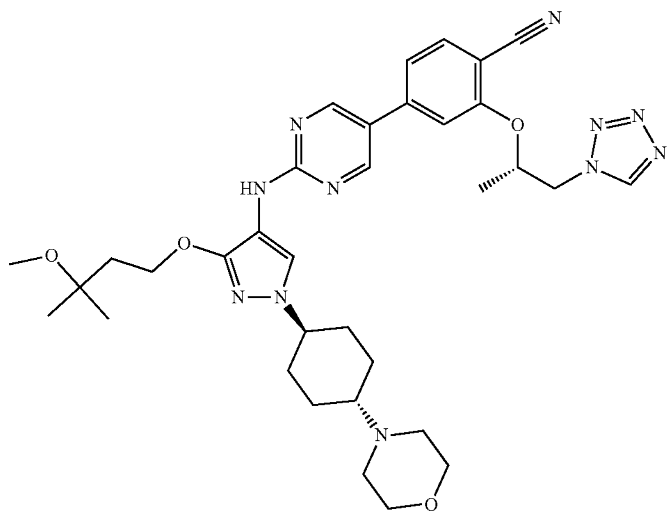 [SMILES: COC(C)(C)CCOc1nn([C@H]2CC[C@H](N3CCOCC3)CC2)cc1Nc1ncc(-c2ccc(C#N)c(O[C@@H](C)Cn3cnnn3)c2)cn1] | A |
| 497 | 5-(3-(((S)-1-(1H-tetrazol-1-yl)propan-2-yl)oxy)-4-chlorophenyl)-N-(1-((1r,4r)-4-morpholinocyclohexyl)-3-((tetrahydro-2H-pyran-4-yl)methoxy)-1H-pyrazol-4-yl)pyrimidin-2-amine | 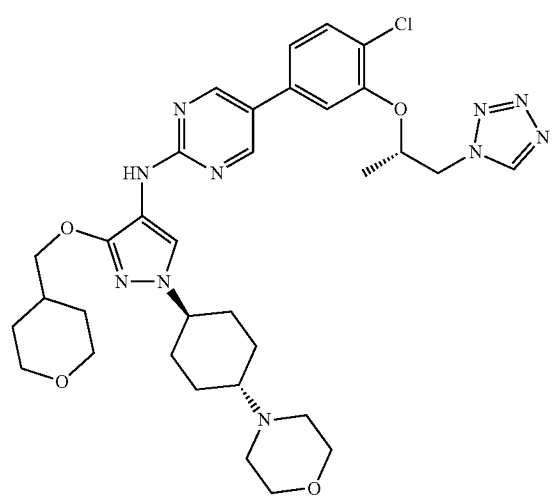 [SMILES: C[C@@H](Cn1cnnn1)Oc1cc(-c2cnc(Nc3cn([C@H]4CC[C@H](N5CCOCC5)CC4)nc3OCC3CCOCC3)nc2)ccc1Cl] | A |

TABLE 4-continued

| Ex. No. | IUPAC NAME | STRUCTURE | ACTIVITY |
|---|---|---|---|
| 498 | 5-(3-(((S)-1-(1H-tetrazol-1-yl)propan-2-yl)oxy)-4-chlorophenyl)-N-(1-((1r,4r)-4-morpholinocyclohexyl)-3-((tetrahydrofuran-3-yl)methoxy)-1H-pyrazol-4-yl)pyrimidin-2-amine | 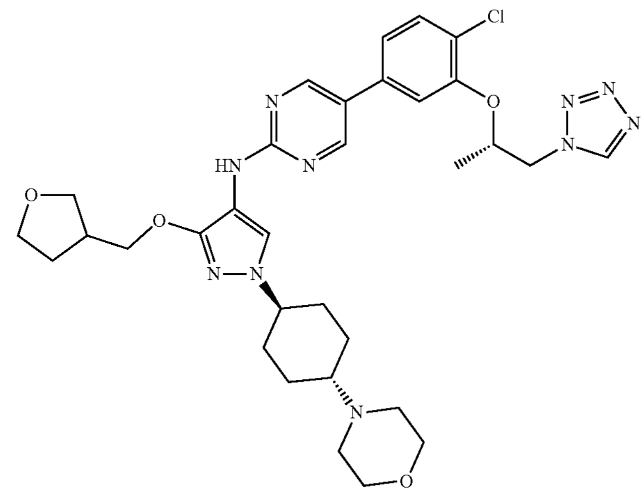 [SMILES: C[C@@H](Cn1cnnn1)Oc1cc(-c2cnc(Nc3cn([C@H]4CC[C@H](N5CCOCC5)CC4)nc3OCC3CCOC3)nc2)ccc1Cl] | A |
| 499 | 5-(3-(((S)-1-(1H-tetrazol-1-yl)propan-2-yl)oxy)-4-chlorophenyl)-N-(1-((1r,4r)-4-morpholinocyclohexyl)-3-((tetrahydro-2H-pyran-3-yl)methoxy)-1H-pyrazol-4-yl)pyrimidin-2-amine | 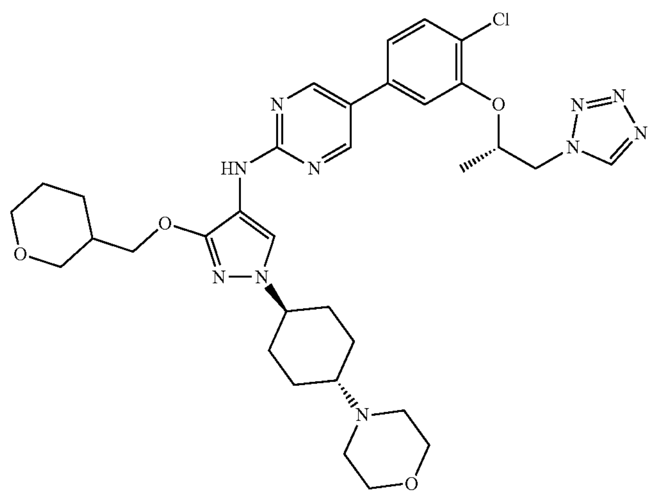 [SMILES: C[C@@H](Cn1cnnn1)Oc1cc(-c2cnc(Nc3cn([C@H]4CC[C@H](N5CCOCC5)CC4)nc3OCC3CCCOC3)nc2)ccc1Cl] | A |
| 500 | 4-((4-((5-(3-(((S)-1-(1H-tetrazol-1-yl)propan-2-yl)oxy)-4-chlorophenyl)pyrimidin-2-yl)amino)-1-((1r,4r)-4-morpholinocyclohexyl)-1H-pyrazol-3-yl)oxy)-2-methylbutan-2-ol | 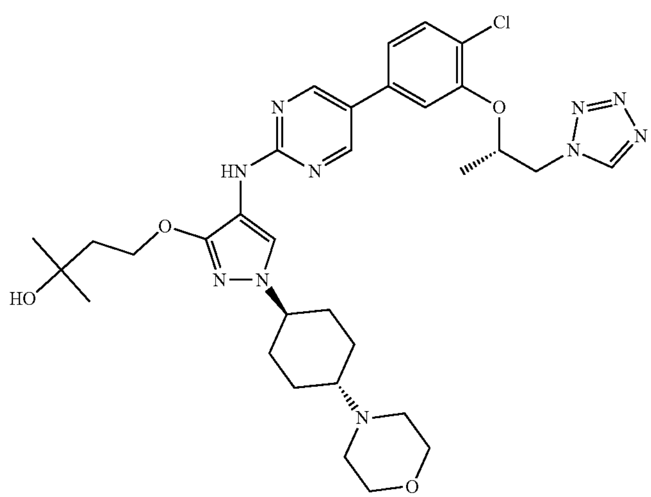 [SMILES: C[C@@H](Cn1cnnn1)Oc1cc(-c2cnc(Nc3cn([C@H]4CC[C@H](N5CCOCC5)CC4)nc3OCCC(C)(C)O)nc2)ccc1Cl] | A |

TABLE 4-continued

| Ex. No. | IUPAC NAME | STRUCTURE | ACTIVITY |
|---|---|---|---|
| 501 | 5-(3-(((S)-1-(1H-tetrazol-1-yl)propan-2-yl)oxy)-4-chlorophenyl)-N-(1-((1r,4r)-4-morpholinocyclohexyl)-3-(thiazol-5-ylmethoxy)-1H-pyrazol-4-yl)pyrimidin-2-amine | 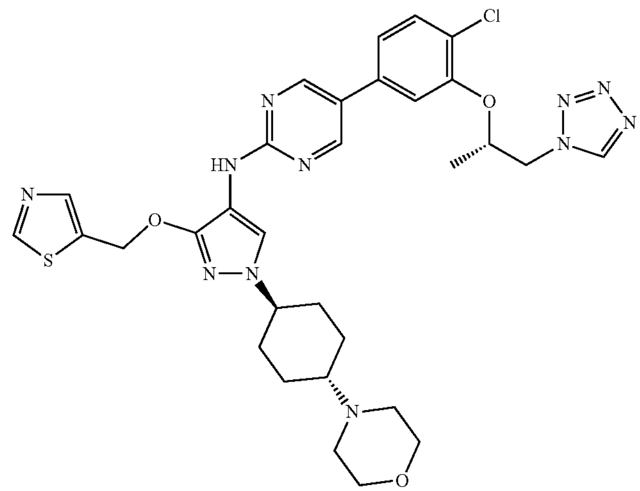 [SMILES: C[C@@H](Cn1cnnn1)Oc1cc(-c2cnc(Nc3cn([C@H]4CC[C@H](N5CCOCC5)CC4)nc3OCc3cncs3)nc2)ccc1Cl] | A |
| 502 | 5-(3-(((S)-1-(1H-tetrazol-1-yl)propan-2-yl)oxy)-4-chlorophenyl)-N-(3-((1-methyl-1H-pyrazol-5-yl)methoxy)-1-((1r,4r)-4-morpholinocyclohexyl)-1H-pyrazol-4-yl)pyrimidin-2-amine | 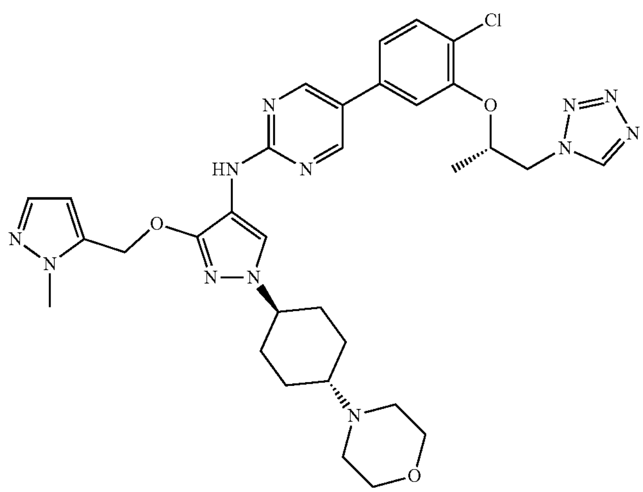 [SMILES: C[C@@H](Cn1cnnn1)Oc1cc(-c2cnc(Nc3cn([C@H]4CC[C@H](N5CCOCC5)CC4)nc3OCc3ccnn3C)nc2)ccc1Cl] | A |
| 503 | 5-(3-(((S)-1-(1H-tetrazol-1-yl)propan-2-yl)oxy)-4-chlorophenyl)-N-(1-((1r,4r)-4-morpholinocyclohexyl)-3-(oxazol-2-ylmethoxy)-1H-pyrazol-4-yl)pyrimidin-2-amine | 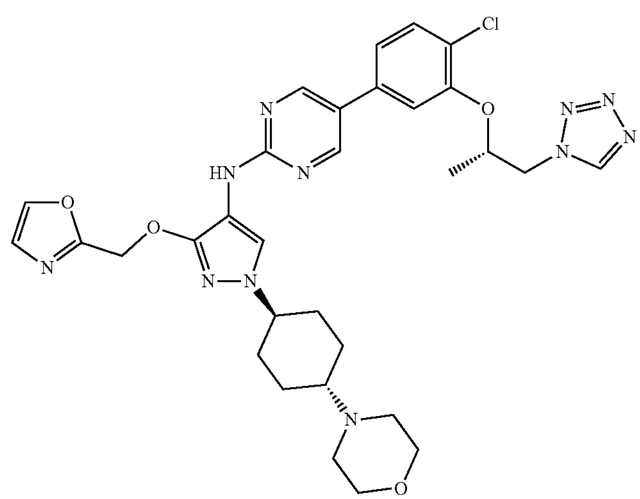 [SMILES: C[C@@H](Cn1cnnn1)Oc1cc(-c2cnc(Nc3cn([C@H]4CC[C@H](N5CCOCC5)CC4)nc3OCc3ncco3)nc2)ccc1Cl] | A |

TABLE 4-continued

| Ex. No. | IUPAC NAME | STRUCTURE | ACTIVITY |
|---|---|---|---|
| 504 | 5-(3-(((S)-1-(1H-tetrazol-1-yl)propan-2-yl)oxy)-4-chlorophenyl)-N-(1-((1r,4r)-4-morpholinocyclohexyl)-3-(thiazol-2-ylmethoxy)-1H-pyrazol-4-yl)pyrimidin-2-amine | 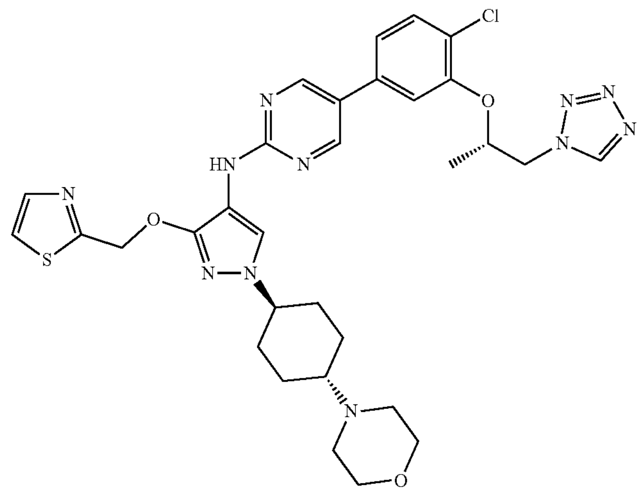 [SMILES: C[C@@H](Cn1cnnn1)Oc1cc(-c2cnc(Nc3cn([C@H]4CC[C@H](N5CCOCC5)CC4)nc3OCc3nccs3)nc2)ccc1Cl] | A |
| 505 | 5-(3-(((S)-1-(1H-tetrazol-1-yl)propan-2-yl)oxy)-4-chlorophenyl)-N-(3-((1-methyl-1H-pyrazol-5-yl)methoxy)-1-((1r,4r)-4-morpholinocyclohexyl)-1H-pyrazol-4-yl)pyrimidin-2-amine | 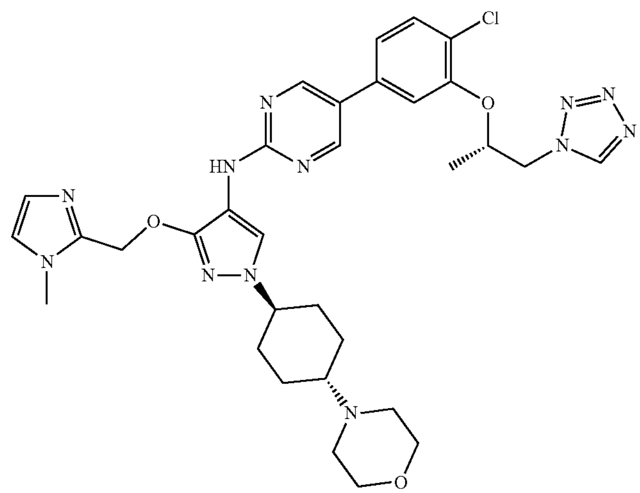 [SMILES: C[C@@H](Cn1cnnn1)Oc1cc(-c2cnc(Nc3cn([C@H]4CC[C@H](N5CCOCC5)CC4)nc3OCc3nccn3C)nc2)ccc1Cl] | A |
| 506 | 5-(3-(((S)-1-(1H-tetrazol-1-yl)propan-2-yl)oxy)-4-chlorophenyl)-N-(3-((3,5-dimethylisoxazol-4-yl)methoxy)-1-((1r,4r)-4-morpholinocyclohexyl)-1H-pyrazol-4-yl)pyrimidin-2-amine | 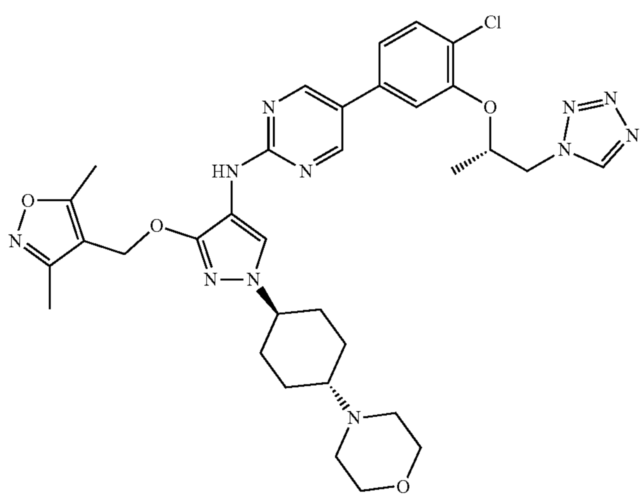 [SMILES: Cc1noc(C)c1COc1nn([C@H]2CC[C@H](N3CCOCC3)CC2)cc1Nc1ncc(-c2ccc(Cl)c(O[C@@H](C)Cn3cnnn3)c2)cn1] | A |

TABLE 4-continued

| Ex. No. | IUPAC NAME | STRUCTURE | ACTIVITY |
|---|---|---|---|
| 507 | N-(3-(2-(1H-imidazol-1-yl)ethoxy)-1-((1r,4r)-4-morpholinocyclohexyl)-1H-pyrazol-4-yl)-5-(3-(((S)-1-(1H-tetrazol-1-yl)propan-2-yl)oxy)-4-chlorophenyl)pyrimidin-2-amine | 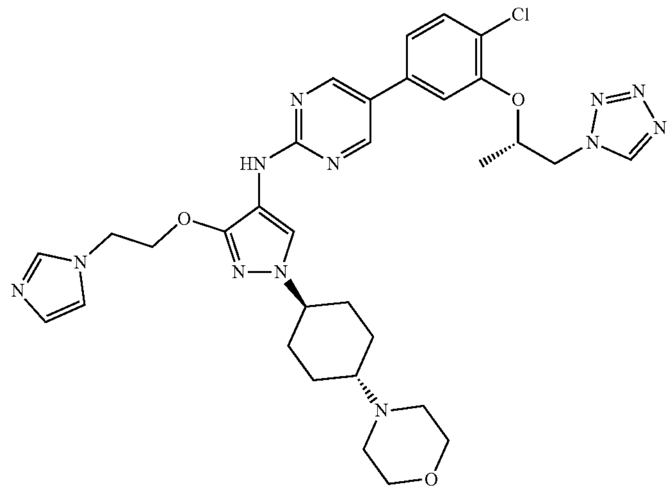 [SMILES: C[C@@H](Cn1cnnn1)Oc1cc(-c2cnc(Nc3cn([C@H]4CC[C@H](N5CCOCC5)CC4)nc3OCCn3ccnc3)nc2)ccc1Cl] | A |
| 508 | N-(3-(3-(1H-1,2,4-triazol-1-yl)propoxy)-1-((1r,4r)-4-morpholinocyclohexyl)-1H-pyrazol-4-yl)-5-(3-(((S)-1-(1H-tetrazol-1-yl)propan-2-yl)oxy)-4-chlorophenyl)pyrimidin-2-amine | 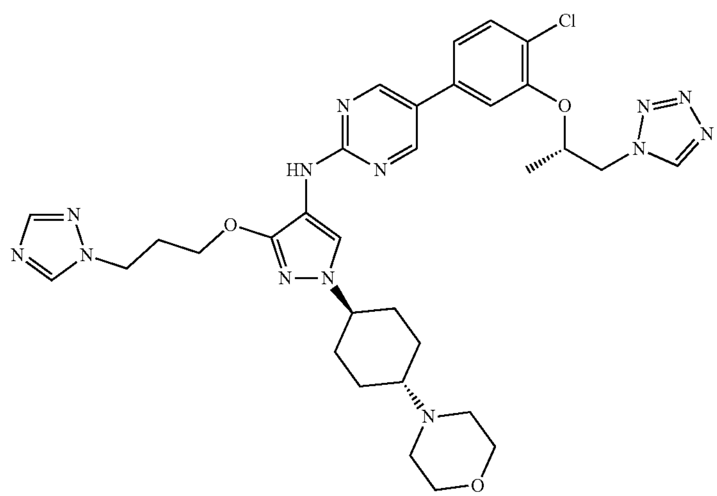 [SMILES: C[C@@H](Cn1cnnn1)Oc1cc(-c2cnc(Nc3cn([C@H]4CC[C@H](N5CCOCC5)CC4)nc3OCCCn3cncn3)nc2)ccc1Cl] | A |
| 509 | 5-(3-(((S)-1-(1H-tetrazol-1-yl)propan-2-yl)oxy)-4-chlorophenyl)-N-(1-((1r,4r)-4-morpholinocyclohexyl)-3-(pyrimidin-2-ylmethoxy)-1H-pyrazol-4-yl)pyrimidin-2-amine | 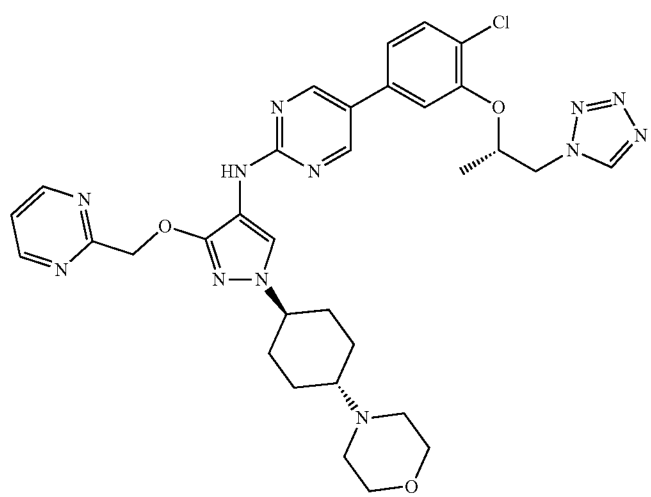 [SMILES: C[C@@H](Cn1cnnn1)Oc1cc(-c2cnc(Nc3cn([C@H]4CC[C@H](N5CCOCC5)CC4)nc3OCc3ncccn3)nc2)ccc1Cl] | B |

TABLE 4-continued

| Ex. No. | IUPAC NAME | STRUCTURE | ACTIVITY |
|---|---|---|---|
| 510 | 5-(3-(((S)-1-(1H-tetrazol-1-yl)propan-2-yl)oxy)-4-chlorophenyl)-N-(1-((1r,4r)-4-morpholinocyclohexyl)-3-(2-(pyridin-3-yl)ethoxy)-1H-pyrazol-4-yl)pyrimidin-2-amine | 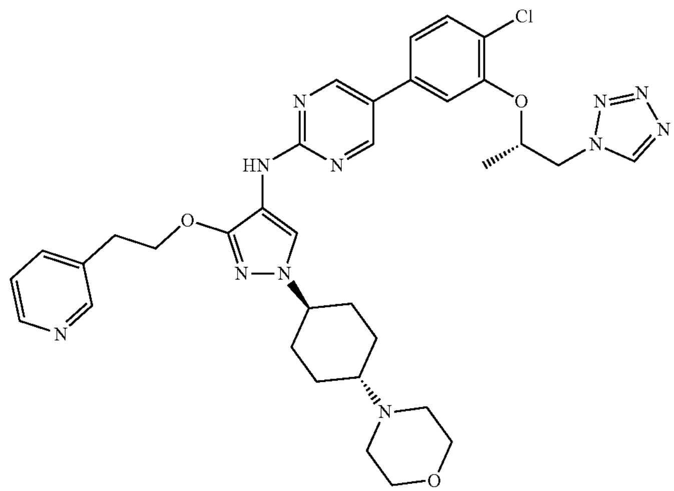 [SMILES: C[C@@H](Cn1cnnn1)Oc1cc(-c2cnc(Nc3cn([C@H]4CC[C@H](N5CCOCC5)CC4)nc3OCCc3cccnc3)nc2)ccc1Cl] | A |
| 511 | 5-(3-(((S)-1-(1H-tetrazol-1-yl)propan-2-yl)oxy)-4-chlorophenyl)-N-(3-(2-(2-(2-methoxyethoxy)ethoxy)ethoxy)-1-((1r,4r)-4-morpholinocyclohexyl)-1H-pyrazol-4-yl)pyrimidin-2-amine | 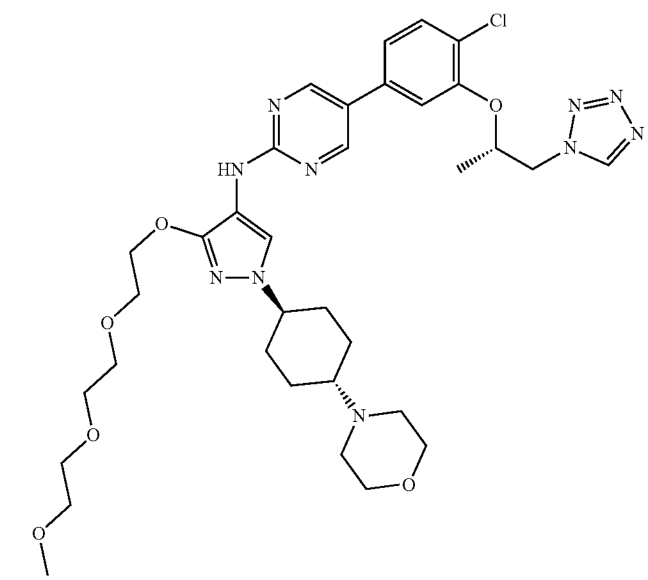 [SMILES: COCCOCCOCCOc1nn([C@H]2CC[C@H](N3CCOCC3)CC2)cc1Nc1ncc(-c2ccc(Cl)c(O[C@@H](C)Cn3cnnn3)c2)cn1] | B |
| 512 | 5-(3-(((S)-1-(1H-tetrazol-1-yl)propan-2-yl)oxy)-4-chlorophenyl)-N-(3-(3-(methoxy-d3)propoxy)-1-((1r,4r)-4-morpholinocyclohexyl)-1H-pyrazol-4-yl)pyrimidin-2-amine | 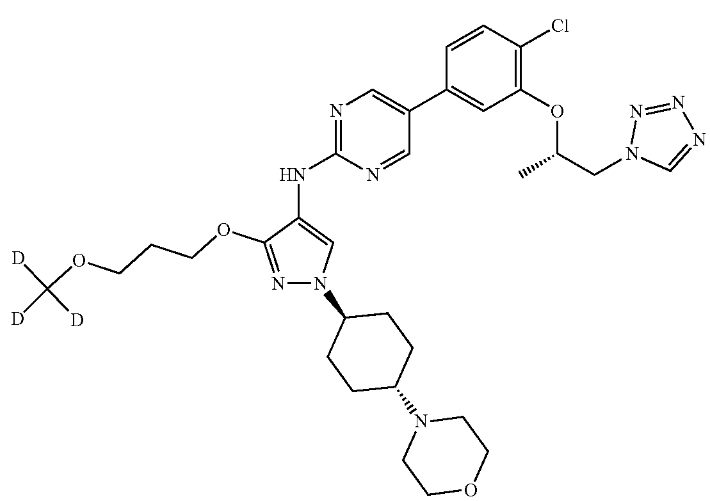 [SMILES: [2H]C([2H])([2H])OCCCOc1nn([C@H]2CC[C@H](N3CCOCC3)CC2)cc1Nc1ncc(-c2ccc(Cl)c(O[C@@H](C)Cn3cnnn3)c2)cn1] | A |

| Ex. No. | IUPAC NAME | STRUCTURE | ACTIVITY |
|---|---|---|---|
| 513 | N-(3-(2-(1H-pyrazol-1-yl)ethoxy)-1-((1r,4r)-4-morpholinocyclohexyl)-1H-pyrazol-4-yl)-5-(3-(((S)-1-(1H-tetrazol-1-yl)propan-2-yl)oxy)-4-chlorophenyl)pyrimidin-2-amine | 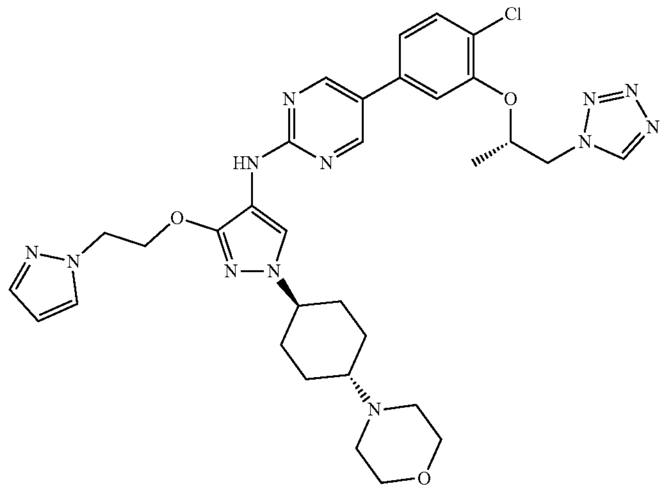 [SMILES: C[C@@H](Cn1cnnn1)Oc1cc(-c2cnc(Nc3cn([C@H]4CC[C@H](N5CCOCC5)CC4)nc3OCCn3cccn3)nc2)ccc1Cl] | A |

Example 514

2-(((S)-1-(1H-tetrazol-1-yl)propan-2-yl)oxy)-4-(2-((3-(3-methoxypropoxy)-1-((1r,4r)-4-morpholinocyclohexyl)-1H-pyrazol-4-yl)amino)pyrimidin-5-yl)benzonitrile hydrochloride 4 M Hydrogen chloride-ethyl acetate (174 uL) was added to a suspension of 2-(((S)-1-(1H-tetrazol-1-yl)propan-2-yl)oxy)-4-(2-((3-(3-methoxypropoxy)-1-((r,4r)-4-morpholinocyclohexyl)-1H-pyrazol-4-yl)amino)pyrimidin-5-yl)benzonitrile (300 mg) in EtOH (5.0 mL) at room temperature. The mixture was stirred at 60° C. for a while. The mixture was stirred at room temperature over night. The precipitate was collected by filtration and washed with cold EtOH to give the title compound (230 mg) as light yellow crystals.

$^1$H NMR (300 MHz, DMSO-$d_6$) δ 9.35 (s, 1H), 8.82 (brs, 1H), 8.79 (s, 2H), 7.77 (s, 1H), 7.74 (s, 1H), 7.46 (s, 1H), 7.37-7.42 (m, 1H), 5.34 (dt, J=3.94, 6.37 Hz, 1H), 4.89-4.99 (m, 1H), 4.81-4.89 (m, 1H), 4.13 (t, J=6.37 Hz, 2H), 3.95-4.06 (m, 2H), 3.71-3.81 (m, 1H), 3.56 (brs, 1H), 3.42 (t, J=6.33 Hz, 3H), 3.21 (s, 3H), 3.02-3.19 (m, 2H), 2.07-2.29 (m, 4H), 1.89 (quin, J=6.28 Hz, 2H), 1.54-1.84 (m, 4H), 1.36 (d, J=6.14 Hz, 3H) 4H were hidden by DMSO; MS m/z 644.5 [M+H]$^+$.

Example 515

2-(((S)-1-(1H-tetrazol-1-yl)propan-2-yl)oxy)-4-(2-((1-((1r,4r)-4-((2S,6R)-2,6-dimethylmorpholino)cyclohexyl)-3-(3-methoxypropoxy)-1H-pyrazol-4-yl)amino)pyrimidin-5-yl)benzonitrile hydrochloride To a solution of 2-(((S)-1-(1H-tetrazol-1-yl)propan-2-yl)oxy)-4-(2-((1-((1r,4r)-4-((2S,6R)-2,6-dimethylmorpholino)cyclohexyl)-3-(3-methoxypropoxy)-1H-pyrazol-4-yl)amino)pyrimidin-5-yl)benzonitrile (13.7 g) in EtOH (150 mL) was added dropwise 4 M hydrogen chloride-ethyl acetate (7.6 mL) at 60° C., and the mixture was stirred at room temperature for 16 hr. The precipitate was collected by filtration and washed with EtOH (50 mL) and dried under reduced pressure to give the title compound (13.9 g) as yellow crystals.

$^1$H NMR (300 MHz, DMSO-$d_6$) δ 10.55-10.73 (m, 1H), 9.35 (s, 1H), 8.79 (s, 3H), 7.68-7.82 (m, 2H), 7.45 (s, 1H), 7.39 (dd, J=8.1, 1.3 Hz, 1H), 5.34 (td, J=6.4, 3.8 Hz, 1H), 4.78-5.00 (m, 2H), 4.13 (t, J=6.4 Hz, 2H), 3.97 (br dd, J=9.4, 6.0 Hz, 3H),3.42 (t, J=6.4 Hz, 4H), 3.21 (s, 4H), 2.57-2.76 (m, 2H), 2.27 (dt, J=3.9, 1.7 Hz, 2H), 2.08-2.20 (m, 2H), 1.89 (quin, J=6.4 Hz, 2H), 1.59-1.83 (m, 4H), 1.36 (d, J=6.4 Hz, 3H), 1.16 (d, J=6.4 Hz, 6H); MS m/z 672.5 [M+H].

Example 516

2-(((S)-1-(1H-tetrazol-1-yl)propan-2-yl)oxy)-4-(2-((1-((1r,4r)-4-((2S,6R)-2,6-dimethylmorpholino)cyclohexyl)-3-(3-methoxypropoxy)-1H-pyrazol-4-yl)amino)pyrimidin-5-yl)benzonitrile phosphate To a solution of 2-(((S)-1-(1H-tetrazol-1-yl)propan-2-yl)oxy)-4-(2-((1-((1r,4r)-4-((2S,6R)-2,6-dimethylmorpholino)cyclohexyl)-3-(3-methoxypropoxy)-1H-pyrazol-4-yl)amino)pyrimidin-5-yl)benzonitrile (1.03 g) in THF (10 mL) was added phosphoric acid (149 mg) at room temperature. The mixture was stirred at room temperature for 1 hr. IPE (30 mL) was added to the mixture, and the mixture was stirred at 0° C. for 1h. The precipitate was collected by filtration, washed with IPE and dried under reduced pressure to give the title compound (910 mg) as yellow crystals.

$^1$H NMR (300 MHz, DMSO-$d_6$) δ 9.33-9.37 (m, 1H), 8.77-8.84 (m, 3H), 7.72-7.79 (m, 2H), 7.44-7.50 (m, 1H), 7.35-7.43 (m, 1H), 5.25-5.42 (m, 1H), 4.79-5.00 (m, 2H), 4.07-4.16 (m, 2H), 3.80-3.97 (m, 2H), 3.47-3.64 (m, 2H), 3.39-3.45 (m, 2H), 2.68-2.82 (m, 2H), 2.25-2.42 (m, 2H), 2.01-2.10 (m, 2H), 1.82-1.98 (m, 4H), 1.61-1.74 (m, 2H), 1.31-1.47 (m, 5H), 1.02-1.09 (m, 9H) 3H were hidden by solvent; MS m/z 672.5 [M+H]+.

An alternative method to produce the Example 515 is described in detail as follows.

Example 517

2-(((S)-1-(1H-tetrazol-1-yl)propan-2-yl)oxy)-4-(2-((1-((1r,4r)-4-((2S,6R)-2,6-dimethylmorpholino)cyclohexyl)-3-(3-methoxypropoxy)-1H-pyrazol-4-yl)amino)pyrimidin-5-yl)benzonitrile hydrochloride

A) 4-hydroxycyclohexan-1-one

To a solution of 1,4-dioxaspiro[4.5]decan-8-one (50.0 g) in MeOH (230 mL) was added portionwise sodium borohydride (9.50 g) at 0° C., and the mixture was stirred at room temperature for 2 hr. The reaction mixture was concentrated under reduced pressure to a volume of ca. 70-80 mL. To the resulting solution was carefully dropwise added 2 M hydrochloric acid (200 mL) at 0° C., and the mixture was stirred at room temperature for 72 hr. An aqueous potassium carbonate solution was carefully added to the mixture, and the mixture was extracted with ethyl acetate. The organic layer was separated, washed with saturated brine, dried over anhydrous sodium sulfate and concentrated under reduced pressure. The residue was passed through a silica gel pad (ethyl acetate) to give the crude title compound (24.8 g).

$^1$H NMR (300 MHz, CDCl$_3$) δ 4.20 (td, J=6.6, 3.0 Hz, 1H), 2.52-2.69 (m, 2H), 2.23-2.39 (m, 2H), 1.89-2.13 (m, 4H), 1.68 (d, J=3.4 Hz, 1H).

B) 4-((tert-butyldimethylsilyl)oxy)cyclohexan-1-one

To a solution of the crude 4-hydroxycyclohexan-1-one (21.2 g), 4-dimethylaminopyridine (7.48 g) and triethylamine (22.5 g) in DMF (350 mL) was slowly added tert-butyldimethylsilyl chloride (30.2 g) at room temperature, and the mixture was stirred at room temperature for 16 hr. Water was added to the mixture, and the mixture was extracted with ethyl acetate. The organic layer was separated, washed with saturated brine, dried over anhydrous sodium sulfate and concentrated under reduced pressure. The residue was passed through a silica gel pad (ethyl acetate/hexane) to give the crude title compound (40.4 g).

$^1$H NMR (300 MHz, CDCl$_3$) δ 4.13 (tt, J=5.0, 2.5 Hz, 1H), 2.58-2.76 (m, 2H), 2.17-2.31 (m, 2H), 1.81-2.05 (m, 4H), 0.92 (s, 9H), 0.10 (s, 6H).

C) 4-(cis-2,6-dimethylmorpholino)cyclohexan-1-ol (A Mixture of Cis and Trans)

A mixture of 4-((tert-butyldimethylsilyl)oxy)cyclohexan-1-one (36.2 g), cis-2,6-dimethylmorpholine (18.3 g), AcOH (9.51 g) and 10% palladium-carbon (8.60 g) in MeOH (700 mL) was stirred under normal pressure of hydrogen atmosphere at room temperature for 16 hr. The catalyst was removed by filtration, and the filtrate was concentrated under reduced pressure. The residue was dissolved in 2 M hydrochloric acid (280 mL) and MeOH (200 mL), and the solution was stirred at room temperature for 90 min. Ethyl acetate and saturated brine were added to the mixture, and the mixture was partitioned. The aqueous layer was washed with ethyl acetate, adjusted to pH 9 with carefully adding potassium carbonate and extracted with ethyl acetate. The extracts were washed with saturated brine, dried over anhydrous sodium sulfate and concentrated under reduced pressure. The residue was dried by azeotroped with toluene to give the title compound (25.3 g, cis:trans=87:13, determined by $^1$H NMR).

MS m/z 214.2 [M+H]$^+$.

D) cis-4-(cis-2,6-dimethylmorpholino)cyclohexan-1-ol

The above obtained 4-(cis-2,6-dimethylmorpholino)cyclohexan-1-ol (32.4 g) was dissolved in hexane (210 mL) at 65° C., and the solution was allowed to cool to room temperature and stirred at room temperature for 16 hr. The precipitate was collected by filtration, washed with cold hexane and dried under reduced pressure to give the title compound (23.5 g, cis:trans=>98:2, determined by $^1$H NMR).

$^1$H NMR (300 MHz, CDCl$_3$) δ 3.90-4.02 (m, 1H), 3.66 (dqd, J=10.1, 6.3, 2.1 Hz, 2H), 2.70-2.80 (m, 2H), 2.15-2.27 (m, 1H), 1.91 (dd, J=11.3, 10.2 Hz, 2H), 1.76-1.86 (m, 2H), 1.47-1.75 (m, 6H), 1.33 (brs, 1H), 1.16 (d, J=6.4 Hz, 6H); MS m/z 214.2 [M+H]$^+$.

E) cis-4-(cis-2,6-dimethylmorpholino)cyclohexyl methanesulfonate

To a solution of cis-4-(cis-2,6-dimethylmorpholino)cyclohexan-1-ol (10.0 g) and triethylamine (6.64 g) in THF (300 mL) was added a solution of methanesulfonyl chloride (7.52 g) in THF (30 mL) at room temperature. The reaction mixture was stirred at room temperature for 3 hr and concentrated under reduced pressure. The mixture was quenched with aqueous potassium carbonate solution at room temperature and extracted with ethyl acetate. The organic layer was separated, washed with saturated brine, dried over anhydrous sodium sulfate and concentrated under reduced pressure. The residue was passed through a NH silica gel pad (ethyl acetate) to give the crude title compound (13.7 g).

MS m/z 292.1 [M+H]$^+$.

F) ethyl 1-((1r,4r)-4-((2S,6R)-2,6-dimethylmorpholino)cyclohexyl)-3-(3-methoxypropoxy)-1H-pyrazole-4-carboxylate To a solution of cis-4-(cis-2,6-dimethylmorpholino)cyclohexyl methanesulfonate (12.0 g) and ethyl 3-(3-methoxypropoxy)-1H-pyrazole-4-carboxylate (4.70 g) in n-butyl acetate (150 mL) was added cesium carbonate (13.4 g) at room temperature. The reaction mixture was stirred at 110° C. for 16 hr. Additional cesium carbonate (4.03 g) was added to the mixture, and the mixture was stirred at 110° C. for 8 hr. DMF (120 mL) was added to the mixture, and the mixture was stirred at 110° C. for 2 hr. The mixture was quenched with saturated aqueous sodium hydrogencarbonate solution and extracted with ethyl acetate. The organic layer was separated, washed with saturated brine and concentrated under reduced pressure. The residue was purified by silica gel column chromatography (NH, ethyl acetate/hexane) to give the title compound (5.50 g).

MS m/z 424.3 [M+H]$^+$.

G) benzyl(1-((1r,4r)-4-((2S,6R)-2,6-dimethylmorpholino)cyclohexyl)-3-(3-methoxypropoxy)-1H-pyrazol-4-yl)carbamate To a solution of ethyl 1-((1r,4r)-4-((2S,6R)-2,6-dimethylmorpholino)cyclohexyl)-3-(3-methoxypropoxy)-1H-pyrazole-4-carboxylate (5.50 g) in EtOH (90 mL) was added a 2 M aqueous sodium hydroxide solution (16.2 mL) at room temperature, and the mixture was stirred at 50° C. for 24 hr.

2 M Hydrochloric acid (32.5 mL) was added to the mixture, and the mixture was stirred at room temperature for 10 min. Triethylamine (6.57 g) was added to the mixture, and the mixture was stirred at room temperature for 15 min. The reaction mixture was concentrated under reduced pressure. The residue was dried by azeotroped with EtOH and with chlorobenzene to remove EtOH. To a suspension of the residue, benzyl alcohol (7.02 g) and triethylamine (2.63 g) in chlorobenzene (200 mL) was added DPPA (5.36 g) at room temperature. After stirred at room temperature for 16 hr, the mixture was stirred at 100° C. for 3 hr. The mixture was quenched with aqueous potassium carbonate solution at room temperature and extracted with ethyl acetate. The organic layer was separated, washed with saturated brine, dried over anhydrous sodium sulfate and concentrated under reduced pressure. IPE and 1 M hydrochloric acid were added to the residue, and the mixture was partitioned. The aqueous layer was basified with potassium carbonate to pH 8 and extracted with ethyl acetate. The organic layer was separated, washed with saturated brine, and concentrated under reduced pressure. The residue was purified by silica gel column chromatography (NH, ethyl acetate/hexane) to give the title compound (6.24 g).

MS m/z 501.3 [M+H]$^+$.

H) 1-((1r,4r)-4-((2S,6R)-2,6-dimethylmorpholino)cyclohexyl)-3-(3-methoxypropoxy)-1H-pyrazol-4-amine dihydrochloride monohydrate A mixture of benzyl(1-((1r,4r)-4-((2S,6R)-2,6-dimethylmorpholino)cyclohexyl)-3-(3-methoxypropoxy)-1H-pyrazol-4-yl)carbamate (6.24 g) and 10% palladium-carbon (1.80 g) in MeOH (120 mL) was stirred under normal pressure of hydrogen atmosphere at room temperature for 16 hr. The catalyst was removed by filtration, and the filtrate was concentrated under reduced pressure. To a solution of the residue in 2-propanol (60 mL) was added 2 M hydrogen chloride-2-propanol (15.6 mL), and the mixture was stirred at room temperature for 10 min. The reaction mixture was concentrated under reduced pressure. To a solution of the residue in 2-propanol (20 mL) was added dropwise ethyl acetate (100 mL) at 60° C. The mixture was allowed to cool to room temperature and stirred at room temperature for 16 hr. The precipitate was collected by filtration, washed with ethyl acetate and dried under reduced pressure to give the title compound (3.96 g).

MS m/z 367.3 [M+H]$^+$.

I) 5-(3-(((S)-1-(1H-tetrazol-1-yl)propan-2-yl)oxy)-4-chlorophenyl)-N-(1-((1r,4r)-4-((2S,6R)-2,6-dimethylmorpholino)cyclohexyl)-3-(3-methoxypropoxy)-1H-pyrazol-4-yl)pyrimidin-2-amine A mixture of 1-((1r,4r)-4-((2S,6R)-2,6-dimethylmorpholino)cyclohexyl)-3-(3-methoxypropoxy)-1H-pyrazol-4-amine dihydrochloride monohydrate (3.00 g) and 2-chloro-5-(4-chloro-3-{[(2S)-1-(1H-tetrazol-1-yl)propan-2-yl]oxy}phenyl)pyrimidine (2.53 g) in NMP (11 mL) was stirred at 110° C. under nitrogen atmosphere for 16 hr. To the mixture were added ethyl acetate and 1 M hydrochloric acid, and the mixture was partitioned. The organic layer was washed with saturated brine. The combined aqueous layer was basified with 2 M aqueous sodium hydroxide solution to pH 8 and extracted with ethyl acetate. The organic layer was washed with saturated brine and concentrated under reduced pressure. The residue was passed through silica pad (NH, ethyl acetate/hexane). To a solution of the residue in EtOH (20 mL) was added 4 M hydrogen chloride-ethyl acetate (3.0 mL) at room temperature, and the mixture was stirred for 10 min. Ethyl acetate was added dropwise to the mixture at 55° C., and the mixture was allowed to cool to room temperature. The mixture was stirred at room temperature for 16 hr. The precipitate was collected by filtration, washed with ethyl acetate and dried under reduced pressure to give a HCl salt of the crude title compound as solids. The solids were dissolved in potassium carbonate solution and extracted with ethyl acetate. The organic layer was separated, washed with saturated brine, and concentrated under reduced pressure to give the title compound (2.71 g).

MS m/z 681.4 [M+H]$^+$.

J) 2-(((S)-1-(1H-tetrazol-1-yl)propan-2-yl)oxy)-4-(2-((1-(1r,4r)-4-((2S,6R)-2,6-dimethylmorpholino)cyclohexyl)-3-(3-methoxypropoxy)-1H-pyrazol-4-yl)amino)pyrimidin-5-yl)benzonitrile hydrochloride To a suspension of 5-(3-(((S)-1-(1H-tetrazol-1-yl)propan-2-yl)oxy)-4-chlorophenyl)-N-(1-((1r,4r)-4-((2S,6R)-2,6-dimethylmorpholino)cyclohexyl)-3-(3-methoxypropoxy)-1H-pyrazol-4-yl)pyrimidin-2-amine (2.71 g), potassium hexacyanoferrate(II) trihydrate (6.72 g) and potassium acetate (1.17 g) in CPME (42 mL) and water (42 mL) were added XPhos (379 mg) and XPhos Pd G2 (313 mg) at room temperature. The mixture was stirred at 100° C. under nitrogen atmosphere for 16 hr. The reaction mixture was partitioned. The organic layer was washed with saturated brine. The aqueous layers were extracted with ethyl acetate. The organic layer was washed with saturated brine. The combined organic layers were washed with aqueous 12% ammonia solution, saturated brine, dried over anhydrous sodium sulfate and concentrated under reduced pressure. The residue was passed through silica pad (NH, ethyl acetate). To a solution of the residue in ethyl acetate (50 mL) was added dropwise a solution of 4 M hydrogen chloride-ethyl acetate (4.0 mL) at room temperature, and the mixture was stirred at room temperature for 30 min. IPE (20 mL) was added dropwise to the mixture, and the mixture was stirred at room temperature for 1 hr. The precipitate was collected by filtration, washed with IPE and dried under reduced pressure to give the crude title compound (2.96 g). To a solution of the crude title compound (2.96 g) in EtOH (45 mL) and water (15 mL) was added dropwise EtOH (60 mL) at 70° C. The mixture was allowed to cool to room temperature and stirred at room temperature for 16 hr. The precipitate was collected by filtration, washed with EtOH and dried under reduced pressure to give the title compound (2.34 g, purity 98.2%). To a solution of the title compound (2.00 g) in ethyl methyl ketone (18 mL) and water (5.0 mL) was added EtOH (1.5 mL) at 70° C. The mixture was allowed to cool to room temperature and stirred at room temperature for 16 hr. After stirred at 5° C. for 2 hr, the precipitate was collected by filtration, washed with ethyl methyl ketone and dried under reduced pressure to give the title compound (1.42 g, purity 99.1%).

$^1$H NMR (300 MHz, DMSO-d$_6$) δ 10.47 (br d, J=1.1 Hz, 1H), 9.35 (s, 1H), 8.79 (s, 3H), 7.71-7.81 (m, 2H), 7.45 (s, 1H), 7.39 (dd, J=8.1, 1.3 Hz, 1H), 5.34 (td, J=6.1, 4.0 Hz, 1H), 4.78-4.99 (m, 2H), 4.13 (t, J=6.4 Hz, 2H), 3.95 (br dd, J=9.3, 7.0 Hz, 3H), 3.42 (t, J=6.4 Hz, 4H), 3.17-3.27 (m, 4H), 2.57-2.76 (m, 2H), 2.20-2.32 (m, 2H), 2.09-2.19 (m, 2H), 1.89 (t, J=6.4 Hz, 2H), 1.60-1.84 (m, 4H), 1.36 (d, J=6.0 Hz, 3H), 1.16 (d, J=6.4 Hz, 6H); MS m/z 672.4 [M+H]+; Anal. Calcd for C34H46Cl1N11O4: C, 57.66; H, 6.55; N, 21.75. Found: C, 57.58; H, 6.54; N, 21.57.

The melting point and the optical rotation of the compounds of Example 26, Example 143 and Example 515 are shown in the following Table 5.

TABLE 5

| Example No. | Melting Point (deg C.) | Optical Rotation (°) |
|---|---|---|
| 26 | 153 | $[\alpha]_D^{25}$ −20.8 (c 1.01, DMSO) |
| 143 | 113 | $[\alpha]_D^{25}$ −19.6 (c 1.01, DMSO) |
| 515 | decomposed around 240 | not measured |

Experimental Example 1

Evaluation of In Vitro CaMKII Inhibitory Activity (Binding Assay)
(i) Objective
In vitro CaMKIIδ inhibitory activity was evaluated by a binding assay.
(ii) Materials
Full-length, glutathione-S-transferase(GST)-tagged, human CaMKIIδ was purchased from Carna Biosciences (product #02-111, Kobe, Japan). Full-length bovine calmodulin was purchased from Wako Pure Chemical Industries (Osaka, Japan). Terbium-labeled anti-GST antibody (Tb-anti-GST Ab) was purchased from Life Technologies (Carlsbad, Calif., USA). Boron-dipyrromethene (BODIPY)-labeled probe ligand was synthesized as described below.

5,5-difluoro-7,9-dimethyl-3-(3-oxo-3-((3-((4-(3-(piperazin-1-yl)phenyl)pyrimidin-2-yl)amino)phenyl)amino)propyl)-5H-dipyrrolo[1,2-c:2',1'-f][1,3,2]diazaborinin-4-ium-5-uide

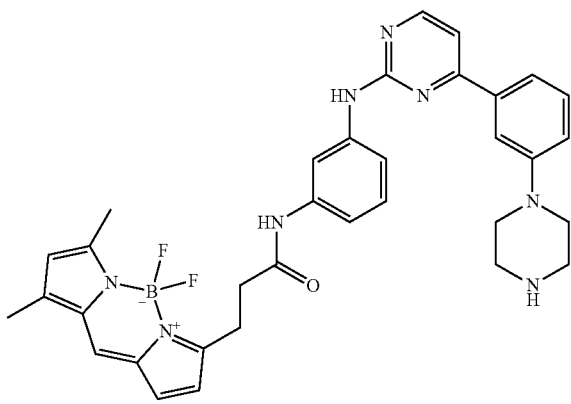

A) tert-butyl 4-(3-(2-chloropyrimidin-4-yl)phenyl)piperazine-1-carboxylate

A mixture of 2,4-dichloropyrimidine (500 mg), tert-butyl 4-(3-(4,4,5,5-tetramethyl-1,3,2-dioxaborolan-2-yl)phenyl)piperazine-1-carboxylate (1.24 g), tetrakis(triphenylphosphine)palladium(0) (739 mg), sodium carbonate (508 mg), THF (20 mL) and water (2.0 mL) was stirred at 60° C. under nitrogen atmosphere for 24 hr. The mixture was quenched with water at room temperature and extracted with ethyl acetate. The organic layer was separated, washed with water and saturated brine, dried over anhydrous magnesium sulfate and concentrated under reduced pressure. The residue was purified by column chromatography (ethyl acetate/hexane) to give the title compound.
MS m/z 375.1 [M+1]⁺.

B) tert-butyl 4-(3-(2-((3-nitrophenyl)amino)pyrimidin-4-yl)phenyl)piperazine-1-carboxylate A mixture of tert-butyl 4-(3-(2-chloropyrimidin-4-yl)phenyl)piperazine-1-carboxylate (704 mg), 3-nitroaniline (285 mg), palladium acetate (63.2 mg), BINAP (234 mg), cesium carbonate (857 mg) and toluene (10 mL) was stirred at 90° C. under nitrogen atmosphere overnight. The mixture was quenched with 1 M aqueous hydrogen chloride solution at room temperature and extracted with ethyl acetate. The organic layer was separated, washed with water and saturated brine, dried over anhydrous magnesium sulfate and concentrated under reduced pressure. The residue was purified by column chromatography (NH, ethyl acetate/hexane) to give the title compound (588 mg) MS m/z 477.2 [M+1]⁺.

C) tert-butyl 4-(3-(2-((3-aminophenyl)amino)pyrimidin-4-yl)phenyl)piperazine-1-carboxylate A mixture of tert-butyl 4-(3-(2-((3-nitrophenyl)amino)pyrimidin-4-yl)phenyl)piperazine-1-carboxylate (588 mg) and 10% palladium-carbon (131 mg) in MeOH (15 mL) was stirred under normal pressure of hydrogen atmosphere at room temperature for 3 hr. The catalyst was removed by filtration, and the filtrate was concentrated under reduced pressure to give the title compound (167 mg).
MS m/z 447.3 [M+1]⁺.

D) 3-(3-((3-((4-(3-(4-(tert-butoxycarbonyl)piperazin-1-yl)phenyl)pyrimidin-2-yl)amino)phenyl)amino)-3-oxopropyl)-5,5-difluoro-7,9-dimethyl-5H-dipyrrolo[1,2-c:2',1'-f][1,3,2]diazaborinin-4-ium-5-uide 1-Propanephosphonic acid cyclic anhydride (0.44 mL) was added to a solution of tert-butyl 4-(3-(2-((3-aminophenyl)amino)pyrimidin-4-yl)phenyl)piperazine-1-carboxylate (167 mg), 3-(2-carboxyethyl)-5,5-difluoro-7,9-dimethyl-5H-dipyrrolo[1,2-c:2',1'-f][1,3,2]diazaborinin-4-ium-5-uide (109 mg), N,N-diisopropylethylamine (0.196 mL) and N,N-dimethylaminopyridine (45.7 mg) in ethyl acetate (4.0 mL) at room temperature. The mixture was stirred at 80° C. under a dry atmosphere (calcium chloride tube) for 5 hr. The mixture was quenched with saturated aqueous sodium hydrogencarbonate solution at room temperature and extracted with ethyl acetate. The organic layer was separated, washed with water and saturated brine, dried over anhydrous magnesium sulfate and concentrated under reduced pressure. The residue was purified by column chromatography (ethyl acetate/hexane) to give the title compound (110 mg).
MS m/z 721.1 [M+1]⁺.

E) 5,5-difluoro-7,9-dimethyl-3-(3-oxo-3-((3-((4-(3-(piperazin-1-yl)phenyl)pyrimidin-2-yl)amino)phenyl)amino)propyl)-5H-dipyrrolo[1,2-c:2',1'-f][1,3,2]diazaborinin-4-ium-5-uide 4 M Hydrogen chloride-cyclopentyl methyl ether (0.382 mL) was added to a solution of 3-(3-((3-((4-(3-(4-(tert-butoxycarbonyl)piperazin-1-yl)phenyl)pyrimidin-2-yl)amino)phenyl)amino)-3-oxopropyl)-5,5-difluoro-7,9-dimethyl-5H-dipyrrolo[1,2-c:2',1'-f][1,3,2]diazaborinin-4-ium- 5-uide (110 mg) in ethyl acetate (2.0 mL) at room temperature. The mixture was stirred at room temperature under a dry atmosphere (calcium chloride tube) for 5 hr. After evaporation of the solvent, the residue was purified by preparative HPLC (water/CH₃CN containing 0.1% TFA). The desired fractions were neutralized with saturated aqueous sodium hydrogencarbonate solution and extracted with ethyl acetate. The organic layer was separated, dried over anhydrous magnesium sulfate and concentrated under reduced pressure to give the title compound (15.0 mg).

$^1$H NMR (300 MHz, DMSO-d$_6$) δ 9.99 (s, 1H), 9.61 (s, 1H), 8.51 (d, J=5.0 Hz, 1H), 8.05 (s, 1H), 7.71 (s, 2H), 7.60 (d, J=8.3 Hz, 1H), 7.49-7.56 (m, 1H), 7.32-7.43 (m, 2H), 7.21 (d, J=7.7 Hz, 2H), 7.10 (d, J=3.9 Hz, 2H), 6.41 (d, J=3.9 Hz, 1H), 6.31 (s, 1H), 3.09-3.23 (m, 6H), 2.82-2.94 (m, 4H), 2.72-2.80 (m, 3H), 2.27 (s, 3H), 1.23 (s, 3H); MS m/z 621.2 [M+1]$^+$.

(iii) Methods

Time-Resolved Fluorescence Resonance Energy Transfer (TR-FRET) Assay

All assays were conducted using 384-well, white, flat-bottomed plates (product #784075, Greiner Bio-One, Frickenhausen, Germany) in kinase assay buffer, which consists of 50 mM HEPES pH 7.6, 10 mM MgCl$_2$, 1 mM EGTA, 0.01% Brig-35, 0.1 mM DTT). The fluorescent probe ligand was added at a final concentration of 300 nM to solutions containing 0.21 nM Tb-anti-GST Ab, 1 mM CaCl$_2$, 10 μg/mL calmodulin, and 0.5 nM GST-tagged CaMKIIδ. After shaded incubation of the protein-probe mixture on ice for 30 min, the premix was dispensed in the assay plate including test inhibitors with 4 fold dilution series of eight concentrations. After 1 hr incubation at room temperature, TR-FRET signals were measured in duplicate using an EnVision microplate reader (Perkin Elmer, Waltham, Mass., USA). The solution in each well was excited with a laser (λ=340 nm) reflected by a dichroic mirror (D400/D505 (Perkin Elmer) through an excitation filter (UV (TRF) 340, (Perkin Elmer)), and fluorescence from Tb and BODIPY were detected through two emission filters (CFP 495 (Perkin Elmer) for Tb, Emission 520 (Perkin Elmer) for BODIPY).

The percentage of inhibition of test compounds was calculated according to equation (1)

$$\text{Inhibition}(\%) = 100 \times (\mu_H - T)/(\mu_H - \mu_L) \quad (1)$$

Where T is the value of the wells containing test compounds and $\mu_H$ and $\mu_L$ are the mean values of the 0% and 100% inhibition control wells, respectively. The values of the 0 and 100% controls were the signals obtained in the absence and presence of 3 μM its parent compound, respectively. The half maximal inhibitory concentration (IC$_{50}$) of test compounds was calculated by fitting the data with the logistic equation using XLfit (IDBS, Guildford, UK). The IC$_{50}$ was classified according to the following activity ranks.

A: less than 10 nM
B: 10 nM or more and less than 100 nM
C: 100 nM or more

The results are shown in Tables 1 and 4.

Experimental Example 2

Evaluation of In Vivo Cardiac CaMKII Inhibition (Oral Administration)

(i) Objective

To evaluate potency of test compounds to inhibit cardiac CaMKII kinase in vivo, phosphorylation levels of CaMKII-specific sites of phospholamban (Thr17, PLN) were measured in the heart of rats administered orally with test compounds.

(ii) Materials and Methods

Test compounds were suspended in 0.5% [w/v]methyl-cellulose/water solution and administered (30 mg/kg) to male CD (SD) IGS rat (6-8 weeks old, n=4) by the p.o. route (5 mL/kg). At 4 hours after the administration, rats were sacrificed and the hearts were harvested. After washing the isolated hearts with ice-cold saline, connective tissues were removed on ice, and the isolated left ventricle were frozen into liquid nitrogen gas and stored at −80° C.

The left ventricle samples were homogenized in RIPA-buffer containing phosphatase inhibitors and protease inhibitors. Samples were analyzed by Western blotting using anti-P-PLN (Thr17, Santa Cruz Biotechnology, sc-17024-R) antibody. The band intensities were quantified using an imaging system and were normalized relative to the vehicle-treated group.

(iii) Results

The results of the in vivo cardiac CaMKII inhibition are shown in Table 6.

TABLE 6

Results of P-PLN reduction rate of each test compound in comparison with vehicle-treated group

| Test compound (Example No.) | Dose | Time after administration | Reduction rate of P-PLN |
|---|---|---|---|
| 12 | 30 mg/kg | 4 hr | >30% |
| 26 | 30 mg/kg | 4 hr | >30% |
| 30 | 30 mg/kg | 4 hr | >30% |
| 33 | 30 mg/kg | 4 hr | >30% |
| 36 | 30 mg/kg | 4 hr | >30% |
| 143 | 30 mg/kg | 4 hr | >30% |
| 486 | 30 mg/kg | 4 hr | >30% |
| 487 | 30 mg/kg | 4 hr | >30% |
| 488 | 30 mg/kg | 4 hr | >30% |
| 489 | 30 mg/kg | 4 hr | >30% |

Experimental Example 3

Evaluation of In Vivo Cardiac CaMKII Inhibition (Intravenous Administration)

(i) Objective

To evaluate potency of test compounds to inhibit cardiac CaMKII kinase in vivo, phosphorylation levels of CaMKII-specific sites of phospholamban (Thr17, PLN) were measured in the heart of rats administered intravenously with test compounds.

(ii) Materials and Methods

Test compounds were dissolved in N,N-dimethylacet-amide and 1,3-butanediol (1:1) solution and were injected (1 mg/kg) to male CD (SD) IGS rats (8 weeks old, n=4) by bolus intravenous injection via the lateral tail vein or the femoral vein (0.5-1 mL/kg). At 0.25 hours after the injection, rats were sacrificed and the hearts were harvested. After washing the isolated hearts with ice-cold saline, connective tissues were removed on ice, and the isolated left ventricle were frozen into liquid nitrogen gas and stored at −80° C.

The left ventricle samples were homogenized in RIPA-buffer containing phosphatase inhibitors and protease inhibitors. Samples were analyzed by Western blotting using anti-P-PLN (Thr17, Santa Cruz Biotechnology, sc-17024-R) antibody. The band intensities were quantified using an imaging system and were normalized relative to the vehicle-treated group.

(iii) Results

The results of the in vivo cardiac CaMKII inhibition are shown in Table 7.

TABLE 7

Results of P-PLN reduction rate of each test compound in comparison with vehicle-treated group

| Test compound (Example No.) | Dose | Time after administration | Reduction rate of P-PLN |
|---|---|---|---|
| 143 | 1 mg/kg | 0.25 hr | >30% |
| 485 | 1 mg/kg | 0.25 hr | >30% |

Experimental Example 4

Evaluation of In Vitro Cytotoxicity (i) Objective

To evaluate in vitro cytotoxicity of test compounds, % ATP reduction was determined in the presence of 33 μM of each test compound after 72 hr incubation.

(ii) Materials and Methods

HepG2 cells were seeded in DMEM (Invitrogen) containing 10% FBS (Corning)+glucose (4.5 g/L) for 24 hr to allow cell adhesion. For compound treatments, compounds were diluted in DMSO and the media, followed by added to the wells (24 hr after the cell seeding) to obtain the desired final concentration (33 μM, n=2). The final DMSO concentration was 1%. After 72 hr, cellular ATP contents were measured using CellTiter-Glo Luminescent Cell Viability Assay (Promega). The % ATP reduction was determined by comparing the ATP contents in the absence and the presence of test compounds.

(iii) Results

The results of cytotoxicity test are shown in Table 8.

TABLE 8

Results of % ATP reduction after 72 hr incubation with each test compound

| Test compound (Example No.) | % ATP reduction |
|---|---|
| 143 | 12% |
| 26 | 9% |
| 241 | −2% |
| 477 | 9% |
| 485 | 7% |
| 488 | 3% |
| Ex. 772 described in WO 2018/183112 A1 | >50% |
| Ex. 817 described in WO 2018/183112 A1 | 40% |

Formulation Examples

Medicaments containing the compound of the present invention as an active ingredient can be produced, for example, by the following formulations.

1. Capsule

| (1) compound obtained in Example 1 | 10 mg |
| (2) lactose | 90 mg |
| (3) microcrystalline cellulose | 70 mg |
| (4) magnesium stearate | 10 mg |
| 1 capsule | 180 mg |

The total amount of the above-mentioned (1), (2) and (3) and 5 mg of (4) are blended and granulated, and 5 mg of the remaining (4) is added. The whole mixture is sealed in a gelatin capsule.

2. Tablet

| (1) compound obtained in Example 1 | 10 mg |
| (2) lactose | 35 mg |
| (3) cornstarch | 150 mg |
| (4) microcrystalline cellulose | 30 mg |
| (5) magnesium stearate | 5 mg |
| 1 tablet | 230 mg |

The total amount of the above-mentioned (1), (2) and (3), 20 mg of (4) and 2.5 mg of (5) are blended and granulated, and 10 mg of the remaining (4) and 2.5 mg of the remaining (5) are added and the mixture is compression formed to give a tablet.

INDUSTRIAL APPLICABILITY

According to the present invention, a compound having a superior CaMKII inhibitory action, which is expected to be useful as an agent for the prophylaxis or treatment of cardiac diseases (particularly catecholaminergic polymorphic ventricular tachycardia, postoperative atrial fibrillation, heart failure, fatal arrhythmia) and the like can be provided.

The invention claimed is:

1. A compound represented by the formula (I):

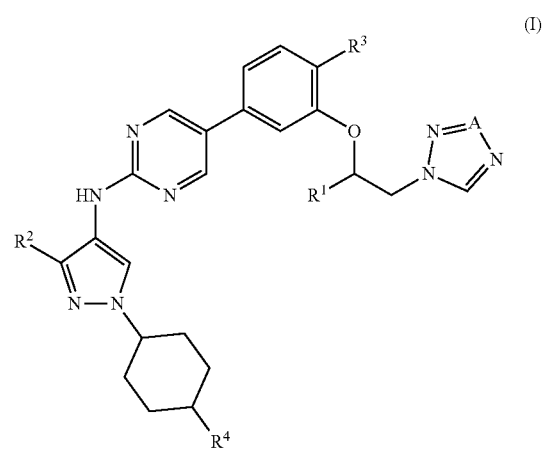

wherein
A is CH or N;
$R^1$ is a $C_{1-3}$ alkyl group;
$R^2$ is
(1) a group represented by the formula: —O—$X^1$—$X^2$—O—$(CH_2$—$CH_2$—$O)_p$—Y:
wherein
$X^1$ is a $C_{1-6}$ alkylene group optionally substituted by 1 to 4 halogen atoms,

491

$X^2$ is
(i) a bond, or
(ii) a group represented by the formula:

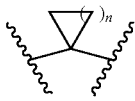

wherein n is an integer of 1 to 4,
p is an integer of 0 to 7, and
Y is
(i) a hydrogen atom, or
(ii) a $C_{1-6}$ alkyl group optionally substituted by 1 to 3 halogen atoms,
(2) a group represented by the formula: —O—$X^3$—$Z^1$:
wherein
$X^3$ is a $C_{1-6}$ alkylene group optionally substituted by 1 to 4 halogen atoms, and
$Z^1$ is
(i) a cyano group,
(ii) a $C_{1-6}$ alkylsulfonyl group, or
(iii) a 3- to 8-membered monocyclic oxygen-containing non-aromatic heterocyclic group,
(3) a group represented by the formula: —O—$X^4$—$Z^2$:
wherein
$X^4$ is a bond or a $C_{1-6}$ alkylene group optionally substituted by 1 to 4 halogen atoms, and
$Z^2$ is a 5- or 6-membered monocyclic nitrogen containing aromatic heterocyclic group optionally substituted by 1 to 3 $C_{1-6}$ alkyl groups, or
(4) a hydroxy group;
$R^3$ is a cyano group or a halogen atom; and
$R^4$ is a morpholinyl group or a bridged morpholinyl group, each optionally substituted by 1 to 3 $C_{1-6}$ alkyl groups;
or a pharmaceutically acceptable salt thereof.

2. The compound or pharmaceutically acceptable salt according to claim 1,
wherein
$R^1$ is a methyl group;
$R^2$ is
(1) a group represented by the formula: —O—$X^1$—$X^2$—O—$(CH_2$-$CH_2$—O$)_p$—Y:
wherein
$X^1$ is a $C_{1-6}$ alkylene group,
$X^2$ is a bond,
p is an integer of 0 or 1, and
Y is
(i) a hydrogen atom, or
(ii) a $C_{1-3}$ alkyl group optionally substituted by 1 to 3 halogen atoms,
(2) a group represented by the formula: —O—$X^3$—$Z^1$:
wherein
$X^3$ is a $C_{1-3}$ alkylene group, and
$Z^1$ is
(i) a cyano group,
(ii) a $C_{1-3}$ alkylsulfonyl group, or
(iii) a 3- to 6-membered monocyclic oxygen-containing non-aromatic heterocyclic group,

492

(3) a group represented by the formula: —O—$X^4$—$Z^2$:
wherein
$X^4$ is a $C_{1-3}$ alkylene group, and
$Z^2$ is a 5- or 6-membered monocyclic nitrogen containing aromatic heterocyclic group optionally substituted by 1 to 3 $C_{1-3}$ alkyl groups, or
(4) a hydroxy group;
$R^3$ is a cyano group or a chlorine atom; and
$R^4$ is a morpholino group or a 3-oxa-8-azabicyclo[3.2.1]octan-8-yl group, each optionally substituted by 1 to 3 $C_{1-6}$ alkyl groups.

3. The compound or pharmaceutically acceptable salt according to claim 1,
wherein
$R^1$ is a methyl group;
$R^2$ is
(1) a group represented by the formula: —O—$X^1$—$X^2$—O—$(CH_2$-$CH_2$—O$)_p$—Y:
wherein
$X^1$ is a $C_{1-6}$ alkylene group,
$X^2$ is a bond,
p is an integer of 0 or 1, and
Y is
(i) a hydrogen atom, or
(ii) a $C_{1-3}$ alkyl group, or
(2) a group represented by the formula: —O—$X^3$—$Z^1$:
wherein
$X^3$ is a $C_{1-3}$ alkylene group, and
$Z^1$ is a 3- to 6-membered monocyclic oxygen-containing non-aromatic heterocyclic group;
$R^3$ is a cyano group or a chlorine atom; and
$R^4$ is a morpholino group, a morpholino group substituted by 1 or 2 $C_{1-6}$ alkyl groups, or a 3-oxa-8-azabicyclo[3.2.1]octan-8-yl group.

4. The compound or pharmaceutically acceptable salt according to claim 3,
wherein $R^2$ is
(1) a group represented by the formula: —O—$X^1$—$X^2$—O—$(CH_2$-$CH_2$—O$)_p$—Y:
wherein
$X^1$ is —$(CH_2)2$—, —$(CH_2)_3$— or *—$CH_2$—$CH_2$—$C(CH_3)_2$—**, wherein * is the bonding site to the oxygen atom, and ** is the bonding site to $X^2$,
$X^2$ is a bond,
p is an integer of 0 or 1, and
Y is a hydrogen atom, a methyl group or an ethyl group, or
(2) a group represented by the formula: —O—$X^3$—$Z^1$:
wherein
$X^3$ is —$CH_2$— or —$(CH_2)_2$—, and
$Z^1$ is an oxetanyl group or a tetrahydropyranyl group.

5. A compound selected from
2-(((S)-1-(1H-tetrazol-1-yl)propan-2-yl)oxy)-4-(2-((1-((1r,4r)-4-((1R,5S)-3-oxa-8-azabicyclo[3.2.1]octan-8-yl)cyclohexyl)-3-(2-ethoxyethoxy)-1H-pyrazol-4-yl)amino)pyrimidin-5-yl)benzonitrile,
2-(((S)-1-(1H-tetrazol-1-yl)propan-2-yl)oxy)-4-(2-((3-(3-methoxypropoxy)-1-((1r,4r-4-morpholinocyclohexyl)-1H-pyrazol-4-yl)amino)pyrimidin-5-yl)benzonitrile,
2-(((S)-1-(1H-tetrazol-1-yl)propan-2-yl)oxy)-4-(2-((1-((1r,4r)-4-((1R,5 S)-3-oxa-8-azabicyclo[3.2.1] octan-8-yl)cyclohexyl)-3-(3-methoxypropoxy)-1H-pyrazol-4-yl)amino)pyrimidin-5-yl)benzonitrile,
2-(((S)-1-(1H-tetrazol-1-yl)propan-2-yl)oxy)-4-(2-((3-(3-ethoxypropoxy)-1-((1r,4r-4-morpholinocyclohexyl)-1H-pyrazol-4-yl)amino)pyrimidin-5-yl)b enzonitrile, 2-(((S)-1-(1H-tetrazol-1-yl)propan-2-yl)oxy)-4-(2-((1-((1r,4r)-4-((1R,5S)-3-oxa-8-azabicyclo[3.0.2.1]octan-8-yl)cyclohexyl)-3-(3-ethoxypropoxy)-1H-pyrazol-4-yl)amino)pyrimidin-5-yl)benzonitrile, 2-(((S)-1-(1H-tetrazol-1-yl)propan-2-yl)oxy)-4-(2-((1-((1r,4r)-4-((2S,6R)-2,6-dimethylmorpholino)cyclohexyl)-3-(3-methoxypropoxy)-1H-pyrazol-4-yl)amino)pyrimidin-5-yl)benzonitrile, 2-(((S)-1-(1H-tetrazol-1-yl)propan-2-yl)oxy)-4-(2-((1-((1r,4r)-4-((2S,6R)-2,6-dimethylmorpholino)cyclohexyl)-3-(2-(2-methoxyethoxy)ethoxy)-1H-pyrazol-4-yl)amino)pyrimidin-5-yl)benzonitrile hydrochloride, 2-(3-((4-((5-(3-(((S)-1-(1H-tetrazol-1-yl)propan-2-yl)oxy)-4-chlorophenyl)pyrimidin-2-yl)amino)-1-((1r,4r)-4-((2S,6R)-2,6-dimethylmorpholino)cyclohexyl)-1H-pyrazol-3-yl)oxy)propoxy)ethan-1-ol, 2-(((S)-1-(1H-tetrazol-1-yl)propan-2-yl)oxy)-4-(2-((1-((1r,4r)-4-((2S,6R)-2,6-dimethylmorpholino)cyclohexyl)-3-(2-(oxetan-3-yl)ethoxy)-1H-pyrazol-4-yl)amino)pyrimidin-5-yl)benzonitrile, 2-(((S)-1-(1H-tetrazol-1-yl)propan-2-yl)oxy)-4-(2-((1-((1r,4r)-4-((2S,6R)-2,6-dimethylmorpholino)cyclohexyl)-3-(oxetan-3-ylmethoxy)-1H-pyrazol-4-yl)amino)pyrimidin-5-yl)benzonitrile, 2-(((S)-1-(1H-tetrazol-1-yl)propan-2-yl)oxy)-4-(2-((1-((1r,4r)-4-((2S,6R)-2,6-dimethylmorpholino)cyclohexyl)-3-((tetrahydro-2H-pyran-4-yl)methoxy)-1H-pyrazol-4-yl)amino)pyrimidin-5-yl)benzonitrile, 2-(((S)-1-(1H-tetrazol-1-yl)propan-2-yl)oxy)-4-(2-((1-((1r,4r)-4-((2S,6R)-2,6-dimethylmorpholino)cyclohexyl)-3-(3-hydroxy-3-methylbutoxy)-1H-pyrazol-4-yl)amino)pyrimidin-5-yl)benzonitrile, 4-((4-((5-(3-(((S)-1-(1H-tetrazol-1-yl)propan-2-yl)oxy)-4-chlorophenyl)pyrimidin-2-yl)amino)-1-((1r,4r)-4-((2S,6R)-2,6-dimethylmorpholino)cyclohexyl)-1H-pyrazol-3-yl)oxy)-2-methylbutan-2-ol, 5-(3-(((S)-1-(1H-tetrazol-1-yl)propan-2-yl)oxy)-4-chlorophenyl)-N-(1-((1r,4r)-4-((2S,6R)-2,6-dimethylmorpholino)cyclohexyl)-3-(3-(2-methoxyethoxy)propoxy)-1H-pyrazol-4-yl)pyrimidin-2-amine, 2-(((S)-1-(1H-tetrazol-1-yl)propan-2-yl)oxy)-4-(2-((1-((1r,4r)-4-((2S,6R)-2,6-dimethylmorpholino)cyclohexyl)-3-(3-(2-methoxyethoxy)propoxy)-1H-pyrazol-4-yl)amino)pyrimidin-5-yl)benzonitrile, and 5-(3-(((S)-1-(1H-tetrazol-1-yl)propan-2-yl)oxy)-4-chlorophenyl)-N-(1-((1r,4r)-4-((2S,6R)-2,6-dimethylmorpholino)cyclohexyl)-3-(3-methoxypropoxy)-1H-pyrazol-4-yl)pyrimidin-2-amine, or a pharmaceutically acceptable salt thereof.

\* \* \* \* \*